US006967088B1

(12) United States Patent
Williams et al.

(10) Patent No.: US 6,967,088 B1
(45) Date of Patent: Nov. 22, 2005

(54) SOLUBLE RECOMBINANT BOTULINUM TOXIN PROTEINS

(75) Inventors: James A. Williams, Lincoln, NE (US); Bruce S. Thalley, Madison, WI (US)

(73) Assignees: Allergan, Inc., Irvine, CA (US); Allergan Botox Limited, Irvine, CA (US)

( * ) Notice: Subject to any disclaimer, the term of this patent is extended or adjusted under 35 U.S.C. 154(b) by 0 days.

(21) Appl. No.: 08/704,159

(22) Filed: Aug. 28, 1996

Related U.S. Application Data

(63) Continuation-in-part of application No. 08/405,496, filed on Mar. 16, 1995, now Pat. No. 5,919,665.

(51) Int. Cl.[7] ........................ C12N 15/09; C12N 15/31; C12N 15/72; C12N 15/74; A61K 39/08

(52) U.S. Cl. .................... 435/69.1; 435/69.7; 435/71.1; 435/71.2; 435/320.1; 424/236.1; 424/247.1

(58) Field of Search ............................ 435/69.1, 320.1, 435/71.1, 252.7; 424/247.1, 236.1, 184.1, 192.1; 530/350

(56) References Cited

U.S. PATENT DOCUMENTS

| | | | | |
|---|---|---|---|---|
| 5,080,895 A | | 1/1992 | Tokoro | |
| 5,310,663 A | * | 5/1994 | Dobeli et al. | 435/69.7 |
| 5,919,665 A | * | 7/1999 | Williams | 435/71.1 |

OTHER PUBLICATIONS

Nassau et al. J. Bacterio. 1996, vol. 178, No. 4, pp. 1047–1052.*

Hill et al. Arch. Biochem. And Biophy. 1996, vol. 336, No. 2, pp. 283–289.*

Kimura et al. Applied and Environmental Microbiology 1991, vol. 57, No. 4, pp. 1168–1172.*

TaKaRa Shuzo Co. Catalog of TAKARA BIO Inc. at the web site: bio:takara.co.jp.*

Plotkin et al (*Vaccines* published by W.B. Saunders Company Philadelphia, p. 571), 1988.*

Nygren, P.–A. et al. Trends in Biotechnology 12 (5): 184–188, May 1994.*

Rudinger, J. in Peptide Hormones, Parsons, J.A. (Ed.), University Park Press, Baltimore, MD, pp. 1–7, 1976.*

Thompson, D. E. et al. Eur. J. Biochem. 189: 73–81, Apr. 1990.*

Binz, T. et al. J. Biol. Chem. 265: 9153–9158, Jun. 1990.*

Roitt, I. Essential Immunology, Sixth Edition, Blackwell Scientific Publications, Boston, MA, pp. 173–178, 1988.*

LeClerc, C. et al., J. Immunol. 144 (8): 3174–3182, Apr. 1990.*

Kleid, D. G. Annals NY Acad. Sci. 413: 23–30, 1983.*

Siegel, L. J. Clin. Microbiol. 26: 2351–2356, Nov. 1988.*

Cato et al. (1986) "Clostridium,"in *Bergey's Manual® of Systematic Bacteriology,* 2:1141–1200, Sneath (ed.), Williams & Wilkins.

Englekirk et al. (1992) "Classification," in *Principles and Practice of Clinical Anaerobic Bacteriology,* pp. 22–23, Star Publishing Co., Belmont, CA.

Stephen and Pietrowski (1986) "Toxins Which Traverse Membranes and Deregulate Cells," in *Bacterial Toxins,* 2d ed., pp. 66–67, American Society for Microbiology.

Berkow and Fletcher (eds.) (1992) "Bacterial Diseases," *in Merck Manual of Diagnosis and Therapy,* 16th ed., pp. 116–126, Merck Research Laboratories, Rahway, NJ.

Sigmund and Fraser (eds.) (1979) "Clostridial Infections," in *Merck Veterinary Manual,* 5th ed., pp. 396–409, Merck & Co., Rahway, N.J.

Hatheway (1990) "Bacteriophages and plasmids and their roles in coding for botulinal neurotoxins," Clin. Microbiol. Rev. 3:73–74.

Arnon (1986) "Infant Botulism: Anticipating the Second Decade," J. Infect. Dis. 154:201–206.

Arnon (1980) "Infant Botulism" Ann. Rev. Med. 31:541–559.

MacDonald et al. (1986) "The Changing Epidemiology of Adult Botulism in the United States," *Am. J. Epidemiol.* 124:794–799.

Tacket et al. (1984) "Equine Antitoxin Use and Other Factors That Predict Outcome in Type A Foodborne Botulism," Am. J. Med. 76:794–798.

Swartz (1990) "Anaerobic Spore–Forming Bacilli: The Clostridia," in B.D. *Microbiology,* 4th edition, pp. 633–646, Davis et al. (eds.), J.B. Lippincott Co.

Holzer (1962) "Botulismus durch Inhalation," Med. Klin. 41:1735–738.

Franz et al. (1993) in *Botulinum and Tetanus Neurotoxins,* pp. 473–476, B.R. DasGupta, ed., Plenum Press, NY.

Arnon et al. (1981) "Infant Botulism: Epidemiology and Relation to Sudden Infant Death Syndrome," Epidemiol. Rev. 3:45–66.

Frankovich and Arnon (1991) "Clinical Trial of Botulism Immune Globulin for Infant Botulism," West. J. Med. 154:103.

Sugiyama (1980) "*Clostridium botoulinum* Neurotoxin," Microbiol. Rev. 44:419–448.

Balady (1991) "Botulism Antitoxin Fielded for Operation Desert Storm," USAMRDC Newsletter, p. 6.

(Continued)

*Primary Examiner*—James Housel
*Assistant Examiner*—Bao Qun Li
(74) *Attorney, Agent, or Firm*—Greg S. Hollrigel

(57) ABSTRACT

The present invention includes recombinant proteins derived from *Clostridium botulinum* toxins. In particular, soluble recombinant *Clostridium botulinum* type A, type B and type E toxin proteins are provided. Methods which allow for the isolation of recombinant proteins free of significant endotoxin contamination are provided. The soluble, endotoxin-free recombinant proteins are used as immunogens for the production of vaccines and antitoxins. These vaccines and antitoxins are useful in the treatment of humans and other animals at risk of intoxication with clostridial toxin.

7 Claims, 40 Drawing Sheets

OTHER PUBLICATIONS

Schwarz and Arnon (1992)( "Botulism Immune Globulin for Infant Botulism Arrives–One Year and A Gulf War Later," Western J. Med. 156:197–198.

Peterson et al. (1979) "The Sudden Infant Death Syndrome and Infant Botulism," Rev. Infect. Dis. 1:630–634.

Arnon et al. (1978) "Intestinal Infection and Toxin Production by *Clostridium Botulinum* as One Cause of Sudden Infant Death Syndrome," Lancet, pp. 1273–1277.

Informational Brochure for the Pentavalent (ABCDE) Botulinum Toxoid, Centers for Disease Control, Rev. 1995, pp. 1–3 and 3 unnumbered pages.

Brooks et al. (eds.) (1991) "Infections Caused by Anaerobic Bacteria," in *Jawetz, Melnick, & Adelberg's Medical Microbiology,* 19th ed., pp. 257–262, Appleton & Lange, San Mateo, CA.

Engelkirk et al. (1992) Principles and Practice of Clinical Anaerobic Bacteriology, pp. 64–67, Star Publishing Co., Belmont, CA.

Lyerly et al. (1992) "Characterization of a Toxin A–Negative, Toxin B–Positive Strain of *Clostridium difficile,*" Infect. Immun. 60:4633–4639.

Borriello et al. (1990 "Virulence Factors of *Clostridium difficile,*" Rev. Infect. Dis., 12(Suppl. 2):S185–S191.

Lyerly et al. (1985) "Effects of *Clostridium difficile* Toxins Given Intragastrically to Animals," Infect. Immun. 47:349–352.

Rolfe (1990) "Binding Kinetics of *Clostridium difficile* Toxins A and B to Intestinal Brush Border Membranes from Infant and Adult Hamsters," Infect. Immun. 59:1223–1230.

Kim and Rolfe (1987) "The Protective Role of Antibody to Toxin A in *Clostridium difficile*—Induced Ileoceeitis," Abstr. Ann. Meet. Am. Soc. Microbiol. 69:62.

Banno et al. (1984) "Biochemical Characterization and Biologic Actions of Two Toxins (D–1 and D–2) From *Clostridium difficile,*" Rev. Infect. Dis. 6(Suppl. 1:S11–S20).

Rihn et al. (1984) "A New Purification Procedure for *Clostridium difficile* Enterotoxin," Biochem. Biophys. Res. Comm. 124:690–695.

Justus et al. (1982) "Myoelectric Effects of *Clostridium difficile:* Motility–Altering Factors Distinct From its Cytotoxin and Enterotoxin in Rabbits," Gasroenterol. 83:836–843.

Finegold et al. (1992) "Antimicrobial–Associated pseudomembranous Colitis," in *Clinical Guide to Anaerobic Infections,* pp. 88–89, Star Publishing Co., Belmont, CA.

United States Pharmacopeia (1990) United States Pharmacopeial Convention, vol. XXII:1515–1516 Rockville, MD.

FDA Guidelines for Parenteral Drugs (Dec. 1987) i.e., Guideline on Validation of the Limulus Ameobycte Lysate Test as an End–Product Endotoxin Test for Human and Animal Parenteral Drugs. Biological Products and Medical Devices.

Pearson (1985) "Equivalency of LAL and USP Rabbit Pyrogen Tests," in *Pyrogens: endotoxins, lal testing and depyrogenation,* Marcel Dekker, NY, pp. 150–155.

Minton (1995) "Molecular Genetics of Clostridial Neurotoxins," Curr. Top. Microbiol. Immunol. 195:161–194.

Benedict and Yamaga (1966) "Immunoglobulins and Antibody Production in Avian Species," in *Comparative Immunology,* pp. 335–375 (JJ. Marchaloni, ed.), Blackwell, Oxford.

Patterson et al. (1962) "Antibody Production and Transfer to Egg Yolk in Chickens," Immunol. 89:272–278.

Carroll and Stollar (1983) "Antibodies of Calf Thymus RNA Polymerase II from Egg Yolks of Immunized Hens," J. Biol. Chem. 258:24–26.

Polson et al. (1980) "Antibodies to Proteins from Yolk of Immunized Hens," Immunol. Comm. 9:495–514.

DasGupta and Sugiyama (1972) "A Common Subunit Structure In *Clostridium Botulinum* Type A, B. and E Toxins," Biochem. Biophys. Res. Commun. 48:108–112.

DasGupta (1990) "Structure and Biological Activity of Botulinum Neurotoxin," J. Physiol. 84:220–228.

Halpern and Loftus (1993) "Characterization of the Receptor–binding Domain of Tetanus Toxin," J. Biol. Chem. 268:11188–11192.

Whelan et al. (1992) "Molecular Cloning of the *Clostridium botulinum* Structural Gene Encoding the Type B Neurotoxin and Determination of Its Entire Nucleotide Sequence," Appl. Environ. Microbiol. 58:2345–2354.

Sakaguchi (1983) "*Clostridium Botulinum* Toxins," Pharmac. Ther. 19:165–194.

Moberg and H. Sugiyama (1978) "Affinity Chromatography Purification of Type A Botulinum Neurotoxin from Crystalline Toxic Complex," Appl. Environ. Microbol. 35:878–880.

Thalley et al. (1993) "Development of an Avian Antitoxin to Type A Botulinum Neurotoxin," in *Botulinum and Tetanus Neurotoxins,* pp. 467–472, B.R. DasGupta, ed., Plenum Press, NY.

Schantz and Johnson (1992) "Properties and Use of Botulinum Toxin and Other Microbial Neurotoxins in Medicine," Microbiol. Rev. 56:80–99.

Makoff et al. (1989) "Expression of Tetanus Toxin Fragment C in *E. Coli:* Its Purification and Potential Use as a Vaccine," Bio/Technology 7:1043–1046.

Makoff et al. (1989) "Expression of tetanus toxin fragment C in *E. coli:* high level expression by removing rare condons," Nucl. Acids Res. 17:10191–10202.

Halpern et al. (1990) "Cloning and Expression of Functional Fragment C of Tetanus Toxin," Infect. Immun. 58:1004–1009.

Romanos et al. (1991) "Expression of tetanus toxin fragment C in yeast: gene synthesis is required to eliminate fortuitous polyadenylation sites in AT–rich DNA," Nucleic Acids Res. 19:1461–1467.

Charles et al. (1991) "Synthesis of Tetanus Toxin Fragment C in Insect Cells by Use of a Baculovirus Expression System," Infect. Immun. 59:1627–1632.

Popoff et al. (1991) "Characterization of the C3 Gene of *Clostridium botulinum* Types C and D and Its Expression in *Escherichia coli,*" Infect. Immun. 59:3673–3679.

LaPenotiere et al. (1993) "Development of a Molecular Engeineered Vaccine for *C. Botulitnum* Neurotoxins," in *Botulinum and Tetanus Neurotoxins,* B.R. DasGupta, ed., Plenum Press, NY, pp. 463–466.

Thompson et al. (1990) The complete amino acid sequence of the *Clostricum botulinum* type A neurotoxin, deduced by nucleotide sequence analysis of the encoding gene, Eur. J. Biochem. 189:73–81.

LaPenotiere et al. (1995) "Expression of a Large, Nontoxic Fragment of Botulinum Neurotoxin Serotype A and Its Use as an Immunogen," Toxicon, 33:1383–1386.

Middlebrook and Brown (1995) "Immunodiagnosis and Immunotherapy of Tetanus and Botulinum Neurotoxins," Curr. Top. Microbiol. Immunol. 195:89–122.

Hutson et al. (1994) "Nucleotide Sequence of the Gene Coding for Non–Proteolytic *Clostridium botulinum* Type B Neurotoxin: Comparison with Other Clostridial Neurotoxins," Curr. Microbiol. 28:101–110.

Poulet et al. (1992) "Sequences of the Botulinal Neurotoxin E Derived from *Clostridium Botulinum* Type E (Strain Beluga) and *Clostridium Butyricum* (Strains ATCC 43181 and ATCC 43755)," Biochem. Biophys. Res. Commun. 183:107–113.

Whelan et al. (1992) "The complete amino acid sequence of the *Clostridium botulinum* type–E neurotoxin, derived by nucleotide–sequence analysis of the encoding gene," Eur. J. Biochem. 204:657–667.

Fujii et al. (1993) "The complete nucleotide sequence of the gene encoding the nontoxic component of *Clostridium botulinum* type E progenitor toxin," J. Gen. Microbiol. 139:79–86.

Delmee et al. (1990) "Characterization of Flagells of *Clostridium difficile* and Their Role in Serogrouping Reactions," J. Clin. Microbiol. 28:2210–2214.

Delmee and Avesani (1990) "Virulence of ten serogroups of *Clostridium difficile* in hamsters," J. Med Microbiol. 33:85–90.

Toma et al., (1988) "Serotyping of *Clostridium difficile,*" J. Clin. Microbiol. 26:426–428.

Delmee et al. (1985) "Serogrouping of *Clostridium difficile* Strains by Slide Agglutination," J. Clin. Microbiol. 21:323–327.

Davies and Borriello (1990) "Detection of Capsule in Strains of *Clostridium difficile* of Varying Virulence and Toxigenicity," Microbial Path. 9:141–146.

Edelstein (1990) "Processing Clinical Specimens for Anaerobic Bacteria: Isolation and Identification Procedures," *in Bailey and Scott's Diagnostic Microbiology,* pp. 477–507, C.V. Mosby Co. Baron and Finegold (eds.).

Padhye et al. (1990) "Production and Characterization of a Monoclonal Antibody Specific for Enterohemorrhagic *Escherchia coli* of Serotypes 0157:H7 and 026:H11," J. Clin. Microbiol. 29:99–103.

Lyerly et al. (1991) "Passive Immunization of Hamsters Against Disease Caused by *Clostridium difficile* by Use of Bovine Immunoglobulin G Concentrate," Infect. Immun. 59:2215–2218.

DasGupta & Sathyamoorthy (1984) "Purification and Amino Acid Composition of Type A Botullinum Neurotoxin," Toxicon, 22:415–424.

Singh & DasGupta (1989) "Molecular Differences Between Type A Botulinum Neurotoxin and Its Toxoid," Toxicon 27:403–410.

Towbin et al. (1979) "Electrophoretic Transfer of Proteins from Polyacrylamide Gels to Nitrocellulose Sheets: Procedure and Some Applications," Proc. Natl. Acad. Sci. USA, 76:4350–4354.

Weber and Osborn (1975) "Proteins and Sodium Dodecyl Sulfate: Molecular Weight Determination on Polyacrylamide Gels and Related Procedures," in *The Proteins,* pp. 179–223, 3d Edition (H. Neurath & R.L. Hill, eds), Academic Press, NY.

Carroll and Laughon (1987) "Production and purification of polyclonal antibodies to the foreign segment of β–galactosidase fusion proteins," in *DNA Cloning: A Practical Approach,* vol. III, pp. 89–111, D. Glover (ed.) IRL Press Oxford.

Thalley and Carroll (1990) "Rattlesnake and Scorpion Antivenoms From The Egg Yolks of Immunized Hens," Bio/Technology 8:934–938.

Ohishi et al. (1977) "Oral Toxicities of *Clostridium botulinum* Toxins in Response to Molecular Size," Infect. Immun. 16:106–107.

Wren et al. (1991) "Antigenic Cross–Reactivity and Functional Inhibition by Antibodies to *Clostridium difficile* Toxin A, *Streptococcus mutans* Glucan–Binding Protein, and a Synthetic Peptide," Infect. Immun. 59:3151–3155.

Ehrich et al. (1980) "Production of *Clostridium difficile* Antitoxin," Infect. Immun. 28:1041–1043.

McGee et al. (1992) "Local induction of tumor necrosis factor as a molecular mechanism of mucosal damage by gonococci," Microb. Path. 12:333–341.

Fekety (1986) "Animal Models of Antibiotic–Induced Colitis," *in Experimental Models in Antimicrobial Chemotherapy,* 2:61–72, Zak and Sande (eds.), Harcourt Brace Jovanovich, NY.

Borriello et al. (1987) "*Clostridium difficile*—a spectrum of virulence and analysis of putative virulence determinants in the hamster model of antibiotic–associated colitis," J. Med. Microbiol. 24:53–64.

Kim et al. (1987) "Immunization of Adult Hamsters Against *Clostridium difficile*—Associated Ileocecitis and Transfer of Protection to Infant Hamsters," Infect. Immun. 55:2984–2992.

Borriello et al. (1988) "Mucosal Association by *Clostridium difficile* in the hamster gastrointestinal tact," J. Med. Microbiol. 25:191–196.

Dove et al. (1990) "Molecular Characterization of the *Clostridium difficile* Toxin A Gene," Infect. Immun. 58:480–488.

Williams et al. (1995) "Expression of foreign proteins in *E. coli* using plasmid vectors and purification of specific polyclonal antibodies," in *DNA Cloning 2: Expression Systems,* pp. 15–58, Glover and Hames (eds.) IRL Press, Oxford.

von Eichel–Streiber and Sauerborn (1990) "*Clostridium difficile* Toxin A Carries a C–Terminal Repetitive Structure Homologous to the Carbohydrate Binding Region of Streptococcal Glycosyltransferases," Gene 96:107–113.

Wren and Tabaqchali (1987) "Restriction Endonuclease DNA Analysis of *Clostridium difficile,*" J. Clin. Microbiol. 25:2402–2404.

Price et al. (1987) "Cloning of the Carbohydrate–binding Portion of the Toxin A Gene of *Clostridium difficile,*" Curr. Microbiol. 16:55–60.

Krivan et al. (1986) "Cell Surface Binding Site for *Clostridium difficile* Enterotoxin: Evidence for a Glycoconjugate Containing the Sequence Galα1–3–Galβ1–4GlcNAc," Infect. Immun., 53:573–581.

von Eichel–Streiber et al. (1989) "Cloning and Characterization of Overlapping DNA Fragments of the Toxin A Gene of *Clostridium difficile,*" J. Gen. Microbiol. 135:55–64.

Lyerly et al. (1989) "Nonspecific Binding of Mouse Monoclonal Antibodies to *Clostridium difficile* Toxins A and B," Curr. Microbiol. 19:303–306.

Lyerly et al. (1990) "Vaccination Against Lethal *Clostridium difficile* Enterocolitis with a Nontoxic Recombinant Peptide to Toxin A," Curr. Microbiol. 21:29–32.

Swanson et al. (1991) "In Vitro and In Vivo Evaluation of Tiacumcins B and C Against *Clostridium difficile,*" Antimicro. Agents and Chemo. 35:1108–1111.

Swanson et al., (1989) "Phenelfamycins, a Novel Complex of Elfamycin–type Antibiotics, III. Activity In Vitro and in a Hamster Colitis Model," J. Antibiotics 42:94–101.
von Eichel–Streiber et al. (1992) "Comparative Sequence Analysis of the *Clostridium difficile* Toxins A and B," Gen. Genetics 233:260–268.
Barroso et al. (1990) "Nucleotide Sequence of *Clostridium difficile* Toxin B Gene," Nucl. Acids Res. 18:4004.
Thompson et al. (1990) "The complete amino acid sequence of the *Clostridium botulinum* type A neurotoxin, deduced by nucleotide sequence analysis of the encoding gene," Eur. J. Biochem. 189:73–81.
Riggs (1989) in *Current Protocols in Molecular Biology,* vol. 2, Ausubel, et al.(Eds.) pp. 16.6.1–16.6.14.
Schantz and Kautter (1978) "Microbiological Methods: Standardized Assay for *Clostridium botulinum* Toxins," J. AOAC 61:96–99.
Investigational New Drug (BB–IND–3703) application by the Surgeon General of the Department of the Army to the Federal Food and Drug Administration.
Pearson (1985) *Pyrogens: ednotoxins, LAL testing and depyrogentaion,* Marcel Dekker, NY, pp. 23–56.
Smith and Corcoran (1994) "Expression and Purification of Glutathione–S–Transferase Fusion Proteins," Current Protocols in Molecular Biology, Supplement 28:16.7.1–16.7.7.
Gragerov et al. (1992) "Cooperation of GroEL/GroEs and DnaK/DnaJ heat shock proteins in preventing protein misfolding in *Escherichia coli,*" Proc. Natl. Acad. Sci. USA 89:10341–10344.
Fujii et al. (1990) "The Nucleotide and Deduced Amino Acid Sequences of EcoRI Fragment Containing the 5'–Terminal Regions of *Clostridium botulinum* Type E Toxin Gene Cloned from Mashike, Iwanai an Otaru Strains," Microbiol. Immunol. 34:1041–1047.
Kimura et al. (1990) "The Complete Nucleotide Sequence of the Gene Coding for Botulinum Type $C_1$ Toxin in the C–St Phage Genome," Biochem. Biophys. Res. Comm. 171:1304–1311.

Sunagawa et al. (1992) "The Complete Amino Acid Sequence of the *Clostridium botulinum* Type D Neurotoxin, Deduced by Nucleotide Sequence Analysis of the Encoding Phage d–16ϕ Genome," J. Vet. Med. Sci. 54:905–913.

Binz et al. (1990) "Nucleotide sequence of the gene encoding *Clostridium botulinum* neurotoxin type D," Nucleic Acids Res. 18:5556.

Campbell et al. (1993) "Nucleotide sequence of the gene coding for *Clostridium botulinum* (*Clostridium argentinense*) type G neurotoxin: genealogical comparison with other clostridial neurotoxins," Biochim. Biophy. Acta 1216:487–491.

East et al. (1992) "Sequence of the gene encoding type F neurotoxin of *Clostridium botulinum,*" FEMS Micro. Letters 96:225–230.

Niemann (1992) "Clostridial Neurotoxins—Proposal of a Common Nomenclature," Toxicon 30:223–225.

Food and Drug Administration Document (Docket No. 79D–0465) 53 FR 5044, Feb. 19, 1988.

Food and Drug Administration Document (Docket No. 79D–0465) 48 FR 27835, Jun. 17, 1983.

* cited by examiner

FIGURE 6

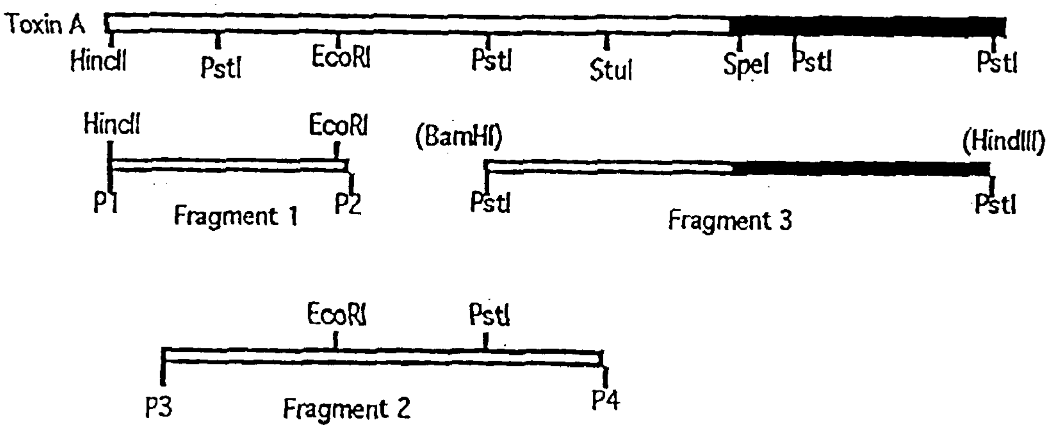

P1-P4 are PCR primers 1-4. P1=5'GGAAATTTAGCTGCAGCATCTGAC3', P2=5'TCTAGCAAATTCGCTTGTGTTGAA3', P3=5'CTCGCATATAGCATTAGACC3', P4=5'CTATCTAGGCCTAAAGTAT3'. Indicated restriction sites in fragments 1 and 2 are internal sites used to clone into pGEX2T vector (fragment 1; construct called pGA30-660) or pMALc vector (fragment 2; construct called pMA660-1100). Bracketed restriction sites at ends of fragment 3 are pUC9 polylinker sites utilized to clone fragment 3 into pET23 vector (construct called pPA1100-2680). Numbers in these constructs refer to toxin A amino acid interval that is expressed. The shaded portion of the toxin A gene corresponds to the repeating ligand binding domain.

pP refers to pET23 vector, pM refers to pMALc vector, A refers to toxin A, and numbers refer to amino acid interval expressed in clone. Endpoints of clones correspond to indicated restriction sites shown of toxin A map.

pP refers to pET23 vector, pM refers to pMALc vector, A refers to toxin A, and numbers refer to amino acid interval expressed in clone. Endpoints of clones correspond to indicated restriction sites shown of toxin A map.

Summary of expression constructs from the toxin B gene

Binding of neutralizing CTB antibodies by recombinant toxin B protein

```
                    P14(1850)                          P8
                    |                                  (2360)
Interval 3   ┌──────┬────────┬────────┬──────────────┐
             SpeI            HindIII  PvuII
             (1750)          (1970)   (2070)
```

pMB1750-2360 pPB1750-2360                                      HHH pMB1750-1970 pMB1970-2360 pPB1850-2360  HHH pMB1850-1970 pPB1850-2070  HHH

SEQUENCE LISTING

```
(1) GENERAL INFORMATION:

   (iii) NUMBER OF SEQUENCES: 82


(2) INFORMATION FOR SEQ ID NO:1:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:1:

GGAAATTTAG CTGCAGCATC TGAC                                            24


(2) INFORMATION FOR SEQ ID NO:2:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:2:

TCTAGCAAAT TCGCTTGTGT TGAA                                            24


(2) INFORMATION FOR SEQ ID NO:3:

     (i) SEQUENCE CHARACTERISTICS:
          (A) LENGTH: 20 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:3:

CTCGCATATA GCATTAGACC                                                 20


(2) INFORMATION FOR SEQ ID NO:4:

     (i) SEQUENCE CHARACTERISTICS:
          (A) LENGTH: 19 base pairs
          (B) TYPE: nucleic acid
```

-continued (C) STRANDEDNESS: single
(D) TOPOLOGY: linear (ii) MOLECULE TYPE: DNA (genomic)

(xi) SEQUENCE DESCRIPTION: SEQ ID NO:4:

```
CTATCTAGGC CTAAAGTAT                                                19
```

(2) INFORMATION FOR SEQ ID NO:5:

(i) SEQUENCE CHARACTERISTICS:
(A) LENGTH: 8133 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..8130

(xi) SEQUENCE DESCRIPTION: SEQ ID NO:5:

```
ATG TCT TTA ATA TCT AAA GAA GAG TTA ATA AAA CTC GCA TAT AGC ATT       48
Met Ser Leu Ile Ser Lys Glu Glu Leu Ile Lys Leu Ala Tyr Ser Ile
  1               5                  10                  15

AGA CCA AGA GAA AAT GAG TAT AAA ACT ATA CTA ACT AAT TTA GAC GAA       96
Arg Pro Arg Glu Asn Glu Tyr Lys Thr Ile Leu Thr Asn Leu Asp Glu
             20                  25                  30

TAT AAT AAG TTA ACT ACA AAC AAT AAT GAA AAT AAA TAT TTG CAA TTA      144
Tyr Asn Lys Leu Thr Thr Asn Asn Asn Glu Asn Lys Tyr Leu Gln Leu
         35                  40                  45

AAA AAA CTA AAT GAA TCA ATT GAT GTT TTT ATG AAT AAA TAT AAA ACT      192
Lys Lys Leu Asn Glu Ser Ile Asp Val Phe Met Asn Lys Tyr Lys Thr
     50                  55                  60

TCA AGC AGA AAT AGA GCA CTC TCT AAT CTA AAA AAA GAT ATA TTA AAA      240
Ser Ser Arg Asn Arg Ala Leu Ser Asn Leu Lys Lys Asp Ile Leu Lys
 65                  70                  75                  80

GAA GTA ATT CTT ATT AAA AAT TCC AAT ACA AGC CCT GTA GAA AAA AAT      288
Glu Val Ile Leu Ile Lys Asn Ser Asn Thr Ser Pro Val Glu Lys Asn
                 85                  90                  95

TTA CAT TTT GTA TGG ATA GGT GGA GAA GTC AGT GAT ATT GCT CTT GAA      336
Leu His Phe Val Trp Ile Gly Gly Glu Val Ser Asp Ile Ala Leu Glu
            100                 105                 110

TAC ATA AAA CAA TGG GCT GAT ATT AAT GCA GAA TAT AAT ATT AAA CTG      384
Tyr Ile Lys Gln Trp Ala Asp Ile Asn Ala Glu Tyr Asn Ile Lys Leu
        115                 120                 125

TGG TAT GAT AGT GAA GCA TTC TTA GTA AAT ACA CTA AAA AAG GCT ATA      432
Trp Tyr Asp Ser Glu Ala Phe Leu Val Asn Thr Leu Lys Lys Ala Ile
    130                 135                 140

GTT GAA TCT TCT ACC ACT GAA GCA TTA CAG CTA CTA GAG GAA GAG ATT      480
Val Glu Ser Ser Thr Thr Glu Ala Leu Gln Leu Leu Glu Glu Glu Ile
145                 150                 155                 160

CAA AAT CCT CAA TTT GAT AAT ATG AAA TTT TAC AAA AAA AGG ATG GAA      528
Gln Asn Pro Gln Phe Asp Asn Met Lys Phe Tyr Lys Lys Arg Met Glu
                165                 170                 175

TTT ATA TAT GAT AGA CAA AAA AGG TTT ATA AAT TAT TAT AAA TCT CAA      576
Phe Ile Tyr Asp Arg Gln Lys Arg Phe Ile Asn Tyr Tyr Lys Ser Gln
            180                 185                 190

ATC AAT AAA CCT ACA GTA CCT ACA ATA GAT GAT ATT ATA AAG TCT CAT      624
Ile Asn Lys Pro Thr Val Pro Thr Ile Asp Asp Ile Ile Lys Ser His
        195                 200                 205

CTA GTA TCT GAA TAT AAT AGA GAT GAA ACT GTA TTA GAA TCA TAT AGA      672
```

-continued

```
Leu Val Ser Glu Tyr Asn Arg Asp Glu Thr Val Leu Glu Ser Tyr Arg
    210                 215                 220

ACA AAT TCT TTG AGA AAA ATA AAT AGT AAT CAT GGG ATA GAT ATC AGG      720
Thr Asn Ser Leu Arg Lys Ile Asn Ser Asn His Gly Ile Asp Ile Arg
225                 230                 235                 240

GCT AAT AGT TTG TTT ACA GAA CAA GAG TTA TTA AAT ATT TAT AGT CAG      768
Ala Asn Ser Leu Phe Thr Glu Gln Glu Leu Leu Asn Ile Tyr Ser Gln
                245                 250                 255

GAG TTG TTA AAT CGT GGA AAT TTA GCT GCA GCA TCT GAC ATA GTA AGA      816
Glu Leu Leu Asn Arg Gly Asn Leu Ala Ala Ala Ser Asp Ile Val Arg
            260                 265                 270

TTA TTA GCC CTA AAA AAT TTT GGC GGA GTA TAT TTA GAT GTT GAT ATG      864
Leu Leu Ala Leu Lys Asn Phe Gly Gly Val Tyr Leu Asp Val Asp Met
        275                 280                 285

CTT CCA GGT ATT CAC TCT GAT TTA TTT AAA ACA ATA TCT AGA CCT AGC      912
Leu Pro Gly Ile His Ser Asp Leu Phe Lys Thr Ile Ser Arg Pro Ser
    290                 295                 300

TCT ATT GGA CTA GAC CGT TGG GAA ATG ATA AAA TTA GAG GCT ATT ATG      960
Ser Ile Gly Leu Asp Arg Trp Glu Met Ile Lys Leu Glu Ala Ile Met
305                 310                 315                 320

AAG TAT AAA AAA TAT ATA AAT AAT TAT ACA TCA GAA AAC TTT GAT AAA     1008
Lys Tyr Lys Lys Tyr Ile Asn Asn Tyr Thr Ser Glu Asn Phe Asp Lys
                325                 330                 335

CTT GAT CAA CAA TTA AAA GAT AAT TTT AAA CTC ATT ATA GAA AGT AAA     1056
Leu Asp Gln Gln Leu Lys Asp Asn Phe Lys Leu Ile Ile Glu Ser Lys
            340                 345                 350

AGT GAA AAA TCT GAG ATA TTT TCT AAA TTA GAA AAT TTA AAT GTA TCT     1104
Ser Glu Lys Ser Glu Ile Phe Ser Lys Leu Glu Asn Leu Asn Val Ser
        355                 360                 365

GAT CTT GAA ATT AAA ATA GCT TTC GCT TTA GGC AGT GTT ATA AAT CAA     1152
Asp Leu Glu Ile Lys Ile Ala Phe Ala Leu Gly Ser Val Ile Asn Gln
    370                 375                 380

GCC TTG ATA TCA AAA CAA GGT TCA TAT CTT ACT AAC CTA GTA ATA GAA     1200
Ala Leu Ile Ser Lys Gln Gly Ser Tyr Leu Thr Asn Leu Val Ile Glu
385                 390                 395                 400

CAA GTA AAA AAT AGA TAT CAA TTT TTA AAC CAA CAC CTT AAC CCA GCC     1248
Gln Val Lys Asn Arg Tyr Gln Phe Leu Asn Gln His Leu Asn Pro Ala
                405                 410                 415

ATA GAG TCT GAT AAT AAC TTC ACA GAT ACT ACT AAA ATT TTT CAT GAT     1296
Ile Glu Ser Asp Asn Asn Phe Thr Asp Thr Thr Lys Ile Phe His Asp
            420                 425                 430

TCA TTA TTT AAT TCA GCT ACC GCA GAA AAC TCT ATG TTT TTA ACA AAA     1344
Ser Leu Phe Asn Ser Ala Thr Ala Glu Asn Ser Met Phe Leu Thr Lys
        435                 440                 445

ATA GCA CCA TAC TTA CAA GTA GGT TTT ATG CCA GAA GCT CGC TCC ACA     1392
Ile Ala Pro Tyr Leu Gln Val Gly Phe Met Pro Glu Ala Arg Ser Thr
    450                 455                 460

ATA AGT TTA AGT GGT CCA GGA GCT TAT GCG TCA GCT TAC TAT GAT TTC     1440
Ile Ser Leu Ser Gly Pro Gly Ala Tyr Ala Ser Ala Tyr Tyr Asp Phe
465                 470                 475                 480

ATA AAT TTA CAA GAA AAT ACT ATA GAA AAA ACT TTA AAA GCA TCA GAT     1488
Ile Asn Leu Gln Glu Asn Thr Ile Glu Lys Thr Leu Lys Ala Ser Asp
                485                 490                 495

TTA ATA GAA TTT AAA TTC CCA GAA AAT AAT CTA TCT CAA TTG ACA GAA     1536
Leu Ile Glu Phe Lys Phe Pro Glu Asn Asn Leu Ser Gln Leu Thr Glu
            500                 505                 510

CAA GAA ATA AAT AGT CTA TGG AGC TTT GAT CAA GCA AGT GCA AAA TAT     1584
Gln Glu Ile Asn Ser Leu Trp Ser Phe Asp Gln Ala Ser Ala Lys Tyr
        515                 520                 525
```

-continued

```
CAA TTT GAG AAA TAT GTA AGA GAT TAT ACT GGT GGA TCT CTT TCT GAA      1632
Gln Phe Glu Lys Tyr Val Arg Asp Tyr Thr Gly Gly Ser Leu Ser Glu
    530                 535                 540

GAC AAT GGG GTA GAC TTT AAT AAA AAT ACT GCC CTC GAC AAA AAC TAT      1680
Asp Asn Gly Val Asp Phe Asn Lys Asn Thr Ala Leu Asp Lys Asn Tyr
545                 550                 555                 560

TTA TTA AAT AAT AAA ATT CCA TCA AAC AAT GTA GAA GAA GCT GGA AGT      1728
Leu Leu Asn Asn Lys Ile Pro Ser Asn Asn Val Glu Glu Ala Gly Ser
                565                 570                 575

AAA AAT TAT GTT CAT TAT ATC ATA CAG TTA CAA GGA GAT GAT ATA AGT      1776
Lys Asn Tyr Val His Tyr Ile Ile Gln Leu Gln Gly Asp Asp Ile Ser
            580                 585                 590

TAT GAA GCA ACA TGC AAT TTA TTT TCT AAA AAT CCT AAA AAT AGT ATT      1824
Tyr Glu Ala Thr Cys Asn Leu Phe Ser Lys Asn Pro Lys Asn Ser Ile
        595                 600                 605

ATT ATA CAA CGA AAT ATG AAT GAA AGT GCA AAA AGC TAC TTT TTA AGT      1872
Ile Ile Gln Arg Asn Met Asn Glu Ser Ala Lys Ser Tyr Phe Leu Ser
    610                 615                 620

GAT GAT GGA GAA TCT ATT TTA GAA TTA AAT AAA TAT AGG ATA CCT GAA      1920
Asp Asp Gly Glu Ser Ile Leu Glu Leu Asn Lys Tyr Arg Ile Pro Glu
625                 630                 635                 640

AGA TTA AAA AAT AAG GAA AAA GTA AAA GTA ACC TTT ATT GGA CAT GGT      1968
Arg Leu Lys Asn Lys Glu Lys Val Lys Val Thr Phe Ile Gly His Gly
                645                 650                 655

AAA GAT GAA TTC AAC ACA AGC GAA TTT GCT AGA TTA AGT GTA GAT TCA      2016
Lys Asp Glu Phe Asn Thr Ser Glu Phe Ala Arg Leu Ser Val Asp Ser
            660                 665                 670

CTT TCC AAT GAG ATA AGT TCA TTT TTA GAT ACC ATA AAA TTA GAT ATA      2064
Leu Ser Asn Glu Ile Ser Ser Phe Leu Asp Thr Ile Lys Leu Asp Ile
        675                 680                 685

TCA CCT AAA AAT GTA GAA GTA AAC TTA CTT GGA TGT AAT ATG TTT AGT      2112
Ser Pro Lys Asn Val Glu Val Asn Leu Leu Gly Cys Asn Met Phe Ser
    690                 695                 700

TAT GAT TTT AAT GTT GAA GAA ACT TAT CCT GGG AAG TTG CTA TTA AGT      2160
Tyr Asp Phe Asn Val Glu Glu Thr Tyr Pro Gly Lys Leu Leu Leu Ser
705                 710                 715                 720

ATT ATG GAC AAA ATT ACT TCC ACT TTA CCT GAT GTA AAT AAA AAT TCT      2208
Ile Met Asp Lys Ile Thr Ser Thr Leu Pro Asp Val Asn Lys Asn Ser
                725                 730                 735

ATT ACT ATA GGA GCA AAT CAA TAT GAA GTA AGA ATT AAT AGT GAG GGA      2256
Ile Thr Ile Gly Ala Asn Gln Tyr Glu Val Arg Ile Asn Ser Glu Gly
            740                 745                 750

AGA AAA GAA CTT CTG GCT CAC TCA GGT AAA TGG ATA AAT AAA GAA GAA      2304
Arg Lys Glu Leu Leu Ala His Ser Gly Lys Trp Ile Asn Lys Glu Glu
        755                 760                 765

GCT ATT ATG AGC GAT TTA TCT AGT AAA GAA TAC ATT TTT TTT GAT TCT      2352
Ala Ile Met Ser Asp Leu Ser Ser Lys Glu Tyr Ile Phe Phe Asp Ser
    770                 775                 780

ATA GAT AAT AAG CTA AAA GCA AAG TCC AAG AAT ATT CCA GGA TTA GCA      2400
Ile Asp Asn Lys Leu Lys Ala Lys Ser Lys Asn Ile Pro Gly Leu Ala
785                 790                 795                 800

TCA ATA TCA GAA GAT ATA AAA ACA TTA TTA CTT GAT GCA AGT GTT AGT      2448
Ser Ile Ser Glu Asp Ile Lys Thr Leu Leu Leu Asp Ala Ser Val Ser
                805                 810                 815

CCT GAT ACA AAA TTT ATT TTA AAT AAT CTT AAG CTT AAT ATT GAA TCT      2496
Pro Asp Thr Lys Phe Ile Leu Asn Asn Leu Lys Leu Asn Ile Glu Ser
            820                 825                 830

TCT ATT GGG GAT TAC ATT TAT TAT GAA AAA TTA GAG CCT GTT AAA AAT      2544
Ser Ile Gly Asp Tyr Ile Tyr Tyr Glu Lys Leu Glu Pro Val Lys Asn
        835                 840                 845
```

-continued

```
ATA ATT CAC AAT TCT ATA GAT GAT TTA ATA GAT GAG TTC AAT CTA CTT      2592
Ile Ile His Asn Ser Ile Asp Asp Leu Ile Asp Glu Phe Asn Leu Leu
    850                 855                 860

GAA AAT GTA TCT GAT GAA TTA TAT GAA TTA AAA AAA TTA AAT AAT CTA      2640
Glu Asn Val Ser Asp Glu Leu Tyr Glu Leu Lys Lys Leu Asn Asn Leu
865                 870                 875                 880

GAT GAG AAG TAT TTA ATA TCT TTT GAA GAT ATC TCA AAA AAT AAT TCA      2688
Asp Glu Lys Tyr Leu Ile Ser Phe Glu Asp Ile Ser Lys Asn Asn Ser
                885                 890                 895

ACT TAC TCT GTA AGA TTT ATT AAC AAA AGT AAT GGT GAG TCA GTT TAT      2736
Thr Tyr Ser Val Arg Phe Ile Asn Lys Ser Asn Gly Glu Ser Val Tyr
            900                 905                 910

GTA GAA ACA GAA AAA GAA ATT TTT TCA AAA TAT AGC GAA CAT ATT ACA      2784
Val Glu Thr Glu Lys Glu Ile Phe Ser Lys Tyr Ser Glu His Ile Thr
        915                 920                 925

AAA GAA ATA AGT ACT ATA AAG AAT AGT ATA ATT ACA GAT GTT AAT GGT      2832
Lys Glu Ile Ser Thr Ile Lys Asn Ser Ile Ile Thr Asp Val Asn Gly
    930                 935                 940

AAT TTA TTG GAT AAT ATA CAG TTA GAT CAT ACT TCT CAA GTT AAT ACA      2880
Asn Leu Leu Asp Asn Ile Gln Leu Asp His Thr Ser Gln Val Asn Thr
945                 950                 955                 960

TTA AAC GCA GCA TTC TTT ATT CAA TCA TTA ATA GAT TAT AGT AGC AAT      2928
Leu Asn Ala Ala Phe Phe Ile Gln Ser Leu Ile Asp Tyr Ser Ser Asn
                965                 970                 975

AAA GAT GTA CTG AAT GAT TTA AGT ACC TCA GTT AAG GTT CAA CTT TAT      2976
Lys Asp Val Leu Asn Asp Leu Ser Thr Ser Val Lys Val Gln Leu Tyr
            980                 985                 990

GCT CAA CTA TTT AGT ACA GGT TTA AAT ACT ATA TAT GAC TCT ATC CAA      3024
Ala Gln Leu Phe Ser Thr Gly Leu Asn Thr Ile Tyr Asp Ser Ile Gln
        995                1000                1005

TTA GTA AAT TTA ATA TCA AAT GCA GTA AAT GAT ACT ATA AAT GTA CTA      3072
Leu Val Asn Leu Ile Ser Asn Ala Val Asn Asp Thr Ile Asn Val Leu
    1010                1015                1020

CCT ACA ATA ACA GAG GGG ATA CCT ATT GTA TCT ACT ATA TTA GAC GGA      3120
Pro Thr Ile Thr Glu Gly Ile Pro Ile Val Ser Thr Ile Leu Asp Gly
1025                1030                1035                1040

ATA AAC TTA GGT GCA GCA ATT AAG GAA TTA CTA GAC GAA CAT GAC CCA      3168
Ile Asn Leu Gly Ala Ala Ile Lys Glu Leu Leu Asp Glu His Asp Pro
                1045                1050                1055

TTA CTA AAA AAA GAA TTA GAA GCT AAG GTG GGT GTT TTA GCA ATA AAT      3216
Leu Leu Lys Lys Glu Leu Glu Ala Lys Val Gly Val Leu Ala Ile Asn
            1060                1065                1070

ATG TCA TTA TCT ATA GCT GCA ACT GTA GCT TCA ATT GTT GGA ATA GGT      3264
Met Ser Leu Ser Ile Ala Ala Thr Val Ala Ser Ile Val Gly Ile Gly
        1075                1080                1085

GCT GAA GTT ACT ATT TTC TTA TTA CCT ATA GCT GGT ATA TCT GCA GGA      3312
Ala Glu Val Thr Ile Phe Leu Leu Pro Ile Ala Gly Ile Ser Ala Gly
    1090                1095                1100

ATA CCT TCA TTA GTT AAT AAT GAA TTA ATA TTG CAT GAT AAG GCA ACT      3360
Ile Pro Ser Leu Val Asn Asn Glu Leu Ile Leu His Asp Lys Ala Thr
1105                1110                1115                1120

TCA GTG GTA AAC TAT TTT AAT CAT TTG TCT GAA TCT AAA AAA TAT GGC      3408
Ser Val Val Asn Tyr Phe Asn His Leu Ser Glu Ser Lys Lys Tyr Gly
                1125                1130                1135

CCT CTT AAA ACA GAA GAT GAT AAA ATT TTA GTT CCT ATT GAT GAT TTA      3456
Pro Leu Lys Thr Glu Asp Asp Lys Ile Leu Val Pro Ile Asp Asp Leu
            1140                1145                1150

GTA ATA TCA GAA ATA GAT TTT AAT AAT AAT TCG ATA AAA CTA GGA ACA      3504
Val Ile Ser Glu Ile Asp Phe Asn Asn Asn Ser Ile Lys Leu Gly Thr
```

-continued

```
        1155                1160                1165

TGT AAT ATA TTA GCA ATG GAG GGG GGA TCA GGA CAC ACA GTG ACT GGT     3552
Cys Asn Ile Leu Ala Met Glu Gly Gly Ser Gly His Thr Val Thr Gly
    1170                1175                1180

AAT ATA GAT CAC TTT TTC TCA TCT CCA TCT ATA AGT TCT CAT ATT CCT     3600
Asn Ile Asp His Phe Phe Ser Ser Pro Ser Ile Ser Ser His Ile Pro
1185                1190                1195                1200

TCA TTA TCA ATT TAT TCT GCA ATA GGT ATA GAA ACA GAA AAT CTA GAT     3648
Ser Leu Ser Ile Tyr Ser Ala Ile Gly Ile Glu Thr Glu Asn Leu Asp
                1205                1210                1215

TTT TCA AAA AAA ATA ATG ATG TTA CCT AAT GCT CCT TCA AGA GTG TTT     3696
Phe Ser Lys Lys Ile Met Met Leu Pro Asn Ala Pro Ser Arg Val Phe
            1220                1225                1230

TGG TGG GAA ACT GGA GCA GTT CCA GGT TTA AGA TCA TTG GAA AAT GAC     3744
Trp Trp Glu Thr Gly Ala Val Pro Gly Leu Arg Ser Leu Glu Asn Asp
        1235                1240                1245

GGA ACT AGA TTA CTT GAT TCA ATA AGA GAT TTA TAC CCA GGT AAA TTT     3792
Gly Thr Arg Leu Leu Asp Ser Ile Arg Asp Leu Tyr Pro Gly Lys Phe
    1250                1255                1260

TAC TGG AGA TTC TAT GCT TTT TTC GAT TAT GCA ATA ACT ACA TTA AAA     3840
Tyr Trp Arg Phe Tyr Ala Phe Phe Asp Tyr Ala Ile Thr Thr Leu Lys
1265                1270                1275                1280

CCA GTT TAT GAA GAC ACT AAT ATT AAA ATT AAA CTA GAT AAA GAT ACT     3888
Pro Val Tyr Glu Asp Thr Asn Ile Lys Ile Lys Leu Asp Lys Asp Thr
                1285                1290                1295

AGA AAC TTC ATA ATG CCA ACT ATA ACT ACT AAC GAA ATT AGA AAC AAA     3936
Arg Asn Phe Ile Met Pro Thr Ile Thr Thr Asn Glu Ile Arg Asn Lys
            1300                1305                1310

TTA TCT TAT TCA TTT GAT GGA GCA GGA GGA ACT TAC TCT TTA TTA TTA     3984
Leu Ser Tyr Ser Phe Asp Gly Ala Gly Gly Thr Tyr Ser Leu Leu Leu
        1315                1320                1325

TCT TCA TAT CCA ATA TCA ACG AAT ATA AAT TTA TCT AAA GAT GAT TTA     4032
Ser Ser Tyr Pro Ile Ser Thr Asn Ile Asn Leu Ser Lys Asp Asp Leu
    1330                1335                1340

TGG ATA TTT AAT ATT GAT AAT GAA GTA AGA GAA ATA TCT ATA GAA AAT     4080
Trp Ile Phe Asn Ile Asp Asn Glu Val Arg Glu Ile Ser Ile Glu Asn
1345                1350                1355                1360

GGT ACT ATT AAA AAA GGA AAG TTA ATA AAA GAT GTT TTA AGT AAA ATT     4128
Gly Thr Ile Lys Lys Gly Lys Leu Ile Lys Asp Val Leu Ser Lys Ile
                1365                1370                1375

GAT ATA AAT AAA AAT AAA CTT ATT ATA GGC AAT CAA ACA ATA GAT TTT     4176
Asp Ile Asn Lys Asn Lys Leu Ile Ile Gly Asn Gln Thr Ile Asp Phe
            1380                1385                1390

TCA GGC GAT ATA GAT AAT AAA GAT AGA TAT ATA TTC TTG ACT TGT GAG     4224
Ser Gly Asp Ile Asp Asn Lys Asp Arg Tyr Ile Phe Leu Thr Cys Glu
        1395                1400                1405

TTA GAT GAT AAA ATT AGT TTA ATA ATA GAA ATA AAT CTT GTT GCA AAA     4272
Leu Asp Asp Lys Ile Ser Leu Ile Ile Glu Ile Asn Leu Val Ala Lys
    1410                1415                1420

TCT TAT AGT TTG TTA TTG TCT GGG GAT AAA AAT TAT TTG ATA TCC AAT     4320
Ser Tyr Ser Leu Leu Leu Ser Gly Asp Lys Asn Tyr Leu Ile Ser Asn
1425                1430                1435                1440

TTA TCT AAT ACT ATT GAG AAA ATC AAT ACT TTA GGC CTA GAT AGT AAA     4368
Leu Ser Asn Thr Ile Glu Lys Ile Asn Thr Leu Gly Leu Asp Ser Lys
                1445                1450                1455

AAT ATA GCG TAC AAT TAC ACT GAT GAA TCT AAT AAT AAA TAT TTT GGA     4416
Asn Ile Ala Tyr Asn Tyr Thr Asp Glu Ser Asn Asn Lys Tyr Phe Gly
            1460                1465                1470

GCT ATA TCT AAA ACA AGT CAA AAA AGC ATA ATA CAT TAT AAA AAA GAC     4464
```

-continued

```
Ala Ile Ser Lys Thr Ser Gln Lys Ser Ile Ile His Tyr Lys Lys Asp
        1475                1480                1485

AGT AAA AAT ATA TTA GAA TTT TAT AAT GAC AGT ACA TTA GAA TTT AAC     4512
Ser Lys Asn Ile Leu Glu Phe Tyr Asn Asp Ser Thr Leu Glu Phe Asn
    1490                1495                1500

AGT AAA GAT TTT ATT GCT GAA GAT ATA AAT GTA TTT ATG AAA GAT GAT     4560
Ser Lys Asp Phe Ile Ala Glu Asp Ile Asn Val Phe Met Lys Asp Asp
1505                1510                1515                1520

ATT AAT ACT ATA ACA GGA AAA TAC TAT GTT GAT AAT AAT ACT GAT AAA     4608
Ile Asn Thr Ile Thr Gly Lys Tyr Tyr Val Asp Asn Asn Thr Asp Lys
                1525                1530                1535

AGT ATA GAT TTC TCT ATT TCT TTA GTT AGT AAA AAT CAA GTA AAA GTA     4656
Ser Ile Asp Phe Ser Ile Ser Leu Val Ser Lys Asn Gln Val Lys Val
            1540                1545                1550

AAT GGA TTA TAT TTA AAT GAA TCC GTA TAC TCA TCT TAC CTT GAT TTT     4704
Asn Gly Leu Tyr Leu Asn Glu Ser Val Tyr Ser Ser Tyr Leu Asp Phe
        1555                1560                1565

GTG AAA AAT TCA GAT GGA CAC CAT AAT ACT TCT AAT TTT ATG AAT TTA     4752
Val Lys Asn Ser Asp Gly His His Asn Thr Ser Asn Phe Met Asn Leu
    1570                1575                1580

TTT TTG GAC AAT ATA AGT TTC TGG AAA TTG TTT GGG TTT GAA AAT ATA     4800
Phe Leu Asp Asn Ile Ser Phe Trp Lys Leu Phe Gly Phe Glu Asn Ile
1585                1590                1595                1600

AAT TTT GTA ATC GAT AAA TAC TTT ACC CTT GTT GGT AAA ACT AAT CTT     4848
Asn Phe Val Ile Asp Lys Tyr Phe Thr Leu Val Gly Lys Thr Asn Leu
                1605                1610                1615

GGA TAT GTA GAA TTT ATT TGT GAC AAT AAT AAA AAT ATA GAT ATA TAT     4896
Gly Tyr Val Glu Phe Ile Cys Asp Asn Asn Lys Asn Ile Asp Ile Tyr
            1620                1625                1630

TTT GGT GAA TGG AAA ACA TCG TCA TCT AAA AGC ACT ATA TTT AGC GGA     4944
Phe Gly Glu Trp Lys Thr Ser Ser Ser Lys Ser Thr Ile Phe Ser Gly
        1635                1640                1645

AAT GGT AGA AAT GTT GTA GTA GAG CCT ATA TAT AAT CCT GAT ACG GGT     4992
Asn Gly Arg Asn Val Val Val Glu Pro Ile Tyr Asn Pro Asp Thr Gly
    1650                1655                1660

GAA GAT ATA TCT ACT TCA CTA GAT TTT TCC TAT GAA CCT CTC TAT GGA     5040
Glu Asp Ile Ser Thr Ser Leu Asp Phe Ser Tyr Glu Pro Leu Tyr Gly
1665                1670                1675                1680

ATA GAT AGA TAT ATA AAT AAA GTA TTG ATA GCA CCT GAT TTA TAT ACA     5088
Ile Asp Arg Tyr Ile Asn Lys Val Leu Ile Ala Pro Asp Leu Tyr Thr
                1685                1690                1695

AGT TTA ATA AAT ATT AAT ACC AAT TAT TAT TCA AAT GAG TAC TAC CCT     5136
Ser Leu Ile Asn Ile Asn Thr Asn Tyr Tyr Ser Asn Glu Tyr Tyr Pro
            1700                1705                1710

GAG ATT ATA GTT CTT AAC CCA AAT ACA TTC CAC AAA AAA GTA AAT ATA     5184
Glu Ile Ile Val Leu Asn Pro Asn Thr Phe His Lys Lys Val Asn Ile
        1715                1720                1725

AAT TTA GAT AGT TCT TCT TTT GAG TAT AAA TGG TCT ACA GAA GGA AGT     5232
Asn Leu Asp Ser Ser Ser Phe Glu Tyr Lys Trp Ser Thr Glu Gly Ser
    1730                1735                1740

GAC TTT ATT TTA GTT AGA TAC TTA GAA GAA AGT AAT AAA AAA ATA TTA     5280
Asp Phe Ile Leu Val Arg Tyr Leu Glu Glu Ser Asn Lys Lys Ile Leu
1745                1750                1755                1760

CAA AAA ATA AGA ATC AAA GGT ATC TTA TCT AAT ACT CAA TCA TTT AAT     5328
Gln Lys Ile Arg Ile Lys Gly Ile Leu Ser Asn Thr Gln Ser Phe Asn
                1765                1770                1775

AAA ATG AGT ATA GAT TTT AAA GAT ATT AAA AAA CTA TCA TTA GGA TAT     5376
Lys Met Ser Ile Asp Phe Lys Asp Ile Lys Lys Leu Ser Leu Gly Tyr
            1780                1785                1790
```

-continued

```
ATA ATG AGT AAT TTT AAA TCA TTT AAT TCT GAA AAT GAA TTA GAT AGA     5424
Ile Met Ser Asn Phe Lys Ser Phe Asn Ser Glu Asn Glu Leu Asp Arg
        1795                1800                1805

GAT CAT TTA GGA TTT AAA ATA ATA GAT AAT AAA ACT TAT TAC TAT GAT     5472
Asp His Leu Gly Phe Lys Ile Ile Asp Asn Lys Thr Tyr Tyr Tyr Asp
    1810                1815                1820

GAA GAT AGT AAA TTA GTT AAA GGA TTA ATC AAT ATA AAT AAT TCA TTA     5520
Glu Asp Ser Lys Leu Val Lys Gly Leu Ile Asn Ile Asn Asn Ser Leu
1825                1830                1835                1840

TTC TAT TTT GAT CCT ATA GAA TTT AAC TTA GTA ACT GGA TGG CAA ACT     5568
Phe Tyr Phe Asp Pro Ile Glu Phe Asn Leu Val Thr Gly Trp Gln Thr
                1845                1850                1855

ATC AAT GGT AAA AAA TAT TAT TTT GAT ATA AAT ACT GGA GCA GCT TTA     5616
Ile Asn Gly Lys Lys Tyr Tyr Phe Asp Ile Asn Thr Gly Ala Ala Leu
            1860                1865                1870

ACT AGT TAT AAA ATT ATT AAT GGT AAA CAC TTT TAT TTT AAT AAT GAT     5664
Thr Ser Tyr Lys Ile Ile Asn Gly Lys His Phe Tyr Phe Asn Asn Asp
        1875                1880                1885

GGT GTG ATG CAG TTG GGA GTA TTT AAA GGA CCT GAT GGA TTT GAA TAT     5712
Gly Val Met Gln Leu Gly Val Phe Lys Gly Pro Asp Gly Phe Glu Tyr
    1890                1895                1900

TTT GCA CCT GCC AAT ACT CAA AAT AAT AAC ATA GAA GGT CAG GCT ATA     5760
Phe Ala Pro Ala Asn Thr Gln Asn Asn Asn Ile Glu Gly Gln Ala Ile
1905                1910                1915                1920

GTT TAT CAA AGT AAA TTC TTA ACT TTG AAT GGC AAA AAA TAT TAT TTT     5808
Val Tyr Gln Ser Lys Phe Leu Thr Leu Asn Gly Lys Lys Tyr Tyr Phe
                1925                1930                1935

GAT AAT AAC TCA AAA GCA GTC ACT GGA TGG AGA ATT ATT AAC AAT GAG     5856
Asp Asn Asn Ser Lys Ala Val Thr Gly Trp Arg Ile Ile Asn Asn Glu
            1940                1945                1950

AAA TAT TAC TTT AAT CCT AAT AAT GCT ATT GCT GCA GTC GGA TTG CAA     5904
Lys Tyr Tyr Phe Asn Pro Asn Asn Ala Ile Ala Ala Val Gly Leu Gln
        1955                1960                1965

GTA ATT GAC AAT AAT AAG TAT TAT TTC AAT CCT GAC ACT GCT ATC ATC     5952
Val Ile Asp Asn Asn Lys Tyr Tyr Phe Asn Pro Asp Thr Ala Ile Ile
    1970                1975                1980

TCA AAA GGT TGG CAG ACT GTT AAT GGT AGT AGA TAC TAC TTT GAT ACT     6000
Ser Lys Gly Trp Gln Thr Val Asn Gly Ser Arg Tyr Tyr Phe Asp Thr
1985                1990                1995                2000

GAT ACC GCT ATT GCC TTT AAT GGT TAT AAA ACT ATT GAT GGT AAA CAC     6048
Asp Thr Ala Ile Ala Phe Asn Gly Tyr Lys Thr Ile Asp Gly Lys His
                2005                2010                2015

TTT TAT TTT GAT AGT GAT TGT GTA GTG AAA ATA GGT GTG TTT AGT ACC     6096
Phe Tyr Phe Asp Ser Asp Cys Val Val Lys Ile Gly Val Phe Ser Thr
            2020                2025                2030

TCT AAT GGA TTT GAA TAT TTT GCA CCT GCT AAT ACT TAT AAT AAT AAC     6144
Ser Asn Gly Phe Glu Tyr Phe Ala Pro Ala Asn Thr Tyr Asn Asn Asn
        2035                2040                2045

ATA GAA GGT CAG GCT ATA GTT TAT CAA AGT AAA TTC TTA ACT TTG AAT     6192
Ile Glu Gly Gln Ala Ile Val Tyr Gln Ser Lys Phe Leu Thr Leu Asn
    2050                2055                2060

GGT AAA AAA TAT TAC TTT GAT AAT AAC TCA AAA GCA GTT ACC GGA TTG     6240
Gly Lys Lys Tyr Tyr Phe Asp Asn Asn Ser Lys Ala Val Thr Gly Leu
2065                2070                2075                2080

CAA ACT ATT GAT AGT AAA AAA TAT TAC TTT AAT ACT AAC ACT GCT GAA     6288
Gln Thr Ile Asp Ser Lys Lys Tyr Tyr Phe Asn Thr Asn Thr Ala Glu
                2085                2090                2095

GCA GCT ACT GGA TGG CAA ACT ATT GAT GGT AAA AAA TAT TAC TTT AAT     6336
Ala Ala Thr Gly Trp Gln Thr Ile Asp Gly Lys Lys Tyr Tyr Phe Asn
            2100                2105                2110
```

-continued

```
ACT AAC ACT GCT GAA GCA GCT ACT GGA TGG CAA ACT ATT GAT GGT AAA      6384
Thr Asn Thr Ala Glu Ala Ala Thr Gly Trp Gln Thr Ile Asp Gly Lys
        2115                2120                2125

AAA TAT TAC TTT AAT ACT AAC ACT GCT ATA GCT TCA ACT GGT TAT ACA      6432
Lys Tyr Tyr Phe Asn Thr Asn Thr Ala Ile Ala Ser Thr Gly Tyr Thr
    2130                2135                2140

ATT ATT AAT GGT AAA CAT TTT TAT TTT AAT ACT GAT GGT ATT ATG CAG      6480
Ile Ile Asn Gly Lys His Phe Tyr Phe Asn Thr Asp Gly Ile Met Gln
2145                2150                2155                2160

ATA GGA GTG TTT AAA GGA CCT AAT GGA TTT GAA TAT TTT GCA CCT GCT      6528
Ile Gly Val Phe Lys Gly Pro Asn Gly Phe Glu Tyr Phe Ala Pro Ala
            2165                2170                2175

AAT ACG GAT GCT AAC AAC ATA GAA GGT CAA GCT ATA CTT TAC CAA AAT      6576
Asn Thr Asp Ala Asn Asn Ile Glu Gly Gln Ala Ile Leu Tyr Gln Asn
            2180                2185                2190

GAA TTC TTA ACT TTG AAT GGT AAA AAA TAT TAC TTT GGT AGT GAC TCA      6624
Glu Phe Leu Thr Leu Asn Gly Lys Lys Tyr Tyr Phe Gly Ser Asp Ser
        2195                2200                2205

AAA GCA GTT ACT GGA TGG AGA ATT ATT AAC AAT AAG AAA TAT TAC TTT      6672
Lys Ala Val Thr Gly Trp Arg Ile Ile Asn Asn Lys Lys Tyr Tyr Phe
    2210                2215                2220

AAT CCT AAT AAT GCT ATT GCT GCA ATT CAT CTA TGC ACT ATA AAT AAT      6720
Asn Pro Asn Asn Ala Ile Ala Ala Ile His Leu Cys Thr Ile Asn Asn
2225                2230                2235                2240

GAC AAG TAT TAC TTT AGT TAT GAT GGA ATT CTT CAA AAT GGA TAT ATT      6768
Asp Lys Tyr Tyr Phe Ser Tyr Asp Gly Ile Leu Gln Asn Gly Tyr Ile
            2245                2250                2255

ACT ATT GAA AGA AAT AAT TTC TAT TTT GAT GCT AAT AAT GAA TCT AAA      6816
Thr Ile Glu Arg Asn Asn Phe Tyr Phe Asp Ala Asn Asn Glu Ser Lys
            2260                2265                2270

ATG GTA ACA GGA GTA TTT AAA GGA CCT AAT GGA TTT GAG TAT TTT GCA      6864
Met Val Thr Gly Val Phe Lys Gly Pro Asn Gly Phe Glu Tyr Phe Ala
        2275                2280                2285

CCT GCT AAT ACT CAC AAT AAT AAC ATA GAA GGT CAG GCT ATA GTT TAC      6912
Pro Ala Asn Thr His Asn Asn Asn Ile Glu Gly Gln Ala Ile Val Tyr
    2290                2295                2300

CAG AAC AAA TTC TTA ACT TTG AAT GGC AAA AAA TAT TAT TTT GAT AAT      6960
Gln Asn Lys Phe Leu Thr Leu Asn Gly Lys Lys Tyr Tyr Phe Asp Asn
2305                2310                2315                2320

GAC TCA AAA GCA GTT ACT GGA TGG CAA ACC ATT GAT GGT AAA AAA TAT      7008
Asp Ser Lys Ala Val Thr Gly Trp Gln Thr Ile Asp Gly Lys Lys Tyr
            2325                2330                2335

TAC TTT AAT CTT AAC ACT GCT GAA GCA GCT ACT GGA TGG CAA ACT ATT      7056
Tyr Phe Asn Leu Asn Thr Ala Glu Ala Ala Thr Gly Trp Gln Thr Ile
            2340                2345                2350

GAT GGT AAA AAA TAT TAC TTT AAT CTT AAC ACT GCT GAA GCA GCT ACT      7104
Asp Gly Lys Lys Tyr Tyr Phe Asn Leu Asn Thr Ala Glu Ala Ala Thr
        2355                2360                2365

GGA TGG CAA ACT ATT GAT GGT AAA AAA TAT TAC TTT AAT ACT AAC ACT      7152
Gly Trp Gln Thr Ile Asp Gly Lys Lys Tyr Tyr Phe Asn Thr Asn Thr
    2370                2375                2380

TTC ATA GCC TCA ACT GGT TAT ACA AGT ATT AAT GGT AAA CAT TTT TAT      7200
Phe Ile Ala Ser Thr Gly Tyr Thr Ser Ile Asn Gly Lys His Phe Tyr
2385                2390                2395                2400

TTT AAT ACT GAT GGT ATT ATG CAG ATA GGA GTG TTT AAA GGA CCT AAT      7248
Phe Asn Thr Asp Gly Ile Met Gln Ile Gly Val Phe Lys Gly Pro Asn
            2405                2410                2415

GGA TTT GAA TAC TTT GCA CCT GCT AAT ACG GAT GCT AAC AAC ATA GAA      7296
Gly Phe Glu Tyr Phe Ala Pro Ala Asn Thr Asp Ala Asn Asn Ile Glu
```

-continued

```
        2420                2425                2430

GGT CAA GCT ATA CTT TAC CAA AAT AAA TTC TTA ACT TTG AAT GGT AAA      7344
Gly Gln Ala Ile Leu Tyr Gln Asn Lys Phe Leu Thr Leu Asn Gly Lys
        2435                2440                2445

AAA TAT TAC TTT GGT AGT GAC TCA AAA GCA GTT ACC GGA CTG CGA ACT      7392
Lys Tyr Tyr Phe Gly Ser Asp Ser Lys Ala Val Thr Gly Leu Arg Thr
    2450                2455                2460

ATT GAT GGT AAA AAA TAT TAC TTT AAT ACT AAC ACT GCT GTT GCA GTT      7440
Ile Asp Gly Lys Lys Tyr Tyr Phe Asn Thr Asn Thr Ala Val Ala Val
2465                2470                2475                2480

ACT GGA TGG CAA ACT ATT AAT GGT AAA AAA TAC TAC TTT AAT ACT AAC      7488
Thr Gly Trp Gln Thr Ile Asn Gly Lys Lys Tyr Tyr Phe Asn Thr Asn
                2485                2490                2495

ACT TCT ATA GCT TCA ACT GGT TAT ACA ATT ATT AGT GGT AAA CAT TTT      7536
Thr Ser Ile Ala Ser Thr Gly Tyr Thr Ile Ile Ser Gly Lys His Phe
            2500                2505                2510

TAT TTT AAT ACT GAT GGT ATT ATG CAG ATA GGA GTG TTT AAA GGA CCT      7584
Tyr Phe Asn Thr Asp Gly Ile Met Gln Ile Gly Val Phe Lys Gly Pro
        2515                2520                2525

GAT GGA TTT GAA TAC TTT GCA CCT GCT AAT ACA GAT GCT AAC AAT ATA      7632
Asp Gly Phe Glu Tyr Phe Ala Pro Ala Asn Thr Asp Ala Asn Asn Ile
    2530                2535                2540

GAA GGT CAA GCT ATA CGT TAT CAA AAT AGA TTC CTA TAT TTA CAT GAC      7680
Glu Gly Gln Ala Ile Arg Tyr Gln Asn Arg Phe Leu Tyr Leu His Asp
2545                2550                2555                2560

AAT ATA TAT TAT TTT GGT AAT AAT TCA AAA GCG GCT ACT GGT TGG GTA      7728
Asn Ile Tyr Tyr Phe Gly Asn Asn Ser Lys Ala Ala Thr Gly Trp Val
                2565                2570                2575

ACT ATT GAT GGT AAT AGA TAT TAC TTC GAG CCT AAT ACA GCT ATG GGT      7776
Thr Ile Asp Gly Asn Arg Tyr Tyr Phe Glu Pro Asn Thr Ala Met Gly
            2580                2585                2590

GCG AAT GGT TAT AAA ACT ATT GAT AAT AAA AAT TTT TAC TTT AGA AAT      7824
Ala Asn Gly Tyr Lys Thr Ile Asp Asn Lys Asn Phe Tyr Phe Arg Asn
        2595                2600                2605

GGT TTA CCT CAG ATA GGA GTG TTT AAA GGG TCT AAT GGA TTT GAA TAC      7872
Gly Leu Pro Gln Ile Gly Val Phe Lys Gly Ser Asn Gly Phe Glu Tyr
    2610                2615                2620

TTT GCA CCT GCT AAT ACG GAT GCT AAC AAT ATA GAA GGT CAA GCT ATA      7920
Phe Ala Pro Ala Asn Thr Asp Ala Asn Asn Ile Glu Gly Gln Ala Ile
2625                2630                2635                2640

CGT TAT CAA AAT AGA TTC CTA CAT TTA CTT GGA AAA ATA TAT TAC TTT      7968
Arg Tyr Gln Asn Arg Phe Leu His Leu Leu Gly Lys Ile Tyr Tyr Phe
                2645                2650                2655

GGT AAT AAT TCA AAA GCA GTT ACT GGA TGG CAA ACT ATT AAT GGT AAA      8016
Gly Asn Asn Ser Lys Ala Val Thr Gly Trp Gln Thr Ile Asn Gly Lys
            2660                2665                2670

GTA TAT TAC TTT ATG CCT GAT ACT GCT ATG GCT GCA GCT GGT GGA CTT      8064
Val Tyr Tyr Phe Met Pro Asp Thr Ala Met Ala Ala Ala Gly Gly Leu
        2675                2680                2685

TTC GAG ATT GAT GGT GTT ATA TAT TTC TTT GGT GTT GAT GGA GTA AAA      8112
Phe Glu Ile Asp Gly Val Ile Tyr Phe Phe Gly Val Asp Gly Val Lys
    2690                2695                2700

GCC CCT GGG ATA TAT GGC TAA                                          8133
Ala Pro Gly Ile Tyr Gly
2705                2710
```

(2) INFORMATION FOR SEQ ID NO:6:

(i) SEQUENCE CHARACTERISTICS:
(A) LENGTH: 2710 amino acids

-continued (B) TYPE: amino acid
(D) TOPOLOGY: linear (ii) MOLECULE TYPE: protein (xi) SEQUENCE DESCRIPTION: SEQ ID NO:6:

```
Met Ser Leu Ile Ser Lys Glu Glu Leu Ile Lys Leu Ala Tyr Ser Ile
  1               5                  10                  15

Arg Pro Arg Glu Asn Glu Tyr Lys Thr Ile Leu Thr Asn Leu Asp Glu
             20                  25                  30

Tyr Asn Lys Leu Thr Thr Asn Asn Asn Glu Asn Lys Tyr Leu Gln Leu
         35                  40                  45

Lys Lys Leu Asn Glu Ser Ile Asp Val Phe Met Asn Lys Tyr Lys Thr
     50                  55                  60

Ser Ser Arg Asn Arg Ala Leu Ser Asn Leu Lys Lys Asp Ile Leu Lys
 65                  70                  75                  80

Glu Val Ile Leu Ile Lys Asn Ser Asn Thr Ser Pro Val Glu Lys Asn
                 85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380
```

-continued

Ala Leu Ile Ser Lys Gln Gly Ser Tyr Leu Thr Asn Leu Val Ile Glu
385 390 395 400

Gln Val Lys Asn Arg Tyr Gln Phe Leu Asn Gln His Leu Asn Pro Ala
405 410 415

Ile Glu Ser Asp Asn Asn Phe Thr Asp Thr Thr Lys Ile Phe His Asp
420 425 430

Ser Leu Phe Asn Ser Ala Thr Ala Glu Asn Ser Met Phe Leu Thr Lys
435 440 445

Ile Ala Pro Tyr Leu Gln Val Gly Phe Met Pro Glu Ala Arg Ser Thr
450 455 460

Ile Ser Leu Ser Gly Pro Gly Ala Tyr Ala Ser Ala Tyr Tyr Asp Phe
465 470 475 480

Ile Asn Leu Gln Glu Asn Thr Ile Glu Lys Thr Leu Lys Ala Ser Asp
485 490 495

Leu Ile Glu Phe Lys Phe Pro Glu Asn Asn Leu Ser Gln Leu Thr Glu
500 505 510

Gln Glu Ile Asn Ser Leu Trp Ser Phe Asp Gln Ala Ser Ala Lys Tyr
515 520 525

Gln Phe Glu Lys Tyr Val Arg Asp Tyr Thr Gly Gly Ser Leu Ser Glu
530 535 540

Asp Asn Gly Val Asp Phe Asn Lys Asn Thr Ala Leu Asp Lys Asn Tyr
545 550 555 560

Leu Leu Asn Asn Lys Ile Pro Ser Asn Asn Val Glu Glu Ala Gly Ser
565 570 575

Lys Asn Tyr Val His Tyr Ile Ile Gln Leu Gln Gly Asp Asp Ile Ser
580 585 590

Tyr Glu Ala Thr Cys Asn Leu Phe Ser Lys Asn Pro Lys Asn Ser Ile
595 600 605

Ile Ile Gln Arg Asn Met Asn Glu Ser Ala Lys Ser Tyr Phe Leu Ser
610 615 620

Asp Asp Gly Glu Ser Ile Leu Glu Leu Asn Lys Tyr Arg Ile Pro Glu
625 630 635 640

Arg Leu Lys Asn Lys Glu Lys Val Lys Val Thr Phe Ile Gly His Gly
645 650 655

Lys Asp Glu Phe Asn Thr Ser Glu Phe Ala Arg Leu Ser Val Asp Ser
660 665 670

Leu Ser Asn Glu Ile Ser Ser Phe Leu Asp Thr Ile Lys Leu Asp Ile
675 680 685

Ser Pro Lys Asn Val Glu Val Asn Leu Leu Gly Cys Asn Met Phe Ser
690 695 700

Tyr Asp Phe Asn Val Glu Glu Thr Tyr Pro Gly Lys Leu Leu Leu Ser
705 710 715 720

Ile Met Asp Lys Ile Thr Ser Thr Leu Pro Asp Val Asn Lys Asn Ser
725 730 735

Ile Thr Ile Gly Ala Asn Gln Tyr Glu Val Arg Ile Asn Ser Glu Gly
740 745 750

Arg Lys Glu Leu Leu Ala His Ser Gly Lys Trp Ile Asn Lys Glu Glu
755 760 765

Ala Ile Met Ser Asp Leu Ser Ser Lys Glu Tyr Ile Phe Phe Asp Ser
770 775 780

Ile Asp Asn Lys Leu Lys Ala Lys Ser Lys Asn Ile Pro Gly Leu Ala
785 790 795 800

Ser Ile Ser Glu Asp Ile Lys Thr Leu Leu Leu Asp Ala Ser Val Ser

-continued

```
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val Leu
    1010                1015                1020

Pro Thr Ile Thr Glu Gly Ile Pro Ile Val Ser Thr Ile Leu Asp Gly
1025                1030                1035                1040

Ile Asn Leu Gly Ala Ala Ile Lys Glu Leu Leu Asp Glu His Asp Pro
                1045                1050                1055

Leu Leu Lys Lys Glu Leu Glu Ala Lys Val Gly Val Leu Ala Ile Asn
            1060                1065                1070

Met Ser Leu Ser Ile Ala Ala Thr Val Ala Ser Ile Val Gly Ile Gly
        1075                1080                1085

Ala Glu Val Thr Ile Phe Leu Leu Pro Ile Ala Gly Ile Ser Ala Gly
    1090                1095                1100

Ile Pro Ser Leu Val Asn Asn Glu Leu Ile Leu His Asp Lys Ala Thr
1105                1110                1115                1120

Ser Val Val Asn Tyr Phe Asn His Leu Ser Glu Ser Lys Lys Tyr Gly
                1125                1130                1135

Pro Leu Lys Thr Glu Asp Asp Lys Ile Leu Val Pro Ile Asp Asp Leu
            1140                1145                1150

Val Ile Ser Glu Ile Asp Phe Asn Asn Asn Ser Ile Lys Leu Gly Thr
        1155                1160                1165

Cys Asn Ile Leu Ala Met Glu Gly Gly Ser Gly His Thr Val Thr Gly
    1170                1175                1180

Asn Ile Asp His Phe Phe Ser Ser Pro Ser Ile Ser Ser His Ile Pro
1185                1190                1195                1200

Ser Leu Ser Ile Tyr Ser Ala Ile Gly Ile Glu Thr Glu Asn Leu Asp
                1205                1210                1215

Phe Ser Lys Lys Ile Met Met Leu Pro Asn Ala Pro Ser Arg Val Phe
            1220                1225                1230
```

-continued

```
Trp Trp Glu Thr Gly Ala Val Pro Gly Leu Arg Ser Leu Glu Asn Asp
        1235                1240                1245

Gly Thr Arg Leu Leu Asp Ser Ile Arg Asp Leu Tyr Pro Gly Lys Phe
    1250                1255                1260

Tyr Trp Arg Phe Tyr Ala Phe Phe Asp Tyr Ala Ile Thr Thr Leu Lys
1265                1270                1275                1280

Pro Val Tyr Glu Asp Thr Asn Ile Lys Ile Lys Leu Asp Lys Asp Thr
                1285                1290                1295

Arg Asn Phe Ile Met Pro Thr Ile Thr Thr Asn Glu Ile Arg Asn Lys
            1300                1305                1310

Leu Ser Tyr Ser Phe Asp Gly Ala Gly Gly Thr Tyr Ser Leu Leu Leu
        1315                1320                1325

Ser Ser Tyr Pro Ile Ser Thr Asn Ile Asn Leu Ser Lys Asp Asp Leu
    1330                1335                1340

Trp Ile Phe Asn Ile Asp Asn Glu Val Arg Glu Ile Ser Ile Glu Asn
1345                1350                1355                1360

Gly Thr Ile Lys Lys Gly Lys Leu Ile Lys Asp Val Leu Ser Lys Ile
                1365                1370                1375

Asp Ile Asn Lys Asn Lys Leu Ile Ile Gly Asn Gln Thr Ile Asp Phe
            1380                1385                1390

Ser Gly Asp Ile Asp Asn Lys Asp Arg Tyr Ile Phe Leu Thr Cys Glu
        1395                1400                1405

Leu Asp Asp Lys Ile Ser Leu Ile Ile Glu Ile Asn Leu Val Ala Lys
    1410                1415                1420

Ser Tyr Ser Leu Leu Leu Ser Gly Asp Lys Asn Tyr Leu Ile Ser Asn
1425                1430                1435                1440

Leu Ser Asn Thr Ile Glu Lys Ile Asn Thr Leu Gly Leu Asp Ser Lys
                1445                1450                1455

Asn Ile Ala Tyr Asn Tyr Thr Asp Glu Ser Asn Asn Lys Tyr Phe Gly
            1460                1465                1470

Ala Ile Ser Lys Thr Ser Gln Lys Ser Ile Ile His Tyr Lys Lys Asp
        1475                1480                1485

Ser Lys Asn Ile Leu Glu Phe Tyr Asn Asp Ser Thr Leu Glu Phe Asn
    1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
                1525                1530                1535

Ser Ile Asp Phe Ser Ile Ser Leu Val Ser Lys Asn Gln Val Lys Val
            1540                1545                1550

Asn Gly Leu Tyr Leu Asn Glu Ser Val Tyr Ser Ser Tyr Leu Asp Phe
        1555                1560                1565

Val Lys Asn Ser Asp Gly His His Asn Thr Ser Asn Phe Met Asn Leu
    1570                1575                1580

Phe Leu Asp Asn Ile Ser Phe Trp Lys Leu Phe Gly Phe Glu Asn Ile
1585                1590                1595                1600

Asn Phe Val Ile Asp Lys Tyr Phe Thr Leu Val Gly Lys Thr Asn Leu
                1605                1610                1615

Gly Tyr Val Glu Phe Ile Cys Asp Asn Asn Lys Asn Ile Asp Ile Tyr
            1620                1625                1630

Phe Gly Glu Trp Lys Thr Ser Ser Ser Lys Ser Thr Ile Phe Ser Gly
        1635                1640                1645
```

-continued

```
Asn Gly Arg Asn Val Val Val Glu Pro Ile Tyr Asn Pro Asp Thr Gly
    1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
                1685                1690                1695

Ser Leu Ile Asn Ile Asn Thr Asn Tyr Tyr Ser Asn Glu Tyr Tyr Pro
            1700                1705                1710

Glu Ile Ile Val Leu Asn Pro Asn Thr Phe His Lys Lys Val Asn Ile
        1715                1720                1725

Asn Leu Asp Ser Ser Ser Phe Glu Tyr Lys Trp Ser Thr Glu Gly Ser
    1730                1735                1740

Asp Phe Ile Leu Val Arg Tyr Leu Glu Glu Ser Asn Lys Lys Ile Leu
1745                1750                1755                1760

Gln Lys Ile Arg Ile Lys Gly Ile Leu Ser Asn Thr Gln Ser Phe Asn
                1765                1770                1775

Lys Met Ser Ile Asp Phe Lys Asp Ile Lys Lys Leu Ser Leu Gly Tyr
            1780                1785                1790

Ile Met Ser Asn Phe Lys Ser Phe Asn Ser Glu Asn Glu Leu Asp Arg
        1795                1800                1805

Asp His Leu Gly Phe Lys Ile Ile Asp Asn Lys Thr Tyr Tyr Tyr Asp
    1810                1815                1820

Glu Asp Ser Lys Leu Val Lys Gly Leu Ile Asn Ile Asn Asn Ser Leu
1825                1830                1835                1840

Phe Tyr Phe Asp Pro Ile Glu Phe Asn Leu Val Thr Gly Trp Gln Thr
                1845                1850                1855

Ile Asn Gly Lys Lys Tyr Tyr Phe Asp Ile Asn Thr Gly Ala Ala Leu
            1860                1865                1870

Thr Ser Tyr Lys Ile Ile Asn Gly Lys His Phe Tyr Phe Asn Asn Asp
        1875                1880                1885

Gly Val Met Gln Leu Gly Val Phe Lys Gly Pro Asp Gly Phe Glu Tyr
    1890                1895                1900

Phe Ala Pro Ala Asn Thr Gln Asn Asn Asn Ile Glu Gly Gln Ala Ile
1905                1910                1915                1920

Val Tyr Gln Ser Lys Phe Leu Thr Leu Asn Gly Lys Lys Tyr Tyr Phe
                1925                1930                1935

Asp Asn Asn Ser Lys Ala Val Thr Gly Trp Arg Ile Ile Asn Asn Glu
            1940                1945                1950

Lys Tyr Tyr Phe Asn Pro Asn Asn Ala Ile Ala Ala Val Gly Leu Gln
        1955                1960                1965

Val Ile Asp Asn Asn Lys Tyr Tyr Phe Asn Pro Asp Thr Ala Ile Ile
    1970                1975                1980

Ser Lys Gly Trp Gln Thr Val Asn Gly Ser Arg Tyr Tyr Phe Asp Thr
1985                1990                1995                2000

Asp Thr Ala Ile Ala Phe Asn Gly Tyr Lys Thr Ile Asp Gly Lys His
                2005                2010                2015

Phe Tyr Phe Asp Ser Asp Cys Val Val Lys Ile Gly Val Phe Ser Thr
            2020                2025                2030

Ser Asn Gly Phe Glu Tyr Phe Ala Pro Ala Asn Thr Tyr Asn Asn Asn
        2035                2040                2045

Ile Glu Gly Gln Ala Ile Val Tyr Gln Ser Lys Phe Leu Thr Leu Asn
    2050                2055                2060

Gly Lys Lys Tyr Tyr Phe Asp Asn Asn Ser Lys Ala Val Thr Gly Leu
```

-continued

```
2065                2070                2075                2080

Gln Thr Ile Asp Ser Lys Lys Tyr Tyr Phe Asn Thr Asn Thr Ala Glu
                2085                2090                2095

Ala Ala Thr Gly Trp Gln Thr Ile Asp Gly Lys Lys Tyr Tyr Phe Asn
            2100                2105                2110

Thr Asn Thr Ala Glu Ala Ala Thr Gly Trp Gln Thr Ile Asp Gly Lys
        2115                2120                2125

Lys Tyr Tyr Phe Asn Thr Asn Thr Ala Ile Ala Ser Thr Gly Tyr Thr
    2130                2135                2140

Ile Ile Asn Gly Lys His Phe Tyr Phe Asn Thr Asp Gly Ile Met Gln
2145                2150                2155                2160

Ile Gly Val Phe Lys Gly Pro Asn Gly Phe Glu Tyr Phe Ala Pro Ala
                2165                2170                2175

Asn Thr Asp Ala Asn Asn Ile Glu Gly Gln Ala Ile Leu Tyr Gln Asn
            2180                2185                2190

Glu Phe Leu Thr Leu Asn Gly Lys Lys Tyr Tyr Phe Gly Ser Asp Ser
        2195                2200                2205

Lys Ala Val Thr Gly Trp Arg Ile Ile Asn Asn Lys Lys Tyr Tyr Phe
    2210                2215                2220

Asn Pro Asn Asn Ala Ile Ala Ala Ile His Leu Cys Thr Ile Asn Asn
2225                2230                2235                2240

Asp Lys Tyr Tyr Phe Ser Tyr Asp Gly Ile Leu Gln Asn Gly Tyr Ile
                2245                2250                2255

Thr Ile Glu Arg Asn Asn Phe Tyr Phe Asp Ala Asn Asn Glu Ser Lys
            2260                2265                2270

Met Val Thr Gly Val Phe Lys Gly Pro Asn Gly Phe Glu Tyr Phe Ala
        2275                2280                2285

Pro Ala Asn Thr His Asn Asn Asn Ile Glu Gly Gln Ala Ile Val Tyr
    2290                2295                2300

Gln Asn Lys Phe Leu Thr Leu Asn Gly Lys Lys Tyr Tyr Phe Asp Asn
2305                2310                2315                2320

Asp Ser Lys Ala Val Thr Gly Trp Gln Thr Ile Asp Gly Lys Lys Tyr
                2325                2330                2335

Tyr Phe Asn Leu Asn Thr Ala Glu Ala Ala Thr Gly Trp Gln Thr Ile
            2340                2345                2350

Asp Gly Lys Lys Tyr Tyr Phe Asn Leu Asn Thr Ala Glu Ala Ala Thr
        2355                2360                2365

Gly Trp Gln Thr Ile Asp Gly Lys Lys Tyr Tyr Phe Asn Thr Asn Thr
    2370                2375                2380

Phe Ile Ala Ser Thr Gly Tyr Thr Ser Ile Asn Gly Lys His Phe Tyr
2385                2390                2395                2400

Phe Asn Thr Asp Gly Ile Met Gln Ile Gly Val Phe Lys Gly Pro Asn
                2405                2410                2415

Gly Phe Glu Tyr Phe Ala Pro Ala Asn Thr Asp Ala Asn Asn Ile Glu
            2420                2425                2430

Gly Gln Ala Ile Leu Tyr Gln Asn Lys Phe Leu Thr Leu Asn Gly Lys
        2435                2440                2445

Lys Tyr Tyr Phe Gly Ser Asp Ser Lys Ala Val Thr Gly Leu Arg Thr
    2450                2455                2460

Ile Asp Gly Lys Lys Tyr Tyr Phe Asn Thr Asn Thr Ala Val Ala Val
2465                2470                2475                2480

Thr Gly Trp Gln Thr Ile Asn Gly Lys Lys Tyr Tyr Phe Asn Thr Asn
                2485                2490                2495
```

-continued

```
Thr Ser Ile Ala Ser Thr Gly Tyr Thr Ile Ile Ser Gly Lys His Phe
            2500                2505                2510

Tyr Phe Asn Thr Asp Gly Ile Met Gln Ile Gly Val Phe Lys Gly Pro
        2515                2520                2525

Asp Gly Phe Glu Tyr Phe Ala Pro Ala Asn Thr Asp Ala Asn Asn Ile
    2530                2535                2540

Glu Gly Gln Ala Ile Arg Tyr Gln Asn Arg Phe Leu Tyr Leu His Asp
2545                2550                2555                2560

Asn Ile Tyr Tyr Phe Gly Asn Asn Ser Lys Ala Ala Thr Gly Trp Val
                2565                2570                2575

Thr Ile Asp Gly Asn Arg Tyr Tyr Phe Glu Pro Asn Thr Ala Met Gly
            2580                2585                2590

Ala Asn Gly Tyr Lys Thr Ile Asp Asn Lys Asn Phe Tyr Phe Arg Asn
        2595                2600                2605

Gly Leu Pro Gln Ile Gly Val Phe Lys Gly Ser Asn Gly Phe Glu Tyr
    2610                2615                2620

Phe Ala Pro Ala Asn Thr Asp Ala Asn Asn Ile Glu Gly Gln Ala Ile
2625                2630                2635                2640

Arg Tyr Gln Asn Arg Phe Leu His Leu Leu Gly Lys Ile Tyr Tyr Phe
                2645                2650                2655

Gly Asn Asn Ser Lys Ala Val Thr Gly Trp Gln Thr Ile Asn Gly Lys
            2660                2665                2670

Val Tyr Tyr Phe Met Pro Asp Thr Ala Met Ala Ala Ala Gly Gly Leu
        2675                2680                2685

Phe Glu Ile Asp Gly Val Ile Tyr Phe Phe Gly Val Asp Gly Val Lys
    2690                2695                2700

Ala Pro Gly Ile Tyr Gly
2705                2710
```

(2) INFORMATION FOR SEQ ID NO:7:

(i) SEQUENCE CHARACTERISTICS:
(A) LENGTH: 811 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:7:

```
Ser Tyr Lys Ile Ile Asn Gly Lys His Phe Tyr Phe Asn Asn Asp Gly
1               5                   10                  15

Val Met Gln Leu Gly Val Phe Lys Gly Pro Asp Gly Phe Glu Tyr Phe
            20                  25                  30

Ala Pro Ala Asn Thr Gln Asn Asn Asn Ile Glu Gly Gln Ala Ile Val
        35                  40                  45

Tyr Gln Ser Lys Phe Leu Thr Leu Asn Gly Lys Lys Tyr Tyr Phe Asp
    50                  55                  60

Asn Asn Ser Lys Ala Val Thr Gly Trp Arg Ile Ile Asn Asn Glu Lys
65                  70                  75                  80

Tyr Tyr Phe Asn Pro Asn Asn Ala Ile Ala Ala Val Gly Leu Gln Val
                85                  90                  95

Ile Asp Asn Asn Lys Tyr Tyr Phe Asn Pro Asp Thr Ala Ile Ile Ser
            100                 105                 110

Lys Gly Trp Gln Thr Val Asn Gly Ser Arg Tyr Tyr Phe Asp Thr Asp
        115                 120                 125
```

-continued

```
Thr Ala Ile Ala Phe Asn Gly Tyr Lys Thr Ile Asp Gly Lys His Phe
    130                 135                 140

Tyr Phe Asp Ser Asp Cys Val Val Lys Ile Gly Val Phe Ser Thr Ser
145                 150                 155                 160

Asn Gly Phe Glu Tyr Phe Ala Pro Ala Asn Thr Tyr Asn Asn Asn Ile
                165                 170                 175

Glu Gly Gln Ala Ile Val Tyr Gln Ser Lys Phe Leu Thr Leu Asn Gly
            180                 185                 190

Lys Lys Tyr Tyr Phe Asp Asn Asn Ser Lys Ala Val Thr Gly Leu Gln
        195                 200                 205

Thr Ile Asp Ser Lys Lys Tyr Tyr Phe Asn Thr Asn Thr Ala Glu Ala
    210                 215                 220

Ala Thr Gly Trp Gln Thr Ile Asp Gly Lys Lys Tyr Tyr Phe Asn Thr
225                 230                 235                 240

Asn Thr Ala Glu Ala Ala Thr Gly Trp Gln Thr Ile Asp Gly Lys Lys
                245                 250                 255

Tyr Tyr Phe Asn Thr Asn Thr Ala Ile Ala Ser Thr Gly Tyr Thr Ile
            260                 265                 270

Ile Asn Gly Lys His Phe Tyr Phe Asn Thr Asp Gly Ile Met Gln Ile
        275                 280                 285

Gly Val Phe Lys Gly Pro Asn Gly Phe Glu Tyr Phe Ala Pro Ala Asn
    290                 295                 300

Thr Asp Ala Asn Asn Ile Glu Gly Gln Ala Ile Leu Tyr Gln Asn Glu
305                 310                 315                 320

Phe Leu Thr Leu Asn Gly Lys Lys Tyr Tyr Phe Gly Ser Asp Ser Lys
                325                 330                 335

Ala Val Thr Gly Trp Arg Ile Ile Asn Asn Lys Lys Tyr Tyr Phe Asn
            340                 345                 350

Pro Asn Asn Ala Ile Ala Ala Ile His Leu Cys Thr Ile Asn Asn Asp
        355                 360                 365

Lys Tyr Tyr Phe Ser Tyr Asp Gly Ile Leu Gln Asn Gly Tyr Ile Thr
    370                 375                 380

Ile Glu Arg Asn Asn Phe Tyr Phe Asp Ala Asn Asn Glu Ser Lys Met
385                 390                 395                 400

Val Thr Gly Val Phe Lys Gly Pro Asn Gly Phe Glu Tyr Phe Ala Pro
                405                 410                 415

Ala Asn Thr His Asn Asn Asn Ile Glu Gly Gln Ala Ile Val Tyr Gln
            420                 425                 430

Asn Lys Phe Leu Thr Leu Asn Gly Lys Lys Tyr Tyr Phe Asp Asn Asp
        435                 440                 445

Ser Lys Ala Val Thr Gly Trp Gln Thr Ile Asp Gly Lys Lys Tyr Tyr
    450                 455                 460

Phe Asn Leu Asn Thr Ala Glu Ala Ala Thr Gly Trp Gln Thr Ile Asp
465                 470                 475                 480

Gly Lys Lys Tyr Tyr Phe Asn Leu Asn Thr Ala Glu Ala Ala Thr Gly
                485                 490                 495

Trp Gln Thr Ile Asp Gly Lys Lys Tyr Tyr Phe Asn Thr Asn Thr Phe
            500                 505                 510

Ile Ala Ser Thr Gly Tyr Thr Ser Ile Asn Gly Lys His Phe Tyr Phe
        515                 520                 525

Asn Thr Asp Gly Ile Met Gln Ile Gly Val Phe Lys Gly Pro Asn Gly
    530                 535                 540
```

-continued

```
Phe Glu Tyr Phe Ala Pro Ala Asn Thr Asp Ala Asn Asn Ile Glu Gly
545                 550                 555                 560

Gln Ala Ile Leu Tyr Gln Asn Lys Phe Leu Thr Leu Asn Gly Lys Lys
                565                 570                 575

Tyr Tyr Phe Gly Ser Asp Ser Lys Ala Val Thr Gly Leu Arg Thr Ile
            580                 585                 590

Asp Gly Lys Lys Tyr Tyr Phe Asn Thr Asn Thr Ala Val Ala Val Thr
        595                 600                 605

Gly Trp Gln Thr Ile Asn Gly Lys Lys Tyr Tyr Phe Asn Thr Asn Thr
    610                 615                 620

Ser Ile Ala Ser Thr Gly Tyr Thr Ile Ile Ser Gly Lys His Phe Tyr
625                 630                 635                 640

Phe Asn Thr Asp Gly Ile Met Gln Ile Gly Val Phe Lys Gly Pro Asp
                645                 650                 655

Gly Phe Glu Tyr Phe Ala Pro Ala Asn Thr Asp Ala Asn Asn Ile Glu
            660                 665                 670

Gly Gln Ala Ile Arg Tyr Gln Asn Arg Phe Leu Tyr Leu His Asp Asn
        675                 680                 685

Ile Tyr Tyr Phe Gly Asn Asn Ser Lys Ala Ala Thr Gly Trp Val Thr
    690                 695                 700

Ile Asp Gly Asn Arg Tyr Tyr Phe Glu Pro Asn Thr Ala Met Gly Ala
705                 710                 715                 720

Asn Gly Tyr Lys Thr Ile Asp Asn Lys Asn Phe Tyr Phe Arg Asn Gly
                725                 730                 735

Leu Pro Gln Ile Gly Val Phe Lys Gly Ser Asn Gly Phe Glu Tyr Phe
            740                 745                 750

Ala Pro Ala Asn Thr Asp Ala Asn Asn Ile Glu Gly Gln Ala Ile Arg
        755                 760                 765

Tyr Gln Asn Arg Phe Leu His Leu Leu Gly Lys Ile Tyr Tyr Phe Gly
    770                 775                 780

Asn Asn Ser Lys Ala Val Thr Gly Trp Gln Thr Ile Asn Gly Lys Val
785                 790                 795                 800

Tyr Tyr Phe Met Pro Asp Thr Ala Met Ala Ala
                805                 810
```

(2) INFORMATION FOR SEQ ID NO:8:

(i) SEQUENCE CHARACTERISTICS:
(A) LENGTH: 91 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:8:

```
Ser Tyr Lys Ile Ile Asn Gly Lys His Phe Tyr Phe Asn Asn Asp Gly
1               5                   10                  15

Val Met Gln Leu Gly Val Phe Lys Gly Pro Asp Gly Phe Glu Tyr Phe
            20                  25                  30

Ala Pro Ala Asn Thr Gln Asn Asn Ile Glu Gly Gln Ala Ile Val
        35                  40                  45

Tyr Gln Ser Lys Phe Leu Thr Leu Asn Gly Lys Lys Tyr Tyr Phe Asp
    50                  55                  60

Asn Asn Ser Lys Ala Val Thr Gly Trp Arg Ile Ile Asn Asn Glu Lys
65                  70                  75                  80
```

-continued

```
Tyr Tyr Phe Asn Pro Asn Asn Ala Ile Ala Ala
                85                  90
```

(2) INFORMATION FOR SEQ ID NO:9:

(i) SEQUENCE CHARACTERISTICS:
(A) LENGTH: 7101 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..7098

(xi) SEQUENCE DESCRIPTION: SEQ ID NO:9:

```
ATG AGT TTA GTT AAT AGA AAA CAG TTA GAA AAA ATG GCA AAT GTA AGA        48
Met Ser Leu Val Asn Arg Lys Gln Leu Glu Lys Met Ala Asn Val Arg
  1               5                  10                  15

TTT CGT ACT CAA GAA GAT GAA TAT GTT GCA ATA TTG GAT GCT TTA GAA        96
Phe Arg Thr Gln Glu Asp Glu Tyr Val Ala Ile Leu Asp Ala Leu Glu
             20                  25                  30

GAA TAT CAT AAT ATG TCA GAG AAT ACT GTA GTC GAA AAA TAT TTA AAA       144
Glu Tyr His Asn Met Ser Glu Asn Thr Val Val Glu Lys Tyr Leu Lys
         35                  40                  45

TTA AAA GAT ATA AAT AGT TTA ACA GAT ATT TAT ATA GAT ACA TAT AAA       192
Leu Lys Asp Ile Asn Ser Leu Thr Asp Ile Tyr Ile Asp Thr Tyr Lys
     50                  55                  60

AAA TCT GGT AGA AAT AAA GCC TTA AAA AAA TTT AAG GAA TAT CTA GTT       240
Lys Ser Gly Arg Asn Lys Ala Leu Lys Lys Phe Lys Glu Tyr Leu Val
 65                  70                  75                  80

ACA GAA GTA TTA GAG CTA AAG AAT AAT AAT TTA ACT CCA GTT GAG AAA       288
Thr Glu Val Leu Glu Leu Lys Asn Asn Asn Leu Thr Pro Val Glu Lys
                 85                  90                  95

AAT TTA CAT TTT GTT TGG ATT GGA GGT CAA ATA AAT GAC ACT GCT ATT       336
Asn Leu His Phe Val Trp Ile Gly Gly Gln Ile Asn Asp Thr Ala Ile
            100                 105                 110

AAT TAT ATA AAT CAA TGG AAA GAT GTA AAT AGT GAT TAT AAT GTT AAT       384
Asn Tyr Ile Asn Gln Trp Lys Asp Val Asn Ser Asp Tyr Asn Val Asn
        115                 120                 125

GTT TTT TAT GAT AGT AAT GCA TTT TTG ATA AAC ACA TTG AAA AAA ACT       432
Val Phe Tyr Asp Ser Asn Ala Phe Leu Ile Asn Thr Leu Lys Lys Thr
    130                 135                 140

GTA GTA GAA TCA GCA ATA AAT GAT ACA CTT GAA TCA TTT AGA GAA AAC       480
Val Val Glu Ser Ala Ile Asn Asp Thr Leu Glu Ser Phe Arg Glu Asn
145                 150                 155                 160

TTA AAT GAC CCT AGA TTT GAC TAT AAT AAA TTC TTC AGA AAA CGT ATG       528
Leu Asn Asp Pro Arg Phe Asp Tyr Asn Lys Phe Phe Arg Lys Arg Met
                165                 170                 175

GAA ATA ATT TAT GAT AAA CAG AAA AAT TTC ATA AAC TAC TAT AAA GCT       576
Glu Ile Ile Tyr Asp Lys Gln Lys Asn Phe Ile Asn Tyr Tyr Lys Ala
            180                 185                 190

CAA AGA GAA GAA AAT CCT GAA CTT ATA ATT GAT GAT ATT GTA AAG ACA       624
Gln Arg Glu Glu Asn Pro Glu Leu Ile Ile Asp Asp Ile Val Lys Thr
        195                 200                 205

TAT CTT TCA AAT GAG TAT TCA AAG GAG ATA GAT GAA CTT AAT ACC TAT       672
Tyr Leu Ser Asn Glu Tyr Ser Lys Glu Ile Asp Glu Leu Asn Thr Tyr
    210                 215                 220

ATT GAA GAA TCC TTA AAT AAA ATT ACA CAG AAT AGT GGA AAT GAT GTT       720
Ile Glu Glu Ser Leu Asn Lys Ile Thr Gln Asn Ser Gly Asn Asp Val
225                 230                 235                 240
```

-continued

```
AGA AAC TTT GAA GAA TTT AAA AAT GGA GAG TCA TTC AAC TTA TAT GAA      768
Arg Asn Phe Glu Glu Phe Lys Asn Gly Glu Ser Phe Asn Leu Tyr Glu
                245                 250                 255

CAA GAG TTG GTA GAA AGG TGG AAT TTA GCT GCT GCT TCT GAC ATA TTA      816
Gln Glu Leu Val Glu Arg Trp Asn Leu Ala Ala Ala Ser Asp Ile Leu
            260                 265                 270

AGA ATA TCT GCA TTA AAA GAA ATT GGT GGT ATG TAT TTA GAT GTT GAT      864
Arg Ile Ser Ala Leu Lys Glu Ile Gly Gly Met Tyr Leu Asp Val Asp
        275                 280                 285

ATG TTA CCA GGA ATA CAA CCA GAC TTA TTT GAG TCT ATA GAG AAA CCT      912
Met Leu Pro Gly Ile Gln Pro Asp Leu Phe Glu Ser Ile Glu Lys Pro
    290                 295                 300

AGT TCA GTA ACA GTG GAT TTT TGG GAA ATG ACA AAG TTA GAA GCT ATA      960
Ser Ser Val Thr Val Asp Phe Trp Glu Met Thr Lys Leu Glu Ala Ile
305                 310                 315                 320

ATG AAA TAC AAA GAA TAT ATA CCA GAA TAT ACC TCA GAA CAT TTT GAC     1008
Met Lys Tyr Lys Glu Tyr Ile Pro Glu Tyr Thr Ser Glu His Phe Asp
                325                 330                 335

ATG TTA GAC GAA GAA GTT CAA AGT AGT TTT GAA TCT GTT CTA GCT TCT     1056
Met Leu Asp Glu Glu Val Gln Ser Ser Phe Glu Ser Val Leu Ala Ser
            340                 345                 350

AAG TCA GAT AAA TCA GAA ATA TTC TCA TCA CTT GGT GAT ATG GAG GCA     1104
Lys Ser Asp Lys Ser Glu Ile Phe Ser Ser Leu Gly Asp Met Glu Ala
        355                 360                 365

TCA CCA CTA GAA GTT AAA ATT GCA TTT AAT AGT AAG GGT ATT ATA AAT     1152
Ser Pro Leu Glu Val Lys Ile Ala Phe Asn Ser Lys Gly Ile Ile Asn
    370                 375                 380

CAA GGG CTA ATT TCT GTG AAA GAC TCA TAT TGT AGC AAT TTA ATA GTA     1200
Gln Gly Leu Ile Ser Val Lys Asp Ser Tyr Cys Ser Asn Leu Ile Val
385                 390                 395                 400

AAA CAA ATC GAG AAT AGA TAT AAA ATA TTG AAT AAT AGT TTA AAT CCA     1248
Lys Gln Ile Glu Asn Arg Tyr Lys Ile Leu Asn Asn Ser Leu Asn Pro
                405                 410                 415

GCT ATT AGC GAG GAT AAT GAT TTT AAT ACT ACA ACG AAT ACC TTT ATT     1296
Ala Ile Ser Glu Asp Asn Asp Phe Asn Thr Thr Thr Asn Thr Phe Ile
            420                 425                 430

GAT AGT ATA ATG GCT GAA GCT AAT GCA GAT AAT GGT AGA TTT ATG ATG     1344
Asp Ser Ile Met Ala Glu Ala Asn Ala Asp Asn Gly Arg Phe Met Met
        435                 440                 445

GAA CTA GGA AAG TAT TTA AGA GTT GGT TTC TTC CCA GAT GTT AAA ACT     1392
Glu Leu Gly Lys Tyr Leu Arg Val Gly Phe Phe Pro Asp Val Lys Thr
    450                 455                 460

ACT ATT AAC TTA AGT GGC CCT GAA GCA TAT GCG GCA GCT TAT CAA GAT     1440
Thr Ile Asn Leu Ser Gly Pro Glu Ala Tyr Ala Ala Ala Tyr Gln Asp
465                 470                 475                 480

TTA TTA ATG TTT AAA GAA GGC AGT ATG AAT ATC CAT TTG ATA GAA GCT     1488
Leu Leu Met Phe Lys Glu Gly Ser Met Asn Ile His Leu Ile Glu Ala
                485                 490                 495

GAT TTA AGA AAC TTT GAA ATC TCT AAA ACT AAT ATT TCT CAA TCA ACT     1536
Asp Leu Arg Asn Phe Glu Ile Ser Lys Thr Asn Ile Ser Gln Ser Thr
            500                 505                 510

GAA CAA GAA ATG GCT AGC TTA TGG TCA TTT GAC GAT GCA AGA GCT AAA     1584
Glu Gln Glu Met Ala Ser Leu Trp Ser Phe Asp Asp Ala Arg Ala Lys
        515                 520                 525

GCT CAA TTT GAA GAA TAT AAA AGG AAT TAT TTT GAA GGT TCT CTT GGT     1632
Ala Gln Phe Glu Glu Tyr Lys Arg Asn Tyr Phe Glu Gly Ser Leu Gly
    530                 535                 540

GAA GAT GAT AAT CTT GAT TTT TCT CAA AAT ATA GTA GTT GAC AAG GAG     1680
Glu Asp Asp Asn Leu Asp Phe Ser Gln Asn Ile Val Val Asp Lys Glu
```

-continued

```
545                 550                 555                 560

TAT CTT TTA GAA AAA ATA TCT TCA TTA GCA AGA AGT TCA GAG AGA GGA     1728
Tyr Leu Leu Glu Lys Ile Ser Ser Leu Ala Arg Ser Ser Glu Arg Gly
                565                 570                 575

TAT ATA CAC TAT ATT GTT CAG TTA CAA GGA GAT AAA ATT AGT TAT GAA     1776
Tyr Ile His Tyr Ile Val Gln Leu Gln Gly Asp Lys Ile Ser Tyr Glu
            580                 585                 590

GCA GCA TGT AAC TTA TTT GCA AAG ACT CCT TAT GAT AGT GTA CTG TTT     1824
Ala Ala Cys Asn Leu Phe Ala Lys Thr Pro Tyr Asp Ser Val Leu Phe
        595                 600                 605

CAG AAA AAT ATA GAA GAT TCA GAA ATT GCA TAT TAT TAT AAT CCT GGA     1872
Gln Lys Asn Ile Glu Asp Ser Glu Ile Ala Tyr Tyr Tyr Asn Pro Gly
    610                 615                 620

GAT GGT GAA ATA CAA GAA ATA GAC AAG TAT AAA ATT CCA AGT ATA ATT     1920
Asp Gly Glu Ile Gln Glu Ile Asp Lys Tyr Lys Ile Pro Ser Ile Ile
625                 630                 635                 640

TCT GAT AGA CCT AAG ATT AAA TTA ACA TTT ATT GGT CAT GGT AAA GAT     1968
Ser Asp Arg Pro Lys Ile Lys Leu Thr Phe Ile Gly His Gly Lys Asp
                645                 650                 655

GAA TTT AAT ACT GAT ATA TTT GCA GGT TTT GAT GTA GAT TCA TTA TCC     2016
Glu Phe Asn Thr Asp Ile Phe Ala Gly Phe Asp Val Asp Ser Leu Ser
            660                 665                 670

ACA GAA ATA GAA GCA GCA ATA GAT TTA GCT AAA GAG GAT ATT TCT CCT     2064
Thr Glu Ile Glu Ala Ala Ile Asp Leu Ala Lys Glu Asp Ile Ser Pro
        675                 680                 685

AAG TCA ATA GAA ATA AAT TTA TTA GGA TGT AAT ATG TTT AGC TAC TCT     2112
Lys Ser Ile Glu Ile Asn Leu Leu Gly Cys Asn Met Phe Ser Tyr Ser
    690                 695                 700

ATC AAC GTA GAG GAG ACT TAT CCT GGA AAA TTA TTA CTT AAA GTT AAA     2160
Ile Asn Val Glu Glu Thr Tyr Pro Gly Lys Leu Leu Leu Lys Val Lys
705                 710                 715                 720

GAT AAA ATA TCA GAA TTA ATG CCA TCT ATA AGT CAA GAC TCT ATT ATA     2208
Asp Lys Ile Ser Glu Leu Met Pro Ser Ile Ser Gln Asp Ser Ile Ile
                725                 730                 735

GTA AGT GCA AAT CAA TAT GAA GTT AGA ATA AAT AGT GAA GGA AGA AGA     2256
Val Ser Ala Asn Gln Tyr Glu Val Arg Ile Asn Ser Glu Gly Arg Arg
            740                 745                 750

GAA TTA TTG GAT CAT TCT GGT GAA TGG ATA AAT AAA GAA GAA AGT ATT     2304
Glu Leu Leu Asp His Ser Gly Glu Trp Ile Asn Lys Glu Glu Ser Ile
        755                 760                 765

ATA AAG GAT ATT TCA TCA AAA GAA TAT ATA TCA TTT AAT CCT AAA GAA     2352
Ile Lys Asp Ile Ser Ser Lys Glu Tyr Ile Ser Phe Asn Pro Lys Glu
    770                 775                 780

AAT AAA ATT ACA GTA AAA TCT AAA AAT TTA CCT GAG CTA TCT ACA TTA     2400
Asn Lys Ile Thr Val Lys Ser Lys Asn Leu Pro Glu Leu Ser Thr Leu
785                 790                 795                 800

TTA CAA GAA ATT AGA AAT AAT TCT AAT TCA AGT GAT ATT GAA CTA GAA     2448
Leu Gln Glu Ile Arg Asn Asn Ser Asn Ser Ser Asp Ile Glu Leu Glu
                805                 810                 815

GAA AAA GTA ATG TTA ACA GAA TGT GAG ATA AAT GTT ATT TCA AAT ATA     2496
Glu Lys Val Met Leu Thr Glu Cys Glu Ile Asn Val Ile Ser Asn Ile
            820                 825                 830

GAT ACG CAA ATT GTT GAG GAA AGG ATT GAA GAA GCT AAG AAT TTA ACT     2544
Asp Thr Gln Ile Val Glu Glu Arg Ile Glu Glu Ala Lys Asn Leu Thr
        835                 840                 845

TCT GAC TCT ATT AAT TAT ATA AAA GAT GAA TTT AAA CTA ATA GAA TCT     2592
Ser Asp Ser Ile Asn Tyr Ile Lys Asp Glu Phe Lys Leu Ile Glu Ser
    850                 855                 860

ATT TCT GAT GCA CTA TGT GAC TTA AAA CAA CAG AAT GAA TTA GAA GAT     2640
```

-continued

```
Ile Ser Asp Ala Leu Cys Asp Leu Lys Gln Gln Asn Glu Leu Glu Asp
865                 870                 875                 880

TCT CAT TTT ATA TCT TTT GAG GAC ATA TCA GAG ACT GAT GAG GGA TTT      2688
Ser His Phe Ile Ser Phe Glu Asp Ile Ser Glu Thr Asp Glu Gly Phe
                885                 890                 895

AGT ATA AGA TTT ATT AAT AAA GAA ACT GGA GAA TCT ATA TTT GTA GAA      2736
Ser Ile Arg Phe Ile Asn Lys Glu Thr Gly Glu Ser Ile Phe Val Glu
            900                 905                 910

ACT GAA AAA ACA ATA TTC TCT GAA TAT GCT AAT CAT ATA ACT GAA GAG      2784
Thr Glu Lys Thr Ile Phe Ser Glu Tyr Ala Asn His Ile Thr Glu Glu
        915                 920                 925

ATT TCT AAG ATA AAA GGT ACT ATA TTT GAT ACT GTA AAT GGT AAG TTA      2832
Ile Ser Lys Ile Lys Gly Thr Ile Phe Asp Thr Val Asn Gly Lys Leu
    930                 935                 940

GTA AAA AAA GTA AAT TTA GAT ACT ACA CAC GAA GTA AAT ACT TTA AAT      2880
Val Lys Lys Val Asn Leu Asp Thr Thr His Glu Val Asn Thr Leu Asn
945                 950                 955                 960

GCT GCA TTT TTT ATA CAA TCA TTA ATA GAA TAT AAT AGT TCT AAA GAA      2928
Ala Ala Phe Phe Ile Gln Ser Leu Ile Glu Tyr Asn Ser Ser Lys Glu
                965                 970                 975

TCT CTT AGT AAT TTA AGT GTA GCA ATG AAA GTC CAA GTT TAC GCT CAA      2976
Ser Leu Ser Asn Leu Ser Val Ala Met Lys Val Gln Val Tyr Ala Gln
            980                 985                 990

TTA TTT AGT ACT GGT TTA AAT ACT ATT ACA GAT GCA GCC AAA GTT GTT      3024
Leu Phe Ser Thr Gly Leu Asn Thr Ile Thr Asp Ala Ala Lys Val Val
        995                 1000                1005

GAA TTA GTA TCA ACT GCA TTA GAT GAA ACT ATA GAC TTA CTT CCT ACA      3072
Glu Leu Val Ser Thr Ala Leu Asp Glu Thr Ile Asp Leu Leu Pro Thr
    1010                1015                1020

TTA TCT GAA GGA TTA CCT ATA ATT GCA ACT ATT ATA GAT GGT GTA AGT      3120
Leu Ser Glu Gly Leu Pro Ile Ile Ala Thr Ile Ile Asp Gly Val Ser
1025                1030                1035                1040

TTA GGT GCA GCA ATC AAA GAG CTA AGT GAA ACG AGT GAC CCA TTA TTA      3168
Leu Gly Ala Ala Ile Lys Glu Leu Ser Glu Thr Ser Asp Pro Leu Leu
                1045                1050                1055

AGA CAA GAA ATA GAA GCT AAG ATA GGT ATA ATG GCA GTA AAT TTA ACA      3216
Arg Gln Glu Ile Glu Ala Lys Ile Gly Ile Met Ala Val Asn Leu Thr
            1060                1065                1070

ACA GCT ACA ACT GCA ATC ATT ACT TCA TCT TTG GGG ATA GCT AGT GGA      3264
Thr Ala Thr Thr Ala Ile Ile Thr Ser Ser Leu Gly Ile Ala Ser Gly
        1075                1080                1085

TTT AGT ATA CTT TTA GTT CCT TTA GCA GGA ATT TCA GCA GGT ATA CCA      3312
Phe Ser Ile Leu Leu Val Pro Leu Ala Gly Ile Ser Ala Gly Ile Pro
    1090                1095                1100

AGC TTA GTA AAC AAT GAA CTT GTA CTT CGA GAT AAG GCA ACA AAG GTT      3360
Ser Leu Val Asn Asn Glu Leu Val Leu Arg Asp Lys Ala Thr Lys Val
1105                1110                1115                1120

GTA GAT TAT TTT AAA CAT GTT TCA TTA GTT GAA ACT GAA GGA GTA TTT      3408
Val Asp Tyr Phe Lys His Val Ser Leu Val Glu Thr Glu Gly Val Phe
                1125                1130                1135

ACT TTA TTA GAT GAT AAA ATA ATG ATG CCA CAA GAT GAT TTA GTG ATA      3456
Thr Leu Leu Asp Asp Lys Ile Met Met Pro Gln Asp Asp Leu Val Ile
            1140                1145                1150

TCA GAA ATA GAT TTT AAT AAT AAT TCA ATA GTT TTA GGT AAA TGT GAA      3504
Ser Glu Ile Asp Phe Asn Asn Asn Ser Ile Val Leu Gly Lys Cys Glu
        1155                1160                1165

ATC TGG AGA ATG GAA GGT GGT TCA GGT CAT ACT GTA ACT GAT GAT ATA      3552
Ile Trp Arg Met Glu Gly Gly Ser Gly His Thr Val Thr Asp Asp Ile
    1170                1175                1180
```

-continued

```
GAT CAC TTC TTT TCA GCA CCA TCA ATA ACA TAT AGA GAG CCA CAC TTA     3600
Asp His Phe Phe Ser Ala Pro Ser Ile Thr Tyr Arg Glu Pro His Leu
1185                1190                1195                1200

TCT ATA TAT GAC GTA TTG GAA GTA CAA AAA GAA GAA CTT GAT TTG TCA     3648
Ser Ile Tyr Asp Val Leu Glu Val Gln Lys Glu Glu Leu Asp Leu Ser
                1205                1210                1215

AAA GAT TTA ATG GTA TTA CCT AAT GCT CCA AAT AGA GTA TTT GCT TGG     3696
Lys Asp Leu Met Val Leu Pro Asn Ala Pro Asn Arg Val Phe Ala Trp
            1220                1225                1230

GAA ACA GGA TGG ACA CCA GGT TTA AGA AGC TTA GAA AAT GAT GGC ACA     3744
Glu Thr Gly Trp Thr Pro Gly Leu Arg Ser Leu Glu Asn Asp Gly Thr
        1235                1240                1245

AAA CTG TTA GAC CGT ATA AGA GAT AAC TAT GAA GGT GAG TTT TAT TGG     3792
Lys Leu Leu Asp Arg Ile Arg Asp Asn Tyr Glu Gly Glu Phe Tyr Trp
    1250                1255                1260

AGA TAT TTT GCT TTT ATA GCT GAT GCT TTA ATA ACA ACA TTA AAA CCA     3840
Arg Tyr Phe Ala Phe Ile Ala Asp Ala Leu Ile Thr Thr Leu Lys Pro
1265                1270                1275                1280

AGA TAT GAA GAT ACT AAT ATA AGA ATA AAT TTA GAT AGT AAT ACT AGA     3888
Arg Tyr Glu Asp Thr Asn Ile Arg Ile Asn Leu Asp Ser Asn Thr Arg
                1285                1290                1295

AGT TTT ATA GTT CCA ATA ATA ACT ACA GAA TAT ATA AGA GAA AAA TTA     3936
Ser Phe Ile Val Pro Ile Ile Thr Thr Glu Tyr Ile Arg Glu Lys Leu
            1300                1305                1310

TCA TAT TCT TTC TAT GGT TCA GGA GGA ACT TAT GCA TTG TCT CTT TCT     3984
Ser Tyr Ser Phe Tyr Gly Ser Gly Gly Thr Tyr Ala Leu Ser Leu Ser
        1315                1320                1325

CAA TAT AAT ATG GGT ATA AAT ATA GAA TTA AGT GAA AGT GAT GTT TGG     4032
Gln Tyr Asn Met Gly Ile Asn Ile Glu Leu Ser Glu Ser Asp Val Trp
    1330                1335                1340

ATT ATA GAT GTT GAT AAT GTT GTG AGA GAT GTA ACT ATA GAA TCT GAT     4080
Ile Ile Asp Val Asp Asn Val Val Arg Asp Val Thr Ile Glu Ser Asp
1345                1350                1355                1360

AAA ATT AAA AAA GGT GAT TTA ATA GAA GGT ATT TTA TCT ACA CTA AGT     4128
Lys Ile Lys Lys Gly Asp Leu Ile Glu Gly Ile Leu Ser Thr Leu Ser
                1365                1370                1375

ATT GAA GAG AAT AAA ATT ATC TTA AAT AGC CAT GAG ATT AAT TTT TCT     4176
Ile Glu Glu Asn Lys Ile Ile Leu Asn Ser His Glu Ile Asn Phe Ser
            1380                1385                1390

GGT GAG GTA AAT GGA AGT AAT GGA TTT GTT TCT TTA ACA TTT TCA ATT     4224
Gly Glu Val Asn Gly Ser Asn Gly Phe Val Ser Leu Thr Phe Ser Ile
        1395                1400                1405

TTA GAA GGA ATA AAT GCA ATT ATA GAA GTT GAT TTA TTA TCT AAA TCA     4272
Leu Glu Gly Ile Asn Ala Ile Ile Glu Val Asp Leu Leu Ser Lys Ser
    1410                1415                1420

TAT AAA TTA CTT ATT TCT GGC GAA TTA AAA ATA TTG ATG TTA AAT TCA     4320
Tyr Lys Leu Leu Ile Ser Gly Glu Leu Lys Ile Leu Met Leu Asn Ser
1425                1430                1435                1440

AAT CAT ATT CAA CAG AAA ATA GAT TAT ATA GGA TTC AAT AGC GAA TTA     4368
Asn His Ile Gln Gln Lys Ile Asp Tyr Ile Gly Phe Asn Ser Glu Leu
                1445                1450                1455

CAG AAA AAT ATA CCA TAT AGC TTT GTA GAT AGT GAA GGA AAA GAG AAT     4416
Gln Lys Asn Ile Pro Tyr Ser Phe Val Asp Ser Glu Gly Lys Glu Asn
            1460                1465                1470

GGT TTT ATT AAT GGT TCA ACA AAA GAA GGT TTA TTT GTA TCT GAA TTA     4464
Gly Phe Ile Asn Gly Ser Thr Lys Glu Gly Leu Phe Val Ser Glu Leu
        1475                1480                1485

CCT GAT GTA GTT CTT ATA AGT AAG GTT TAT ATG GAT GAT AGT AAG CCT     4512
Pro Asp Val Val Leu Ile Ser Lys Val Tyr Met Asp Asp Ser Lys Pro
    1490                1495                1500
```

-continued

```
TCA TTT GGA TAT TAT AGT AAT AAT TTG AAA GAT GTC AAA GTT ATA ACT     4560
Ser Phe Gly Tyr Tyr Ser Asn Asn Leu Lys Asp Val Lys Val Ile Thr
1505                1510                1515                1520

AAA GAT AAT GTT AAT ATA TTA ACA GGT TAT TAT CTT AAG GAT GAT ATA     4608
Lys Asp Asn Val Asn Ile Leu Thr Gly Tyr Tyr Leu Lys Asp Asp Ile
                1525                1530                1535

AAA ATC TCT CTT TCT TTG ACT CTA CAA GAT GAA AAA ACT ATA AAG TTA     4656
Lys Ile Ser Leu Ser Leu Thr Leu Gln Asp Glu Lys Thr Ile Lys Leu
            1540                1545                1550

AAT AGT GTG CAT TTA GAT GAA AGT GGA GTA GCT GAG ATT TTG AAG TTC     4704
Asn Ser Val His Leu Asp Glu Ser Gly Val Ala Glu Ile Leu Lys Phe
        1555                1560                1565

ATG AAT AGA AAA GGT AAT ACA AAT ACT TCA GAT TCT TTA ATG AGC TTT     4752
Met Asn Arg Lys Gly Asn Thr Asn Thr Ser Asp Ser Leu Met Ser Phe
    1570                1575                1580

TTA GAA AGT ATG AAT ATA AAA AGT ATT TTC GTT AAT TTC TTA CAA TCT     4800
Leu Glu Ser Met Asn Ile Lys Ser Ile Phe Val Asn Phe Leu Gln Ser
1585                1590                1595                1600

AAT ATT AAG TTT ATA TTA GAT GCT AAT TTT ATA ATA AGT GGT ACT ACT     4848
Asn Ile Lys Phe Ile Leu Asp Ala Asn Phe Ile Ile Ser Gly Thr Thr
                1605                1610                1615

TCT ATT GGC CAA TTT GAG TTT ATT TGT GAT GAA AAT GAT AAT ATA CAA     4896
Ser Ile Gly Gln Phe Glu Phe Ile Cys Asp Glu Asn Asp Asn Ile Gln
            1620                1625                1630

CCA TAT TTC ATT AAG TTT AAT ACA CTA GAA ACT AAT TAT ACT TTA TAT     4944
Pro Tyr Phe Ile Lys Phe Asn Thr Leu Glu Thr Asn Tyr Thr Leu Tyr
        1635                1640                1645

GTA GGA AAT AGA CAA AAT ATG ATA GTG GAA CCA AAT TAT GAT TTA GAT     4992
Val Gly Asn Arg Gln Asn Met Ile Val Glu Pro Asn Tyr Asp Leu Asp
    1650                1655                1660

GAT TCT GGA GAT ATA TCT TCA ACT GTT ATC AAT TTC TCT CAA AAG TAT     5040
Asp Ser Gly Asp Ile Ser Ser Thr Val Ile Asn Phe Ser Gln Lys Tyr
1665                1670                1675                1680

CTT TAT GGA ATA GAC AGT TGT GTT AAT AAA GTT GTA ATT TCA CCA AAT     5088
Leu Tyr Gly Ile Asp Ser Cys Val Asn Lys Val Val Ile Ser Pro Asn
                1685                1690                1695

ATT TAT ACA GAT GAA ATA AAT ATA ACG CCT GTA TAT GAA ACA AAT AAT     5136
Ile Tyr Thr Asp Glu Ile Asn Ile Thr Pro Val Tyr Glu Thr Asn Asn
            1700                1705                1710

ACT TAT CCA GAA GTT ATT GTA TTA GAT GCA AAT TAT ATA AAT GAA AAA     5184
Thr Tyr Pro Glu Val Ile Val Leu Asp Ala Asn Tyr Ile Asn Glu Lys
        1715                1720                1725

ATA AAT GTT AAT ATC AAT GAT CTA TCT ATA CGA TAT GTA TGG AGT AAT     5232
Ile Asn Val Asn Ile Asn Asp Leu Ser Ile Arg Tyr Val Trp Ser Asn
    1730                1735                1740

GAT GGT AAT GAT TTT ATT CTT ATG TCA ACT AGT GAA GAA AAT AAG GTG     5280
Asp Gly Asn Asp Phe Ile Leu Met Ser Thr Ser Glu Glu Asn Lys Val
1745                1750                1755                1760

TCA CAA GTT AAA ATA AGA TTC GTT AAT GTT TTT AAA GAT AAG ACT TTG     5328
Ser Gln Val Lys Ile Arg Phe Val Asn Val Phe Lys Asp Lys Thr Leu
                1765                1770                1775

GCA AAT AAG CTA TCT TTT AAC TTT AGT GAT AAA CAA GAT GTA CCT GTA     5376
Ala Asn Lys Leu Ser Phe Asn Phe Ser Asp Lys Gln Asp Val Pro Val
            1780                1785                1790

AGT GAA ATA ATC TTA TCA TTT ACA CCT TCA TAT TAT GAG GAT GGA TTG     5424
Ser Glu Ile Ile Leu Ser Phe Thr Pro Ser Tyr Tyr Glu Asp Gly Leu
        1795                1800                1805

ATT GGC TAT GAT TTG GGT CTA GTT TCT TTA TAT AAT GAG AAA TTT TAT     5472
Ile Gly Tyr Asp Leu Gly Leu Val Ser Leu Tyr Asn Glu Lys Phe Tyr
```

-continued

```
    1810                1815                1820

ATT AAT AAC TTT GGA ATG ATG GTA TCT GGA TTA ATA TAT ATT AAT GAT     5520
Ile Asn Asn Phe Gly Met Met Val Ser Gly Leu Ile Tyr Ile Asn Asp
1825                1830                1835                1840

TCA TTA TAT TAT TTT AAA CCA CCA GTA AAT AAT TTG ATA ACT GGA TTT     5568
Ser Leu Tyr Tyr Phe Lys Pro Pro Val Asn Asn Leu Ile Thr Gly Phe
                1845                1850                1855

GTG ACT GTA GGC GAT GAT AAA TAC TAC TTT AAT CCA ATT AAT GGT GGA     5616
Val Thr Val Gly Asp Asp Lys Tyr Tyr Phe Asn Pro Ile Asn Gly Gly
            1860                1865                1870

GCT GCT TCA ATT GGA GAG ACA ATA ATT GAT GAC AAA AAT TAT TAT TTC     5664
Ala Ala Ser Ile Gly Glu Thr Ile Ile Asp Asp Lys Asn Tyr Tyr Phe
        1875                1880                1885

AAC CAA AGT GGA GTG TTA CAA ACA GGT GTA TTT AGT ACA GAA GAT GGA     5712
Asn Gln Ser Gly Val Leu Gln Thr Gly Val Phe Ser Thr Glu Asp Gly
    1890                1895                1900

TTT AAA TAT TTT GCC CCA GCT AAT ACA CTT GAT GAA AAC CTA GAA GGA     5760
Phe Lys Tyr Phe Ala Pro Ala Asn Thr Leu Asp Glu Asn Leu Glu Gly
1905                1910                1915                1920

GAA GCA ATT GAT TTT ACT GGA AAA TTA ATT ATT GAC GAA AAT ATT TAT     5808
Glu Ala Ile Asp Phe Thr Gly Lys Leu Ile Ile Asp Glu Asn Ile Tyr
                1925                1930                1935

TAT TTT GAT GAT AAT TAT AGA GGA GCT GTA GAA TGG AAA GAA TTA GAT     5856
Tyr Phe Asp Asp Asn Tyr Arg Gly Ala Val Glu Trp Lys Glu Leu Asp
            1940                1945                1950

GGT GAA ATG CAC TAT TTT AGC CCA GAA ACA GGT AAA GCT TTT AAA GGT     5904
Gly Glu Met His Tyr Phe Ser Pro Glu Thr Gly Lys Ala Phe Lys Gly
        1955                1960                1965

CTA AAT CAA ATA GGT GAT TAT AAA TAC TAT TTC AAT TCT GAT GGA GTT     5952
Leu Asn Gln Ile Gly Asp Tyr Lys Tyr Tyr Phe Asn Ser Asp Gly Val
    1970                1975                1980

ATG CAA AAA GGA TTT GTT AGT ATA AAT GAT AAT AAA CAC TAT TTT GAT     6000
Met Gln Lys Gly Phe Val Ser Ile Asn Asp Asn Lys His Tyr Phe Asp
1985                1990                1995                2000

GAT TCT GGT GTT ATG AAA GTA GGT TAC ACT GAA ATA GAT GGC AAG CAT     6048
Asp Ser Gly Val Met Lys Val Gly Tyr Thr Glu Ile Asp Gly Lys His
                2005                2010                2015

TTC TAC TTT GCT GAA AAC GGA GAA ATG CAA ATA GGA GTA TTT AAT ACA     6096
Phe Tyr Phe Ala Glu Asn Gly Glu Met Gln Ile Gly Val Phe Asn Thr
            2020                2025                2030

GAA GAT GGA TTT AAA TAT TTT GCT CAT CAT AAT GAA GAT TTA GGA AAT     6144
Glu Asp Gly Phe Lys Tyr Phe Ala His His Asn Glu Asp Leu Gly Asn
        2035                2040                2045

GAA GAA GGT GAA GAA ATC TCA TAT TCT GGT ATA TTA AAT TTC AAT AAT     6192
Glu Glu Gly Glu Glu Ile Ser Tyr Ser Gly Ile Leu Asn Phe Asn Asn
    2050                2055                2060

AAA ATT TAC TAT TTT GAT GAT TCA TTT ACA GCT GTA GTT GGA TGG AAA     6240
Lys Ile Tyr Tyr Phe Asp Asp Ser Phe Thr Ala Val Val Gly Trp Lys
2065                2070                2075                2080

GAT TTA GAG GAT GGT TCA AAG TAT TAT TTT GAT GAA GAT ACA GCA GAA     6288
Asp Leu Glu Asp Gly Ser Lys Tyr Tyr Phe Asp Glu Asp Thr Ala Glu
                2085                2090                2095

GCA TAT ATA GGT TTG TCA TTA ATA AAT GAT GGT CAA TAT TAT TTT AAT     6336
Ala Tyr Ile Gly Leu Ser Leu Ile Asn Asp Gly Gln Tyr Tyr Phe Asn
            2100                2105                2110

GAT GAT GGA ATT ATG CAA GTT GGA TTT GTC ACT ATA AAT GAT AAA GTC     6384
Asp Asp Gly Ile Met Gln Val Gly Phe Val Thr Ile Asn Asp Lys Val
        2115                2120                2125

TTC TAC TTC TCT GAC TCT GGA ATT ATA GAA TCT GGA GTA CAA AAC ATA     6432
```

-continued

```
Phe Tyr Phe Ser Asp Ser Gly Ile Ile Glu Ser Gly Val Gln Asn Ile
    2130                2135                2140

GAT GAC AAT TAT TTC TAT ATA GAT GAT AAT GGT ATA GTT CAA ATT GGT     6480
Asp Asp Asn Tyr Phe Tyr Ile Asp Asp Asn Gly Ile Val Gln Ile Gly
2145                2150                2155                2160

GTA TTT GAT ACT TCA GAT GGA TAT AAA TAT TTT GCA CCT GCT AAT ACT     6528
Val Phe Asp Thr Ser Asp Gly Tyr Lys Tyr Phe Ala Pro Ala Asn Thr
                2165                2170                2175

GTA AAT GAT AAT ATT TAC GGA CAA GCA GTT GAA TAT AGT GGT TTA GTT     6576
Val Asn Asp Asn Ile Tyr Gly Gln Ala Val Glu Tyr Ser Gly Leu Val
            2180                2185                2190

AGA GTT GGG GAA GAT GTA TAT TAT TTT GGA GAA ACA TAT ACA ATT GAG     6624
Arg Val Gly Glu Asp Val Tyr Tyr Phe Gly Glu Thr Tyr Thr Ile Glu
        2195                2200                2205

ACT GGA TGG ATA TAT GAT ATG GAA AAT GAA AGT GAT AAA TAT TAT TTC     6672
Thr Gly Trp Ile Tyr Asp Met Glu Asn Glu Ser Asp Lys Tyr Tyr Phe
    2210                2215                2220

AAT CCA GAA ACT AAA AAA GCA TGC AAA GGT ATT AAT TTA ATT GAT GAT     6720
Asn Pro Glu Thr Lys Lys Ala Cys Lys Gly Ile Asn Leu Ile Asp Asp
2225                2230                2235                2240

ATA AAA TAT TAT TTT GAT GAG AAG GGC ATA ATG AGA ACG GGT CTT ATA     6768
Ile Lys Tyr Tyr Phe Asp Glu Lys Gly Ile Met Arg Thr Gly Leu Ile
                2245                2250                2255

TCA TTT GAA AAT AAT AAT TAT TAC TTT AAT GAG AAT GGT GAA ATG CAA     6816
Ser Phe Glu Asn Asn Asn Tyr Tyr Phe Asn Glu Asn Gly Glu Met Gln
            2260                2265                2270

TTT GGT TAT ATA AAT ATA GAA GAT AAG ATG TTC TAT TTT GGT GAA GAT     6864
Phe Gly Tyr Ile Asn Ile Glu Asp Lys Met Phe Tyr Phe Gly Glu Asp
        2275                2280                2285

GGT GTC ATG CAG ATT GGA GTA TTT AAT ACA CCA GAT GGA TTT AAA TAC     6912
Gly Val Met Gln Ile Gly Val Phe Asn Thr Pro Asp Gly Phe Lys Tyr
    2290                2295                2300

TTT GCA CAT CAA AAT ACT TTG GAT GAG AAT TTT GAG GGA GAA TCA ATA     6960
Phe Ala His Gln Asn Thr Leu Asp Glu Asn Phe Glu Gly Glu Ser Ile
2305                2310                2315                2320

AAC TAT ACT GGT TGG TTA GAT TTA GAT GAA AAG AGA TAT TAT TTT ACA     7008
Asn Tyr Thr Gly Trp Leu Asp Leu Asp Glu Lys Arg Tyr Tyr Phe Thr
                2325                2330                2335

GAT GAA TAT ATT GCA GCA ACT GGT TCA GTT ATT ATT GAT GGT GAG GAG     7056
Asp Glu Tyr Ile Ala Ala Thr Gly Ser Val Ile Ile Asp Gly Glu Glu
            2340                2345                2350

TAT TAT TTT GAT CCT GAT ACA GCT CAA TTA GTG ATT AGT GAA             7098
Tyr Tyr Phe Asp Pro Asp Thr Ala Gln Leu Val Ile Ser Glu
        2355                2360                2365

TAG                                                                 7101
```

(2) INFORMATION FOR SEQ ID NO:10:

(i) SEQUENCE CHARACTERISTICS:
(A) LENGTH: 2366 amino acids
(B) TYPE: amino acid
(D) TOPOLOGY: linear (ii) MOLECULE TYPE: protein (xi) SEQUENCE DESCRIPTION: SEQ ID NO:10:

```
Met Ser Leu Val Asn Arg Lys Gln Leu Glu Lys Met Ala Asn Val Arg
  1               5                  10                  15

Phe Arg Thr Gln Glu Asp Glu Tyr Val Ala Ile Leu Asp Ala Leu Glu
             20                  25                  30
```

-continued

```
Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
```

-continued

```
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880
```

-continued

```
Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro Thr
    1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
                1045                1050                1055

Arg Gln Glu Ile Glu Ala Lys Ile Gly Ile Met Ala Val Asn Leu Thr
            1060                1065                1070

Thr Ala Thr Thr Ala Ile Ile Thr Ser Ser Leu Gly Ile Ala Ser Gly
        1075                1080                1085

Phe Ser Ile Leu Leu Val Pro Leu Ala Gly Ile Ser Ala Gly Ile Pro
    1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
                1125                1130                1135

Thr Leu Leu Asp Asp Lys Ile Met Met Pro Gln Asp Asp Leu Val Ile
            1140                1145                1150

Ser Glu Ile Asp Phe Asn Asn Asn Ser Ile Val Leu Gly Lys Cys Glu
        1155                1160                1165

Ile Trp Arg Met Glu Gly Gly Ser Gly His Thr Val Thr Asp Asp Ile
    1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Glu Leu Asp Leu Ser
                1205                1210                1215

Lys Asp Leu Met Val Leu Pro Asn Ala Pro Asn Arg Val Phe Ala Trp
            1220                1225                1230

Glu Thr Gly Trp Thr Pro Gly Leu Arg Ser Leu Glu Asn Asp Gly Thr
        1235                1240                1245

Lys Leu Leu Asp Arg Ile Arg Asp Asn Tyr Glu Gly Glu Phe Tyr Trp
    1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
                1285                1290                1295
```

-continued

```
Ser Phe Ile Val Pro Ile Ile Thr Thr Glu Tyr Ile Arg Glu Lys Leu
            1300                1305                1310

Ser Tyr Ser Phe Tyr Gly Ser Gly Gly Thr Tyr Ala Leu Ser Leu Ser
        1315                1320                1325

Gln Tyr Asn Met Gly Ile Asn Ile Glu Leu Ser Glu Ser Asp Val Trp
    1330                1335                1340

Ile Ile Asp Val Asp Asn Val Val Arg Asp Val Thr Ile Glu Ser Asp
1345                1350                1355                1360

Lys Ile Lys Lys Gly Asp Leu Ile Glu Gly Ile Leu Ser Thr Leu Ser
                1365                1370                1375

Ile Glu Glu Asn Lys Ile Ile Leu Asn Ser His Glu Ile Asn Phe Ser
            1380                1385                1390

Gly Glu Val Asn Gly Ser Asn Gly Phe Val Ser Leu Thr Phe Ser Ile
        1395                1400                1405

Leu Glu Gly Ile Asn Ala Ile Ile Glu Val Asp Leu Leu Ser Lys Ser
    1410                1415                1420

Tyr Lys Leu Leu Ile Ser Gly Glu Leu Lys Ile Leu Met Leu Asn Ser
1425                1430                1435                1440

Asn His Ile Gln Gln Lys Ile Asp Tyr Ile Gly Phe Asn Ser Glu Leu
                1445                1450                1455

Gln Lys Asn Ile Pro Tyr Ser Phe Val Asp Ser Glu Gly Lys Glu Asn
            1460                1465                1470

Gly Phe Ile Asn Gly Ser Thr Lys Glu Gly Leu Phe Val Ser Glu Leu
        1475                1480                1485

Pro Asp Val Val Leu Ile Ser Lys Val Tyr Met Asp Asp Ser Lys Pro
    1490                1495                1500

Ser Phe Gly Tyr Tyr Ser Asn Asn Leu Lys Asp Val Lys Val Ile Thr
1505                1510                1515                1520

Lys Asp Asn Val Asn Ile Leu Thr Gly Tyr Tyr Leu Lys Asp Asp Ile
                1525                1530                1535

Lys Ile Ser Leu Ser Leu Thr Leu Gln Asp Glu Lys Thr Ile Lys Leu
            1540                1545                1550

Asn Ser Val His Leu Asp Glu Ser Gly Val Ala Glu Ile Leu Lys Phe
        1555                1560                1565

Met Asn Arg Lys Gly Asn Thr Asn Thr Ser Asp Ser Leu Met Ser Phe
    1570                1575                1580

Leu Glu Ser Met Asn Ile Lys Ser Ile Phe Val Asn Phe Leu Gln Ser
1585                1590                1595                1600

Asn Ile Lys Phe Ile Leu Asp Ala Asn Phe Ile Ile Ser Gly Thr Thr
                1605                1610                1615

Ser Ile Gly Gln Phe Glu Phe Ile Cys Asp Glu Asn Asp Asn Ile Gln
            1620                1625                1630

Pro Tyr Phe Ile Lys Phe Asn Thr Leu Glu Thr Asn Tyr Thr Leu Tyr
        1635                1640                1645

Val Gly Asn Arg Gln Asn Met Ile Val Glu Pro Asn Tyr Asp Leu Asp
    1650                1655                1660

Asp Ser Gly Asp Ile Ser Ser Thr Val Ile Asn Phe Ser Gln Lys Tyr
1665                1670                1675                1680

Leu Tyr Gly Ile Asp Ser Cys Val Asn Lys Val Val Ile Ser Pro Asn
                1685                1690                1695

Ile Tyr Thr Asp Glu Ile Asn Ile Thr Pro Val Tyr Glu Thr Asn Asn
            1700                1705                1710

Thr Tyr Pro Glu Val Ile Val Leu Asp Ala Asn Tyr Ile Asn Glu Lys
```

-continued

```
        1715                1720                1725

Ile Asn Val Asn Ile Asn Asp Leu Ser Ile Arg Tyr Val Trp Ser Asn
    1730                1735                1740

Asp Gly Asn Asp Phe Ile Leu Met Ser Thr Ser Glu Glu Asn Lys Val
1745                1750                1755                1760

Ser Gln Val Lys Ile Arg Phe Val Asn Val Phe Lys Asp Lys Thr Leu
                1765                1770                1775

Ala Asn Lys Leu Ser Phe Asn Phe Ser Asp Lys Gln Asp Val Pro Val
            1780                1785                1790

Ser Glu Ile Ile Leu Ser Phe Thr Pro Ser Tyr Tyr Glu Asp Gly Leu
        1795                1800                1805

Ile Gly Tyr Asp Leu Gly Leu Val Ser Leu Tyr Asn Glu Lys Phe Tyr
    1810                1815                1820

Ile Asn Asn Phe Gly Met Met Val Ser Gly Leu Ile Tyr Ile Asn Asp
1825                1830                1835                1840

Ser Leu Tyr Tyr Phe Lys Pro Pro Val Asn Asn Leu Ile Thr Gly Phe
                1845                1850                1855

Val Thr Val Gly Asp Asp Lys Tyr Tyr Phe Asn Pro Ile Asn Gly Gly
            1860                1865                1870

Ala Ala Ser Ile Gly Glu Thr Ile Ile Asp Asp Lys Asn Tyr Tyr Phe
        1875                1880                1885

Asn Gln Ser Gly Val Leu Gln Thr Gly Val Phe Ser Thr Glu Asp Gly
    1890                1895                1900

Phe Lys Tyr Phe Ala Pro Ala Asn Thr Leu Asp Glu Asn Leu Glu Gly
1905                1910                1915                1920

Glu Ala Ile Asp Phe Thr Gly Lys Leu Ile Ile Asp Glu Asn Ile Tyr
                1925                1930                1935

Tyr Phe Asp Asp Asn Tyr Arg Gly Ala Val Glu Trp Lys Glu Leu Asp
            1940                1945                1950

Gly Glu Met His Tyr Phe Ser Pro Glu Thr Gly Lys Ala Phe Lys Gly
        1955                1960                1965

Leu Asn Gln Ile Gly Asp Tyr Lys Tyr Tyr Phe Asn Ser Asp Gly Val
    1970                1975                1980

Met Gln Lys Gly Phe Val Ser Ile Asn Asp Asn Lys His Tyr Phe Asp
1985                1990                1995                2000

Asp Ser Gly Val Met Lys Val Gly Tyr Thr Glu Ile Asp Gly Lys His
                2005                2010                2015

Phe Tyr Phe Ala Glu Asn Gly Glu Met Gln Ile Gly Val Phe Asn Thr
            2020                2025                2030

Glu Asp Gly Phe Lys Tyr Phe Ala His His Asn Glu Asp Leu Gly Asn
        2035                2040                2045

Glu Glu Gly Glu Glu Ile Ser Tyr Ser Gly Ile Leu Asn Phe Asn Asn
    2050                2055                2060

Lys Ile Tyr Tyr Phe Asp Asp Ser Phe Thr Ala Val Val Gly Trp Lys
2065                2070                2075                2080

Asp Leu Glu Asp Gly Ser Lys Tyr Tyr Phe Asp Glu Asp Thr Ala Glu
                2085                2090                2095

Ala Tyr Ile Gly Leu Ser Leu Ile Asn Asp Gly Gln Tyr Tyr Phe Asn
            2100                2105                2110

Asp Asp Gly Ile Met Gln Val Gly Phe Val Thr Ile Asn Asp Lys Val
        2115                2120                2125

Phe Tyr Phe Ser Asp Ser Gly Ile Ile Glu Ser Gly Val Gln Asn Ile
    2130                2135                2140
```

-continued

```
Asp Asp Asn Tyr Phe Tyr Ile Asp Asp Asn Gly Ile Val Gln Ile Gly
2145                2150                2155                2160

Val Phe Asp Thr Ser Asp Gly Tyr Lys Tyr Phe Ala Pro Ala Asn Thr
                2165                2170                2175

Val Asn Asp Asn Ile Tyr Gly Gln Ala Val Glu Tyr Ser Gly Leu Val
            2180                2185                2190

Arg Val Gly Glu Asp Val Tyr Tyr Phe Gly Glu Thr Tyr Thr Ile Glu
        2195                2200                2205

Thr Gly Trp Ile Tyr Asp Met Glu Asn Glu Ser Asp Lys Tyr Tyr Phe
    2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
                2245                2250                2255

Ser Phe Glu Asn Asn Asn Tyr Tyr Phe Asn Glu Asn Gly Glu Met Gln
            2260                2265                2270

Phe Gly Tyr Ile Asn Ile Glu Asp Lys Met Phe Tyr Phe Gly Glu Asp
        2275                2280                2285

Gly Val Met Gln Ile Gly Val Phe Asn Thr Pro Asp Gly Phe Lys Tyr
    2290                2295                2300

Phe Ala His Gln Asn Thr Leu Asp Glu Asn Phe Glu Gly Glu Ser Ile
2305                2310                2315                2320

Asn Tyr Thr Gly Trp Leu Asp Leu Asp Glu Lys Arg Tyr Tyr Phe Thr
                2325                2330                2335

Asp Glu Tyr Ile Ala Ala Thr Gly Ser Val Ile Ile Asp Gly Glu Glu
            2340                2345                2350

Tyr Tyr Phe Asp Pro Asp Thr Ala Gln Leu Val Ile Ser Glu
        2355                2360                2365
```

(2) INFORMATION FOR SEQ ID NO:11:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

TAGAAAAAAT GGCAAATGT 19

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

TTTCATCTTG TAGAGTCAAA G 21

(2) INFORMATION FOR SEQ ID NO:13:

(i) SEQUENCE CHARACTERISTICS:
(A) LENGTH: 22 base pairs
(B) TYPE: nucleic acid

-continued (C) STRANDEDNESS: single
(D) TOPOLOGY: linear (ii) MOLECULE TYPE: DNA (genomic)

(xi) SEQUENCE DESCRIPTION: SEQ ID NO:13:

GATGCCACAA GATGATTTAG TG 22

(2) INFORMATION FOR SEQ ID NO:14:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

CTAATTGAGC TGTATCAGGA TC 22

(2) INFORMATION FOR SEQ ID NO:15:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

CGGAATTCCT AGAAAAAATG GCAAATG 27

(2) INFORMATION FOR SEQ ID NO:16:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

GCTCTAGAAT GACCATAAGC TAGCCA 26

(2) INFORMATION FOR SEQ ID NO:17:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

CGGAATTCGA GTTGGTAGAA AGGTGGA 27

(2) INFORMATION FOR SEQ ID NO:18:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO:18:

CGGAATTCGG TTATTATCTT AAGGATG 27

(2) INFORMATION FOR SEQ ID NO:19:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

CGGAATTCTT GATAACTGGA TTTGTGAC 28

(2) INFORMATION FOR SEQ ID NO:20:

(i) SEQUENCE CHARACTERISTICS:
(A) LENGTH: 511 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:20:

```
Leu Ile Thr Gly Phe Val Thr Val Gly Asp Asp Lys Tyr Tyr Phe Asn
1               5                   10                  15

Pro Ile Asn Gly Gly Ala Ala Ser Ile Gly Glu Thr Ile Ile Asp Asp
            20                  25                  30

Lys Asn Tyr Tyr Phe Asn Gln Ser Gly Val Leu Gln Thr Gly Val Phe
        35                  40                  45

Ser Thr Glu Asp Gly Phe Lys Tyr Phe Ala Pro Ala Asn Thr Leu Asp
    50                  55                  60

Glu Asn Leu Glu Gly Glu Ala Ile Asp Phe Thr Gly Lys Leu Ile Ile
65                  70                  75                  80

Asp Glu Asn Ile Tyr Tyr Phe Asp Asp Asn Tyr Arg Gly Ala Val Glu
                85                  90                  95

Trp Lys Glu Leu Asp Gly Glu Met His Tyr Phe Ser Pro Glu Thr Gly
            100                 105                 110

Lys Ala Phe Lys Gly Leu Asn Gln Ile Gly Asp Tyr Lys Tyr Tyr Phe
        115                 120                 125

Asn Ser Asp Gly Val Met Gln Lys Gly Phe Val Ser Ile Asn Asp Asn
    130                 135                 140

Lys His Tyr Phe Asp Asp Ser Gly Val Met Lys Val Gly Tyr Thr Glu
145                 150                 155                 160

Ile Asp Gly Lys His Phe Tyr Phe Ala Glu Asn Gly Glu Met Gln Ile
                165                 170                 175

Gly Val Phe Asn Thr Glu Asp Gly Phe Lys Tyr Phe Ala His His Asn
            180                 185                 190

Glu Asp Leu Gly Asn Glu Glu Gly Glu Glu Ile Ser Tyr Ser Gly Ile
        195                 200                 205

Leu Asn Phe Asn Asn Lys Ile Tyr Tyr Phe Asp Asp Ser Phe Thr Ala
    210                 215                 220

Val Val Gly Trp Lys Asp Leu Glu Asp Gly Ser Lys Tyr Tyr Phe Asp
225                 230                 235                 240

Glu Asp Thr Ala Glu Ala Tyr Ile Gly Leu Ser Leu Ile Asn Asp Gly
```

-continued

```
                245                 250                 255

Gln Tyr Tyr Phe Asn Asp Asp Gly Ile Met Gln Val Gly Phe Val Thr
            260                 265                 270

Ile Asn Asp Lys Val Phe Tyr Phe Ser Asp Ser Gly Ile Ile Glu Ser
        275                 280                 285

Gly Val Gln Asn Ile Asp Asp Asn Tyr Phe Tyr Ile Asp Asp Asn Gly
    290                 295                 300

Ile Val Gln Ile Gly Val Phe Asp Thr Ser Asp Gly Tyr Lys Tyr Phe
305                 310                 315                 320

Ala Pro Ala Asn Thr Val Asn Asp Asn Ile Tyr Gly Gln Ala Val Glu
                325                 330                 335

Tyr Ser Gly Leu Val Arg Val Gly Glu Asp Val Tyr Tyr Phe Gly Glu
            340                 345                 350

Thr Tyr Thr Ile Glu Thr Gly Trp Ile Tyr Asp Met Glu Asn Glu Ser
        355                 360                 365

Asp Lys Tyr Tyr Phe Asn Pro Glu Thr Lys Lys Ala Cys Lys Gly Ile
    370                 375                 380

Asn Leu Ile Asp Asp Ile Lys Tyr Tyr Phe Asp Glu Lys Gly Ile Met
385                 390                 395                 400

Arg Thr Gly Leu Ile Ser Phe Glu Asn Asn Asn Tyr Tyr Phe Asn Glu
                405                 410                 415

Asn Gly Glu Met Gln Phe Gly Tyr Ile Asn Ile Glu Asp Lys Met Phe
            420                 425                 430

Tyr Phe Gly Glu Asp Gly Val Met Gln Ile Gly Val Phe Asn Thr Pro
        435                 440                 445

Asp Gly Phe Lys Tyr Phe Ala His Gln Asn Thr Leu Asp Glu Asn Phe
    450                 455                 460

Glu Gly Glu Ser Ile Asn Tyr Thr Gly Trp Leu Asp Leu Asp Glu Lys
465                 470                 475                 480

Arg Tyr Tyr Phe Thr Asp Glu Tyr Ile Ala Ala Thr Gly Ser Val Ile
                485                 490                 495

Ile Asp Gly Glu Glu Tyr Tyr Phe Asp Pro Asp Thr Ala Gln Leu
            500                 505                 510
```

(2) INFORMATION FOR SEQ ID NO:21:

(i) SEQUENCE CHARACTERISTICS:
(A) LENGTH: 608 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:21:

```
Ser Glu Glu Asn Lys Val Ser Gln Val Lys Ile Arg Phe Val Asn Val
1               5                   10                  15

Phe Lys Asp Lys Thr Leu Ala Asn Lys Leu Ser Phe Asn Phe Ser Asp
            20                  25                  30

Lys Gln Asp Val Pro Val Ser Glu Ile Ile Leu Ser Phe Thr Pro Ser
        35                  40                  45

Tyr Tyr Glu Asp Gly Leu Ile Gly Tyr Asp Leu Gly Leu Val Ser Leu
    50                  55                  60

Tyr Asn Glu Lys Phe Tyr Ile Asn Asn Phe Gly Met Met Val Ser Gly
65                  70                  75                  80

Leu Ile Tyr Ile Asn Asp Ser Leu Tyr Tyr Phe Lys Pro Pro Val Asn
```

-continued

```
                85                  90                  95

Asn Leu Ile Thr Gly Phe Val Thr Val Gly Asp Asp Lys Tyr Tyr Phe
            100                 105                 110

Asn Pro Ile Asn Gly Gly Ala Ala Ser Ile Gly Glu Thr Ile Ile Asp
        115                 120                 125

Asp Lys Asn Tyr Tyr Phe Asn Gln Ser Gly Val Leu Gln Thr Gly Val
    130                 135                 140

Phe Ser Thr Glu Asp Gly Phe Lys Tyr Phe Ala Pro Ala Asn Thr Leu
145                 150                 155                 160

Asp Glu Asn Leu Glu Gly Glu Ala Ile Asp Phe Thr Gly Lys Leu Ile
                165                 170                 175

Ile Asp Glu Asn Ile Tyr Tyr Phe Asp Asp Asn Tyr Arg Gly Ala Val
            180                 185                 190

Glu Trp Lys Glu Leu Asp Gly Glu Met His Tyr Phe Ser Pro Glu Thr
        195                 200                 205

Gly Lys Ala Phe Lys Gly Leu Asn Gln Ile Gly Asp Tyr Lys Tyr Tyr
    210                 215                 220

Phe Asn Ser Asp Gly Val Met Gln Lys Gly Phe Val Ser Ile Asn Asp
225                 230                 235                 240

Asn Lys His Tyr Phe Asp Asp Ser Gly Val Met Lys Val Gly Tyr Thr
                245                 250                 255

Glu Ile Asp Gly Lys His Phe Tyr Phe Ala Glu Asn Gly Glu Met Gln
            260                 265                 270

Ile Gly Val Phe Asn Thr Glu Asp Gly Phe Lys Tyr Phe Ala His His
        275                 280                 285

Asn Glu Asp Leu Gly Asn Glu Glu Gly Glu Glu Ile Ser Tyr Ser Gly
    290                 295                 300

Ile Leu Asn Phe Asn Asn Lys Ile Tyr Tyr Phe Asp Asp Ser Phe Thr
305                 310                 315                 320

Ala Val Val Gly Trp Lys Asp Leu Glu Asp Gly Ser Lys Tyr Tyr Phe
                325                 330                 335

Asp Glu Asp Thr Ala Glu Ala Tyr Ile Gly Leu Ser Leu Ile Asn Asp
            340                 345                 350

Gly Gln Tyr Tyr Phe Asn Asp Asp Gly Ile Met Gln Val Gly Phe Val
        355                 360                 365

Thr Ile Asn Asp Lys Val Phe Tyr Phe Ser Asp Ser Gly Ile Ile Glu
    370                 375                 380

Ser Gly Val Gln Asn Ile Asp Asp Asn Tyr Phe Tyr Ile Asp Asp Asn
385                 390                 395                 400

Gly Ile Val Gln Ile Gly Val Phe Asp Thr Ser Asp Gly Tyr Lys Tyr
                405                 410                 415

Phe Ala Pro Ala Asn Thr Val Asn Asp Asn Ile Tyr Gly Gln Ala Val
            420                 425                 430

Glu Tyr Ser Gly Leu Val Arg Val Gly Glu Asp Val Tyr Tyr Phe Gly
        435                 440                 445

Glu Thr Tyr Thr Ile Glu Thr Gly Trp Ile Tyr Asp Met Glu Asn Glu
    450                 455                 460

Ser Asp Lys Tyr Tyr Phe Asn Pro Glu Thr Lys Lys Ala Cys Lys Gly
465                 470                 475                 480

Ile Asn Leu Ile Asp Asp Ile Lys Tyr Tyr Phe Asp Glu Lys Gly Ile
                485                 490                 495

Met Arg Thr Gly Leu Ile Ser Phe Glu Asn Asn Asn Tyr Tyr Phe Asn
            500                 505                 510
```

```
Glu Asn Gly Glu Met Gln Phe Gly Tyr Ile Asn Ile Glu Asp Lys Met
        515                 520                 525

Phe Tyr Phe Gly Glu Asp Gly Val Met Gln Ile Gly Val Phe Asn Thr
    530                 535                 540

Pro Asp Gly Phe Lys Tyr Phe Ala His Gln Asn Thr Leu Asp Glu Asn
545                 550                 555                 560

Phe Glu Gly Glu Ser Ile Asn Tyr Thr Gly Trp Leu Asp Leu Asp Glu
                565                 570                 575

Lys Arg Tyr Tyr Phe Thr Asp Glu Tyr Ile Ala Ala Thr Gly Ser Val
            580                 585                 590

Ile Ile Asp Gly Glu Glu Tyr Tyr Phe Asp Pro Asp Thr Ala Gln Leu
        595                 600                 605


(2) INFORMATION FOR SEQ ID NO:22:

     (i) SEQUENCE CHARACTERISTICS:
          (A) LENGTH: 1330 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 1..1314

    (xi) SEQUENCE DESCRIPTION: SEQ ID NO:22:

ATG GCT CGT CTG CTG TCT ACC TTC ACT GAA TAC ATC AAG AAC ATC ATC       48
Met Ala Arg Leu Leu Ser Thr Phe Thr Glu Tyr Ile Lys Asn Ile Ile
  1               5                  10                  15

AAT ACC TCC ATC CTG AAC CTG CGC TAC GAA TCC AAT CAC CTG ATC GAC       96
Asn Thr Ser Ile Leu Asn Leu Arg Tyr Glu Ser Asn His Leu Ile Asp
             20                  25                  30

CTG TCT CGC TAC GCT TCC AAA ATC AAC ATC GGT TCT AAA GTT AAC TTC      144
Leu Ser Arg Tyr Ala Ser Lys Ile Asn Ile Gly Ser Lys Val Asn Phe
         35                  40                  45

GAT CCG ATC GAC AAG AAT CAG ATC CAG CTG TTC AAT CTG GAA TCT TCC      192
Asp Pro Ile Asp Lys Asn Gln Ile Gln Leu Phe Asn Leu Glu Ser Ser
     50                  55                  60

AAA ATC GAA GTT ATC CTG AAG AAT GCT ATC GTA TAC AAC TCT ATG TAC      240
Lys Ile Glu Val Ile Leu Lys Asn Ala Ile Val Tyr Asn Ser Met Tyr
 65                  70                  75                  80

GAA AAC TTC TCC ACC TCC TTC TGG ATC CGT ATC CCG AAA TAC TTC AAC      288
Glu Asn Phe Ser Thr Ser Phe Trp Ile Arg Ile Pro Lys Tyr Phe Asn
                 85                  90                  95

TCC ATC TCT CTG AAC AAT GAA TAC ACC ATC ATC AAC TGC ATG GAA AAC      336
Ser Ile Ser Leu Asn Asn Glu Tyr Thr Ile Ile Asn Cys Met Glu Asn
            100                 105                 110

AAT TCT GGT TGG AAA GTA TCT CTG AAC TAC GGT GAA ATC ATC TGG ACT      384
Asn Ser Gly Trp Lys Val Ser Leu Asn Tyr Gly Glu Ile Ile Trp Thr
        115                 120                 125

CTG CAG GAC ACT CAG GAA ATC AAA CAG CGT GTT GTA TTC AAA TAC TCT      432
Leu Gln Asp Thr Gln Glu Ile Lys Gln Arg Val Val Phe Lys Tyr Ser
    130                 135                 140

CAG ATG ATC AAC ATC TCT GAC TAC ATC AAT CGC TGG ATC TTC GTT ACC      480
Gln Met Ile Asn Ile Ser Asp Tyr Ile Asn Arg Trp Ile Phe Val Thr
145                 150                 155                 160

ATC ACC AAC AAT CGT CTG AAT AAC TCC AAA ATC TAC ATC AAC GGC CGT      528
Ile Thr Asn Asn Arg Leu Asn Asn Ser Lys Ile Tyr Ile Asn Gly Arg
                165                 170                 175
```

-continued

```
CTG ATC GAC CAG AAA CCG ATC TCC AAT CTG GGT AAC ATC CAC GCT TCT      576
Leu Ile Asp Gln Lys Pro Ile Ser Asn Leu Gly Asn Ile His Ala Ser
            180                 185                 190

AAT AAC ATC ATG TTC AAA CTG GAC GGT TGT CGT GAC ACT CAC CGC TAC      624
Asn Asn Ile Met Phe Lys Leu Asp Gly Cys Arg Asp Thr His Arg Tyr
        195                 200                 205

ATC TGG ATC AAA TAC TTC AAT CTG TTC GAC AAA GAA CTG AAC GAA AAA      672
Ile Trp Ile Lys Tyr Phe Asn Leu Phe Asp Lys Glu Leu Asn Glu Lys
    210                 215                 220

GAA ATC AAA GAC CTG TAC GAC AAC CAG TCC AAT TCT GGT ATC CTG AAA      720
Glu Ile Lys Asp Leu Tyr Asp Asn Gln Ser Asn Ser Gly Ile Leu Lys
225                 230                 235                 240

GAC TTC TGG GGT GAC TAC CTG CAG TAC GAC AAA CCG TAC TAC ATG CTG      768
Asp Phe Trp Gly Asp Tyr Leu Gln Tyr Asp Lys Pro Tyr Tyr Met Leu
                245                 250                 255

AAT CTG TAC GAT CCG AAC AAA TAC GTT GAC GTC AAC AAT GTA GGT ATC      816
Asn Leu Tyr Asp Pro Asn Lys Tyr Val Asp Val Asn Asn Val Gly Ile
            260                 265                 270

CGC GGT TAC ATG TAC CTG AAA GGT CCG CGT GGT TCT GTT ATG ACT ACC      864
Arg Gly Tyr Met Tyr Leu Lys Gly Pro Arg Gly Ser Val Met Thr Thr
        275                 280                 285

AAC ATC TAC CTG AAC TCT TCC CTG TAC CGT GGT ACC AAA TTC ATC ATC      912
Asn Ile Tyr Leu Asn Ser Ser Leu Tyr Arg Gly Thr Lys Phe Ile Ile
    290                 295                 300

AAG AAA TAC GCG TCT GGT AAC AAG GAC AAT ATC GTT CGC AAC AAT GAT      960
Lys Lys Tyr Ala Ser Gly Asn Lys Asp Asn Ile Val Arg Asn Asn Asp
305                 310                 315                 320

CGT GTA TAC ATC AAT GTT GTA GTT AAG AAC AAA GAA TAC CGT CTG GCT     1008
Arg Val Tyr Ile Asn Val Val Val Lys Asn Lys Glu Tyr Arg Leu Ala
                325                 330                 335

ACC AAT GCT TCT CAG GCT GGT GTA GAA AAG ATC TTG TCT GCT CTG GAA     1056
Thr Asn Ala Ser Gln Ala Gly Val Glu Lys Ile Leu Ser Ala Leu Glu
            340                 345                 350

ATC CCG GAC GTT GGT AAT CTG TCT CAG GTA GTT GTA ATG AAA TCC AAG     1104
Ile Pro Asp Val Gly Asn Leu Ser Gln Val Val Val Met Lys Ser Lys
        355                 360                 365

AAC GAC CAG GGT ATC ACT AAC AAA TGC AAA ATG AAT CTG CAG GAC AAC     1152
Asn Asp Gln Gly Ile Thr Asn Lys Cys Lys Met Asn Leu Gln Asp Asn
    370                 375                 380

AAT GGT AAC GAT ATC GGT TTC ATC GGT TTC CAC CAG TTC AAC AAT ATC     1200
Asn Gly Asn Asp Ile Gly Phe Ile Gly Phe His Gln Phe Asn Asn Ile
385                 390                 395                 400

GCT AAA CTG GTT GCT TCC AAC TGG TAC AAT CGT CAG ATC GAA CGT TCC     1248
Ala Lys Leu Val Ala Ser Asn Trp Tyr Asn Arg Gln Ile Glu Arg Ser
                405                 410                 415

TCT CGC ACT CTG GGT TGC TCT TGG GAG TTC ATC CCG GTT GAT GAC GGT     1296
Ser Arg Thr Leu Gly Cys Ser Trp Glu Phe Ile Pro Val Asp Asp Gly
            420                 425                 430

TGG GGT GAA CGT CCG CTG TAACCCGGGA AAGCTT                           1330
Trp Gly Glu Arg Pro Leu
        435
```

(2) INFORMATION FOR SEQ ID NO:23:

(i) SEQUENCE CHARACTERISTICS:
(A) LENGTH: 438 amino acids
(B) TYPE: amino acid
(D) TOPOLOGY: linear (ii) MOLECULE TYPE: protein -continued (xi) SEQUENCE DESCRIPTION: SEQ ID NO:23:

```
Met Ala Arg Leu Leu Ser Thr Phe Thr Glu Tyr Ile Lys Asn Ile Ile
  1               5                  10                  15

Asn Thr Ser Ile Leu Asn Leu Arg Tyr Glu Ser Asn His Leu Ile Asp
             20                  25                  30

Leu Ser Arg Tyr Ala Ser Lys Ile Asn Ile Gly Ser Lys Val Asn Phe
         35                  40                  45

Asp Pro Ile Asp Lys Asn Gln Ile Gln Leu Phe Asn Leu Glu Ser Ser
     50                  55                  60

Lys Ile Glu Val Ile Leu Lys Asn Ala Ile Val Tyr Asn Ser Met Tyr
 65                  70                  75                  80

Glu Asn Phe Ser Thr Ser Phe Trp Ile Arg Ile Pro Lys Tyr Phe Asn
                 85                  90                  95

Ser Ile Ser Leu Asn Asn Glu Tyr Thr Ile Ile Asn Cys Met Glu Asn
            100                 105                 110

Asn Ser Gly Trp Lys Val Ser Leu Asn Tyr Gly Glu Ile Ile Trp Thr
        115                 120                 125

Leu Gln Asp Thr Gln Glu Ile Lys Gln Arg Val Val Phe Lys Tyr Ser
    130                 135                 140

Gln Met Ile Asn Ile Ser Asp Tyr Ile Asn Arg Trp Ile Phe Val Thr
145                 150                 155                 160

Ile Thr Asn Asn Arg Leu Asn Asn Ser Lys Ile Tyr Ile Asn Gly Arg
                165                 170                 175

Leu Ile Asp Gln Lys Pro Ile Ser Asn Leu Gly Asn Ile His Ala Ser
            180                 185                 190

Asn Asn Ile Met Phe Lys Leu Asp Gly Cys Arg Asp Thr His Arg Tyr
        195                 200                 205

Ile Trp Ile Lys Tyr Phe Asn Leu Phe Asp Lys Glu Leu Asn Glu Lys
    210                 215                 220

Glu Ile Lys Asp Leu Tyr Asp Asn Gln Ser Asn Ser Gly Ile Leu Lys
225                 230                 235                 240

Asp Phe Trp Gly Asp Tyr Leu Gln Tyr Asp Lys Pro Tyr Tyr Met Leu
                245                 250                 255

Asn Leu Tyr Asp Pro Asn Lys Tyr Val Asp Val Asn Asn Val Gly Ile
            260                 265                 270

Arg Gly Tyr Met Tyr Leu Lys Gly Pro Arg Gly Ser Val Met Thr Thr
        275                 280                 285

Asn Ile Tyr Leu Asn Ser Ser Leu Tyr Arg Gly Thr Lys Phe Ile Ile
    290                 295                 300

Lys Lys Tyr Ala Ser Gly Asn Lys Asp Asn Ile Val Arg Asn Asn Asp
305                 310                 315                 320

Arg Val Tyr Ile Asn Val Val Val Lys Asn Lys Glu Tyr Arg Leu Ala
                325                 330                 335

Thr Asn Ala Ser Gln Ala Gly Val Glu Lys Ile Leu Ser Ala Leu Glu
            340                 345                 350

Ile Pro Asp Val Gly Asn Leu Ser Gln Val Val Val Met Lys Ser Lys
        355                 360                 365

Asn Asp Gln Gly Ile Thr Asn Lys Cys Lys Met Asn Leu Gln Asp Asn
    370                 375                 380

Asn Gly Asn Asp Ile Gly Phe Ile Gly Phe His Gln Phe Asn Asn Ile
385                 390                 395                 400

Ala Lys Leu Val Ala Ser Asn Trp Tyr Asn Arg Gln Ile Glu Arg Ser
                405                 410                 415
```

-continued

```
Ser Arg Thr Leu Gly Cys Ser Trp Glu Phe Ile Pro Val Asp Asp Gly
            420                 425                 430

Trp Gly Glu Arg Pro Leu
        435


(2) INFORMATION FOR SEQ ID NO:24:

     (i) SEQUENCE CHARACTERISTICS:
          (A) LENGTH: 23 amino acids
          (B) TYPE: amino acid
          (C) STRANDEDNESS: unknown
          (D) TOPOLOGY: linear

    (ii) MOLECULE TYPE: protein

    (xi) SEQUENCE DESCRIPTION: SEQ ID NO:24:

Met Gly His His His His His His His His His His Ser Ser Gly His
1               5                   10                  15

Ile Glu Gly Arg His Met Ala
            20


(2) INFORMATION FOR SEQ ID NO:25:

     (i) SEQUENCE CHARACTERISTICS:
          (A) LENGTH: 1402 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 1..1386

    (xi) SEQUENCE DESCRIPTION: SEQ ID NO:25:

ATG GGC CAT CAT CAT CAT CAT CAT CAT CAT CAT CAC AGC AGC GGC CAT        48
Met Gly His His His His His His His His His His Ser Ser Gly His
  1               5                  10                  15

ATC GAA GGT CGT CAT ATG GCT AGC ATG GCT CGT CTG CTG TCT ACC TTC        96
Ile Glu Gly Arg His Met Ala Ser Met Ala Arg Leu Leu Ser Thr Phe
             20                  25                  30

ACT GAA TAC ATC AAG AAC ATC ATC AAT ACC TCC ATC CTG AAC CTG CGC       144
Thr Glu Tyr Ile Lys Asn Ile Ile Asn Thr Ser Ile Leu Asn Leu Arg
         35                  40                  45

TAC GAA TCC AAT CAC CTG ATC GAC CTG TCT CGC TAC GCT TCC AAA ATC       192
Tyr Glu Ser Asn His Leu Ile Asp Leu Ser Arg Tyr Ala Ser Lys Ile
     50                  55                  60

AAC ATC GGT TCT AAA GTT AAC TTC GAT CCG ATC GAC AAG AAT CAG ATC       240
Asn Ile Gly Ser Lys Val Asn Phe Asp Pro Ile Asp Lys Asn Gln Ile
 65                  70                  75                  80

CAG CTG TTC AAT CTG GAA TCT TCC AAA ATC GAA GTT ATC CTG AAG AAT       288
Gln Leu Phe Asn Leu Glu Ser Ser Lys Ile Glu Val Ile Leu Lys Asn
                 85                  90                  95

GCT ATC GTA TAC AAC TCT ATG TAC GAA AAC TTC TCC ACC TCC TTC TGG       336
Ala Ile Val Tyr Asn Ser Met Tyr Glu Asn Phe Ser Thr Ser Phe Trp
            100                 105                 110

ATC CGT ATC CCG AAA TAC TTC AAC TCC ATC TCT CTG AAC AAT GAA TAC       384
Ile Arg Ile Pro Lys Tyr Phe Asn Ser Ile Ser Leu Asn Asn Glu Tyr
        115                 120                 125

ACC ATC ATC AAC TGC ATG GAA AAC AAT TCT GGT TGG AAA GTA TCT CTG       432
Thr Ile Ile Asn Cys Met Glu Asn Asn Ser Gly Trp Lys Val Ser Leu
    130                 135                 140
```

-continued

```
AAC TAC GGT GAA ATC ATC TGG ACT CTG CAG GAC ACT CAG GAA ATC AAA       480
Asn Tyr Gly Glu Ile Ile Trp Thr Leu Gln Asp Thr Gln Glu Ile Lys
145                 150                 155                 160

CAG CGT GTT GTA TTC AAA TAC TCT CAG ATG ATC AAC ATC TCT GAC TAC       528
Gln Arg Val Val Phe Lys Tyr Ser Gln Met Ile Asn Ile Ser Asp Tyr
                165                 170                 175

ATC AAT CGC TGG ATC TTC GTT ACC ATC ACC AAC AAT CGT CTG AAT AAC       576
Ile Asn Arg Trp Ile Phe Val Thr Ile Thr Asn Asn Arg Leu Asn Asn
            180                 185                 190

TCC AAA ATC TAC ATC AAC GGC CGT CTG ATC GAC CAG AAA CCG ATC TCC       624
Ser Lys Ile Tyr Ile Asn Gly Arg Leu Ile Asp Gln Lys Pro Ile Ser
        195                 200                 205

AAT CTG GGT AAC ATC CAC GCT TCT AAT AAC ATC ATG TTC AAA CTG GAC       672
Asn Leu Gly Asn Ile His Ala Ser Asn Asn Ile Met Phe Lys Leu Asp
    210                 215                 220

GGT TGT CGT GAC ACT CAC CGC TAC ATC TGG ATC AAA TAC TTC AAT CTG       720
Gly Cys Arg Asp Thr His Arg Tyr Ile Trp Ile Lys Tyr Phe Asn Leu
225                 230                 235                 240

TTC GAC AAA GAA CTG AAC GAA AAA GAA ATC AAA GAC CTG TAC GAC AAC       768
Phe Asp Lys Glu Leu Asn Glu Lys Glu Ile Lys Asp Leu Tyr Asp Asn
                245                 250                 255

CAG TCC AAT TCT GGT ATC CTG AAA GAC TTC TGG GGT GAC TAC CTG CAG       816
Gln Ser Asn Ser Gly Ile Leu Lys Asp Phe Trp Gly Asp Tyr Leu Gln
            260                 265                 270

TAC GAC AAA CCG TAC TAC ATG CTG AAT CTG TAC GAT CCG AAC AAA TAC       864
Tyr Asp Lys Pro Tyr Tyr Met Leu Asn Leu Tyr Asp Pro Asn Lys Tyr
        275                 280                 285

GTT GAC GTC AAC AAT GTA GGT ATC CGC GGT TAC ATG TAC CTG AAA GGT       912
Val Asp Val Asn Asn Val Gly Ile Arg Gly Tyr Met Tyr Leu Lys Gly
    290                 295                 300

CCG CGT GGT TCT GTT ATG ACT ACC AAC ATC TAC CTG AAC TCT TCC CTG       960
Pro Arg Gly Ser Val Met Thr Thr Asn Ile Tyr Leu Asn Ser Ser Leu
305                 310                 315                 320

TAC CGT GGT ACC AAA TTC ATC ATC AAG AAA TAC GCG TCT GGT AAC AAG      1008
Tyr Arg Gly Thr Lys Phe Ile Ile Lys Lys Tyr Ala Ser Gly Asn Lys
                325                 330                 335

GAC AAT ATC GTT CGC AAC AAT GAT CGT GTA TAC ATC AAT GTT GTA GTT      1056
Asp Asn Ile Val Arg Asn Asn Asp Arg Val Tyr Ile Asn Val Val Val
            340                 345                 350

AAG AAC AAA GAA TAC CGT CTG GCT ACC AAT GCT TCT CAG GCT GGT GTA      1104
Lys Asn Lys Glu Tyr Arg Leu Ala Thr Asn Ala Ser Gln Ala Gly Val
        355                 360                 365

GAA AAG ATC TTG TCT GCT CTG GAA ATC CCG GAC GTT GGT AAT CTG TCT      1152
Glu Lys Ile Leu Ser Ala Leu Glu Ile Pro Asp Val Gly Asn Leu Ser
    370                 375                 380

CAG GTA GTT GTA ATG AAA TCC AAG AAC GAC CAG GGT ATC ACT AAC AAA      1200
Gln Val Val Val Met Lys Ser Lys Asn Asp Gln Gly Ile Thr Asn Lys
385                 390                 395                 400

TGC AAA ATG AAT CTG CAG GAC AAC AAT GGT AAC GAT ATC GGT TTC ATC      1248
Cys Lys Met Asn Leu Gln Asp Asn Asn Gly Asn Asp Ile Gly Phe Ile
                405                 410                 415

GGT TTC CAC CAG TTC AAC AAT ATC GCT AAA CTG GTT GCT TCC AAC TGG      1296
Gly Phe His Gln Phe Asn Asn Ile Ala Lys Leu Val Ala Ser Asn Trp
            420                 425                 430

TAC AAT CGT CAG ATC GAA CGT TCC TCT CGC ACT CTG GGT TGC TCT TGG      1344
Tyr Asn Arg Gln Ile Glu Arg Ser Ser Arg Thr Leu Gly Cys Ser Trp
        435                 440                 445

GAG TTC ATC CCG GTT GAT GAC GGT TGG GGT GAA CGT CCG CTG              1386
Glu Phe Ile Pro Val Asp Asp Gly Trp Gly Glu Arg Pro Leu
    450                 455                 460
```

-continued

TAACCCGGGA AAGCTT 1402

(2) INFORMATION FOR SEQ ID NO:26:

(i) SEQUENCE CHARACTERISTICS:
(A) LENGTH: 462 amino acids
(B) TYPE: amino acid
(D) TOPOLOGY: linear (ii) MOLECULE TYPE: protein (xi) SEQUENCE DESCRIPTION: SEQ ID NO:26:

Met Gly His His His His His His His His His His Ser Ser Gly His
1 5 10 15

Ile Glu Gly Arg His Met Ala Ser Met Ala Arg Leu Leu Ser Thr Phe
20 25 30

Thr Glu Tyr Ile Lys Asn Ile Ile Asn Thr Ser Ile Leu Asn Leu Arg
35 40 45

Tyr Glu Ser Asn His Leu Ile Asp Leu Ser Arg Tyr Ala Ser Lys Ile
50 55 60

Asn Ile Gly Ser Lys Val Asn Phe Asp Pro Ile Asp Lys Asn Gln Ile
65 70 75 80

Gln Leu Phe Asn Leu Glu Ser Ser Lys Ile Glu Val Ile Leu Lys Asn
85 90 95

Ala Ile Val Tyr Asn Ser Met Tyr Glu Asn Phe Ser Thr Ser Phe Trp
100 105 110

Ile Arg Ile Pro Lys Tyr Phe Asn Ser Ile Ser Leu Asn Asn Glu Tyr
115 120 125

Thr Ile Ile Asn Cys Met Glu Asn Asn Ser Gly Trp Lys Val Ser Leu
130 135 140

Asn Tyr Gly Glu Ile Ile Trp Thr Leu Gln Asp Thr Gln Glu Ile Lys
145 150 155 160

Gln Arg Val Val Phe Lys Tyr Ser Gln Met Ile Asn Ile Ser Asp Tyr
165 170 175

Ile Asn Arg Trp Ile Phe Val Thr Ile Thr Asn Asn Arg Leu Asn Asn
180 185 190

Ser Lys Ile Tyr Ile Asn Gly Arg Leu Ile Asp Gln Lys Pro Ile Ser
195 200 205

Asn Leu Gly Asn Ile His Ala Ser Asn Asn Ile Met Phe Lys Leu Asp
210 215 220

Gly Cys Arg Asp Thr His Arg Tyr Ile Trp Ile Lys Tyr Phe Asn Leu
225 230 235 240

Phe Asp Lys Glu Leu Asn Glu Lys Glu Ile Lys Asp Leu Tyr Asp Asn
245 250 255

Gln Ser Asn Ser Gly Ile Leu Lys Asp Phe Trp Gly Asp Tyr Leu Gln
260 265 270

Tyr Asp Lys Pro Tyr Tyr Met Leu Asn Leu Tyr Asp Pro Asn Lys Tyr
275 280 285

Val Asp Val Asn Asn Val Gly Ile Arg Gly Tyr Met Tyr Leu Lys Gly
290 295 300

Pro Arg Gly Ser Val Met Thr Thr Asn Ile Tyr Leu Asn Ser Ser Leu
305 310 315 320

Tyr Arg Gly Thr Lys Phe Ile Ile Lys Lys Tyr Ala Ser Gly Asn Lys
325 330 335

Asp Asn Ile Val Arg Asn Asn Asp Arg Val Tyr Ile Asn Val Val Val

-continued

```
            340                 345                 350

Lys Asn Lys Glu Tyr Arg Leu Ala Thr Asn Ala Ser Gln Ala Gly Val
        355                 360                 365

Glu Lys Ile Leu Ser Ala Leu Glu Ile Pro Asp Val Gly Asn Leu Ser
    370                 375                 380

Gln Val Val Val Met Lys Ser Lys Asn Asp Gln Gly Ile Thr Asn Lys
385                 390                 395                 400

Cys Lys Met Asn Leu Gln Asp Asn Asn Gly Asn Asp Ile Gly Phe Ile
                405                 410                 415

Gly Phe His Gln Phe Asn Asn Ile Ala Lys Leu Val Ala Ser Asn Trp
            420                 425                 430

Tyr Asn Arg Gln Ile Glu Arg Ser Ser Arg Thr Leu Gly Cys Ser Trp
        435                 440                 445

Glu Phe Ile Pro Val Asp Asp Gly Trp Gly Glu Arg Pro Leu
    450                 455                 460
```

(2) INFORMATION FOR SEQ ID NO:27:

(i) SEQUENCE CHARACTERISTICS:
(A) LENGTH: 3891 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3888

(xi) SEQUENCE DESCRIPTION: SEQ ID NO:27:

```
ATG CAA TTT GTT AAT AAA CAA TTT AAT TAT AAA GAT CCT GTA AAT GGT        48
Met Gln Phe Val Asn Lys Gln Phe Asn Tyr Lys Asp Pro Val Asn Gly
  1               5                  10                  15

GTT GAT ATT GCT TAT ATA AAA ATT CCA AAT GTA GGA CAA ATG CAA CCA        96
Val Asp Ile Ala Tyr Ile Lys Ile Pro Asn Val Gly Gln Met Gln Pro
             20                  25                  30

GTA AAA GCT TTT AAA ATT CAT AAT AAA ATA TGG GTT ATT CCA GAA AGA       144
Val Lys Ala Phe Lys Ile His Asn Lys Ile Trp Val Ile Pro Glu Arg
         35                  40                  45

GAT ACA TTT ACA AAT CCT GAA GAA GGA GAT TTA AAT CCA CCA CCA GAA       192
Asp Thr Phe Thr Asn Pro Glu Glu Gly Asp Leu Asn Pro Pro Pro Glu
     50                  55                  60

GCA AAA CAA GTT CCA GTT TCA TAT TAT GAT TCA ACA TAT TTA AGT ACA       240
Ala Lys Gln Val Pro Val Ser Tyr Tyr Asp Ser Thr Tyr Leu Ser Thr
 65                  70                  75                  80

GAT AAT GAA AAA GAT AAT TAT TTA AAG GGA GTT ACA AAA TTA TTT GAG       288
Asp Asn Glu Lys Asp Asn Tyr Leu Lys Gly Val Thr Lys Leu Phe Glu
                 85                  90                  95

AGA ATT TAT TCA ACT GAT CTT GGA AGA ATG TTG TTA ACA TCA ATA GTA       336
Arg Ile Tyr Ser Thr Asp Leu Gly Arg Met Leu Leu Thr Ser Ile Val
            100                 105                 110

AGG GGA ATA CCA TTT TGG GGT GGA AGT ACA ATA GAT ACA GAA TTA AAA       384
Arg Gly Ile Pro Phe Trp Gly Gly Ser Thr Ile Asp Thr Glu Leu Lys
        115                 120                 125

GTT ATT GAT ACT AAT TGT ATT AAT GTG ATA CAA CCA GAT GGT AGT TAT       432
Val Ile Asp Thr Asn Cys Ile Asn Val Ile Gln Pro Asp Gly Ser Tyr
    130                 135                 140

AGA TCA GAA GAA CTT AAT CTA GTA ATA ATA GGA CCC TCA GCT GAT ATT       480
Arg Ser Glu Glu Leu Asn Leu Val Ile Ile Gly Pro Ser Ala Asp Ile
145                 150                 155                 160
```

-continued

ATA CAG TTT GAA TGT AAA AGC TTT GGA CAT GAA GTT TTG AAT CTT ACG      528
Ile Gln Phe Glu Cys Lys Ser Phe Gly His Glu Val Leu Asn Leu Thr
                165                 170                 175

CGA AAT GGT TAT GGC TCT ACT CAA TAC ATT AGA TTT AGC CCA GAT TTT      576
Arg Asn Gly Tyr Gly Ser Thr Gln Tyr Ile Arg Phe Ser Pro Asp Phe
            180                 185                 190

ACA TTT GGT TTT GAG GAG TCA CTT GAA GTT GAT ACA AAT CCT CTT TTA      624
Thr Phe Gly Phe Glu Glu Ser Leu Glu Val Asp Thr Asn Pro Leu Leu
        195                 200                 205

GGT GCA GGC AAA TTT GCT ACA GAT CCA GCA GTA ACA TTA GCA CAT GAA      672
Gly Ala Gly Lys Phe Ala Thr Asp Pro Ala Val Thr Leu Ala His Glu
    210                 215                 220

CTT ATA CAT GCT GGA CAT AGA TTA TAT GGA ATA GCA ATT AAT CCA AAT      720
Leu Ile His Ala Gly His Arg Leu Tyr Gly Ile Ala Ile Asn Pro Asn
225                 230                 235                 240

AGG GTT TTT AAA GTA AAT ACT AAT GCC TAT TAT GAA ATG AGT GGG TTA      768
Arg Val Phe Lys Val Asn Thr Asn Ala Tyr Tyr Glu Met Ser Gly Leu
                245                 250                 255

GAA GTA AGC TTT GAG GAA CTT AGA ACA TTT GGG GGA CAT GAT GCA AAG      816
Glu Val Ser Phe Glu Glu Leu Arg Thr Phe Gly Gly His Asp Ala Lys
            260                 265                 270

TTT ATA GAT AGT TTA CAG GAA AAC GAA TTT CGT CTA TAT TAT TAT AAT      864
Phe Ile Asp Ser Leu Gln Glu Asn Glu Phe Arg Leu Tyr Tyr Tyr Asn
        275                 280                 285

AAG TTT AAA GAT ATA GCA AGT ACA CTT AAT AAA GCT AAA TCA ATA GTA      912
Lys Phe Lys Asp Ile Ala Ser Thr Leu Asn Lys Ala Lys Ser Ile Val
    290                 295                 300

GGT ACT ACT GCT TCA TTA CAG TAT ATG AAA AAT GTT TTT AAA GAG AAA      960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA     1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT     1056
Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT     1104
Asn Phe Val Lys Phe Phe Lys Val Leu Asn Arg Lys Thr Tyr Leu Asn
        355                 360                 365

TTT GAT AAA GCC GTA TTT AAG ATA AAT ATA GTA CCT AAG GTA AAT TAC     1152
Phe Asp Lys Ala Val Phe Lys Ile Asn Ile Val Pro Lys Val Asn Tyr
    370                 375                 380

ACA ATA TAT GAT GGA TTT AAT TTA AGA AAT ACA AAT TTA GCA GCA AAC     1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA     1248
Phe Asn Gly Gln Asn Thr Glu Ile Asn Asn Met Asn Phe Thr Lys Leu
                405                 410                 415

AAA AAT TTT ACT GGA TTG TTT GAA TTT TAT AAG TTG CTA TGT GTA AGA     1296
Lys Asn Phe Thr Gly Leu Phe Glu Phe Tyr Lys Leu Leu Cys Val Arg
            420                 425                 430

GGG ATA ATA ACT TCT AAA ACT AAA TCA TTA GAT AAA GGA TAC AAT AAG     1344
Gly Ile Ile Thr Ser Lys Thr Lys Ser Leu Asp Lys Gly Tyr Asn Lys
        435                 440                 445

GCA TTA AAT GAT TTA TGT ATC AAA GTT AAT AAT TGG GAC TTG TTT TTT     1392
Ala Leu Asn Asp Leu Cys Ile Lys Val Asn Asn Trp Asp Leu Phe Phe
    450                 455                 460

AGT CCT TCA GAA GAT AAT TTT ACT AAT GAT CTA AAT AAA GGA GAA GAA     1440
Ser Pro Ser Glu Asp Asn Phe Thr Asn Asp Leu Asn Lys Gly Glu Glu

-continued

```
465                 470                 475                 480

ATT ACA TCT GAT ACT AAT ATA GAA GCA GCA GAA GAA AAT ATT AGT TTA      1488
Ile Thr Ser Asp Thr Asn Ile Glu Ala Ala Glu Glu Asn Ile Ser Leu
                485                 490                 495

GAT TTA ATA CAA CAA TAT TAT TTA ACC TTT AAT TTT GAT AAT GAA CCT      1536
Asp Leu Ile Gln Gln Tyr Tyr Leu Thr Phe Asn Phe Asp Asn Glu Pro
            500                 505                 510

GAA AAT ATT TCA ATA GAA AAT CTT TCA AGT GAC ATT ATA GGC CAA TTA      1584
Glu Asn Ile Ser Ile Glu Asn Leu Ser Ser Asp Ile Ile Gly Gln Leu
        515                 520                 525

GAA CTT ATG CCT AAT ATA GAA AGA TTT CCT AAT GGA AAA AAG TAT GAG      1632
Glu Leu Met Pro Asn Ile Glu Arg Phe Pro Asn Gly Lys Lys Tyr Glu
    530                 535                 540

TTA GAT AAA TAT ACT ATG TTC CAT TAT CTT CGT GCT CAA GAA TTT GAA      1680
Leu Asp Lys Tyr Thr Met Phe His Tyr Leu Arg Ala Gln Glu Phe Glu
545                 550                 555                 560

CAT GGT AAA TCT AGG ATT GCT TTA ACA AAT TCT GTT AAC GAA GCA TTA      1728
His Gly Lys Ser Arg Ile Ala Leu Thr Asn Ser Val Asn Glu Ala Leu
                565                 570                 575

TTA AAT CCT AGT CGT GTT TAT ACA TTT TTT TCT TCA GAC TAT GTA AAG      1776
Leu Asn Pro Ser Arg Val Tyr Thr Phe Phe Ser Ser Asp Tyr Val Lys
            580                 585                 590

AAA GTT AAT AAA GCT ACG GAG GCA GCT ATG TTT TTA GGC TGG GTA GAA      1824
Lys Val Asn Lys Ala Thr Glu Ala Ala Met Phe Leu Gly Trp Val Glu
        595                 600                 605

CAA TTA GTA TAT GAT TTT ACC GAT GAA ACT AGC GAA GTA AGT ACT ACG      1872
Gln Leu Val Tyr Asp Phe Thr Asp Glu Thr Ser Glu Val Ser Thr Thr
    610                 615                 620

GAT AAA ATT GCG GAT ATA ACT ATA ATT ATT CCA TAT ATA GGA CCT GCT      1920
Asp Lys Ile Ala Asp Ile Thr Ile Ile Ile Pro Tyr Ile Gly Pro Ala
625                 630                 635                 640

TTA AAT ATA GGT AAT ATG TTA TAT AAA GAT GAT TTT GTA GGT GCT TTA      1968
Leu Asn Ile Gly Asn Met Leu Tyr Lys Asp Asp Phe Val Gly Ala Leu
                645                 650                 655

ATA TTT TCA GGA GCT GTT ATT CTG TTA GAA TTT ATA CCA GAG ATT GCA      2016
Ile Phe Ser Gly Ala Val Ile Leu Leu Glu Phe Ile Pro Glu Ile Ala
            660                 665                 670

ATA CCT GTA TTA GGT ACT TTT GCA CTT GTA TCA TAT ATT GCG AAT AAG      2064
Ile Pro Val Leu Gly Thr Phe Ala Leu Val Ser Tyr Ile Ala Asn Lys
        675                 680                 685

GTT CTA ACC GTT CAA ACA ATA GAT AAT GCT TTA AGT AAA AGA AAT GAA      2112
Val Leu Thr Val Gln Thr Ile Asp Asn Ala Leu Ser Lys Arg Asn Glu
    690                 695                 700

AAA TGG GAT GAG GTC TAT AAA TAT ATA GTA ACA AAT TGG TTA GCA AAG      2160
Lys Trp Asp Glu Val Tyr Lys Tyr Ile Val Thr Asn Trp Leu Ala Lys
705                 710                 715                 720

GTT AAT ACA CAG ATT GAT CTA ATA AGA AAA AAA ATG AAA GAA GCT TTA      2208
Val Asn Thr Gln Ile Asp Leu Ile Arg Lys Lys Met Lys Glu Ala Leu
                725                 730                 735

GAA AAT CAA GCA GAA GCA ACA AAG GCT ATA ATA AAC TAT CAG TAT AAT      2256
Glu Asn Gln Ala Glu Ala Thr Lys Ala Ile Ile Asn Tyr Gln Tyr Asn
            740                 745                 750

CAA TAT ACT GAG GAA GAG AAA AAT AAT ATT AAT TTT AAT ATT GAT GAT      2304
Gln Tyr Thr Glu Glu Glu Lys Asn Asn Ile Asn Phe Asn Ile Asp Asp
        755                 760                 765

TTA AGT TCG AAA CTT AAT GAG TCT ATA AAT AAA GCT ATG ATT AAT ATA      2352
Leu Ser Ser Lys Leu Asn Glu Ser Ile Asn Lys Ala Met Ile Asn Ile
    770                 775                 780

AAT AAA TTT TTG AAT CAA TGC TCT GTT TCA TAT TTA ATG AAT TCT ATG      2400
```

-continued

```
Asn Lys Phe Leu Asn Gln Cys Ser Val Ser Tyr Leu Met Asn Ser Met
785                 790                 795                 800

ATC CCT TAT GGT GTT AAA CGG TTA GAA GAT TTT GAT GCT AGT CTT AAA      2448
Ile Pro Tyr Gly Val Lys Arg Leu Glu Asp Phe Asp Ala Ser Leu Lys
                805                 810                 815

GAT GCA TTA TTA AAG TAT ATA TAT GAT AAT AGA GGA ACT TTA ATT GGT      2496
Asp Ala Leu Leu Lys Tyr Ile Tyr Asp Asn Arg Gly Thr Leu Ile Gly
            820                 825                 830

CAA GTA GAT AGA TTA AAA GAT AAA GTT AAT AAT ACA CTT AGT ACA GAT      2544
Gln Val Asp Arg Leu Lys Asp Lys Val Asn Asn Thr Leu Ser Thr Asp
        835                 840                 845

ATA CCT TTT CAG CTT TCC AAA TAC GTA GAT AAT CAA AGA TTA TTA TCT      2592
Ile Pro Phe Gln Leu Ser Lys Tyr Val Asp Asn Gln Arg Leu Leu Ser
    850                 855                 860

ACA TTT ACT GAA TAT ATT AAG AAT ATT ATT AAT ACT TCT ATA TTG AAT      2640
Thr Phe Thr Glu Tyr Ile Lys Asn Ile Ile Asn Thr Ser Ile Leu Asn
865                 870                 875                 880

TTA AGA TAT GAA AGT AAT CAT TTA ATA GAC TTA TCT AGG TAT GCA TCA      2688
Leu Arg Tyr Glu Ser Asn His Leu Ile Asp Leu Ser Arg Tyr Ala Ser
                885                 890                 895

AAA ATA AAT ATT GGT AGT AAA GTA AAT TTT GAT CCA ATA GAT AAA AAT      2736
Lys Ile Asn Ile Gly Ser Lys Val Asn Phe Asp Pro Ile Asp Lys Asn
            900                 905                 910

CAA ATT CAA TTA TTT AAT TTA GAA AGT AGT AAA ATT GAG GTA ATT TTA      2784
Gln Ile Gln Leu Phe Asn Leu Glu Ser Ser Lys Ile Glu Val Ile Leu
        915                 920                 925

AAA AAT GCT ATT GTA TAT AAT AGT ATG TAT GAA AAT TTT AGT ACT AGC      2832
Lys Asn Ala Ile Val Tyr Asn Ser Met Tyr Glu Asn Phe Ser Thr Ser
    930                 935                 940

TTT TGG ATA AGA ATT CCT AAG TAT TTT AAC AGT ATA AGT CTA AAT AAT      2880
Phe Trp Ile Arg Ile Pro Lys Tyr Phe Asn Ser Ile Ser Leu Asn Asn
945                 950                 955                 960

GAA TAT ACA ATA ATA AAT TGT ATG GAA AAT AAT TCA GGA TGG AAA GTA      2928
Glu Tyr Thr Ile Ile Asn Cys Met Glu Asn Asn Ser Gly Trp Lys Val
                965                 970                 975

TCA CTT AAT TAT GGT GAA ATA ATC TGG ACT TTA CAG GAT ACT CAG GAA      2976
Ser Leu Asn Tyr Gly Glu Ile Ile Trp Thr Leu Gln Asp Thr Gln Glu
            980                 985                 990

ATA AAA CAA AGA GTA GTT TTT AAA TAC AGT CAA ATG ATT AAT ATA TCA      3024
Ile Lys Gln Arg Val Val Phe Lys Tyr Ser Gln Met Ile Asn Ile Ser
        995                 1000                1005

GAT TAT ATA AAC AGA TGG ATT TTT GTA ACT ATC ACT AAT AAT AGA TTA      3072
Asp Tyr Ile Asn Arg Trp Ile Phe Val Thr Ile Thr Asn Asn Arg Leu
    1010                1015                1020

AAT AAC TCT AAA ATT TAT ATA AAT GGA AGA TTA ATA GAT CAA AAA CCA      3120
Asn Asn Ser Lys Ile Tyr Ile Asn Gly Arg Leu Ile Asp Gln Lys Pro
1025                1030                1035                1040

ATT TCA AAT TTA GGT AAT ATT CAT GCT AGT AAT AAT ATA ATG TTT AAA      3168
Ile Ser Asn Leu Gly Asn Ile His Ala Ser Asn Asn Ile Met Phe Lys
                1045                1050                1055

TTA GAT GGT TGT AGA GAT ACA CAT AGA TAT ATT TGG ATA AAA TAT TTT      3216
Leu Asp Gly Cys Arg Asp Thr His Arg Tyr Ile Trp Ile Lys Tyr Phe
            1060                1065                1070

AAT CTT TTT GAT AAG GAA TTA AAT GAA AAA GAA ATC AAA GAT TTA TAT      3264
Asn Leu Phe Asp Lys Glu Leu Asn Glu Lys Glu Ile Lys Asp Leu Tyr
        1075                1080                1085

GAT AAT CAA TCA AAT TCA GGT ATT TTA AAA GAC TTT TGG GGT GAT TAT      3312
Asp Asn Gln Ser Asn Ser Gly Ile Leu Lys Asp Phe Trp Gly Asp Tyr
    1090                1095                1100
```

-continued

```
TTA CAA TAT GAT AAA CCA TAC TAT ATG TTA AAT TTA TAT GAT CCA AAT      3360
Leu Gln Tyr Asp Lys Pro Tyr Tyr Met Leu Asn Leu Tyr Asp Pro Asn
1105                1110                1115                1120

AAA TAT GTC GAT GTA AAT AAT GTA GGT ATT AGA GGT TAT ATG TAT CTT      3408
Lys Tyr Val Asp Val Asn Asn Val Gly Ile Arg Gly Tyr Met Tyr Leu
                1125                1130                1135

AAA GGG CCT AGA GGT AGC GTA ATG ACT ACA AAC ATT TAT TTA AAT TCA      3456
Lys Gly Pro Arg Gly Ser Val Met Thr Thr Asn Ile Tyr Leu Asn Ser
            1140                1145                1150

AGT TTG TAT AGG GGG ACA AAA TTT ATT ATA AAA AAA TAT GCT TCT GGA      3504
Ser Leu Tyr Arg Gly Thr Lys Phe Ile Ile Lys Lys Tyr Ala Ser Gly
        1155                1160                1165

AAT AAA GAT AAT ATT GTT AGA AAT AAT GAT CGT GTA TAT ATT AAT GTA      3552
Asn Lys Asp Asn Ile Val Arg Asn Asn Asp Arg Val Tyr Ile Asn Val
    1170                1175                1180

GTA GTT AAA AAT AAA GAA TAT AGG TTA GCT ACT AAT GCA TCA CAG GCA      3600
Val Val Lys Asn Lys Glu Tyr Arg Leu Ala Thr Asn Ala Ser Gln Ala
1185                1190                1195                1200

GGC GTA GAA AAA ATA CTA AGT GCA TTA GAA ATA CCT GAT GTA GGA AAT      3648
Gly Val Glu Lys Ile Leu Ser Ala Leu Glu Ile Pro Asp Val Gly Asn
                1205                1210                1215

CTA AGT CAA GTA GTA GTA ATG AAG TCA AAA AAT GAT CAA GGA ATA ACA      3696
Leu Ser Gln Val Val Val Met Lys Ser Lys Asn Asp Gln Gly Ile Thr
            1220                1225                1230

AAT AAA TGC AAA ATG AAT TTA CAA GAT AAT AAT GGG AAT GAT ATA GGC      3744
Asn Lys Cys Lys Met Asn Leu Gln Asp Asn Asn Gly Asn Asp Ile Gly
        1235                1240                1245

TTT ATA GGA TTT CAT CAG TTT AAT AAT ATA GCT AAA CTA GTA GCA AGT      3792
Phe Ile Gly Phe His Gln Phe Asn Asn Ile Ala Lys Leu Val Ala Ser
    1250                1255                1260

AAT TGG TAT AAT AGA CAA ATA GAA AGA TCT AGT AGG ACT TTG GGT TGC      3840
Asn Trp Tyr Asn Arg Gln Ile Glu Arg Ser Ser Arg Thr Leu Gly Cys
1265                1270                1275                1280

TCA TGG GAA TTT ATT CCT GTA GAT GAT GGA TGG GGA GAA AGG CCA CTG      3888
Ser Trp Glu Phe Ile Pro Val Asp Asp Gly Trp Gly Glu Arg Pro Leu
                1285                1290                1295

TAA                                                                  3891
```

(2) INFORMATION FOR SEQ ID NO:28:

(i) SEQUENCE CHARACTERISTICS:
(A) LENGTH: 1296 amino acids
(B) TYPE: amino acid
(D) TOPOLOGY: linear (ii) MOLECULE TYPE: protein (xi) SEQUENCE DESCRIPTION: SEQ ID NO:28:

```
Met Gln Phe Val Asn Lys Gln Phe Asn Tyr Lys Asp Pro Val Asn Gly
  1               5                  10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95
```

-continued

```
Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510
```

-continued

```
Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
```

-continued

```
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295
```

(2) INFORMATION FOR SEQ ID NO:29:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

-continued (xi) SEQUENCE DESCRIPTION: SEQ ID NO:29:

CGCCATGGCT AGATTATTAT CTACATTTAC 30

(2) INFORMATION FOR SEQ ID NO:30:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:30:

GCAAGCTTCT TGACAGACTC ATGTAG 26

(2) INFORMATION FOR SEQ ID NO:31:

(i) SEQUENCE CHARACTERISTICS:
(A) LENGTH: 1546 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:31:

AGATCTCGAT CCCGCGAAAT TAATACGACT CACTATAGGG GAATTGTGAG CGGATAACAA 60

TTCCCCTCTA GAAATAATTT TGTTTAACTT TAAGAAGGAG ATATACCATG GGCCATCATC 120

ATCATCATCA TCATCATCAT CACAGCAGCG GCCATATCGA AGGTCGTCAT ATGGCTAGCA 180

TGGCTAGATT ATTATCTACA TTTACTGAAT ATATTAAGAA TATTATTAAT ACTTCTATAT 240

TGAATTTAAG ATATGAAAGT AATCATTTAA TAGACTTATC TAGGTATGCA TCAAAAATAA 300

ATATTGGTAG TAAAGTAAAT TTTGATCCAA TAGATAAAAA TCAAATTCAA TTATTTAATT 360

TAGAAAGTAG TAAAATTGAG GTAATTTTAA AAAATGCTAT TGTATATAAT AGTATGTATG 420

AAAATTTTAG TACTAGCTTT TGGATAAGAA TTCCTAAGTA TTTTAACAGT ATAAGTCTAA 480

ATAATGAATA TACAATAATA AATTGTATGG AAAATAATTC AGGATGGAAA GTATCACTTA 540

ATTATGGTGA AATAATCTGG ACTTTACAGG ATACTCAGGA AATAAAACAA AGAGTAGTTT 600

TTAAATACAG TCAAATGATT AATATATCAG ATTATATAAA CAGATGGATT TTTGTAACTA 660

TCACTAATAA TAGATTAAAT AACTCTAAAA TTTATATAAA TGGAAGATTA ATAGATCAAA 720

AACCAATTTC AAATTTAGGT AATATTCATG CTAGTAATAA TATAATGTTT AAATTAGATG 780

GTTGTAGAGA TACACATAGA TATATTTGGA TAAAATATTT TAATCTTTTT GATAAGGAAT 840

TAAATGAAAA AGAAATCAAA GATTTATATG ATAATCAATC AAATTCAGGT ATTTTAAAAG 900

ACTTTTGGGG TGATTATTTA CAATATGATA AACCATACTA TATGTTAAAT TTATATGATC 960

CAAATAAATA TGTCGATGTA AATAATGTAG GTATTAGAGG TTATATGTAT CTTAAAGGGC 1020

CTAGAGGTAG CGTAATGACT ACAAACATTT ATTTAAATTC AAGTTTGTAT AGGGGGACAA 1080

AATTTATTAT AAAAAAATAT GCTTCTGGAA ATAAAGATAA TATTGTTAGA AATAATGATC 1140

GTGTATATAT TAATGTAGTA GTTAAAAATA AAGAATATAG GTTAGCTACT AATGCATCAC 1200

AGGCAGGCGT AGAAAAAATA CTAAGTGCAT TAGAAATACC TGATGTAGGA AATCTAAGTC 1260

AAGTAGTAGT AATGAAGTCA AAAAATGATC AAGGAATAAC AAATAAATGC AAAATGAATT 1320

TACAAGATAA TAATGGGAAT GATATAGGCT TTATAGGATT TCATCAGTTT AATAATATAG 1380

-continued

```
CTAAACTAGT AGCAAGTAAT TGGTATAATA GACAAATAGA AAGATCTAGT AGGACTTTGG   1440

GTTGCTCATG GGAATTTATT CCTGTAGATG ATGGATGGGG AGAAAGGCCA CTGTAATTAA   1500

TCTCAAACTA CATGAGTCTG TCAAGAAGCT TGCGGCCGCA CTCGAG                  1546


(2) INFORMATION FOR SEQ ID NO:32:

     (i) SEQUENCE CHARACTERISTICS:
          (A) LENGTH: 9 amino acids
          (B) TYPE: amino acid
          (C) STRANDEDNESS: Not Relevant
          (D) TOPOLOGY: Not Relevant

    (ii) MOLECULE TYPE: peptide

    (xi) SEQUENCE DESCRIPTION: SEQ ID NO:32:

Met His His His His His His Met Ala
1               5


(2) INFORMATION FOR SEQ ID NO:33:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "DNA"

    (xi) SEQUENCE DESCRIPTION: SEQ ID NO:33:

TATGCATCAC CATCACCATC A                                               21


(2) INFORMATION FOR SEQ ID NO:34:

     (i) SEQUENCE CHARACTERISTICS:
          (A) LENGTH: 23 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "DNA"

    (xi) SEQUENCE DESCRIPTION: SEQ ID NO:34:

CATGTGATGG TGATGGTGAT GCA                                             23


(2) INFORMATION FOR SEQ ID NO:35:

     (i) SEQUENCE CHARACTERISTICS:
          (A) LENGTH: 1351 base pairs
          (B) TYPE: nucleic acid
          (C) STRANDEDNESS: double
          (D) TOPOLOGY: linear

    (ii) MOLECULE TYPE: other nucleic acid
          (A) DESCRIPTION: /desc = "DNA"

    (ix) FEATURE:
          (A) NAME/KEY: CDS
          (B) LOCATION: 1..1335

    (xi) SEQUENCE DESCRIPTION: SEQ ID NO:35:

ATG CAT CAC CAT CAC CAT CAC ATG GCT CGT CTG CTG TCT ACC TTC ACT       48
Met His His His His His His Met Ala Arg Leu Leu Ser Thr Phe Thr
  1               5                  10                  15

GAA TAC ATC AAG AAC ATC ATC AAT ACC TCC ATC CTG AAC CTG CGC TAC       96
Glu Tyr Ile Lys Asn Ile Ile Asn Thr Ser Ile Leu Asn Leu Arg Tyr
```

-continued

```
                 20                  25                  30

GAA TCC AAT CAC CTG ATC GAC CTG TCT CGC TAC GCT TCC AAA ATC AAC      144
Glu Ser Asn His Leu Ile Asp Leu Ser Arg Tyr Ala Ser Lys Ile Asn
            35                  40                  45

ATC GGT TCT AAA GTT AAC TTC GAT CCG ATC GAC AAG AAT CAG ATC CAG      192
Ile Gly Ser Lys Val Asn Phe Asp Pro Ile Asp Lys Asn Gln Ile Gln
        50                  55                  60

CTG TTC AAT CTG GAA TCT TCC AAA ATC GAA GTT ATC CTG AAG AAT GCT      240
Leu Phe Asn Leu Glu Ser Ser Lys Ile Glu Val Ile Leu Lys Asn Ala
 65                  70                  75                  80

ATC GTA TAC AAC TCT ATG TAC GAA AAC TTC TCC ACC TCC TTC TGG ATC      288
Ile Val Tyr Asn Ser Met Tyr Glu Asn Phe Ser Thr Ser Phe Trp Ile
                 85                  90                  95

CGT ATC CCG AAA TAC TTC AAC TCC ATC TCT CTG AAC AAT GAA TAC ACC      336
Arg Ile Pro Lys Tyr Phe Asn Ser Ile Ser Leu Asn Asn Glu Tyr Thr
            100                 105                 110

ATC ATC AAC TGC ATG GAA AAC AAT TCT GGT TGG AAA GTA TCT CTG AAC      384
Ile Ile Asn Cys Met Glu Asn Asn Ser Gly Trp Lys Val Ser Leu Asn
        115                 120                 125

TAC GGT GAA ATC ATC TGG ACT CTG CAG GAC ACT CAG GAA ATC AAA CAG      432
Tyr Gly Glu Ile Ile Trp Thr Leu Gln Asp Thr Gln Glu Ile Lys Gln
    130                 135                 140

CGT GTT GTA TTC AAA TAC TCT CAG ATG ATC AAC ATC TCT GAC TAC ATC      480
Arg Val Val Phe Lys Tyr Ser Gln Met Ile Asn Ile Ser Asp Tyr Ile
145                 150                 155                 160

AAT CGC TGG ATC TTC GTT ACC ATC ACC AAC AAT CGT CTG AAT AAC TCC      528
Asn Arg Trp Ile Phe Val Thr Ile Thr Asn Asn Arg Leu Asn Asn Ser
                165                 170                 175

AAA ATC TAC ATC AAC GGC CGT CTG ATC GAC CAG AAA CCG ATC TCC AAT      576
Lys Ile Tyr Ile Asn Gly Arg Leu Ile Asp Gln Lys Pro Ile Ser Asn
            180                 185                 190

CTG GGT AAC ATC CAC GCT TCT AAT AAC ATC ATG TTC AAA CTG GAC GGT      624
Leu Gly Asn Ile His Ala Ser Asn Asn Ile Met Phe Lys Leu Asp Gly
        195                 200                 205

TGT CGT GAC ACT CAC CGC TAC ATC TGG ATC AAA TAC TTC AAT CTG TTC      672
Cys Arg Asp Thr His Arg Tyr Ile Trp Ile Lys Tyr Phe Asn Leu Phe
    210                 215                 220

GAC AAA GAA CTG AAC GAA AAA GAA ATC AAA GAC CTG TAC GAC AAC CAG      720
Asp Lys Glu Leu Asn Glu Lys Glu Ile Lys Asp Leu Tyr Asp Asn Gln
225                 230                 235                 240

TCC AAT TCT GGT ATC CTG AAA GAC TTC TGG GGT GAC TAC CTG CAG TAC      768
Ser Asn Ser Gly Ile Leu Lys Asp Phe Trp Gly Asp Tyr Leu Gln Tyr
                245                 250                 255

GAC AAA CCG TAC TAC ATG CTG AAT CTG TAC GAT CCG AAC AAA TAC GTT      816
Asp Lys Pro Tyr Tyr Met Leu Asn Leu Tyr Asp Pro Asn Lys Tyr Val
            260                 265                 270

GAC GTC AAC AAT GTA GGT ATC CGC GGT TAC ATG TAC CTG AAA GGT CCG      864
Asp Val Asn Asn Val Gly Ile Arg Gly Tyr Met Tyr Leu Lys Gly Pro
        275                 280                 285

CGT GGT TCT GTT ATG ACT ACC AAC ATC TAC CTG AAC TCT TCC CTG TAC      912
Arg Gly Ser Val Met Thr Thr Asn Ile Tyr Leu Asn Ser Ser Leu Tyr
    290                 295                 300

CGT GGT ACC AAA TTC ATC ATC AAG AAA TAC GCG TCT GGT AAC AAG GAC      960
Arg Gly Thr Lys Phe Ile Ile Lys Lys Tyr Ala Ser Gly Asn Lys Asp
305                 310                 315                 320

AAT ATC GTT CGC AAC AAT GAT CGT GTA TAC ATC AAT GTT GTA GTT AAG     1008
Asn Ile Val Arg Asn Asn Asp Arg Val Tyr Ile Asn Val Val Val Lys
                325                 330                 335

AAC AAA GAA TAC CGT CTG GCT ACC AAT GCT TCT CAG GCT GGT GTA GAA     1056
```

-continued

```
Asn Lys Glu Tyr Arg Leu Ala Thr Asn Ala Ser Gln Ala Gly Val Glu
            340                 345                 350

AAG ATC TTG TCT GCT CTG GAA ATC CCG GAC GTT GGT AAT CTG TCT CAG      1104
Lys Ile Leu Ser Ala Leu Glu Ile Pro Asp Val Gly Asn Leu Ser Gln
        355                 360                 365

GTA GTT GTA ATG AAA TCC AAG AAC GAC CAG GGT ATC ACT AAC AAA TGC      1152
Val Val Val Met Lys Ser Lys Asn Asp Gln Gly Ile Thr Asn Lys Cys
    370                 375                 380

AAA ATG AAT CTG CAG GAC AAC AAT GGT AAC GAT ATC GGT TTC ATC GGT      1200
Lys Met Asn Leu Gln Asp Asn Asn Gly Asn Asp Ile Gly Phe Ile Gly
385                 390                 395                 400

TTC CAC CAG TTC AAC AAT ATC GCT AAA CTG GTT GCT TCC AAC TGG TAC      1248
Phe His Gln Phe Asn Asn Ile Ala Lys Leu Val Ala Ser Asn Trp Tyr
                405                 410                 415

AAT CGT CAG ATC GAA CGT TCC TCT CGC ACT CTG GGT TGC TCT TGG GAG      1296
Asn Arg Gln Ile Glu Arg Ser Ser Arg Thr Leu Gly Cys Ser Trp Glu
            420                 425                 430

TTC ATC CCG GTT GAT GAC GGT TGG GGT GAA CGT CCG CTG TAACCCGGGA      1345
Phe Ile Pro Val Asp Asp Gly Trp Gly Glu Arg Pro Leu
        435                 440                 445

AAGCTT                                                               1351
```

(2) INFORMATION FOR SEQ ID NO:36:

(i) SEQUENCE CHARACTERISTICS:
(A) LENGTH: 445 amino acids
(B) TYPE: amino acid
(D) TOPOLOGY: linear (ii) MOLECULE TYPE: protein (xi) SEQUENCE DESCRIPTION: SEQ ID NO:36:

```
Met His His His His His His Met Ala Arg Leu Leu Ser Thr Phe Thr
  1               5                  10                  15

Glu Tyr Ile Lys Asn Ile Ile Asn Thr Ser Ile Leu Asn Leu Arg Tyr
             20                  25                  30

Glu Ser Asn His Leu Ile Asp Leu Ser Arg Tyr Ala Ser Lys Ile Asn
         35                  40                  45

Ile Gly Ser Lys Val Asn Phe Asp Pro Ile Asp Lys Asn Gln Ile Gln
     50                  55                  60

Leu Phe Asn Leu Glu Ser Ser Lys Ile Glu Val Ile Leu Lys Asn Ala
 65                  70                  75                  80

Ile Val Tyr Asn Ser Met Tyr Glu Asn Phe Ser Thr Ser Phe Trp Ile
                 85                  90                  95

Arg Ile Pro Lys Tyr Phe Asn Ser Ile Ser Leu Asn Asn Glu Tyr Thr
            100                 105                 110

Ile Ile Asn Cys Met Glu Asn Asn Ser Gly Trp Lys Val Ser Leu Asn
        115                 120                 125

Tyr Gly Glu Ile Ile Trp Thr Leu Gln Asp Thr Gln Glu Ile Lys Gln
    130                 135                 140

Arg Val Val Phe Lys Tyr Ser Gln Met Ile Asn Ile Ser Asp Tyr Ile
145                 150                 155                 160

Asn Arg Trp Ile Phe Val Thr Ile Thr Asn Asn Arg Leu Asn Asn Ser
                165                 170                 175

Lys Ile Tyr Ile Asn Gly Arg Leu Ile Asp Gln Lys Pro Ile Ser Asn
            180                 185                 190

Leu Gly Asn Ile His Ala Ser Asn Asn Ile Met Phe Lys Leu Asp Gly
        195                 200                 205
```

-continued

```
Cys Arg Asp Thr His Arg Tyr Ile Trp Ile Lys Tyr Phe Asn Leu Phe
    210                 215                 220

Asp Lys Glu Leu Asn Glu Lys Glu Ile Lys Asp Leu Tyr Asp Asn Gln
225                 230                 235                 240

Ser Asn Ser Gly Ile Leu Lys Asp Phe Trp Gly Asp Tyr Leu Gln Tyr
                245                 250                 255

Asp Lys Pro Tyr Tyr Met Leu Asn Leu Tyr Asp Pro Asn Lys Tyr Val
            260                 265                 270

Asp Val Asn Asn Val Gly Ile Arg Gly Tyr Met Tyr Leu Lys Gly Pro
        275                 280                 285

Arg Gly Ser Val Met Thr Thr Asn Ile Tyr Leu Asn Ser Ser Leu Tyr
    290                 295                 300

Arg Gly Thr Lys Phe Ile Ile Lys Lys Tyr Ala Ser Gly Asn Lys Asp
305                 310                 315                 320

Asn Ile Val Arg Asn Asn Asp Arg Val Tyr Ile Asn Val Val Val Lys
                325                 330                 335

Asn Lys Glu Tyr Arg Leu Ala Thr Asn Ala Ser Gln Ala Gly Val Glu
            340                 345                 350

Lys Ile Leu Ser Ala Leu Glu Ile Pro Asp Val Gly Asn Leu Ser Gln
        355                 360                 365

Val Val Val Met Lys Ser Lys Asn Asp Gln Gly Ile Thr Asn Lys Cys
    370                 375                 380

Lys Met Asn Leu Gln Asp Asn Asn Gly Asn Asp Ile Gly Phe Ile Gly
385                 390                 395                 400

Phe His Gln Phe Asn Asn Ile Ala Lys Leu Val Ala Ser Asn Trp Tyr
                405                 410                 415

Asn Arg Gln Ile Glu Arg Ser Ser Arg Thr Leu Gly Cys Ser Trp Glu
            420                 425                 430

Phe Ile Pro Val Asp Asp Gly Trp Gly Glu Arg Pro Leu
        435                 440                 445
```

(2) INFORMATION FOR SEQ ID NO:37:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “DNA”

(xi) SEQUENCE DESCRIPTION: SEQ ID NO:37:

CGCATATGAA TATTCGTCCA TTGCATG 27

(2) INFORMATION FOR SEQ ID NO:38:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “DNA”

(xi) SEQUENCE DESCRIPTION: SEQ ID NO:38:

GGAAGCTTGC AGGGCAATTA CATCATG 27

-continued (2) INFORMATION FOR SEQ ID NO:39:

(i) SEQUENCE CHARACTERISTICS:
(A) LENGTH: 3876 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3873

(xi) SEQUENCE DESCRIPTION: SEQ ID NO:39:

```
ATG CCA GTT ACA ATA AAT AAT TTT AAT TAT AAT GAT CCT ATT GAT AAT       48
Met Pro Val Thr Ile Asn Asn Phe Asn Tyr Asn Asp Pro Ile Asp Asn
  1               5                  10                  15

GAC AAT ATT ATT ATG ATG GAA CCT CCA TTT GCA AGG GGT ACG GGG AGA       96
Asp Asn Ile Ile Met Met Glu Pro Pro Phe Ala Arg Gly Thr Gly Arg
             20                  25                  30

TAT TAT AAA GCT TTT AAA ATC ACA GAT CGT ATT TGG ATA ATA CCC GAA      144
Tyr Tyr Lys Ala Phe Lys Ile Thr Asp Arg Ile Trp Ile Ile Pro Glu
         35                  40                  45

AGA TAT ACT TTT GGA TAT AAA CCT GAG GAT TTT AAT AAA AGT TCC GGT      192
Arg Tyr Thr Phe Gly Tyr Lys Pro Glu Asp Phe Asn Lys Ser Ser Gly
     50                  55                  60

ATT TTT AAT AGA GAT GTT TGT GAA TAT TAT GAT CCA GAT TAC TTA AAT      240
Ile Phe Asn Arg Asp Val Cys Glu Tyr Tyr Asp Pro Asp Tyr Leu Asn
 65                  70                  75                  80

ACC AAT GAT AAA AAG AAT ATA TTT TTC CAA ACA TTG ATC AAG TTA TTT      288
Thr Asn Asp Lys Lys Asn Ile Phe Phe Gln Thr Leu Ile Lys Leu Phe
                 85                  90                  95

AAT AGA ATC AAA TCA AAA CCA TTG GGT GAA AAG TTA TTA GAG ATG ATT      336
Asn Arg Ile Lys Ser Lys Pro Leu Gly Glu Lys Leu Leu Glu Met Ile
            100                 105                 110

ATA AAT GGT ATA CCT TAT CTT GGA GAT AGA CGT GTT CCA CTC GAA GAG      384
Ile Asn Gly Ile Pro Tyr Leu Gly Asp Arg Arg Val Pro Leu Glu Glu
        115                 120                 125

TTT AAC ACA AAC ATT GCT AGT GTA ACT GTT AAT AAA TTA ATT AGT AAT      432
Phe Asn Thr Asn Ile Ala Ser Val Thr Val Asn Lys Leu Ile Ser Asn
    130                 135                 140

CCA GGA GAA GTG GAG CGA AAA AAA GGT ATT TTC GCA AAT TTA ATA ATA      480
Pro Gly Glu Val Glu Arg Lys Lys Gly Ile Phe Ala Asn Leu Ile Ile
145                 150                 155                 160

TTT GGA CCT GGG CCA GTT TTA AAT GAA AAT GAG ACT ATA GAT ATA GGT      528
Phe Gly Pro Gly Pro Val Leu Asn Glu Asn Glu Thr Ile Asp Ile Gly
                165                 170                 175

ATA CAA AAT CAT TTT GCA TCA AGG GAA GGC TTT GGG GGT ATA ATG CAA      576
Ile Gln Asn His Phe Ala Ser Arg Glu Gly Phe Gly Gly Ile Met Gln
            180                 185                 190

ATG AAA TTT TGT CCA GAA TAT GTA AGC GTA TTT AAT AAT GTT CAA GAA      624
Met Lys Phe Cys Pro Glu Tyr Val Ser Val Phe Asn Asn Val Gln Glu
        195                 200                 205

AAC AAA GGC GCA AGT ATA TTT AAT AGA CGT GGA TAT TTT TCA GAT CCA      672
Asn Lys Gly Ala Ser Ile Phe Asn Arg Arg Gly Tyr Phe Ser Asp Pro
    210                 215                 220

GCC TTG ATA TTA ATG CAT GAA CTT ATA CAT GTT TTG CAT GGA TTA TAT      720
Ala Leu Ile Leu Met His Glu Leu Ile His Val Leu His Gly Leu Tyr
225                 230                 235                 240

GGC ATT AAA GTA GAT GAT TTA CCA ATT GTA CCA AAT GAA AAA AAA TTT      768
Gly Ile Lys Val Asp Asp Leu Pro Ile Val Pro Asn Glu Lys Lys Phe
                245                 250                 255
```

-continued

```
TTT ATG CAA TCT ACA GAT ACT ATA CAG GCA GAA GAA CTA TAT ACA TTT      816
Phe Met Gln Ser Thr Asp Thr Ile Gln Ala Glu Glu Leu Tyr Thr Phe
            260                 265                 270

GGA GGA CAA GAT CCC AGC ATC ATA TCT CCT TCT ACA GAT AAA AGT ATC      864
Gly Gly Gln Asp Pro Ser Ile Ile Ser Pro Ser Thr Asp Lys Ser Ile
        275                 280                 285

TAT GAT AAA GTT TTG CAA AAT TTT AGG GGG ATA GTT GAT AGA CTT AAC      912
Tyr Asp Lys Val Leu Gln Asn Phe Arg Gly Ile Val Asp Arg Leu Asn
    290                 295                 300

AAG GTT TTA GTT TGC ATA TCA GAT CCT AAC ATT AAC ATT AAT ATA TAT      960
Lys Val Leu Val Cys Ile Ser Asp Pro Asn Ile Asn Ile Asn Ile Tyr
305                 310                 315                 320

AAA AAT AAA TTT AAA GAT AAA TAT AAA TTC GTT GAA GAT TCT GAA GGA     1008
Lys Asn Lys Phe Lys Asp Lys Tyr Lys Phe Val Glu Asp Ser Glu Gly
                325                 330                 335

AAA TAT AGT ATA GAT GTA GAA AGT TTC AAT AAA TTA TAT AAA AGC TTA     1056
Lys Tyr Ser Ile Asp Val Glu Ser Phe Asn Lys Leu Tyr Lys Ser Leu
            340                 345                 350

ATG TTA GGT TTT ACA GAA ATT AAT ATA GCA GAA AAT TAT AAA ATA AAA     1104
Met Leu Gly Phe Thr Glu Ile Asn Ile Ala Glu Asn Tyr Lys Ile Lys
        355                 360                 365

ACT AGA GCT TCT TAT TTT AGT GAT TCC TTA CCA CCA GTA AAA ATA AAA     1152
Thr Arg Ala Ser Tyr Phe Ser Asp Ser Leu Pro Pro Val Lys Ile Lys
    370                 375                 380

AAT TTA TTA GAT AAT GAA ATC TAT ACT ATA GAG GAA GGG TTT AAT ATA     1200
Asn Leu Leu Asp Asn Glu Ile Tyr Thr Ile Glu Glu Gly Phe Asn Ile
385                 390                 395                 400

TCT GAT AAA AAT ATG GGA AAA GAA TAT AGG GGT CAG AAT AAA GCT ATA     1248
Ser Asp Lys Asn Met Gly Lys Glu Tyr Arg Gly Gln Asn Lys Ala Ile
                405                 410                 415

AAT AAA CAA GCT TAT GAA GAA ATC AGC AAG GAG CAT TTG GCT GTA TAT     1296
Asn Lys Gln Ala Tyr Glu Glu Ile Ser Lys Glu His Leu Ala Val Tyr
            420                 425                 430

AAG ATA CAA ATG TGT AAA AGT GTT AAA GTT CCA GGA ATA TGT ATT GAT     1344
Lys Ile Gln Met Cys Lys Ser Val Lys Val Pro Gly Ile Cys Ile Asp
        435                 440                 445

GTC GAT AAT GAA AAT TTG TTC TTT ATA GCT GAT AAA AAT AGT TTT TCA     1392
Val Asp Asn Glu Asn Leu Phe Phe Ile Ala Asp Lys Asn Ser Phe Ser
    450                 455                 460

GAT GAT TTA TCT AAA AAT GAA AGA GTA GAA TAT AAT ACA CAG AAT AAT     1440
Asp Asp Leu Ser Lys Asn Glu Arg Val Glu Tyr Asn Thr Gln Asn Asn
465                 470                 475                 480

TAT ATA GGA AAT GAC TTT CCT ATA AAT GAA TTA ATT TTA GAT ACT GAT     1488
Tyr Ile Gly Asn Asp Phe Pro Ile Asn Glu Leu Ile Leu Asp Thr Asp
                485                 490                 495

TTA ATA AGT AAA ATA GAA TTA CCA AGT GAA AAT ACA GAA TCA CTT ACT     1536
Leu Ile Ser Lys Ile Glu Leu Pro Ser Glu Asn Thr Glu Ser Leu Thr
            500                 505                 510

GAT TTT AAT GTA GAT GTT CCA GTA TAT GAA AAA CAA CCC GCT ATA AAA     1584
Asp Phe Asn Val Asp Val Pro Val Tyr Glu Lys Gln Pro Ala Ile Lys
        515                 520                 525

AAA GTT TTT ACA GAT GAA AAT ACC ATC TTT CAA TAT TTA TAC TCT CAG     1632
Lys Val Phe Thr Asp Glu Asn Thr Ile Phe Gln Tyr Leu Tyr Ser Gln
    530                 535                 540

ACA TTT CCT CTA AAT ATA AGA GAT ATA AGT TTA ACA TCT TCA TTT GAT     1680
Thr Phe Pro Leu Asn Ile Arg Asp Ile Ser Leu Thr Ser Ser Phe Asp
545                 550                 555                 560

GAT GCA TTA TTA GTT TCT AGC AAA GTT TAT TCA TTT TTT TCT ATG GAT     1728
Asp Ala Leu Leu Val Ser Ser Lys Val Tyr Ser Phe Phe Ser Met Asp
```

-continued

```
              565                 570                 575

TAT ATT AAA ACT GCT AAT AAA GTA GTA GAA GCA GGA TTA TTT GCA GGT      1776
Tyr Ile Lys Thr Ala Asn Lys Val Val Glu Ala Gly Leu Phe Ala Gly
            580                 585                 590

TGG GTG AAA CAG ATA GTA GAT GAT TTT GTA ATC GAA GCT AAT AAA AGC      1824
Trp Val Lys Gln Ile Val Asp Asp Phe Val Ile Glu Ala Asn Lys Ser
        595                 600                 605

AGT ACT ATG GAT AAA ATT GCA GAT ATA TCT CTA ATT GTT CCT TAT ATA      1872
Ser Thr Met Asp Lys Ile Ala Asp Ile Ser Leu Ile Val Pro Tyr Ile
    610                 615                 620

GGA TTA GCT TTA AAT GTA GGA GAT GAA ACA GCT AAA GGA AAT TTT GAA      1920
Gly Leu Ala Leu Asn Val Gly Asp Glu Thr Ala Lys Gly Asn Phe Glu
625                 630                 635                 640

AGT GCT TTT GAG ATT GCA GGA TCC AGT ATT TTA CTA GAA TTT ATA CCA      1968
Ser Ala Phe Glu Ile Ala Gly Ser Ser Ile Leu Leu Glu Phe Ile Pro
                645                 650                 655

GAA CTT TTA ATA CCT GTA GTT GGA GTC TTT TTA TTA GAA TCA TAT ATT      2016
Glu Leu Leu Ile Pro Val Val Gly Val Phe Leu Leu Glu Ser Tyr Ile
            660                 665                 670

GAC AAT AAA AAT AAA ATT ATT AAA ACA ATA GAT AAT GCT TTA ACT AAA      2064
Asp Asn Lys Asn Lys Ile Ile Lys Thr Ile Asp Asn Ala Leu Thr Lys
        675                 680                 685

AGA GTG GAA AAA TGG ATT GAT ATG TAC GGA TTA ATA GTA GCG CAA TGG      2112
Arg Val Glu Lys Trp Ile Asp Met Tyr Gly Leu Ile Val Ala Gln Trp
    690                 695                 700

CTC TCA ACA GTT AAT ACT CAA TTT TAT ACA ATA AAA GAG GGA ATG TAT      2160
Leu Ser Thr Val Asn Thr Gln Phe Tyr Thr Ile Lys Glu Gly Met Tyr
705                 710                 715                 720

AAG GCT TTA AAT TAT CAA GCA CAA GCA TTG GAA GAA ATA ATA AAA TAC      2208
Lys Ala Leu Asn Tyr Gln Ala Gln Ala Leu Glu Glu Ile Ile Lys Tyr
                725                 730                 735

AAA TAT AAT ATA TAT TCT GAA GAG GAA AAG TCA AAT ATT AAC ATC AAT      2256
Lys Tyr Asn Ile Tyr Ser Glu Glu Glu Lys Ser Asn Ile Asn Ile Asn
            740                 745                 750

TTT AAT GAT ATA AAT TCT AAA CTT AAT GAT GGT ATT AAC CAA GCT ATG      2304
Phe Asn Asp Ile Asn Ser Lys Leu Asn Asp Gly Ile Asn Gln Ala Met
        755                 760                 765

GAT AAT ATA AAT GAT TTT ATA AAT GAA TGT TCT GTA TCA TAT TTA ATG      2352
Asp Asn Ile Asn Asp Phe Ile Asn Glu Cys Ser Val Ser Tyr Leu Met
    770                 775                 780

AAA AAA ATG ATT CCA TTA GCT GTA AAA AAA TTA CTA GAC TTT GAT AAT      2400
Lys Lys Met Ile Pro Leu Ala Val Lys Lys Leu Leu Asp Phe Asp Asn
785                 790                 795                 800

ACT CTC AAA AAA AAT TTA TTA AAT TAT ATA GAT GAA AAT AAA TTA TAT      2448
Thr Leu Lys Lys Asn Leu Leu Asn Tyr Ile Asp Glu Asn Lys Leu Tyr
                805                 810                 815

TTA ATT GGA AGT GTA GAA GAT GAA AAA TCA AAA GTA GAT AAA TAC TTG      2496
Leu Ile Gly Ser Val Glu Asp Glu Lys Ser Lys Val Asp Lys Tyr Leu
            820                 825                 830

AAA ACC ATT ATA CCA TTT GAT CTT TCA ACG TAT TCT AAT ATT GAA ATA      2544
Lys Thr Ile Ile Pro Phe Asp Leu Ser Thr Tyr Ser Asn Ile Glu Ile
        835                 840                 845

CTA ATA AAA ATA TTT AAT AAA TAT AAT AGC GAA ATT TTA AAT AAT ATT      2592
Leu Ile Lys Ile Phe Asn Lys Tyr Asn Ser Glu Ile Leu Asn Asn Ile
    850                 855                 860

ATC TTA AAT TTA AGA TAT AGA GAT AAT AAT TTA ATA GAT TTA TCA GGA      2640
Ile Leu Asn Leu Arg Tyr Arg Asp Asn Asn Leu Ile Asp Leu Ser Gly
865                 870                 875                 880

TAT GGA GCA AAG GTA GAG GTA TAT GAT GGG GTC AAG CTT AAT GAT AAA      2688
```

-continued

```
Tyr Gly Ala Lys Val Glu Val Tyr Asp Gly Val Lys Leu Asn Asp Lys
                885                 890                 895

AAT CAA TTT AAA TTA ACT AGT TCA GCA GAT AGT AAG ATT AGA GTC ACT      2736
Asn Gln Phe Lys Leu Thr Ser Ser Ala Asp Ser Lys Ile Arg Val Thr
            900                 905                 910

CAA AAT CAG AAT ATT ATA TTT AAT AGT ATG TTC CTT GAT TTT AGC GTT      2784
Gln Asn Gln Asn Ile Ile Phe Asn Ser Met Phe Leu Asp Phe Ser Val
        915                 920                 925

AGC TTT TGG ATA AGG ATA CCT AAA TAT AGG AAT GAT GAT ATA CAA AAT      2832
Ser Phe Trp Ile Arg Ile Pro Lys Tyr Arg Asn Asp Asp Ile Gln Asn
    930                 935                 940

TAT ATT CAT AAT GAA TAT ACG ATA ATT AAT TGT ATG AAA AAT AAT TCA      2880
Tyr Ile His Asn Glu Tyr Thr Ile Ile Asn Cys Met Lys Asn Asn Ser
945                 950                 955                 960

GGC TGG AAA ATA TCT ATT AGG GGT AAT AGG ATA ATA TGG ACC TTA ATT      2928
Gly Trp Lys Ile Ser Ile Arg Gly Asn Arg Ile Ile Trp Thr Leu Ile
                965                 970                 975

GAT ATA AAT GGA AAA ACC AAA TCA GTA TTT TTT GAA TAT AAC ATA AGA      2976
Asp Ile Asn Gly Lys Thr Lys Ser Val Phe Phe Glu Tyr Asn Ile Arg
            980                 985                 990

GAA GAT ATA TCA GAG TAT ATA AAT AGA TGG TTT TTT GTA ACT ATT ACT      3024
Glu Asp Ile Ser Glu Tyr Ile Asn Arg Trp Phe Phe Val Thr Ile Thr
        995                 1000                1005

AAT AAT TTG GAT AAT GCT AAA ATT TAT ATT AAT GGC ACG TTA GAA TCA      3072
Asn Asn Leu Asp Asn Ala Lys Ile Tyr Ile Asn Gly Thr Leu Glu Ser
    1010                1015                1020

AAT ATG GAT ATT AAA GAT ATA GGA GAA GTT ATT GTT AAT GGT GAA ATA      3120
Asn Met Asp Ile Lys Asp Ile Gly Glu Val Ile Val Asn Gly Glu Ile
1025                1030                1035                1040

ACA TTT AAA TTA GAT GGT GAT GTA GAT AGA ACA CAA TTT ATT TGG ATG      3168
Thr Phe Lys Leu Asp Gly Asp Val Asp Arg Thr Gln Phe Ile Trp Met
                1045                1050                1055

AAA TAT TTT AGT ATT TTT AAT ACG CAA TTA AAT CAA TCA AAT ATT AAA      3216
Lys Tyr Phe Ser Ile Phe Asn Thr Gln Leu Asn Gln Ser Asn Ile Lys
            1060                1065                1070

GAG ATA TAT AAA ATT CAA TCA TAT AGC GAA TAC TTA AAA GAT TTT TGG      3264
Glu Ile Tyr Lys Ile Gln Ser Tyr Ser Glu Tyr Leu Lys Asp Phe Trp
        1075                1080                1085

GGA AAT CCT TTA ATG TAT AAT AAA GAA TAT TAT ATG TTT AAT GCG GGG      3312
Gly Asn Pro Leu Met Tyr Asn Lys Glu Tyr Tyr Met Phe Asn Ala Gly
    1090                1095                1100

AAT AAA AAT TCA TAT ATT AAA CTA GTG AAA GAT TCA TCT GTA GGT GAA      3360
Asn Lys Asn Ser Tyr Ile Lys Leu Val Lys Asp Ser Ser Val Gly Glu
1105                1110                1115                1120

ATA TTA ATA CGT AGC AAA TAT AAT CAG AAT TCC AAT TAT ATA AAT TAT      3408
Ile Leu Ile Arg Ser Lys Tyr Asn Gln Asn Ser Asn Tyr Ile Asn Tyr
                1125                1130                1135

AGA AAT TTA TAT ATT GGA GAA AAA TTT ATT ATA AGA AGA GAG TCA AAT      3456
Arg Asn Leu Tyr Ile Gly Glu Lys Phe Ile Ile Arg Arg Glu Ser Asn
            1140                1145                1150

TCT CAA TCT ATA AAT GAT GAT ATA GTT AGA AAA GAA GAT TAT ATA CAT      3504
Ser Gln Ser Ile Asn Asp Asp Ile Val Arg Lys Glu Asp Tyr Ile His
        1155                1160                1165

CTA GAT TTG GTA CTT CAC CAT GAA GAG TGG AGA GTA TAT GCC TAT AAA      3552
Leu Asp Leu Val Leu His His Glu Glu Trp Arg Val Tyr Ala Tyr Lys
    1170                1175                1180

TAT TTT AAG GAA CAG GAA GAA AAA TTG TTT TTA TCT ATT ATA AGT GAT      3600
Tyr Phe Lys Glu Gln Glu Glu Lys Leu Phe Leu Ser Ile Ile Ser Asp
1185                1190                1195                1200
```

-continued

```
TCT AAT GAA TTT TAT AAG ACT ATA GAA ATA AAA GAA TAT GAT GAA CAG      3648
Ser Asn Glu Phe Tyr Lys Thr Ile Glu Ile Lys Glu Tyr Asp Glu Gln
                1205                1210                1215

CCA TCA TAT AGT TGT CAG TTG CTT TTT AAA AAA GAT GAA GAA AGT ACT      3696
Pro Ser Tyr Ser Cys Gln Leu Leu Phe Lys Lys Asp Glu Glu Ser Thr
            1220                1225                1230

GAT GAT ATA GGA TTG ATT GGT ATT CAT CGT TTC TAC GAA TCT GGA GTT      3744
Asp Asp Ile Gly Leu Ile Gly Ile His Arg Phe Tyr Glu Ser Gly Val
        1235                1240                1245

TTA CGT AAA AAG TAT AAA GAT TAT TTT TGT ATA AGT AAA TGG TAC TTA      3792
Leu Arg Lys Lys Tyr Lys Asp Tyr Phe Cys Ile Ser Lys Trp Tyr Leu
    1250                1255                1260

AAA GAG GTA AAA AGG AAA CCA TAT AAG TCA AAT TTG GGA TGT AAT TGG      3840
Lys Glu Val Lys Arg Lys Pro Tyr Lys Ser Asn Leu Gly Cys Asn Trp
1265                1270                1275                1280

CAG TTT ATT CCT AAA GAT GAA GGG TGG ACT GAA TAA                      3876
Gln Phe Ile Pro Lys Asp Glu Gly Trp Thr Glu
                1285                1290
```

(2) INFORMATION FOR SEQ ID NO:40:

(i) SEQUENCE CHARACTERISTICS:
(A) LENGTH: 1291 amino acids
(B) TYPE: amino acid
(D) TOPOLOGY: linear (ii) MOLECULE TYPE: protein (xi) SEQUENCE DESCRIPTION: SEQ ID NO:40:

```
Met Pro Val Thr Ile Asn Asn Phe Asn Tyr Asn Asp Pro Ile Asp Asn
  1               5                  10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Phe Gln Thr Leu Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
```

-continued

```
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
            340                 345                 350

Met Leu Gly Phe Thr Glu Ile Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Val Pro Gly Ile Cys Ile Asp
        435                 440                 445

Val Asp Asn Glu Asn Leu Phe Phe Ile Ala Asp Lys Asn Ser Phe Ser
    450                 455                 460

Asp Asp Leu Ser Lys Asn Glu Arg Val Glu Tyr Asn Thr Gln Asn Asn
465                 470                 475                 480

Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Val Phe Thr Asp Glu Asn Thr Ile Phe Gln Tyr Leu Tyr Ser Gln
    530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
                645                 650                 655
```

-continued

```
Glu Leu Leu Ile Pro Val Val Gly Val Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Val Glu Lys Trp Ile Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Glu Glu Lys Ser Asn Ile Asn Ile Asn
            740                 745                 750

Phe Asn Asp Ile Asn Ser Lys Leu Asn Asp Gly Ile Asn Gln Ala Met
        755                 760                 765

Asp Asn Ile Asn Asp Phe Ile Asn Glu Cys Ser Val Ser Tyr Leu Met
    770                 775                 780

Lys Lys Met Ile Pro Leu Ala Val Lys Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Val Glu Asp Glu Lys Ser Lys Val Asp Lys Tyr Leu
            820                 825                 830

Lys Thr Ile Ile Pro Phe Asp Leu Ser Thr Tyr Ser Asn Ile Glu Ile
        835                 840                 845

Leu Ile Lys Ile Phe Asn Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asp Ser Lys Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Arg Asn Asp Asp Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asp Asn Ala Lys Ile Tyr Ile Asn Gly Thr Leu Glu Ser
    1010                1015                1020

Asn Met Asp Ile Lys Asp Ile Gly Glu Val Ile Val Asn Gly Glu Ile
1025                1030                1035                1040

Thr Phe Lys Leu Asp Gly Asp Val Asp Arg Thr Gln Phe Ile Trp Met
                1045                1050                1055

Lys Tyr Phe Ser Ile Phe Asn Thr Gln Leu Asn Gln Ser Asn Ile Lys
            1060                1065                1070
```

-continued

```
Glu Ile Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Val Lys Asp Ser Ser Val Gly Glu
1105                1110                1115                1120

Ile Leu Ile Arg Ser Lys Tyr Asn Gln Asn Ser Asn Tyr Ile Asn Tyr
                1125                1130                1135

Arg Asn Leu Tyr Ile Gly Glu Lys Phe Ile Ile Arg Arg Glu Ser Asn
            1140                1145                1150

Ser Gln Ser Ile Asn Asp Asp Ile Val Arg Lys Glu Asp Tyr Ile His
        1155                1160                1165

Leu Asp Leu Val Leu His His Glu Glu Trp Arg Val Tyr Ala Tyr Lys
    1170                1175                1180

Tyr Phe Lys Glu Gln Glu Glu Lys Leu Phe Leu Ser Ile Ile Ser Asp
1185                1190                1195                1200

Ser Asn Glu Phe Tyr Lys Thr Ile Glu Ile Lys Glu Tyr Asp Glu Gln
                1205                1210                1215

Pro Ser Tyr Ser Cys Gln Leu Leu Phe Lys Lys Asp Glu Glu Ser Thr
            1220                1225                1230

Asp Asp Ile Gly Leu Ile Gly Ile His Arg Phe Tyr Glu Ser Gly Val
        1235                1240                1245

Leu Arg Lys Lys Tyr Lys Asp Tyr Phe Cys Ile Ser Lys Trp Tyr Leu
    1250                1255                1260

Lys Glu Val Lys Arg Lys Pro Tyr Lys Ser Asn Leu Gly Cys Asn Trp
1265                1270                1275                1280

Gln Phe Ile Pro Lys Asp Glu Gly Trp Thr Glu
                1285                1290
```

(2) INFORMATION FOR SEQ ID NO:41:

(i) SEQUENCE CHARACTERISTICS:
(A) LENGTH: 3876 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3873

(xi) SEQUENCE DESCRIPTION: SEQ ID NO:41:

```
ATG CCA GTT ACA ATA AAT AAT TTT AAT TAT AAT GAT CCT ATT GAT AAT        48
Met Pro Val Thr Ile Asn Asn Phe Asn Tyr Asn Asp Pro Ile Asp Asn
  1               5                  10                  15

AAT AAT ATT ATT ATG ATG GAG CCT CCA TTT GCG AGA GGT ACG GGG AGA        96
Asn Asn Ile Ile Met Met Glu Pro Pro Phe Ala Arg Gly Thr Gly Arg
             20                  25                  30

TAT TAT AAA GCT TTT AAA ATC ACA GAT CGT ATT TGG ATA ATA CCG GAA       144
Tyr Tyr Lys Ala Phe Lys Ile Thr Asp Arg Ile Trp Ile Ile Pro Glu
         35                  40                  45

AGA TAT ACT TTT GGA TAT AAA CCT GAG GAT TTT AAT AAA AGT TCC GGT       192
Arg Tyr Thr Phe Gly Tyr Lys Pro Glu Asp Phe Asn Lys Ser Ser Gly
     50                  55                  60

ATT TTT AAT AGA GAT GTT TGT GAA TAT TAT GAT CCA GAT TAC TTA AAT       240
Ile Phe Asn Arg Asp Val Cys Glu Tyr Tyr Asp Pro Asp Tyr Leu Asn
 65                  70                  75                  80
```

-continued

```
ACT AAT GAT AAA AAG AAT ATA TTT TTA CAA ACA ATG ATC AAG TTA TTT       288
Thr Asn Asp Lys Lys Asn Ile Phe Leu Gln Thr Met Ile Lys Leu Phe
                 85                  90                  95

AAT AGA ATC AAA TCA AAA CCA TTG GGT GAA AAG TTA TTA GAG ATG ATT       336
Asn Arg Ile Lys Ser Lys Pro Leu Gly Glu Lys Leu Leu Glu Met Ile
            100                 105                 110

ATA AAT GGT ATA CCT TAT CTT GGA GAT AGA CGT GTT CCA CTC GAA GAG       384
Ile Asn Gly Ile Pro Tyr Leu Gly Asp Arg Arg Val Pro Leu Glu Glu
        115                 120                 125

TTT AAC ACA AAC ATT GCT AGT GTA ACT GTT AAT AAA TTA ATC AGT AAT       432
Phe Asn Thr Asn Ile Ala Ser Val Thr Val Asn Lys Leu Ile Ser Asn
    130                 135                 140

CCA GGA GAA GTG GAG CGA AAA AAA GGT ATT TTC GCA AAT TTA ATA ATA       480
Pro Gly Glu Val Glu Arg Lys Lys Gly Ile Phe Ala Asn Leu Ile Ile
145                 150                 155                 160

TTT GGA CCT GGG CCA GTT TTA AAT GAA AAT GAG ACT ATA GAT ATA GGT       528
Phe Gly Pro Gly Pro Val Leu Asn Glu Asn Glu Thr Ile Asp Ile Gly
                165                 170                 175

ATA CAA AAT CAT TTT GCA TCA AGG GAA GGC TTC GGG GGT ATA ATG CAA       576
Ile Gln Asn His Phe Ala Ser Arg Glu Gly Phe Gly Gly Ile Met Gln
            180                 185                 190

ATG AAG TTT TGC CCA GAA TAT GTA AGC GTA TTT AAT AAT GTT CAA GAA       624
Met Lys Phe Cys Pro Glu Tyr Val Ser Val Phe Asn Asn Val Gln Glu
        195                 200                 205

AAC AAA GGC GCA AGT ATA TTT AAT AGA CGT GGA TAT TTT TCA GAT CCA       672
Asn Lys Gly Ala Ser Ile Phe Asn Arg Arg Gly Tyr Phe Ser Asp Pro
    210                 215                 220

GCC TTG ATA TTA ATG CAT GAA CTT ATA CAT GTT TTA CAT GGA TTA TAT       720
Ala Leu Ile Leu Met His Glu Leu Ile His Val Leu His Gly Leu Tyr
225                 230                 235                 240

GGC ATT AAA GTA GAT GAT TTA CCA ATT GTA CCA AAT GAA AAA AAA TTT       768
Gly Ile Lys Val Asp Asp Leu Pro Ile Val Pro Asn Glu Lys Lys Phe
                245                 250                 255

TTT ATG CAA TCT ACA GAT GCT ATA CAG GCA GAA GAA CTA TAT ACA TTT       816
Phe Met Gln Ser Thr Asp Ala Ile Gln Ala Glu Glu Leu Tyr Thr Phe
            260                 265                 270

GGA GGA CAA GAT CCC AGC ATC ATA ACT CCT TCT ACG GAT AAA AGT ATC       864
Gly Gly Gln Asp Pro Ser Ile Ile Thr Pro Ser Thr Asp Lys Ser Ile
        275                 280                 285

TAT GAT AAA GTT TTG CAA AAT TTT AGA GGG ATA GTT GAT AGA CTT AAC       912
Tyr Asp Lys Val Leu Gln Asn Phe Arg Gly Ile Val Asp Arg Leu Asn
    290                 295                 300

AAG GTT TTA GTT TGC ATA TCA GAT CCT AAC ATT AAT ATT AAT ATA TAT       960
Lys Val Leu Val Cys Ile Ser Asp Pro Asn Ile Asn Ile Asn Ile Tyr
305                 310                 315                 320

AAA AAT AAA TTT AAA GAT AAA TAT AAA TTC GTT GAA GAT TCT GAG GGA      1008
Lys Asn Lys Phe Lys Asp Lys Tyr Lys Phe Val Glu Asp Ser Glu Gly
                325                 330                 335

AAA TAT AGT ATA GAT GTA GAA AGT TTT GAT AAA TTA TAT AAA AGC TTA      1056
Lys Tyr Ser Ile Asp Val Glu Ser Phe Asp Lys Leu Tyr Lys Ser Leu
            340                 345                 350

ATG TTT GGT TTT ACA GAA ACT AAT ATA GCA GAA AAT TAT AAA ATA AAA      1104
Met Phe Gly Phe Thr Glu Thr Asn Ile Ala Glu Asn Tyr Lys Ile Lys
        355                 360                 365

ACT AGA GCT TCT TAT TTT AGT GAT TCC TTA CCA CCA GTA AAA ATA AAA      1152
Thr Arg Ala Ser Tyr Phe Ser Asp Ser Leu Pro Pro Val Lys Ile Lys
    370                 375                 380

AAT TTA TTA GAT AAT GAA ATC TAT ACT ATA GAG GAA GGG TTT AAT ATA      1200
Asn Leu Leu Asp Asn Glu Ile Tyr Thr Ile Glu Glu Gly Phe Asn Ile
385                 390                 395                 400
```

-continued

```
TCT GAT AAA GAT ATG GAA AAA GAA TAT AGA GGT CAG AAT AAA GCT ATA      1248
Ser Asp Lys Asp Met Glu Lys Glu Tyr Arg Gly Gln Asn Lys Ala Ile
                405                 410                 415

AAT AAA CAA GCT TAT GAA GAA ATT AGC AAG GAG CAT TTG GCT GTA TAT      1296
Asn Lys Gln Ala Tyr Glu Glu Ile Ser Lys Glu His Leu Ala Val Tyr
            420                 425                 430

AAG ATA CAA ATG TGT AAA AGT GTT AAA GCT CCA GGA ATA TGT ATT GAT      1344
Lys Ile Gln Met Cys Lys Ser Val Lys Ala Pro Gly Ile Cys Ile Asp
        435                 440                 445

GTT GAT AAT GAA GAT TTG TTC TTT ATA GCT GAT AAA AAT AGT TTT TCA      1392
Val Asp Asn Glu Asp Leu Phe Phe Ile Ala Asp Lys Asn Ser Phe Ser
    450                 455                 460

GAT GAT TTA TCT AAA AAC GAA AGA ATA GAA TAT AAT ACA CAG AGT AAT      1440
Asp Asp Leu Ser Lys Asn Glu Arg Ile Glu Tyr Asn Thr Gln Ser Asn
465                 470                 475                 480

TAT ATA GAA AAT GAC TTC CCT ATA AAT GAA TTA ATT TTA GAT ACT GAT      1488
Tyr Ile Glu Asn Asp Phe Pro Ile Asn Glu Leu Ile Leu Asp Thr Asp
                485                 490                 495

TTA ATA AGT AAA ATA GAA TTA CCA AGT GAA AAT ACA GAA TCA CTT ACT      1536
Leu Ile Ser Lys Ile Glu Leu Pro Ser Glu Asn Thr Glu Ser Leu Thr
            500                 505                 510

GAT TTT AAT GTA GAT GTT CCA GTA TAT GAA AAA CAA CCC GCT ATA AAA      1584
Asp Phe Asn Val Asp Val Pro Val Tyr Glu Lys Gln Pro Ala Ile Lys
        515                 520                 525

AAA ATT TTT ACA GAT GAA AAT ACC ATC TTT CAA TAT TTA TAC TCT CAG      1632
Lys Ile Phe Thr Asp Glu Asn Thr Ile Phe Gln Tyr Leu Tyr Ser Gln
    530                 535                 540

ACA TTT CTC TTA GAT ATA AGA GAT ATA AGT TTA ACA TCT TCA TTT GAT      1680
Thr Phe Leu Leu Asp Ile Arg Asp Ile Ser Leu Thr Ser Ser Phe Asp
545                 550                 555                 560

GAT GCA TTA TTA TTT TCT AAC AAA GTT TAT TCA TTT TTT TCT ATG GAT      1728
Asp Ala Leu Leu Phe Ser Asn Lys Val Tyr Ser Phe Phe Ser Met Asp
                565                 570                 575

TAT ATT AAA ACT GCT AAT AAA GTG GTA GAA GCA GGA TTA TTT GCA GGT      1776
Tyr Ile Lys Thr Ala Asn Lys Val Val Glu Ala Gly Leu Phe Ala Gly
            580                 585                 590

TGG GTG AAA CAG ATA GTA AAT GAT TTT GTA ATC GAA GCT AAT AAA AGC      1824
Trp Val Lys Gln Ile Val Asn Asp Phe Val Ile Glu Ala Asn Lys Ser
        595                 600                 605

AAT ACT ATG GAT AAA ATT GCA GAT ATA TCT CTA ATT GTT CCT TAT ATA      1872
Asn Thr Met Asp Lys Ile Ala Asp Ile Ser Leu Ile Val Pro Tyr Ile
    610                 615                 620

GGA TTA GCT TTA AAT GTA GGA AAT GAA ACA GCT AAA GGA AAT TTT GAA      1920
Gly Leu Ala Leu Asn Val Gly Asn Glu Thr Ala Lys Gly Asn Phe Glu
625                 630                 635                 640

AAT GCT TTT GAG ATT GCA GGA GCC AGT ATT CTA CTA GAA TTT ATA CCA      1968
Asn Ala Phe Glu Ile Ala Gly Ala Ser Ile Leu Leu Glu Phe Ile Pro
                645                 650                 655

GAA CTT TTA ATA CCT GTA GTT GGA GCC TTT TTA TTA GAA TCA TAT ATT      2016
Glu Leu Leu Ile Pro Val Val Gly Ala Phe Leu Leu Glu Ser Tyr Ile
            660                 665                 670

GAC AAT AAA AAT AAA ATT ATT AAA ACA ATA GAT AAT GCT TTA ACT AAA      2064
Asp Asn Lys Asn Lys Ile Ile Lys Thr Ile Asp Asn Ala Leu Thr Lys
        675                 680                 685

AGA AAT GAA AAA TGG AGT GAT ATG TAC GGA TTA ATA GTA GCG CAA TGG      2112
Arg Asn Glu Lys Trp Ser Asp Met Tyr Gly Leu Ile Val Ala Gln Trp
    690                 695                 700

CTC TCA ACA GTT AAT ACT CAA TTT TAT ACA ATA AAA GAG GGA ATG TAT      2160
Leu Ser Thr Val Asn Thr Gln Phe Tyr Thr Ile Lys Glu Gly Met Tyr
```

-continued

```
705                 710                 715                 720

AAG GCT TTA AAT TAT CAA GCA CAA GCA TTG GAA GAA ATA ATA AAA TAC      2208
Lys Ala Leu Asn Tyr Gln Ala Gln Ala Leu Glu Glu Ile Ile Lys Tyr
            725                 730                 735

AGA TAT AAT ATA TAT TCT GAA AAA GAA AAG TCA AAT ATT AAC ATC GAT      2256
Arg Tyr Asn Ile Tyr Ser Glu Lys Glu Lys Ser Asn Ile Asn Ile Asp
            740                 745                 750

TTT AAT GAT ATA AAT TCT AAA CTT AAT GAG GGT ATT AAC CAA GCT ATA      2304
Phe Asn Asp Ile Asn Ser Lys Leu Asn Glu Gly Ile Asn Gln Ala Ile
        755                 760                 765

GAT AAT ATA AAT AAT TTT ATA AAT GGA TGT TCT GTA TCA TAT TTA ATG      2352
Asp Asn Ile Asn Asn Phe Ile Asn Gly Cys Ser Val Ser Tyr Leu Met
    770                 775                 780

AAA AAA ATG ATT CCA TTA GCT GTA GAA AAA TTA CTA GAC TTT GAT AAT      2400
Lys Lys Met Ile Pro Leu Ala Val Glu Lys Leu Leu Asp Phe Asp Asn
785                 790                 795                 800

ACT CTC AAA AAA AAT TTG TTA AAT TAT ATA GAT GAA AAT AAA TTA TAT      2448
Thr Leu Lys Lys Asn Leu Leu Asn Tyr Ile Asp Glu Asn Lys Leu Tyr
            805                 810                 815

TTG ATT GGA AGT GCA GAA TAT GAA AAA TCA AAA GTA AAT AAA TAC TTG      2496
Leu Ile Gly Ser Ala Glu Tyr Glu Lys Ser Lys Val Asn Lys Tyr Leu
            820                 825                 830

AAA ACC ATT ATG CCG TTT GAT CTT TCA ATA TAT ACC AAT GAT ACA ATA      2544
Lys Thr Ile Met Pro Phe Asp Leu Ser Ile Tyr Thr Asn Asp Thr Ile
        835                 840                 845

CTA ATA GAA ATG TTT AAT AAA TAT AAT AGC GAA ATT TTA AAT AAT ATT      2592
Leu Ile Glu Met Phe Asn Lys Tyr Asn Ser Glu Ile Leu Asn Asn Ile
    850                 855                 860

ATC TTA AAT TTA AGA TAT AAG GAT AAT AAT TTA ATA GAT TTA TCA GGA      2640
Ile Leu Asn Leu Arg Tyr Lys Asp Asn Asn Leu Ile Asp Leu Ser Gly
865                 870                 875                 880

TAT GGG GCA AAG GTA GAG GTA TAT GAT GGA GTC GAG CTT AAT GAT AAA      2688
Tyr Gly Ala Lys Val Glu Val Tyr Asp Gly Val Glu Leu Asn Asp Lys
            885                 890                 895

AAT CAA TTT AAA TTA ACT AGT TCA GCA AAT AGT AAG ATT AGA GTG ACT      2736
Asn Gln Phe Lys Leu Thr Ser Ser Ala Asn Ser Lys Ile Arg Val Thr
            900                 905                 910

CAA AAT CAG AAT ATC ATA TTT AAT AGT GTG TTC CTT GAT TTT AGC GTT      2784
Gln Asn Gln Asn Ile Ile Phe Asn Ser Val Phe Leu Asp Phe Ser Val
        915                 920                 925

AGC TTT TGG ATA AGA ATA CCT AAA TAT AAG AAT GAT GGT ATA CAA AAT      2832
Ser Phe Trp Ile Arg Ile Pro Lys Tyr Lys Asn Asp Gly Ile Gln Asn
    930                 935                 940

TAT ATT CAT AAT GAA TAT ACA ATA ATT AAT TGT ATG AAA AAT AAT TCG      2880
Tyr Ile His Asn Glu Tyr Thr Ile Ile Asn Cys Met Lys Asn Asn Ser
945                 950                 955                 960

GGC TGG AAA ATA TCT ATT AGG GGT AAT AGG ATA ATA TGG ACT TTA ATT      2928
Gly Trp Lys Ile Ser Ile Arg Gly Asn Arg Ile Ile Trp Thr Leu Ile
            965                 970                 975

GAT ATA AAT GGA AAA ACC AAA TCG GTA TTT TTT GAA TAT AAC ATA AGA      2976
Asp Ile Asn Gly Lys Thr Lys Ser Val Phe Phe Glu Tyr Asn Ile Arg
            980                 985                 990

GAA GAT ATA TCA GAG TAT ATA AAT AGA TGG TTT TTT GTA ACT ATT ACT      3024
Glu Asp Ile Ser Glu Tyr Ile Asn Arg Trp Phe Phe Val Thr Ile Thr
        995                 1000                1005

AAT AAT TTG AAT AAC GCT AAA ATT TAT ATT AAT GGT AAG CTA GAA TCA      3072
Asn Asn Leu Asn Asn Ala Lys Ile Tyr Ile Asn Gly Lys Leu Glu Ser
    1010                1015                1020

AAT ACA GAT ATT AAA GAT ATA AGA GAA GTT ATT GCT AAT GGT GAA ATA      3120
```

-continued

```
Asn Thr Asp Ile Lys Asp Ile Arg Glu Val Ile Ala Asn Gly Glu Ile
1025                1030                1035                1040

ATA TTT AAA TTA GAT GGT GAT ATA GAT AGA ACA CAA TTT ATT TGG ATG      3168
Ile Phe Lys Leu Asp Gly Asp Ile Asp Arg Thr Gln Phe Ile Trp Met
                1045                1050                1055

AAA TAT TTC AGT ATT TTT AAT ACG GAA TTA AGT CAA TCA AAT ATT GAA      3216
Lys Tyr Phe Ser Ile Phe Asn Thr Glu Leu Ser Gln Ser Asn Ile Glu
            1060                1065                1070

GAA AGA TAT AAA ATT CAA TCA TAT AGC GAA TAT TTA AAA GAT TTT TGG      3264
Glu Arg Tyr Lys Ile Gln Ser Tyr Ser Glu Tyr Leu Lys Asp Phe Trp
        1075                1080                1085

GGA AAT CCT TTA ATG TAC AAT AAA GAA TAT TAT ATG TTT AAT GCG GGG      3312
Gly Asn Pro Leu Met Tyr Asn Lys Glu Tyr Tyr Met Phe Asn Ala Gly
    1090                1095                1100

AAT AAA AAT TCA TAT ATT AAA CTA AAG AAA GAT TCA CCT GTA GGT GAA      3360
Asn Lys Asn Ser Tyr Ile Lys Leu Lys Lys Asp Ser Pro Val Gly Glu
1105                1110                1115                1120

ATT TTA ACA CGT AGC AAA TAT AAT CAA AAT TCT AAA TAT ATA AAT TAT      3408
Ile Leu Thr Arg Ser Lys Tyr Asn Gln Asn Ser Lys Tyr Ile Asn Tyr
                1125                1130                1135

AGA GAT TTA TAT ATT GGA GAA AAA TTT ATT ATA AGA AGA AAG TCA AAT      3456
Arg Asp Leu Tyr Ile Gly Glu Lys Phe Ile Ile Arg Arg Lys Ser Asn
            1140                1145                1150

TCT CAA TCT ATA AAT GAT GAT ATA GTT AGA AAA GAA GAT TAT ATA TAT      3504
Ser Gln Ser Ile Asn Asp Asp Ile Val Arg Lys Glu Asp Tyr Ile Tyr
        1155                1160                1165

CTA GAT TTT TTT AAT TTA AAT CAA GAG TGG AGA GTA TAT ACC TAT AAA      3552
Leu Asp Phe Phe Asn Leu Asn Gln Glu Trp Arg Val Tyr Thr Tyr Lys
    1170                1175                1180

TAT TTT AAG AAA GAG GAA GAA AAA TTG TTT TTA GCT CCT ATA AGT GAT      3600
Tyr Phe Lys Lys Glu Glu Glu Lys Leu Phe Leu Ala Pro Ile Ser Asp
1185                1190                1195                1200

TCT GAT GAG TTT TAC AAT ACT ATA CAA ATA AAA GAA TAT GAT GAA CAG      3648
Ser Asp Glu Phe Tyr Asn Thr Ile Gln Ile Lys Glu Tyr Asp Glu Gln
                1205                1210                1215

CCA ACA TAT AGT TGT CAG TTG CTT TTT AAA AAA GAT GAA GAA AGT ACT      3696
Pro Thr Tyr Ser Cys Gln Leu Leu Phe Lys Lys Asp Glu Glu Ser Thr
            1220                1225                1230

GAT GAG ATA GGA TTG ATT GGT ATT CAT CGT TTC TAC GAA TCT GGA ATT      3744
Asp Glu Ile Gly Leu Ile Gly Ile His Arg Phe Tyr Glu Ser Gly Ile
        1235                1240                1245

GTA TTT GAA GAG TAT AAA GAT TAT TTT TGT ATA AGT AAA TGG TAC TTA      3792
Val Phe Glu Glu Tyr Lys Asp Tyr Phe Cys Ile Ser Lys Trp Tyr Leu
    1250                1255                1260

AAA GAG GTA AAA AGG AAA CCA TAT AAT TTA AAA TTG GGA TGT AAT TGG      3840
Lys Glu Val Lys Arg Lys Pro Tyr Asn Leu Lys Leu Gly Cys Asn Trp
1265                1270                1275                1280

CAG TTT ATT CCT AAA GAT GAA GGG TGG ACT GAA TAA                      3876
Gln Phe Ile Pro Lys Asp Glu Gly Trp Thr Glu
                1285                1290
```

(2) INFORMATION FOR SEQ ID NO:42:

(i) SEQUENCE CHARACTERISTICS:
(A) LENGTH: 1291 amino acids
(B) TYPE: amino acid
(D) TOPOLOGY: linear (ii) MOLECULE TYPE: protein (xi) SEQUENCE DESCRIPTION: SEQ ID NO:42:

-continued

```
Met Pro Val Thr Ile Asn Asn Phe Asn Tyr Asn Asp Pro Ile Asp Asn
  1             5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
```

-continued

```
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Leu Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845
```

-continued

```
Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu Ser
    1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
    1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Thr Tyr Lys
    1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr Leu
    1250                1255                1260
```

-continued

```
Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290
```

(2) INFORMATION FOR SEQ ID NO:43:

(i) SEQUENCE CHARACTERISTICS:
(A) LENGTH: 1526 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(ix) FEATURE:
(A) NAME/KEY: CDS
(B) LOCATION: 108..1523

(xi) SEQUENCE DESCRIPTION: SEQ ID NO:43:

```
AGATCTCGAT CCCGCGAAAT TAATACGACT CACTATAGGG GAATTGTGAG CGGATAACAA      60

TTCCCCTCTA GAAATAATTT TGTTTAACTT TAAGAAGGAG ATATACC ATG GGC CAT       116
                                                    Met Gly His
                                                      1

CAT CAT CAT CAT CAT CAT CAT CAT CAC AGC AGC GGC CAT ATC GAA GGT       164
His His His His His His His His His Ser Ser Gly His Ile Glu Gly
      5                  10                  15

CGT CAT ATG GCT AGC ATG GCT GAT ACA ATA CTA ATA GAA ATG TTT AAT       212
Arg His Met Ala Ser Met Ala Asp Thr Ile Leu Ile Glu Met Phe Asn
 20                  25                  30                  35

AAA TAT AAT AGC GAA ATT TTA AAT AAT ATT ATC TTA AAT TTA AGA TAT       260
Lys Tyr Asn Ser Glu Ile Leu Asn Asn Ile Ile Leu Asn Leu Arg Tyr
                 40                  45                  50

AGA GAT AAT AAT TTA ATA GAT TTA TCA GGA TAT GGA GCA AAG GTA GAG       308
Arg Asp Asn Asn Leu Ile Asp Leu Ser Gly Tyr Gly Ala Lys Val Glu
             55                  60                  65

GTA TAT GAT GGG GTC AAG CTT AAT GAT AAA AAT CAA TTT AAA TTA ACT       356
Val Tyr Asp Gly Val Lys Leu Asn Asp Lys Asn Gln Phe Lys Leu Thr
         70                  75                  80

AGT TCA GCA GAT AGT AAG ATT AGA GTC ACT CAA AAT CAG AAT ATT ATA       404
Ser Ser Ala Asp Ser Lys Ile Arg Val Thr Gln Asn Gln Asn Ile Ile
     85                  90                  95

TTT AAT AGT ATG TTC CTT GAT TTT AGC GTT AGC TTT TGG ATA AGG ATA       452
Phe Asn Ser Met Phe Leu Asp Phe Ser Val Ser Phe Trp Ile Arg Ile
100                 105                 110                 115

CCT AAA TAT AGG AAT GAT GAT ATA CAA AAT TAT ATT CAT AAT GAA TAT       500
Pro Lys Tyr Arg Asn Asp Asp Ile Gln Asn Tyr Ile His Asn Glu Tyr
                120                 125                 130

ACG ATA ATT AAT TGT ATG AAA AAT AAT TCA GGC TGG AAA ATA TCT ATT       548
Thr Ile Ile Asn Cys Met Lys Asn Asn Ser Gly Trp Lys Ile Ser Ile
            135                 140                 145

AGG GGT AAT AGG ATA ATA TGG ACC TTA ATT GAT ATA AAT GGA AAA ACC       596
Arg Gly Asn Arg Ile Ile Trp Thr Leu Ile Asp Ile Asn Gly Lys Thr
        150                 155                 160

AAA TCA GTA TTT TTT GAA TAT AAC ATA AGA GAA GAT ATA TCA GAG TAT       644
Lys Ser Val Phe Phe Glu Tyr Asn Ile Arg Glu Asp Ile Ser Glu Tyr
    165                 170                 175

ATA AAT AGA TGG TTT TTT GTA ACT ATT ACT AAT AAT TTG GAT AAT GCT       692
Ile Asn Arg Trp Phe Phe Val Thr Ile Thr Asn Asn Leu Asp Asn Ala
180                 185                 190                 195

AAA ATT TAT ATT AAT GGC ACG TTA GAA TCA AAT ATG GAT ATT AAA GAT       740
```

-continued

```
Lys Ile Tyr Ile Asn Gly Thr Leu Glu Ser Asn Met Asp Ile Lys Asp
                200                 205                 210

ATA GGA GAA GTT ATT GTT AAT GGT GAA ATA ACA TTT AAA TTA GAT GGT      788
Ile Gly Glu Val Ile Val Asn Gly Glu Ile Thr Phe Lys Leu Asp Gly
            215                 220                 225

GAT GTA GAT AGA ACA CAA TTT ATT TGG ATG AAA TAT TTT AGT ATT TTT      836
Asp Val Asp Arg Thr Gln Phe Ile Trp Met Lys Tyr Phe Ser Ile Phe
        230                 235                 240

AAT ACG CAA TTA AAT CAA TCA AAT ATT AAA GAG ATA TAT AAA ATT CAA      884
Asn Thr Gln Leu Asn Gln Ser Asn Ile Lys Glu Ile Tyr Lys Ile Gln
    245                 250                 255

TCA TAT AGC GAA TAC TTA AAA GAT TTT TGG GGA AAT CCT TTA ATG TAT      932
Ser Tyr Ser Glu Tyr Leu Lys Asp Phe Trp Gly Asn Pro Leu Met Tyr
260                 265                 270                 275

AAT AAA GAA TAT TAT ATG TTT AAT GCG GGG AAT AAA AAT TCA TAT ATT      980
Asn Lys Glu Tyr Tyr Met Phe Asn Ala Gly Asn Lys Asn Ser Tyr Ile
                280                 285                 290

AAA CTA GTG AAA GAT TCA TCT GTA GGT GAA ATA TTA ATA CGT AGC AAA     1028
Lys Leu Val Lys Asp Ser Ser Val Gly Glu Ile Leu Ile Arg Ser Lys
            295                 300                 305

TAT AAT CAG AAT TCC AAT TAT ATA AAT TAT AGA AAT TTA TAT ATT GGA     1076
Tyr Asn Gln Asn Ser Asn Tyr Ile Asn Tyr Arg Asn Leu Tyr Ile Gly
        310                 315                 320

GAA AAA TTT ATT ATA AGA AGA GAG TCA AAT TCT CAA TCT ATA AAT GAT     1124
Glu Lys Phe Ile Ile Arg Arg Glu Ser Asn Ser Gln Ser Ile Asn Asp
    325                 330                 335

GAT ATA GTT AGA AAA GAA GAT TAT ATA CAT CTA GAT TTG GTA CTT CAC     1172
Asp Ile Val Arg Lys Glu Asp Tyr Ile His Leu Asp Leu Val Leu His
340                 345                 350                 355

CAT GAA GAG TGG AGA GTA TAT GCC TAT AAA TAT TTT AAG GAA CAG GAA     1220
His Glu Glu Trp Arg Val Tyr Ala Tyr Lys Tyr Phe Lys Glu Gln Glu
                360                 365                 370

GAA AAA TTG TTT TTA TCT ATT ATA AGT GAT TCT AAT GAA TTT TAT AAG     1268
Glu Lys Leu Phe Leu Ser Ile Ile Ser Asp Ser Asn Glu Phe Tyr Lys
            375                 380                 385

ACT ATA GAA ATA AAA GAA TAT GAT GAA CAG CCA TCA TAT AGT TGT CAG     1316
Thr Ile Glu Ile Lys Glu Tyr Asp Glu Gln Pro Ser Tyr Ser Cys Gln
        390                 395                 400

TTG CTT TTT AAA AAA GAT GAA GAA AGT ACT GAT GAT ATA GGA TTG ATT     1364
Leu Leu Phe Lys Lys Asp Glu Glu Ser Thr Asp Asp Ile Gly Leu Ile
    405                 410                 415

GGT ATT CAT CGT TTC TAC GAA TCT GGA GTT TTA CGT AAA AAG TAT AAA     1412
Gly Ile His Arg Phe Tyr Glu Ser Gly Val Leu Arg Lys Lys Tyr Lys
420                 425                 430                 435

GAT TAT TTT TGT ATA AGT AAA TGG TAC TTA AAA GAG GTA AAA AGG AAA     1460
Asp Tyr Phe Cys Ile Ser Lys Trp Tyr Leu Lys Glu Val Lys Arg Lys
                440                 445                 450

CCA TAT AAG TCA AAT TTG GGA TGT AAT TGG CAG TTT ATT CCT AAA GAT     1508
Pro Tyr Lys Ser Asn Leu Gly Cys Asn Trp Gln Phe Ile Pro Lys Asp
            455                 460                 465

GAA GGG TGG ACT GAA TAA                                             1526
Glu Gly Trp Thr Glu
        470
```

(2) INFORMATION FOR SEQ ID NO:44:

(i) SEQUENCE CHARACTERISTICS:
(A) LENGTH: 472 amino acids
(B) TYPE: amino acid
(D) TOPOLOGY: linear -continued (ii) MOLECULE TYPE: protein (xi) SEQUENCE DESCRIPTION: SEQ ID NO:44:

```
Met Gly His His His His His His His His His His Ser Ser Gly His
  1               5                  10                  15

Ile Glu Gly Arg His Met Ala Ser Met Ala Asp Thr Ile Leu Ile Glu
             20                  25                  30

Met Phe Asn Lys Tyr Asn Ser Glu Ile Leu Asn Asn Ile Ile Leu Asn
         35                  40                  45

Leu Arg Tyr Arg Asp Asn Asn Leu Ile Asp Leu Ser Gly Tyr Gly Ala
     50                  55                  60

Lys Val Glu Val Tyr Asp Gly Val Lys Leu Asn Asp Lys Asn Gln Phe
 65                  70                  75                  80

Lys Leu Thr Ser Ser Ala Asp Ser Lys Ile Arg Val Thr Gln Asn Gln
                 85                  90                  95

Asn Ile Ile Phe Asn Ser Met Phe Leu Asp Phe Ser Val Ser Phe Trp
            100                 105                 110

Ile Arg Ile Pro Lys Tyr Arg Asn Asp Asp Ile Gln Asn Tyr Ile His
        115                 120                 125

Asn Glu Tyr Thr Ile Ile Asn Cys Met Lys Asn Asn Ser Gly Trp Lys
    130                 135                 140

Ile Ser Ile Arg Gly Asn Arg Ile Ile Trp Thr Leu Ile Asp Ile Asn
145                 150                 155                 160

Gly Lys Thr Lys Ser Val Phe Phe Glu Tyr Asn Ile Arg Glu Asp Ile
                165                 170                 175

Ser Glu Tyr Ile Asn Arg Trp Phe Phe Val Thr Ile Thr Asn Asn Leu
            180                 185                 190

Asp Asn Ala Lys Ile Tyr Ile Asn Gly Thr Leu Glu Ser Asn Met Asp
        195                 200                 205

Ile Lys Asp Ile Gly Glu Val Ile Val Asn Gly Glu Ile Thr Phe Lys
    210                 215                 220

Leu Asp Gly Asp Val Asp Arg Thr Gln Phe Ile Trp Met Lys Tyr Phe
225                 230                 235                 240

Ser Ile Phe Asn Thr Gln Leu Asn Gln Ser Asn Ile Lys Glu Ile Tyr
                245                 250                 255

Lys Ile Gln Ser Tyr Ser Glu Tyr Leu Lys Asp Phe Trp Gly Asn Pro
            260                 265                 270

Leu Met Tyr Asn Lys Glu Tyr Tyr Met Phe Asn Ala Gly Asn Lys Asn
        275                 280                 285

Ser Tyr Ile Lys Leu Val Lys Asp Ser Ser Val Gly Glu Ile Leu Ile
    290                 295                 300

Arg Ser Lys Tyr Asn Gln Asn Ser Asn Tyr Ile Asn Tyr Arg Asn Leu
305                 310                 315                 320

Tyr Ile Gly Glu Lys Phe Ile Ile Arg Arg Glu Ser Asn Ser Gln Ser
                325                 330                 335

Ile Asn Asp Asp Ile Val Arg Lys Glu Asp Tyr Ile His Leu Asp Leu
            340                 345                 350

Val Leu His His Glu Glu Trp Arg Val Tyr Ala Tyr Lys Tyr Phe Lys
        355                 360                 365

Glu Gln Glu Glu Lys Leu Phe Leu Ser Ile Ile Ser Asp Ser Asn Glu
    370                 375                 380

Phe Tyr Lys Thr Ile Glu Ile Lys Glu Tyr Asp Glu Gln Pro Ser Tyr
385                 390                 395                 400
```

-continued

```
Ser Cys Gln Leu Leu Phe Lys Lys Asp Glu Glu Ser Thr Asp Asp Ile
                405                 410                 415

Gly Leu Ile Gly Ile His Arg Phe Tyr Glu Ser Gly Val Leu Arg Lys
            420                 425                 430

Lys Tyr Lys Asp Tyr Phe Cys Ile Ser Lys Trp Tyr Leu Lys Glu Val
        435                 440                 445

Lys Arg Lys Pro Tyr Lys Ser Asn Leu Gly Cys Asn Trp Gln Phe Ile
    450                 455                 460

Pro Lys Asp Glu Gly Trp Thr Glu
465                 470


(2) INFORMATION FOR SEQ ID NO:45:

     (i) SEQUENCE CHARACTERISTICS:
          (A) LENGTH: 1547 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 108..1523

    (xi) SEQUENCE DESCRIPTION: SEQ ID NO:45:

AGATCTCGAT CCCGCGAAAT TAATACGACT CACTATAGGG GAATTGTGAG CGGATAACAA     60

TTCCCCTCTA GAAATAATTT TGTTTAACTT TAAGAAGGAG ATATACC ATG GGC CAT      116
                                                    Met Gly His
                                                      1

CAT CAT CAT CAT CAT CAT CAT CAT CAC AGC AGC GGC CAT ATC GAA GGT      164
His His His His His His His His His Ser Ser Gly His Ile Glu Gly
      5                  10                  15

CGT CAT ATG GCT AGC ATG GCT GAT ACA ATA CTA ATA GAA ATG TTT AAT      212
Arg His Met Ala Ser Met Ala Asp Thr Ile Leu Ile Glu Met Phe Asn
 20                  25                  30                  35

AAA TAT AAT AGC GAA ATT TTA AAT AAT ATT ATC TTA AAT TTA AGA TAT      260
Lys Tyr Asn Ser Glu Ile Leu Asn Asn Ile Ile Leu Asn Leu Arg Tyr
                 40                  45                  50

AAG GAT AAT AAT TTA ATA GAT TTA TCA GGA TAT GGG GCA AAG GTA GAG      308
Lys Asp Asn Asn Leu Ile Asp Leu Ser Gly Tyr Gly Ala Lys Val Glu
             55                  60                  65

GTA TAT GAT GGA GTC GAG CTT AAT GAT AAA AAT CAA TTT AAA TTA ACT      356
Val Tyr Asp Gly Val Glu Leu Asn Asp Lys Asn Gln Phe Lys Leu Thr
         70                  75                  80

AGT TCA GCA AAT AGT AAG ATT AGA GTG ACT CAA AAT CAG AAT ATC ATA      404
Ser Ser Ala Asn Ser Lys Ile Arg Val Thr Gln Asn Gln Asn Ile Ile
     85                  90                  95

TTT AAT AGT GTG TTC CTT GAT TTT AGC GTT AGC TTT TGG ATA AGA ATA      452
Phe Asn Ser Val Phe Leu Asp Phe Ser Val Ser Phe Trp Ile Arg Ile
100                 105                 110                 115

CCT AAA TAT AAG AAT GAT GGT ATA CAA AAT TAT ATT CAT AAT GAA TAT      500
Pro Lys Tyr Lys Asn Asp Gly Ile Gln Asn Tyr Ile His Asn Glu Tyr
                120                 125                 130

ACA ATA ATT AAT TGT ATG AAA AAT AAT TCG GGC TGG AAA ATA TCT ATT      548
Thr Ile Ile Asn Cys Met Lys Asn Asn Ser Gly Trp Lys Ile Ser Ile
            135                 140                 145

AGG GGT AAT AGG ATA ATA TGG ACT TTA ATT GAT ATA AAT GGA AAA ACC      596
Arg Gly Asn Arg Ile Ile Trp Thr Leu Ile Asp Ile Asn Gly Lys Thr
        150                 155                 160

AAA TCG GTA TTT TTT GAA TAT AAC ATA AGA GAA GAT ATA TCA GAG TAT      644
```

-continued

```
Lys Ser Val Phe Phe Glu Tyr Asn Ile Arg Glu Asp Ile Ser Glu Tyr
    165                 170                 175

ATA AAT AGA TGG TTT TTT GTA ACT ATT ACT AAT AAT TTG AAT AAC GCT      692
Ile Asn Arg Trp Phe Phe Val Thr Ile Thr Asn Asn Leu Asn Asn Ala
180                 185                 190                 195

AAA ATT TAT ATT AAT GGT AAG CTA GAA TCA AAT ACA GAT ATT AAA GAT      740
Lys Ile Tyr Ile Asn Gly Lys Leu Glu Ser Asn Thr Asp Ile Lys Asp
                200                 205                 210

ATA AGA GAA GTT ATT GCT AAT GGT GAA ATA ATA TTT AAA TTA GAT GGT      788
Ile Arg Glu Val Ile Ala Asn Gly Glu Ile Ile Phe Lys Leu Asp Gly
            215                 220                 225

GAT ATA GAT AGA ACA CAA TTT ATT TGG ATG AAA TAT TTC AGT ATT TTT      836
Asp Ile Asp Arg Thr Gln Phe Ile Trp Met Lys Tyr Phe Ser Ile Phe
        230                 235                 240

AAT ACG GAA TTA AGT CAA TCA AAT ATT GAA GAA AGA TAT AAA ATT CAA      884
Asn Thr Glu Leu Ser Gln Ser Asn Ile Glu Glu Arg Tyr Lys Ile Gln
    245                 250                 255

TCA TAT AGC GAA TAT TTA AAA GAT TTT TGG GGA AAT CCT TTA ATG TAC      932
Ser Tyr Ser Glu Tyr Leu Lys Asp Phe Trp Gly Asn Pro Leu Met Tyr
260                 265                 270                 275

AAT AAA GAA TAT TAT ATG TTT AAT GCG GGG AAT AAA AAT TCA TAT ATT      980
Asn Lys Glu Tyr Tyr Met Phe Asn Ala Gly Asn Lys Asn Ser Tyr Ile
                280                 285                 290

AAA CTA AAG AAA GAT TCA CCT GTA GGT GAA ATT TTA ACA CGT AGC AAA     1028
Lys Leu Lys Lys Asp Ser Pro Val Gly Glu Ile Leu Thr Arg Ser Lys
            295                 300                 305

TAT AAT CAA AAT TCT AAA TAT ATA AAT TAT AGA GAT TTA TAT ATT GGA     1076
Tyr Asn Gln Asn Ser Lys Tyr Ile Asn Tyr Arg Asp Leu Tyr Ile Gly
        310                 315                 320

GAA AAA TTT ATT ATA AGA AGA AAG TCA AAT TCT CAA TCT ATA AAT GAT     1124
Glu Lys Phe Ile Ile Arg Arg Lys Ser Asn Ser Gln Ser Ile Asn Asp
    325                 330                 335

GAT ATA GTT AGA AAA GAA GAT TAT ATA TAT CTA GAT TTT TTT AAT TTA     1172
Asp Ile Val Arg Lys Glu Asp Tyr Ile Tyr Leu Asp Phe Phe Asn Leu
340                 345                 350                 355

AAT CAA GAG TGG AGA GTA TAT ACC TAT AAA TAT TTT AAG AAA GAG GAA     1220
Asn Gln Glu Trp Arg Val Tyr Thr Tyr Lys Tyr Phe Lys Lys Glu Glu
                360                 365                 370

GAA AAA TTG TTT TTA GCT CCT ATA AGT GAT TCT GAT GAG TTT TAC AAT     1268
Glu Lys Leu Phe Leu Ala Pro Ile Ser Asp Ser Asp Glu Phe Tyr Asn
            375                 380                 385

ACT ATA CAA ATA AAA GAA TAT GAT GAA CAG CCA ACA TAT AGT TGT CAG     1316
Thr Ile Gln Ile Lys Glu Tyr Asp Glu Gln Pro Thr Tyr Ser Cys Gln
        390                 395                 400

TTG CTT TTT AAA AAA GAT GAA GAA AGT ACT GAT GAG ATA GGA TTG ATT     1364
Leu Leu Phe Lys Lys Asp Glu Glu Ser Thr Asp Glu Ile Gly Leu Ile
    405                 410                 415

GGT ATT CAT CGT TTC TAC GAA TCT GGA ATT GTA TTT GAA GAG TAT AAA     1412
Gly Ile His Arg Phe Tyr Glu Ser Gly Ile Val Phe Glu Glu Tyr Lys
420                 425                 430                 435

GAT TAT TTT TGT ATA AGT AAA TGG TAC TTA AAA GAG GTA AAA AGG AAA     1460
Asp Tyr Phe Cys Ile Ser Lys Trp Tyr Leu Lys Glu Val Lys Arg Lys
                440                 445                 450

CCA TAT AAT TTA AAA TTG GGA TGT AAT TGG CAG TTT ATT CCT AAA GAT     1508
Pro Tyr Asn Leu Lys Leu Gly Cys Asn Trp Gln Phe Ile Pro Lys Asp
            455                 460                 465

GAA GGG TGG ACT GAA TAAAAGCTTG CGGCCGCACT CGAG                      1547
Glu Gly Trp Thr Glu
        470
```

(2) INFORMATION FOR SEQ ID NO:46:

(i) SEQUENCE CHARACTERISTICS:
(A) LENGTH: 472 amino acids
(B) TYPE: amino acid
(D) TOPOLOGY: linear (ii) MOLECULE TYPE: protein (xi) SEQUENCE DESCRIPTION: SEQ ID NO:46:

```
Met Gly His His His His His His His His His His Ser Ser Gly His
  1               5                  10                  15

Ile Glu Gly Arg His Met Ala Ser Met Ala Asp Thr Ile Leu Ile Glu
             20                  25                  30

Met Phe Asn Lys Tyr Asn Ser Glu Ile Leu Asn Asn Ile Ile Leu Asn
         35                  40                  45

Leu Arg Tyr Lys Asp Asn Asn Leu Ile Asp Leu Ser Gly Tyr Gly Ala
     50                  55                  60

Lys Val Glu Val Tyr Asp Gly Val Glu Leu Asn Asp Lys Asn Gln Phe
 65                  70                  75                  80

Lys Leu Thr Ser Ser Ala Asn Ser Lys Ile Arg Val Thr Gln Asn Gln
                 85                  90                  95

Asn Ile Ile Phe Asn Ser Val Phe Leu Asp Phe Ser Val Ser Phe Trp
            100                 105                 110

Ile Arg Ile Pro Lys Tyr Lys Asn Asp Gly Ile Gln Asn Tyr Ile His
        115                 120                 125

Asn Glu Tyr Thr Ile Ile Asn Cys Met Lys Asn Asn Ser Gly Trp Lys
    130                 135                 140

Ile Ser Ile Arg Gly Asn Arg Ile Ile Trp Thr Leu Ile Asp Ile Asn
145                 150                 155                 160

Gly Lys Thr Lys Ser Val Phe Phe Glu Tyr Asn Ile Arg Glu Asp Ile
                165                 170                 175

Ser Glu Tyr Ile Asn Arg Trp Phe Phe Val Thr Ile Thr Asn Asn Leu
            180                 185                 190

Asn Asn Ala Lys Ile Tyr Ile Asn Gly Lys Leu Glu Ser Asn Thr Asp
        195                 200                 205

Ile Lys Asp Ile Arg Glu Val Ile Ala Asn Gly Glu Ile Ile Phe Lys
    210                 215                 220

Leu Asp Gly Asp Ile Asp Arg Thr Gln Phe Ile Trp Met Lys Tyr Phe
225                 230                 235                 240

Ser Ile Phe Asn Thr Glu Leu Ser Gln Ser Asn Ile Glu Glu Arg Tyr
                245                 250                 255

Lys Ile Gln Ser Tyr Ser Glu Tyr Leu Lys Asp Phe Trp Gly Asn Pro
            260                 265                 270

Leu Met Tyr Asn Lys Glu Tyr Tyr Met Phe Asn Ala Gly Asn Lys Asn
        275                 280                 285

Ser Tyr Ile Lys Leu Lys Lys Asp Ser Pro Val Gly Glu Ile Leu Thr
    290                 295                 300

Arg Ser Lys Tyr Asn Gln Asn Ser Lys Tyr Ile Asn Tyr Arg Asp Leu
305                 310                 315                 320

Tyr Ile Gly Glu Lys Phe Ile Ile Arg Arg Lys Ser Asn Ser Gln Ser
                325                 330                 335

Ile Asn Asp Asp Ile Val Arg Lys Glu Asp Tyr Ile Tyr Leu Asp Phe
            340                 345                 350

Phe Asn Leu Asn Gln Glu Trp Arg Val Tyr Thr Tyr Lys Tyr Phe Lys
```

-continued

```
        355                 360                 365

Lys Glu Glu Glu Lys Leu Phe Leu Ala Pro Ile Ser Asp Ser Asp Glu
    370                 375                 380

Phe Tyr Asn Thr Ile Gln Ile Lys Glu Tyr Asp Glu Gln Pro Thr Tyr
385                 390                 395                 400

Ser Cys Gln Leu Leu Phe Lys Lys Asp Glu Glu Ser Thr Asp Glu Ile
                405                 410                 415

Gly Leu Ile Gly Ile His Arg Phe Tyr Glu Ser Gly Ile Val Phe Glu
            420                 425                 430

Glu Tyr Lys Asp Tyr Phe Cys Ile Ser Lys Trp Tyr Leu Lys Glu Val
        435                 440                 445

Lys Arg Lys Pro Tyr Asn Leu Lys Leu Gly Cys Asn Trp Gln Phe Ile
    450                 455                 460

Pro Lys Asp Glu Gly Trp Thr Glu
465                 470
```

(2) INFORMATION FOR SEQ ID NO:47:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “DNA”

(xi) SEQUENCE DESCRIPTION: SEQ ID NO:47:

```
CGCCATGGCT GATACAATAC TAATAGAAAT G                                 31
```

(2) INFORMATION FOR SEQ ID NO:48:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “DNA”

(xi) SEQUENCE DESCRIPTION: SEQ ID NO:48:

```
GCAAGCTTTT ATTCAGTCCA CCCTTCATC                                    29
```

(2) INFORMATION FOR SEQ ID NO:49:

(i) SEQUENCE CHARACTERISTICS:
(A) LENGTH: 3753 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3750

(xi) SEQUENCE DESCRIPTION: SEQ ID NO:49:

```
ATG CCA ACA ATT AAT AGT TTT AAT TAT AAT GAT CCT GTT AAT AAT AGA       48
Met Pro Thr Ile Asn Ser Phe Asn Tyr Asn Asp Pro Val Asn Asn Arg
  1               5                  10                  15

ACA ATT TTA TAT ATT AAA CCA GGC GGT TGT CAA CAA TTT TAT AAA TCA       96
Thr Ile Leu Tyr Ile Lys Pro Gly Gly Cys Gln Gln Phe Tyr Lys Ser
             20                  25                  30
```

-continued

```
TTT AAT ATT ATG AAA AAT ATT TGG ATA ATT CCA GAG AGA AAT GTA ATT      144
Phe Asn Ile Met Lys Asn Ile Trp Ile Ile Pro Glu Arg Asn Val Ile
         35                  40                  45

GGT ACA ATT CCC CAA GAT TTT CTT CCG CCT ACT TCA TTG AAA AAT GGA      192
Gly Thr Ile Pro Gln Asp Phe Leu Pro Pro Thr Ser Leu Lys Asn Gly
     50                  55                  60

GAT AGT AGT TAT TAT GAC CCT AAT TAT TTA CAA AGT GAT CAA GAA AAG      240
Asp Ser Ser Tyr Tyr Asp Pro Asn Tyr Leu Gln Ser Asp Gln Glu Lys
 65                  70                  75                  80

GAT AAA TTT TTA AAA ATA GTC ACA AAA ATA TTT AAT AGA ATA AAT GAT      288
Asp Lys Phe Leu Lys Ile Val Thr Lys Ile Phe Asn Arg Ile Asn Asp
                 85                  90                  95

AAT CTT TCA GGA AGG ATT TTA TTA GAA GAA CTG TCA AAA GCT AAT CCA      336
Asn Leu Ser Gly Arg Ile Leu Leu Glu Glu Leu Ser Lys Ala Asn Pro
            100                 105                 110

TAT TTA GGA AAT GAT AAT ACT CCA GAT GGT GAC TTC ATT ATT AAT GAT      384
Tyr Leu Gly Asn Asp Asn Thr Pro Asp Gly Asp Phe Ile Ile Asn Asp
        115                 120                 125

GCA TCA GCA GTT CCA ATT CAA TTC TCA AAT GGT AGC CAA AGC ATA CTA      432
Ala Ser Ala Val Pro Ile Gln Phe Ser Asn Gly Ser Gln Ser Ile Leu
    130                 135                 140

TTA CCT AAT GTT ATT ATA ATG GGA GCA GAG CCT GAT TTA TTT GAA ACT      480
Leu Pro Asn Val Ile Ile Met Gly Ala Glu Pro Asp Leu Phe Glu Thr
145                 150                 155                 160

AAC AGT TCC AAT ATT TCT CTA AGA AAT AAT TAT ATG CCA AGC AAT CAC      528
Asn Ser Ser Asn Ile Ser Leu Arg Asn Asn Tyr Met Pro Ser Asn His
                165                 170                 175

GGT TTT GGA TCA ATA GCT ATA GTA ACA TTC TCA CCT GAA TAT TCT TTT      576
Gly Phe Gly Ser Ile Ala Ile Val Thr Phe Ser Pro Glu Tyr Ser Phe
            180                 185                 190

AGA TTT AAA GAT AAT AGT ATG AAT GAA TTT ATT CAA GAT CCT GCT CTT      624
Arg Phe Lys Asp Asn Ser Met Asn Glu Phe Ile Gln Asp Pro Ala Leu
        195                 200                 205

ACA TTA ATG CAT GAA TTA ATA CAT TCA TTA CAT GGA CTA TAT GGG GCT      672
Thr Leu Met His Glu Leu Ile His Ser Leu His Gly Leu Tyr Gly Ala
    210                 215                 220

AAA GGG ATT ACT ACA AAG TAT ACT ATA ACA CAA AAA CAA AAT CCC CTA      720
Lys Gly Ile Thr Thr Lys Tyr Thr Ile Thr Gln Lys Gln Asn Pro Leu
225                 230                 235                 240

ATA ACA AAT ATA AGA GGT ACA AAT ATT GAA GAA TTC TTA ACT TTT GGA      768
Ile Thr Asn Ile Arg Gly Thr Asn Ile Glu Glu Phe Leu Thr Phe Gly
                245                 250                 255

GGT ACT GAT TTA AAC ATT ATT ACT AGT GCT CAG TCC AAT GAT ATC TAT      816
Gly Thr Asp Leu Asn Ile Ile Thr Ser Ala Gln Ser Asn Asp Ile Tyr
            260                 265                 270

ACT AAT CTT CTA GCT GAT TAT AAA AAA ATA GCG TCT AAA CTT AGC AAA      864
Thr Asn Leu Leu Ala Asp Tyr Lys Lys Ile Ala Ser Lys Leu Ser Lys
        275                 280                 285

GTA CAA GTA TCT AAT CCA CTA CTT AAT CCT TAT AAA GAT GTT TTT GAA      912
Val Gln Val Ser Asn Pro Leu Leu Asn Pro Tyr Lys Asp Val Phe Glu
    290                 295                 300

GCA AAG TAT GGA TTA GAT AAA GAT GCT AGC GGA ATT TAT TCG GTA AAT      960
Ala Lys Tyr Gly Leu Asp Lys Asp Ala Ser Gly Ile Tyr Ser Val Asn
305                 310                 315                 320

ATA AAC AAA TTT AAT GAT ATT TTT AAA AAA TTA TAC AGC TTT ACG GAA     1008
Ile Asn Lys Phe Asn Asp Ile Phe Lys Lys Leu Tyr Ser Phe Thr Glu
                325                 330                 335

TTT GAT TTA GCA ACT AAA TTT CAA GTT AAA TGT AGG CAA ACT TAT ATT     1056
Phe Asp Leu Ala Thr Lys Phe Gln Val Lys Cys Arg Gln Thr Tyr Ile
```

-continued

```
            340                 345                 350

GGA CAG TAT AAA TAC TTC AAA CTT TCA AAC TTG TTA AAT GAT TCT ATT     1104
Gly Gln Tyr Lys Tyr Phe Lys Leu Ser Asn Leu Leu Asn Asp Ser Ile
        355                 360                 365

TAT AAT ATA TCA GAA GGC TAT AAT ATA AAT AAT TTA AAG GTA AAT TTT     1152
Tyr Asn Ile Ser Glu Gly Tyr Asn Ile Asn Asn Leu Lys Val Asn Phe
    370                 375                 380

AGA GGA CAG AAT GCA AAT TTA AAT CCT AGA ATT ATT ACA CCA ATT ACA     1200
Arg Gly Gln Asn Ala Asn Leu Asn Pro Arg Ile Ile Thr Pro Ile Thr
385                 390                 395                 400

GGT AGA GGA CTA GTA AAA AAA ATC ATT AGA TTT TGT AAA AAT ATT GTT     1248
Gly Arg Gly Leu Val Lys Lys Ile Ile Arg Phe Cys Lys Asn Ile Val
                405                 410                 415

TCT GTA AAA GGC ATA AGG AAA TCA ATA TGT ATC GAA ATA AAT AAT GGT     1296
Ser Val Lys Gly Ile Arg Lys Ser Ile Cys Ile Glu Ile Asn Asn Gly
            420                 425                 430

GAG TTA TTT TTT GTG GCT TCC GAG AAT AGT TAT AAT GAT GAT AAT ATA     1344
Glu Leu Phe Phe Val Ala Ser Glu Asn Ser Tyr Asn Asp Asp Asn Ile
        435                 440                 445

AAT ACT CCT AAA GAA ATT GAC GAT ACA GTA ACT TCA AAT AAT AAT TAT     1392
Asn Thr Pro Lys Glu Ile Asp Asp Thr Val Thr Ser Asn Asn Asn Tyr
    450                 455                 460

GAA AAT GAT TTA GAT CAG GTT ATT TTA AAT TTT AAT AGT GAA TCA GCA     1440
Glu Asn Asp Leu Asp Gln Val Ile Leu Asn Phe Asn Ser Glu Ser Ala
465                 470                 475                 480

CCT GGA CTT TCA GAT GAA AAA TTA AAT TTA ACT ATC CAA AAT GAT GCT     1488
Pro Gly Leu Ser Asp Glu Lys Leu Asn Leu Thr Ile Gln Asn Asp Ala
                485                 490                 495

TAT ATA CCA AAA TAT GAT TCT AAT GGA ACA AGT GAT ATA GAA CAA CAT     1536
Tyr Ile Pro Lys Tyr Asp Ser Asn Gly Thr Ser Asp Ile Glu Gln His
            500                 505                 510

GAT GTT AAT GAA CTT AAT GTA TTT TTC TAT TTA GAT GCA CAG AAA GTG     1584
Asp Val Asn Glu Leu Asn Val Phe Phe Tyr Leu Asp Ala Gln Lys Val
        515                 520                 525

CCC GAA GGT GAA AAT AAT GTC AAT CTC ACC TCT TCA ATT GAT ACA GCA     1632
Pro Glu Gly Glu Asn Asn Val Asn Leu Thr Ser Ser Ile Asp Thr Ala
    530                 535                 540

TTA TTA GAA CAA CCT AAA ATA TAT ACA TTT TTT TCA TCA GAA TTT ATT     1680
Leu Leu Glu Gln Pro Lys Ile Tyr Thr Phe Phe Ser Ser Glu Phe Ile
545                 550                 555                 560

AAT AAT GTC AAT AAA CCT GTG CAA GCA GCA TTA TTT GTA AGC TGG ATA     1728
Asn Asn Val Asn Lys Pro Val Gln Ala Ala Leu Phe Val Ser Trp Ile
                565                 570                 575

CAA CAA GTA TTA GTA GAT TTT ACT ACT GAA GCT AAC CAA AAA AGT ACT     1776
Gln Gln Val Leu Val Asp Phe Thr Thr Glu Ala Asn Gln Lys Ser Thr
            580                 585                 590

GTT GAT AAA ATT GCA GAT ATT TCT ATA GTT GTT CCA TAT ATA GGT CTT     1824
Val Asp Lys Ile Ala Asp Ile Ser Ile Val Val Pro Tyr Ile Gly Leu
        595                 600                 605

GCT TTA AAT ATA GGA AAT GAA GCA CAA AAA GGA AAT TTT AAA GAT GCA     1872
Ala Leu Asn Ile Gly Asn Glu Ala Gln Lys Gly Asn Phe Lys Asp Ala
    610                 615                 620

CTT GAA TTA TTA GGA GCA GGT ATT TTA TTA GAA TTT GAA CCC GAG CTT     1920
Leu Glu Leu Leu Gly Ala Gly Ile Leu Leu Glu Phe Glu Pro Glu Leu
625                 630                 635                 640

TTA ATT CCT ACA ATT TTA GTA TTC ACG ATA AAA TCT TTT TTA GGT TCA     1968
Leu Ile Pro Thr Ile Leu Val Phe Thr Ile Lys Ser Phe Leu Gly Ser
                645                 650                 655

TCT GAT AAT AAA AAT AAA GTT ATT AAA GCA ATA AAT AAT GCA TTG AAA     2016
```

-continued

```
Ser Asp Asn Lys Asn Lys Val Ile Lys Ala Ile Asn Asn Ala Leu Lys
            660                 665                 670

GAA AGA GAT GAA AAA TGG AAA GAA GTA TAT AGT TTT ATA GTA TCG AAT      2064
Glu Arg Asp Glu Lys Trp Lys Glu Val Tyr Ser Phe Ile Val Ser Asn
        675                 680                 685

TGG ATG ACT AAA ATT AAT ACA CAA TTT AAT AAA AGA AAA GAA CAA ATG      2112
Trp Met Thr Lys Ile Asn Thr Gln Phe Asn Lys Arg Lys Glu Gln Met
    690                 695                 700

TAT CAA GCT TTA CAA AAT CAA GTA AAT GCA CTT AAA GCA ATA ATA GAA      2160
Tyr Gln Ala Leu Gln Asn Gln Val Asn Ala Leu Lys Ala Ile Ile Glu
705                 710                 715                 720

TCT AAG TAT AAT AGT TAT ACT TTA GAA GAA AAA AAT GAG CTT ACA AAT      2208
Ser Lys Tyr Asn Ser Tyr Thr Leu Glu Glu Lys Asn Glu Leu Thr Asn
                725                 730                 735

AAA TAT GAT ATT GAG CAA ATA GAA AAT GAA CTT AAT CAA AAG GTT TCT      2256
Lys Tyr Asp Ile Glu Gln Ile Glu Asn Glu Leu Asn Gln Lys Val Ser
            740                 745                 750

ATA GCA ATG AAT AAT ATA GAC AGG TTC TTA ACT GAA AGT TCT ATA TCT      2304
Ile Ala Met Asn Asn Ile Asp Arg Phe Leu Thr Glu Ser Ser Ile Ser
        755                 760                 765

TAT TTA ATG AAA TTA ATA AAT GAA GTA AAA ATT AAT AAA TTA AGA GAA      2352
Tyr Leu Met Lys Leu Ile Asn Glu Val Lys Ile Asn Lys Leu Arg Glu
    770                 775                 780

TAT GAT GAA AAT GTT AAA ACG TAT TTA TTA GAT TAT ATT ATA AAA CAT      2400
Tyr Asp Glu Asn Val Lys Thr Tyr Leu Leu Asp Tyr Ile Ile Lys His
785                 790                 795                 800

GGA TCA ATC TTG GGA GAG AGT CAG CAA GAA CTA AAT TCT ATG GTA ATT      2448
Gly Ser Ile Leu Gly Glu Ser Gln Gln Glu Leu Asn Ser Met Val Ile
                805                 810                 815

GAT ACC CTA AAT AAT AGT ATT CCT TTT AAG CTT TCT TCT TAT ACA GAT      2496
Asp Thr Leu Asn Asn Ser Ile Pro Phe Lys Leu Ser Ser Tyr Thr Asp
            820                 825                 830

GAT AAA ATT TTA ATT TCA TAT TTT AAT AAG TTC TTT AAG AGA ATT AAA      2544
Asp Lys Ile Leu Ile Ser Tyr Phe Asn Lys Phe Phe Lys Arg Ile Lys
        835                 840                 845

AGT AGT TCT GTT TTA AAT ATG AGA TAT AAA AAT GAT AAA TAC GTA GAT      2592
Ser Ser Ser Val Leu Asn Met Arg Tyr Lys Asn Asp Lys Tyr Val Asp
    850                 855                 860

ACT TCA GGA TAT GAT TCA AAT ATA AAT ATT AAT GGA GAT GTA TAT AAA      2640
Thr Ser Gly Tyr Asp Ser Asn Ile Asn Ile Asn Gly Asp Val Tyr Lys
865                 870                 875                 880

TAT CCA ACT AAT AAA AAT CAA TTT GGA ATA TAT AAT GAT AAA CTT AGT      2688
Tyr Pro Thr Asn Lys Asn Gln Phe Gly Ile Tyr Asn Asp Lys Leu Ser
                885                 890                 895

GAA GTT AAT ATA TCT CAA AAT GAT TAC ATT ATA TAT GAT AAT AAA TAT      2736
Glu Val Asn Ile Ser Gln Asn Asp Tyr Ile Ile Tyr Asp Asn Lys Tyr
            900                 905                 910

AAA AAT TTT AGT ATT AGT TTT TGG GTA AGA ATT CCT AAC TAT GAT AAT      2784
Lys Asn Phe Ser Ile Ser Phe Trp Val Arg Ile Pro Asn Tyr Asp Asn
        915                 920                 925

AAG ATA GTA AAT GTT AAT AAT GAA TAC ACT ATA ATA AAT TGT ATG AGG      2832
Lys Ile Val Asn Val Asn Asn Glu Tyr Thr Ile Ile Asn Cys Met Arg
    930                 935                 940

GAT AAT AAT TCA GGA TGG AAA GTA TCT CTT AAT CAT AAT GAA ATA ATT      2880
Asp Asn Asn Ser Gly Trp Lys Val Ser Leu Asn His Asn Glu Ile Ile
945                 950                 955                 960

TGG ACA TTG CAA GAT AAT TCA GGA ATT AAT CAA AAA TTA GCA TTT AAC      2928
Trp Thr Leu Gln Asp Asn Ser Gly Ile Asn Gln Lys Leu Ala Phe Asn
                965                 970                 975
```

-continued

```
TAT GGT AAC GCA AAT GGT ATT TCT GAT TAT ATA AAT AAG TGG ATT TTT     2976
Tyr Gly Asn Ala Asn Gly Ile Ser Asp Tyr Ile Asn Lys Trp Ile Phe
            980                 985                 990

GTA ACT ATA ACT AAT GAT AGA TTA GGA GAT TCT AAA CTT TAT ATT AAT     3024
Val Thr Ile Thr Asn Asp Arg Leu Gly Asp Ser Lys Leu Tyr Ile Asn
        995                1000                1005

GGA AAT TTA ATA GAT AAA AAA TCA ATT TTA AAT TTA GGT AAT ATT CAT     3072
Gly Asn Leu Ile Asp Lys Lys Ser Ile Leu Asn Leu Gly Asn Ile His
    1010                1015                1020

GTT AGT GAC AAT ATA TTA TTT AAA ATA GTT AAT TGT AGT TAT ACA AGA     3120
Val Ser Asp Asn Ile Leu Phe Lys Ile Val Asn Cys Ser Tyr Thr Arg
1025                1030                1035                1040

TAT ATT GGT ATT AGA TAT TTT AAT ATT TTT GAT AAA GAA TTA GAT GAA     3168
Tyr Ile Gly Ile Arg Tyr Phe Asn Ile Phe Asp Lys Glu Leu Asp Glu
                1045                1050                1055

ACA GAA ATT CAA ACT TTA TAT AAC AAT GAA CCT AAT GCA AAT ATT TTA     3216
Thr Glu Ile Gln Thr Leu Tyr Asn Asn Glu Pro Asn Ala Asn Ile Leu
            1060                1065                1070

AAG GAT TTT TGG GGA AAT TAT TTG CTT TAT GAC AAA GAA TAC TAT TTA     3264
Lys Asp Phe Trp Gly Asn Tyr Leu Leu Tyr Asp Lys Glu Tyr Tyr Leu
        1075                1080                1085

TTA AAT GTG TTA AAA CCA AAT AAC TTT ATT AAT AGG AGA ACA GAT TCT     3312
Leu Asn Val Leu Lys Pro Asn Asn Phe Ile Asn Arg Arg Thr Asp Ser
    1090                1095                1100

ACT TTA AGC ATT AAT AAT ATA AGA AGC ACT ATT CTT TTA GCT AAT AGA     3360
Thr Leu Ser Ile Asn Asn Ile Arg Ser Thr Ile Leu Leu Ala Asn Arg
1105                1110                1115                1120

TTA TAT AGT GGA ATA AAA GTT AAA ATA CAA AGA GTT AAT AAT AGT AGT     3408
Leu Tyr Ser Gly Ile Lys Val Lys Ile Gln Arg Val Asn Asn Ser Ser
                1125                1130                1135

ACT AAC GAT AAT CTT GTT AGA AAG AAT GAT CAG GTA TAT ATT AAT TTT     3456
Thr Asn Asp Asn Leu Val Arg Lys Asn Asp Gln Val Tyr Ile Asn Phe
            1140                1145                1150

GTA GCC AGC AAA ACT CAC TTA CTT CCA TTA TAT GCT GAT ACA GCT ACC     3504
Val Ala Ser Lys Thr His Leu Leu Pro Leu Tyr Ala Asp Thr Ala Thr
        1155                1160                1165

ACA AAT AAA GAG AAA ACA ATA AAA ATA TCA TCA TCT GGC AAT AGA TTT     3552
Thr Asn Lys Glu Lys Thr Ile Lys Ile Ser Ser Ser Gly Asn Arg Phe
    1170                1175                1180

AAT CAA GTA GTA GTT ATG AAT TCA GTA GGA TGT ACA ATG AAT TTT AAA     3600
Asn Gln Val Val Val Met Asn Ser Val Gly Cys Thr Met Asn Phe Lys
1185                1190                1195                1200

AAT AAT AAT GGA AAT AAT ATT GGG TTG TTA GGT TTC AAG GCA GAT ACT     3648
Asn Asn Asn Gly Asn Asn Ile Gly Leu Leu Gly Phe Lys Ala Asp Thr
                1205                1210                1215

GTA GTT GCT AGT ACT TGG TAT TAT ACA CAT ATG AGA GAT AAT ACA AAC     3696
Val Val Ala Ser Thr Trp Tyr Tyr Thr His Met Arg Asp Asn Thr Asn
            1220                1225                1230

AGC AAT GGA TTT TTT TGG AAC TTT ATT TCT GAA GAA CAT GGA TGG CAA     3744
Ser Asn Gly Phe Phe Trp Asn Phe Ile Ser Glu Glu His Gly Trp Gln
        1235                1240                1245

GAA AAA TAA                                                         3753
Glu Lys
    1250
```

(2) INFORMATION FOR SEQ ID NO:50:

(i) SEQUENCE CHARACTERISTICS:
(A) LENGTH: 1250 amino acids
(B) TYPE: amino acid
(D) TOPOLOGY: linear -continued (ii) MOLECULE TYPE: protein (xi) SEQUENCE DESCRIPTION: SEQ ID NO:50:

```
Met Pro Thr Ile Asn Ser Phe Asn Tyr Asn Asp Pro Val Asn Asn Arg
  1               5                  10                  15

Thr Ile Leu Tyr Ile Lys Pro Gly Gly Cys Gln Gln Phe Tyr Lys Ser
             20                  25                  30

Phe Asn Ile Met Lys Asn Ile Trp Ile Ile Pro Glu Arg Asn Val Ile
         35                  40                  45

Gly Thr Ile Pro Gln Asp Phe Leu Pro Pro Thr Ser Leu Lys Asn Gly
     50                  55                  60

Asp Ser Ser Tyr Tyr Asp Pro Asn Tyr Leu Gln Ser Asp Gln Glu Lys
 65                  70                  75                  80

Asp Lys Phe Leu Lys Ile Val Thr Lys Ile Phe Asn Arg Ile Asn Asp
                 85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400
```

-continued

```
Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Leu Lys Ala Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815
```

-continued

```
Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Lys Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Asn Asn Glu Pro Asn Ala Asn Ile Leu
            1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asn Arg Arg Thr Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Leu Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Cys Thr Met Asn Phe Lys
1185                1190                1195                1200

Asn Asn Asn Gly Asn Asn Ile Gly Leu Leu Gly Phe Lys Ala Asp Thr
                1205                1210                1215

Val Val Ala Ser Thr Trp Tyr Tyr Thr His Met Arg Asp Asn Thr Asn
            1220                1225                1230

Ser Asn Gly Phe Phe Trp Asn Phe Ile Ser Glu Glu His Gly Trp Gln
```

-continued

```
        1235                1240                1245

Glu Lys
    1250


(2) INFORMATION FOR SEQ ID NO:51:

     (i) SEQUENCE CHARACTERISTICS:
          (A) LENGTH: 3759 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 1..3756

    (xi) SEQUENCE DESCRIPTION: SEQ ID NO:51:

ATG CCA AAA ATT AAT AGT TTT AAT TAT AAT GAT CCT GTT AAT GAT AGA        48
Met Pro Lys Ile Asn Ser Phe Asn Tyr Asn Asp Pro Val Asn Asp Arg
  1               5                  10                  15

ACA ATT TTA TAT ATT AAA CCA GGC GGT TGT CAA GAA TTT TAT AAA TCA        96
Thr Ile Leu Tyr Ile Lys Pro Gly Gly Cys Gln Glu Phe Tyr Lys Ser
             20                  25                  30

TTT AAT ATT ATG AAA AAT ATT TGG ATA ATT CCA GAG AGA AAT GTA ATT       144
Phe Asn Ile Met Lys Asn Ile Trp Ile Ile Pro Glu Arg Asn Val Ile
         35                  40                  45

GGT ACA ACC CCC CAA GAT TTT CAT CCG CCT ACT TCA TTA AAA AAT GGA       192
Gly Thr Thr Pro Gln Asp Phe His Pro Pro Thr Ser Leu Lys Asn Gly
     50                  55                  60

GAT AGT AGT TAT TAT GAC CCT AAT TAT TTA CAA AGT GAT GAA GAA AAG       240
Asp Ser Ser Tyr Tyr Asp Pro Asn Tyr Leu Gln Ser Asp Glu Glu Lys
 65                  70                  75                  80

GAT AGA TTT TTA AAA ATA GTC ACA AAA ATA TTT AAT AGA ATA AAT AAT       288
Asp Arg Phe Leu Lys Ile Val Thr Lys Ile Phe Asn Arg Ile Asn Asn
                 85                  90                  95

AAT CTT TCA GGA GGG ATT TTA TTA GAA GAA CTG TCA AAA GCT AAT CCA       336
Asn Leu Ser Gly Gly Ile Leu Leu Glu Glu Leu Ser Lys Ala Asn Pro
            100                 105                 110

TAT TTA GGG AAT GAT AAT ACT CCA GAT AAT CAA TTC CAT ATT GGT GAT       384
Tyr Leu Gly Asn Asp Asn Thr Pro Asp Asn Gln Phe His Ile Gly Asp
        115                 120                 125

GCA TCA GCA GTT GAG ATT AAA TTC TCA AAT GGT AGC CAA GAC ATA CTA       432
Ala Ser Ala Val Glu Ile Lys Phe Ser Asn Gly Ser Gln Asp Ile Leu
    130                 135                 140

TTA CCT AAT GTT ATT ATA ATG GGA GCA GAG CCT GAT TTA TTT GAA ACT       480
Leu Pro Asn Val Ile Ile Met Gly Ala Glu Pro Asp Leu Phe Glu Thr
145                 150                 155                 160

AAC AGT TCC AAT ATT TCT CTA AGA AAT AAT TAT ATG CCA AGC AAT CAC       528
Asn Ser Ser Asn Ile Ser Leu Arg Asn Asn Tyr Met Pro Ser Asn His
                165                 170                 175

GGT TTT GGA TCA ATA GCT ATA GTA ACA TTC TCA CCT GAA TAT TCT TTT       576
Gly Phe Gly Ser Ile Ala Ile Val Thr Phe Ser Pro Glu Tyr Ser Phe
            180                 185                 190

AGA TTT AAT GAT AAT AGT ATG AAT GAA TTT ATT CAA GAT CCT GCT CTT       624
Arg Phe Asn Asp Asn Ser Met Asn Glu Phe Ile Gln Asp Pro Ala Leu
        195                 200                 205

ACA TTA ATG CAT GAA TTA ATA CAT TCA TTA CAT GGA CTA TAT GGG GCT       672
Thr Leu Met His Glu Leu Ile His Ser Leu His Gly Leu Tyr Gly Ala
    210                 215                 220

AAA GGG ATT ACT ACA AAG TAT ACT ATA ACA CAA AAA CAA AAT CCC CTA       720
```

-continued

```
Lys Gly Ile Thr Thr Lys Tyr Thr Ile Thr Gln Lys Gln Asn Pro Leu
225                 230                 235                 240

ATA ACA AAT ATA AGA GGT ACA AAT ATT GAA GAA TTC TTA ACT TTT GGA      768
Ile Thr Asn Ile Arg Gly Thr Asn Ile Glu Glu Phe Leu Thr Phe Gly
                245                 250                 255

GGT ACT GAT TTA AAC ATT ATT ACT AGT GCT CAG TCC AAT GAT ATC TAT      816
Gly Thr Asp Leu Asn Ile Ile Thr Ser Ala Gln Ser Asn Asp Ile Tyr
            260                 265                 270

ACT AAT CTT CTA GCT GAT TAT AAA AAA ATA GCG TCT AAA CTT AGC AAA      864
Thr Asn Leu Leu Ala Asp Tyr Lys Lys Ile Ala Ser Lys Leu Ser Lys
        275                 280                 285

GTA CAA GTA TCT AAT CCA CTA CTT AAT CCT TAT AAA GAT GTT TTT GAA      912
Val Gln Val Ser Asn Pro Leu Leu Asn Pro Tyr Lys Asp Val Phe Glu
    290                 295                 300

GCA AAG TAT GGA TTA GAT AAA GAT GCT AGC GGA ATT TAT TCG GTA AAT      960
Ala Lys Tyr Gly Leu Asp Lys Asp Ala Ser Gly Ile Tyr Ser Val Asn
305                 310                 315                 320

ATA AAC AAA TTT AAT GAT ATT TTT AAA AAA TTA TAC AGC TTT ACG GAA     1008
Ile Asn Lys Phe Asn Asp Ile Phe Lys Lys Leu Tyr Ser Phe Thr Glu
                325                 330                 335

TTT GAT TTA GCA ACT AAA TTT CAA GTT AAA TGT AGG CAA ACT TAT ATT     1056
Phe Asp Leu Ala Thr Lys Phe Gln Val Lys Cys Arg Gln Thr Tyr Ile
            340                 345                 350

GGA CAG TAT AAA TAC TTC AAA CTT TCA AAC TTG TTA AAT GAT TCT ATT     1104
Gly Gln Tyr Lys Tyr Phe Lys Leu Ser Asn Leu Leu Asn Asp Ser Ile
        355                 360                 365

TAT AAT ATA TCA GAA GGC TAT AAT ATA AAT AAT TTA AAG GTA AAT TTT     1152
Tyr Asn Ile Ser Glu Gly Tyr Asn Ile Asn Asn Leu Lys Val Asn Phe
    370                 375                 380

AGA GGA CAG AAT GCA AAT TTA AAT CCT AGA ATT ATT ACA CCA ATT ACA     1200
Arg Gly Gln Asn Ala Asn Leu Asn Pro Arg Ile Ile Thr Pro Ile Thr
385                 390                 395                 400

GGT AGA GGA CTA GTA AAA AAA ATC ATT AGA TTT TGT AAA AAT ATT GTT     1248
Gly Arg Gly Leu Val Lys Lys Ile Ile Arg Phe Cys Lys Asn Ile Val
                405                 410                 415

TCT GTA AAA GGC ATA AGG AAA TCA ATA TGT ATC GAA ATA AAT AAT GGT     1296
Ser Val Lys Gly Ile Arg Lys Ser Ile Cys Ile Glu Ile Asn Asn Gly
            420                 425                 430

GAG TTA TTT TTT GTG GCT TCC GAG AAT AGT TAT AAT GAT GAT AAT ATA     1344
Glu Leu Phe Phe Val Ala Ser Glu Asn Ser Tyr Asn Asp Asp Asn Ile
        435                 440                 445

AAT ACT CCT AAA GAA ATT GAC GAT ACA GTA ACT TCA AAT AAT AAT TAT     1392
Asn Thr Pro Lys Glu Ile Asp Asp Thr Val Thr Ser Asn Asn Asn Tyr
    450                 455                 460

GAA AAT GAT TTA GAT CAG GTT ATT TTA AAT TTT AAT AGT GAA TCA GCA     1440
Glu Asn Asp Leu Asp Gln Val Ile Leu Asn Phe Asn Ser Glu Ser Ala
465                 470                 475                 480

CCT GGA CTT TCA GAT GAA AAA TTA AAT TTA ACT ATC CAA AAT GAT GCT     1488
Pro Gly Leu Ser Asp Glu Lys Leu Asn Leu Thr Ile Gln Asn Asp Ala
                485                 490                 495

TAT ATA CCA AAA TAT GAT TCT AAT GGA ACA AGT GAT ATA GAA CAA CAT     1536
Tyr Ile Pro Lys Tyr Asp Ser Asn Gly Thr Ser Asp Ile Glu Gln His
            500                 505                 510

GAT GTT AAT GAA CTT AAT GTA TTT TTC TAT TTA GAT GCA CAG AAA GTG     1584
Asp Val Asn Glu Leu Asn Val Phe Phe Tyr Leu Asp Ala Gln Lys Val
        515                 520                 525

CCC GAA GGT GAA AAT AAT GTC AAT CTC ACC TCT TCA ATT GAT ACA GCA     1632
Pro Glu Gly Glu Asn Asn Val Asn Leu Thr Ser Ser Ile Asp Thr Ala
    530                 535                 540
```

-continued

```
TTA TTA GAA CAA CCT AAA ATA TAT ACA TTT TTT TCA TCA GAA TTT ATT      1680
Leu Leu Glu Gln Pro Lys Ile Tyr Thr Phe Phe Ser Ser Glu Phe Ile
545                 550                 555                 560

AAT AAT GTC AAT AAA CCT GTG CAA GCA GCA TTA TTT GTA AGC TGG ATA      1728
Asn Asn Val Asn Lys Pro Val Gln Ala Ala Leu Phe Val Ser Trp Ile
                565                 570                 575

CAA CAA GTG TTA GTA GAT TTT ACT ACT GAA GCT AAC CAA AAA AGT ACT      1776
Gln Gln Val Leu Val Asp Phe Thr Thr Glu Ala Asn Gln Lys Ser Thr
            580                 585                 590

GTT GAT AAA ATT GCA GAT ATT TCT ATA GTT GTT CCA TAT ATA GGT CTT      1824
Val Asp Lys Ile Ala Asp Ile Ser Ile Val Val Pro Tyr Ile Gly Leu
        595                 600                 605

GCT TTA AAT ATA GGA AAT GAA GCA CAA AAA GGA AAT TTT AAA GAT GCA      1872
Ala Leu Asn Ile Gly Asn Glu Ala Gln Lys Gly Asn Phe Lys Asp Ala
    610                 615                 620

CTT GAA TTA TTA GGA GCA GGT ATT TTA TTA GAA TTT GAA CCC GAG CTT      1920
Leu Glu Leu Leu Gly Ala Gly Ile Leu Leu Glu Phe Glu Pro Glu Leu
625                 630                 635                 640

TTA ATT CCT ACA ATT TTA GTA TTC ACG ATA AAA TCT TTT TTA GGT TCA      1968
Leu Ile Pro Thr Ile Leu Val Phe Thr Ile Lys Ser Phe Leu Gly Ser
                645                 650                 655

TCT GAT AAT AAA AAT AAA GTT ATT AAA GCA ATA AAT AAT GCA TTG AAA      2016
Ser Asp Asn Lys Asn Lys Val Ile Lys Ala Ile Asn Asn Ala Leu Lys
            660                 665                 670

GAA AGA GAT GAA AAA TGG AAA GAA GTA TAT AGT TTT ATA GTA TCG AAT      2064
Glu Arg Asp Glu Lys Trp Lys Glu Val Tyr Ser Phe Ile Val Ser Asn
        675                 680                 685

TGG ATG ACT AAA ATT AAT ACA CAA TTT AAT AAA AGA AAA GAA CAA ATG      2112
Trp Met Thr Lys Ile Asn Thr Gln Phe Asn Lys Arg Lys Glu Gln Met
    690                 695                 700

TAT CAA GCT TTA CAA AAT CAA GTA AAT GCA ATT AAA ACA ATA ATA GAA      2160
Tyr Gln Ala Leu Gln Asn Gln Val Asn Ala Ile Lys Thr Ile Ile Glu
705                 710                 715                 720

TCT AAG TAT AAT AGT TAT ACT TTA GAG GAA AAA AAT GAG CTT ACA AAT      2208
Ser Lys Tyr Asn Ser Tyr Thr Leu Glu Glu Lys Asn Glu Leu Thr Asn
                725                 730                 735

AAA TAT GAT ATT AAG CAA ATA GAA AAT GAA CTT AAT CAA AAG GTT TCT      2256
Lys Tyr Asp Ile Lys Gln Ile Glu Asn Glu Leu Asn Gln Lys Val Ser
            740                 745                 750

ATA GCA ATG AAT AAT ATA GAC AGG TTC TTA ACT GAA AGT TCT ATA TCC      2304
Ile Ala Met Asn Asn Ile Asp Arg Phe Leu Thr Glu Ser Ser Ile Ser
        755                 760                 765

TAT TTA ATG AAA TTA ATA AAT GAA GTA AAA ATT AAT AAA TTA AGA GAA      2352
Tyr Leu Met Lys Leu Ile Asn Glu Val Lys Ile Asn Lys Leu Arg Glu
    770                 775                 780

TAT GAT GAG AAT GTC AAA ACG TAT TTA TTG AAT TAT ATT ATA CAA CAT      2400
Tyr Asp Glu Asn Val Lys Thr Tyr Leu Leu Asn Tyr Ile Ile Gln His
785                 790                 795                 800

GGA TCA ATC TTG GGA GAG AGT CAG CAA GAA CTA AAT TCT ATG GTA ACT      2448
Gly Ser Ile Leu Gly Glu Ser Gln Gln Glu Leu Asn Ser Met Val Thr
                805                 810                 815

GAT ACC CTA AAT AAT AGT ATT CCT TTT AAG CTT TCT TCT TAT ACA GAT      2496
Asp Thr Leu Asn Asn Ser Ile Pro Phe Lys Leu Ser Ser Tyr Thr Asp
            820                 825                 830

GAT AAA ATT TTA ATT TCA TAT TTT AAT AAA TTC TTT AAG AGA ATT AAA      2544
Asp Lys Ile Leu Ile Ser Tyr Phe Asn Lys Phe Phe Lys Arg Ile Lys
        835                 840                 845

AGT AGT TCA GTT TTA AAT ATG AGA TAT AAA AAT GAT AAA TAC GTA GAT      2592
Ser Ser Ser Val Leu Asn Met Arg Tyr Lys Asn Asp Lys Tyr Val Asp
    850                 855                 860
```

-continued

```
ACT TCA GGA TAT GAT TCA AAT ATA AAT ATT AAT GGA GAT GTA TAT AAA     2640
Thr Ser Gly Tyr Asp Ser Asn Ile Asn Ile Asn Gly Asp Val Tyr Lys
865                 870                 875                 880

TAT CCA ACT AAT AAA AAT CAA TTT GGA ATA TAT AAT GAT AAA CTT AGT     2688
Tyr Pro Thr Asn Lys Asn Gln Phe Gly Ile Tyr Asn Asp Lys Leu Ser
                885                 890                 895

GAA GTT AAT ATA TCT CAA AAT GAT TAC ATT ATA TAT GAT AAT AAA TAT     2736
Glu Val Asn Ile Ser Gln Asn Asp Tyr Ile Ile Tyr Asp Asn Lys Tyr
            900                 905                 910

AAA AAT TTT AGT ATT AGT TTT TGG GTA AGA ATT CCT AAC TAT GAT AAT     2784
Lys Asn Phe Ser Ile Ser Phe Trp Val Arg Ile Pro Asn Tyr Asp Asn
        915                 920                 925

AAG ATA GTA AAT GTT AAT AAT GAA TAC ACT ATA ATA AAT TGT ATG AGA     2832
Lys Ile Val Asn Val Asn Asn Glu Tyr Thr Ile Ile Asn Cys Met Arg
    930                 935                 940

GAT AAT AAT TCA GGA TGG AAA GTA TCT CTT AAT CAT AAT GAA ATA ATT     2880
Asp Asn Asn Ser Gly Trp Lys Val Ser Leu Asn His Asn Glu Ile Ile
945                 950                 955                 960

TGG ACA TTG CAA GAT AAT GCA GGA ATT AAT CAA AAA TTA GCA TTT AAC     2928
Trp Thr Leu Gln Asp Asn Ala Gly Ile Asn Gln Lys Leu Ala Phe Asn
                965                 970                 975

TAT GGT AAC GCA AAT GGT ATT TCT GAT TAT ATA AAT AAG TGG ATT TTT     2976
Tyr Gly Asn Ala Asn Gly Ile Ser Asp Tyr Ile Asn Lys Trp Ile Phe
            980                 985                 990

GTA ACT ATA ACT AAT GAT AGA TTA GGA GAT TCT AAA CTT TAT ATT AAT     3024
Val Thr Ile Thr Asn Asp Arg Leu Gly Asp Ser Lys Leu Tyr Ile Asn
        995                 1000                1005

GGA AAT TTA ATA GAT CAA AAA TCA ATT TTA AAT TTA GGT AAT ATT CAT     3072
Gly Asn Leu Ile Asp Gln Lys Ser Ile Leu Asn Leu Gly Asn Ile His
    1010                1015                1020

GTT AGT GAC AAT ATA TTA TTT AAA ATA GTT AAT TGT AGT TAT ACA AGA     3120
Val Ser Asp Asn Ile Leu Phe Lys Ile Val Asn Cys Ser Tyr Thr Arg
1025                1030                1035                1040

TAT ATT GGT ATT AGA TAT TTT AAT ATT TTT GAT AAA GAA TTA GAT GAA     3168
Tyr Ile Gly Ile Arg Tyr Phe Asn Ile Phe Asp Lys Glu Leu Asp Glu
                1045                1050                1055

ACA GAA ATT CAA ACT TTA TAT AGC AAT GAA CCT AAT ACA AAT ATT TTG     3216
Thr Glu Ile Gln Thr Leu Tyr Ser Asn Glu Pro Asn Thr Asn Ile Leu
            1060                1065                1070

AAG GAT TTT TGG GGA AAT TAT TTG CTT TAT GAC AAA GAA TAC TAT TTA     3264
Lys Asp Phe Trp Gly Asn Tyr Leu Leu Tyr Asp Lys Glu Tyr Tyr Leu
        1075                1080                1085

TTA AAT GTG TTA AAA CCA AAT AAC TTT ATT GAT AGG AGA AAA GAT TCT     3312
Leu Asn Val Leu Lys Pro Asn Asn Phe Ile Asp Arg Arg Lys Asp Ser
    1090                1095                1100

ACT TTA AGC ATT AAT AAT ATA AGA AGC ACT ATT CTT TTA GCT AAT AGA     3360
Thr Leu Ser Ile Asn Asn Ile Arg Ser Thr Ile Leu Leu Ala Asn Arg
1105                1110                1115                1120

TTA TAT AGT GGA ATA AAA GTT AAA ATA CAA AGA GTT AAT AAT AGT AGT     3408
Leu Tyr Ser Gly Ile Lys Val Lys Ile Gln Arg Val Asn Asn Ser Ser
                1125                1130                1135

ACT AAC GAT AAT CTT GTT AGA AAG AAT GAT CAG GTA TAT ATT AAT TTT     3456
Thr Asn Asp Asn Leu Val Arg Lys Asn Asp Gln Val Tyr Ile Asn Phe
            1140                1145                1150

GTA GCC AGC AAA ACT CAC TTA TTT CCA TTA TAT GCT GAT ACA GCT ACC     3504
Val Ala Ser Lys Thr His Leu Phe Pro Leu Tyr Ala Asp Thr Ala Thr
        1155                1160                1165

ACA AAT AAA GAG AAA ACA ATA AAA ATA TCA TCA TCT GGC AAT AGA TTT     3552
Thr Asn Lys Glu Lys Thr Ile Lys Ile Ser Ser Ser Gly Asn Arg Phe
```

-continued

```
    1170                1175                1180

AAT CAA GTA GTA GTT ATG AAT TCA GTA GGA AAT AAT TGT ACA ATG AAT      3600
Asn Gln Val Val Val Met Asn Ser Val Gly Asn Asn Cys Thr Met Asn
1185                1190                1195                1200

TTT AAA AAT AAT AAT GGA AAT AAT ATT GGG TTG TTA GGT TTC AAG GCA      3648
Phe Lys Asn Asn Asn Gly Asn Asn Ile Gly Leu Leu Gly Phe Lys Ala
                1205                1210                1215

GAT ACT GTA GTT GCT AGT ACT TGG TAT TAT ACA CAT ATG AGA GAT CAT      3696
Asp Thr Val Val Ala Ser Thr Trp Tyr Tyr Thr His Met Arg Asp His
            1220                1225                1230

ACA AAC AGC AAT GGA TGT TTT TGG AAC TTT ATT TCT GAA GAA CAT GGA      3744
Thr Asn Ser Asn Gly Cys Phe Trp Asn Phe Ile Ser Glu Glu His Gly
        1235                1240                1245

TGG CAA GAA AAA TAA                                                  3759
Trp Gln Glu Lys
    1250


(2) INFORMATION FOR SEQ ID NO:52:

     (i) SEQUENCE CHARACTERISTICS:
          (A) LENGTH: 1252 amino acids
          (B) TYPE: amino acid
          (D) TOPOLOGY: linear

    (ii) MOLECULE TYPE: protein

    (xi) SEQUENCE DESCRIPTION: SEQ ID NO:52:

Met Pro Lys Ile Asn Ser Phe Asn Tyr Asn Asp Pro Val Asn Asp Arg
  1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240
```

-continued

```
Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
```

-continued

```
        660                 665                 670

Glu Arg Asp Glu Lys Trp Lys Glu Val Tyr Ser Phe Ile Val Ser Asn
    675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
            1060                1065                1070

Lys Asp Phe Trp Gly Asn Tyr Leu Leu Tyr Asp Lys Glu Tyr Tyr Leu
        1075                1080                1085
```

-continued

```
Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Phe Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
                1205                1210                1215

Asp Thr Val Val Ala Ser Thr Trp Tyr Tyr Thr His Met Arg Asp His
            1220                1225                1230

Thr Asn Ser Asn Gly Cys Phe Trp Asn Phe Ile Ser Glu Glu His Gly
        1235                1240                1245

Trp Gln Glu Lys
    1250
```

(2) INFORMATION FOR SEQ ID NO:53:

(i) SEQUENCE CHARACTERISTICS:
(A) LENGTH: 1463 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(ix) FEATURE:
(A) NAME/KEY: CDS
(B) LOCATION: 108..1460

(xi) SEQUENCE DESCRIPTION: SEQ ID NO:53:

```
AGATCTCGAT CCCGCGAAAT TAATACGACT CACTATAGGG GAATTGTGAG CGGATAACAA     60

TTCCCCTCTA GAAATAATTT TGTTTAACTT TAAGAAGGAG ATATACC ATG GGC CAT      116
                                                    Met Gly His
                                                      1

CAT CAT CAT CAT CAT CAT CAT CAT CAC AGC AGC GGC CAT ATC GAA GGT      164
His His His His His His His His His Ser Ser Gly His Ile Glu Gly
      5                  10                  15

CGT CAT ATG GCT AGC ATG GCT CTT TCT TCT TAT ACA GAT GAT AAA ATT      212
Arg His Met Ala Ser Met Ala Leu Ser Ser Tyr Thr Asp Asp Lys Ile
 20                  25                  30                  35

TTA ATT TCA TAT TTT AAT AAG TTC TTT AAG AGA ATT AAA AGT AGT TCT      260
Leu Ile Ser Tyr Phe Asn Lys Phe Phe Lys Arg Ile Lys Ser Ser Ser
                 40                  45                  50

GTT TTA AAT ATG AGA TAT AAA AAT GAT AAA TAC GTA GAT ACT TCA GGA      308
Val Leu Asn Met Arg Tyr Lys Asn Asp Lys Tyr Val Asp Thr Ser Gly
             55                  60                  65

TAT GAT TCA AAT ATA AAT ATT AAT GGA GAT GTA TAT AAA TAT CCA ACT      356
Tyr Asp Ser Asn Ile Asn Ile Asn Gly Asp Val Tyr Lys Tyr Pro Thr
         70                  75                  80

AAT AAA AAT CAA TTT GGA ATA TAT AAT GAT AAA CTT AGT GAA GTT AAT      404
```

-continued

```
Asn Lys Asn Gln Phe Gly Ile Tyr Asn Asp Lys Leu Ser Glu Val Asn
     85                  90                  95

ATA TCT CAA AAT GAT TAC ATT ATA TAT GAT AAT AAA TAT AAA AAT TTT       452
Ile Ser Gln Asn Asp Tyr Ile Ile Tyr Asp Asn Lys Tyr Lys Asn Phe
100                 105                 110                 115

AGT ATT AGT TTT TGG GTA AGA ATT CCT AAC TAT GAT AAT AAG ATA GTA       500
Ser Ile Ser Phe Trp Val Arg Ile Pro Asn Tyr Asp Asn Lys Ile Val
                120                 125                 130

AAT GTT AAT AAT GAA TAC ACT ATA ATA AAT TGT ATG AGG GAT AAT AAT       548
Asn Val Asn Asn Glu Tyr Thr Ile Ile Asn Cys Met Arg Asp Asn Asn
            135                 140                 145

TCA GGA TGG AAA GTA TCT CTT AAT CAT AAT GAA ATA ATT TGG ACA TTG       596
Ser Gly Trp Lys Val Ser Leu Asn His Asn Glu Ile Ile Trp Thr Leu
        150                 155                 160

CAA GAT AAT TCA GGA ATT AAT CAA AAA TTA GCA TTT AAC TAT GGT AAC       644
Gln Asp Asn Ser Gly Ile Asn Gln Lys Leu Ala Phe Asn Tyr Gly Asn
    165                 170                 175

GCA AAT GGT ATT TCT GAT TAT ATA AAT AAG TGG ATT TTT GTA ACT ATA       692
Ala Asn Gly Ile Ser Asp Tyr Ile Asn Lys Trp Ile Phe Val Thr Ile
180                 185                 190                 195

ACT AAT GAT AGA TTA GGA GAT TCT AAA CTT TAT ATT AAT GGA AAT TTA       740
Thr Asn Asp Arg Leu Gly Asp Ser Lys Leu Tyr Ile Asn Gly Asn Leu
                200                 205                 210

ATA GAT AAA AAA TCA ATT TTA AAT TTA GGT AAT ATT CAT GTT AGT GAC       788
Ile Asp Lys Lys Ser Ile Leu Asn Leu Gly Asn Ile His Val Ser Asp
            215                 220                 225

AAT ATA TTA TTT AAA ATA GTT AAT TGT AGT TAT ACA AGA TAT ATT GGT       836
Asn Ile Leu Phe Lys Ile Val Asn Cys Ser Tyr Thr Arg Tyr Ile Gly
        230                 235                 240

ATT AGA TAT TTT AAT ATT TTT GAT AAA GAA TTA GAT GAA ACA GAA ATT       884
Ile Arg Tyr Phe Asn Ile Phe Asp Lys Glu Leu Asp Glu Thr Glu Ile
    245                 250                 255

CAA ACT TTA TAT AAC AAT GAA CCT AAT GCA AAT ATT TTA AAG GAT TTT       932
Gln Thr Leu Tyr Asn Asn Glu Pro Asn Ala Asn Ile Leu Lys Asp Phe
260                 265                 270                 275

TGG GGA AAT TAT TTG CTT TAT GAC AAA GAA TAC TAT TTA TTA AAT GTG       980
Trp Gly Asn Tyr Leu Leu Tyr Asp Lys Glu Tyr Tyr Leu Leu Asn Val
                280                 285                 290

TTA AAA CCA AAT AAC TTT ATT AAT AGG AGA ACA GAT TCT ACT TTA AGC      1028
Leu Lys Pro Asn Asn Phe Ile Asn Arg Arg Thr Asp Ser Thr Leu Ser
            295                 300                 305

ATT AAT AAT ATA AGA AGC ACT ATT CTT TTA GCT AAT AGA TTA TAT AGT      1076
Ile Asn Asn Ile Arg Ser Thr Ile Leu Leu Ala Asn Arg Leu Tyr Ser
        310                 315                 320

GGA ATA AAA GTT AAA ATA CAA AGA GTT AAT AAT AGT AGT ACT AAC GAT      1124
Gly Ile Lys Val Lys Ile Gln Arg Val Asn Asn Ser Ser Thr Asn Asp
    325                 330                 335

AAT CTT GTT AGA AAG AAT GAT CAG GTA TAT ATT AAT TTT GTA GCC AGC      1172
Asn Leu Val Arg Lys Asn Asp Gln Val Tyr Ile Asn Phe Val Ala Ser
340                 345                 350                 355

AAA ACT CAC TTA CTT CCA TTA TAT GCT GAT ACA GCT ACC ACA AAT AAA      1220
Lys Thr His Leu Leu Pro Leu Tyr Ala Asp Thr Ala Thr Thr Asn Lys
                360                 365                 370

GAG AAA ACA ATA AAA ATA TCA TCA TCT GGC AAT AGA TTT AAT CAA GTA      1268
Glu Lys Thr Ile Lys Ile Ser Ser Ser Gly Asn Arg Phe Asn Gln Val
            375                 380                 385

GTA GTT ATG AAT TCA GTA GGA AAT TGT ACA ATG AAT TTT AAA AAT AAT      1316
Val Val Met Asn Ser Val Gly Asn Cys Thr Met Asn Phe Lys Asn Asn
        390                 395                 400
```

-continued

```
AAT GGA AAT AAT ATT GGG TTG TTA GGT TTC AAG GCA GAT ACT GTA GTT      1364
Asn Gly Asn Asn Ile Gly Leu Leu Gly Phe Lys Ala Asp Thr Val Val
    405                 410                 415

GCT AGT ACT TGG TAT TAT ACA CAT ATG AGA GAT AAT ACA AAC AGC AAT      1412
Ala Ser Thr Trp Tyr Tyr Thr His Met Arg Asp Asn Thr Asn Ser Asn
420                 425                 430                 435

GGA TTT TTT TGG AAC TTT ATT TCT GAA GAA CAT GGA TGG CAA GAA AAA      1460
Gly Phe Phe Trp Asn Phe Ile Ser Glu Glu His Gly Trp Gln Glu Lys
                440                 445                 450

TAA                                                                  1463
```

(2) INFORMATION FOR SEQ ID NO:54:

(i) SEQUENCE CHARACTERISTICS:
(A) LENGTH: 451 amino acids
(B) TYPE: amino acid
(D) TOPOLOGY: linear (ii) MOLECULE TYPE: protein (xi) SEQUENCE DESCRIPTION: SEQ ID NO:54:

```
Met Gly His His His His His His His His His His Ser Ser Gly His
  1               5                  10                  15

Ile Glu Gly Arg His Met Ala Ser Met Ala Leu Ser Ser Tyr Thr Asp
             20                  25                  30

Asp Lys Ile Leu Ile Ser Tyr Phe Asn Lys Phe Phe Lys Arg Ile Lys
         35                  40                  45

Ser Ser Ser Val Leu Asn Met Arg Tyr Lys Asn Asp Lys Tyr Val Asp
     50                  55                  60

Thr Ser Gly Tyr Asp Ser Asn Ile Asn Ile Asn Gly Asp Val Tyr Lys
 65                  70                  75                  80

Tyr Pro Thr Asn Lys Asn Gln Phe Gly Ile Tyr Asn Asp Lys Leu Ser
                 85                  90                  95

Glu Val Asn Ile Ser Gln Asn Asp Tyr Ile Ile Tyr Asp Asn Lys Tyr
            100                 105                 110

Lys Asn Phe Ser Ile Ser Phe Trp Val Arg Ile Pro Asn Tyr Asp Asn
        115                 120                 125

Lys Ile Val Asn Val Asn Asn Glu Tyr Thr Ile Ile Asn Cys Met Arg
    130                 135                 140

Asp Asn Asn Ser Gly Trp Lys Val Ser Leu Asn His Asn Glu Ile Ile
145                 150                 155                 160

Trp Thr Leu Gln Asp Asn Ser Gly Ile Asn Gln Lys Leu Ala Phe Asn
                165                 170                 175

Tyr Gly Asn Ala Asn Gly Ile Ser Asp Tyr Ile Asn Lys Trp Ile Phe
            180                 185                 190

Val Thr Ile Thr Asn Asp Arg Leu Gly Asp Ser Lys Leu Tyr Ile Asn
        195                 200                 205

Gly Asn Leu Ile Asp Lys Lys Ser Ile Leu Asn Leu Gly Asn Ile His
    210                 215                 220

Val Ser Asp Asn Ile Leu Phe Lys Ile Val Asn Cys Ser Tyr Thr Arg
225                 230                 235                 240

Tyr Ile Gly Ile Arg Tyr Phe Asn Ile Phe Asp Lys Glu Leu Asp Glu
                245                 250                 255

Thr Glu Ile Gln Thr Leu Tyr Asn Asn Glu Pro Asn Ala Asn Ile Leu
            260                 265                 270

Lys Asp Phe Trp Gly Asn Tyr Leu Leu Tyr Asp Lys Glu Tyr Tyr Leu
        275                 280                 285
```

-continued

```
Leu Asn Val Leu Lys Pro Asn Asn Phe Ile Asn Arg Arg Thr Asp Ser
    290                 295                 300

Thr Leu Ser Ile Asn Asn Ile Arg Ser Thr Ile Leu Leu Ala Asn Arg
305                 310                 315                 320

Leu Tyr Ser Gly Ile Lys Val Lys Ile Gln Arg Val Asn Asn Ser Ser
                325                 330                 335

Thr Asn Asp Asn Leu Val Arg Lys Asn Asp Gln Val Tyr Ile Asn Phe
            340                 345                 350

Val Ala Ser Lys Thr His Leu Leu Pro Leu Tyr Ala Asp Thr Ala Thr
        355                 360                 365

Thr Asn Lys Glu Lys Thr Ile Lys Ile Ser Ser Ser Gly Asn Arg Phe
    370                 375                 380

Asn Gln Val Val Val Met Asn Ser Val Gly Asn Cys Thr Met Asn Phe
385                 390                 395                 400

Lys Asn Asn Asn Gly Asn Asn Ile Gly Leu Leu Gly Phe Lys Ala Asp
                405                 410                 415

Thr Val Val Ala Ser Thr Trp Tyr Tyr Thr His Met Arg Asp Asn Thr
            420                 425                 430

Asn Ser Asn Gly Phe Phe Trp Asn Phe Ile Ser Glu Glu His Gly Trp
        435                 440                 445

Gln Glu Lys
    450
```

(2) INFORMATION FOR SEQ ID NO:55:

(i) SEQUENCE CHARACTERISTICS:
(A) LENGTH: 1472 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "DNA"

(ix) FEATURE:
(A) NAME/KEY: CDS
(B) LOCATION: 108..1463

(xi) SEQUENCE DESCRIPTION: SEQ ID NO:55:

```
AGATCTCGAT CCCGCGAAAT TAATACGACT CACTATAGGG GAATTGTGAG CGGATAACAA      60

TTCCCCTCTA GAAATAATTT TGTTTAACTT TAAGAAGGAG ATATACC ATG GGC CAT       116
                                                    Met Gly His
                                                      1

CAT CAT CAT CAT CAT CAT CAT CAT CAC AGC AGC GGC CAT ATC GAA GGT       164
His His His His His His His His His Ser Ser Gly His Ile Glu Gly
      5                  10                  15

CGT CAT ATG GCT AGC ATG GCT CTT TCT TCT TAT ACA GAT GAT AAA ATT       212
Arg His Met Ala Ser Met Ala Leu Ser Ser Tyr Thr Asp Asp Lys Ile
 20                  25                  30                  35

TTA ATT TCA TAT TTT AAT AAA TTC TTT AAG AGA ATT AAA AGT AGT TCA       260
Leu Ile Ser Tyr Phe Asn Lys Phe Phe Lys Arg Ile Lys Ser Ser Ser
                 40                  45                  50

GTT TTA AAT ATG AGA TAT AAA AAT GAT AAA TAC GTA GAT ACT TCA GGA       308
Val Leu Asn Met Arg Tyr Lys Asn Asp Lys Tyr Val Asp Thr Ser Gly
             55                  60                  65

TAT GAT TCA AAT ATA AAT ATT AAT GGA GAT GTA TAT AAA TAT CCA ACT       356
Tyr Asp Ser Asn Ile Asn Ile Asn Gly Asp Val Tyr Lys Tyr Pro Thr
         70                  75                  80

AAT AAA AAT CAA TTT GGA ATA TAT AAT GAT AAA CTT AGT GAA GTT AAT       404
```

-continued

```
Asn Lys Asn Gln Phe Gly Ile Tyr Asn Asp Lys Leu Ser Glu Val Asn
     85                  90                  95

ATA TCT CAA AAT GAT TAC ATT ATA TAT GAT AAT AAA TAT AAA AAT TTT      452
Ile Ser Gln Asn Asp Tyr Ile Ile Tyr Asp Asn Lys Tyr Lys Asn Phe
100                 105                 110                 115

AGT ATT AGT TTT TGG GTA AGA ATT CCT AAC TAT GAT AAT AAG ATA GTA      500
Ser Ile Ser Phe Trp Val Arg Ile Pro Asn Tyr Asp Asn Lys Ile Val
                120                 125                 130

AAT GTT AAT AAT GAA TAC ACT ATA ATA AAT TGT ATG AGA GAT AAT AAT      548
Asn Val Asn Asn Glu Tyr Thr Ile Ile Asn Cys Met Arg Asp Asn Asn
            135                 140                 145

TCA GGA TGG AAA GTA TCT CTT AAT CAT AAT GAA ATA ATT TGG ACA TTG      596
Ser Gly Trp Lys Val Ser Leu Asn His Asn Glu Ile Ile Trp Thr Leu
        150                 155                 160

CAA GAT AAT GCA GGA ATT AAT CAA AAA TTA GCA TTT AAC TAT GGT AAC      644
Gln Asp Asn Ala Gly Ile Asn Gln Lys Leu Ala Phe Asn Tyr Gly Asn
    165                 170                 175

GCA AAT GGT ATT TCT GAT TAT ATA AAT AAG TGG ATT TTT GTA ACT ATA      692
Ala Asn Gly Ile Ser Asp Tyr Ile Asn Lys Trp Ile Phe Val Thr Ile
180                 185                 190                 195

ACT AAT GAT AGA TTA GGA GAT TCT AAA CTT TAT ATT AAT GGA AAT TTA      740
Thr Asn Asp Arg Leu Gly Asp Ser Lys Leu Tyr Ile Asn Gly Asn Leu
                200                 205                 210

ATA GAT CAA AAA TCA ATT TTA AAT TTA GGT AAT ATT CAT GTT AGT GAC      788
Ile Asp Gln Lys Ser Ile Leu Asn Leu Gly Asn Ile His Val Ser Asp
            215                 220                 225

AAT ATA TTA TTT AAA ATA GTT AAT TGT AGT TAT ACA AGA TAT ATT GGT      836
Asn Ile Leu Phe Lys Ile Val Asn Cys Ser Tyr Thr Arg Tyr Ile Gly
        230                 235                 240

ATT AGA TAT TTT AAT ATT TTT GAT AAA GAA TTA GAT GAA ACA GAA ATT      884
Ile Arg Tyr Phe Asn Ile Phe Asp Lys Glu Leu Asp Glu Thr Glu Ile
    245                 250                 255

CAA ACT TTA TAT AGC AAT GAA CCT AAT ACA AAT ATT TTG AAG GAT TTT      932
Gln Thr Leu Tyr Ser Asn Glu Pro Asn Thr Asn Ile Leu Lys Asp Phe
260                 265                 270                 275

TGG GGA AAT TAT TTG CTT TAT GAC AAA GAA TAC TAT TTA TTA AAT GTG      980
Trp Gly Asn Tyr Leu Leu Tyr Asp Lys Glu Tyr Tyr Leu Leu Asn Val
                280                 285                 290

TTA AAA CCA AAT AAC TTT ATT GAT AGG AGA AAA GAT TCT ACT TTA AGC     1028
Leu Lys Pro Asn Asn Phe Ile Asp Arg Arg Lys Asp Ser Thr Leu Ser
            295                 300                 305

ATT AAT AAT ATA AGA AGC ACT ATT CTT TTA GCT AAT AGA TTA TAT AGT     1076
Ile Asn Asn Ile Arg Ser Thr Ile Leu Leu Ala Asn Arg Leu Tyr Ser
        310                 315                 320

GGA ATA AAA GTT AAA ATA CAA AGA GTT AAT AAT AGT AGT ACT AAC GAT     1124
Gly Ile Lys Val Lys Ile Gln Arg Val Asn Asn Ser Ser Thr Asn Asp
    325                 330                 335

AAT CTT GTT AGA AAG AAT GAT CAG GTA TAT ATT AAT TTT GTA GCC AGC     1172
Asn Leu Val Arg Lys Asn Asp Gln Val Tyr Ile Asn Phe Val Ala Ser
340                 345                 350                 355

AAA ACT CAC TTA TTT CCA TTA TAT GCT GAT ACA GCT ACC ACA AAT AAA     1220
Lys Thr His Leu Phe Pro Leu Tyr Ala Asp Thr Ala Thr Thr Asn Lys
                360                 365                 370

GAG AAA ACA ATA AAA ATA TCA TCA TCT GGC AAT AGA TTT AAT CAA GTA     1268
Glu Lys Thr Ile Lys Ile Ser Ser Ser Gly Asn Arg Phe Asn Gln Val
            375                 380                 385

GTA GTT ATG AAT TCA GTA GGA AAT AAT TGT ACA ATG AAT TTT AAA AAT     1316
Val Val Met Asn Ser Val Gly Asn Asn Cys Thr Met Asn Phe Lys Asn
        390                 395                 400
```

-continued

```
AAT AAT GGA AAT AAT ATT GGG TTG TTA GGT TTC AAG GCA GAT ACT GTA      1364
Asn Asn Gly Asn Asn Ile Gly Leu Leu Gly Phe Lys Ala Asp Thr Val
    405                 410                 415

GTT GCT AGT ACT TGG TAT TAT ACA CAT ATG AGA GAT CAT ACA AAC AGC      1412
Val Ala Ser Thr Trp Tyr Tyr Thr His Met Arg Asp His Thr Asn Ser
420                 425                 430                 435

AAT GGA TGT TTT TGG AAC TTT ATT TCT GAA GAA CAT GGA TGG CAA GAA      1460
Asn Gly Cys Phe Trp Asn Phe Ile Ser Glu Glu His Gly Trp Gln Glu
                440                 445                 450

AAA TAAAAGCTT                                                        1472
Lys
```

(2) INFORMATION FOR SEQ ID NO:56:

(i) SEQUENCE CHARACTERISTICS:
(A) LENGTH: 452 amino acids
(B) TYPE: amino acid
(D) TOPOLOGY: linear (ii) MOLECULE TYPE: protein (xi) SEQUENCE DESCRIPTION: SEQ ID NO:56:

```
Met Gly His His His His His His His His His His Ser Ser Gly His
  1               5                  10                  15

Ile Glu Gly Arg His Met Ala Ser Met Ala Leu Ser Ser Tyr Thr Asp
             20                  25                  30

Asp Lys Ile Leu Ile Ser Tyr Phe Asn Lys Phe Phe Lys Arg Ile Lys
         35                  40                  45

Ser Ser Ser Val Leu Asn Met Arg Tyr Lys Asn Asp Lys Tyr Val Asp
     50                  55                  60

Thr Ser Gly Tyr Asp Ser Asn Ile Asn Ile Asn Gly Asp Val Tyr Lys
 65                  70                  75                  80

Tyr Pro Thr Asn Lys Asn Gln Phe Gly Ile Tyr Asn Asp Lys Leu Ser
                 85                  90                  95

Glu Val Asn Ile Ser Gln Asn Asp Tyr Ile Ile Tyr Asp Asn Lys Tyr
            100                 105                 110

Lys Asn Phe Ser Ile Ser Phe Trp Val Arg Ile Pro Asn Tyr Asp Asn
        115                 120                 125

Lys Ile Val Asn Val Asn Asn Glu Tyr Thr Ile Ile Asn Cys Met Arg
    130                 135                 140

Asp Asn Asn Ser Gly Trp Lys Val Ser Leu Asn His Asn Glu Ile Ile
145                 150                 155                 160

Trp Thr Leu Gln Asp Asn Ala Gly Ile Asn Gln Lys Leu Ala Phe Asn
                165                 170                 175

Tyr Gly Asn Ala Asn Gly Ile Ser Asp Tyr Ile Asn Lys Trp Ile Phe
            180                 185                 190

Val Thr Ile Thr Asn Asp Arg Leu Gly Asp Ser Lys Leu Tyr Ile Asn
        195                 200                 205

Gly Asn Leu Ile Asp Gln Lys Ser Ile Leu Asn Leu Gly Asn Ile His
    210                 215                 220

Val Ser Asp Asn Ile Leu Phe Lys Ile Val Asn Cys Ser Tyr Thr Arg
225                 230                 235                 240

Tyr Ile Gly Ile Arg Tyr Phe Asn Ile Phe Asp Lys Glu Leu Asp Glu
                245                 250                 255

Thr Glu Ile Gln Thr Leu Tyr Ser Asn Glu Pro Asn Thr Asn Ile Leu
            260                 265                 270

Lys Asp Phe Trp Gly Asn Tyr Leu Leu Tyr Asp Lys Glu Tyr Tyr Leu
```

-continued

```
        275                 280                 285

Leu Asn Val Leu Lys Pro Asn Asn Phe Ile Asp Arg Arg Lys Asp Ser
    290                 295                 300

Thr Leu Ser Ile Asn Asn Ile Arg Ser Thr Ile Leu Leu Ala Asn Arg
305                 310                 315                 320

Leu Tyr Ser Gly Ile Lys Val Lys Ile Gln Arg Val Asn Asn Ser Ser
                325                 330                 335

Thr Asn Asp Asn Leu Val Arg Lys Asn Asp Gln Val Tyr Ile Asn Phe
            340                 345                 350

Val Ala Ser Lys Thr His Leu Phe Pro Leu Tyr Ala Asp Thr Ala Thr
        355                 360                 365

Thr Asn Lys Glu Lys Thr Ile Lys Ile Ser Ser Ser Gly Asn Arg Phe
    370                 375                 380

Asn Gln Val Val Val Met Asn Ser Val Gly Asn Asn Cys Thr Met Asn
385                 390                 395                 400

Phe Lys Asn Asn Asn Gly Asn Asn Ile Gly Leu Leu Gly Phe Lys Ala
                405                 410                 415

Asp Thr Val Val Ala Ser Thr Trp Tyr Tyr Thr His Met Arg Asp His
            420                 425                 430

Thr Asn Ser Asn Gly Cys Phe Trp Asn Phe Ile Ser Glu Glu His Gly
        435                 440                 445

Trp Gln Glu Lys
    450
```

(2) INFORMATION FOR SEQ ID NO:57:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:57:

CGCCATGGCT CTTTCTTCTT ATACAGATGA T 31

(2) INFORMATION FOR SEQ ID NO:58:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:58:

GCAAGCTTTT ATTTTTCTTG CCATCCATG 29

(2) INFORMATION FOR SEQ ID NO:59:

(i) SEQUENCE CHARACTERISTICS:
(A) LENGTH: 3876 base pairs
(B) TYPE: nucleic acid
(C) STRANDEDNESS: double
(D) TOPOLOGY: linear (ii) MOLECULE TYPE: DNA (genomic)

(ix) FEATURE:

-continued

```
        (A) NAME/KEY: CDS
        (B) LOCATION: 1..3873

    (xi) SEQUENCE DESCRIPTION: SEQ ID NO:59:

ATG CCA ATA ACA ATT AAC AAC TTT AAT TAT TCA GAT CCT GTT GAT AAT        48
Met Pro Ile Thr Ile Asn Asn Phe Asn Tyr Ser Asp Pro Val Asp Asn
  1               5                  10                  15

AAA AAT ATT TTA TAT TTA GAT ACT CAT TTA AAT ACA CTA GCT AAT GAG        96
Lys Asn Ile Leu Tyr Leu Asp Thr His Leu Asn Thr Leu Ala Asn Glu
             20                  25                  30

CCT GAA AAA GCC TTT CGC ATT ACA GGA AAT ATA TGG GTA ATA CCT GAT       144
Pro Glu Lys Ala Phe Arg Ile Thr Gly Asn Ile Trp Val Ile Pro Asp
         35                  40                  45

AGA TTT TCA AGA AAT TCT AAT CCA AAT TTA AAT AAA CCT CCT CGA GTT       192
Arg Phe Ser Arg Asn Ser Asn Pro Asn Leu Asn Lys Pro Pro Arg Val
     50                  55                  60

ACA AGC CCT AAA AGT GGT TAT TAT GAT CCT AAT TAT TTG AGT ACT GAT       240
Thr Ser Pro Lys Ser Gly Tyr Tyr Asp Pro Asn Tyr Leu Ser Thr Asp
 65                  70                  75                  80

TCT GAC AAA GAT ACA TTT TTA AAA GAA ATT ATA AAG TTA TTT AAA AGA       288
Ser Asp Lys Asp Thr Phe Leu Lys Glu Ile Ile Lys Leu Phe Lys Arg
                 85                  90                  95

ATT AAT TCT AGA GAA ATA GGA GAA GAA TTA ATA TAT AGA CTT TCG ACA       336
Ile Asn Ser Arg Glu Ile Gly Glu Glu Leu Ile Tyr Arg Leu Ser Thr
            100                 105                 110

GAT ATA CCC TTT CCT GGG AAT AAC AAT ACT CCA ATT AAT ACT TTT GAT       384
Asp Ile Pro Phe Pro Gly Asn Asn Asn Thr Pro Ile Asn Thr Phe Asp
        115                 120                 125

TTT GAT GTA GAT TTT AAC AGT GTT GAT GTT AAA ACT AGA CAA GGT AAC       432
Phe Asp Val Asp Phe Asn Ser Val Asp Val Lys Thr Arg Gln Gly Asn
    130                 135                 140

AAC TGG GTT AAA ACT GGT AGC ATA AAT CCT AGT GTT ATA ATA ACT GGA       480
Asn Trp Val Lys Thr Gly Ser Ile Asn Pro Ser Val Ile Ile Thr Gly
145                 150                 155                 160

CCT AGA GAA AAC ATT ATA GAT CCA GAA ACT TCT ACG TTT AAA TTA ACT       528
Pro Arg Glu Asn Ile Ile Asp Pro Glu Thr Ser Thr Phe Lys Leu Thr
                165                 170                 175

AAC AAT ACT TTT GCG GCA CAA GAA GGA TTT GGT GCT TTA TCA ATA ATT       576
Asn Asn Thr Phe Ala Ala Gln Glu Gly Phe Gly Ala Leu Ser Ile Ile
            180                 185                 190

TCA ATA TCA CCT AGA TTT ATG CTA ACA TAT AGT AAT GCA ACT AAT GAT       624
Ser Ile Ser Pro Arg Phe Met Leu Thr Tyr Ser Asn Ala Thr Asn Asp
        195                 200                 205

GTA GGA GAG GGT AGA TTT TCT AAG TCT GAA TTT TGC ATG GAT CCA ATA       672
Val Gly Glu Gly Arg Phe Ser Lys Ser Glu Phe Cys Met Asp Pro Ile
    210                 215                 220

CTA ATT TTA ATG CAT GAA CTT AAT CAT GCA ATG CAT AAT TTA TAT GGA       720
Leu Ile Leu Met His Glu Leu Asn His Ala Met His Asn Leu Tyr Gly
225                 230                 235                 240

ATA GCT ATA CCA AAT GAT CAA ACA ATT TCA TCT GTA ACT AGT AAT ATT       768
Ile Ala Ile Pro Asn Asp Gln Thr Ile Ser Ser Val Thr Ser Asn Ile
                245                 250                 255

TTT TAT TCT CAA TAT AAT GTG AAA TTA GAG TAT GCA GAA ATA TAT GCA       816
Phe Tyr Ser Gln Tyr Asn Val Lys Leu Glu Tyr Ala Glu Ile Tyr Ala
            260                 265                 270

TTT GGA GGT CCA ACT ATA GAC CTT ATT CCT AAA AGT GCA AGG AAA TAT       864
Phe Gly Gly Pro Thr Ile Asp Leu Ile Pro Lys Ser Ala Arg Lys Tyr
        275                 280                 285

TTT GAG GAA AAG GCA TTG GAT TAT TAT AGA TCT ATA GCT AAA AGA CTT       912
Phe Glu Glu Lys Ala Leu Asp Tyr Tyr Arg Ser Ile Ala Lys Arg Leu
```

-continued

```
    290                 295                 300

AAT AGT ATA ACT ACT GCA AAT CCT TCA AGC TTT AAT AAA TAT ATA GGG      960
Asn Ser Ile Thr Thr Ala Asn Pro Ser Ser Phe Asn Lys Tyr Ile Gly
305                 310                 315                 320

GAA TAT AAA CAG AAA CTT ATT AGA AAG TAT AGA TTC GTA GTA GAA TCT     1008
Glu Tyr Lys Gln Lys Leu Ile Arg Lys Tyr Arg Phe Val Val Glu Ser
                325                 330                 335

TCA GGT GAA GTT ACA GTA AAT CGT AAT AAG TTT GTT GAG TTA TAT AAT     1056
Ser Gly Glu Val Thr Val Asn Arg Asn Lys Phe Val Glu Leu Tyr Asn
            340                 345                 350

GAA CTT ACA CAA ATA TTT ACA GAA TTT AAC TAC GCT AAA ATA TAT AAT     1104
Glu Leu Thr Gln Ile Phe Thr Glu Phe Asn Tyr Ala Lys Ile Tyr Asn
        355                 360                 365

GTA CAA AAT AGG AAA ATA TAT CTT TCA AAT GTA TAT ACT CCG GTT ACG     1152
Val Gln Asn Arg Lys Ile Tyr Leu Ser Asn Val Tyr Thr Pro Val Thr
    370                 375                 380

GCG AAT ATA TTA GAC GAT AAT GTT TAT GAT ATA CAA AAT GGA TTT AAT     1200
Ala Asn Ile Leu Asp Asp Asn Val Tyr Asp Ile Gln Asn Gly Phe Asn
385                 390                 395                 400

ATA CCT AAA AGT AAT TTA AAT GTA CTA TTT ATG GGT CAA AAT TTA TCT     1248
Ile Pro Lys Ser Asn Leu Asn Val Leu Phe Met Gly Gln Asn Leu Ser
                405                 410                 415

CGA AAT CCA GCA TTA AGA AAA GTC AAT CCT GAA AAT ATG CTT TAT TTA     1296
Arg Asn Pro Ala Leu Arg Lys Val Asn Pro Glu Asn Met Leu Tyr Leu
            420                 425                 430

TTT ACA AAA TTT TGT CAT AAA GCA ATA GAT GGT AGA TCA TTA TAT AAT     1344
Phe Thr Lys Phe Cys His Lys Ala Ile Asp Gly Arg Ser Leu Tyr Asn
        435                 440                 445

AAA ACA TTA GAT TGT AGA GAG CTT TTA GTT AAA AAT ACT GAC TTA CCC     1392
Lys Thr Leu Asp Cys Arg Glu Leu Leu Val Lys Asn Thr Asp Leu Pro
    450                 455                 460

TTT ATA GGT GAT ATT AGT GAT GTT AAA ACT GAT ATA TTT TTA AGA AAA     1440
Phe Ile Gly Asp Ile Ser Asp Val Lys Thr Asp Ile Phe Leu Arg Lys
465                 470                 475                 480

GAT ATT AAT GAA GAA ACT GAA GTT ATA TAC TAT CCG GAC AAT GTT TCA     1488
Asp Ile Asn Glu Glu Thr Glu Val Ile Tyr Tyr Pro Asp Asn Val Ser
                485                 490                 495

GTA GAT CAA GTT ATT CTC AGT AAG AAT ACC TCA GAA CAT GGA CAA CTA     1536
Val Asp Gln Val Ile Leu Ser Lys Asn Thr Ser Glu His Gly Gln Leu
            500                 505                 510

GAT TTA TTA TAC CCT AGT ATT GAC AGT GAG AGT GAA ATA TTA CCA GGG     1584
Asp Leu Leu Tyr Pro Ser Ile Asp Ser Glu Ser Glu Ile Leu Pro Gly
        515                 520                 525

GAG AAT CAA GTC TTT TAT GAT AAT AGA ACT CAA AAT GTT GAT TAT TTG     1632
Glu Asn Gln Val Phe Tyr Asp Asn Arg Thr Gln Asn Val Asp Tyr Leu
    530                 535                 540

AAT TCT TAT TAT TAC CTA GAA TCT CAA AAA CTA AGT GAT AAT GTT GAA     1680
Asn Ser Tyr Tyr Tyr Leu Glu Ser Gln Lys Leu Ser Asp Asn Val Glu
545                 550                 555                 560

GAT TTT ACT TTT ACG AGA TCA ATT GAG GAG GCT TTG GAT AAT AGT GCA     1728
Asp Phe Thr Phe Thr Arg Ser Ile Glu Glu Ala Leu Asp Asn Ser Ala
                565                 570                 575

AAA GTA TAT ACT TAC TTT CCT ACA CTA GCT AAT AAA GTA AAT GCG GGT     1776
Lys Val Tyr Thr Tyr Phe Pro Thr Leu Ala Asn Lys Val Asn Ala Gly
            580                 585                 590

GTT CAA GGT GGT TTA TTT TTA ATG TGG GCA AAT GAT GTA GTT GAA GAT     1824
Val Gln Gly Gly Leu Phe Leu Met Trp Ala Asn Asp Val Val Glu Asp
        595                 600                 605

TTT ACT ACA AAT ATT CTA AGA AAA GAT ACA TTA GAT AAA ATA TCA GAT     1872
```

-continued

```
Phe Thr Thr Asn Ile Leu Arg Lys Asp Thr Leu Asp Lys Ile Ser Asp
    610                 615                 620

GTA TCA GCT ATT ATT CCC TAT ATA GGA CCC GCA TTA AAT ATA AGT AAT      1920
Val Ser Ala Ile Ile Pro Tyr Ile Gly Pro Ala Leu Asn Ile Ser Asn
625                 630                 635                 640

TCT GTA AGA AGA GGA AAT TTT ACT GAA GCA TTT GCA GTT ACT GGT GTA      1968
Ser Val Arg Arg Gly Asn Phe Thr Glu Ala Phe Ala Val Thr Gly Val
                645                 650                 655

ACT ATT TTA TTA GAA GCA TTT CCT GAA TTT ACA ATA CCT GCA CTT GGT      2016
Thr Ile Leu Leu Glu Ala Phe Pro Glu Phe Thr Ile Pro Ala Leu Gly
            660                 665                 670

GCA TTT GTG ATT TAT AGT AAG GTT CAA GAA AGA AAC GAG ATT ATT AAA      2064
Ala Phe Val Ile Tyr Ser Lys Val Gln Glu Arg Asn Glu Ile Ile Lys
        675                 680                 685

ACT ATA GAT AAT TGT TTA GAA CAA AGG ATT AAG AGA TGG AAA GAT TCA      2112
Thr Ile Asp Asn Cys Leu Glu Gln Arg Ile Lys Arg Trp Lys Asp Ser
    690                 695                 700

TAT GAA TGG ATG ATG GGA ACG TGG TTA TCC AGG ATT ATT ACT CAA TTT      2160
Tyr Glu Trp Met Met Gly Thr Trp Leu Ser Arg Ile Ile Thr Gln Phe
705                 710                 715                 720

AAT AAT ATA AGT TAT CAA ATG TAT GAT TCT TTA AAT TAT CAG GCA GGT      2208
Asn Asn Ile Ser Tyr Gln Met Tyr Asp Ser Leu Asn Tyr Gln Ala Gly
                725                 730                 735

GCA ATC AAA GCT AAA ATA GAT TTA GAA TAT AAA AAA TAT TCA GGA AGT      2256
Ala Ile Lys Ala Lys Ile Asp Leu Glu Tyr Lys Lys Tyr Ser Gly Ser
            740                 745                 750

GAT AAA GAA AAT ATA AAA AGT CAA GTT GAA AAT TTA AAA AAT AGT TTA      2304
Asp Lys Glu Asn Ile Lys Ser Gln Val Glu Asn Leu Lys Asn Ser Leu
        755                 760                 765

GAT GTA AAA ATT TCG GAA GCA ATG AAT AAT ATA AAT AAA TTT ATA CGA      2352
Asp Val Lys Ile Ser Glu Ala Met Asn Asn Ile Asn Lys Phe Ile Arg
    770                 775                 780

GAA TGT TCC GTA ACA TAT TTA TTT AAA AAT ATG TTA CCT AAA GTA ATT      2400
Glu Cys Ser Val Thr Tyr Leu Phe Lys Asn Met Leu Pro Lys Val Ile
785                 790                 795                 800

GAT GAA TTA AAT GAG TTT GAT CGA AAT ACT AAA GCA AAA TTA ATT AAT      2448
Asp Glu Leu Asn Glu Phe Asp Arg Asn Thr Lys Ala Lys Leu Ile Asn
                805                 810                 815

CTT ATA GAT AGT CAT AAT ATT ATT CTA GTT GGT GAA GTA GAT AAA TTA      2496
Leu Ile Asp Ser His Asn Ile Ile Leu Val Gly Glu Val Asp Lys Leu
            820                 825                 830

AAA GCA AAA GTA AAT AAT AGC TTT CAA AAT ACA ATA CCC TTT AAT ATT      2544
Lys Ala Lys Val Asn Asn Ser Phe Gln Asn Thr Ile Pro Phe Asn Ile
        835                 840                 845

TTT TCA TAT ACT AAT AAT TCT TTA TTA AAA GAT ATA ATT AAT GAA TAT      2592
Phe Ser Tyr Thr Asn Asn Ser Leu Leu Lys Asp Ile Ile Asn Glu Tyr
    850                 855                 860

TTC AAT AAT ATT AAT GAT TCA AAA ATT TTG AGC CTA CAA AAC AGA AAA      2640
Phe Asn Asn Ile Asn Asp Ser Lys Ile Leu Ser Leu Gln Asn Arg Lys
865                 870                 875                 880

AAT ACT TTA GTG GAT ACA TCA GGA TAT AAT GCA GAA GTG AGT GAA GAA      2688
Asn Thr Leu Val Asp Thr Ser Gly Tyr Asn Ala Glu Val Ser Glu Glu
                885                 890                 895

GGC GAT GTT CAG CTT AAT CCA ATA TTT CCA TTT GAC TTT AAA TTA GGT      2736
Gly Asp Val Gln Leu Asn Pro Ile Phe Pro Phe Asp Phe Lys Leu Gly
            900                 905                 910

AGT TCA GGG GAG GAT AGA GGT AAA GTT ATA GTA ACC CAG AAT GAA AAT      2784
Ser Ser Gly Glu Asp Arg Gly Lys Val Ile Val Thr Gln Asn Glu Asn
        915                 920                 925
```

-continued

```
ATT GTA TAT AAT TCT ATG TAT GAA AGT TTT AGC ATT AGT TTT TGG ATT      2832
Ile Val Tyr Asn Ser Met Tyr Glu Ser Phe Ser Ile Ser Phe Trp Ile
    930                 935                 940

AGA ATA AAT AAA TGG GTA AGT AAT TTA CCT GGA TAT ACT ATA ATT GAT      2880
Arg Ile Asn Lys Trp Val Ser Asn Leu Pro Gly Tyr Thr Ile Ile Asp
945                 950                 955                 960

AGT GTT AAA AAT AAC TCA GGT TGG AGT ATA GGT ATT ATT AGT AAT TTT      2928
Ser Val Lys Asn Asn Ser Gly Trp Ser Ile Gly Ile Ile Ser Asn Phe
                965                 970                 975

TTA GTA TTT ACT TTA AAA CAA AAT GAA GAT AGT GAA CAA AGT ATA AAT      2976
Leu Val Phe Thr Leu Lys Gln Asn Glu Asp Ser Glu Gln Ser Ile Asn
            980                 985                 990

TTT AGT TAT GAT ATA TCA AAT AAT GCT CCT GGA TAC AAT AAA TGG TTT      3024
Phe Ser Tyr Asp Ile Ser Asn Asn Ala Pro Gly Tyr Asn Lys Trp Phe
        995                 1000                1005

TTT GTA ACT GTT ACT AAC AAT ATG ATG GGA AAT ATG AAG ATT TAT ATA      3072
Phe Val Thr Val Thr Asn Asn Met Met Gly Asn Met Lys Ile Tyr Ile
    1010                1015                1020

AAT GGA AAA TTA ATA GAT ACT ATA AAA GTT AAA GAA CTA ACT GGA ATT      3120
Asn Gly Lys Leu Ile Asp Thr Ile Lys Val Lys Glu Leu Thr Gly Ile
1025                1030                1035                1040

AAT TTT AGC AAA ACT ATA ACA TTT GAA ATA AAT AAA ATT CCA GAT ACC      3168
Asn Phe Ser Lys Thr Ile Thr Phe Glu Ile Asn Lys Ile Pro Asp Thr
                1045                1050                1055

GGT TTG ATT ACT TCA GAT TCT GAT AAC ATC AAT ATG TGG ATA AGA GAT      3216
Gly Leu Ile Thr Ser Asp Ser Asp Asn Ile Asn Met Trp Ile Arg Asp
            1060                1065                1070

TTT TAT ATA TTT GCT AAA GAA TTA GAT GGT AAA GAT ATT AAT ATA TTA      3264
Phe Tyr Ile Phe Ala Lys Glu Leu Asp Gly Lys Asp Ile Asn Ile Leu
        1075                1080                1085

TTT AAT AGC TTG CAA TAT ACT AAT GTT GTA AAA GAT TAT TGG GGA AAT      3312
Phe Asn Ser Leu Gln Tyr Thr Asn Val Val Lys Asp Tyr Trp Gly Asn
    1090                1095                1100

GAT TTA AGA TAT AAT AAA GAA TAT TAT ATG GTT AAT ATA GAT TAT TTA      3360
Asp Leu Arg Tyr Asn Lys Glu Tyr Tyr Met Val Asn Ile Asp Tyr Leu
1105                1110                1115                1120

AAT AGA TAT ATG TAT GCG AAC TCA CGA CAA ATT GTT TTT AAT ACA CGT      3408
Asn Arg Tyr Met Tyr Ala Asn Ser Arg Gln Ile Val Phe Asn Thr Arg
                1125                1130                1135

AGA AAT AAT AAT GAC TTC AAT GAA GGA TAT AAA ATT ATA ATA AAA AGA      3456
Arg Asn Asn Asn Asp Phe Asn Glu Gly Tyr Lys Ile Ile Ile Lys Arg
            1140                1145                1150

ATC AGA GGA AAT ACA AAT GAT ACT AGA GTA CGA GGA GGA GAT ATT TTA      3504
Ile Arg Gly Asn Thr Asn Asp Thr Arg Val Arg Gly Gly Asp Ile Leu
        1155                1160                1165

TAT TTT GAT ATG ACA ATT AAT AAC AAA GCA TAT AAT TTG TTT ATG AAG      3552
Tyr Phe Asp Met Thr Ile Asn Asn Lys Ala Tyr Asn Leu Phe Met Lys
    1170                1175                1180

AAT GAA ACT ATG TAT GCA GAT AAT CAT AGT ACT GAA GAT ATA TAT GCT      3600
Asn Glu Thr Met Tyr Ala Asp Asn His Ser Thr Glu Asp Ile Tyr Ala
1185                1190                1195                1200

ATA GGT TTA AGA GAA CAA ACA AAG GAT ATA AAT GAT AAT ATT ATA TTT      3648
Ile Gly Leu Arg Glu Gln Thr Lys Asp Ile Asn Asp Asn Ile Ile Phe
                1205                1210                1215

CAA ATA CAA CCA ATG AAT AAT ACT TAT TAT TAC GCA TCT CAA ATA TTT      3696
Gln Ile Gln Pro Met Asn Asn Thr Tyr Tyr Tyr Ala Ser Gln Ile Phe
            1220                1225                1230

AAA TCA AAT TTT AAT GGA GAA AAT ATT TCT GGA ATA TGT TCA ATA GGT      3744
Lys Ser Asn Phe Asn Gly Glu Asn Ile Ser Gly Ile Cys Ser Ile Gly
        1235                1240                1245
```

-continued

```
ACT TAT CGT TTT AGA CTT GGA GGT GAT TGG TAT AGA CAC AAT TAT TTG      3792
Thr Tyr Arg Phe Arg Leu Gly Gly Asp Trp Tyr Arg His Asn Tyr Leu
    1250                1255                1260

GTG CCT ACT GTG AAG CAA GGA AAT TAT GCT TCA TTA TTA GAA TCA ACA      3840
Val Pro Thr Val Lys Gln Gly Asn Tyr Ala Ser Leu Leu Glu Ser Thr
1265                1270                1275                1280

TCA ACT CAT TGG GGT TTT GTA CCT GTA AGT GAA TAA                      3876
Ser Thr His Trp Gly Phe Val Pro Val Ser Glu
                1285                1290
```

(2) INFORMATION FOR SEQ ID NO:60:

(i) SEQUENCE CHARACTERISTICS:
(A) LENGTH: 1291 amino acids
(B) TYPE: amino acid
(D) TOPOLOGY: linear (ii) MOLECULE TYPE: protein (xi) SEQUENCE DESCRIPTION: SEQ ID NO:60:

```
Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
             20                  25                  30

Pro Glu Lys Ala Phe Arg Ile Thr Gly Asn Ile Trp Val Ile Pro Asp
         35                  40                  45

Arg Phe Ser Arg Asn Ser Asn Pro Asn Leu Asn Lys Pro Pro Arg Val
     50                  55                  60

Thr Ser Pro Lys Ser Gly Tyr Tyr Asp Pro Asn Tyr Leu Ser Thr Asp
 65                  70                  75                  80

Ser Asp Lys Asp Thr Phe Leu Lys Glu Ile Ile Lys Leu Phe Lys Arg
                 85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285
```

-continued

```
Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
```

-continued

```
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005

Phe Val Thr Val Thr Asn Asn Met Met Gly Asn Met Lys Ile Tyr Ile
    1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
                1045                1050                1055

Gly Leu Ile Thr Ser Asp Ser Asp Asn Ile Asn Met Trp Ile Arg Asp
            1060                1065                1070

Phe Tyr Ile Phe Ala Lys Glu Leu Asp Gly Lys Asp Ile Asn Ile Leu
        1075                1080                1085

Phe Asn Ser Leu Gln Tyr Thr Asn Val Val Lys Asp Tyr Trp Gly Asn
    1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135
```

-continued

```
Arg Asn Asn Asn Asp Phe Asn Glu Gly Tyr Lys Ile Ile Ile Lys Arg
            1140                1145                1150

Ile Arg Gly Asn Thr Asn Asp Thr Arg Val Arg Gly Gly Asp Ile Leu
        1155                1160                1165

Tyr Phe Asp Met Thr Ile Asn Asn Lys Ala Tyr Asn Leu Phe Met Lys
    1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
        1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290
```

(2) INFORMATION FOR SEQ ID NO:61:

(i) SEQUENCE CHARACTERISTICS:
(A) LENGTH: 1502 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 108..1493

(xi) SEQUENCE DESCRIPTION: SEQ ID NO:61:

```
AGATCTCGAT CCCGCGAAAT TAATACGACT CACTATAGGG GAATTGTGAG CGGATAACAA      60

TTCCCCTCTA GAAATAATTT TGTTTAACTT TAAGAAGGAG ATATACC ATG GGC CAT       116
                                                    Met Gly His
                                                      1

CAT CAT CAT CAT CAT CAT CAT CAT CAC AGC AGC GGC CAT ATC GAA GGT       164
His His His His His His His His His Ser Ser Gly His Ile Glu Gly
      5                   10                  15

CGT CAT ATG GCT AGC ATG GCT TTA TTA AAA GAT ATA ATT AAT GAA TAT       212
Arg His Met Ala Ser Met Ala Leu Leu Lys Asp Ile Ile Asn Glu Tyr
 20                  25                  30                  35

TTC AAT AAT ATT AAT GAT TCA AAA ATT TTG AGC CTA CAA AAC AGA AAA       260
Phe Asn Asn Ile Asn Asp Ser Lys Ile Leu Ser Leu Gln Asn Arg Lys
                 40                  45                  50

AAT ACT TTA GTG GAT ACA TCA GGA TAT AAT GCA GAA GTG AGT GAA GAA       308
Asn Thr Leu Val Asp Thr Ser Gly Tyr Asn Ala Glu Val Ser Glu Glu
             55                  60                  65

GGC GAT GTT CAG CTT AAT CCA ATA TTT CCA TTT GAC TTT AAA TTA GGT       356
Gly Asp Val Gln Leu Asn Pro Ile Phe Pro Phe Asp Phe Lys Leu Gly
         70                  75                  80

AGT TCA GGG GAG GAT AGA GGT AAA GTT ATA GTA ACC CAG AAT GAA AAT       404
Ser Ser Gly Glu Asp Arg Gly Lys Val Ile Val Thr Gln Asn Glu Asn
     85                  90                  95

ATT GTA TAT AAT TCT ATG TAT GAA AGT TTT AGC ATT AGT TTT TGG ATT       452
```

-continued

```
Ile Val Tyr Asn Ser Met Tyr Glu Ser Phe Ser Ile Ser Phe Trp Ile
100                 105                 110                 115

AGA ATA AAT AAA TGG GTA AGT AAT TTA CCT GGA TAT ACT ATA ATT GAT      500
Arg Ile Asn Lys Trp Val Ser Asn Leu Pro Gly Tyr Thr Ile Ile Asp
                120                 125                 130

AGT GTT AAA AAT AAC TCA GGT TGG AGT ATA GGT ATT ATT AGT AAT TTT      548
Ser Val Lys Asn Asn Ser Gly Trp Ser Ile Gly Ile Ile Ser Asn Phe
            135                 140                 145

TTA GTA TTT ACT TTA AAA CAA AAT GAA GAT AGT GAA CAA AGT ATA AAT      596
Leu Val Phe Thr Leu Lys Gln Asn Glu Asp Ser Glu Gln Ser Ile Asn
        150                 155                 160

TTT AGT TAT GAT ATA TCA AAT AAT GCT CCT GGA TAC AAT AAA TGG TTT      644
Phe Ser Tyr Asp Ile Ser Asn Asn Ala Pro Gly Tyr Asn Lys Trp Phe
    165                 170                 175

TTT GTA ACT GTT ACT AAC AAT ATG ATG GGA AAT ATG AAG ATT TAT ATA      692
Phe Val Thr Val Thr Asn Asn Met Met Gly Asn Met Lys Ile Tyr Ile
180                 185                 190                 195

AAT GGA AAA TTA ATA GAT ACT ATA AAA GTT AAA GAA CTA ACT GGA ATT      740
Asn Gly Lys Leu Ile Asp Thr Ile Lys Val Lys Glu Leu Thr Gly Ile
                200                 205                 210

AAT TTT AGC AAA ACT ATA ACA TTT GAA ATA AAT AAA ATT CCA GAT ACC      788
Asn Phe Ser Lys Thr Ile Thr Phe Glu Ile Asn Lys Ile Pro Asp Thr
            215                 220                 225

GGT TTG ATT ACT TCA GAT TCT GAT AAC ATC AAT ATG TGG ATA AGA GAT      836
Gly Leu Ile Thr Ser Asp Ser Asp Asn Ile Asn Met Trp Ile Arg Asp
        230                 235                 240

TTT TAT ATA TTT GCT AAA GAA TTA GAT GGT AAA GAT ATT AAT ATA TTA      884
Phe Tyr Ile Phe Ala Lys Glu Leu Asp Gly Lys Asp Ile Asn Ile Leu
    245                 250                 255

TTT AAT AGC TTG CAA TAT ACT AAT GTT GTA AAA GAT TAT TGG GGA AAT      932
Phe Asn Ser Leu Gln Tyr Thr Asn Val Val Lys Asp Tyr Trp Gly Asn
260                 265                 270                 275

GAT TTA AGA TAT AAT AAA GAA TAT TAT ATG GTT AAT ATA GAT TAT TTA      980
Asp Leu Arg Tyr Asn Lys Glu Tyr Tyr Met Val Asn Ile Asp Tyr Leu
                280                 285                 290

AAT AGA TAT ATG TAT GCG AAC TCA CGA CAA ATT GTT TTT AAT ACA CGT     1028
Asn Arg Tyr Met Tyr Ala Asn Ser Arg Gln Ile Val Phe Asn Thr Arg
            295                 300                 305

AGA AAT AAT AAT GAC TTC AAT GAA GGA TAT AAA ATT ATA ATA AAA AGA     1076
Arg Asn Asn Asn Asp Phe Asn Glu Gly Tyr Lys Ile Ile Ile Lys Arg
        310                 315                 320

ATC AGA GGA AAT ACA AAT GAT ACT AGA GTA CGA GGA GGA GAT ATT TTA     1124
Ile Arg Gly Asn Thr Asn Asp Thr Arg Val Arg Gly Gly Asp Ile Leu
    325                 330                 335

TAT TTT GAT ATG ACA ATT AAT AAC AAA GCA TAT AAT TTG TTT ATG AAG     1172
Tyr Phe Asp Met Thr Ile Asn Asn Lys Ala Tyr Asn Leu Phe Met Lys
340                 345                 350                 355

AAT GAA ACT ATG TAT GCA GAT AAT CAT AGT ACT GAA GAT ATA TAT GCT     1220
Asn Glu Thr Met Tyr Ala Asp Asn His Ser Thr Glu Asp Ile Tyr Ala
                360                 365                 370

ATA GGT TTA AGA GAA CAA ACA AAG GAT ATA AAT GAT AAT ATT ATA TTT     1268
Ile Gly Leu Arg Glu Gln Thr Lys Asp Ile Asn Asp Asn Ile Ile Phe
            375                 380                 385

CAA ATA CAA CCA ATG AAT AAT ACT TAT TAT TAC GCA TCT CAA ATA TTT     1316
Gln Ile Gln Pro Met Asn Asn Thr Tyr Tyr Tyr Ala Ser Gln Ile Phe
        390                 395                 400

AAA TCA AAT TTT AAT GGA GAA AAT ATT TCT GGA ATA TGT TCA ATA GGT     1364
Lys Ser Asn Phe Asn Gly Glu Asn Ile Ser Gly Ile Cys Ser Ile Gly
    405                 410                 415
```

-continued

```
ACT TAT CGT TTT AGA CTT GGA GGT GAT TGG TAT AGA CAC AAT TAT TTG      1412
Thr Tyr Arg Phe Arg Leu Gly Gly Asp Trp Tyr Arg His Asn Tyr Leu
420                 425                 430                 435

GTG CCT ACT GTG AAG CAA GGA AAT TAT GCT TCA TTA TTA GAA TCA ACA      1460
Val Pro Thr Val Lys Gln Gly Asn Tyr Ala Ser Leu Leu Glu Ser Thr
                440                 445                 450

TCA ACT CAT TGG GGT TTT GTA CCT GTA AGT GAA TAAAAGCTT                1502
Ser Thr His Trp Gly Phe Val Pro Val Ser Glu
            455                 460
```

(2) INFORMATION FOR SEQ ID NO:62:

(i) SEQUENCE CHARACTERISTICS:
(A) LENGTH: 462 amino acids
(B) TYPE: amino acid
(D) TOPOLOGY: linear (ii) MOLECULE TYPE: protein (xi) SEQUENCE DESCRIPTION: SEQ ID NO:62:

```
Met Gly His His His His His His His His His His Ser Ser Gly His
  1               5                  10                  15

Ile Glu Gly Arg His Met Ala Ser Met Ala Leu Leu Lys Asp Ile Ile
             20                  25                  30

Asn Glu Tyr Phe Asn Asn Ile Asn Asp Ser Lys Ile Leu Ser Leu Gln
         35                  40                  45

Asn Arg Lys Asn Thr Leu Val Asp Thr Ser Gly Tyr Asn Ala Glu Val
     50                  55                  60

Ser Glu Glu Gly Asp Val Gln Leu Asn Pro Ile Phe Pro Phe Asp Phe
 65                  70                  75                  80

Lys Leu Gly Ser Ser Gly Glu Asp Arg Gly Lys Val Ile Val Thr Gln
                 85                  90                  95

Asn Glu Asn Ile Val Tyr Asn Ser Met Tyr Glu Ser Phe Ser Ile Ser
            100                 105                 110

Phe Trp Ile Arg Ile Asn Lys Trp Val Ser Asn Leu Pro Gly Tyr Thr
        115                 120                 125

Ile Ile Asp Ser Val Lys Asn Asn Ser Gly Trp Ser Ile Gly Ile Ile
    130                 135                 140

Ser Asn Phe Leu Val Phe Thr Leu Lys Gln Asn Glu Asp Ser Glu Gln
145                 150                 155                 160

Ser Ile Asn Phe Ser Tyr Asp Ile Ser Asn Asn Ala Pro Gly Tyr Asn
                165                 170                 175

Lys Trp Phe Phe Val Thr Val Thr Asn Asn Met Met Gly Asn Met Lys
            180                 185                 190

Ile Tyr Ile Asn Gly Lys Leu Ile Asp Thr Ile Lys Val Lys Glu Leu
        195                 200                 205

Thr Gly Ile Asn Phe Ser Lys Thr Ile Thr Phe Glu Ile Asn Lys Ile
    210                 215                 220

Pro Asp Thr Gly Leu Ile Thr Ser Asp Ser Asp Asn Ile Asn Met Trp
225                 230                 235                 240

Ile Arg Asp Phe Tyr Ile Phe Ala Lys Glu Leu Asp Gly Lys Asp Ile
                245                 250                 255

Asn Ile Leu Phe Asn Ser Leu Gln Tyr Thr Asn Val Val Lys Asp Tyr
            260                 265                 270

Trp Gly Asn Asp Leu Arg Tyr Asn Lys Glu Tyr Tyr Met Val Asn Ile
        275                 280                 285

Asp Tyr Leu Asn Arg Tyr Met Tyr Ala Asn Ser Arg Gln Ile Val Phe
```

-continued

```
    290                 295                 300

Asn Thr Arg Arg Asn Asn Asn Asp Phe Asn Glu Gly Tyr Lys Ile Ile
305                 310                 315                 320

Ile Lys Arg Ile Arg Gly Asn Thr Asn Asp Thr Arg Val Arg Gly Gly
                325                 330                 335

Asp Ile Leu Tyr Phe Asp Met Thr Ile Asn Asn Lys Ala Tyr Asn Leu
            340                 345                 350

Phe Met Lys Asn Glu Thr Met Tyr Ala Asp Asn His Ser Thr Glu Asp
        355                 360                 365

Ile Tyr Ala Ile Gly Leu Arg Glu Gln Thr Lys Asp Ile Asn Asp Asn
    370                 375                 380

Ile Ile Phe Gln Ile Gln Pro Met Asn Asn Thr Tyr Tyr Tyr Ala Ser
385                 390                 395                 400

Gln Ile Phe Lys Ser Asn Phe Asn Gly Glu Asn Ile Ser Gly Ile Cys
                405                 410                 415

Ser Ile Gly Thr Tyr Arg Phe Arg Leu Gly Gly Asp Trp Tyr Arg His
            420                 425                 430

Asn Tyr Leu Val Pro Thr Val Lys Gln Gly Asn Tyr Ala Ser Leu Leu
        435                 440                 445

Glu Ser Thr Ser Thr His Trp Gly Phe Val Pro Val Ser Glu
    450                 455                 460
```

(2) INFORMATION FOR SEQ ID NO:63:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:63:

```
CGCCATGGCT TTATTAAAAG ATATAATTAA TG                                32
```

(2) INFORMATION FOR SEQ ID NO:64:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:64:

```
GCAAGCTTTT ATTCACTTAC AGGTACAAAA CC                                32
```

(2) INFORMATION FOR SEQ ID NO:65:

(i) SEQUENCE CHARACTERISTICS:
(A) LENGTH: 3831 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3828

-continued (xi) SEQUENCE DESCRIPTION: SEQ ID NO:65:

```
ATG ACA TGG CCA GTA AAA GAT TTT AAT TAT AGT GAT CCT GTT AAT GAC        48
Met Thr Trp Pro Val Lys Asp Phe Asn Tyr Ser Asp Pro Val Asn Asp
  1               5                  10                  15

AAT GAT ATA TTA TAT TTA AGA ATA CCA CAA AAT AAG TTA ATT ACT ACA        96
Asn Asp Ile Leu Tyr Leu Arg Ile Pro Gln Asn Lys Leu Ile Thr Thr
             20                  25                  30

CCT GTA AAA GCT TTT ATG ATT ACT CAA AAT ATT TGG GTA ATA CCA GAA       144
Pro Val Lys Ala Phe Met Ile Thr Gln Asn Ile Trp Val Ile Pro Glu
         35                  40                  45

AGA TTT TCA TCA GAT ACT AAT CCA AGT TTA AGT AAA CCG CCC AGA CCT       192
Arg Phe Ser Ser Asp Thr Asn Pro Ser Leu Ser Lys Pro Pro Arg Pro
     50                  55                  60

ACT TCA AAG TAT CAA AGT TAT TAT GAT CCT AGT TAT TTA TCT ACT GAT       240
Thr Ser Lys Tyr Gln Ser Tyr Tyr Asp Pro Ser Tyr Leu Ser Thr Asp
 65                  70                  75                  80

GAA CAA AAA GAT ACA TTT TTA AAA GGG ATT ATA AAA TTA TTT AAA AGA       288
Glu Gln Lys Asp Thr Phe Leu Lys Gly Ile Ile Lys Leu Phe Lys Arg
                 85                  90                  95

ATT AAT GAA AGA GAT ATA GGA AAA AAA TTA ATA AAT TAT TTA GTA GTT       336
Ile Asn Glu Arg Asp Ile Gly Lys Lys Leu Ile Asn Tyr Leu Val Val
            100                 105                 110

GGT TCA CCT TTT ATG GGA GAT TCA AGT ACG CCT GAA GAT ACA TTT GAT       384
Gly Ser Pro Phe Met Gly Asp Ser Ser Thr Pro Glu Asp Thr Phe Asp
        115                 120                 125

TTT ACA CGT CAT ACT ACT AAT ATT GCA GTT GAA AAG TTT GAA AAT GGT       432
Phe Thr Arg His Thr Thr Asn Ile Ala Val Glu Lys Phe Glu Asn Gly
    130                 135                 140

AGT TGG AAA GTA ACA AAT ATT ATA ACA CCA AGT GTA TTG ATA TTT GGA       480
Ser Trp Lys Val Thr Asn Ile Ile Thr Pro Ser Val Leu Ile Phe Gly
145                 150                 155                 160

CCA CTT CCT AAT ATA TTA GAC TAT ACA GCA TCC CTT ACA TTG CAA GGA       528
Pro Leu Pro Asn Ile Leu Asp Tyr Thr Ala Ser Leu Thr Leu Gln Gly
                165                 170                 175

CAA CAA TCA AAT CCA TCA TTT GAA GGG TTT GGA ACA TTA TCT ATA CTA       576
Gln Gln Ser Asn Pro Ser Phe Glu Gly Phe Gly Thr Leu Ser Ile Leu
            180                 185                 190

AAA GTA GCA CCT GAA TTT TTG TTA ACA TTT AGT GAT GTA ACA TCT AAT       624
Lys Val Ala Pro Glu Phe Leu Leu Thr Phe Ser Asp Val Thr Ser Asn
        195                 200                 205

CAA AGT TCA GCT GTA TTA GGC AAA TCT ATA TTT TGT ATG GAT CCA GTA       672
Gln Ser Ser Ala Val Leu Gly Lys Ser Ile Phe Cys Met Asp Pro Val
    210                 215                 220

ATA GCT TTA ATG CAT GAG TTA ACA CAT TCT TTG CAT CAA TTA TAT GGA       720
Ile Ala Leu Met His Glu Leu Thr His Ser Leu His Gln Leu Tyr Gly
225                 230                 235                 240

ATA AAT ATA CCA TCT GAT AAA AGG ATT CGT CCA CAA GTT AGC GAG GGA       768
Ile Asn Ile Pro Ser Asp Lys Arg Ile Arg Pro Gln Val Ser Glu Gly
                245                 250                 255

TTT TTC TCT CAA GAT GGA CCC AAC GTA CAA TTT GAG GAA TTA TAT ACA       816
Phe Phe Ser Gln Asp Gly Pro Asn Val Gln Phe Glu Glu Leu Tyr Thr
            260                 265                 270

TTT GGA GGA TTA GAT GTT GAA ATA ATA CCT CAA ATT GAA AGA TCA CAA       864
Phe Gly Gly Leu Asp Val Glu Ile Ile Pro Gln Ile Glu Arg Ser Gln
        275                 280                 285

TTA AGA GAA AAA GCA TTA GGT CAC TAT AAA GAT ATA GCG AAA AGA CTT       912
Leu Arg Glu Lys Ala Leu Gly His Tyr Lys Asp Ile Ala Lys Arg Leu
    290                 295                 300

AAT AAT ATT AAT AAA ACT ATT CCT TCT AGT TGG ATT AGT AAT ATA GAT       960
```

-continued

```
Asn Asn Ile Asn Lys Thr Ile Pro Ser Ser Trp Ile Ser Asn Ile Asp
305                 310                 315                 320

AAA TAT AAA AAA ATA TTT TCT GAA AAG TAT AAT TTT GAT AAA GAT AAT     1008
Lys Tyr Lys Lys Ile Phe Ser Glu Lys Tyr Asn Phe Asp Lys Asp Asn
                325                 330                 335

ACA GGA AAT TTT GTT GTA AAT ATT GAT AAA TTC AAT AGC TTA TAT TCA     1056
Thr Gly Asn Phe Val Val Asn Ile Asp Lys Phe Asn Ser Leu Tyr Ser
            340                 345                 350

GAC TTG ACT AAT GTT ATG TCA GAA GTT GTT TAT TCT TCG CAA TAT AAT     1104
Asp Leu Thr Asn Val Met Ser Glu Val Val Tyr Ser Ser Gln Tyr Asn
        355                 360                 365

GTT AAA AAC AGG ACT CAT TAT TTT TCA AGG CAT TAT CTA CCT GTA TTT     1152
Val Lys Asn Arg Thr His Tyr Phe Ser Arg His Tyr Leu Pro Val Phe
    370                 375                 380

GCA AAT ATA TTA GAT GAT AAT ATT TAT ACT ATA AGA GAT GGT TTT AAT     1200
Ala Asn Ile Leu Asp Asp Asn Ile Tyr Thr Ile Arg Asp Gly Phe Asn
385                 390                 395                 400

TTA ACA AAT AAA GGT TTT AAT ATA GAA AAT TCG GGT CAG AAT ATA GAA     1248
Leu Thr Asn Lys Gly Phe Asn Ile Glu Asn Ser Gly Gln Asn Ile Glu
                405                 410                 415

AGG AAT CCT GCA CTA CAA AAG CTT AGT TCA GAA AGT GTA GTA GAT TTA     1296
Arg Asn Pro Ala Leu Gln Lys Leu Ser Ser Glu Ser Val Val Asp Leu
            420                 425                 430

TTT ACA AAA GTA TGT TTA AGA TTA ACA AAA AAT AGT AGA GAT GAT TCA     1344
Phe Thr Lys Val Cys Leu Arg Leu Thr Lys Asn Ser Arg Asp Asp Ser
        435                 440                 445

ACA TGT ATT AAA GTT AAA AAT AAT AGA TTA CCT TAT GTA GCT GAT AAA     1392
Thr Cys Ile Lys Val Lys Asn Asn Arg Leu Pro Tyr Val Ala Asp Lys
    450                 455                 460

GAT AGC ATT TCA CAA GAA ATA TTT GAA AAT AAA ATT ATT ACA GAT GAG     1440
Asp Ser Ile Ser Gln Glu Ile Phe Glu Asn Lys Ile Ile Thr Asp Glu
465                 470                 475                 480

ACT AAT GTA CAA AAT TAT TCA GAT AAT TTT TCA TTA GAT GAA TCT ATT     1488
Thr Asn Val Gln Asn Tyr Ser Asp Asn Phe Ser Leu Asp Glu Ser Ile
                485                 490                 495

TTA GAT GGG CAA GTT CCT ATT AAT CCT GAA ATA GTA GAT CCA CTA TTA     1536
Leu Asp Gly Gln Val Pro Ile Asn Pro Glu Ile Val Asp Pro Leu Leu
            500                 505                 510

CCC AAT GTT AAT ATG GAA CCT TTA AAT CTT CCA GGT GAA GAA ATA GTA     1584
Pro Asn Val Asn Met Glu Pro Leu Asn Leu Pro Gly Glu Glu Ile Val
        515                 520                 525

TTT TAT GAT GAT ATT ACT AAA TAT GTT GAT TAT TTA AAT TCT TAT TAT     1632
Phe Tyr Asp Asp Ile Thr Lys Tyr Val Asp Tyr Leu Asn Ser Tyr Tyr
    530                 535                 540

TAT TTG GAA TCT CAA AAA TTA AGT AAT AAT GTT GAA AAT ATT ACT CTT     1680
Tyr Leu Glu Ser Gln Lys Leu Ser Asn Asn Val Glu Asn Ile Thr Leu
545                 550                 555                 560

ACA ACT TCA GTT GAA GAA GCA TTA GGT TAT AGC AAT AAG ATA TAC ACA     1728
Thr Thr Ser Val Glu Glu Ala Leu Gly Tyr Ser Asn Lys Ile Tyr Thr
                565                 570                 575

TTT TTA CCT AGC TTA GCT GAA AAA GTG AAT AAA GGT GTT CAA GCA GGT     1776
Phe Leu Pro Ser Leu Ala Glu Lys Val Asn Lys Gly Val Gln Ala Gly
            580                 585                 590

TTA TTC TTA AAT TGG GCG AAT GAA GTA GTT GAG GAT TTT ACT ACA AAT     1824
Leu Phe Leu Asn Trp Ala Asn Glu Val Val Glu Asp Phe Thr Thr Asn
        595                 600                 605

ATT ATG AAG AAA GAT ACA TTG GAT AAA ATA TCA GAT GTA TCA GTA ATA     1872
Ile Met Lys Lys Asp Thr Leu Asp Lys Ile Ser Asp Val Ser Val Ile
    610                 615                 620
```

-continued

```
ATT CCA TAT ATA GGA CCT GCC TTA AAT ATA GGA AAT TCA GCA TTA AGG      1920
Ile Pro Tyr Ile Gly Pro Ala Leu Asn Ile Gly Asn Ser Ala Leu Arg
625                 630                 635                 640

GGA AAT TTT AAG CAA GCA TTT GCA ACA GCT GGT GTA GCT TTT TTA TTA      1968
Gly Asn Phe Lys Gln Ala Phe Ala Thr Ala Gly Val Ala Phe Leu Leu
                645                 650                 655

GAG GGA TTT CCA GAG TTT ACT ATA CCT GCA CTC GGT GTA TTT ACC TTT      2016
Glu Gly Phe Pro Glu Phe Thr Ile Pro Ala Leu Gly Val Phe Thr Phe
            660                 665                 670

TAT AGT TCT ATT CAA GAA AGA GAG AAA ATT ATT AAA ACT ATA GAA AAT      2064
Tyr Ser Ser Ile Gln Glu Arg Glu Lys Ile Ile Lys Thr Ile Glu Asn
        675                 680                 685

TGT TTG GAA CAA AGA GTT AAG AGA TGG AAA GAT TCA TAT CAA TGG ATG      2112
Cys Leu Glu Gln Arg Val Lys Arg Trp Lys Asp Ser Tyr Gln Trp Met
    690                 695                 700

GTA TCA AAT TGG TTG TCA AGA ATT ACT ACT CAA TTT AAT CAT ATA AAT      2160
Val Ser Asn Trp Leu Ser Arg Ile Thr Thr Gln Phe Asn His Ile Asn
705                 710                 715                 720

TAT CAA ATG TAT GAT TCT TTA AGT TAT CAG GCA GAT GCA ATC AAA GCT      2208
Tyr Gln Met Tyr Asp Ser Leu Ser Tyr Gln Ala Asp Ala Ile Lys Ala
                725                 730                 735

AAA ATA GAT TTA GAA TAT AAA AAA TAC TCA GGA AGT GAT AAA GAA AAT      2256
Lys Ile Asp Leu Glu Tyr Lys Lys Tyr Ser Gly Ser Asp Lys Glu Asn
            740                 745                 750

ATA AAA AGT CAA GTT GAA AAT TTA AAA AAT AGT TTA GAT GTA AAA ATT      2304
Ile Lys Ser Gln Val Glu Asn Leu Lys Asn Ser Leu Asp Val Lys Ile
        755                 760                 765

TCG GAA GCA ATG AAT AAT ATA AAT AAA TTT ATA CGA GAA TGT TCT GTA      2352
Ser Glu Ala Met Asn Asn Ile Asn Lys Phe Ile Arg Glu Cys Ser Val
    770                 775                 780

ACA TAC TTA TTT AAA AAT ATG CTC CCT AAA GTA ATT GAC GAA TTA AAT      2400
Thr Tyr Leu Phe Lys Asn Met Leu Pro Lys Val Ile Asp Glu Leu Asn
785                 790                 795                 800

AAG TTT GAT TTA AGA ACT AAA ACA GAA TTA ATT AAT CTT ATA GAT AGT      2448
Lys Phe Asp Leu Arg Thr Lys Thr Glu Leu Ile Asn Leu Ile Asp Ser
                805                 810                 815

CAT AAT ATT ATT CTA GTT GGT GAA GTA GAT AGA TTA AAA GCA AAA GTA      2496
His Asn Ile Ile Leu Val Gly Glu Val Asp Arg Leu Lys Ala Lys Val
            820                 825                 830

AAT GAG AGT TTT GAA AAT ACA ATG CCT TTT AAT ATT TTT TCA TAT ACT      2544
Asn Glu Ser Phe Glu Asn Thr Met Pro Phe Asn Ile Phe Ser Tyr Thr
        835                 840                 845

AAT AAT TCT TTA TTA AAA GAT ATA ATT AAT GAA TAT TTC AAT AGT ATT      2592
Asn Asn Ser Leu Leu Lys Asp Ile Ile Asn Glu Tyr Phe Asn Ser Ile
    850                 855                 860

AAT GAT TCA AAA ATT TTG AGC TTA CAA AAC AAA AAA AAT GCT TTA GTG      2640
Asn Asp Ser Lys Ile Leu Ser Leu Gln Asn Lys Lys Asn Ala Leu Val
865                 870                 875                 880

GAT ACA TCA GGA TAT AAT GCA GAA GTG AGG GTA GGA GAT AAT GTT CAA      2688
Asp Thr Ser Gly Tyr Asn Ala Glu Val Arg Val Gly Asp Asn Val Gln
                885                 890                 895

CTT AAT ACG ATA TAT ACA AAT GAC TTT AAA TTA AGT AGT TCA GGA GAT      2736
Leu Asn Thr Ile Tyr Thr Asn Asp Phe Lys Leu Ser Ser Ser Gly Asp
            900                 905                 910

AAA ATT ATA GTA AAT TTA AAT AAT AAT ATT TTA TAT AGC GCT ATT TAT      2784
Lys Ile Ile Val Asn Leu Asn Asn Asn Ile Leu Tyr Ser Ala Ile Tyr
        915                 920                 925

GAG AAC TCT AGT GTT AGT TTT TGG ATT AAG ATA TCT AAA GAT TTA ACT      2832
Glu Asn Ser Ser Val Ser Phe Trp Ile Lys Ile Ser Lys Asp Leu Thr
    930                 935                 940
```

-continued

```
AAT TCT CAT AAT GAA TAT ACA ATA ATT AAC AGT ATA GAA CAA AAT TCT     2880
Asn Ser His Asn Glu Tyr Thr Ile Ile Asn Ser Ile Glu Gln Asn Ser
945                 950                 955                 960

GGG TGG AAA TTA TGT ATT AGG AAT GGC AAT ATA GAA TGG ATT TTA CAA     2928
Gly Trp Lys Leu Cys Ile Arg Asn Gly Asn Ile Glu Trp Ile Leu Gln
                965                 970                 975

GAT GTT AAT AGA AAG TAT AAA AGT TTA ATT TTT GAT TAT AGT GAA TCA     2976
Asp Val Asn Arg Lys Tyr Lys Ser Leu Ile Phe Asp Tyr Ser Glu Ser
            980                 985                 990

TTA AGT CAT ACA GGA TAT ACA AAT AAA TGG TTT TTT GTT ACT ATA ACT     3024
Leu Ser His Thr Gly Tyr Thr Asn Lys Trp Phe Phe Val Thr Ile Thr
        995                 1000                1005

AAT AAT ATA ATG GGG TAT ATG AAA CTT TAT ATA AAT GGA GAA TTA AAG     3072
Asn Asn Ile Met Gly Tyr Met Lys Leu Tyr Ile Asn Gly Glu Leu Lys
    1010                1015                1020

CAG AGT CAA AAA ATT GAA GAT TTA GAT GAG GTT AAG TTA GAT AAA ACC     3120
Gln Ser Gln Lys Ile Glu Asp Leu Asp Glu Val Lys Leu Asp Lys Thr
1025                1030                1035                1040

ATA GTA TTT GGA ATA GAT GAG AAT ATA GAT GAG AAT CAG ATG CTT TGG     3168
Ile Val Phe Gly Ile Asp Glu Asn Ile Asp Glu Asn Gln Met Leu Trp
                1045                1050                1055

ATT AGA GAT TTT AAT ATT TTT TCT AAA GAA TTA AGT AAT GAA GAT ATT     3216
Ile Arg Asp Phe Asn Ile Phe Ser Lys Glu Leu Ser Asn Glu Asp Ile
            1060                1065                1070

AAT ATT GTA TAT GAG GGA CAA ATA TTA AGA AAT GTT ATT AAA GAT TAT     3264
Asn Ile Val Tyr Glu Gly Gln Ile Leu Arg Asn Val Ile Lys Asp Tyr
        1075                1080                1085

TGG GGA AAT CCT TTG AAG TTT GAT ACA GAA TAT TAT ATT ATT AAT GAT     3312
Trp Gly Asn Pro Leu Lys Phe Asp Thr Glu Tyr Tyr Ile Ile Asn Asp
    1090                1095                1100

AAT TAT ATA GAT AGG TAT ATT GCA CCT GAA AGT AAT GTA CTT GTA CTT     3360
Asn Tyr Ile Asp Arg Tyr Ile Ala Pro Glu Ser Asn Val Leu Val Leu
1105                1110                1115                1120

GTT CGG TAT CCA GAT AGA TCT AAA TTA TAT ACT GGA AAT CCT ATT ACT     3408
Val Arg Tyr Pro Asp Arg Ser Lys Leu Tyr Thr Gly Asn Pro Ile Thr
                1125                1130                1135

ATT AAA TCA GTA TCT GAT AAG AAT CCT TAT AGT AGA ATT TTA AAT GGA     3456
Ile Lys Ser Val Ser Asp Lys Asn Pro Tyr Ser Arg Ile Leu Asn Gly
            1140                1145                1150

GAT AAT ATA ATT CTT CAT ATG TTA TAT AAT AGT AGG AAA TAT ATG ATA     3504
Asp Asn Ile Ile Leu His Met Leu Tyr Asn Ser Arg Lys Tyr Met Ile
        1155                1160                1165

ATA AGA GAT ACT GAT ACA ATA TAT GCA ACA CAA GGA GGA GAG TGT TCA     3552
Ile Arg Asp Thr Asp Thr Ile Tyr Ala Thr Gln Gly Gly Glu Cys Ser
    1170                1175                1180

CAA AAT TGT GTA TAT GCA TTA AAA TTA CAG AGT AAT TTA GGT AAT TAT     3600
Gln Asn Cys Val Tyr Ala Leu Lys Leu Gln Ser Asn Leu Gly Asn Tyr
1185                1190                1195                1200

GGT ATA GGT ATA TTT AGT ATA AAA AAT ATT GTA TCT AAA AAT AAA TAT     3648
Gly Ile Gly Ile Phe Ser Ile Lys Asn Ile Val Ser Lys Asn Lys Tyr
                1205                1210                1215

TGT AGT CAA ATT TTC TCT AGT TTT AGG GAA AAT ACA ATG CTT CTA GCA     3696
Cys Ser Gln Ile Phe Ser Ser Phe Arg Glu Asn Thr Met Leu Leu Ala
            1220                1225                1230

GAT ATA TAT AAA CCT TGG AGA TTT TCT TTT AAA AAT GCA TAC ACG CCA     3744
Asp Ile Tyr Lys Pro Trp Arg Phe Ser Phe Lys Asn Ala Tyr Thr Pro
        1235                1240                1245

GTT GCA GTA ACT AAT TAT GAA ACA AAA CTA TTA TCA ACT TCA TCT TTT     3792
Val Ala Val Thr Asn Tyr Glu Thr Lys Leu Leu Ser Thr Ser Ser Phe
```

-continued

```
    1250                1255                1260

TGG AAA TTT ATT TCT AGG GAT CCA GGA TGG GTA GAG TAA                3831
Trp Lys Phe Ile Ser Arg Asp Pro Gly Trp Val Glu
1265                1270                1275


(2) INFORMATION FOR SEQ ID NO:66:

     (i) SEQUENCE CHARACTERISTICS:
          (A) LENGTH: 1276 amino acids
          (B) TYPE: amino acid
          (D) TOPOLOGY: linear

    (ii) MOLECULE TYPE: protein

    (xi) SEQUENCE DESCRIPTION: SEQ ID NO:66:

Met Thr Trp Pro Val Lys Asp Phe Asn Tyr Ser Asp Pro Val Asn Asp
  1               5                  10                  15

Asn Asp Ile Leu Tyr Leu Arg Ile Pro Gln Asn Lys Leu Ile Thr Thr
             20                  25                  30

Pro Val Lys Ala Phe Met Ile Thr Gln Asn Ile Trp Val Ile Pro Glu
         35                  40                  45

Arg Phe Ser Ser Asp Thr Asn Pro Ser Leu Ser Lys Pro Pro Arg Pro
     50                  55                  60

Thr Ser Lys Tyr Gln Ser Tyr Tyr Asp Pro Ser Tyr Leu Ser Thr Asp
 65                  70                  75                  80

Glu Gln Lys Asp Thr Phe Leu Lys Gly Ile Ile Lys Leu Phe Lys Arg
                 85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
```

-continued

```
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Asn Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750
```

-continued

```
Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
    850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu Lys
    1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
            1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
    1090                1095                1100

Asn Tyr Ile Asp Arg Tyr Ile Ala Pro Glu Ser Asn Val Leu Val Leu
1105                1110                1115                1120

Val Arg Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
            1140                1145                1150

Asp Asn Ile Ile Leu His Met Leu Tyr Asn Ser Arg Lys Tyr Met Ile
        1155                1160                1165
```

-continued

```
Ile Arg Asp Thr Asp Thr Ile Tyr Ala Thr Gln Gly Gly Glu Cys Ser
    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                1205                1210                1215

Cys Ser Gln Ile Phe Ser Ser Phe Arg Glu Asn Thr Met Leu Leu Ala
            1220                1225                1230

Asp Ile Tyr Lys Pro Trp Arg Phe Ser Phe Lys Asn Ala Tyr Thr Pro
        1235                1240                1245

Val Ala Val Thr Asn Tyr Glu Thr Lys Leu Leu Ser Thr Ser Ser Phe
    1250                1255                1260

Trp Lys Phe Ile Ser Arg Asp Pro Gly Trp Val Glu
1265                1270                1275
```

(2) INFORMATION FOR SEQ ID NO:67:

(i) SEQUENCE CHARACTERISTICS:
(A) LENGTH: 1469 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 108..1460

(xi) SEQUENCE DESCRIPTION: SEQ ID NO:67:

```
AGATCTCGAT CCCGCGAAAT TAATACGACT CACTATAGGG GAATTGTGAG CGGATAACAA      60

TTCCCCTCTA GAAATAATTT TGTTTAACTT TAAGAAGGAG ATATACC ATG GGC CAT      116
                                                    Met Gly His
                                                      1

CAT CAT CAT CAT CAT CAT CAT CAT CAC AGC AGC GGC CAT ATC GAA GGT      164
His His His His His His His His His Ser Ser Gly His Ile Glu Gly
      5                  10                  15

CGT CAT ATG GCT AGC ATG GCT TTA TTA AAA GAT ATA ATT AAT GAA TAT      212
Arg His Met Ala Ser Met Ala Leu Leu Lys Asp Ile Ile Asn Glu Tyr
 20                  25                  30                  35

TTC AAT AGT ATT AAT GAT TCA AAA ATT TTG AGC TTA CAA AAC AAA AAA      260
Phe Asn Ser Ile Asn Asp Ser Lys Ile Leu Ser Leu Gln Asn Lys Lys
                 40                  45                  50

AAT GCT TTA GTG GAT ACA TCA GGA TAT AAT GCA GAA GTG AGG GTA GGA      308
Asn Ala Leu Val Asp Thr Ser Gly Tyr Asn Ala Glu Val Arg Val Gly
             55                  60                  65

GAT AAT GTT CAA CTT AAT ACG ATA TAT ACA AAT GAC TTT AAA TTA AGT      356
Asp Asn Val Gln Leu Asn Thr Ile Tyr Thr Asn Asp Phe Lys Leu Ser
         70                  75                  80

AGT TCA GGA GAT AAA ATT ATA GTA AAT TTA AAT AAT AAT ATT TTA TAT      404
Ser Ser Gly Asp Lys Ile Ile Val Asn Leu Asn Asn Asn Ile Leu Tyr
     85                  90                  95

AGC GCT ATT TAT GAG AAC TCT AGT GTT AGT TTT TGG ATT AAG ATA TCT      452
Ser Ala Ile Tyr Glu Asn Ser Ser Val Ser Phe Trp Ile Lys Ile Ser
100                 105                 110                 115

AAA GAT TTA ACT AAT TCT CAT AAT GAA TAT ACA ATA ATT AAC AGT ATA      500
Lys Asp Leu Thr Asn Ser His Asn Glu Tyr Thr Ile Ile Asn Ser Ile
                120                 125                 130

GAA CAA AAT TCT GGG TGG AAA TTA TGT ATT AGG AAT GGC AAT ATA GAA      548
Glu Gln Asn Ser Gly Trp Lys Leu Cys Ile Arg Asn Gly Asn Ile Glu
            135                 140                 145
```

-continued

```
TGG ATT TTA CAA GAT GTT AAT AGA AAG TAT AAA AGT TTA ATT TTT GAT       596
Trp Ile Leu Gln Asp Val Asn Arg Lys Tyr Lys Ser Leu Ile Phe Asp
        150                 155                 160

TAT AGT GAA TCA TTA AGT CAT ACA GGA TAT ACA AAT AAA TGG TTT TTT       644
Tyr Ser Glu Ser Leu Ser His Thr Gly Tyr Thr Asn Lys Trp Phe Phe
    165                 170                 175

GTT ACT ATA ACT AAT AAT ATA ATG GGG TAT ATG AAA CTT TAT ATA AAT       692
Val Thr Ile Thr Asn Asn Ile Met Gly Tyr Met Lys Leu Tyr Ile Asn
180                 185                 190                 195

GGA GAA TTA AAG CAG AGT CAA AAA ATT GAA GAT TTA GAT GAG GTT AAG       740
Gly Glu Leu Lys Gln Ser Gln Lys Ile Glu Asp Leu Asp Glu Val Lys
                200                 205                 210

TTA GAT AAA ACC ATA GTA TTT GGA ATA GAT GAG AAT ATA GAT GAG AAT       788
Leu Asp Lys Thr Ile Val Phe Gly Ile Asp Glu Asn Ile Asp Glu Asn
            215                 220                 225

CAG ATG CTT TGG ATT AGA GAT TTT AAT ATT TTT TCT AAA GAA TTA AGT       836
Gln Met Leu Trp Ile Arg Asp Phe Asn Ile Phe Ser Lys Glu Leu Ser
        230                 235                 240

AAT GAA GAT ATT AAT ATT GTA TAT GAG GGA CAA ATA TTA AGA AAT GTT       884
Asn Glu Asp Ile Asn Ile Val Tyr Glu Gly Gln Ile Leu Arg Asn Val
    245                 250                 255

ATT AAA GAT TAT TGG GGA AAT CCT TTG AAG TTT GAT ACA GAA TAT TAT       932
Ile Lys Asp Tyr Trp Gly Asn Pro Leu Lys Phe Asp Thr Glu Tyr Tyr
260                 265                 270                 275

ATT ATT AAT GAT AAT TAT ATA GAT AGG TAT ATT GCA CCT GAA AGT AAT       980
Ile Ile Asn Asp Asn Tyr Ile Asp Arg Tyr Ile Ala Pro Glu Ser Asn
                280                 285                 290

GTA CTT GTA CTT GTT CGG TAT CCA GAT AGA TCT AAA TTA TAT ACT GGA      1028
Val Leu Val Leu Val Arg Tyr Pro Asp Arg Ser Lys Leu Tyr Thr Gly
            295                 300                 305

AAT CCT ATT ACT ATT AAA TCA GTA TCT GAT AAG AAT CCT TAT AGT AGA      1076
Asn Pro Ile Thr Ile Lys Ser Val Ser Asp Lys Asn Pro Tyr Ser Arg
        310                 315                 320

ATT TTA AAT GGA GAT AAT ATA ATT CTT CAT ATG TTA TAT AAT AGT AGG      1124
Ile Leu Asn Gly Asp Asn Ile Ile Leu His Met Leu Tyr Asn Ser Arg
    325                 330                 335

AAA TAT ATG ATA ATA AGA GAT ACT GAT ACA ATA TAT GCA ACA CAA GGA      1172
Lys Tyr Met Ile Ile Arg Asp Thr Asp Thr Ile Tyr Ala Thr Gln Gly
340                 345                 350                 355

GGA GAG TGT TCA CAA AAT TGT GTA TAT GCA TTA AAA TTA CAG AGT AAT      1220
Gly Glu Cys Ser Gln Asn Cys Val Tyr Ala Leu Lys Leu Gln Ser Asn
                360                 365                 370

TTA GGT AAT TAT GGT ATA GGT ATA TTT AGT ATA AAA AAT ATT GTA TCT      1268
Leu Gly Asn Tyr Gly Ile Gly Ile Phe Ser Ile Lys Asn Ile Val Ser
            375                 380                 385

AAA AAT AAA TAT TGT AGT CAA ATT TTC TCT AGT TTT AGG GAA AAT ACA      1316
Lys Asn Lys Tyr Cys Ser Gln Ile Phe Ser Ser Phe Arg Glu Asn Thr
        390                 395                 400

ATG CTT CTA GCA GAT ATA TAT AAA CCT TGG AGA TTT TCT TTT AAA AAT      1364
Met Leu Leu Ala Asp Ile Tyr Lys Pro Trp Arg Phe Ser Phe Lys Asn
    405                 410                 415

GCA TAC ACG CCA GTT GCA GTA ACT AAT TAT GAA ACA AAA CTA TTA TCA      1412
Ala Tyr Thr Pro Val Ala Val Thr Asn Tyr Glu Thr Lys Leu Leu Ser
420                 425                 430                 435

ACT TCA TCT TTT TGG AAA TTT ATT TCT AGG GAT CCA GGA TGG GTA GAG      1460
Thr Ser Ser Phe Trp Lys Phe Ile Ser Arg Asp Pro Gly Trp Val Glu
                440                 445                 450

TAAAAGCTT                                                            1469
```

-continued (2) INFORMATION FOR SEQ ID NO:68:

(i) SEQUENCE CHARACTERISTICS:
(A) LENGTH: 451 amino acids
(B) TYPE: amino acid
(D) TOPOLOGY: linear (ii) MOLECULE TYPE: protein (xi) SEQUENCE DESCRIPTION: SEQ ID NO:68:

```
Met Gly His His His His His His His His His His Ser Ser Gly His
  1               5                  10                  15

Ile Glu Gly Arg His Met Ala Ser Met Ala Leu Leu Lys Asp Ile Ile
             20                  25                  30

Asn Glu Tyr Phe Asn Ser Ile Asn Asp Ser Lys Ile Leu Ser Leu Gln
         35                  40                  45

Asn Lys Lys Asn Ala Leu Val Asp Thr Ser Gly Tyr Asn Ala Glu Val
     50                  55                  60

Arg Val Gly Asp Asn Val Gln Leu Asn Thr Ile Tyr Thr Asn Asp Phe
 65                  70                  75                  80

Lys Leu Ser Ser Ser Gly Asp Lys Ile Ile Val Asn Leu Asn Asn Asn
                 85                  90                  95

Ile Leu Tyr Ser Ala Ile Tyr Glu Asn Ser Ser Val Ser Phe Trp Ile
            100                 105                 110

Lys Ile Ser Lys Asp Leu Thr Asn Ser His Asn Glu Tyr Thr Ile Ile
        115                 120                 125

Asn Ser Ile Glu Gln Asn Ser Gly Trp Lys Leu Cys Ile Arg Asn Gly
    130                 135                 140

Asn Ile Glu Trp Ile Leu Gln Asp Val Asn Arg Lys Tyr Lys Ser Leu
145                 150                 155                 160

Ile Phe Asp Tyr Ser Glu Ser Leu Ser His Thr Gly Tyr Thr Asn Lys
                165                 170                 175

Trp Phe Phe Val Thr Ile Thr Asn Asn Ile Met Gly Tyr Met Lys Leu
            180                 185                 190

Tyr Ile Asn Gly Glu Leu Lys Gln Ser Gln Lys Ile Glu Asp Leu Asp
        195                 200                 205

Glu Val Lys Leu Asp Lys Thr Ile Val Phe Gly Ile Asp Glu Asn Ile
    210                 215                 220

Asp Glu Asn Gln Met Leu Trp Ile Arg Asp Phe Asn Ile Phe Ser Lys
225                 230                 235                 240

Glu Leu Ser Asn Glu Asp Ile Asn Ile Val Tyr Glu Gly Gln Ile Leu
                245                 250                 255

Arg Asn Val Ile Lys Asp Tyr Trp Gly Asn Pro Leu Lys Phe Asp Thr
            260                 265                 270

Glu Tyr Tyr Ile Ile Asn Asp Asn Tyr Ile Asp Arg Tyr Ile Ala Pro
        275                 280                 285

Glu Ser Asn Val Leu Val Leu Val Arg Tyr Pro Asp Arg Ser Lys Leu
    290                 295                 300

Tyr Thr Gly Asn Pro Ile Thr Ile Lys Ser Val Ser Asp Lys Asn Pro
305                 310                 315                 320

Tyr Ser Arg Ile Leu Asn Gly Asp Asn Ile Ile Leu His Met Leu Tyr
                325                 330                 335

Asn Ser Arg Lys Tyr Met Ile Ile Arg Asp Thr Asp Thr Ile Tyr Ala
            340                 345                 350

Thr Gln Gly Gly Glu Cys Ser Gln Asn Cys Val Tyr Ala Leu Lys Leu
```

-continued

```
        355                 360                 365

Gln Ser Asn Leu Gly Asn Tyr Gly Ile Gly Ile Phe Ser Ile Lys Asn
    370                 375                 380

Ile Val Ser Lys Asn Lys Tyr Cys Ser Gln Ile Phe Ser Ser Phe Arg
385                 390                 395                 400

Glu Asn Thr Met Leu Leu Ala Asp Ile Tyr Lys Pro Trp Arg Phe Ser
                405                 410                 415

Phe Lys Asn Ala Tyr Thr Pro Val Ala Val Thr Asn Tyr Glu Thr Lys
            420                 425                 430

Leu Leu Ser Thr Ser Ser Phe Trp Lys Phe Ile Ser Arg Asp Pro Gly
        435                 440                 445

Trp Val Glu
    450
```

(2) INFORMATION FOR SEQ ID NO:69:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:69:

```
GCAAGCTTTT ACTCTACCCA TCCTGGATCC CT                                 32
```

(2) INFORMATION FOR SEQ ID NO:70:

(i) SEQUENCE CHARACTERISTICS:
(A) LENGTH: 3825 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3822

(xi) SEQUENCE DESCRIPTION: SEQ ID NO:70:

```
ATG CCA GTT GCA ATA AAT AGT TTT AAT TAT AAT GAC CCT GTT AAT GAT       48
Met Pro Val Ala Ile Asn Ser Phe Asn Tyr Asn Asp Pro Val Asn Asp
  1               5                  10                  15

GAT ACA ATT TTA TAC ATG CAG ATA CCA TAT GAA GAA AAA AGT AAA AAA       96
Asp Thr Ile Leu Tyr Met Gln Ile Pro Tyr Glu Glu Lys Ser Lys Lys
             20                  25                  30

TAT TAT AAA GCT TTT GAG ATT ATG CGT AAT GTT TGG ATA ATT CCT GAG      144
Tyr Tyr Lys Ala Phe Glu Ile Met Arg Asn Val Trp Ile Ile Pro Glu
         35                  40                  45

AGA AAT ACA ATA GGA ACG AAT CCT AGT GAT TTT GAT CCA CCG GCT TCA      192
Arg Asn Thr Ile Gly Thr Asn Pro Ser Asp Phe Asp Pro Pro Ala Ser
     50                  55                  60

TTA AAG AAC GGA AGC AGT GCT TAT TAT GAT CCT AAT TAT TTA ACC ACT      240
Leu Lys Asn Gly Ser Ser Ala Tyr Tyr Asp Pro Asn Tyr Leu Thr Thr
 65                  70                  75                  80

GAT GCT GAA AAA GAT AGA TAT TTA AAA ACA ACG ATA AAA TTA TTT AAG      288
Asp Ala Glu Lys Asp Arg Tyr Leu Lys Thr Thr Ile Lys Leu Phe Lys
                 85                  90                  95

AGA ATT AAT AGT AAT CCT GCA GGG AAA GTT TTG TTA CAA GAA ATA TCA      336
Arg Ile Asn Ser Asn Pro Ala Gly Lys Val Leu Leu Gln Glu Ile Ser
```

-continued

```
            100                 105                 110

TAT GCT AAA CCA TAT TTA GGA AAT GAC CAC ACG CCA ATT GAT GAA TTC      384
Tyr Ala Lys Pro Tyr Leu Gly Asn Asp His Thr Pro Ile Asp Glu Phe
        115                 120                 125

TCT CCA GTT ACT AGA ACT ACA AGT GTT AAT ATA AAA TTA TCA ACT AAT      432
Ser Pro Val Thr Arg Thr Thr Ser Val Asn Ile Lys Leu Ser Thr Asn
    130                 135                 140

GTT GAA AGT TCA ATG TTA TTG AAT CTT CTT GTA TTG GGA GCA GGA CCT      480
Val Glu Ser Ser Met Leu Leu Asn Leu Leu Val Leu Gly Ala Gly Pro
145                 150                 155                 160

GAT ATA TTT GAA AGT TGT TGT TAC CCC GTT AGA AAA CTA ATA GAT CCA      528
Asp Ile Phe Glu Ser Cys Cys Tyr Pro Val Arg Lys Leu Ile Asp Pro
                165                 170                 175

GAT GTA GTT TAT GAT CCA AGT AAT TAT GGT TTT GGA TCA ATT AAT ATC      576
Asp Val Val Tyr Asp Pro Ser Asn Tyr Gly Phe Gly Ser Ile Asn Ile
            180                 185                 190

GTG ACA TTT TCA CCT GAG TAT GAA TAT ACT TTT AAT GAT ATT AGT GGA      624
Val Thr Phe Ser Pro Glu Tyr Glu Tyr Thr Phe Asn Asp Ile Ser Gly
        195                 200                 205

GGG CAT AAT AGT AGT ACA GAA TCA TTT ATT GCA GAT CCT GCA ATT TCA      672
Gly His Asn Ser Ser Thr Glu Ser Phe Ile Ala Asp Pro Ala Ile Ser
    210                 215                 220

CTA GCT CAT GAA TTG ATA CAT GCA CTG CAT GGA TTA TAC GGG GCT AGG      720
Leu Ala His Glu Leu Ile His Ala Leu His Gly Leu Tyr Gly Ala Arg
225                 230                 235                 240

GGA GTT ACT TAT GAA GAG ACT ATA GAA GTA AAG CAA GCA CCT CTT ATG      768
Gly Val Thr Tyr Glu Glu Thr Ile Glu Val Lys Gln Ala Pro Leu Met
                245                 250                 255

ATA GCC GAA AAA CCC ATA AGG CTA GAA GAA TTT TTA ACC TTT GGA GGT      816
Ile Ala Glu Lys Pro Ile Arg Leu Glu Glu Phe Leu Thr Phe Gly Gly
            260                 265                 270

CAG GAT TTA AAT ATT ATT ACT AGT GCT ATG AAG GAA AAA ATA TAT AAC      864
Gln Asp Leu Asn Ile Ile Thr Ser Ala Met Lys Glu Lys Ile Tyr Asn
        275                 280                 285

AAT CTT TTA GCT AAC TAT GAA AAA ATA GCT ACT AGA CTT AGT GAA GTT      912
Asn Leu Leu Ala Asn Tyr Glu Lys Ile Ala Thr Arg Leu Ser Glu Val
    290                 295                 300

AAT AGT GCT CCT CCT GAA TAT GAT ATT AAT GAA TAT AAA GAT TAT TTT      960
Asn Ser Ala Pro Pro Glu Tyr Asp Ile Asn Glu Tyr Lys Asp Tyr Phe
305                 310                 315                 320

CAA TGG AAG TAT GGG CTA GAT AAA AAT GCT GAT GGA AGT TAT ACT GTA     1008
Gln Trp Lys Tyr Gly Leu Asp Lys Asn Ala Asp Gly Ser Tyr Thr Val
                325                 330                 335

AAT GAA AAT AAA TTT AAT GAA ATT TAT AAA AAA TTA TAT AGT TTT ACA     1056
Asn Glu Asn Lys Phe Asn Glu Ile Tyr Lys Lys Leu Tyr Ser Phe Thr
            340                 345                 350

GAG AGT GAC TTA GCA AAT AAA TTT AAA GTA AAA TGT AGA AAT ACT TAT     1104
Glu Ser Asp Leu Ala Asn Lys Phe Lys Val Lys Cys Arg Asn Thr Tyr
        355                 360                 365

TTT ATT AAA TAT GAA TTT TTA AAA GTT CCA AAT TTG TTA GAT GAT GAT     1152
Phe Ile Lys Tyr Glu Phe Leu Lys Val Pro Asn Leu Leu Asp Asp Asp
    370                 375                 380

ATT TAT ACT GTA TCA GAG GGG TTT AAT ATA GGT AAT TTA GCA GTA AAC     1200
Ile Tyr Thr Val Ser Glu Gly Phe Asn Ile Gly Asn Leu Ala Val Asn
385                 390                 395                 400

AAT CGC GGA CAA AGT ATA AAG TTA AAT CCT AAA ATT ATT GAT TCC ATT     1248
Asn Arg Gly Gln Ser Ile Lys Leu Asn Pro Lys Ile Ile Asp Ser Ile
                405                 410                 415

CCA GAT AAA GGT CTA GTA GAA AAG ATC GTT AAA TTT TGT AAG AGC GTT     1296
```

-continued

```
Pro Asp Lys Gly Leu Val Glu Lys Ile Val Lys Phe Cys Lys Ser Val
            420                 425                 430

ATT CCT AGA AAA GGT ACA AAG GCG CCA CCG CGA CTA TGC ATT AGA GTA      1344
Ile Pro Arg Lys Gly Thr Lys Ala Pro Pro Arg Leu Cys Ile Arg Val
        435                 440                 445

AAT AAT AGT GAG TTA TTT TTT GTA GCT TCA GAA AGT AGC TAT AAT GAA      1392
Asn Asn Ser Glu Leu Phe Phe Val Ala Ser Glu Ser Ser Tyr Asn Glu
    450                 455                 460

AAT GAT ATT AAT ACA CCT AAA GAA ATT GAC GAT ACA ACA AAT CTA AAT      1440
Asn Asp Ile Asn Thr Pro Lys Glu Ile Asp Asp Thr Thr Asn Leu Asn
465                 470                 475                 480

AAT AAT TAT AGA AAT AAT TTA GAT GAA GTT ATT TTA GAT TAT AAT AGT      1488
Asn Asn Tyr Arg Asn Asn Leu Asp Glu Val Ile Leu Asp Tyr Asn Ser
                485                 490                 495

CAG ACA ATA CCT CAA ATA TCA AAT CGA ACA TTA AAT ACA CTT GTA CAA      1536
Gln Thr Ile Pro Gln Ile Ser Asn Arg Thr Leu Asn Thr Leu Val Gln
            500                 505                 510

GAC AAT AGT TAT GTG CCA AGA TAT GAT TCT AAT GGA ACA AGT GAA ATA      1584
Asp Asn Ser Tyr Val Pro Arg Tyr Asp Ser Asn Gly Thr Ser Glu Ile
        515                 520                 525

GAG GAA TAT GAT GTT GTT GAC TTT AAT GTA TTT TTC TAT TTA CAT GCA      1632
Glu Glu Tyr Asp Val Val Asp Phe Asn Val Phe Phe Tyr Leu His Ala
    530                 535                 540

CAA AAA GTG CCA GAA GGT GAA ACC AAT ATA AGT TTA ACT TCT TCA ATT      1680
Gln Lys Val Pro Glu Gly Glu Thr Asn Ile Ser Leu Thr Ser Ser Ile
545                 550                 555                 560

GAT ACA GCA TTA TTA GAA GAA TCC AAA GAT ATA TTT TTT TCT TCA GAG      1728
Asp Thr Ala Leu Leu Glu Glu Ser Lys Asp Ile Phe Phe Ser Ser Glu
                565                 570                 575

TTT ATC GAT ACT ATC AAT AAA CCT GTA AAT GCA GCA CTA TTT ATA GAT      1776
Phe Ile Asp Thr Ile Asn Lys Pro Val Asn Ala Ala Leu Phe Ile Asp
            580                 585                 590

TGG ATA AGC AAA GTA ATA AGA GAT TTT ACC ACT GAA GCT ACA CAA AAA      1824
Trp Ile Ser Lys Val Ile Arg Asp Phe Thr Thr Glu Ala Thr Gln Lys
        595                 600                 605

AGT ACT GTT GAT AAG ATT GCA GAC ATA TCT TTA ATT GTA CCC TAT GTA      1872
Ser Thr Val Asp Lys Ile Ala Asp Ile Ser Leu Ile Val Pro Tyr Val
    610                 615                 620

GGT CTT GCT TTG AAT ATA ATT ATT GAG GCA GAA AAA GGA AAT TTT GAG      1920
Gly Leu Ala Leu Asn Ile Ile Ile Glu Ala Glu Lys Gly Asn Phe Glu
625                 630                 635                 640

GAG GCA TTT GAA TTA TTA GGA GTG GGT ATT TTA TTA GAA TTT GTG CCA      1968
Glu Ala Phe Glu Leu Leu Gly Val Gly Ile Leu Leu Glu Phe Val Pro
                645                 650                 655

GAA CTT ACA ATT CCT GTA ATT TTA GTG TTT ACG ATA AAA TCC TAT ATA      2016
Glu Leu Thr Ile Pro Val Ile Leu Val Phe Thr Ile Lys Ser Tyr Ile
            660                 665                 670

GAT TCA TAT GAG AAT AAA AAT AAA GCA ATT AAA GCA ATA AAT AAT TCA      2064
Asp Ser Tyr Glu Asn Lys Asn Lys Ala Ile Lys Ala Ile Asn Asn Ser
        675                 680                 685

TTA ATC GAA AGA GAA GCA AAG TGG AAA GAA ATA TAT AGT TGG ATA GTA      2112
Leu Ile Glu Arg Glu Ala Lys Trp Lys Glu Ile Tyr Ser Trp Ile Val
    690                 695                 700

TCA AAT TGG CTT ACT AGA ATT AAT ACT CAA TTT AAT AAA AGA AAA GAG      2160
Ser Asn Trp Leu Thr Arg Ile Asn Thr Gln Phe Asn Lys Arg Lys Glu
705                 710                 715                 720

CAA ATG TAT CAG GCT TTA CAA AAT CAA GTA GAT GCA ATA AAA ACA GCA      2208
Gln Met Tyr Gln Ala Leu Gln Asn Gln Val Asp Ala Ile Lys Thr Ala
                725                 730                 735
```

-continued

```
ATA GAA TAT AAA TAT AAT AAT TAT ACT TCA GAT GAG AAA AAT AGA CTT     2256
Ile Glu Tyr Lys Tyr Asn Asn Tyr Thr Ser Asp Glu Lys Asn Arg Leu
            740                 745                 750

GAA TCT GAA TAT AAT ATC AAT AAT ATA GAA GAA GAA TTG AAT AAA AAA     2304
Glu Ser Glu Tyr Asn Ile Asn Asn Ile Glu Glu Glu Leu Asn Lys Lys
        755                 760                 765

GTT TCT TTA GCA ATG AAA AAT ATA GAA AGA TTT ATG ACA GAA AGT TCT     2352
Val Ser Leu Ala Met Lys Asn Ile Glu Arg Phe Met Thr Glu Ser Ser
    770                 775                 780

ATA TCT TAT TTA ATG AAA TTA ATA AAT GAA GCC AAA GTT GGT AAA TTA     2400
Ile Ser Tyr Leu Met Lys Leu Ile Asn Glu Ala Lys Val Gly Lys Leu
785                 790                 795                 800

AAA AAA TAT GAT AAC CAT GTT AAG AGC GAT TTA TTA AAC TAT ATT CTC     2448
Lys Lys Tyr Asp Asn His Val Lys Ser Asp Leu Leu Asn Tyr Ile Leu
                805                 810                 815

GAC CAT AGA TCA ATC TTA GGA GAG CAG ACA AAT GAA TTA AGT GAT TTG     2496
Asp His Arg Ser Ile Leu Gly Glu Gln Thr Asn Glu Leu Ser Asp Leu
            820                 825                 830

GTG ACT AGT ACT TTG AAT AGT AGT ATT CCA TTT GAA CTT TCT TCA TAT     2544
Val Thr Ser Thr Leu Asn Ser Ser Ile Pro Phe Glu Leu Ser Ser Tyr
        835                 840                 845

ACT AAT GAT AAA ATT CTA ATT ATA TAT TTT AAT AGA TTA TAT AAA AAA     2592
Thr Asn Asp Lys Ile Leu Ile Ile Tyr Phe Asn Arg Leu Tyr Lys Lys
    850                 855                 860

ATT AAA GAT AGT TCT ATT TTA GAT ATG CGA TAT GAA AAT AAT AAA TTT     2640
Ile Lys Asp Ser Ser Ile Leu Asp Met Arg Tyr Glu Asn Asn Lys Phe
865                 870                 875                 880

ATA GAT ATC TCT GGA TAT GGT TCA AAT ATA AGC ATT AAT GGA AAC GTA     2688
Ile Asp Ile Ser Gly Tyr Gly Ser Asn Ile Ser Ile Asn Gly Asn Val
                885                 890                 895

TAT ATT TAT TCA ACA AAT AGA AAT CAA TTT GGA ATA TAT AAT AGT AGG     2736
Tyr Ile Tyr Ser Thr Asn Arg Asn Gln Phe Gly Ile Tyr Asn Ser Arg
            900                 905                 910

CTT AGT GAA GTT AAT ATA GCT CAA AAT AAT GAT ATT ATA TAC AAT AGT     2784
Leu Ser Glu Val Asn Ile Ala Gln Asn Asn Asp Ile Ile Tyr Asn Ser
        915                 920                 925

AGA TAT CAA AAT TTT AGT ATT AGT TTC TGG GTA AGG ATT CCT AAA CAC     2832
Arg Tyr Gln Asn Phe Ser Ile Ser Phe Trp Val Arg Ile Pro Lys His
    930                 935                 940

TAC AAA CCT ATG AAT CAT AAT CGG GAA TAC ACT ATA ATA AAT TGT ATG     2880
Tyr Lys Pro Met Asn His Asn Arg Glu Tyr Thr Ile Ile Asn Cys Met
945                 950                 955                 960

GGG AAT AAT AAT TCG GGA TGG AAA ATA TCA CTT AGA ACT GTT AGA GAT     2928
Gly Asn Asn Asn Ser Gly Trp Lys Ile Ser Leu Arg Thr Val Arg Asp
                965                 970                 975

TGT GAA ATA ATT TGG ACT TTA CAA GAT ACT TCT GGA AAT AAG GAA AAT     2976
Cys Glu Ile Ile Trp Thr Leu Gln Asp Thr Ser Gly Asn Lys Glu Asn
            980                 985                 990

TTA ATT TTT AGG TAT GAA GAA CTT AAT AGG ATA TCT AAT TAT ATA AAT     3024
Leu Ile Phe Arg Tyr Glu Glu Leu Asn Arg Ile Ser Asn Tyr Ile Asn
        995                 1000                1005

AAA TGG ATT TTT GTA ACT ATT ACT AAT AAT AGA TTA GGC AAT TCT AGA     3072
Lys Trp Ile Phe Val Thr Ile Thr Asn Asn Arg Leu Gly Asn Ser Arg
    1010                1015                1020

ATT TAC ATC AAT GGA AAT TTA ATA GTT GAA AAA TCA ATT TCG AAT TTA     3120
Ile Tyr Ile Asn Gly Asn Leu Ile Val Glu Lys Ser Ile Ser Asn Leu
1025                1030                1035                1040

GGT GAT ATT CAT GTT AGT GAT AAT ATA TTA TTT AAA ATT GTT GGT TGT     3168
Gly Asp Ile His Val Ser Asp Asn Ile Leu Phe Lys Ile Val Gly Cys
                1045                1050                1055
```

-continued

```
GAT GAT GAA ACG TAT GTT GGT ATA AGA TAT TTT AAA GTT TTT AAT ACG     3216
Asp Asp Glu Thr Tyr Val Gly Ile Arg Tyr Phe Lys Val Phe Asn Thr
            1060                1065                1070

GAA TTA GAT AAA ACA GAA ATT GAG ACT TTA TAT AGT AAT GAG CCA GAT     3264
Glu Leu Asp Lys Thr Glu Ile Glu Thr Leu Tyr Ser Asn Glu Pro Asp
        1075                1080                1085

CCA AGT ATC TTA AAA AAC TAT TGG GGA AAT TAT TTG CTA TAT AAT AAA     3312
Pro Ser Ile Leu Lys Asn Tyr Trp Gly Asn Tyr Leu Leu Tyr Asn Lys
    1090                1095                1100

AAA TAT TAT TTA TTC AAT TTA CTA AGA AAA GAT AAG TAT ATT ACT CTG     3360
Lys Tyr Tyr Leu Phe Asn Leu Leu Arg Lys Asp Lys Tyr Ile Thr Leu
1105                1110                1115                1120

AAT TCA GGC ATT TTA AAT ATT AAT CAA CAA AGA GGT GTT ACT GAA GGC     3408
Asn Ser Gly Ile Leu Asn Ile Asn Gln Gln Arg Gly Val Thr Glu Gly
                1125                1130                1135

TCT GTT TTT TTG AAC TAT AAA TTA TAT GAA GGA GTA GAA GTC ATT ATA     3456
Ser Val Phe Leu Asn Tyr Lys Leu Tyr Glu Gly Val Glu Val Ile Ile
            1140                1145                1150

AGA AAA AAT GGT CCT ATA GAT ATA TCT AAT ACA GAT AAT TTT GTT AGA     3504
Arg Lys Asn Gly Pro Ile Asp Ile Ser Asn Thr Asp Asn Phe Val Arg
        1155                1160                1165

AAA AAC GAT CTA GCA TAC ATT AAT GTA GTA GAT CGT GGT GTA GAA TAT     3552
Lys Asn Asp Leu Ala Tyr Ile Asn Val Val Asp Arg Gly Val Glu Tyr
    1170                1175                1180

CGG TTA TAT GCT GAT ACA AAA TCA GAG AAA GAG AAA ATA ATA AGA ACA     3600
Arg Leu Tyr Ala Asp Thr Lys Ser Glu Lys Glu Lys Ile Ile Arg Thr
1185                1190                1195                1200

TCT AAT CTA AAC GAT AGC TTA GGT CAA ATT ATA GTT ATG GAT TCA ATA     3648
Ser Asn Leu Asn Asp Ser Leu Gly Gln Ile Ile Val Met Asp Ser Ile
                1205                1210                1215

GGA AAT AAT TGC ACA ATG AAT TTT CAA AAC AAT AAT GGG AGC AAT ATA     3696
Gly Asn Asn Cys Thr Met Asn Phe Gln Asn Asn Asn Gly Ser Asn Ile
            1220                1225                1230

GGA TTA CTA GGT TTT CAT TCA AAT AAT TTG GTT GCT AGT AGT TGG TAT     3744
Gly Leu Leu Gly Phe His Ser Asn Asn Leu Val Ala Ser Ser Trp Tyr
        1235                1240                1245

TAT AAC AAT ATA CGA AGA AAT ACT AGC AGT AAT GGA TGC TTT TGG AGT     3792
Tyr Asn Asn Ile Arg Arg Asn Thr Ser Ser Asn Gly Cys Phe Trp Ser
    1250                1255                1260

TCT ATT TCT AAA GAG AAT GGA TGG AAA GAA TGA                         3825
Ser Ile Ser Lys Glu Asn Gly Trp Lys Glu
1265                1270
```

(2) INFORMATION FOR SEQ ID NO:71:

(i) SEQUENCE CHARACTERISTICS:
(A) LENGTH: 1274 amino acids
(B) TYPE: amino acid
(D) TOPOLOGY: linear (ii) MOLECULE TYPE: protein (xi) SEQUENCE DESCRIPTION: SEQ ID NO:71:

```
Met Pro Val Ala Ile Asn Ser Phe Asn Tyr Asn Asp Pro Val Asn Asp
  1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
```

-continued

```
        50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480
```

-continued

```
Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
        595                 600                 605

Ser Thr Val Asp Lys Ile Ala Asp Ile Ser Leu Ile Val Pro Tyr Val
    610                 615                 620

Gly Leu Ala Leu Asn Ile Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
        675                 680                 685

Leu Ile Glu Arg Glu Ala Lys Trp Lys Glu Ile Tyr Ser Trp Ile Val
    690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Glu Leu Asn Lys Lys
        755                 760                 765

Val Ser Leu Ala Met Lys Asn Ile Glu Arg Phe Met Thr Glu Ser Ser
    770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
            820                 825                 830

Val Thr Ser Thr Leu Asn Ser Ser Ile Pro Phe Glu Leu Ser Ser Tyr
        835                 840                 845

Thr Asn Asp Lys Ile Leu Ile Ile Tyr Phe Asn Arg Leu Tyr Lys Lys
    850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895
```

-continued

```
Tyr Ile Tyr Ser Thr Asn Arg Asn Gln Phe Gly Ile Tyr Asn Ser Arg
            900                 905                 910

Leu Ser Glu Val Asn Ile Ala Gln Asn Asn Asp Ile Ile Tyr Asn Ser
        915                 920                 925

Arg Tyr Gln Asn Phe Ser Ile Ser Phe Trp Val Arg Ile Pro Lys His
    930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
        995                 1000                1005

Lys Trp Ile Phe Val Thr Ile Thr Asn Asn Arg Leu Gly Asn Ser Arg
    1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
            1060                1065                1070

Glu Leu Asp Lys Thr Glu Ile Glu Thr Leu Tyr Ser Asn Glu Pro Asp
        1075                1080                1085

Pro Ser Ile Leu Lys Asn Tyr Trp Gly Asn Tyr Leu Leu Tyr Asn Lys
    1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                1125                1130                1135

Ser Val Phe Leu Asn Tyr Lys Leu Tyr Glu Gly Val Glu Val Ile Ile
            1140                1145                1150

Arg Lys Asn Gly Pro Ile Asp Ile Ser Asn Thr Asp Asn Phe Val Arg
        1155                1160                1165

Lys Asn Asp Leu Ala Tyr Ile Asn Val Val Asp Arg Gly Val Glu Tyr
    1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
                1205                1210                1215

Gly Asn Asn Cys Thr Met Asn Phe Gln Asn Asn Asn Gly Ser Asn Ile
            1220                1225                1230

Gly Leu Leu Gly Phe His Ser Asn Asn Leu Val Ala Ser Ser Trp Tyr
        1235                1240                1245

Tyr Asn Asn Ile Arg Arg Asn Thr Ser Ser Asn Gly Cys Phe Trp Ser
    1250                1255                1260

Ser Ile Ser Lys Glu Asn Gly Trp Lys Glu
1265                1270
```

(2) INFORMATION FOR SEQ ID NO:72:

(i) SEQUENCE CHARACTERISTICS:
(A) LENGTH: 1460 base pairs
(B) TYPE: nucleic acid
(C) STRANDEDNESS: double -continued (D) TOPOLOGY: linear (ii) MOLECULE TYPE: DNA (genomic)

(ix) FEATURE:
(A) NAME/KEY: CDS
(B) LOCATION: 108..1451

(xi) SEQUENCE DESCRIPTION: SEQ ID NO:72:

```
AGATCTCGAT CCCGCGAAAT TAATACGACT CACTATAGGG GAATTGTGAG CGGATAACAA      60

TTCCCCTCTA GAAATAATTT TGTTTAACTT TAAGAAGGAG ATATACC ATG GGC CAT      116
                                                    Met Gly His
                                                     1

CAT CAT CAT CAT CAT CAT CAT CAT CAC AGC AGC GGC CAT ATC GAA GGT      164
His His His His His His His His His Ser Ser Gly His Ile Glu Gly
      5                  10                  15

CGT CAT ATG GCT AGC ATG GCT ATT CTA ATT ATA TAT TTT AAT AGA TTA      212
Arg His Met Ala Ser Met Ala Ile Leu Ile Ile Tyr Phe Asn Arg Leu
 20                  25                  30                  35

TAT AAA AAA ATT AAA GAT AGT TCT ATT TTA GAT ATG CGA TAT GAA AAT      260
Tyr Lys Lys Ile Lys Asp Ser Ser Ile Leu Asp Met Arg Tyr Glu Asn
                 40                  45                  50

AAT AAA TTT ATA GAT ATC TCT GGA TAT GGT TCA AAT ATA AGC ATT AAT      308
Asn Lys Phe Ile Asp Ile Ser Gly Tyr Gly Ser Asn Ile Ser Ile Asn
             55                  60                  65

GGA AAC GTA TAT ATT TAT TCA ACA AAT AGA AAT CAA TTT GGA ATA TAT      356
Gly Asn Val Tyr Ile Tyr Ser Thr Asn Arg Asn Gln Phe Gly Ile Tyr
         70                  75                  80

AAT AGT AGG CTT AGT GAA GTT AAT ATA GCT CAA AAT AAT GAT ATT ATA      404
Asn Ser Arg Leu Ser Glu Val Asn Ile Ala Gln Asn Asn Asp Ile Ile
     85                  90                  95

TAC AAT AGT AGA TAT CAA AAT TTT AGT ATT AGT TTC TGG GTA AGG ATT      452
Tyr Asn Ser Arg Tyr Gln Asn Phe Ser Ile Ser Phe Trp Val Arg Ile
100                 105                 110                 115

CCT AAA CAC TAC AAA CCT ATG AAT CAT AAT CGG GAA TAC ACT ATA ATA      500
Pro Lys His Tyr Lys Pro Met Asn His Asn Arg Glu Tyr Thr Ile Ile
                120                 125                 130

AAT TGT ATG GGG AAT AAT AAT TCG GGA TGG AAA ATA TCA CTT AGA ACT      548
Asn Cys Met Gly Asn Asn Asn Ser Gly Trp Lys Ile Ser Leu Arg Thr
            135                 140                 145

GTT AGA GAT TGT GAA ATA ATT TGG ACT TTA CAA GAT ACT TCT GGA AAT      596
Val Arg Asp Cys Glu Ile Ile Trp Thr Leu Gln Asp Thr Ser Gly Asn
        150                 155                 160

AAG GAA AAT TTA ATT TTT AGG TAT GAA GAA CTT AAT AGG ATA TCT AAT      644
Lys Glu Asn Leu Ile Phe Arg Tyr Glu Glu Leu Asn Arg Ile Ser Asn
    165                 170                 175

TAT ATA AAT AAA TGG ATT TTT GTA ACT ATT ACT AAT AAT AGA TTA GGC      692
Tyr Ile Asn Lys Trp Ile Phe Val Thr Ile Thr Asn Asn Arg Leu Gly
180                 185                 190                 195

AAT TCT AGA ATT TAC ATC AAT GGA AAT TTA ATA GTT GAA AAA TCA ATT      740
Asn Ser Arg Ile Tyr Ile Asn Gly Asn Leu Ile Val Glu Lys Ser Ile
                200                 205                 210

TCG AAT TTA GGT GAT ATT CAT GTT AGT GAT AAT ATA TTA TTT AAA ATT      788
Ser Asn Leu Gly Asp Ile His Val Ser Asp Asn Ile Leu Phe Lys Ile
            215                 220                 225

GTT GGT TGT GAT GAT GAA ACG TAT GTT GGT ATA AGA TAT TTT AAA GTT      836
Val Gly Cys Asp Asp Glu Thr Tyr Val Gly Ile Arg Tyr Phe Lys Val
        230                 235                 240

TTT AAT ACG GAA TTA GAT AAA ACA GAA ATT GAG ACT TTA TAT AGT AAT      884
Phe Asn Thr Glu Leu Asp Lys Thr Glu Ile Glu Thr Leu Tyr Ser Asn
    245                 250                 255
```

-continued

```
GAG CCA GAT CCA AGT ATC TTA AAA AAC TAT TGG GGA AAT TAT TTG CTA      932
Glu Pro Asp Pro Ser Ile Leu Lys Asn Tyr Trp Gly Asn Tyr Leu Leu
260                 265                 270                 275

TAT AAT AAA AAA TAT TAT TTA TTC AAT TTA CTA AGA AAA GAT AAG TAT      980
Tyr Asn Lys Lys Tyr Tyr Leu Phe Asn Leu Leu Arg Lys Asp Lys Tyr
                280                 285                 290

ATT ACT CTG AAT TCA GGC ATT TTA AAT ATT AAT CAA CAA AGA GGT GTT     1028
Ile Thr Leu Asn Ser Gly Ile Leu Asn Ile Asn Gln Gln Arg Gly Val
            295                 300                 305

ACT GAA GGC TCT GTT TTT TTG AAC TAT AAA TTA TAT GAA GGA GTA GAA     1076
Thr Glu Gly Ser Val Phe Leu Asn Tyr Lys Leu Tyr Glu Gly Val Glu
        310                 315                 320

GTC ATT ATA AGA AAA AAT GGT CCT ATA GAT ATA TCT AAT ACA GAT AAT     1124
Val Ile Ile Arg Lys Asn Gly Pro Ile Asp Ile Ser Asn Thr Asp Asn
    325                 330                 335

TTT GTT AGA AAA AAC GAT CTA GCA TAC ATT AAT GTA GTA GAT CGT GGT     1172
Phe Val Arg Lys Asn Asp Leu Ala Tyr Ile Asn Val Val Asp Arg Gly
340                 345                 350                 355

GTA GAA TAT CGG TTA TAT GCT GAT ACA AAA TCA GAG AAA GAG AAA ATA     1220
Val Glu Tyr Arg Leu Tyr Ala Asp Thr Lys Ser Glu Lys Glu Lys Ile
                360                 365                 370

ATA AGA ACA TCT AAT CTA AAC GAT AGC TTA GGT CAA ATT ATA GTT ATG     1268
Ile Arg Thr Ser Asn Leu Asn Asp Ser Leu Gly Gln Ile Ile Val Met
            375                 380                 385

GAT TCA ATA GGA AAT AAT TGC ACA ATG AAT TTT CAA AAC AAT AAT GGG     1316
Asp Ser Ile Gly Asn Asn Cys Thr Met Asn Phe Gln Asn Asn Asn Gly
        390                 395                 400

AGC AAT ATA GGA TTA CTA GGT TTT CAT TCA AAT AAT TTG GTT GCT AGT     1364
Ser Asn Ile Gly Leu Leu Gly Phe His Ser Asn Asn Leu Val Ala Ser
    405                 410                 415

AGT TGG TAT TAT AAC AAT ATA CGA AGA AAT ACT AGC AGT AAT GGA TGC     1412
Ser Trp Tyr Tyr Asn Asn Ile Arg Arg Asn Thr Ser Ser Asn Gly Cys
420                 425                 430                 435

TTT TGG AGT TCT ATT TCT AAA GAG AAT GGA TGG AAA GAA TGAAAGCTT       1460
Phe Trp Ser Ser Ile Ser Lys Glu Asn Gly Trp Lys Glu
                440                 445
```

(2) INFORMATION FOR SEQ ID NO:73:

(i) SEQUENCE CHARACTERISTICS:
(A) LENGTH: 448 amino acids
(B) TYPE: amino acid
(D) TOPOLOGY: linear (ii) MOLECULE TYPE: protein (xi) SEQUENCE DESCRIPTION: SEQ ID NO:73:

```
Met Gly His His His His His His His His His His Ser Ser Gly His
  1               5                  10                  15

Ile Glu Gly Arg His Met Ala Ser Met Ala Ile Leu Ile Ile Tyr Phe
            20                  25                  30

Asn Arg Leu Tyr Lys Lys Ile Lys Asp Ser Ser Ile Leu Asp Met Arg
        35                  40                  45

Tyr Glu Asn Asn Lys Phe Ile Asp Ile Ser Gly Tyr Gly Ser Asn Ile
    50                  55                  60

Ser Ile Asn Gly Asn Val Tyr Ile Tyr Ser Thr Asn Arg Asn Gln Phe
 65                  70                  75                  80

Gly Ile Tyr Asn Ser Arg Leu Ser Glu Val Asn Ile Ala Gln Asn Asn
                 85                  90                  95
```

-continued

```
Asp Ile Ile Tyr Asn Ser Arg Tyr Gln Asn Phe Ser Ile Ser Phe Trp
            100                 105                 110

Val Arg Ile Pro Lys His Tyr Lys Pro Met Asn His Asn Arg Glu Tyr
        115                 120                 125

Thr Ile Ile Asn Cys Met Gly Asn Asn Asn Ser Gly Trp Lys Ile Ser
    130                 135                 140

Leu Arg Thr Val Arg Asp Cys Glu Ile Ile Trp Thr Leu Gln Asp Thr
145                 150                 155                 160

Ser Gly Asn Lys Glu Asn Leu Ile Phe Arg Tyr Glu Glu Leu Asn Arg
                165                 170                 175

Ile Ser Asn Tyr Ile Asn Lys Trp Ile Phe Val Thr Ile Thr Asn Asn
            180                 185                 190

Arg Leu Gly Asn Ser Arg Ile Tyr Ile Asn Gly Asn Leu Ile Val Glu
        195                 200                 205

Lys Ser Ile Ser Asn Leu Gly Asp Ile His Val Ser Asp Asn Ile Leu
    210                 215                 220

Phe Lys Ile Val Gly Cys Asp Asp Glu Thr Tyr Val Gly Ile Arg Tyr
225                 230                 235                 240

Phe Lys Val Phe Asn Thr Glu Leu Asp Lys Thr Glu Ile Glu Thr Leu
                245                 250                 255

Tyr Ser Asn Glu Pro Asp Pro Ser Ile Leu Lys Asn Tyr Trp Gly Asn
            260                 265                 270

Tyr Leu Leu Tyr Asn Lys Lys Tyr Tyr Leu Phe Asn Leu Leu Arg Lys
        275                 280                 285

Asp Lys Tyr Ile Thr Leu Asn Ser Gly Ile Leu Asn Ile Asn Gln Gln
    290                 295                 300

Arg Gly Val Thr Glu Gly Ser Val Phe Leu Asn Tyr Lys Leu Tyr Glu
305                 310                 315                 320

Gly Val Glu Val Ile Ile Arg Lys Asn Gly Pro Ile Asp Ile Ser Asn
                325                 330                 335

Thr Asp Asn Phe Val Arg Lys Asn Asp Leu Ala Tyr Ile Asn Val Val
            340                 345                 350

Asp Arg Gly Val Glu Tyr Arg Leu Tyr Ala Asp Thr Lys Ser Glu Lys
        355                 360                 365

Glu Lys Ile Ile Arg Thr Ser Asn Leu Asn Asp Ser Leu Gly Gln Ile
    370                 375                 380

Ile Val Met Asp Ser Ile Gly Asn Asn Cys Thr Met Asn Phe Gln Asn
385                 390                 395                 400

Asn Asn Gly Ser Asn Ile Gly Leu Leu Gly Phe His Ser Asn Asn Leu
                405                 410                 415

Val Ala Ser Ser Trp Tyr Tyr Asn Asn Ile Arg Arg Asn Thr Ser Ser
            420                 425                 430

Asn Gly Cys Phe Trp Ser Ser Ile Ser Lys Glu Asn Gly Trp Lys Glu
        435                 440                 445
```

(2) INFORMATION FOR SEQ ID NO:74:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA"

(xi) SEQUENCE DESCRIPTION: SEQ ID NO:74:

-continued

```
CGCCATGGCT ATTCTAATTA TATATTTTAA TAG                                   33


(2) INFORMATION FOR SEQ ID NO:75:

     (i) SEQUENCE CHARACTERISTICS:
          (A) LENGTH: 29 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "DNA"

    (xi) SEQUENCE DESCRIPTION: SEQ ID NO:75:

GCAAGCTTTC ATTCTTTCCA TCCATTCTC                                        29


(2) INFORMATION FOR SEQ ID NO:76:

     (i) SEQUENCE CHARACTERISTICS:
          (A) LENGTH: 3894 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 1..3891

    (xi) SEQUENCE DESCRIPTION: SEQ ID NO:76:

ATG CCA GTT AAT ATA AAA AAC TTT AAT TAT AAT GAC CCT ATT AAT AAT        48
Met Pro Val Asn Ile Lys Asn Phe Asn Tyr Asn Asp Pro Ile Asn Asn
  1               5                  10                  15

GAT GAC ATT ATT ATG ATG GAA CCA TTC AAT GAC CCA GGG CCA GGA ACA        96
Asp Asp Ile Ile Met Met Glu Pro Phe Asn Asp Pro Gly Pro Gly Thr
             20                  25                  30

TAT TAT AAA GCT TTT AGG ATT ATA GAT CGT ATT TGG ATA GTA CCA GAA       144
Tyr Tyr Lys Ala Phe Arg Ile Ile Asp Arg Ile Trp Ile Val Pro Glu
         35                  40                  45

AGG TTT ACT TAT GGA TTT CAA CCT GAC CAA TTT AAT GCC AGT ACA GGA       192
Arg Phe Thr Tyr Gly Phe Gln Pro Asp Gln Phe Asn Ala Ser Thr Gly
     50                  55                  60

GTT TTT AGT AAA GAT GTC TAC GAA TAT TAC GAT CCA ACT TAT TTA AAA       240
Val Phe Ser Lys Asp Val Tyr Glu Tyr Tyr Asp Pro Thr Tyr Leu Lys
 65                  70                  75                  80

ACC GAT GCT GAA AAA GAT AAA TTT TTA AAA ACA ATG ATT AAA TTA TTT       288
Thr Asp Ala Glu Lys Asp Lys Phe Leu Lys Thr Met Ile Lys Leu Phe
                 85                  90                  95

AAT AGA ATT AAT TCA AAA CCA TCA GGA CAG AGA TTA CTG GAT ATG ATA       336
Asn Arg Ile Asn Ser Lys Pro Ser Gly Gln Arg Leu Leu Asp Met Ile
            100                 105                 110

GTA GAT GCT ATA CCT TAT CTT GGA AAT GCA TCT ACA CCG CCC GAC AAA       384
Val Asp Ala Ile Pro Tyr Leu Gly Asn Ala Ser Thr Pro Pro Asp Lys
        115                 120                 125

TTT GCA GCA AAT GTT GCA AAT GTA TCT ATT AAT AAA AAA ATT ATC CAA       432
Phe Ala Ala Asn Val Ala Asn Val Ser Ile Asn Lys Lys Ile Ile Gln
    130                 135                 140

CCT GGA GCT GAA GAT CAA ATA AAA GGT TTA ATG ACA AAT TTA ATA ATA       480
Pro Gly Ala Glu Asp Gln Ile Lys Gly Leu Met Thr Asn Leu Ile Ile
145                 150                 155                 160

TTT GGA CCA GGA CCA GTT CTA AGT GAT AAT TTT ACT GAT AGT ATG ATT       528
Phe Gly Pro Gly Pro Val Leu Ser Asp Asn Phe Thr Asp Ser Met Ile
                165                 170                 175
```

-continued

```
ATG AAT GGC CAT TCC CCA ATA TCA GAA GGA TTT GGT GCA AGA ATG ATG      576
Met Asn Gly His Ser Pro Ile Ser Glu Gly Phe Gly Ala Arg Met Met
            180                 185                 190

ATA AGA TTT TGT CCT AGT TGT TTA AAT GTA TTT AAT AAT GTT CAG GAA      624
Ile Arg Phe Cys Pro Ser Cys Leu Asn Val Phe Asn Asn Val Gln Glu
        195                 200                 205

AAT AAA GAT ACA TCT ATA TTT AGT AGA CGC GCG TAT TTT GCA GAT CCA      672
Asn Lys Asp Thr Ser Ile Phe Ser Arg Arg Ala Tyr Phe Ala Asp Pro
    210                 215                 220

GCT CTA ACG TTA ATG CAT GAA CTT ATA CAT GTG TTA CAT GGA TTA TAT      720
Ala Leu Thr Leu Met His Glu Leu Ile His Val Leu His Gly Leu Tyr
225                 230                 235                 240

GGA ATT AAG ATA AGT AAT TTA CCA ATT ACT CCA AAT ACA AAA GAA TTT      768
Gly Ile Lys Ile Ser Asn Leu Pro Ile Thr Pro Asn Thr Lys Glu Phe
                245                 250                 255

TTC ATG CAA CAT AGC GAT CCT GTA CAA GCA GAA GAA CTA TAT ACA TTC      816
Phe Met Gln His Ser Asp Pro Val Gln Ala Glu Glu Leu Tyr Thr Phe
            260                 265                 270

GGA GGA CAT GAT CCT AGT GTT ATA AGT CCT TCT ACG GAT ATG AAT ATT      864
Gly Gly His Asp Pro Ser Val Ile Ser Pro Ser Thr Asp Met Asn Ile
        275                 280                 285

TAT AAT AAA GCG TTA CAA AAT TTT CAA GAT ATA GCT AAT AGG CTT AAT      912
Tyr Asn Lys Ala Leu Gln Asn Phe Gln Asp Ile Ala Asn Arg Leu Asn
    290                 295                 300

ATT GTT TCA AGT GCC CAA GGG AGT GGA ATT GAT ATT TCC TTA TAT AAA      960
Ile Val Ser Ser Ala Gln Gly Ser Gly Ile Asp Ile Ser Leu Tyr Lys
305                 310                 315                 320

CAA ATA TAT AAA AAT AAA TAT GAT TTT GTT GAA GAT CCT AAT GGA AAA     1008
Gln Ile Tyr Lys Asn Lys Tyr Asp Phe Val Glu Asp Pro Asn Gly Lys
                325                 330                 335

TAT AGT GTA GAT AAG GAT AAG TTT GAT AAA TTA TAT AAG GCC TTA ATG     1056
Tyr Ser Val Asp Lys Asp Lys Phe Asp Lys Leu Tyr Lys Ala Leu Met
            340                 345                 350

TTT GGC TTT ACT GAA ACT AAT CTA GCT GGT GAA TAT GGA ATA AAA ACT     1104
Phe Gly Phe Thr Glu Thr Asn Leu Ala Gly Glu Tyr Gly Ile Lys Thr
        355                 360                 365

AGG TAT TCT TAT TTT AGT GAA TAT TTG CCA CCG ATA AAA ACT GAA AAA     1152
Arg Tyr Ser Tyr Phe Ser Glu Tyr Leu Pro Pro Ile Lys Thr Glu Lys
    370                 375                 380

TTG TTA GAC AAT ACA ATT TAT ACT CAA AAT GAA GGC TTT AAC ATA GCT     1200
Leu Leu Asp Asn Thr Ile Tyr Thr Gln Asn Glu Gly Phe Asn Ile Ala
385                 390                 395                 400

AGT AAA AAT CTC AAA ACG GAA TTT AAT GGT CAG AAT AAG GCG GTA AAT     1248
Ser Lys Asn Leu Lys Thr Glu Phe Asn Gly Gln Asn Lys Ala Val Asn
                405                 410                 415

AAA GAG GCT TAT GAA GAA ATC AGC CTA GAA CAT CTC GTT ATA TAT AGA     1296
Lys Glu Ala Tyr Glu Glu Ile Ser Leu Glu His Leu Val Ile Tyr Arg
            420                 425                 430

ATA GCA ATG TGC AAG CCT GTA ATG TAC AAA AAT ACC GGT AAA TCT GAA     1344
Ile Ala Met Cys Lys Pro Val Met Tyr Lys Asn Thr Gly Lys Ser Glu
        435                 440                 445

CAG TGT ATT ATT GTT AAT AAT GAG GAT TTA TTT TTC ATA GCT AAT AAA     1392
Gln Cys Ile Ile Val Asn Asn Glu Asp Leu Phe Phe Ile Ala Asn Lys
    450                 455                 460

GAT AGT TTT TCA AAA GAT TTA GCT AAA GCA GAA ACT ATA GCA TAT AAT     1440
Asp Ser Phe Ser Lys Asp Leu Ala Lys Ala Glu Thr Ile Ala Tyr Asn
465                 470                 475                 480

ACA CAA AAT AAT ACT ATA GAA AAT AAT TTT TCT ATA GAT CAG TTG ATT     1488
Thr Gln Asn Asn Thr Ile Glu Asn Asn Phe Ser Ile Asp Gln Leu Ile
```

-continued

```
                485                     490                     495

TTA GAT AAT GAT TTA AGC AGT GGC ATA GAC TTA CCA AAT GAA AAC ACA     1536
Leu Asp Asn Asp Leu Ser Ser Gly Ile Asp Leu Pro Asn Glu Asn Thr
            500                     505                     510

GAA CCA TTT ACA AAT TTT GAC GAC ATA GAT ATC CCT GTG TAT ATT AAA     1584
Glu Pro Phe Thr Asn Phe Asp Asp Ile Asp Ile Pro Val Tyr Ile Lys
        515                     520                     525

CAA TCT GCT TTA AAA AAA ATT TTT GTG GAT GGA GAT AGC CTT TTT GAA     1632
Gln Ser Ala Leu Lys Lys Ile Phe Val Asp Gly Asp Ser Leu Phe Glu
    530                     535                     540

TAT TTA CAT GCT CAA ACA TTT CCT TCT AAT ATA GAA AAT CTA CAA CTA     1680
Tyr Leu His Ala Gln Thr Phe Pro Ser Asn Ile Glu Asn Leu Gln Leu
545                     550                     555                     560

ACG AAT TCA TTA AAT GAT GCT TTA AGA AAT AAT AAT AAA GTC TAT ACT     1728
Thr Asn Ser Leu Asn Asp Ala Leu Arg Asn Asn Asn Lys Val Tyr Thr
                565                     570                     575

TTT TTT TCT ACA AAC CTT GTT GAA AAA GCT AAT ACA GTT GTA GGT GCT     1776
Phe Phe Ser Thr Asn Leu Val Glu Lys Ala Asn Thr Val Val Gly Ala
            580                     585                     590

TCA CTT TTT GTA AAC TGG GTA AAA GGA GTA ATA GAT GAT TTT ACA TCT     1824
Ser Leu Phe Val Asn Trp Val Lys Gly Val Ile Asp Asp Phe Thr Ser
        595                     600                     605

GAA TCC ACA CAA AAA AGT ACT ATA GAT AAA GTT TCA GAT GTA TCC ATA     1872
Glu Ser Thr Gln Lys Ser Thr Ile Asp Lys Val Ser Asp Val Ser Ile
    610                     615                     620

ATT ATT CCC TAT ATA GGA CCT GCT TTG AAT GTA GGA AAT GAA ACA GCT     1920
Ile Ile Pro Tyr Ile Gly Pro Ala Leu Asn Val Gly Asn Glu Thr Ala
625                     630                     635                     640

AAA GAA AAT TTT AAA AAT GCT TTT GAA ATA GGT GGA GCC GCT ATC TTA     1968
Lys Glu Asn Phe Lys Asn Ala Phe Glu Ile Gly Gly Ala Ala Ile Leu
                645                     650                     655

ATG GAG TTT ATT CCA GAA CTT ATT GTA CCT ATA GTT GGA TTT TTT ACA     2016
Met Glu Phe Ile Pro Glu Leu Ile Val Pro Ile Val Gly Phe Phe Thr
            660                     665                     670

TTA GAA TCA TAT GTA GGA AAT AAA GGG CAT ATT ATT ATG ACG ATA TCC     2064
Leu Glu Ser Tyr Val Gly Asn Lys Gly His Ile Ile Met Thr Ile Ser
        675                     680                     685

AAT GCT TTA AAG AAA AGG GAT CAA AAA TGG ACA GAT ATG TAT GGT TTG     2112
Asn Ala Leu Lys Lys Arg Asp Gln Lys Trp Thr Asp Met Tyr Gly Leu
    690                     695                     700

ATA GTA TCG CAG TGG CTC TCA ACG GTT AAT ACT CAA TTT TAT ACA ATA     2160
Ile Val Ser Gln Trp Leu Ser Thr Val Asn Thr Gln Phe Tyr Thr Ile
705                     710                     715                     720

AAA GAA AGA ATG TAC AAT GCT TTA AAT AAT CAA TCA CAA GCA ATA GAA     2208
Lys Glu Arg Met Tyr Asn Ala Leu Asn Asn Gln Ser Gln Ala Ile Glu
                725                     730                     735

AAA ATA ATA GAA GAT CAA TAT AAT AGA TAT AGT GAA GAA GAT AAA ATG     2256
Lys Ile Ile Glu Asp Gln Tyr Asn Arg Tyr Ser Glu Glu Asp Lys Met
            740                     745                     750

AAT ATT AAC ATT GAT TTT AAT GAT ATA GAT TTT AAA CTT AAT CAA AGT     2304
Asn Ile Asn Ile Asp Phe Asn Asp Ile Asp Phe Lys Leu Asn Gln Ser
        755                     760                     765

ATA AAT TTA GCA ATA AAC AAT ATA GAT GAT TTT ATA AAC CAA TGT TCT     2352
Ile Asn Leu Ala Ile Asn Asn Ile Asp Asp Phe Ile Asn Gln Cys Ser
    770                     775                     780

ATA TCA TAT CTA ATG AAT AGA ATG ATT CCA TTA GCT GTA AAA AAG TTA     2400
Ile Ser Tyr Leu Met Asn Arg Met Ile Pro Leu Ala Val Lys Lys Leu
785                     790                     795                     800

AAA GAC TTT GAT GAT AAT CTT AAG AGA GAT TTA TTG GAG TAT ATA GAT     2448
```

-continued

```
Lys Asp Phe Asp Asp Asn Leu Lys Arg Asp Leu Leu Glu Tyr Ile Asp
                805                 810                 815

ACA AAT GAA CTA TAT TTA CTT GAT GAA GTA AAT ATT CTA AAA TCA AAA     2496
Thr Asn Glu Leu Tyr Leu Leu Asp Glu Val Asn Ile Leu Lys Ser Lys
            820                 825                 830

GTA AAT AGA CAC CTA AAA GAC AGT ATA CCA TTT GAT CTT TCA CTA TAT     2544
Val Asn Arg His Leu Lys Asp Ser Ile Pro Phe Asp Leu Ser Leu Tyr
        835                 840                 845

ACC AAG GAC ACA ATT TTA ATA CAA GTT TTT AAT AAT TAT ATT AGT AAT     2592
Thr Lys Asp Thr Ile Leu Ile Gln Val Phe Asn Asn Tyr Ile Ser Asn
    850                 855                 860

ATT AGT AGT AAT GCT ATT TTA AGT TTA AGT TAT AGA GGT GGG CGT TTA     2640
Ile Ser Ser Asn Ala Ile Leu Ser Leu Ser Tyr Arg Gly Gly Arg Leu
865                 870                 875                 880

ATA GAT TCA TCT GGA TAT GGT GCA ACT ATG AAT GTA GGT TCA GAT GTT     2688
Ile Asp Ser Ser Gly Tyr Gly Ala Thr Met Asn Val Gly Ser Asp Val
                885                 890                 895

ATC TTT AAT GAT ATA GGA AAT GGT CAA TTT AAA TTA AAT AAT TCT GAA     2736
Ile Phe Asn Asp Ile Gly Asn Gly Gln Phe Lys Leu Asn Asn Ser Glu
            900                 905                 910

AAT AGT AAT ATT ACG GCA CAT CAA AGT AAA TTC GTT GTA TAT GAT AGT     2784
Asn Ser Asn Ile Thr Ala His Gln Ser Lys Phe Val Val Tyr Asp Ser
        915                 920                 925

ATG TTT GAT AAT TTT AGC ATT AAC TTT TGG GTA AGG ACT CCT AAA TAT     2832
Met Phe Asp Asn Phe Ser Ile Asn Phe Trp Val Arg Thr Pro Lys Tyr
    930                 935                 940

AAT AAT AAT GAT ATA CAA ACT TAT CTT CAA AAT GAG TAT ACA ATA ATT     2880
Asn Asn Asn Asp Ile Gln Thr Tyr Leu Gln Asn Glu Tyr Thr Ile Ile
945                 950                 955                 960

AGT TGT ATA AAA AAT GAC TCA GGA TGG AAA GTA TCT ATT AAG GGA AAT     2928
Ser Cys Ile Lys Asn Asp Ser Gly Trp Lys Val Ser Ile Lys Gly Asn
                965                 970                 975

AGA ATA ATA TGG ACA TTA ATA GAT GTT AAT GCA AAA TCT AAA TCA ATA     2976
Arg Ile Ile Trp Thr Leu Ile Asp Val Asn Ala Lys Ser Lys Ser Ile
            980                 985                 990

TTT TTC GAA TAT AGT ATA AAA GAT AAT ATA TCA GAT TAT ATA AAT AAA     3024
Phe Phe Glu Tyr Ser Ile Lys Asp Asn Ile Ser Asp Tyr Ile Asn Lys
        995                 1000                1005

TGG TTT TCC ATA ACT ATT ACT AAT GAT AGA TTA GGT AAC GCA AAT ATT     3072
Trp Phe Ser Ile Thr Ile Thr Asn Asp Arg Leu Gly Asn Ala Asn Ile
    1010                1015                1020

TAT ATA AAT GGA AGT TTG AAA AAA AGT GAA AAA ATT TTA AAC TTA GAT     3120
Tyr Ile Asn Gly Ser Leu Lys Lys Ser Glu Lys Ile Leu Asn Leu Asp
1025                1030                1035                1040

AGA ATT AAT TCT AGT AAT GAT ATA GAC TTC AAA TTA ATT AAT TGT ACA     3168
Arg Ile Asn Ser Ser Asn Asp Ile Asp Phe Lys Leu Ile Asn Cys Thr
                1045                1050                1055

GAT ACT ACT AAA TTT GTT TGG ATT AAG GAT TTT AAT ATT TTT GGT AGA     3216
Asp Thr Thr Lys Phe Val Trp Ile Lys Asp Phe Asn Ile Phe Gly Arg
            1060                1065                1070

GAA TTA AAT GCT ACA GAA GTA TCT TCA CTA TAT TGG ATT CAA TCA TCT     3264
Glu Leu Asn Ala Thr Glu Val Ser Ser Leu Tyr Trp Ile Gln Ser Ser
        1075                1080                1085

ACA AAT ACT TTA AAA GAT TTT TGG GGG AAT CCT TTA AGA TAC GAT ACA     3312
Thr Asn Thr Leu Lys Asp Phe Trp Gly Asn Pro Leu Arg Tyr Asp Thr
    1090                1095                1100

CAA TAC TAT CTG TTT AAT CAA GGT ATG CAA AAT ATC TAT ATA AAG TAT     3360
Gln Tyr Tyr Leu Phe Asn Gln Gly Met Gln Asn Ile Tyr Ile Lys Tyr
1105                1110                1115                1120
```

-continued

```
TTT AGT AAA GCT TCT ATG GGG GAA ACT GCA CCA CGT ACA AAC TTT AAT      3408
Phe Ser Lys Ala Ser Met Gly Glu Thr Ala Pro Arg Thr Asn Phe Asn
                1125                1130                1135

AAT GCA GCA ATA AAT TAT CAA AAT TTA TAT CTT GGT TTA CGA TTT ATT      3456
Asn Ala Ala Ile Asn Tyr Gln Asn Leu Tyr Leu Gly Leu Arg Phe Ile
            1140                1145                1150

ATA AAA AAA GCA TCA AAT TCT CGG AAT ATA AAT AAT GAT AAT ATA GTC      3504
Ile Lys Lys Ala Ser Asn Ser Arg Asn Ile Asn Asn Asp Asn Ile Val
        1155                1160                1165

AGA GAA GGA GAT TAT ATA TAT CTT AAT ATT GAT AAT ATT TCT GAT GAA      3552
Arg Glu Gly Asp Tyr Ile Tyr Leu Asn Ile Asp Asn Ile Ser Asp Glu
    1170                1175                1180

TCT TAC AGA GTA TAT GTT TTG GTG AAT TCT AAA GAA ATT CAA ACT CAA      3600
Ser Tyr Arg Val Tyr Val Leu Val Asn Ser Lys Glu Ile Gln Thr Gln
1185                1190                1195                1200

TTA TTT TTA GCA CCC ATA AAT GAT GAT CCT ACG TTC TAT GAT GTA CTA      3648
Leu Phe Leu Ala Pro Ile Asn Asp Asp Pro Thr Phe Tyr Asp Val Leu
                1205                1210                1215

CAA ATA AAA AAA TAT TAT GAA AAA ACA ACA TAT AAT TGT CAG ATA CTT      3696
Gln Ile Lys Lys Tyr Tyr Glu Lys Thr Thr Tyr Asn Cys Gln Ile Leu
            1220                1225                1230

TGC GAA AAA GAT ACT AAA ACA TTT GGG CTG TTT GGA ATT GGT AAA TTT      3744
Cys Glu Lys Asp Thr Lys Thr Phe Gly Leu Phe Gly Ile Gly Lys Phe
        1235                1240                1245

GTT AAA GAT TAT GGA TAT GTT TGG GAT ACC TAT GAT AAT TAT TTT TGC      3792
Val Lys Asp Tyr Gly Tyr Val Trp Asp Thr Tyr Asp Asn Tyr Phe Cys
    1250                1255                1260

ATA AGT CAG TGG TAT CTC AGA AGA ATA TCT GAA AAT ATA AAT AAA TTA      3840
Ile Ser Gln Trp Tyr Leu Arg Arg Ile Ser Glu Asn Ile Asn Lys Leu
1265                1270                1275                1280

AGG TTG GGA TGT AAT TGG CAA TTC ATT CCC GTG GAT GAA GGA TGG ACA      3888
Arg Leu Gly Cys Asn Trp Gln Phe Ile Pro Val Asp Glu Gly Trp Thr
                1285                1290                1295

GAA TAA                                                              3894
Glu
```

(2) INFORMATION FOR SEQ ID NO:77:

(i) SEQUENCE CHARACTERISTICS:
(A) LENGTH: 1297 amino acids
(B) TYPE: amino acid
(D) TOPOLOGY: linear (ii) MOLECULE TYPE: protein (xi) SEQUENCE DESCRIPTION: SEQ ID NO:77:

```
Met Pro Val Asn Ile Lys Asn Phe Asn Tyr Asn Asp Pro Ile Asn Asn
  1               5                  10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
     50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110
```

-continued

```
Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525
```

-continued

```
Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
```

-continued

```
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
        995                 1000                1005

Trp Phe Ser Ile Thr Ile Thr Asn Asp Arg Leu Gly Asn Ala Asn Ile
    1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
                1045                1050                1055

Asp Thr Thr Lys Phe Val Trp Ile Lys Asp Phe Asn Ile Phe Gly Arg
            1060                1065                1070

Glu Leu Asn Ala Thr Glu Val Ser Ser Leu Tyr Trp Ile Gln Ser Ser
        1075                1080                1085

Thr Asn Thr Leu Lys Asp Phe Trp Gly Asn Pro Leu Arg Tyr Asp Thr
    1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
                1125                1130                1135

Asn Ala Ala Ile Asn Tyr Gln Asn Leu Tyr Leu Gly Leu Arg Phe Ile
            1140                1145                1150

Ile Lys Lys Ala Ser Asn Ser Arg Asn Ile Asn Asn Asp Asn Ile Val
        1155                1160                1165

Arg Glu Gly Asp Tyr Ile Tyr Leu Asn Ile Asp Asn Ile Ser Asp Glu
    1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
                1205                1210                1215

Gln Ile Lys Lys Tyr Tyr Glu Lys Thr Thr Tyr Asn Cys Gln Ile Leu
            1220                1225                1230

Cys Glu Lys Asp Thr Lys Thr Phe Gly Leu Phe Gly Ile Gly Lys Phe
        1235                1240                1245

Val Lys Asp Tyr Gly Tyr Val Trp Asp Thr Tyr Asp Asn Tyr Phe Cys
    1250                1255                1260

Ile Ser Gln Trp Tyr Leu Arg Arg Ile Ser Glu Asn Ile Asn Lys Leu
1265                1270                1275                1280

Arg Leu Gly Cys Asn Trp Gln Phe Ile Pro Val Asp Glu Gly Trp Thr
                1285                1290                1295

Glu
```

(2) INFORMATION FOR SEQ ID NO:78:

(i) SEQUENCE CHARACTERISTICS:
(A) LENGTH: 1535 base pairs
(B) TYPE: nucleic acid
(C) STRANDEDNESS: double
(D) TOPOLOGY: linear (ii) MOLECULE TYPE: DNA (genomic)

(ix) FEATURE:

-continued

```
        (A) NAME/KEY: CDS
        (B) LOCATION: 108..1526

    (xi) SEQUENCE DESCRIPTION: SEQ ID NO:78:

AGATCTCGAT CCCGCGAAAT TAATACGACT CACTATAGGG GAATTGTGAG CGGATAACAA      60

TTCCCCTCTA GAAATAATTT TGTTTAACTT TAAGAAGGAG ATATACC ATG GGC CAT       116
                                                    Met Gly His
                                                      1

CAT CAT CAT CAT CAT CAT CAT CAT CAC AGC AGC GGC CAT ATC GAA GGT       164
His His His His His His His His His Ser Ser Gly His Ile Glu Gly
      5                  10                  15

CGT CAT ATG GCT AGC ATG GCT GAC ACA ATT TTA ATA CAA GTT TTT AAT       212
Arg His Met Ala Ser Met Ala Asp Thr Ile Leu Ile Gln Val Phe Asn
 20                  25                  30                  35

AAT TAT ATT AGT AAT ATT AGT AGT AAT GCT ATT TTA AGT TTA AGT TAT       260
Asn Tyr Ile Ser Asn Ile Ser Ser Asn Ala Ile Leu Ser Leu Ser Tyr
                 40                  45                  50

AGA GGT GGG CGT TTA ATA GAT TCA TCT GGA TAT GGT GCA ACT ATG AAT       308
Arg Gly Gly Arg Leu Ile Asp Ser Ser Gly Tyr Gly Ala Thr Met Asn
             55                  60                  65

GTA GGT TCA GAT GTT ATC TTT AAT GAT ATA GGA AAT GGT CAA TTT AAA       356
Val Gly Ser Asp Val Ile Phe Asn Asp Ile Gly Asn Gly Gln Phe Lys
         70                  75                  80

TTA AAT AAT TCT GAA AAT AGT AAT ATT ACG GCA CAT CAA AGT AAA TTC       404
Leu Asn Asn Ser Glu Asn Ser Asn Ile Thr Ala His Gln Ser Lys Phe
     85                  90                  95

GTT GTA TAT GAT AGT ATG TTT GAT AAT TTT AGC ATT AAC TTT TGG GTA       452
Val Val Tyr Asp Ser Met Phe Asp Asn Phe Ser Ile Asn Phe Trp Val
100                 105                 110                 115

AGG ACT CCT AAA TAT AAT AAT AAT GAT ATA CAA ACT TAT CTT CAA AAT       500
Arg Thr Pro Lys Tyr Asn Asn Asn Asp Ile Gln Thr Tyr Leu Gln Asn
                120                 125                 130

GAG TAT ACA ATA ATT AGT TGT ATA AAA AAT GAC TCA GGA TGG AAA GTA       548
Glu Tyr Thr Ile Ile Ser Cys Ile Lys Asn Asp Ser Gly Trp Lys Val
            135                 140                 145

TCT ATT AAG GGA AAT AGA ATA ATA TGG ACA TTA ATA GAT GTT AAT GCA       596
Ser Ile Lys Gly Asn Arg Ile Ile Trp Thr Leu Ile Asp Val Asn Ala
        150                 155                 160

AAA TCT AAA TCA ATA TTT TTC GAA TAT AGT ATA AAA GAT AAT ATA TCA       644
Lys Ser Lys Ser Ile Phe Phe Glu Tyr Ser Ile Lys Asp Asn Ile Ser
    165                 170                 175

GAT TAT ATA AAT AAA TGG TTT TCC ATA ACT ATT ACT AAT GAT AGA TTA       692
Asp Tyr Ile Asn Lys Trp Phe Ser Ile Thr Ile Thr Asn Asp Arg Leu
180                 185                 190                 195

GGT AAC GCA AAT ATT TAT ATA AAT GGA AGT TTG AAA AAA AGT GAA AAA       740
Gly Asn Ala Asn Ile Tyr Ile Asn Gly Ser Leu Lys Lys Ser Glu Lys
                200                 205                 210

ATT TTA AAC TTA GAT AGA ATT AAT TCT AGT AAT GAT ATA GAC TTC AAA       788
Ile Leu Asn Leu Asp Arg Ile Asn Ser Ser Asn Asp Ile Asp Phe Lys
            215                 220                 225

TTA ATT AAT TGT ACA GAT ACT ACT AAA TTT GTT TGG ATT AAG GAT TTT       836
Leu Ile Asn Cys Thr Asp Thr Thr Lys Phe Val Trp Ile Lys Asp Phe
        230                 235                 240

AAT ATT TTT GGT AGA GAA TTA AAT GCT ACA GAA GTA TCT TCA CTA TAT       884
Asn Ile Phe Gly Arg Glu Leu Asn Ala Thr Glu Val Ser Ser Leu Tyr
    245                 250                 255

TGG ATT CAA TCA TCT ACA AAT ACT TTA AAA GAT TTT TGG GGG AAT CCT       932
Trp Ile Gln Ser Ser Thr Asn Thr Leu Lys Asp Phe Trp Gly Asn Pro
260                 265                 270                 275
```

-continued

```
TTA AGA TAC GAT ACA CAA TAC TAT CTG TTT AAT CAA GGT ATG CAA AAT      980
Leu Arg Tyr Asp Thr Gln Tyr Tyr Leu Phe Asn Gln Gly Met Gln Asn
                280                 285                 290

ATC TAT ATA AAG TAT TTT AGT AAA GCT TCT ATG GGG GAA ACT GCA CCA     1028
Ile Tyr Ile Lys Tyr Phe Ser Lys Ala Ser Met Gly Glu Thr Ala Pro
            295                 300                 305

CGT ACA AAC TTT AAT AAT GCA GCA ATA AAT TAT CAA AAT TTA TAT CTT     1076
Arg Thr Asn Phe Asn Asn Ala Ala Ile Asn Tyr Gln Asn Leu Tyr Leu
        310                 315                 320

GGT TTA CGA TTT ATT ATA AAA AAA GCA TCA AAT TCT CGG AAT ATA AAT     1124
Gly Leu Arg Phe Ile Ile Lys Lys Ala Ser Asn Ser Arg Asn Ile Asn
    325                 330                 335

AAT GAT AAT ATA GTC AGA GAA GGA GAT TAT ATA TAT CTT AAT ATT GAT     1172
Asn Asp Asn Ile Val Arg Glu Gly Asp Tyr Ile Tyr Leu Asn Ile Asp
340                 345                 350                 355

AAT ATT TCT GAT GAA TCT TAC AGA GTA TAT GTT TTG GTG AAT TCT AAA     1220
Asn Ile Ser Asp Glu Ser Tyr Arg Val Tyr Val Leu Val Asn Ser Lys
                360                 365                 370

GAA ATT CAA ACT CAA TTA TTT TTA GCA CCC ATA AAT GAT GAT CCT ACG     1268
Glu Ile Gln Thr Gln Leu Phe Leu Ala Pro Ile Asn Asp Asp Pro Thr
            375                 380                 385

TTC TAT GAT GTA CTA CAA ATA AAA AAA TAT TAT GAA AAA ACA ACA TAT     1316
Phe Tyr Asp Val Leu Gln Ile Lys Lys Tyr Tyr Glu Lys Thr Thr Tyr
        390                 395                 400

AAT TGT CAG ATA CTT TGC GAA AAA GAT ACT AAA ACA TTT GGG CTG TTT     1364
Asn Cys Gln Ile Leu Cys Glu Lys Asp Thr Lys Thr Phe Gly Leu Phe
    405                 410                 415

GGA ATT GGT AAA TTT GTT AAA GAT TAT GGA TAT GTT TGG GAT ACC TAT     1412
Gly Ile Gly Lys Phe Val Lys Asp Tyr Gly Tyr Val Trp Asp Thr Tyr
420                 425                 430                 435

GAT AAT TAT TTT TGC ATA AGT CAG TGG TAT CTC AGA AGA ATA TCT GAA     1460
Asp Asn Tyr Phe Cys Ile Ser Gln Trp Tyr Leu Arg Arg Ile Ser Glu
                440                 445                 450

AAT ATA AAT AAA TTA AGG TTG GGA TGT AAT TGG CAA TTC ATT CCC GTG     1508
Asn Ile Asn Lys Leu Arg Leu Gly Cys Asn Trp Gln Phe Ile Pro Val
            455                 460                 465

GAT GAA GGA TGG ACA GAA TAACTCGAG                                   1535
Asp Glu Gly Trp Thr Glu
        470
```

(2) INFORMATION FOR SEQ ID NO:79:

(i) SEQUENCE CHARACTERISTICS:
(A) LENGTH: 473 amino acids
(B) TYPE: amino acid
(D) TOPOLOGY: linear (ii) MOLECULE TYPE: protein (xi) SEQUENCE DESCRIPTION: SEQ ID NO:79:

```
Met Gly His His His His His His His His His His Ser Ser Gly His
  1               5                  10                  15

Ile Glu Gly Arg His Met Ala Ser Met Ala Asp Thr Ile Leu Ile Gln
            20                  25                  30

Val Phe Asn Asn Tyr Ile Ser Asn Ile Ser Ser Asn Ala Ile Leu Ser
        35                  40                  45

Leu Ser Tyr Arg Gly Gly Arg Leu Ile Asp Ser Ser Gly Tyr Gly Ala
    50                  55                  60

Thr Met Asn Val Gly Ser Asp Val Ile Phe Asn Asp Ile Gly Asn Gly
 65                  70                  75                  80
```

-continued

```
Gln Phe Lys Leu Asn Asn Ser Glu Asn Ser Asn Ile Thr Ala His Gln
                85                  90                  95

Ser Lys Phe Val Val Tyr Asp Ser Met Phe Asp Asn Phe Ser Ile Asn
            100                 105                 110

Phe Trp Val Arg Thr Pro Lys Tyr Asn Asn Asn Asp Ile Gln Thr Tyr
        115                 120                 125

Leu Gln Asn Glu Tyr Thr Ile Ile Ser Cys Ile Lys Asn Asp Ser Gly
    130                 135                 140

Trp Lys Val Ser Ile Lys Gly Asn Arg Ile Ile Trp Thr Leu Ile Asp
145                 150                 155                 160

Val Asn Ala Lys Ser Lys Ser Ile Phe Phe Glu Tyr Ser Ile Lys Asp
                165                 170                 175

Asn Ile Ser Asp Tyr Ile Asn Lys Trp Phe Ser Ile Thr Ile Thr Asn
            180                 185                 190

Asp Arg Leu Gly Asn Ala Asn Ile Tyr Ile Asn Gly Ser Leu Lys Lys
        195                 200                 205

Ser Glu Lys Ile Leu Asn Leu Asp Arg Ile Asn Ser Ser Asn Asp Ile
    210                 215                 220

Asp Phe Lys Leu Ile Asn Cys Thr Asp Thr Thr Lys Phe Val Trp Ile
225                 230                 235                 240

Lys Asp Phe Asn Ile Phe Gly Arg Glu Leu Asn Ala Thr Glu Val Ser
                245                 250                 255

Ser Leu Tyr Trp Ile Gln Ser Ser Thr Asn Thr Leu Lys Asp Phe Trp
            260                 265                 270

Gly Asn Pro Leu Arg Tyr Asp Thr Gln Tyr Tyr Leu Phe Asn Gln Gly
        275                 280                 285

Met Gln Asn Ile Tyr Ile Lys Tyr Phe Ser Lys Ala Ser Met Gly Glu
    290                 295                 300

Thr Ala Pro Arg Thr Asn Phe Asn Asn Ala Ala Ile Asn Tyr Gln Asn
305                 310                 315                 320

Leu Tyr Leu Gly Leu Arg Phe Ile Ile Lys Lys Ala Ser Asn Ser Arg
                325                 330                 335

Asn Ile Asn Asn Asp Asn Ile Val Arg Glu Gly Asp Tyr Ile Tyr Leu
            340                 345                 350

Asn Ile Asp Asn Ile Ser Asp Glu Ser Tyr Arg Val Tyr Val Leu Val
        355                 360                 365

Asn Ser Lys Glu Ile Gln Thr Gln Leu Phe Leu Ala Pro Ile Asn Asp
    370                 375                 380

Asp Pro Thr Phe Tyr Asp Val Leu Gln Ile Lys Lys Tyr Tyr Glu Lys
385                 390                 395                 400

Thr Thr Tyr Asn Cys Gln Ile Leu Cys Glu Lys Asp Thr Lys Thr Phe
                405                 410                 415

Gly Leu Phe Gly Ile Gly Lys Phe Val Lys Asp Tyr Gly Tyr Val Trp
            420                 425                 430

Asp Thr Tyr Asp Asn Tyr Phe Cys Ile Ser Gln Trp Tyr Leu Arg Arg
        435                 440                 445

Ile Ser Glu Asn Ile Asn Lys Leu Arg Leu Gly Cys Asn Trp Gln Phe
    450                 455                 460

Ile Pro Val Asp Glu Gly Trp Thr Glu
465                 470
```

(2) INFORMATION FOR SEQ ID NO:80:

(i) SEQUENCE CHARACTERISTICS:

-continued

```
          (A) LENGTH: 30 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "DNA"

    (xi) SEQUENCE DESCRIPTION: SEQ ID NO:80:

CGCCATGGCT GACACAATTT TAATACAAGT                                      30


(2) INFORMATION FOR SEQ ID NO:81:

     (i) SEQUENCE CHARACTERISTICS:
          (A) LENGTH: 32 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "DNA"

    (xi) SEQUENCE DESCRIPTION: SEQ ID NO:81:

GCCTCGAGTT ATTCTGTCCA TCCTTCATCC AC                                   32


(2) INFORMATION FOR SEQ ID NO:82:

     (i) SEQUENCE CHARACTERISTICS:
          (A) LENGTH: 12 amino acids
          (B) TYPE: amino acid
          (C) STRANDEDNESS: Not Relevant
          (D) TOPOLOGY: Not Relevant

    (ii) MOLECULE TYPE: peptide

    (ix) FEATURE:
          (A) NAME/KEY: Modified-site
          (B) LOCATION: 12
          (D) OTHER INFORMATION: /note= "The asparagine residue at
               this position contains an amide group."

    (xi) SEQUENCE DESCRIPTION: SEQ ID NO:82:

Cys Gln Thr Ile Asp Gly Lys Lys Tyr Tyr Phe Asn
1               5                   10
```

SOLUBLE RECOMBINANT BOTULINUM TOXIN PROTEINS

This Application is a Continuation-In-Part of application Ser. No. 08/405,496, filed on Mar. 16, 1995 now U.S. Pat. No. 5,919,665.

FIELD OF THE INVENTION

The present invention relates to the isolation of polypeptides derived from *Clostridium botulinum* neurotoxins and the use thereof as immunogens for the production of vaccines, including multivalent vaccines, and antitoxins.

BACKGROUND OF THE INVENTION

The genus *Clostridium* is comprised of gram-positive, anaerobic, spore-forming bacilli. The natural habitat of these organisms is the environment and the intestinal tracts of humans and other animals. Indeed, clostridia are ubiquitous; they are commonly found in soil, dust, sewage, marine sediments, decaying vegetation, and mud. [See e.g. P. H. A. Sneath et al., "*Clostridium,*" *Bergey's Manual® of Systematic Bacteriology*, Vol. 2, pp. 1141–1200, Williams & Wilkins (1986).] Despite the identification of approximately 100 species of *Clostridium*, only a small number have been recognized as etiologic agents of medical and veterinary importance. Nonetheless, these species are associated with very serious diseases, Including botulism, tetanus, anaerobic cellulitis, gas gangrene, bacteremia, pseudomembranous colitis, and clostridial gastroenteritis. Table 1 lists some of the species of medical and veterinary importance and the diseases with which they are associated. As virtually all of these species have been isolated from fecal samples of apparently healthy persons, some of these isolates may be transient, rather than permanent residents of the colonic flora.

TABLE 1

*Clostridium* Species Of Medical And Veterinary Importance*

| Species | Disease |
| --- | --- |
| C. aminovalericum | Bacteriuria (pregnant women) |
| C. argentinense | Infected wounds; Bacteremia; Botulism; Infections of amniotic fluid |
| C. baratii | Infected war wounds; Peritonitis; Infectious processes of the eye, ear and prostate |
| C. beijerinckikii | Infected wounds |
| C. bifermentans | Infected wounds; Abscesses; Gas Gangrene; Bacteremia |
| C. botulinum | Food poisoning; Botulism (wound, food, infant) |
| C. butyricum | Urinary tract, lower respiratory tract, pleural cavity, and abdominal infections; Infected wounds; Abscesses; Bacteremia |
| C. cadaveris | Abscesses; Infected wounds |
| C. carnis | Soft tissue infections; Bacteremia |
| C. chauvoei | Blackleg |
| C. clostridioforme | Abdominal, cervical, scrotal, pleural, and other infections; Septicemia; Peritonitis; Appendicitis |
| C. cochlearium | Isolated from human disease processes, but role in disease unknown. |
| C. difficile | Antimicrobial-associated diarrhea; Pseudomembranous enterocolitis; Bacteremia; Pyogenic infections |
| C. fallax | Soft tissue infections |
| C. ghnoii | Soft tissue infections |
| C. glycolicum | Wound infections; Abscesses; Peritonitis |
| C. hastiforme | Infected war wounds; Bacteremia; Abscesses |
| C. histolyticum | Infected war wounds; Gas gangrene; Gingival plaque isolate |
| C. indolis | Gastrointestinal tract infections |
| C. innocuum | Gastrointestinal tract infections; Empyema |
| C. irregulare | Penile lesions |
| C. leptum | Isolated from human disease processes, but role in disease unknown. |
| C. limosum | Bacteremia; Peritonitis; Pulmonary infections |
| C. malenominatum | Various infectious processes |
| C. novyi | Infected wounds; Gas gangrene; Blackleg, Big head (ovine); Redwater disease (bovine) |
| C. oroticum | Urinary tract infections; Rectal abscesses |
| C. paraputrificum | Bacteremia; Peritonitis; Infected wounds; Appendicitis |
| C. perfringens | Gas gangrene; Anaerobic cellulitis; Intra-abdominal abscesses; Soft tissue infections; Food poisoning; Necrotizing pneumonia; Empyema; Meningitis; Bacteremia; Uterine Infections; Enteritis necrotans; Lamb dysentery; Struck; Ovine Enterotoxemia; |
| C. putrefaciens | Bacteriuria (Pregnant women with bacteremia) |
| C. putrificum | Abscesses; Infected wounds; Bacteremia |
| C. ramosum | Infections of the abdominal cavity, genital tract, lung, and biliary tract; Bacteremia |
| C. sartagoforme | Isolated from human disease processes, but role in disease unknown. |
| C. septicum | Gas gangrene; Bacteremia; Suppurative infections; Necrotizing enterocolitis; Braxy |
| C. sordellii | Gas gangrene; Wound infections; Penile lesions; Bacteremia; Abscesses; Abdominal and vaginal infections |

TABLE 1-continued

*Clostridium* Species Of Medical And Veterinary Importance*

| Species | Disease |
|---|---|
| *C. sphenoides* | Appendicitis; Bacteremia; Bone and soft tissue infections; Intraperitoneal infections; Infected war wounds; Visceral gas gangrene; Renal abscesses |
| *C. sporogenes* | Gas gangrene; Bacteremia; Endocarditis; central nervous system and pleuropulmonary infections; Penile lesions; Infected war wounds; Other pyogenic infections |
| *C. subterminale* | Bacteremia; Empyema; Biliary tract, soft tissue and bone infections |
| *C. symbiosum* | Liver abscesses; Bacteremia; Infections resulting due to bowel flora |
| *C. tertium* | Gas gangrene; Appendicitis; Brain abscesses; Intestinal tract and soft tissue infections; Infected war wounds; Periodontitis; Bacteremia |
| *C. tetani* | Tetanus; Infected gums and teeth; Corneal ulcerations; Mastoid and middle ear infections; Intraperitoneal infections; Tetanus neonatorum; Postpartum uterine infections; Soft tissue infections, especially related to trauma (including abrasions and lacerations); Infections related to use of contaminated needles |
| *C. thermosaccharolyticum* | Isolated from human disease processes, but role in disease unknown. |

*Compiled from P. G. Engelkirk et al. "Classification", Principles and Practice of Clinical Anaerobic Bacteriology, pp. 22–23, Star Publishing Co., Belmont, CA (1992); J. Stephen and R. A. Petrowski, "Toxins Which Traverse Membranes and Deregulate Cells," in Bacterial Toxins, 2d ed., pp. 66–67, American Society for Microbiology (1986); R. Berkow and A. J. Fletcher (eds.), "Bacterial Diseases," Merck Manual of Diagnosis and Therapy, 16th ed., pp. 116–126, Merck Research Laboratories, Rahway, N. J. (1992); and O. H. Sigmund and C. M. Fraser (eds.), "Clostridial Infections," Merck Veterinary Manual, 5th ed., pp. 396–409, Merck & Co., Rahway, N. J. (1979).

In most cases, the pathogenicity of these organisms is related to the release of powerful exotoxins or highly destructive enzymes. Indeed, several species of the genus *Clostridium* produce toxins and other enzymes of great medical and veterinary significance. [C. L. Hatheway, Clin. Microbiol. Rev. 3:66–98 (1990).]

Perhaps because of their significance for human and veterinary medicine, much research has been conducted on these toxins, in particular those of *C. botulinum* and *C. difficile.*

*C. botulinum*

Several strains of *Clostridium botulinum* produce toxins of significance to human and animal health. [C. L. Hatheway, Clin. Microbiol. Rev. 3:66–98 (1990)] The effects of these toxins range from diarrheal diseases that can cause destruction of the colon, to paralytic effects that can cause death. Particularly at risk for developing clostridial diseases are neonates and humans and animals in poor health (e.g., those suffering from diseases associated with old age or immunodeficiency diseases).

*Clostridium botulinum* produces the most poisonous biological toxin known. The lethal human dose is a mere $10^{-9}$ mg/kg bodyweight for toxin in the bloodstream. Botulinal toxin blocks nerve transmission to the muscles, resulting in flaccid paralysis. When the toxin reaches airway and respiratory muscles, it results in respiratory failure that can cause death. [S. Arnon, J. Infect. Dis. 154:201–206 (1986)]

*C. botulinum* spores are carried by dust and are found on vegetables taken from the soil, on fresh fruits, and on agricultural products such as honey. Under conditions favorable to the organism, the spores germinate to vegetative cells which produces toxin. [S. Arnon, Ann. Rev. Med. 31:541 (1980)]

Botulism disease may be grouped into four types, based on the method of introduction of toxin into the bloodstream. Food-borne botulism results from ingesting improperly preserved and inadequately heated food that contains botulinal toxin. There were 355 cases of food-borne botulism in the United States between 1976 and 1984. [K. L. MacDonald et al., Am. J. Epidemiol. 124:794 (1986).] The death rate due to botulinal toxin is 12% and can be higher in particular risk groups. [C. O. Tacket et al., Am. J. Med. 76:794 (1984).] Wound-induced botulism results from *C. botulinum* penetrating traumatized tissue and producing toxin that is absorbed into the bloodstream. Since 1950, thirty cases of wound botulism have been reported. [M. N. Swartz, "*Anaerobic Spore-Forming Bacilli: The Clostridia*," pp. 633–646, in B. D. Davis et al.,(eds.), *Microbiology,* 4th edition, J. B. Lippincott Co. (1990).] Inhalation botulism results when the toxin is inhaled. Inhalation botulism has been reported as the result of accidental exposure in the laboratory [E. Holzer, Med. Klin. 41:1735 (1962)] and could arise if the toxin is used as an agent of biological warfare [D. R. Franz et al., in *Botulinum and Tetanus Neurotoxins*, B. R. DasGupta, ed., Plenum Press, New York (1993), pp. 473–476]. Infectious infant botulism results from *C. botulinum* colonization of the infant intestine with production of toxin and its absorption into the bloodstream. It is likely that the bacterium gains entry when spores are ingested and subsequently germinate. [S. Arnon, J. Infect. Dis. 154:201 (1986).] There have been 500 cases reported since it was first recognized in 1976. [M. N. Swartz, supra.]

Infant botulism strikes infants who are three weeks to eleven months old (greater than 90% of the cases are infants less than six months). [S. Arnon, J. Infect. Dis. 154:201 (1986).] It is believed that infants are susceptible, due, in large part, to the absence of the full adult complement of intestinal microflora. The benign microflora present in the adult intestine provide an acidic environment that is not favorable to colonization by *C. botulinum*. Infants begin life with a sterile intestine which is gradually colonized by microflora. Because of the limited microflora present in early infancy, the intestinal environment is not as acidic, allowing for *C. botulinum* spore germination, growth, and toxin production. In this regard, some adults who have undergone antibiotic therapy which alters intestinal microflora become more susceptible to botulism.

An additional factor accounting for infant susceptibility to infectious botulism is the immaturity of the infant immune system. The mature immune system is sensitized to bacterial antigens and produces protective antibodies. Secretory IgA produced in the adult intestine has the ability to agglutinate vegetative cells of *C. botulinum*. [S. Arnon, J. Infect. Dis. 154:201 (1986).] Secretory IgA may also act by preventing intestinal bacteria and their products from crossing the cells of the intestine. [S. Arnon, Epidemiol. Rev. 3:45 (1981).] The infant immune system is not primed to do this.

Clinical symptoms of infant botulism range from mild paralysis, to moderate and severe paralysis requiring hospitalization, to fulminant paralysis, leading to sudden death. [S. Arnon, Epidemiol. Rev. 3:45 (1981).]

The chief therapy for severe infant botulism is ventilatory assistance using a mechanical respirator and concurrent elimination of toxin and bacteria using cathartics, enemas, and gastric lavage. There were 68 hospitalizations in California for infant botulism in a single year with a total cost of over $4 million for treatment. [T. L. Frankovich and S. Arnon, West. J. Med. 154:103 (1991).]

Different strains of *Clostridium botulinum* each produce antigenically distinct toxin designated by the letters A–G. Serotype A toxin has been implicated in 26% of the cases of food botulism; types B, E and F have also been implicated in a smaller percentage of the food botulism cases [H. Sugiyama, Microbiol. Rev. 44:419 (1980)]. Wound botulism has been reportedly caused by only types A or B toxins [H. Sugiyama, supra]. Nearly all cases of infant botulism have been caused by bacteria producing either type A or type B toxin. (Exceptionally, one New Mexico case was caused by *Clostridium botulinum* producing type F toxin and another by *Clostridium botulinum* producing a type B-type F hybrid.) [S. Arnon, Epidemiol. Rev. 3:45 (1981).] Type C toxin affects waterfowl, cattle, horses and mink. Type D toxin affects cattle, and type E toxin affects both humans and birds.

A trivalent antitoxin derived from horse plasma is commercially available from Connaught Industries Ltd. as a therapy for toxin types A, B, and E. However, the antitoxin has several disadvantages. First, extremely large dosages must be injected intravenously and/or intramuscularly. Second, the antitoxin has serious side effects such as acute anaphylaxis which can lead to death, and serum sickness. Finally, the efficacy of the antitoxin is uncertain and the treatment is costly. [C. O. Tacket et al., Am. J. Med. 76:794 (1984).]

A heptavalent equine botulinal antitoxin which uses only the $F(ab')_2$ portion of the antibody molecule has been tested by the United States Military. [M. Balady, USAMRDC Newsletter, p. 6 (1991).] This was raised against impure toxoids in those large animals and is not a high titer preparation.

A pentavalent human antitoxin has been collected from immunized human subjects for use as a treatment for infant botulism. The supply of this antitoxin is limited and cannot be expected to meet the needs of all individuals stricken with botulism disease. In addition, collection of human sera must involve screening out HIV and other potentially serious human pathogens. [P. J. Schwarz and S. S. Arnon, Western J. Med. 156:197 (1992).]

Infant botulism has been implicated as the cause of mortality in some cases of Sudden Infant Death Syndrome (SIDS, also known as crib death). SIDS is officially recognized as infant death that is sudden and unexpected and that remained unexplained despite complete post-mortem examination. The link of SIDS to infant botulism came when fecal or blood specimens taken at autopsy from SIDS infants were found to contain *C. botulinum* organisms and/or toxin in 3–4% of cases analyzed. [D. R. Peterson et al., Rev. Infect. Dis. 1:630 (1979).] In contrast, only 1 of 160 healthy infants (0.6%) had *C. botulinum* organisms in the feces and no botulinal toxin. (S. Arnon et al., Lancet, pp. 1273–76, Jun. 17, 1978.)

In developed countries, SIDS is the number one cause of death in children between one month and one year old. (S. Arnon et al, Lancet, pp. 1273–77, Jun. 17, 1978.) More children die from SIDS in the first year than from any other single cause of death in the first fourteen years of life. In the United States, there are 8,000–10,000 SIDS victims annually. Id.

What is needed is an effective therapy against infant botulism that is free of dangerous side effects, is available in large supply at a reasonable price, and can be safely and gently delivered so that prophylactic application to infants is feasible.

Immunization of subjects with toxin preparations has been done in an attempt to induce immunity against botulinal toxins. A *C. botulinum* vaccine comprising chemically inactivated (i.e., formaldehyde-treated) type A, B, C, D and E toxin is commercially available for human usage. However, this vaccine preparation has several disadvantages. First, the efficacy of this vaccine is variable (in particular, only 78% of recipients produce protective levels of anti-type B antibodies following administration of the primary series). Second, immunization is painful (deep subcutaneous inoculation is required for administration), with adverse reactions being common (moderate to severe local reactions occur in approximately 6% of recipients upon initial injection; this number rises to approximately 11% of individuals who receive booster injections) [Informational Brochure for the Pentavalent (ABCDE) Botulinum Toxoid, Centers for Disease Control]. Third, preparation of the vaccine is dangerous as active toxin must be handled by laboratory workers.

What is needed are safe and effective vaccine preparations for administration to those at risk of exposure to *C. botulinum* toxins.

*C. difficile*

*C. difficile*, an organism which gained its name due to difficulties encountered in its isolation, has recently been proven to be an etiologic agent of diarrheal disease. (Sneath et al., p. 1165.). *C. difficile* is present in the gastrointestinal tract of approximately 3% of healthy adults, and 10–30% of neonates without adverse effect (Swartz, at p. 644); by other estimates, *C. difficile* is a part of the normal gastrointestinal flora of 2–10% of humans. [G. F. Brooks et al., (eds.) "*Infections Caused by Anaerobic Bacteria,*" *Jawetz, Melnick, & Adelberg's Medical Microbiology,* 19th ed., pp. 257–262, Appleton & Lange, San Mateo, Calif. (1991).] As these organisms are relatively resistant to most commonly used antimicrobials, when a patient is treated with antibiotics, the other members of the normal gastrointestinal flora are suppressed and *C. difficile* flourishes, producing cytopathic toxins and enterotoxins. It has been found in 25% of cases of moderate diarrhea resulting from treatment with antibiotics, especially the cephalosporins, clindamycin, and ampicillin. [M. N. Swartz at 644.1

Importantly, *C. difficile* is commonly associated with nosocomial infections. The organism is often present in the hospital and nursing home environments and may be carried on the hands and clothing of hospital personnel who care for debilitated and immunocompromised patients. As many of these patients are being treated with antimicrobials or other chemotherapeutic agents, such transmission of *C. difficile* represents a significant risk factor for disease. (Engelkirk et al., pp. 64–67.)

*C. difficile* is associated with a range of diarrhetic illness, ranging from diarrhea alone to marked diarrhea and necrosis of the gastrointestinal mucosa with the accumulation of inflammatory cells and fibrin, which forms a pseudomembrane in the affected area. (Brooks et al.) It has been found in over 95% of pseudomembranous enterocolitis cases. (Swartz, at p. 644.) This occasionally fatal disease is characterized by diarrhea, multiple small colonic plaques, and toxic megacolon. (Swartz, at p. 644.) Although stool cultures are sometimes used for diagnosis, diagnosis is best made by detection of the heat labile toxins present in fecal filtrates from patients with enterocolitis due to *C. difficile*. (Swartz, at p. 644–645; and Brooks et al., at p. 260.) *C. difficile* toxins are cytotoxic for tissue/cell cultures and cause enterocolitis when injected intracecally into hamsters. (Swartz, at p. 644.)

The enterotoxicity of *C. difficile* is primarily due to the action of two toxins, designated A and B, each of approximately 300,000 in molecular weight. Both are potent cytotoxins, with toxin A possessing direct enterocytotoxic activity. [Lyerly et al., Infect. Immun. 60:4633 (1992).] Unlike toxin A of *C. perfringens*, an organism rarely associated with antimicrobial-associated diarrhea, the toxin of *C. difficile* is not a spore coat constituent and is not produced during sporulation. (Swartz, at p. 644.) *C. difficile* toxin A causes hemorrhage, fluid accumulation and mucosal damage in rabbit ileal loops and appears to increase the uptake of toxin B by the intestinal mucosa. Toxin B does not cause intestinal fluid accumulation, but it is 1000 times more toxic than toxin A to tissue culture cells and causes membrane damage. Although both toxins induce similar cellular effects such as actin disaggregation, differences in cell specificity occurs.

Both toxins are important in disease. [Borriello et al., Rev. Infect. Dis., 12(suppl. 2):S185 (1990); Lyerly et al., Infect. Immun., 47:349 (1985); and Rolfe, Infect. Immun., 59:1223 (1990).] Toxin A is thought to act first by binding to brush border receptors, destroying the outer mucosal layer, then allowing toxin B to gain access to the underlying tissue. These steps in pathogenesis would indicate that the production of neutralizing antibodies against toxin A may be sufficient in the prophylactic therapy of CDAD. However, antibodies against toxin B may be a necessary additional component for an effective therapeutic against later stage colonic disease. Indeed, it has been reported that animals require antibodies to both toxin A and toxin B to be completely protected against the disease. [Kim and Rolfe, Abstr. Ann. Meet. Am. Soc. Microbiol., 69:62 (1987).]

*C. difficile* has also been reported to produce other toxins such as an enterotoxin different from toxins A and B [Banno et al., Rev. Infect. Dis., 6(Suppl. 1:S 11–S20 (1984)], a low molecular weight toxin [Rihn et al., Biochem. Biophys. Res. Comm., 124:690–695 (1984)], a motility altering factor [Justus et al., Gastroenterol., 83:836–843 (1982)], and perhaps other toxins. Regardless, *C. difficile* gastrointestinal disease is of primary concern.

It is significant that due to its resistance to most commonly used antimicrobials, *C. difficile* is associated with antimicrobial therapy with virtually all antimicrobial agents (although most commonly ampicillin, clindamycin and cephalosporins). It is also associated with disease in patients undergoing chemotherapy with such compounds as methotrexate, 5-fluorouracil, cyclophosphamide, and doxorubicin. [S. M. Finegold et al., *Clinical Guide to Anaerobic Infections*, pp. 88–89, Star Publishing Co., Belmont, Calif. (1992)]

Treatment of *C. difficile* disease is problematic, given the high resistance of the organism. Oral metronidazole, bacitracin and vancomycin have been reported to be effective. (Finegold et al., p. 89.) However there are problems associated with treatment utilizing these compounds. Vancomycin is very expensive, some patients are unable to take oral medication, and the relapse rate is high (20–25%), although it may not occur for several weeks. Id

*C. difficile* disease would be prevented or treated by neutralizing the effects of these toxins in the gastrointestinal tract. Thus, what is needed is an effective therapy against *C. difficile* toxin that is free of dangerous side effects, is available in large supply at a reasonable price, and can be safely delivered so that prophylactic application to patients at risk of developing pseudomembranous enterocolitis can be effectively treated.

DESCRIPTION OF THE DRAWINGS

FIG. 6 is a restriction map of *C. difficile* toxin A gene, showing sequences of primers 1–4 (SEQ ID NOS:1–4).

DEFINITIONS

Figure 1:
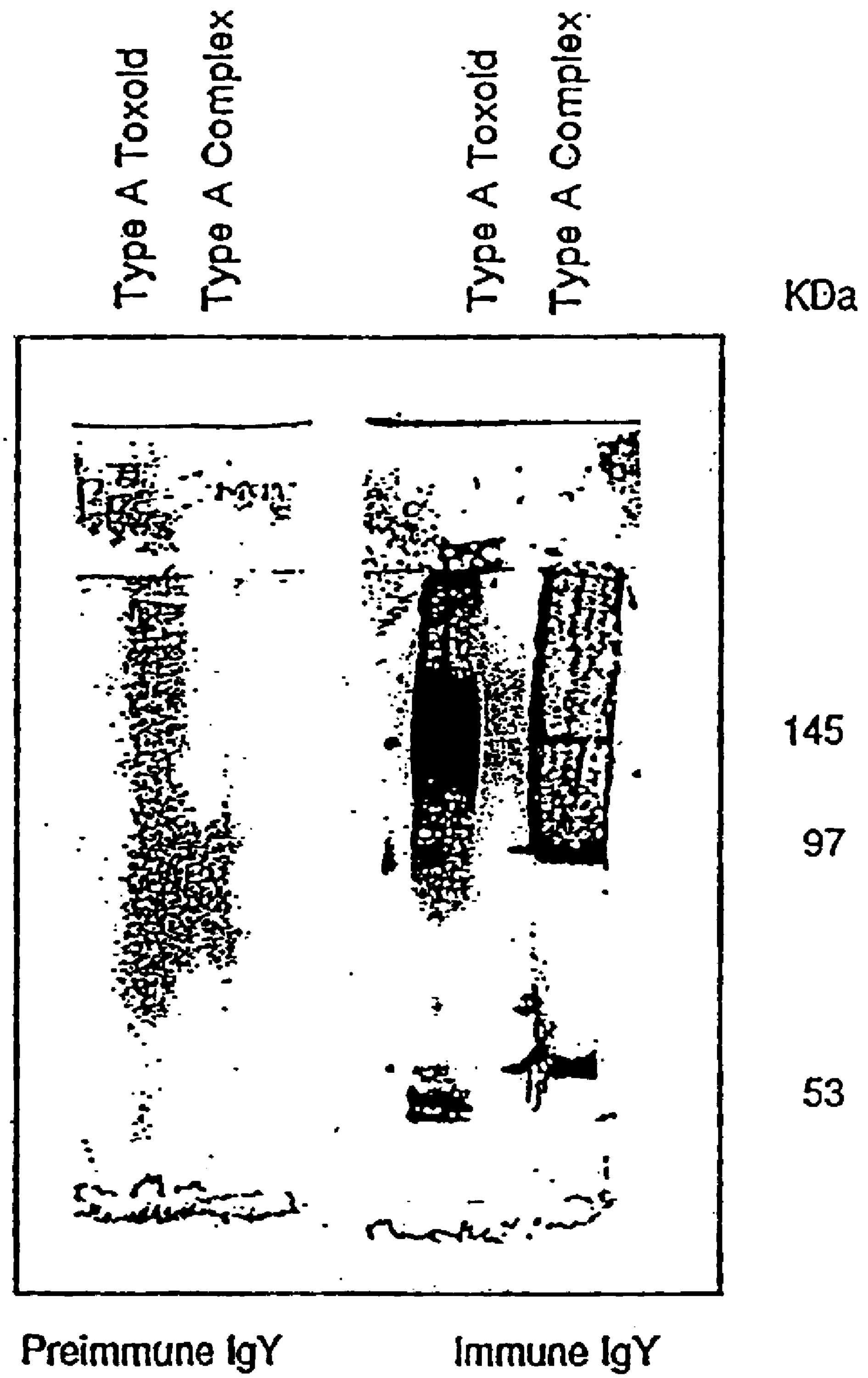
FIG. 1 shows the reactivity of anti-*C. botulinum* IgY by Western blot.

To facilitate understanding of the invention, a number of terms are defined below.

As used herein, the term "neutralizing" is used in reference to antitoxins, particularly antitoxins comprising antibodies, which have the ability to prevent the pathological actions of the toxin against which the antitoxin is directed.

As used herein, the term "overproducing" is used in reference to the production of clostridial toxin polypeptides in a host cell and indicates that the host cell is producing more of the clostridial toxin by virtue of the introduction of nucleic acid sequences encoding said clostridial toxin polypeptide than would be expressed by said host cell absent the introduction of said nucleic acid sequences. To allow ease of purification of toxin polypeptides produced in a host cell it is preferred that the host cell express or overproduce said toxin polypeptide at a level greater than 1 mg/liter of host cell culture.

"A host cell capable of expressing a recombinant protein at a level greater than or equal to 5% of the total cellular protein" is a host cell in which the recombinant protein represents at least 5% of the total cellular protein. To determine what percentage of total cellular protein the recombinant protein represents, the following steps are taken. A total of 10 $OD_{600}$ units of recombinant host cells (e.g., 200 μl of cells at $OD_{600}$=50/ml) are removed (at a timepoint known to represent the peak of expression of the desired recombinant protein) to a 1.5 ml microfuge tube and pelleted for 2 min at maximum rpm in a microfuge. The pellets are resuspended in 1 ml of 50 mM $NaHPO_4$, 0.5 M NaCl, 40 mM imidazole buffer (pH 6.8) containing 1 mg/ml lysozyme. The samples are incubated for 20 min at room temperature and stored ON at −70° C. Samples are thawed completely at room temperature and sonicated 2×10 seconds with a Branson Sonifier 450 microtip probe at # 3 power setting. The samples are centrifuged for 5 min. at maximum rpm in a microfuge. An aliquot (20 μl) of the protein sample is removed to 20 μl 2× sample buffer (this represents the total protein extract). The samples are heated to 95° C. for 5 min, then cooled and 5 or 10 μl are loaded onto 12.5% SDS-PAGE gels. High molecular weight protein markers are also loaded to allow for estimation of the MW of identified recombinant proteins. After electrophoresis, protein is detected generally by staining with Coomassie blue and the stained gel is scanned using a densitometer to determine the percentage of protein present in each band. In this manner, the percentage of protein present in the band corresponding to the recombinant protein of interest may be determined. It is not necessary that Coomassie blue be employed for the detection of protein, a number of fluorescent dyes [e.g., Sypro orange S-6651 (Molecular Probes, Eugene, Oreg.] may be employed and the stained gel scanned using a fluoroimager [e.g., Fluor Imager SI (Molecular Dynamics, Sunnyvale, Calif.)].

"A host cell capable of expressing a recombinant protein as a soluble protein at a level greater than or equal to 0.25% of the total soluble cellular protein" is a host cell in which the amount of soluble recombinant protein present represents at least 0.25% of the total cellular protein. As used herein "total soluble cellular protein" refers to a clarified PEI lysate prepared as described in Example 31(c)(iv). Briefly, cells are harvested following induction of expression of recombinant protein (at a point of maximal expression). The cells are resuspended in cell resuspension buffer (CRB: 50 mM $NaPO_4$, 0.5 M NaCl, 40 mM imidazole, pH 6.8) to create a 20% cell suspension (wet weight of cells/volume of CRB) and cell lysates are prepared as described in Example 31(c)(iv) (i.e., sonication or homogenization followed by centrifugation). The cell lysate is then flocculated utilizing polyethyleneimine (PEI) prior to centrifugation. PEI (a 2% solution in $dH_2O$, pH 7.5 with HCl) is added to the cell lysate to a final concentration of 0.2%, and stirred for 20 min at room temperature prior to centrifugation [8,500 rpm in JA10 rotor (Beckman) for 30 minutes at 4° C.]. This treatment removes RNA, DNA and cell wall components, resulting in a clarified, low viscosity lysate ("PEI clarified lysate"). The recombinant protein present in the PEI clarified lysate is then purified (e.g., by chromatography on an IDA column for his-tagged proteins). The amount of purified recombinant protein (i.e., the eluted protein) is divided by the concentration of protein present in the PEI clarified lysate (typically 8 mg/ml when using a 20% cell suspension as the starting material) and multiplied by 100 to determine what percentage of total soluble cellular protein is comprised of the soluble recombinant protein (see Example 33b).

As used herein, the term "fusion protein" refers to a chimeric protein containing the protein of interest (i.e., *C. botulinum* toxin A, B, C, D, E, F, or G and fragments thereof) joined to an exogenous protein fragment (the fusion partner which consists of a non-toxin protein). The fusion partner may enhance solubility of the *C. botulinum* protein as expressed in a host cell, may provide an affinity tag to allow purification of the recombinant fusion protein from the host cell or culture supernatant, or both. If desired, the fusion protein may be removed from the protein of interest (i.e., toxin protein or fragments thereof) prior to immunization by a variety of enzymatic or chemical means known to the art.

As used herein, the term "non-toxin protein" or "non-toxin protein sequence" refers to that portion of a fusion protein which comprises a protein or protein sequence which is not derived from a bacterial toxin protein.

The term "protein of interest", as used herein, refers to the protein whose expression is desired within the fusion protein. In a fusion protein the protein of interest will be joined or fused with another protein or protein domain, the fusion partner, to allow for enhanced stability of the protein of interest and/or ease of purification of the fusion protein.

As used herein, the term "maltose binding protein" refers to the maltose binding protein of *E. coli*. A portion of the maltose binding protein may be added to a protein of interest to generate a fusion protein; a portion of the maltose binding protein may merely enhance the solubility of the resulting fusion protein when expressed in a bacterial host. On the other hand, a portion of the maltose binding protein may allow affinity purification of the fusion protein on an amylose resin.

As used herein, the term "poly-histidine tract" when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate or IDA column.

As used herein, the term "purified" or "to purify" refers to the removal of contaminants from a sample. For example, antitoxins are purified by removal of contaminating non-immunoglobulin proteins; they are also purified by the removal of immunoglobulin that does not bind toxin. The removal of non-immunoglobulin proteins and/or the removal of immunoglobulins that do not bind toxin results in an increase in the percent of toxin-reactive immunoglobulins in the sample. In another example, recombinant toxin polypeptides are expressed in bacterial host cells and the toxin polypeptides are purified by the removal of host cell proteins; the percent of recombinant toxin polypeptides is thereby increased in the sample. Additionally, the recombinant toxin polypeptides are purified by the removal of host cell components such as lipopolysaccharide (e.g., endotoxin).

The term "recombinant DNA molecule", as used herein, refers to a DNA molecule which is comprised of segments of DNA joined together by means of molecular biological techniques.

The term "recombinant protein" or "recombinant polypeptide", as used herein, refers to a protein molecule which is expressed from a recombinant DNA molecule.

The term "native protein", as used herein, refers to a protein which is isolated from a natural source as opposed to the production of a protein by recombinant means.

As used herein, the term "portion" when used in reference to a protein (as in "a portion of a given protein") refers to fragments of that protein. The fragments may range in size from four amino acid residues to the entire amino acid sequence minus one amino acid.

As used herein, the term "soluble" when used in reference to a protein produced by recombinant DNA technology in a host cell is a protein which exists in solution in the cytoplasm of the host cell; if the protein contains a signal sequence the soluble protein is exported to the periplasmic space in bacteria hosts and is secreted into the culture medium in eucaryotic cells capable of secretion or by bacterial host possessing the appropriate genes (i.e., the kil gene). In contrast, an insoluble protein is one which exists in denatured form inside cytoplasmic granules (called inclusion bodies) in the host cell. High level expression (i.e., greater than 10–20 mg recombinant protein/liter of bacterial culture) of recombinant proteins often results in the expressed protein being found in inclusion bodies in the bacterial host cells. A soluble protein is a protein which is not found in an inclusion body inside the host cell or is found both in the cytoplasm and in inclusion bodies and in this case the protein may be present at high or low levels in the cytoplasm.

A distinction is drawn between a soluble protein (i.e., a protein which when expressed in a host cell is produced in a soluble form) and a "solubilized" protein. An insoluble recombinant protein found inside an inclusion body may be solubilized (i.e., rendered into a soluble form) by treating purified inclusion bodies with denaturants such as guanidine hydrochloride, urea or sodium dodecyl sulfate (SDS). These denaturants must then be removed from the solubilized protein preparation to allow the recovered protein to renature (refold). Not all proteins will refold into an active conformation after solubilization in a denaturant and removal of the denaturant. Many proteins precipitate upon removal of the denaturant. SDS may be used to solubilize inclusion bodies and will maintain the proteins in solution at low concentration. However, dialysis will not always remove all of the SDS (SDS can form micelles which do not dialyze out); therefore, SDS-solubilized inclusion body protein is soluble but not refolded.

A distinction is drawn between proteins which are soluble (i.e., dissolved) in a solution devoid of significant amounts of ionic detergents (e.g., SDS) or denaturants (e.g., urea, guanidine hydrochloride) and proteins which exist as a suspension of insoluble protein molecules dispersed within the solution. A soluble protein will not be removed from a solution containing the protein by centrifugation using conditions sufficient to remove bacteria present in a liquid medium (i.e., centrifugation at 12,000 x g for 4–5 minutes). For example, to test whether two proteins, protein A and protein B, are soluble in solution, the two proteins are placed into a solution selected from the group consisting of PBS-NaCl (PBS containing 0.5 M NaCl), PBS-NaCl containing 0.2% Tween 20, PBS, PBS containing 0.2% Tween 20, PBS-C (PBS containing 2 mM $CaCl_2$), PBS-C containing either 0.1 or 0.5% Tween 20, PBS-C containing either 0.1 or 0.5% NP-40, PBS-C containing either 0.1 or 0.5% Triton X-100, PBS-C containing 0.1% sodium deoxycholate. The mixture containing proteins A and B is then centrifuged at 5000×g for 5 minutes. The supernatant and pellet formed by centrifugation are then assayed for the presence of protein A and B. If protein A is found in the supernatant and not in the pellet [except for minor amounts (i.e., less than 10%) as a result of trapping], protein is said to be soluble in the solution tested. If the majority of protein B is found in the pellet (i.e., greater than 90%), then protein B is said to exist as a suspension in the solution tested.

As used herein, the term "therapeutic amount" refers to that amount of antitoxin required to neutralize the pathologic effects of one or more clostridial toxins in a subject.

The term "pyrogen", as used herein, refers to a fever-producing substance. Pyrogens may be endogenous to the host (e.g., prostaglandins) or may be exogenous compounds (e.g., bacterial endo- and exotoxins, nonbacterial compounds such as antigens and certain steroid compounds, etc.). The presence of pyrogen in a pharmaceutical solution may be detected using the U.S. Pharmacopeia (USP) rabbit fever test (United States Pharmacopeia, Vol. XXII (1990) United States Pharmacopeial Convention, Rockville, Md., p. 151).

The term "endotoxin", as used herein, refers to the high molecular weight complexes associated with the outer membrane of gram-negative bacteria. Unpurified endotoxin contains lipids, proteins and carbohydrates. Highly purified endotoxin does not contain protein and is referred to as lipopolysaccharide (LPS). Because unpurified endotoxin is of concern in the production of pharmaceutical compounds (e.g., proteins produced in *E. coli* using recombinant DNA technology), the term endotoxin as used herein refers to unpurified endotoxin. Bacterial endotoxin is a well known pyrogen.

As used herein, the term "endotoxin-free" when used in reference to a composition to be administered parenterally (with the exception of intrathecal administration) to a host means that the dose to be delivered contains less than 5 EU/kg body weight [FDA Guidelines for Parenteral Drugs (December 1987)]. Assuming a weight of 70 kg for an adult human, the dose must contain less than 350 EU to meet FDA Guidelines for parenteral administration. Endotoxin levels are measured herein using the Limulus Amebocyte Lysate (LAL) test (Limulus Amebocyte Lysate Pyrochrome™, Associates of Cape Cod, Inc. Woods Hole, Mass.). To measure endotoxin levels in preparations of recombinant proteins, 0.5 ml of a solution comprising 0.5 mg of purified recombinant protein in 50 mM $NaPO_4$, pH 7.0, 0.3M NaCl and 10% glycerol is used in the LAL assay according to the manufacturer's instructions for the endpoint chromogenic without diazo-coupling method [the specific components of the buffer containing recombinant protein to be analyzed in the LAL test are not important; any buffer having a neutral pH may be employed (see for example, alternative buffers employed in Examples 34, 40 and 45)]. Compositions containing less than or equal to 250 endotoxin units (EU)/mg of purified recombinant protein are herein defined as "substantially endotoxin-free." Preferably the composition contains less than or equal to 100, and most preferably less than or equal to 60, (EU)/mg of purified recombinant protein. Typically, administration of bacterial toxins or toxoids to adult humans for the purpose of vaccination involves doses of about 10–500 $\mu$g protein/dose. Therefore, administration of 10–500 $\mu$g of a purified recombinant protein to a 70 kg human, wherein said purified recombinant protein preparation contains 60 EU/mg protein, results in the introduction of only 0.6 to 30 EU (i.e., 0.2 to 8.6% of the maximum allowable endotoxin burden per parenteral dose). Administration of 10–500 $\mu$g of a purified recombinant protein to a 70 kg human, wherein said purified recombinant protein preparation contains 250 EU/mg protein, results in the introduction of only 2.5 to 125 EU (i.e., 0.7 to 36% of the maximum allowable endotoxin burden per parenteral dose).

The LAL test is accepted by the U.S. FDA as a means of detecting bacterial endotoxins (21 C.F.R. §§ 660.100–105). Studies have shown that the LAL test is equivalent or superior to the USP rabbit pyrogen test for the detection of endotoxin and thus the LAL test can be used as a surrogate for pyrogenicity studies in animals [F. C. Perason, *Pyrogens: endotoxins, LAL testing and depyrogenation*, Marcel Dekker, New York (1985), pp.150–155]. The FDA Bureau of Biologics accepts the LAL assay in place of the USP rabbit pyrogen test so long as the LAL assay utilized is shown to be as sensitive as, or more sensitive as the rabbit test [Fed. Reg., 38, 26130 (1980)].

The term "monovalent" when used in reference to a clostridial vaccine refers to a vaccine which is capable of provoking an immune response in a host animal directed against a single type of clostridial toxin. For example, if immunization of a host with *C. botulinum* type A toxin vaccine induces antibodies in the immunized host which protect against a challenge with type A toxin but not against challenge with type B, C, D, E, F or G toxins, then the type A vaccine is said to be monovalent. In contrast, a "multivalent" vaccine provokes an immune response in a host animal directed against several (i.e., more than one) clostridial toxins. For example, if immunization of a host with a vaccine comprising *C. botulinum* type A and B toxins induces the production of antibodies which protect the host against a challenge with both type A and B toxin, the vaccine is said to be multivalent (in particular, this hypothetical vaccine is bivalent).

As used herein, the term "immunogenically-effective amount" refers to that amount of an immunogen required to invoke the production of protective levels of antibodies in a host upon vaccination.

The term "protective level", when used in reference to the level of antibodies induced upon immunization of the host with an immunogen which comprises a bacterial toxin, means a level of circulating antibodies sufficient to protect the host from challenge with a lethal dose of the toxin.

As used herein, the terms "protein" and "polypeptide" refer to compounds comprising amino acids joined via peptide bonds and are used interchangeably.

The terms "toxin" and "neurotoxin" when used in reference to toxins produced by members (ie., species and strains) of the genus *Clostridium* are used interchangeably and refer to the proteins which are poisonous to nerve tissue.

The term "receptor-binding domain" when used in reference to a *C. botulinum* toxin refers to the carboxy-terminal portion of the heavy chain ($H_C$ or the C fragment) of the toxin which is presumed to be responsible for the binding of the active toxin (i.e., the derivative toxin comprising the H and L chains joined via disulfide bonds) to receptors on the surface of synaptosomes. The receptor-binding domain for *C. botulinum* type A toxin is defined herein as comprising amino acid residues 861 through 1296 of SEQ ID NO:28. The receptor-binding domain for *C. botulinum* type B toxin is defined herein as comprising amino acid residues 848 through 1291 of SEQ ID NO:40 (strain Eklund 17B). The receptor-binding domain of *C. botulinum* type C1 toxin is defined herein as comprising amino acid residues 856 through 1291 of SEQ ID NO:60. The receptor-binding domain of *C. botulinum* type D toxin is defined herein as comprising amino acid residues 852 through 1276 of SEQ ID NO:66. The receptor-binding domain of *C. botulinum* type E toxin is defined herein as comprising amino acid residues 835 through 1250 of SEQ ID NO:50 (Beluga strain). The receptor-binding domain of *C. botulinum* type F toxin is defined herein as comprising amino acid residues 853 through 1274 of SEQ ID NO:71. The receptor-binding domain of *C. botulinum* type G toxin is defined herein as comprising amino acid residues 853 through 1297 of SEQ ID NO:77. Within a given serotype, small variations in the primary amino acid sequence of the botulinal toxins isolated from different strains has been reported [Whelan et al. (1992), supra and Minton (1995) Curr. Top. Microbiol. Immunol. 195:161–194]. The present invention contemplates fusion proteins comprising the receptor-binding domain of *C. botulinum* toxins from serotypes A–G including the variants found among different strains within a given serotype. The receptor-binding domains listed above are used as the prototype for each strain within a serotype. Fusion proteins containing an analogous region from a strain other than the prototype strain are encompassed by the present invention.

Fusion proteins comprising the receptor binding domain (i.e., C fragment) of botulinal toxins may include amino acid residues located beyond the termini of the domains defined above. For example, the pHisBotB protein contains amino acid residues 846–1291 of SEQ ID NO:40; this fusion protein thus comprises the receptor-binding domain for *C. botulinum* type B toxin as defined above (i.e., Ile-848 through Glu-1291). Similarly, pHisBotE contains amino acid residues 827–1252 of SEQ ID NO:50 and pHisBotG contains amino acid residues 851–1297 of SEQ ID NO:77. Thus, both pHisBotE and pHisBotG fusion proteins contain a few amino acids located beyond the N-terminus of the defined receptor-binding domain.

The terms "native gene" or "native gene sequences" are used to indicate DNA sequences encoding a particular gene which contain the same DNA sequences as found in the gene as isolated from nature. In contrast, "synthetic gene sequences" are DNA sequences which are used to replace the naturally occurring DNA sequences when the naturally occurring sequences cause expression problems in a given host cell. For example, naturally-occurring DNA sequences encoding codons which are rarely used in a host cell may be replaced (e.g., by site-directed mutagenesis) such that the synthetic DNA sequence represents a more frequently used codon. The native DNA sequence and the synthetic DNA sequence will preferably encode the same amino acid sequence.

SUMMARY OF THE INVENTION

The present invention relates to the production of polypeptides derived from toxins particularly in recombinant host cells. In one embodiment, the present invention provides a host cell containing a recombinant expression vector, said vector encoding a protein comprising at least a portion of a *Clostridium botulinum* toxin, said toxin selected from the group consisting of type B toxin and type E toxin. The present invention is not limited by the nature of sequences encoding portions of the *C. botulinum* toxin. These sequences may be derived from the native gene sequences or alternatively they may comprise synthetic gene sequences. Synthetic gene sequences are employed when expression of the native gene sequences is problematic in a given host cell (e.g., when the native gene sequences contain sequences resembling yeast transcription termination signals and the desired host cell is a yeast cell).

In one embodiment, the host cell is capable of expressing the recombinant *C. botulinum* toxin protein at a level greater than or equal to 2% to 40% of the total cellular protein and preferably at a level greater than or equal to 5% of the total cellular protein. In another embodiment, the host cell is capable of expressing the recombinant *C. botulinum* toxin protein as a soluble protein at a level greater than or equal to 0.25% of the total cellular protein and preferably at a level greater than or equal to 0.25% to 10% of the total cellular protein.

The present invention is not limited by the nature of the host cell employed for the production of recombinant *C. botulinum* toxin proteins. In a preferred embodiment, the host cell is an *E. coli* cell. In another preferred embodiment, the host cell is an insect cell; particularly preferred insect host cells are *Spodoptera frugiperda* (Sf9) cells. In another preferred embodiment, the host cell is a yeast cell; particularly preferred yeast cells are *Pichia pastoris* cells.

In another embodiment, the invention provides a host cell containing a recombinant expression vector, said vector encoding a fusion protein comprising a non-toxin protein sequence and at least a portion of a *Clostridium botulinum* toxin, said toxin selected from the group consisting of type B toxin and type E toxin. The invention is not limited by the nature of the portion of the *Clostridium botulinum* toxin selected. In a preferred embodiment, the portion of the toxin comprises the receptor binding domain (i.e., the C fragment of the toxin). The present invention is not limited by the nature of the non-toxin protein sequence employed. In a preferred embodiment, the non-toxin protein sequence comprises a poly-histidine tract. A number of alternative fusion tags or fusion partners are known to the art (e.g., MBP, GST, protein A, etc.) and may be employed for the production of fusion proteins comprising a portion of a botulinal toxin.

The present invention further provides a vaccine comprising a fusion protein, said fusion protein comprising a non-toxin protein sequence and at least a portion of a *Clostridium botulinum* toxin, said toxin selected from the group consisting of type B toxin and type E toxin. The vaccine may be a monovalent vaccine (i.e., containing only a toxin B fusion protein or a toxin E fusion protein), a bivalent vaccine (i.e., containing both a toxin B fusion protein and a toxin E fusion protein) or a trivalent or higher valency vaccine. In a preferred embodiment, the toxin B fusion protein and/or toxin E fusion protein is combined with a fusion protein comprising a non-toxin protein sequence and at least a portion of *Clostridium botulinum* type A toxin. The present invention is not limited by the nature of the portion of the *Clostridium botulinum* toxin selected. In a preferred embodiment, the portion of the toxin comprises the receptor binding domain (i.e., the C fragment of the toxin). The present invention is not limited by the nature of the non-toxin protein sequence employed. In a preferred embodiment, the non-toxin protein sequence comprises a poly-histidine tract. A number of alternative fusion tags or fusion partners are known to the art (e.g., MBP, GST, protein A, etc.) and may be employed for the generation of fusion proteins comprising vaccines. When a fusion partner (i.e., the non-toxin protein sequence) is employed for the production of a recombinant *C. botulinal* toxin protein, the fusion partner may be removed from the recombinant *C. botulinal* toxin protein if desired (i.e., prior to administration of the protein to a subject) using a variety of methods known to the art (e.g., digestion of fusion proteins containing FactorXa or thrombin recognition sites with the appropriate enzyme). A number of the pETHis vectors employed herein provide an N-terminal his-tag followed by a FactorXa cleavage site (see Example 28a); the botulinal C fragment sequences follow the FactorXa site and thus, FactorXa can be used to remove the his-tag from the botulinal fusion protein. In a preferred embodiment, the vaccine is substantially endotoxin-free.

The present invention is not limited by the method employed for the generation of vaccine comprising fusion proteins comprising a non-toxin protein sequence and at least a portion of a *Clostridium botulinum* toxin. The fusion proteins may be produced by recombinant DNA means using either native or synthetic gene sequences expressed in a host cell. The present invention is not limited to the production of vaccines using recombinant host cells; cell free in vitro transcription/translation systems may be employed for the expression of the nucleic acid constructs encoding the fusion proteins of the present invention. An example of such a cell-free system is the commercially available TnT™ Coupled Reticulocyte Lysate System (Promega Corporation, Madison, Wis.). Alternatively, the fusion proteins of the present invention may be generated by synthetic means (i.e., peptide synthesis).

The present invention further provides a method of generating antibody directed against a *Clostridium botulinum* toxin comprising: a) providing in any order: i) an antigen comprising a fusion protein comprising a non-toxin protein sequence and at least a portion of a *Clostridium botulinum* toxin, said toxin selected from the group consisting of type B toxin and type E toxin, and ii) a host; and by immunizing the host with the antigen so as to generate an antibody. In a preferred embodiment, the antigen used to immunize the host also contains a fusion protein comprising a non-toxin protein sequence and at least a portion of *Clostridium botulinum* type A toxin. The present invention is not limited by the nature of the portion of the *Clostridium botulinum* toxin selected. In a preferred embodiment, the portion of the toxin comprises the receptor binding domain (i.e., the C fragment of the toxin). The present invention is not limited by the nature of the non-toxin protein sequence employed. In a preferred embodiment, the non-toxin protein sequence comprises a poly-histidine tract. A number of alternative fusion tags or fusion partners are known to the art (e.g., MBP, GST, protein A, etc.) and may be employed for the generation of fusion proteins comprising vaccines. When a fusion partner (i.e., the non-toxin protein sequence) is employed for the production of a recombinant *C. botulinal* toxin protein, the fusion partner may be removed from the recombinant *C. botulinal* toxin protein if desired (i.e., prior to administration of the protein to a subject) using a variety of methods known to the art (e.g., digestion of fusion proteins containing FactorXa or thrombin recognition sites with the appropriate enzyme).

The present invention is not limited by the nature of the host employed for the production of the antibodies of the invention. In a preferred embodiment, the host is a mammal, preferably a human. The antibodies of the present invention may be generated using non-mammalian hosts such as birds, preferably chickens. In a preferred embodiment the method of the present invention further comprised the step c) of collecting the antibodies from the host. In yet another embodiment, the method of the present invention further comprises the step d) of purifying the antibodies.

The present invention further provides antibodies raised according to the above methods.

The present invention further contemplates multivalent vaccines comprising at least two recombinant *C. botulinum* toxin proteins derived from the group consisting of *C. botulinum* serotypes A, B, C, D, E, F, and G. The invention contemplates bivalent, trivalent, quadravalent, pentavalent, heptavalent and septivalent vaccines comprising recombinant *C. botulinum* toxin proteins. Preferably the recombinant *C. botulinum* toxin protein comprises the receptor binding domain (i.e., C fragment) of the toxin.

DESCRIPTION OF THE INVENTION

The present invention contemplates vaccinating humans and other animals with polypeptides derived from *C. botulinum* neurotoxins which are substantially endotoxin-free. These botulinal peptides are also useful for the production of antitoxin. Anti-botulinal toxin antitoxin is useful for the treatment of patients effected by or at risk of symptoms due to the action of *C. botulinum* toxins. The organisms, toxins and individual steps of the present invention are described separately below.

I. *Clostridium* Species, Clostridial Diseases and Associated Toxins

A preferred embodiment of the method of the present invention is directed toward obtaining antibodies against *Clostridium* species, their toxins, enzymes or other metabolic by-products, cell wall components, or synthetic or recombinant versions of any of these compounds. It is contemplated that these antibodies will be produced by immunization of humans or other animals. It is not intended that the present invention be limited to any particular toxin or any species of organism. In one embodiment, toxins from all *Clostridium* species are contemplated as immunogens. Examples of these toxins include the neuraminidase toxin of *C. butyricum, C. sordellii* toxins HT and LT, toxins A, B, C, D, E, F, and G of *C. botulinum* and the numerous *C. perfringens* toxins. In one preferred embodiment, toxins A, B, and E of *C. botulinum* are contemplated as immunogens. Table 2 below lists various *Clostridium* species, their toxins and some antigens associated with disease.

TABLE 2

Clostridial Toxins

| Organism | Toxins and Disease-Associated Antigens |
|---|---|
| *C. botulinum* | A, B, $C_1$, $C_2$, D, E, F, G |
| *C. butyricum* | Neuraminidase |
| *C. difficile* | A, B, Enterotoxin (not A nor B), Motility Altering Factor, Low Molecular Weight Toxin, Others |
| *C. perfringens* | α, β, ϵ, t, γ, δ, ν, θ, κ, λ, μ, υ |
| *C. sordelli/ C. bifermentans* | HT, LT, α, β, γ |
| *C. novyi* | α, β, γ, δ, ϵ, ζ, ν, θ |
| *C. septicum* | α, β, γ, δ |
| *C. histolyticum* | α, β, γ, δ, ϵ plus additional enzymes |
| *C. chauvoei* | α, β, γ, δ |

It is not intended that antibodies produced against one toxin will only be used against that toxin. It is contemplated that antibodies directed against one toxin (e.g., *C. perfringens* type A enterotoxin) may be used as an effective therapeutic against one or more toxin(s) produced by other members of the genus *Clostridium* or other toxin producing organisms (e.g., *Bacillus cereus, Staphylococcus aureus, Streptococcus mutans, Acinetobacter calcoaceticus, Pseudomonas aeruginosa*, other *Pseudomonas* species, etc.). It is further contemplated that antibodies directed against the portion of the toxin which binds to mammalian membranes (e.g., *C. perfringens* enterotoxin A) can also be used against other organisms. It is contemplated that these membrane binding domains are produced synthetically and used as immunogens.

II. Obtaining Antibodies in Non-Mammals

A preferred embodiment of the method of the present invention for obtaining antibodies involves immunization. However, it is also contemplated that antibodies could be obtained from non-mammals without immunization. In the case where no immunization is contemplated, the present invention may use non-mammals with preexisting antibodies to toxins as well as non-mammals that have antibodies to whole organisms by virtue of reactions with the administered antigen. An example of the latter involves immunization with synthetic peptides or recombinant proteins sharing epitopes with whole organism components.

In a preferred embodiment, the method of the present invention contemplates immunizing non-mammals with bacterial toxin(s). It is not intended that the present invention be limited to any particular toxin. In one embodiment, toxin from all clostridial bacteria sources (see Table 2) are contemplated as immunogens. Examples of these toxins are *C. butyricum* neuraminidase toxin, toxins A, B, C, D, E, F, and G from *C. botulinum, C. perfringens* toxins α, β, ε, and ι, and *C. sordellii* toxins HT and LT. In a preferred embodiment, *C. botulinum* toxins A, B, C, D, E, and F (or fragments thereof) are contemplated as immunogens.

A particularly preferred embodiment involves the use of bacterial toxin protein or fragments of toxin proteins produced by molecular biological means (i.e., recombinant toxin proteins). In a preferred embodiment, the immunogen comprises the receptor-binding domain (i.e., the ~50 kD carboxy-terminal portion of the heavy chain; also referred to as the C fragment) of *C. botulinum* serotype A neurotoxin produced by recombinant DNA technology. In another preferred embodiment, the immunogen comprises the receptor-binding domain of *C. botulinum* serotype B neurotoxin produced by recombinant DNA technology. In yet another preferred embodiment, the immunogen comprises the receptor-binding domain region of *C. botulinum* serotype E neurotoxin produced by recombinant DNA technology. In yet another preferred embodiment, the immunogen comprises the receptor-binding domain region of *C. botulinum* serotype C1 neurotoxin produced by recombinant DNA technology. In yet another preferred embodiment, the immunogen comprises the receptor-binding domain region of *C. botulinum* serotype C2 neurotoxin produced by recombinant DNA technology. In yet another preferred embodiment, the immunogen comprises the receptor-binding domain region of *C. botulinum* serotype D neurotoxin produced by recombinant DNA technology. In yet another preferred embodiment, the immunogen comprises the receptor-binding domain region of *C. botulinum* serotype F neurotoxin produced by recombinant DNA technology. In yet another preferred embodiment, the immunogen comprises the receptor-binding domain region of *C. botulinum* serotype G neurotoxin produced by recombinant DNA technology. In a preferred embodiment, the recombinant botulinal toxin proteins are expressed as fusion proteins (e.g., as histidine-tagged proteins). In a still further preferred embodiment, the immunogen is a multivalent vaccine comprising the receptor-binding domain region of *C. botulinum* toxin from two or more toxins selected from the group consisting of type A, type B, type C (including C1 and C2), type D, type E, and type F toxin.

When immunization is used, the preferred non-mammal is from the class Aves. All birds are contemplated (e.g., duck, ostrich, emu, turkey, etc.). A preferred bird is a chicken. Importantly, chicken antibody does not fix mammalian complement. [See H. N. Benson et al., J. Immunol. 87:616 (1961).] Thus, chicken antibody will normally not cause a complement-dependent reaction. [A. A. Benedict and K. Yamaga, "*Immunoglobulins and Antibody Production in Avian Species,* "in *Comparative Immunology* (J. J. Marchaloni, ed.), pp. 335–375, Blackwell, Oxford (1966).] Thus, the preferred antitoxins of the present invention will not exhibit complement-related side effects observed with antitoxins known presently.

When birds are used, it is contemplated that the antibody will be obtained from either the bird serum or the egg. A preferred embodiment involves collection of the antibody from the egg. Laying hens transport immunoglobulin to the egg yolk ("IgY") in concentrations equal to or exceeding that found in serum. [See R. Patterson et al., J. Immunol. 89:272 (1962); and S. B. Carroll and B. D. Stollar, J. Biol. Chem. 258:24 (1983).] In addition, the large volume of egg yolk produced vastly exceeds the volume of serum that can be safely obtained from the bird over any given time period. Finally, the antibody from eggs is purer and more homogeneous; there is far less non-immunoglobulin protein (as compared to serum) and only one class of immunoglobulin is transported to the yolk.

When considering immunization with toxins, one may consider modification of the toxins to reduce the toxicity. In this regard, it is not intended that the present invention be limited by immunization with modified toxin. Unmodified ("native") toxin is also contemplated as an immunogen.

It is also not intended that the present invention be limited by the type of modification—if modification is used. The present invention contemplates all types of toxin modification, including chemical and heat treatment of the toxin. The preferred modification, however, is formaldehyde treatment.

It is not intended that the present invention be limited to a particular mode of immunization; the present invention contemplates all modes of immunization, including subcutaneous, intramuscular, intraperitoneal, and intravenous or intravascular injection, as well as per os administration of immunogen.

The present invention further contemplates immunization with or without adjuvant. (Adjuvant is defined as a substance known to increase the immune response to other antigens when administered with other antigens.) If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant. Another preferred use of adjuvant is the use of Gerbu Adjuvant. The invention also contemplates the use of RIBI fowl adjuvant and Quil A adjuvant.

When immunization is used, the present invention contemplates a wide variety of immunization schedules. In one embodiment, a chicken is administered toxin(s) on day zero and subsequently receives toxin(s) in intervals thereafter. It is not intended that the present invention be limited by the particular intervals or doses. Similarly, it is not intended that the present invention be limited to any particular schedule for collecting antibody. The preferred collection time is sometime after day 100.

Where birds are used and collection of antibody is performed by collecting eggs, the eggs may be stored prior to processing for antibody. It is preferred that eggs be stored at 4° C. for less than one year.

It is contemplated that chicken antibody produced in this manner can be buffer-extracted and used analytically. While unpurified, this preparation can serve as a reference for activity of the antibody prior to further manipulations (e.g., immunoaffinity purification).

III. Increasing the Effectiveness of Antibodies

When purification is used, the present invention contemplates purifying to increase the effectiveness of both non-mammalian antitoxins and mammalian antitoxins. Specifically, the present invention contemplates increasing the percent of toxin-reactive immunoglobulin. The preferred purification approach for avian antibody is polyethylene glycol (PEG) separation.

The present invention contemplates that avian antibody be initially purified using simple, inexpensive procedures. In one embodiment, chicken antibody from eggs is purified by extraction and precipitation with PEG. PEG purification exploits the differential solubility of lipids (which are abundant in egg yolks) and yolk proteins in high concentrations of PEG 8000. [Polson et al., Immunol. Comm. 9:495 (1980) .] The technique is rapid, simple, and relatively inexpensive and yields an immunoglobulin fraction that is significantly purer in terms of contaminating non-immunoglobulin proteins than the comparable ammonium sulfate fractions of mammalian sera and horse antibodies. The majority of the PEG is removed from the precipitated chicken immunoglobulin by treatment with ethanol. Indeed, PEG-purified antibody is sufficiently pure that the present invention contemplates the use of PEG-purified antitoxins in the passive immunization of intoxicated humans and animals.

IV. Treatment

The present invention contemplates antitoxin therapy for humans and other animals intoxicated by bacterial toxins. A preferred method of treatment is by intravenous administration of anti-boutlinal antitoxin; oral administration is also contemplated for other clostridial antitoxins.

A. Dosage of Antitoxin

It was noted by way of background that a balance must be struck when administering currently available antitoxin which is usually produced in large animals such as horses; sufficient antitoxin must be administered to neutralize the toxin, but not so much antitoxin as to increase the risk of untoward side effects. These side effects are caused by: i) patient sensitivity to foreign (e.g, horse) proteins; ii) anaphylactic or immunogenic properties of non-immunoglobulin proteins; iii) the complement fixing properties of mammalian antibodies; and/or iv) the overall burden of foreign protein administered. It is extremely difficult to strike this balance when, as noted above, the degree of intoxication (and hence the level of antitoxin therapy needed) can only be approximated.

The present invention contemplates significantly reducing side effects so that this balance is more easily achieved. Treatment according to the present invention contemplates reducing side effects by using PEG-purified antitoxin from birds.

In one embodiment, the treatment of the present invention contemplates the use of PEG-purified antitoxin from birds. The use of yolk-derived, PEG-purified antibody as antitoxin allows for the administration of: 1) non(mammalian)-complement-fixing, avian antibody; 2) a less heterogeneous mixture of non-immunoglobulin proteins; and 3) less total protein to deliver the equivalent weight of active antibody present in currently available antitoxins. The non-mammalian source of the antitoxin makes it useful for treating patients who are sensitive to horse or other mammalian sera.

B. Delivery of Antitoxin

Although it is not intended to limit the route of delivery, the present invention contemplates a method for antitoxin treatment of bacterial intoxication in which delivery of antitoxin is oral. In one embodiment, antitoxin is delivered in a solid form (e.g., tablets). In an alternative embodiment antitoxin is delivered in an aqueous solution. When an aqueous solution is used, the solution has sufficient ionic strength to solubilize antibody protein, yet is made palatable for oral administration. The delivery solution may also be buffered (e.g., carbonate buffer pH 9.5) which can neutralize stomach acids and stabilize the antibodies when the antibodies are administered orally. In one embodiment the delivery solution is an aqueous solution. In another embodiment the delivery solution is a nutritional formula. Preferably, the delivery solution is infant formula. Yet another embodiment contemplates the delivery of lyophilized antibody encapsulated or microencapsulated inside acid-resistant compounds.

Methods of applying enteric coatings to pharmaceutical compounds are well known to the art [companies specializing in the coating of pharmaceutical compounds are available; for example, The Coating Place (Verona, Wis.) and AAI (Wilmington, N.C.)]. Enteric coatings which are resistant to gastric fluid and whose release (ie., dissolution of the coating to release the pharmaceutical compound) is pH dependent are commercially available [for example, the polymethacrylates Eudragit® L and Eudragit® S (Röhm GmbH)]. Eudragit® S is soluble in intestinal fluid from pH 7.0; this coating can be used to microencapsulate lyophilized antitoxin antibodies and the particles are suspended in a solution having a pH above or below pH 7.0 for oral administration. The microparticles will remain intact and undissolved until they reached the intestines where the intestinal pH would cause them to dissolve thereby releasing the antitoxin.

The invention contemplates a method of treatment which can be administered for treatment of acute intoxication. In one embodiment, antitoxin is administered orally in either a delivery solution or in tablet form, in therapeutic dosage, to a subject intoxicated by the bacterial toxin which served as immunogen for the antitoxin.

The invention also contemplates a method of treatment which can be administered prophylactically. In one embodiment, antitoxin is administered orally, in a delivery solution, in therapeutic dosage, to a subject, to prevent intoxication of the subject by the bacterial toxin which served as immunogen for the production of antitoxin. In another embodiment, antitoxin is administered orally in solid form such as tablets or as microencapsulated particles. Microencapsulation of lyophilized antibody using compounds such as Eudragit® (Rohm GmbH) or polyethylene glycol, which dissolve at a wide range of pH units, allows the oral administration of solid antitoxin in a liquid form (i.e., a suspension) to recipients unable to tolerate administration of tablets (e.g., children or patients on feeding tubes). In one preferred embodiment the subject is a child. In another embodiment, antibody raised against whole bacterial organism is administered orally to a subject, in a delivery solution, in therapeutic dosage.

V. Vaccines Against Clostridial Species

The invention contemplates the generation of mono- and multivalent vaccines for the protection of an animal particularly humans) against several clostridial species. Of particular interest are vaccines which stimulate the production of a humoral immune response to *C. botulinum, C. tetani* and *C. difficile* in humans. The antigens comprising the vaccine preparation may be native or recombinantly produced toxin proteins from the clostridial species listed above. When toxin proteins are used as immunogens they are generally modified to reduce the toxicity. This modification may be by chemical or genetic (i.e., recombinant DNA technology) means. In general genetic detoxification (i.e., the expression of nontoxic fragments in a host cell) is preferred as the expression of nontoxic fragments in a host cell precludes the presence of intact, active toxin in the final preparation. However, when chemical modification is desired, the preferred toxin modification is formaldehyde treatment.

The invention contemplates that recombinant *C. botulinum* toxin proteins be used as antigens in mono- and multivalent vaccine preparations. Soluble, substantially endotoxin-free recombinant *C. botulinum* toxin proteins derived from serotypes A, B and E may be used individually (i.e., as mono-valent vaccines) or in combination (i.e., as a multi-valent vaccine). In addition, the recombinant *C. botulinum* toxin proteins derived from serotpes A, B and E may be used in conjunction with either recombinant or native toxins or toxoids from other serotypes of *C. botulinum, C. difficile* and *C. tetani* as antigens for the preparation of these mono- and multivalent vaccines. It is contemplated that, due to the structural similarity of *C. botulinum* and *C. tetani* toxin proteins, a vaccine comprising *C. difficile* and botulinum toxin proteins (native or recombinant or a mixture thereof) be used to stimulate an immune response against *C. botulinum, C. tetani* and *C. difficile.*

The present invention further contemplates multi-valent vaccines comprising two or more botulinal toxin proteins selected from the group comprising recombinant *C. botulinum* toxin proteins derived from serotypes A, B, C (including C1 and C2), D, E, F and G.

The adverse consequences of exposure to botulinal toxin would be avoided by immunization of subjects at risk of exposure to the toxin with nontoxic preparations which confer immunity such as chemically or genetically detoxified toxin.

Vaccines which confer immunity against one or more of the toxin types A, B, E, F and G would be useful as a means of protecting humans from the deleterious effects of those *C. botulinum* toxins known to affect man. Indeed as the possibility exists that humans could be exposed to any of the seven serotypes of *C. botulinum* toxin (e.g., during biological warfare or the production of toxin in a laboratory setting), multivalent vaccines capable of conferring immunity against toxin types A–G (including both C1 and C2 toxins) would be useful for the protection of humans. Vaccines which confer immunity against one or more of the toxin types C, D and E would be useful for veterinary applications.

The botulinal neurotoxin is synthesized as a single polypeptide chain which is processed into a heavy (H; ~100 kD) and a light (L; ~50 kD) chain by cleavage with proteolytic enzymes; these two chains are held together via disulfide bonds in the active toxin (referred to as derivative toxin) [B. R. DasGupta and H. Sugiyama, Biochem. Biophys. Res. Commun. 48:108 (1972); reviewed in B. R. DasGupta, J. Physiol. 84:220 (1990), H. Sugiyama, Microbiol. Rev. 44:419 (1980) and C. L. Hatheway, Clin. Microbiol. Rev. 3:66 (1990)]. The heavy chain of the active toxin is cleaved by trypsin to produce two fragments termed $H_C$ (also referred to as $H_1$ or C) and $H_N$ (also referred to as $H_2$ or B). The $H_C$ fragment (~46 kD) comprises the carboxy end of the H chain. The $H_N$ fragment (~49 kD) comprises the animo end and remains attached to the L chain ($H_NL$). Neither $H_C$ or $H_NL$ is toxic. $H_C$ competes with whole derivative toxin for binding to synaptosomes and therefore $H_C$ is said to contain the receptor binding site. The $H_C$ and $H_N$ fragments of botulinal toxin are analogous to the fragments C and B of tetanus toxin which are produced by papain cleavage. The C fragment of tetanus toxin has been shown to be responsible for the binding of tetanus toxin to purified gangliosides and neuronal cells [Halpern and Loftus, J. Biol. Chem. 288:11188 (1993)].

Antisera raised against purified preparations of isolated botulinal H and L chains have been shown to protect mice against the lethal effects of the toxin; however, the effectiveness of the two antisera differ with the anti-H sera being more potent (H. Sugiyama, supra). While the different botulinal toxins show structural similarity to one another, the different serotypes are reported to be immunologically distinct (i.e., sera raised against one toxin type does not cross-react to a significant degree with other types). Thus, the generation of multivalent vaccines may require the use of more than one type of toxin.

*C. botulinum* toxin genes from all seven serotypes have been cloned and sequenced (Minton (1995), supra); in addition, partial amino acid sequence is available for a number of *C. botulinum* toxins isolated from different strains within a given serotype. The *C. botulinum* toxins contain about 1250–1300 amino acid residues. On the DNA level, the overall degree of homology between *C. botulinum* serotypes A, B, C, D and E toxins averages between 50 and 60% identity with a greater degree of homology being found between H chain-encoding regions than between those encoding L chains [Whelan et al. (1992) Appl. Environ. Microbiol. 58:2345]. The degree of identity between *C. botulinum* toxins on the amino acid level reflects the level of DNA sequence homology. The most divergent area of DNA and amino acid sequence is found within the carboxy-terminal area of the various *C. botulinum* H chain genes. This portion of the toxin (i.e., $H_C$ or the C fragment) plays a major role in cell binding. As toxin from different serotypes is thought to bind to distinct cell receptor molecules, it is not surprising that the toxins diverge significantly over this region.

Within a given serotype, small variations in the primary amino acid sequence of the botulinal toxins isolated from different strains has been reported [Whelan et al. (1992), supra and Minton (1995), supra]. The present invention contemplates fusion proteins comprising portions of *C. botulinum* toxins from serotypes A–G including the variants found among different strains within a given serotype. The present invention provides oligonucleotide primers which may be used to amplify the C fragment or receptor-binding region of the toxin gene from various strains of *C. botulinum* serotype A, serotype B, serotype C(C1 and C2), serotype D, serotype E, serotype F and serotype G. A large number of different strains of *C. botulinum* serotype A, serotype B, serotype C, serotype D serotype E and serotype F are available from the American Type Culture Collection (ATCC; Rockville, Md.). For example, the ATCC provides the following: Type A strains: 174 (ATCC 3502), 457 (ATCC 17862), and NCTC 7272 (ATCC 19397); Type B strains: 34 (ATCC 439), 62A (ATCC 7948), NCA 213 B (ATCC 7949), 13114 (ATCC 8083), 3137 (ATCC 17780), 1347 (ATCC 17841), 2017 (ATCC 17843), 2217 (ATCC 17844), 2254 (ATCC 17845) and VP 1731 (ATCC 25765); Type C strains: 2220 (ATCC 17782), 2239 (ATCC 17783), 2223 (ATCC 17784; a type C-β strain; C-β strains produce C2 toxin), 662 (ATCC 17849; a type C-α strain; C-α strains produce mainly C1 toxin and a small amount of C2 toxin), 2021 (ATCC 17850; a type C-α strain) and VPI 3803 (ATCC 25766); Type D strains: ATCC 9633, 2023 (ATCC 17851), and VPI 5995 (ATCC 27517); Type E strains: ATCC 43181, 36208 (ATCC 9564), 2231 (ATCC 17786), 2229 (ATCC 17852), 2279 (ATCC 17854) and 2285 (ATCC 17855) and Type F strains: 202F (ATCC 23387), VPI 4404 (ATCC 25764), VPI 2382 (ATCC 27321) and Langeland (ATCC 35415). Type G strain, 113/30 (NCFB 3012) may be obtained from the National Collection of Food Bacteria (NCFB, AFRC Institute of Food Research, Reading, United Kingdom).

Purification methods have been reported for native toxin types A, B, C, D, E, and F [reviewed in G. Sakaguchi, Pharmac. Ther. 19:165 (1983)]. As the different botulinal toxins are structurally related, the invention contemplates the expression of any of the botulinal toxins (e.g., types A–G) as soluble recombinant fusion proteins.

In particular, methods for purification of the type A botulinum neurotoxin have been developed [L. J. Moberg and H. Sugiyama, Appl. Environ. Microbiol. 35:878 (1978)]. Immunization of hens with detoxified purified protein results in the generation of neutralizing antibodies [B. S. Thalley et al., in *Botulinum and Tetanus Neurotoxins*, B. R. DasGupta, ed., Plenum Press, New York (1993), p. 467].

The currently available *C. botulinum* pentavalent vaccine comprising chemically inactivated (i.e., formaldehyde treated) type A, B, C, D and E toxins is not adequate. The efficacy is variable (in particular, only 78% of recipients produce protective levels of anti-type B antibodies following administration of the primary series) and immunization is painful (deep subcutaneous inoculation is required for administration), with adverse reactions being common (moderate to severe local reactions occur in approximately 6% of recipients upon initial injection; this number rises to approximately 11% of individuals who receive booster injections) [Informational Brochure for the Pentavalent (ABCDE) Botulinum Toxoid, Centers for Disease Control]. Preparation of this vaccine is dangerous as active toxin must be handled by laboratory workers.

In general, chemical detoxification of bacterial toxins using agents such as formaldehyde, glutaraldehyde or hydrogen peroxide is not optimal for the generation of vaccines or antitoxins. A delicate balance must be struck between too much and too little chemical modification. If the treatment is insufficient, the vaccine may retain residual toxicity. If the treatment is too excessive, the vaccine may lose potency due to destruction of native immunogenic determinants. Another major limitation of using botulinal toxoids for the generation of antitoxins or vaccines is the high production expense. For the above reasons, the development of methods for the production of nontoxic but immunogenic *C. botulinum* toxin proteins is desirable.

The *C. botulinum* and *C. tetanus* toxin proteins have similar structures [reviewed in E. J. Schantz and E. A. Johnson, Microbiol. Rev. 56:80 (1992)]. The carboxy-terminal 50 kD fragment of the tetanus toxin heavy chain (fragment C) is released by papain cleavage and has been shown to be non-toxic and immunogenic. Recombinant tetanus toxin fragment C has been developed as a candidate vaccine antigen [A. J. Makoff et al., Bio/Technology 7:1043 (1989)). Mice immunized with recombinant tetanus toxin fragment C were protected from challenge with lethal doses of tetanus toxin. No studies have demonstrated that the recombinant tetanus fragment C protein confers immunity against other botulinal toxins such as the *C. botulinum* toxins.

Recombinant tetanus fragment C has been expressed in *E. coli* (A. J. Makoff et al., Bio/Technology, supra and Nucleic Acids Res. 17:10191 (1989); J. L. Halpern et al., Infect. Immun. 58:1004 (1990)], yeast [M. A. Romanos et al., Nucleic Acids Res. 19:1461 (1991)] and baculovirus [I. G. Charles et al., Infect. Immun. 59:1627 (1991)]. Synthetic tetanus toxin genes had to be constructed to facilitate expression in yeast (M. A. Romanos et al., supra) and *E. coli* [A. J. Makoff et al., Nucleic Acids Res., supra], due to the high A–T content of the tetanus toxin gene sequences. High A–T content is a common feature of clostridial genes (M. R. Popoff et al., Infect. Immun. 59:3673 (1991); H. F. LaPenotiere et al., in *Botulinum and Tetanus Neurotoxins*, B. R. DasGupta, ed., Plenum Press, New York (1993), p. 463] which creates expression difficulties in *E. coli* and yeast due primarily to altered codon usage frequency and fortuitous polyadenylation sites, respectively.

The C fragment of the *C. botulinum* type A neurotoxin heavy chain has been evaluated as a vaccine candidate. The *C. botulinum* type A neurotoxin gene has been cloned and sequenced [D. E. Thompson et al., Eur. J. Biochem. 189:73 (1990)]. The C fragment of the type A toxin was expressed as either a fusion protein comprising the botulinal C fragment fused with the maltose binding protein (MBP) or as a native protein [H. F. LaPenotiere et al., (1993) supra, H. F. LaPenotiere et al., Toxicon. 33:1383 (1995) and Middlebrook and Brown (1995), Curr. Top. Microbiol. Immunol. 195:89–122]. The plasmid construct encoding the native protein was reported to be unstable, while the fusion protein was expressed primarily in inclusion bodies as insoluble protein. Immunization of mice with crudely purified MBP fusion protein resulted in protection against IP challenge with 3 $LD_{50}$ doses of toxin [LaPenotiere et al., (1993) and (1995), supra]. However, this recombinant *C. botulinum* type A toxin C fragment/MBP fusion protein is not a suitable immunogen for the production of vaccines as it is expressed as an insoluble protein in *E. coli*. Furthermore, this recombinant *C. botulinum* type A toxin C fragment/MBP fusion protein was not shown to be substantially free of endotoxin contamination. Experience with recombinant *C. botulinum* type A toxin C fragment/MBP fusion proteins shows that the presence of the MBP on the fusion protein greatly complicates the removal of endotoxin from preparations of the recombinant fusion protein (see Ex. 24, infra). Expression of a synthetic gene encoding *C. botulinum* type A toxin C fragment as a soluble protein excreted from insect cells has been reported [Middlebrook and Brown (1995), supra]; no details regarding the level of expression achieved or the presence of endotoxin or other pyrogens were provided. Like the insoluble protein expressed in *E. coli*, immunization with the recombinant protein produced in insect cells was reported to protect mice from challenge with *C. botulinum* toxin A.

Inclusion body protein must be solubilized prior to purification and/or administration to a host. The harsh treatment of inclusion body protein needed to accomplish this solubilization may reduce the immunogenicity of the purified protein. Ideally, recombinant proteins to be used as vaccines are expressed as soluble proteins at high levels (i.e., greater than or equal to about 0.75% of total cellular protein) in *E. coli* or other host cells (e.g., yeast, insect cells, etc.). This facilitates the production and isolation of sufficient quantities of the immunogen in a highly purified form (i.e., substantially free of endotoxin or other pyrogen contamination). The ability to express recombinant toxin proteins as soluble proteins in *E. coli* is advantageous due to the low cost of growth compared to insect or mammalian tissue culture cells.

The *C. botulinum* type B neurotoxin gene has been cloned and sequenced from two strains of *C. botulinum* type B

[Whelan et al. (1992) Appl. Environ. Microbiol. 58:2345 (Danish strain) and Hutson et al. (1994) Curr. Microbiol. 28:101 (Eklund 17B strain)]. The nucleotide sequence of the toxin gene derived from the Eklund 17B strain (ATCC 25765) is available from the EMBL/GenBank sequence data banks under the accession number X71343; the nucleotide sequence of the coding region is listed in SEQ ID NO:39. The amino acid sequence of the *C. botulinum* type B neurotoxin derived from the strain Eklund 17B is listed in SEQ ID NO:40. The nucleotide sequence of the *C. botulinum* serotype B toxin gene derived from the Danish strain is listed in SEQ ID NO:41. The amino acid sequence of the *C. botulinum* type B neurotoxin derived from the Danish strain is listed in SEQ ID NO:42.

The *C. botulinum* type B neurotoxin gene is synthesized as a single polypeptide chain which is processed to form a dimer composed of a light and a heavy chain linked via disulfide bonds. The light chain is responsible for pharmacological activity (i.e., inhibition of the release of acetylcholine at the neuromuscular junction). The N-terminal portion of the heavy chain is thought to mediate channel formation while the C-terminal portion mediates toxin binding; the type B neurotoxin has been reported to exist as a mixture of predominantly single chain with some double chain (Whelan et al., supra). The 50 kD carboxy-terminal portion of the heavy chain is referred to as the C fragment or the $H_C$ domain. The present invention reports for the first time, the expression of the C fragment of *C. botulinum* type B toxin in heterologous hosts (e.g., *E. coli*).

The *C. botulinum* type E neurotoxin gene has been cloned and sequenced from a number of different strains [Poulet et al. (1992) Biochem. Biophys. Res. Commun. 183:107; Whelan et al. (1992) Eur. J. Biochem. 204:657; and Fujii et al. (1993) J. Gen. Microbiol. 139:79]. The nucleotide sequence of the type E toxin gene is available from the EMBL sequence data bank under accession numbers X62089 (strain Beluga) and X62683 (strain NCTC 11219); the nucleotide sequence of the coding region (strain Beluga) is listed in SEQ ID NO:45. The amino acid sequence of the *C. botulinum* type E neurotoxin derived from strain Beluga is listed in SEQ ID NO:46. The type E neurotoxin gene is synthesized as a single polypeptide chain which may be converted to a double-chain form (i.e., a heavy chain and a light chain) by cleavage with trypsin; unlike the type A neurotoxin, the type E neurotoxin exists essentially only in the single-chain form. The 50 kD carboxy-terminal portion of the heavy chain is referred to as the C fragment or the $H_C$ domain. The present invention reports for the first time, the expression of the C fragment of *C. botulinum* type E toxin in heterologous hosts (e.g., *E. coli*).

The *C. botulinum* type C1, D, F and G neurotoxin genes have been cloned and sequenced. The nucleotide and amino acid sequences of these genes and toxins are provided herein. The invention provides methods for the expression of the C fragment from each of these toxin genes in heterologous hosts and the purification of the resulting recombinant proteins.

The subject invention provides methods which allow the production of soluble *C. botulinum* toxin proteins in economical host cells (e.g., *E. coli*). In addition the subject invention provides methods which allow the production of soluble botulinal toxin proteins in yeast and insect cells. Further, methods for the isolation of purified soluble *C. botulinum* toxin proteins which are suitable for immunization of humans and other animals are provided. These soluble, purified preparations of *C. botulinum* toxin proteins provide the basis for improved vaccine preparations and facilitate the production of antitoxin.

When recombinant clostridial toxin proteins produced in gram-negative bacteria (e.g., *E. coli*) are used as vaccines, they are purified to remove endotoxin prior to administration to a host animal. In order to vaccinate a host, an immunogenically-effective amount of purified substantially endotoxin-free recombinant clostridial toxin protein is administered in any of a number of physiologically acceptable carriers known to the art. When administered for the purpose of vaccination, the purified substantially endotoxin-free recombinant clostridial toxin protein may be used alone or in conjunction with known adjutants, including potassium alum, aluminum phosphate, aluminum hydroxide, Gerbu adjuvant (GmDP; C.C. Biotech Corp.), RIBI adjuvant (MPL; RIBI Immunochemical Research, Inc.), QS21 (Cambridge Biotech). The alum and aluminum-based adjutants are particularly preferred when vaccines are to be administered to humans; however, any adjuvant approved for use in humans may be employed. The route of immunization may be nasal, oral, intramuscular, intraperitoneal or subcutaneous.

The invention contemplates the use of soluble, substantially endotoxin-free preparations of fusion proteins comprising the C fragment of the *C. botulinum* type A, B, C, D, E, F, and G toxin as vaccines. In one embodiment, the vaccine comprises the C fragment of either the *C. botulinum* type A, B, C, D, E, F, or G toxin and a poly-histidine tract (also called a histidine tag). In a particularly preferred embodiment, a fusion protein comprising the histidine tagged C fragment is expressed using the pET series of expression vectors (Novagen). The pET expression system utilizes a vector containing the T7 promoter which encodes the fusion protein and a host cell which can be induced to express the T7 DNA polymerase (i.e., a DE3 host strain). The production of C fragment fusion proteins containing a histidine tract is not limited to the use of a particular expression vector and host strain. Several commercially available expression vectors and host strains can be used to express the C fragment protein sequences as a fusion protein containing a histidine tract (For example, the pQE series (pQE-8, 12, 16, 17, 18, 30, 31, 32, 40, 41, 42, 50, 51, 52, 60 and 70) of expression vectors (Qiagen) which are used with the host strains M15[pREP4] (Qiagen) and SG13009 [pREP4] (Qiagen) can be used to express fusion proteins containing six histidine residues at the amino-terminus of the fusion protein). Furthermore a number of commercially available expression vectors which provide a histidine tract also provide a protease cleavage site between the histidine tract and the protein of interest (e.g., botulinal toxin sequences). Cleavage of the resulting fusion protein with the appropriate protease will remove the histidine tag from the protein of interest (e.g., botulinal toxin sequences) (see Example 28a, infra). Removal of the histidine tag may be desirable prior to administration of the recombinant botulinal toxin protein to a subject (e.g., a human).

VI. Detection of Toxin

The invention contemplates detecting bacterial toxin in a sample. The term "sample" in the present specification and claims is used in its broadest sense. On the one hand it is meant to include a specimen or culture. On the other hand, it is meant to include both biological and environmental samples.

Biological samples may be animal, including human, fluid, solid (e.g., stool) or tissue; liquid and solid food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

The invention contemplates detecting bacterial toxin by a competitive immunoassay method that utilizes recombinant toxin A and toxin B proteins, antibodies raised against recombinant bacterial toxin proteins. A fixed a mount of the recombinant toxin proteins are immobilized to a solid support (e.g., a microtiter plate) followed by the addition of a biological sample suspected of containing a bacterial toxin. The biological sample is first mixed with affinity-purified or PEG fractionated antibodies directed against the recombinant toxin protein. A reporter reagent is then added which is capable of detecting the presence of antibody bound to the immobilized toxin protein. The reporter substance may comprise an antibody with binding specificity for the antitoxin attached to a molecule which is used to identify the presence of the reporter substance. If toxin is present in the sample, this toxin will compete with the immobilized recombinant toxin protein for binding to the anti-recombinant antibody thereby reducing the signal obtained following the addition of the reporter reagent. A control is employed where the antibody is not mixed with the sample. This gives the highest (or reference) signal.

The invention also contemplates detecting bacterial toxin by a "sandwich" immunoassay method that utilizes antibodies directed against recombinant bacterial toxin proteins. Affinity-purified antibodies directed against recombinant bacterial toxin proteins are immobilized to a solid support (e.g., microtiter plates). Biological samples suspected of containing bacterial toxins are then added followed by a washing step to remove substantially all unbound antitoxin. The biological sample is next exposed to the reporter substance, which binds to antitoxin and is then washed free of substantially all unbound reporter substance. The reporter substance may comprise an antibody with binding specificity for the antitoxin attached to a molecule which is used to identify the presence of the reporter substance. Identification of the reporter substance in the biological tissue indicates the presence of the bacterial toxin.

It is also contemplated that bacterial toxin be detected by pouring liquids (e.g., soups and other fluid foods and feeds including nutritional supplements for humans and other animals) over immobilized antibody which is directed against the bacterial toxin. It is contemplated that the immobilized antibody will be present in or on such supports as cartridges, columns, beads, or any other solid support medium. In one embodiment, following the exposure of the liquid to the immobilized antibody, unbound toxin is substantially removed by washing. The exposure of the liquid is then exposed to a reporter substance which detects the presence of bound toxin. In a preferred embodiment the reporter substance is an enzyme, fluorescent dye, or radioactive compound attached to an antibody which is directed against the toxin (i.e., in a "sandwich" immunoassay). It is also contemplated that the detection system will Experimental The following examples serve to illustrate certain preferred embodiments and aspects of the present invention and are not to be construed as limiting the scope thereof.

In the disclosure which follows, the following abbreviations apply: ° C. (degrees Centigrade); rpm (revolutions per minute); BBS-Tween (borate buffered saline containing Tween); BSA (bovine serum albumin); ELISA (enzyme-linked immunosorbent assay); CFA (complete Freund's adjuvant); IFA (incomplete Freund's adjuvant); IgG (immunoglobulin G); IgY (immunoglobulin Y); IM (intramuscular); IP (intraperitoneal); IV (intravenous or intravascular); SC (subcutaneous); $H_2O$ (water); HCl (hydrochloric acid); $LD_{100}$ (lethal dose for 100% of experimental animals); aa (amino acid); HPLC (high performance liquid chromatography); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); MW (molecular weight); sec (seconds); min(s) (minute/minutes); hr(s) (hour/hours); $MgCl_2$ (magnesium chloride); NaCl (sodium chloride); $Na_2CO_3$ (sodium carbonate); $OD_{280}$ (optical density at 280 nm); $OD_{600}$ (optical density at 600 nm); PAGE (polyacrylamide gel electrophoresis); PBS [phosphate buffered saline (150 mM NaCl, 10 mM sodium phosphate buffer, pH 7.2)]; PEG (polyethylene glycol); PMSF (phenylmethylsulfonyl fluoride); SDS (sodium dodecyl sulfate); Tris (tris (hydroxymethyl)aminomethane); Ensure® (Ensure®, Ross Laboratories, Columbus Ohio); Enfamil® (Enfamil®, Mead Johnson); w/v (weight to volume); v/v (volume to volume); Amicon (Amicon, Inc., Beverly, Mass.); Amresco (Amresco, Inc., Solon, Ohio); ATCC (American Type Culture Collection, Rockville, Md.); BBL (Baltimore Biologics Laboratory, (a division of Becton Dickinson), Cockeysville, Md.); Becton Dickinson (Becton Dickinson Labware, Lincoln Park, N.J.); BioRad (BioRad, Richmond, Calif.); Biotech (C—C Biotech Corp., Poway, Calif.); Charles River (Charles River Laboratories, Wilmington, Mass.); Cocalico (Cocalico Biologicals Inc., Reamstown, Pa.); CytRx (CytRx Corp., Norcross, Ga.); Falcon (e.g. Baxter Healthcare Corp., McGaw Park, Ill. and Becton Dickinson); FDA (Federal Food and Drug Administration); Fisher Biotech (Fisher Biotech, Springfield, N.J.); GIBCO (Grand Island Biologic Company/BRL, Grand Island, N.Y.); Gibco-BRL (Life Technologies, Inc., Gaithersburg, Md.); Harlan Sprague Dawley (Harlan Sprague Dawley, Inc., Madison, Wis.); Mallinckrodt (a division of Baxter Healthcare Corp., McGaw Park, Ill.); Millipore (Millipore Corp., Marlborough, Mass.); New England Biolabs (New England Biolabs, Inc., Beverly, Mass.); Novagen (Novagen, Inc., Madison, Wis.); Pharmacia (Pharmacia, Inc., Piscataway, N.J.); Qiagen (Qiagen, Chatsworth, Calif.); Sasco (Sasco, Omaha, Nebr.); Showdex (Showa Denko America, Inc., New York, N.Y.); Sigma (Sigma Chemical Co., St. Louis, Mo.); Sterogene (Sterogene, Inc., Arcadia, Calif.); Tech Lab (Tech Lab, Inc., Blacksburg, Va.); and Vaxcell (Vaxcell, Inc., a subsidiary of CytRX Corp., Norcross, Ga.).

When a recombinant protein is described in the specification it is referred to in a short-hand manner by the amino acids in the toxin sequence present in the recombinant protein rounded to the nearest 10. For example, the recombinant protein pMB1850–2360 contains amino acids 1.852 through 2362 of the *C. difficile* toxin B protein. The specification gives detailed construction details for all recombinant proteins such that one skilled in the art will know precisely which amino acids are present in a given recombinant protein.

EXAMPLE 1

Production of High-Titer Antibodies to *Clostridium difficile* Organisms in a Hen Antibodies to certain pathogenic organisms have been shown to be effective in treating diseases caused by those organisms. It has not been shown whether antibodies can be raised, against *Clostridium difficile*, which would be effective in treating infection by this organism. Accordingly, *C. difficile* was tested as immunogen for production of hen antibodies.

To determine the best course for raising high-titer egg antibodies against whole *C. difficile* organisms, different immunizing strains and different immunizing concentrations were examined. The example involved (a) preparation of the bacterial immunogen, (b) immunization, (c) purification of anti-bacterial chicken antibodies, and (d) detection of anti-bacterial antibodies in the purified IgY preparations.

a) Preparation of Bacterial Immunogen

*C. difficile* strains 43594 (serogroup A) and 43596 (serogroup C) were originally obtained from the ATCC. These two strains were selected because they represent two of the most commonly-occurring serogroups isolated from patients with antibiotic-associated pseudomembranous colitis. [Delmee et al., J. Clin. Microbiol., 28(10):2210 (1990).] Additionally, both of these strains have been previously characterized with respect to their virulence in the Syrian hamster model for *C. difficile* infection. [Delmee et al., J. Med Microbiol., 33:85 (1990).]

The bacterial strains were separately cultured on brain heart infusion agar for 48 hours at 37° C. in a Gas Pack 100 Jar (BBL, Cockeysville, Md.) equipped with a Gas Pack Plus anaerobic envelope (BBL). Forty-eight hour cultures were used because they produce better growth and the organisms have been found to be more cross-reactive with respect to their surface antigen presentation. The greater the degree of cross-reactivity of our IgY preparations, the better the probability of a broad range of activity against different strains/serogroups. [Toma et al., J. Clin. Microbiol., 26(3):426 (1988).]

The resulting organisms were removed from the agar surface using a sterile dacron-tip swab, and were suspended in a solution containing 0.4% formaldehyde in PBS, pH 7.2. This concentration of formaldehyde has been reported as producing good results for the purpose of preparing whole-organism immunogen suspensions for the generation of polyclonal anti-*C. difficile* antisera in rabbits. [Delmee et al., J. Clin. Microbiol., 21:323 (1985); Davies et al., Microbial Path., 9:141 (1990).] In this manner, two separate bacterial suspensions were prepared, one for each strain. The two suspensions were then incubated at 4° C. for 1 hour. Following this period of formalin-treatment, the suspensions were centrifuged at 4,200×g for 20 min., and the resulting pellets were washed twice in normal saline. The washed pellets, which contained formalin-treated whole organisms, were resuspended in fresh normal saline such that the visual turbidity of each suspension corresponded to a #7 McFarland standard. [M. A. C. Edelstein, "*Processing Clinical Specimens for Anaerobic Bacteria: Isolation and Identification Procedures*," in S. M. Finegold et al (eds.)., *Bailey and Scott's Diagnostic Microbiology*, pp. 477–507, C. V. Mosby Co., (1990). The preparation of McFarland nephelometer standards and the corresponding approximate number of organisms for each tube are described in detail at pp. 172–173 of this volume.] Each of the two #7 suspensions was then split into two separate volumes. One volume of each suspension was volumetrically adjusted, by the addition of saline, to correspond to the visual turbidity of a #1 McFarland standard. [Id.] The #1 suspensions contained approximately $3\times10^8$ organisms/ml, and the #7 suspensions contained approximately $2\times10^9$ organisms/ml. [Id.] The four resulting concentration-adjusted suspensions of formalin-treated *C. difficile* organisms were considered to be "bacterial immunogen suspensions." These suspensions were used immediately after preparation for the initial immunization. [See section (b).]

The formalin-treatment procedure did not result in 100% non-viable bacteria in the immunogen suspensions. In order to increase the level of killing, the formalin concentration and length of treatment were both increased for subsequent immunogen preparations, as described below in Table 3. (Although viability was decreased with the stronger formalin treatment, 100% inviability of the bacterial immunogen suspensions was not reached.) Also, in subsequent immunogen preparations, the formalin solutions were prepared in normal saline instead of PBS. At day 49, the day of the fifth immunization, the excess volumes of the four previous bacterial immunogen suspensions were stored frozen at −70° C. for use during all subsequent immunizations.

b) Immunization

For the initial immunization, 1.0 ml volumes of each of the four bacterial immunogen suspensions described above were separately emulsified in 1.2 ml volumes of CFA (GIBCO). For each of the four emulsified immunogen suspensions, two four-month old White Leghorn hens (pre-laying) were immunized. (It is not necessary to use pre-laying hens; actively-laying hens can also be utilized.) Each hen received a total volume of approximately 1.0 ml of a single emulsified immunogen suspension via four injections (two subcutaneous and two intramuscular) of approximately 250 $\mu$l per site. In this manner, a total of four different immunization combinations, using two hens per combination, were initiated for the purpose of evaluating both the effect of immunizing concentration on egg yolk antibody (IgY) production, and interstrain cross-reactivity of IgY raised against heterologous strains. The four immunization groups are summarized in Table 3.

TABLE 3

Immunization Groups

| Group Designation | Immunizing Strain | Approximate Immunizing Dose |
|---|---|---|
| CD 43594, #1 | *C. difficile* strain 43594 | $1.5\times10^8$ organisms/hen |
| CD 43594, #7 | *C. difficile* strain 43594 | $1.0\times10^9$ organisms/hen |
| CD 43596, #1 | *C. difficile* strain 43596 | $1.5\times10^8$ organisms/hen |
| CD 43596, #7 | *C. difficile* strain 43596 | $1.0\times10^9$ organisms/hen |

The time point for the first series of immunizations was designated as "day zero." All subsequent immunizations were performed as described above except that the bacterial immunogen suspensions were emulsified using IFA (GIBCO) instead of CFA, and for the later time point immunization, the stored frozen suspensions were used instead of freshly-prepared suspensions. The immunization schedule used is listed in Table 4.

TABLE 4

Immunization Schedule

| Day Of Immunization | Formalin-Treatment | Immunogen Preparation Used |
|---|---|---|
| 0 | 1%, 1 hr. | freshly-prepared |
| 14 | 1%, overnight | " |
| 21 | 1%, overnight | " |

TABLE 4-continued

Immunization Schedule

| Day Of Immunization | Formalin-Treatment | Immunogen Preparation Used |
|---|---|---|
| 35 | 1%, 48 hrs. | " |
| 49 | 1%, 72 hrs. | " |
| 70 | " | stored frozen |
| 85 | " | " |
| 105 | " | " |

c) Purification of Anti-Bacterial Chicken Antibodies

Groups of four eggs were collected per immunization group between days 80 and 84 post-initial immunization, and chicken immunoglobulin (IgY) was extracted according to a modification of the procedure of A. Poison et al., Immunol. Comm., 9:495 (1980). A gentle stream of distilled water from a squirt bottle was used to separate the yolks from the whites, and the yolks were broken by dropping them through a funnel into a graduated cylinder. The four individual yolks were pooled for each group. The pooled, broken yolks were blended with 4 volumes of egg extraction buffer to improve antibody yield (egg extraction buffer is 0.01 M sodium phosphate, 0.1 M NaCl, pH 7.5, containing 0.005% thimerosal), and PEG 8000 (Amresco) was added to a concentration of 3.5%. When all the PEG dissolved, the protein precipitates that formed were pelleted by centrifugation at 13,000×g for 10 minutes. The supernatants were decanted and filtered through cheesecloth to remove the lipid layer, and the PEG was added to the supernatants to a final concentration of 12% (the supernatants were assumed to contain 3.5% PEG). After a second centrifugation, the supernatants were discarded and the pellets were centrifuged a final time to extrude the remaining PEG. These crude IgY pellets were then dissolved in the original yolk volume of egg extraction buffer and stored at 4° C. As an additional control, a preimmune IgY solution was prepared as described above, using eggs collected from unimmunized hens.

d) Detection of Anti-Bacterial Antibodies in the Purified IgY Preparations

In order to evaluate the relative levels of specific anti-*C. difficile* activity in the IgY preparations described above, a modified version of the whole-organism ELISA procedure of N. V. Padhye et al., J. Clin. Microbiol. 29:99–103 (1990) was used. Frozen organisms of both *C. difficile* strains described above were thawed and diluted to a concentration of approximately $1\times10^7$ organisms/ml using PBS, pH 7.2. In this way, two separate coating suspensions were prepared, one for each immunizing strain. Into the wells of 96-well microtiter plates (Falcon, Pro-Bind Assay Plates) were placed 100 μl volumes of the coating suspensions. In this manner, each plate well received a total of approximately $1\times10^6$ organisms of one strain or the other. The plates were then incubated at 4° C. overnight. The next morning, the coating suspensions were decanted, and all wells were washed three times using PBS. In order to block non-specific binding sites, 100 μl of 0.5% BSA (Sigma) in PBS was then added to each well, and the plates were incubated for 2 hours at room temperature. The blocking solution was decanted, and 100 μl volumes of the IgY preparations described above were initially diluted 1:500 with a solution of 0.1% BSA in PBS, and then serially diluted in 1:5 steps. The following dilutions were placed in the wells: 1:500, 1:2,500, 1:62, 5000, 1:312,500, and 1:1,562,500. The plates were again incubated for 2 hours at room temperature. Following this incubation, the IgY-containing solutions were decanted, and the wells were washed three times using BBS-Tween (0.1 M boric acid, 0.025 M sodium borate, 1.0 M NaCl, 0.1% Tween-20), followed by two washes using PBS-Tween (0.1% Tween-20), and finally, two washes using PBS only. To each well, 100 μl of a 1:750 dilution of rabbit anti-chicken IgG (whole-molecule)-alkaline phosphatase conjugate (Sigma) (diluted in 0.1% BSA in PBS) was added. The plates were again incubated for 2 hours at room temperature. The conjugate solutions were decanted and the plates were washed as described above, substituting 50 mM $Na_2CO_3$, pH 9.5 for the PBS in the final wash. The plates were developed by the addition of 100 μl of a solution containing 1 mg/ml para-nitrophenyl phosphate (Sigma) dissolved in 50 mM $Na_2CO_3$, 10 mM $MgCl_2$, pH 9.5 to each well, and incubating the plates at room temperature in the dark for 45 minutes. The absorbance of each well was measured at 410 nm using a Dynatech MR 700 plate reader. In this manner, each of the four IgY preparations described above was tested for reactivity against both of the immunizing *C. difficile* strains; strain-specific, as well as cross-reactive activity was determined.

Table 5 shows the results of the whole-organism ELISA. All four IgY preparations demonstrated significant levels of activity, to a dilution of 1:62,500 or greater against both of the immunizing organism strains. Therefore, antibodies raised against one strain were highly cross-reactive with the other strain, and vice versa. The immunizing concentration of organisms did not have a significant effect on organism-specific IgY production, as both concentrations produced approximately equivalent responses. Therefore, the lower immunizing concentration of approximately $1.5\times10^8$ organisms/hen is the preferred immunizing concentration of the two tested. The preimmune IgY preparation appeared to possess relatively low levels of *C. difficile*-reactive activity to a dilution of 1:500, probably due to prior exposure of the animals to environmental clostridia.

An initial whole-organism ELISA was performed using IgY preparations made from single CD 43594, #1 and CD 43596, #1 eggs collected around day 50 (data not shown). Specific titers were found to be 5 to 10-fold lower than those reported in Table 5. These results demonstrate that it is possible to begin immunizing hens prior to the time that they begin to lay eggs, and to obtain high titer specific IgY from the first eggs that are laid. In other words, it is not necessary to wait for the hens to begin laying before the immunization schedule is started.

TABLE 5

Results Of The Anti-*C. difficile* Whole-Organism ELISA

| IgY Preparation | Dilution Of IgY Prep | 43594-Coated Wells | 43596-Coated Wells |
|---|---|---|---|
| CD 43594, #1 | 1:500 | 1.746 | 1.801 |
| | 1:2,500 | 1.092 | 1.670 |
| | 1:12,500 | 0.202 | 0.812 |
| | 1:62,500 | 0.136 | 0.179 |
| | 1:312,500 | 0.012 | 0.080 |
| | 1:1,562,500 | 0.002 | 0.020 |
| CD 43594, #7 | 1:500 | 1.780 | 1.771 |
| | 1:2,500 | 1.025 | 1.078 |
| | 1:12,500 | 0.188 | 0.382 |
| | 1:62,500 | 0.052 | 0.132 |
| | 1:312,500 | 0.022 | 0.043 |
| | 1:1,562,500 | 0.005 | 0.024 |

TABLE 5-continued

Results Of The Anti-*C. difficile* Whole-Organism ELISA

| IgY Preparation | Dilution Of IgY Prep | 43594-Coated Wells | 43596-Coated Wells |
|---|---|---|---|
| CD 43596, #1 | 1:500 | 1.526 | 1.790 |
| | 1:2,500 | 0.832 | 1.477 |
| | 1:12,500 | 0.247 | 0.452 |
| | 1:62,500 | 0.050 | 0.242 |
| | 1:312,500 | 0.010 | 0.067 |
| | 1:1,562,500 | 0.000 | 0.036 |
| CD 43596, #7 | 1:500 | 1.702 | 1.505 |
| | 1:2,500 | 0.706 | 0.866 |
| | 1:12,500 | 0.250 | 0.282 |
| | 1:62,500 | 0.039 | 0.078 |
| | 1:312,500 | 0.002 | 0.017 |
| | 1:1,562,500 | 0.000 | 0.010 |
| Preimmune IgY | 1:500 | 0.142 | 0.309 |
| | 1:2,500 | 0.032 | 0.077 |
| | 1:12,500 | 0.006 | 0.024 |
| | 1:62,500 | 0.002 | 0.012 |
| | 1:312,500 | 0.004 | 0.010 |
| | 1:1,562,500 | 0.002 | 0.014 |

EXAMPLE 2

Treatment Of *C. difficile* Infection with Anti-*C. difficile* Antibody

In order to determine whether the immune IgY antibodies raised against whole *C. difficile* organisms were capable of inhibiting the infection of hamsters by *C. difficile*, hamsters infected by these bacteria were utilized. [Lyerly et al., Infect. Immun., 59:2215–2218 (1991).] This example involved: (a) determination of the lethal dose of *C. difficile* organisms; and (b) treatment of infected animals with immune antibody or control antibody in nutritional solution.

a) Determination of the Lethal Dose of *C. difficile* Organisms

Determination of the lethal dose of *C. difficile* organisms was carried out according to the model described by D. M. Lyerly et al., Infect. Immun., 59:2215–2218 (1991). *C. difficile* strain ATCC 43596 (serogroup C, ATCC) was plated on BHI agar and grown anaerobically (BBL Gas Pak 100 system) at 37° C. for 42 hours. Organisms were removed from the agar surface using a sterile dacron-tip swab and suspended in sterile 0.9% NaCl solution to a density of 108 organisms/ml.

In order to determine the lethal dose of *C. difficile* in the presence of control antibody and nutritional formula, non-immune eggs were obtained from unimmunized hens and a 12% PEG preparation made as described in Example 1(c). This preparation was redissolved in one fourth the original yolk volume of vanilla flavor Ensure®.

Starting on day one, groups of female Golden Syrian hamsters (Harlan Sprague Dawley), 8–9 weeks old and weighing approximately 100 gm, were orally administered 1 ml of the preimmune/Ensure® formula at time zero, 2 hours, 6 hours, and 10 hours. At 1 hour, animals were orally administered 3.0 mg clindamycin HCl (Sigma) in 1 ml of water. This drug predisposes hamsters to *C. difficile* infection by altering the normal intestinal flora. On day two, the animals were given 1 ml of the preimmune IgY/Ensure® formula at time zero, 2 hours, 6 hours, and 10 hours. At 1 hour on day two, different groups of animals were inoculated orally with saline (control), or $10^2$, $10^4$, $10^6$, or $10^8$ *C. difficile* organisms in 1 ml of saline. From days 3–12, animals were given 1 ml of the preimmune IgY/Ensure® formula three times daily and observed for the onset of diarrhea and death. Each animal was housed in an individual cage and was offered food and water ad libitum.

Administration of $10^6$–$10^8$ organisms resulted in death in 3–4 days while the lower doses of $10^2$–$10^4$ organisms caused death in 5 days. Cecal swabs taken from dead animals indicated the presence of *C. difficile*. Given the effectiveness of the 102 dose, this number of organisms was chosen for the following experiment to see if hyperimmune anti-*C. difficile* antibody could block infection.

b) Treatment of Infected Animals with Immune Antibody or Control Antibody in Nutritional Formula The experiment in (a) was repeated using three groups of seven hamsters each. Group A received no clindanycin or *C. difficile* and was the survival control. Group B received clindamycin, $10^2$ *C. difficile* organisms and preimmune IgY on the same schedule as the animals in (a) above. Group C received clindamycin, $10^2$ *C. difficile* organisms, and hyperimmune anti-*C. difficile* IgY on the same schedule as Group B. The anti-*C. difficile* IgY was prepared as described in Example 1 except that the 12% PEG preparation was dissolved in one fourth the original yolk volume of Ensure®.

All animals were observed for the onset of diarrhea or other disease symptoms and death. Each animal was housed in an individual cage and was offered food and water ad libitum. The results are shown in Table 6.

TABLE 6

The Effect Of Oral Feeding Of Hyperimmune IgY Antibody on *C. difficile* Infection

| | Animal Group | Time To Diarrhea[a] | Time To Death[a] |
|---|---|---|---|
| A | pre-immune IgY only | no diarrhea | no deaths |
| B | Clindamycin, *C. difficile*, preimmune IgY | 30 hrs. | 49 hrs. |
| C | Clindamycin, *C. difficile*, immune IgY | 33 hrs. | 56 hrs. |

[a]Mean of seven animals.

Hamsters in the control group A did not develop diarrhea and remained healthy during the experimental period. Hamsters in groups B and C developed diarrheal disease. Anti-*C. difficile* IgY did not protect the animals from diarrhea or death, all animals succumbed in the same time interval as the animals treated with preimmune IgY. Thus, while immunization with whole organisms apparently can improve sublethal symptoms with particular bacteria (see U.S. Pat. No. 5,080,895 to H. Tokoro), such an approach does not prove to be productive to protect against the lethal effects of *C. difficile.*

EXAMPLE 3

Production of *C. botulinum* Type A Antitoxin in Hens

In order to determine whether antibodies could be raised against the toxin produced by clostridial pathogens, which would be effective in treating clostridial diseases, antitoxin to *C. botulinum* type A toxin was produced. This example involves: (a) toxin modification; (b) immunization; (c) antitoxin collection; (d) antigenicity assessment; and (e) assay of antitoxin titer.

a) Toxin Modification

*C. botulinum* type A toxoid was obtain ed from B. R. DasGupta. From this, the active type A neurotoxin (M.W. approximately 150 kD) was purified to greater than 99% purity, according to published methods. [B. R. DasGupta & V. Sathyamoorthy, Toxicon, 22:415 (1984).] The neurotoxin was detoxified with formaldehyde according to published methods. [B. R. Singh & B. R. DasGupta, Toxicon, 27:403 (1989).]

b) Immunization

*C. botulinum* toxoid for immunization was dissolved in PBS (1 mg/ml) and was emulsified with an approximately equal volume of CFA (GIBCO) for initial immunization or IFA for booster immunization. On day zero, two white leghorn hens, obtained from local breeders, were each injected at multiple sites (intramuscular and subcutaneous) with 1 ml inactivated toxoid emulsified in 1 ml CFA. Subsequent booster immunizations were made according to the following schedule for day of injection and toxoid amount: days 14 and 21–0.5 mg; day 171–0.75 mg; days 394, 401, 409–0.25 mg. One hen received an additional booster of 0.150 mg on day 544.

c) Antitoxin Collection

Total yolk immunoglobulin (IgY) was extracted as described in Example 1(c) and the IgY pellet was dissolved in the original yolk volume of PBS with thimerosal.

d) Antigenicity Assessment

Eggs were collected from day 409 through day 423 to assess whether the toxoid was sufficiently immunogenic to raise antibody. Eggs from the two hens were pooled and antibody was collected as described in the standard PEG protocol. [Example 1(c).] Antigenicity of the botulinal toxin was assessed on Western blots. The 150 kD detoxified type A neurotoxin and unmodified, toxic, 300 kD botulinal type A complex (toxin used for intragastric route administration for animal gut neutralization experiments; see Example 6) were separated on a SDS-polyacrylamide reducing gel. The Western blot technique was performed according to the method of Towbin. [H. Towbin et al., Proc. Natl. Acad. Sci. USA, 76:4350 (1979).] Ten μg samples of *C. botulinum* complex and toxoid were dissolved in SDS reducing sample buffer (1% SDS, 0.5% 2-mercaptoethanol, 50 mM Tris, pH 6.8, 10% glycerol, 0.025% w/v bromphenol blue, 10% β-mercaptoethanol), heated at 95° C. for 10 min and separated on a 1 mm thick 5% SDS-polyacrylamide gel. [K. Weber and M. Osborn, "*Proteins and Sodium Dodecyl Sulfate: Molecular Weight Determination on Polyacrylamide Gels and Related Procedures,*" *in The Proteins,* 3d Edition (H. Neurath & R. L. Hill, eds), pp. 179–223, (Academic Press, NY, 1975).] Part of the gel was cut off and the proteins were stained with Coomassie Blue. The proteins in the remainder of the gel were transferred to nitrocellulose using the Milliblot-SDE electro-blotting system (Millipore) according to manufacturer's directions. The nitrocellulose was temporarily stained with 10% Ponceau S [S. B. Carroll and A. Laughon, "*Production and Purification of Polyclonal Antibodies to the Foreign Segment of* β*-galactosidase Fusion Proteins,*" *in DNA Cloning: A Practical Approach,* Vol.III, (D. Glover, ed.), pp. 89–111, IRL Press, Oxford, (1987)] to visualize the lanes, then destained by running a gentle stream of distilled water over the blot for several minutes. The nitrocellulose was immersed in PBS containing 3% BSA overnight at 4° C. to block any remaining protein binding sites.

The blot was cut into strips and each strip was incubated with the appropriate primary antibody. The avian anti-*C. botulinum* antibodies [described in (c)] and pre-immune chicken antibody (as control) were diluted 1:125 in PBS containing 1 mg/ml BSA for 2 hours at room temperature. The blots were washed with two changes each of large volumes of PBS, BBS-Tween and PBS, successively (10 min/wash). Goat anti-chicken IgG alkaline phosphatase conjugated secondary antibody (Fisher Biotech) was diluted 1:500 in PBS containing 1 mg/ml BSA and incubated with the blot for 2 hours at room temperature. The blots were washed with two changes each of large volumes of PBS and BBS-Tween, followed by one change of PBS and 0.1 M Tris-HCl, pH 9.5. Blots were developed in freshly prepared alkaline phosphatase substrate buffer (100 μg/ml nitroblue tetrazolium (Sigma), 50 μg/ml 5-bromo-4-chloro-3-indolyl phosphate (Sigma), 5 mM $MgCl_2$ in 50 mM $Na_2CO_3$, pH 9.5).

The Western blots are shown in FIG. 1. The anti-*C. botulinum* IgY reacted to the toxoid to give a broad immunoreactive band at about 145–150 kD on the reducing gel. This toxoid is refractive to disulfide cleavage by reducing agents due to formalin crosslinking. The immune IgY reacted with the active toxin complex, a 97 kD *C. botulinum* type A heavy chain and a 53 kD light chain. The preimmune IgY was unreactive to the *C. botulinum* complex or toxoid in the Western blot.

e) Antitoxin Antibody Titer

The IgY antibody titer to *C. botulinum* type A toxoid of eggs harvested between day 409 and 423 was evaluated by ELISA, prepared as follows. Ninety-six-well Falcon Probind plates were coated overnight at 4° C. with 100 μl/well toxoid [B. R. Singh & B. R. Das Gupta, Toxicon 27:403 (1989)] at 2.5 μg/ml in PBS, pH 7.5 containing 0.005% thimerosal. The following day the wells were blocked with PBS containing 1% BSA for 1 hour at 37° C. The IgY from immune or preimmune eggs was diluted in PBS containing 1% BSA and 0.05% Tween 20 and the plates were incubated for 1 hour at 37° C. The plates were washed three times with PBS containing 0.05% Tween 20 and three times with PBS alone. Alkaline phosphatase-conjugated goat-anti-chicken IgG (Fisher Biotech) was diluted 1:750 in PBS containing 1% BSA and 0.05% Tween 20, added to the plates, and incubated 1 hour at 37° C. The plates were washed as before, and p-nitrophenyl phosphate (Sigma) at 1 mg/ml in 0.05 M $Na_2CO_3$, pH 9.5, 10 mM $MgCl_2$ was added.

Figure 2:
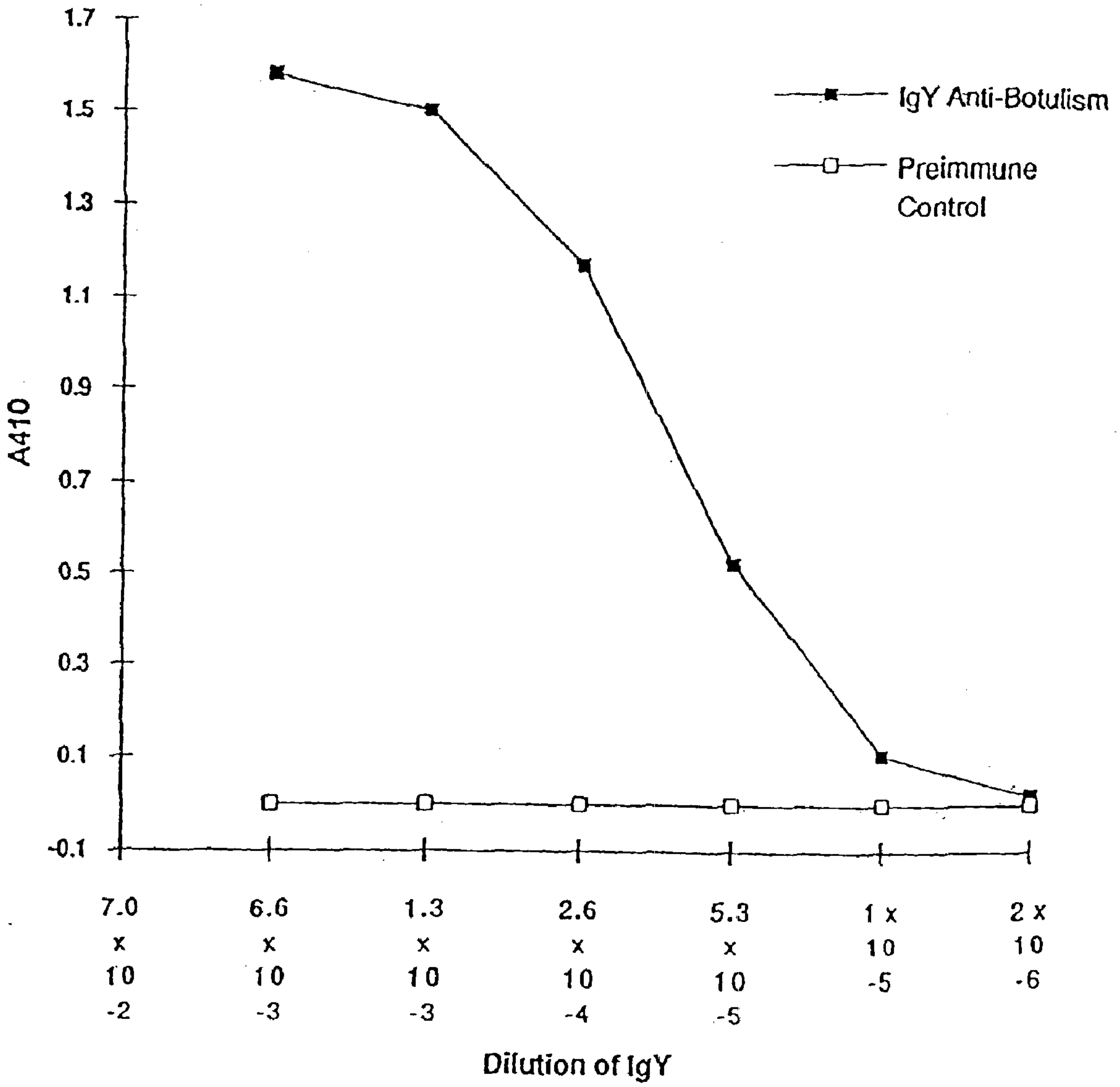
FIG. 2 shows the IgY antibody titer to *C. botulinum* type A toxoid in eggs, measured by ELISA.

The results are shown in FIG. 2. Chickens immunized with the toxoid generated high titers of antibody to the immunogen. Importantly, eggs from both immunized hens had significant anti-immunogen antibody titers as compared to preimmune control eggs. The anti-*C. botulinum* IgY possessed significant activity, to a dilution of 1:93,750 or greater.

EXAMPLE 4

Preparation of Avian Egg Yolk Immunoglobulin in an Orally Administrable Form In order to administer avian IgY antibodies orally to experimental mice, an effective delivery formula for the IgY had to be determined. The concern was that if the crude IgY was dissolved in PBS, the saline in PBS would dehydrate the mice, which might prove harmful over the duration of the study. Therefore, alternative methods of oral administration of IgY were tested. The example involved: (a) isolation of immune IgY; (b) solubilization of IgY in water or PBS, including subsequent dialysis of the IgY-PBS solution with water to eliminate or reduce the salts (salt and phosphate) in the buffer; and (c) comparison of the quantity and activity of recovered IgY by absorbance at 280 run and PAGE, and enzyme-linked immunoassay (ELISA).

a) Isolation of Immune IgY

In order to investigate the most effective delivery formula for IgY, we used IgY which was raised against *Crotalus durissus terrificus* venom. Three eggs were collected from hens immunized with the *C. durissus terrificus* venom and IgY was extracted from the yolks using the modified Polson procedure described by Thalley and Carroll [Bio/Technology, 8:934–938 (1990)] as described in Example 1(c).

The egg yolks were separated from the whites, pooled, and blended with four volumes of PBS. Powdered PEG 8000 was added to a concentration of 3.5%. The mixture was centrifuged at 10,000 rpm for 10 minutes to pellet the precipitated protein, and the supernatant was filtered through cheesecloth to remove the lipid layer. Powdered PEG 8000 was added to the supernatant to bring the final PEG concentration to 12% (assuming a PEG concentration of 3.5% in the supernatant). The 12% PEG/IgY mixture was divided into two equal volumes and centrifuged to pellet the IgY.

b) Solubilization of the IgY in Water or PBS

One pellet was resuspended in ½ the original yolk volume of PBS, and the other pellet was resuspended in ½ the original yolk volume of water. The pellets were then centrifuged to remove any particles or insoluble material. The IgY in PBS solution dissolved readily but the fraction resuspended in water remained cloudy.

In order to satisfy anticipated sterility requirements for orally administered antibodies, the antibody solution needs to be filter-sterilized (as an alternative to heat sterilization which would destroy the antibodies). The preparation of IgY resuspended in water was too cloudy to pass through either a 0.2 or 0.45 μm membrane filter, so 10 ml of the PBS resuspended fraction was dialyzed overnight at room temperature against 250 ml of water. The following morning the dialysis chamber was emptied and refilled with 250 ml of fresh $H_2O$ for a second dialysis. Thereafter, the yields of soluble antibody were determined at $OD_{280}$ and are compared in Table 7.

TABLE 7

Dependence Of IgY Yield On Solvents

| Fraction | Absorbance Of 1:10 Dilution At 280 nm | Percent Recovery |
|---|---|---|
| PBS dissolved | 1.149 | 100% |
| $H_2O$ dissolved | 0.706 | 61% |
| PBS dissolved/$H_2O$ dialyzed | 0.885 | 77% |

Resuspending the pellets in PBS followed by dialysis against water recovered more antibody than directly resuspending the pellets in water (77% versus 61%). Equivalent volumes of the IgY preparation in PBS or water were compared by PAGE, and these results were in accordance with the absorbance values (data not shown).

c) Activity of IgY Prepared with Different Solvents

An ELISA was performed to compare the binding activity of the IgY extracted by each procedure described above. *C. durissus terrificus* (C.d.t.) venom at 2.5 μg/ml in PBS was used to coat each well of a 96-well microtiter plate. The remaining protein binding sites were blocked with PBS containing 5 mg/ml BSA. Primary antibody dilutions (in PBS containing 1 mg/ml BSA) were added in duplicate. After 2 hours of incubation at room temperature, the unbound primary antibodies were removed by washing the wells with PBS, BBS-Tween, and PBS. The species specific secondary antibody (goat anti-chicken immunoglobulin alkaline-phosphatase conjugate (Sigma) was diluted 1:750 in PBS containing 1 mg/ml BSA and added to each well of the microtiter plate. After 2 hours of incubation at room temperature, the unbound secondary antibody was removed by washing the plate as before, and freshly prepared alkaline phosphatase substrate (Sigma) at 1 mg/ml in 50 mM $Na_2CO_3$, 10 mM $MgCl_2$, pH 9.5 was added to each well. The color development was measured on a Dynatech MR 700 microplate reader using a 412 nm filter. The results are shown in Table 8.

The binding assay results parallel the recovery values in Table 7, with PBS-dissolved IgY showing slightly more activity than the PBS-dissolved/$H_2O$ dialyzed antibody. The water-dissolved antibody had considerably less binding activity than the other preparations.

EXAMPLE 5

Survival of Antibody Activity after Passage Through the Gastrointestinal Tract In order to determine the feasibility of oral administration of antibody, it was of interest to determine whether orally administered IgY survived passage through the gastrointestinal tract. The example involved: (a) oral administration of specific immune antibody mixed with a nutritional formula; and (b) assay of antibody activity extracted from feces.

TABLE 8

Antigen-Binding Activity Of IgY Prepared With Different Solvents

| Dilution | Preimmune | PBS Dissolved | $H_2O$ Dissolved | PBS/$H_2O$ |
|---|---|---|---|---|
| 1:500 | 0.005 | 1.748 | 1.577 | 1.742 |
| 1:2,500 | 0.004 | 0.644 | 0.349 | 0.606 |
| 1:12,500 | 0.001 | 0.144 | 0.054 | 0.090 |
| 1:62,500 | 0.001 | 0.025 | 0.007 | 0.016 |
| 1:312,500 | 0.010 | 0.000 | 0.000 | 0.002 |

a) Oral Administration of Antibody

The IgY preparations used in this example are the same PBS-dissolved/$H_2O$ dialyzed antivenom materials obtained in Example 4 above, mixed with an equal volume of Enfamil®. Two mice were used in this experiment, each receiving a different diet as follows:

1) water and food as usual;
2) immune IgY preparation dialyzed against water and mixed 1:1 with Enfamil®. (The mice were given the corresponding mixture as their only source of food and water).

b) Antibody Activity after Ingestion

After both mice had ingested their respective fluids, each tube was refilled with approximately 10 ml of the appropriate fluid first thing in the morning. By mid-morning there was about 4 to 5 ml of liquid left in each tube. At this point stool samples were collected from each mouse, weighed, and dissolved in approximately 500 μl PBS per 100 mg stool sample. One hundred and sixty mg of control stools (no antibody) and 99 mg of experimental stools (specific antibody) in 1.5 ml microfuge tubes were dissolved in 800 and 500 μl PBS, respectively. The samples were heated at 37° C. for 10 minutes and vortexed vigorously. The experimental stools were also broken up with a narrow spatula. Each sample was centrifuged for 5 minutes in a microfuge and the supernatants, presumably containing the antibody extracts, were collected. The pellets were saved at 2–8° C. in case future extracts were needed. Because the supernatants were tinted, they were diluted five-fold in PBS containing 1 mg/ml BSA for the initial dilution in the enzyme immunoassay (ELISA). The primary extracts were then diluted five-fold serially from this initial dilution. The volume of primary extract added to each well was 190 μl. The ELISA was performed exactly as described in Example 4.

TABLE 9

Specific Antibody Activity After Passage Through The Gastrointestinal Tract

| Dilution | Preimmune IgY | Control Fecal Extract | EXP. Fecal Extract |
|---|---|---|---|
| 1:5 | <0 | 0.000 | 0.032 |
| 1:25 | 0.016 | <0 | 0.016 |
| 1:125 | <0 | <0 | 0.009 |
| 1:625 | <0 | 0.003 | 0.001 |
| 1:3125 | <0 | <0 | 0.000 |

There was some active antibody in the fecal extract from the mouse given the specific antibody in Enfamil® formula, but it was present at a very low level. Since the samples were assayed at an initial 1:5 dilution, the binding observed could have been higher with less dilute samples. Consequently, the mice were allowed to continue ingesting either regular food and water or the specific IgY in Enfamil® formula, as appropriate, so the assay could be repeated. Another ELISA plate was coated overnight with 5 μg/ml of C.d.t. venom in PBS.

The following morning the ELISA plate was blocked with 5 mg/ml BSA, and the fecal samples were extracted as before, except that instead of heating the extracts at 37° C., the samples were kept on ice to limit proteolysis. The samples were assayed undiluted initially, and in 5× serial dilutions thereafter. Otherwise the assay was carried out as before.

TABLE 10

Specific Antibody Survives Passage Through The Gastrointestinal Tract

| Dilution | Preimmune IgY | Control Extract | Exp. Extract |
|---|---|---|---|
| undiluted | 0.003 | <0 | 0.379 |
| 1:5 | <0 | <0 | 0.071 |
| 1:25 | 0.000 | <0 | 0.027 |
| 1:125 | 0.003 | <0 | 0.017 |
| 1:625 | 0.000 | <0 | 0.008 |
| 1:3125 | 0.002 | <0 | 0.002 |

The experiment confirmed the previous results, with the antibody activity markedly higher. The control fecal extract showed no anti-C.d.t. activity, even undiluted, while the fecal extract from the anti-C.d.t. IgY/Enfamil®-fed mouse showed considerable anti-C.d.t. activity. This experiment (and the previous experiment) clearly demonstrate that active IgY antibody survives passage through the mouse digestive tract, a finding with favorable implications for the success of IgY antibodies administered orally as a therapeutic or prophylactic.

EXAMPLE 6

In Vivo Neutralization of Type *C. botulinum* Type A Neurotoxin by Avian Antitoxin Antibody This example demonstrated the ability of PEG-purified antitoxin, collected as described in Example 3, to neutralize the lethal effect of *C. botulinum* neurotoxin type A in mice. To determine the oral lethal dose ($LD_{100}$) of toxin A, groups of BALB/c mice were given different doses of toxin per unit body weight (average body weight of 24 grams). For oral administration, toxin A complex, which contains the neurotoxin associated with other non-toxin proteins was used. This complex is markedly more toxic than purified neurotoxin when given by the oral route. [I. Ohishi et al., Infect. Immun., 16:106 (1977).] *C. botulinum* toxin type A complex, obtained from Eric Johnson (University Of Wisconsin, Madison) was 250 μg/ml in 50 mM sodium citrate, pH 5.5, specific toxicity $3\times10^7$ mouse $LD_{50}$/mg with parenteral administration. Approximately 40–50 ng/gm body weight was usually fatal within 48 hours in mice maintained on conventional food and water. When mice were given a diet ad libitum of only Enfamil® the concentration needed to produce lethality was approximately 2.5 times higher (125 ng/gm body weight). Botulinal toxin concentrations of approximately 200 ng/gm body weight were fatal in mice fed Enfamil® containing preimmune IgY (resuspended in Enfamil® at the original yolk volume).

The oral $LD_{100}$ of *C. botulinum* toxin was also determined in mice that received known amounts of a mixture of preimmune IgY-Ensure® delivered orally through feeding needles. Using a 22 gauge feeding needle, mice were given 250 μl each of a preimmune IgY-Ensure® mixture (preimmune IgY dissolved in ¼ original yolk volume) 1 hour before and ½ hour and 5 hours after administering botulinal toxin. Toxin concentrations given orally ranged from approximately 12 to 312 ng/gm body weight (0.3 to 7.5 μg per mouse). Botulinal toxin complex concentration of approximately 40 ng/gm body weight (1 μg per mouse) was lethal in all mice in less than 36 hours.

Two groups of BALB/c mice, 10 per group, were each given orally a single dose of 1 μg each of botulinal toxin complex in 100 μl of 50 mM sodium citrate pH 5.5. The mice received 250 μl treatments of a mixture of either preimmune or immune IgY in Ensure® (¼ original yolk volume) 1 hour before and ½ hour, 4 hours, and 8 hours after botulinal toxin administration. The mice received three treatments per day for two more days. The mice were observed for 96 hours. The survival and mortality are shown in Table 11.

TABLE 11

Neutralization Of Botulinal Toxin A In Vivo

| Toxin Dose ng/gm | Antibody Type | Number Of Mice Alive | Number Of Mice Dead |
|---|---|---|---|
| 41.6 | non-immune | 0 | 10 |
| 41.6 | anti-botulinal toxin | 10 | 0 |

All mice treated with the preimmune IgY-Ensure® mixture died within 46 hours post-toxin administration. The average time of death in the mice was 32 hours post toxin administration. Treatments of preimmune IgY-Ensure® mixture did not continue beyond 24 hours due to extensive paralysis of the mouth in mice of this group. In contrast, all ten mice treated with the immune anti-botulinal toxin IgY-Ensure® mixture survived past 96 hours. Only 4 mice in this group exhibited symptoms of botulism toxicity (two mice about 2 days after and two mice 4 days after toxin administration). These mice eventually died 5 and 6 days later. Six of the mice in this immune group displayed no adverse effects to the toxin and remained alive and healthy long term. Thus, the avian anti-botulinal toxin antibody demonstrated very good protection from the lethal effects of the toxin in the experimental mice.

EXAMPLE 7

Production of an Avian Antitoxin Against *Clostridium difficile* Toxin A

Toxin A is a potent cytotoxin secreted by pathogenic strains of *C. difficile*, that plays a direct role in damaging gastrointestinal tissues. In more severe cases of *C. difficile* intoxication, pseudomembranous colitis can develop which may be fatal. This would be prevented by neutralizing the effects of this toxin in the gastrointestinal tract. As a first step, antibodies were produced against a portion of the toxin. The example involved: (a) conjugation of a synthetic peptide of toxin A to bovine serum albumin; (b) immunization of hens with the peptide-BSA conjugate; and (c) detection of antitoxin peptide antibodies by ELISA.

a) Conjugation of a Synthetic Peptide of Toxin A to Bovine Serum Albumin

The synthetic peptide CQTIDGKKYYFN-$NH_2$ (SEQ ID NO:82) was prepared commercially (Multiple Peptide Systems, San Diego, Calif.) and validated to be >80% pure by high-pressure liquid chromatography. The eleven amino acids following the cysteine residue represent a consensus sequence of a repeated amino acid sequence found in Toxin A. [Wren et al., Infect. Immun., 59:3151–3155 (1991).] The cysteine was added to facilitate conjugation to carrier protein.

In order to prepare the carrier for conjugation, BSA (Sigma) was dissolved in 0.01 M $NaPO_4$, pH 7.0 to a final concentration of 20 mg/ml and n-maleimidobenzoyl-N-hydroxysuccinimide ester (MBS; Pierce) was dissolved in N,N-dimethyl formamide to a concentration of 5 mg/ml. MBS solution, 0.51 ml, was added to 3.25 ml of the BSA solution and incubated for 30 minutes at room temperature with stirring every 5 minutes. The MBS-activated BSA was then purified by chromatography on a Bio-Gel P-10 column (Bio-Rad; 40 ml bed volume) equilibrated with 50 mM $NaPO_4$, pH 7.0 buffer. Peak fractions were pooled (6.0 ml).

Lyophilized toxin A peptide (20 mg) was added to the activated BSA mixture, stirred until the peptide dissolved and incubated 3 hours at room temperature. Within 20 minutes, the reaction mixture became cloudy and precipitates formed. After 3 hours, the reaction mixture was centrifuged at 10,000×g for 10 min and the supernatant analyzed for protein content. No significant protein could be detected at 280 nm. The conjugate precipitate was washed three times with PBS and stored at 4° C. A second conjugation was performed with 15 mg of activated BSA and 5 mg of peptide and the conjugates pooled and suspended at a peptide concentration of 10 mg/ml in 10 mM $NaPO_4$, pH 7.2.

b) Immunization of Hens with Peptide Conjugate

Two hens were each initially immunized on day zero by injection into two subcutaneous and two intramuscular sites with 1 mg of peptide conjugate that was emulsified in CFA (GIBCO). The hens were boosted on day 14 and day 21 with 1 mg of peptide conjugate emulsified in IFA (GIBCO).

c) Detection of Antitoxin Peptide Antibodies by ELISA

IgY was purified from two eggs obtained before immunization (pre-immune) and two eggs obtained 31 and 32 days after the initial immunization using PEG fractionation as described in Example 1.

Wells of a 96-well microtiter plate (Falcon Pro-Bind Assay Plate) were coated overnight at 4° C. with 100 μg/ml solution of the toxin A synthetic peptide in PBS, pH 7.2 prepared by dissolving 1 mg of the peptide in 1.0 ml of $H_2O$ and dilution of PBS. The pre-immune and immune IgY preparations were diluted in a five-fold series in a buffer containing 1% PEG 8000 and 0.1% Tween-20 (v/v) in PBS, pH 7.2. The wells were blocked for 2 hours at room temperature with 150 μl of a solution containing 5% (v/v) Carnation® nonfat dry milk and 1% PEG 8000 in PBS, pH 7.2. After incubation for 2 hours at room temperature, the wells were washed, secondary rabbit anti-chicken IgG-alkaline phosphatase (1:750) added, the wells washed again and the color development obtained as described in Example 1. The results are shown in Table 12.

TABLE 12

Reactivity Of IgY With Toxin Peptide

| | Absorbance At 410 nm | |
|---|---|---|
| Dilution Of PEG Prep | Preimmune | Immune Anti-Peptide |
| 1:100 | 0.013 | 0.253 |
| 1:500 | 0.004 | 0.039 |
| 1:2500 | 0.004 | 0.005 |

Clearly, the immune antibodies contain titers against this repeated epitope of toxin A.

EXAMPLE 8

Production of Avian Antitoxins Against *Clostridium difficile* Native Toxins A And B To determine whether avian antibodies are effective for the neutralization of *C. difficile* toxins, hens were immunized using native *C. difficile* toxins A and B. The resulting egg yolk antibodies were then extracted and assessed for their ability to neutralize toxins A and B in vitro. The Example involved (a) preparation of the toxin immunogens, (b) immunization, (c) purification of the antitoxins, and (d) assay of toxin neutralization activity.

a) Preparation of the Toxin Immunogens

Both *C. difficile* native toxins A and B, and *C. difficile* toxoids, prepared by the treatment of the native toxins with formaldehyde, were employed as immunogens. *C. difficile* toxoids A and B were prepared by a procedure which was modified from published methods (Ehrich et al., Infect. Immun. 28:104.1 (1980). Separate solutions (in PBS) of native *C. difficile* toxin A and toxin B (Tech Lab) were each adjusted to a concentration of 0.20 mg/ml, and formaldehyde was added to a final concentration of 0.4%. The toxin/formaldehyde solutions were then incubated at 37° C. for 40 hrs. Free formaldehyde was then removed from the resulting toxoid solutions by dialysis against PBS at 4° C. In previously published reports, this dialysis step was not performed. Therefore, free formaldehyde must have been present in their toxoid preparations. The toxoid solutions were concentrated, using a Centriprep concentrator unit (Amicon), to a final toxoid concentration of 4.0 mg/ml. The two resulting preparations were designated as toxoid A and toxoid B.

*C. difficile* native toxins were prepared by concentrating stock solutions of toxin A and toxin B (Tech Lab, Inc), using Centriprep concentrator units (Amicon), to a final concentration of 4.0 mg/ml.

b) Immunization

The first two immunizations were performed using the toxoid A and toxoid B immunogens described above. A total of 3 different immunization combinations were employed. For the first immunization group, 0.2 ml of toxoid A was emulsified in an equal volume of Titer Max adjuvant (CytRx). Titer Max was used in order to conserve the amount of immunogen used, and to simplify the immunization procedure. This immunization group was designated "CTA." For the second immunization group, 0.1 ml of toxoid B was emulsified in an equal volume of Titer Max adjuvant. This group was designated "CTB." For the third immunization group, 0.2 ml of toxoid A was first mixed with 0.2 ml of toxoid B, and the resulting mixture was emulsified in 0.4 ml of Titer Max adjuvant. This group was designated "CTAB." In this way, three separate immunogen emulsions were prepared, with each emulsion containing a final concentration of 2.0 mg/ml of toxoid A (CTA) or toxoid B (CTB) or a mixture of 2.0 mg/ml toxoid A and 2.0 mg/ml toxoid B (CTAB).

On day 0, White Leghorn hens, obtained from a local breeder, were immunized as follows: Group CTA. Four hens were immunized, with each hen receiving 200 μg of toxoid A, via two intramuscular (I.M.) injections of 50 μl of CTA emulsion in the breast area Group CTB. One hen was immunized with 200 μg of toxoid B, via two I.M. injections of 50 μl of CTB emulsion in the breast area. Group CTAB. Four hens were immunized, with each hen receiving a mixture containing 200 μg of toxoid A and 200 μg of toxoid B, via two I.M. injections of 100 μl of CTAB emulsion in the breast area. The second immunization was performed 5 weeks later, on day 35, exactly as described for the first immunization above.

In order to determine whether hens previously immunized with *C. difficile* toxoids could tolerate subsequent booster immunizations using native toxins, a single hen from group CTAB was immunized for a third time, this time using a mixture of the native toxin A and native toxin B described in section (a) above (these toxins were not formaldehyde-treated, and were used in their active form). This was done in order to increase the amount (titer) and affinity of specific antitoxin antibody produced by the hen over that achieved by immunizing with toxoids only. On day 62, 0.1 ml of a toxin mixture was prepared which contained 200 μg of native toxin A and 200 μg of native toxin B. This toxin mixture was then emulsified in 0.1 ml of Titer Max adjuvant A single CTAB hen was then immunized with the resulting immunogen emulsion, via two I.M. injections of 100 μl each, into the breast area. This hen was marked with a wing band, and observed for adverse effects for a period of approximately 1 week, after which time the hen appeared to be in good health.

Because the CTAB hen described above tolerated the booster immunization with native toxins A and B with no adverse effects, it was decided to boost the remaining hens with native toxin as well. On day 70, booster immunizations were performed as follows: Group CTA. A 0.2 ml volume of the 4 mg/ml native toxin A solution was emulsified in an equal volume of Titer Max adjuvant. Each of the 4 hens was then immunized with 200 μg of native toxin A, as described for the toxoid A immunizations above. Group CTB. A 50 μl volume of the 4 mg/ml native toxin B solution was emulsified in an equal volume of Titer Max adjuvant. The hen was then immunized with 200 μg of native toxin B, as described for the toxoid B immunizations above. Group CTAB. A 0.15 ml volume of the 4 mg/ml native toxin A solution was first mixed with a 0.15 ml volume the 4 mg/ml native toxin B solution. The resulting toxin mixture was then emulsified in 0.3 ml of Titer Max adjuvant. The 3 remaining hens (the hen with the wing band was not immunized this time) were then immunized with 200 μg of native toxin A and 200 μg of native toxin B as described for the toxoid A+toxoid B immunizations (CTAB) above. On day 85, all hens received a second booster immunization using native toxins, done exactly as described for the first boost with native toxins above.

All hens tolerated both booster immunizations with native toxins with no adverse effects. As previous literature references describe the use of formaldehyde-treated toxoids, this is apparently the first time that any immunizations have been performed using native *C. difficile* toxins.

c) Purification of Antitoxins

Eggs were collected from the hen in group CTB 10–12 days following the second immunization with toxoid (day 35 immunization described in section (b) above), and from the hens in groups CTA and CTAB 20–21 days following the second immunization with toxoid. To be used as a pre-immune (negative) control, eggs were also collected from unimmunized hens from the same flock. Egg yolk immunoglobulin (IgY) was extracted from the 4 groups of eggs as described in Example 1 (c), and the final IgY pellets were solubilized in the original yolk volume of PBS without thimerosal. Importantly, thimerosal was excluded because it would have been toxic to the CHO cells used in the toxin neutralization assays described in section (d) below.

d) Assay of Toxin Neutralization Activity

The toxin neutralization activity of the IgY solutions prepared in section (c) above was determined using an assay system that was modified from published methods. [Ehrich et al., Infect. Immun. 28:1041–1043 (1992); and McGee et al. Microb. Path. 12:333–341 (1992).] As additional controls, affinity-purified goat anti-*C. difficile* toxin A (Tech Lab) and affinity-purified goat anti-*C. difficile* toxin B (Tech Lab) were also assayed for toxin neutralization activity.

The IgY solutions and goat antibodies were serially diluted using F 12 medium (GIBCO) which was supplemented with 2% FCS (GIBCO)(this solution will be referred to as "medium" for the remainder of this Example). The resulting antibody solutions were then mixed with a standardized concentration of either native *C. difficile* toxin A (Tech Lab), or native *C. difficile* toxin B (Tech Lab), at the concentrations indicated below. Following incubation at 37° C. for 60 min., 100 μl volumes of the toxin+antibody mixtures were added to the wells of 96-well microtiter plates (Falcon Microtest III) which contained $2.5\times10^4$ Chinese Hamster Ovary (CHO) cells per well (the CHO cells were plated on the previous day to allow them to adhere to the plate wells). The final concentration of toxin, or dilution of antibody indicated below refers to the final test concentration of each reagent present in the respective microtiter plate wells. Toxin reference wells were prepared which contained CHO cells and toxin A or toxin B at the same concentration used for the toxin plus antibody mixtures (these wells contained no antibody). Separate control wells were also prepared which contained CHO cells and medium only. The assay plates were then incubated for 18–24 hrs. in a 37° C., humidified, 5% $CO_2$ incubator. On the following day, the remaining adherent (viable) cells in the plate wells were stained using 0.2% crystal violet (Mallinckrodt) dissolved in 2% ethanol, for 10 min. Excess stain was then removed by rinsing with water, and the stained cells were solubilized by adding 100 μl of 1% SDS (dissolved in water) to each well. The absorbance of each well was then measured at 570 nm, and the percent cytotoxicity of each test sample or mixture was calculated using the following formula:

$$\%\ \text{CHO Cell Cytotoxicity} = \left[1 - \left(\frac{\text{Abs. Sample}}{\text{Abs. Control}}\right)\right] \times 100$$

Figure 3:
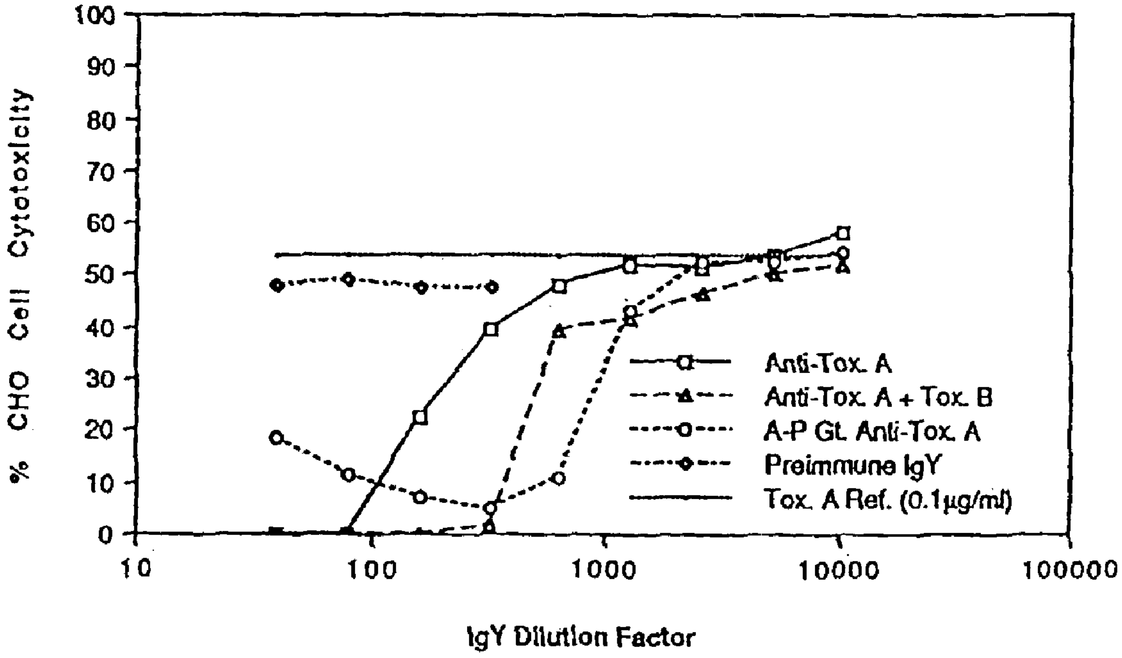
FIG. 3 shows the results of *C. difficile* toxin A neutralization assays.

Unlike previous reports which quantitate results visually by counting cell rounding by microscopy, this Example utilized spectrophotometric methods to quantitate the *C. difficile* toxin bioassay. In order to determine the toxin A neutralizing activity of the CTA, CTAB, and pre-immune IgY preparations, as well as the affinity-purified goat antitoxin A control, dilutions of these antibodies were reacted against a 0.1 μg/ml concentration of native toxin A (this is the approx. 50% cytotoxic dose of toxin A in this assay system). The results are shown in FIG. 3.

Complete neutralization of toxin A occurred with the CTA IgY (antitoxin A, above) at dilutions of 1:80 and lower, while significant neutralization occurred out to the 1:320 dilution. The CTAB IgY (antitoxin A+ toxin B, above) demonstrated complete neutralization at the 1:320–1:160 and lower dilutions, and significant neutralization occurred out to the 1:1280 dilution. The commercially available affinity-purified goat antitoxin A did not completely neutralize toxin A at any of the dilutions tested, but demonstrated significant neutralization out to a dilution of 1:1,280. The preimmune IgY did not show any toxin A neutralizing activity at any of the concentrations tested. These results demonstrate that IgY purified from eggs laid by hens immunized with toxin A alone, or simultaneously with toxin A and toxin B, is an effective toxin A antitoxin.

Figure 4:
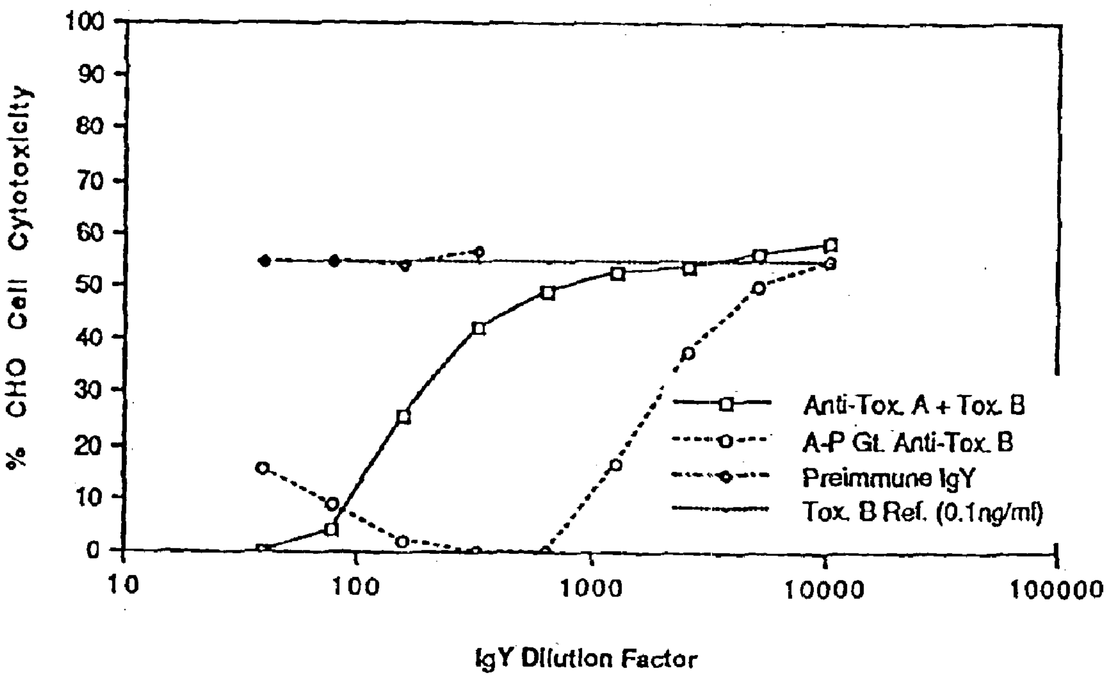
FIG. 4 shows the results of *C. difficile* toxin B neutralization assays.

The toxin B neutralizing activity of the CTAB and preimmune IgY preparations, and also the affinity-purified goat antitoxin B control was determined by reacting dilutions of these antibodies against a concentration of native toxin B of 0.1 ng/ml (approximately the 50% cytotoxic dose of toxin B in the assay system). The results are shown in FIG. 4.

Complete neutralization of toxin B occurred with the CTAB IgY (antitoxin A+ toxin B, above) at the 1:40 and lower dilutions, and significant neutralization occurred out to the 1:320 dilution. The affinity-purified goat antitoxin B demonstrated complete neutralization at dilutions of 1:640 and lower, and significant neutralization occurred out to a dilution of 1:2,560. The preimmune IgY did not show any toxin B neutralizing activity at any of the concentrations tested. These results demonstrate that IgY purified from eggs laid by hens immunized simultaneously with toxin A and toxin B is an effective toxin B antitoxin.

Figure 5:
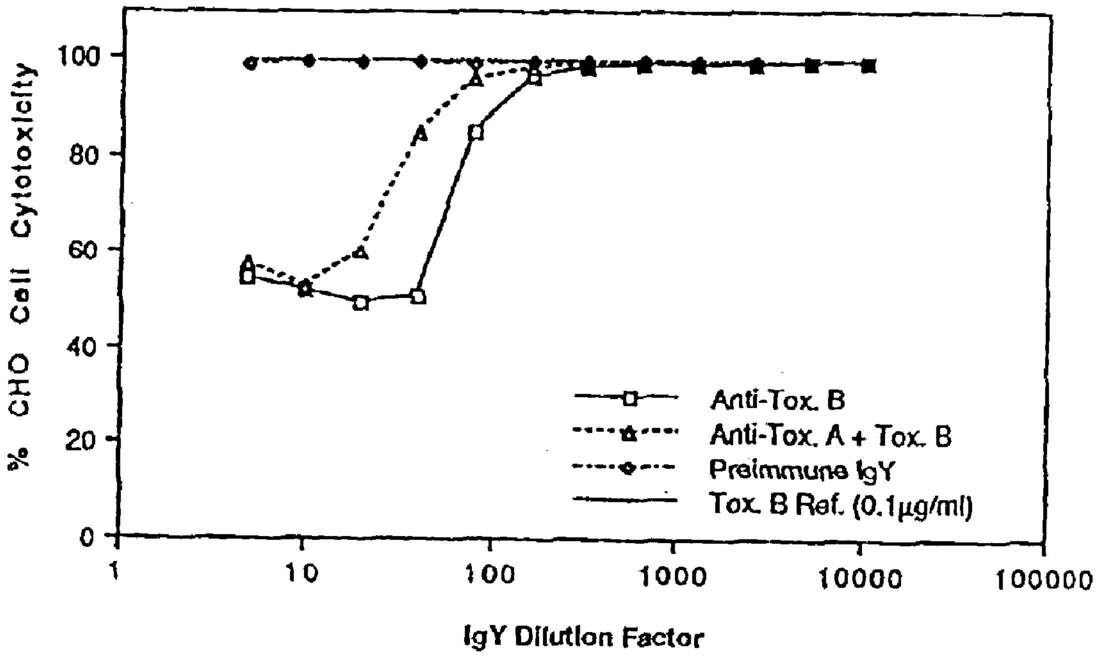
FIG. 5 shows the results of *C. difficile* toxin B neutralization assays.

In a separate study, the toxin B neutralizing activity of CTB, CTAB, and pre-immune IgY preparations was determined by reacting dilutions of these antibodies against a native toxin B concentration of 0.1 g/ml (approximately 100% cytotoxic dose of toxin B in this assay system). The results are shown in FIG. 5.

Significant neutralization of toxin B occurred with the CTB IgY (antitoxin B, above) at dilutions of 1:80 and lower, while the CTAB IgY (antitoxin A+ toxin B, above) was found to have significant neutralizing activity at dilutions of 1:40 and lower. The preimmune IgY did not show any toxin B neutralizing activity at any of the concentrations tested. These results demonstrate that IgY purified from eggs laid by hens immunized with toxin B alone, or simultaneously with toxin A and toxin B, is an effective toxin B antitoxin.

EXAMPLE 9

In vivo Protection of Golden Syrian Hamsters from *C. difficile* Disease by Avian Antitoxins Against *C. difficile* Toxins A and B The most extensively used animal model to study *C. difficile* disease is the hamster. [Lyerly et al., Infect. Immun. 47:349–352 (1992).] Several other animal models for antibiotic-induced diarrhea exist, but none mimic the human form of the disease as closely as the hamster model. [R. Fekety, "*Animal Models of Antibiotic-Induced Colitis*," in 0. Zak and M. Sande (eds.), *Experimental Models in Antimicrobial Chemotherapy*, Vol. 2, pp.61–72, (1986).] In this model, the animals are first predisposed to the disease by the oral administration of an antibiotic, such as clindamycin, which alters the population of normally-occurring gastrointestinal flora (Fekety, at 61–72). Following the oral challenge of these animals with viable *C. difficile* organisms, the hamsters develop cecitis, and hemorrhage, ulceration, and inflammation are evident in the intestinal mucosa. [Lyerly et al., Infect. Immun. 47:349–352 (1985).] The animals become lethargic, develop severe diarrhea, and a high percentage of them die from the disease. [Lyerly et al., Infect. Immun. 47:349–352 (1985).] This model is therefore ideally suited for the evaluation of therapeutic agents designed for the treatment or prophylaxis of *C. difficile* disease.

The ability of the avian *C. difficile* antitoxins, described in Example 1 above, to protect hamsters from *C. difficile* disease was evaluated using the Golden Syrian hamster model of *C. difficile* infection. The Example involved (a) preparation of the avian *C. difficile antitoxins*, (b) in vivo protection of hamsters from *C. difficile* disease by treatment with avian antitoxins, and (c) long-term survival of treated hamsters.

a) Preparation of the Avian *C. difficile* Antitoxins

Eggs were collected from hens in groups CTA and CTAB described in Example 1 (b) above. To be used as a preimmune (negative) control, eggs were also purchased from a local supermarket. Egg yolk immunoglobulin (IgY) was extracted from the 3 groups of eggs as described in Example 1 (c), and the final IgY pellets were solubilized in one fourth the original yolk volume of Ensures nutritional formula.

b) In vivo Protection of Hamsters Against *C. difficile* Disease by Treatment with Avian Antitoxins The avian *C. difficile* antitoxins prepared in section (a) above were evaluated for their ability to protect hamsters from *C. difficile* disease using an animal model system which was modified from published procedures. [Fekety, at 61–72; Borriello et al., J. Med. Microbiol., 24:53–64 (1987); Kim et al., Infect. Immun., 55:2984–2992 (1987); Borriello et al., J. Med. Microbiol., 25:191–196 (1988); Delmee and Avesani, J. Med. Microbiol., 33:85–90 (1990); and Lyerly et al., Infect. Immun., 59:2215–2218 (1991).] For the study, three separate experimental groups were used, with each group consisting of 7 female Golden Syrian hamsters (Charles River), approximately 10 weeks old and weighing approximately 100 gms. each. The three groups were designated "CTA," "CTAB" and "Pre-immune." These designations corresponded to the antitoxin preparations with which the animals in each group were treated. Each animal was housed in an individual cage, and was offered food and water ad libitum through the entire length of the study. On day 1, each animal was orally administered 1.0 ml of one of the three antitoxin preparations (prepared in section (a) above) at the following timepoints: 0 hrs., 4 hrs., and 8 hrs. On day 2, the day 1 treatment was repeated. On day 3, at the 0 hr. timepoint, each animal was again administered antitoxin, as described above. At 1 hr., each animal was orally administered 3.0 mg of clindamycin-HCl (Sigma) in 1 ml of water. This treatment predisposed the animals to infection with *C. difficile*. As a control for possible endogenous *C. difficile* colonization, an additional animal from the same shipment (untreated) was also administered 3.0 mg of clindamycin-HCl in the same manner. This clindamycin control animal was left untreated (and uninfected) for the remainder of the study. At the 4 hr. and 8 hr. timepoints, the animals were administered antitoxin as described above. On day 4, at the 0 hr. timepoint, each animal was again administered antitoxin as described above. At 1 hr., each animal was orally challenged with 1 ml of *C. difficile* inoculum, which contained approx. 100 *C. difficile* strain 43596 organisms in sterile saline. *C. difficile* strain 43596, which is a serogroup C strain, was chosen because it is representative of one of the most frequently-occurring serogroups isolated from patients with antibiotic-associated pseudomembranous colitis. [Delmee et al., J. Clin. Microbiol., 28:2210–2214 (1985).] In addition, this strain has been previously demonstrated to be virulent in the hamster model of infection. [Delmee and Avesani, J. Med. Microbiol., 33:85–90 (1990).] At the 4 hr. and 8 hr. timepoints, the animals were administered antitoxin as described above. On days 5 through 13, the animals were administered antitoxin 3× per day as described for day 1 above, and observed for the onset of diarrhea and death. On the morning of day 14, the final results of the study were tabulated. These results are shown in Table 13.

Representative animals from those that died in the Pre-Immune and CTA groups were necropsied. Viable *C. difficile* organisms were cultured from the ceca of these animals, and the gross pathology of the gastrointestinal tracts of these animals was consistent with that expected for *C. difficile* disease (inflamed, distended, hemorrhagic cecum, filled with watery diarrhea-like material). In addition, the clindamycin control animal remained healthy throughout the entire study period, therefore indicating that the hamsters used in the study had not previously been colonized with endogenous *C. difficile* organisms prior to the start of the study. Following the final antitoxin treatment on day 13, a single surviving animal from the CTA group, and also from the CTAB group, was sacrificed and necropsied. No pathology was noted in either animal.

TABLE 13

| | Treatment Results | |
|---|---|---|
| Treatment Group | No. Animals Surviving | No. Animals Dead |
| Pre-Immune | 1 | 6 |
| CTA (Antitoxin A only) | 5 | 2 |
| CTAB (Antitoxin A + Antitoxin B) | 7 | 0 |

Treatment of hamsters with orally-administered toxin A and toxin B antitoxin (group CTAB) successfully protected 7 out of 7 (100%) of the animals from *C. difficile* disease. Treatment of hamsters with orally-administered toxin A antitoxin (group CTA) protected 5 out of 7 (71%) of these animals from *C. difficile* disease. Treatment using pre-immune IgY was not protective against *C. difficile* disease, as only 1 out of 7 (14%) of these animals survived. These results demonstrate that the avian toxin A antitoxin and the avian toxin A+toxin B antitoxin effectively protected the hamsters from *C. difficile* disease. These results also suggest that although the neutralization of toxin A alone confers some degree of protection against *C. difficile* disease, in order to achieve maximal protection, simultaneous antitoxin A and antitoxin B activity is necessary.

c) Long-Term Survival of Treated Hamsters

It has been previously reported in the literature that hamsters treated with orally-administered bovine antitoxin IgG concentrate are protected from *C. difficile* disease as long as the treatment is continued, but when the treatment is stopped, the animals develop diarrhea and subsequently die within 72 hrs. [Lyerly et al., Infect. Immun., 59(6):2215–2218 (1991).]

In order to determine whether treatment of *C. difficile* disease using avian antitoxins promotes long-term survival following the discontinuation of treatment, the 4 surviving animals in group CTA, and the 6 surviving animals in group CTAB were observed for a period of 11 days (264 hrs.) following the discontinuation of antitoxin treatment described in section (b) above. All hamsters remained healthy through the entire post-treatment period. This result demonstrates that not only does treatment with avian antitoxin protect against the onset of *C. difficile* disease (i.e., it is effective as a prophylactic), it also promotes long-term survival beyond the treatment period, and thus provides a lasting cure.

EXAMPLE 10

In vivo Treatment of Established *C. difficile* Infection in Golden Syrian Hamsters with Avian Antitoxins Against *C. difficile* Toxins A and B The ability of the avian *C. difficile* antitoxins, described in Example 8 above, to treat an established *C. difficile* infection was evaluated using the Golden Syrian hamster model. The Example involved (a) preparation of the avian *C. difficile* antitoxins, (b) in vivo treatment of hamsters with established *C. difficile* infection, and (c) histologic evaluation of cecal tissue.

a) Preparation of the Avian *C. difficile* Antitoxins Eggs were collected from hens in group CTAB described in Example 8 (b) above, which were immunized with *C. difficile* toxoids and native toxins A and B. Eggs purchased from a local supermarket were used as a pre-immune (negative) control. Egg yolk immunoglobulin (IgY) was extracted from the 2 groups of eggs as described in Example 1 (c), and the final IgY pellets were solubilized in one-fourth the original yolk volume of Ensure® nutritional formula.

b) In vivo Treatment of Hamsters with Established *C .difficile* Infection

The avian *C. difficile* antitoxins prepared in section (a) above were evaluated for the ability to treat established *C. difficile* infection in hamsters using an animal model system which was modified from the procedure which was described for the hamster protection study in Example 8(b) above.

For the study, four separate experimental groups were used, with each group consisting of 7 female Golden Syrian hamsters (Charles River), approx. 10 weeks old, weighing approximately 100 gms. each. Each animal was housed separately, and was offered food and water ad libitum through the entire length of the study.

On day 1 of the study, the animals in all four groups were each predisposed to *C. difficile* infection by the oral administration of 3.0 mg of clindamycin-HCl (Sigma) in 1 ml of water.

On day 2, each animal in all four groups was orally challenged with 1 ml of *C. difficile* inoculum, which contained approximately 100 *C. difficile* strain 43596 organisms in sterile saline. *C. difficile* strain 43596 was chosen because it is representative of one of the most frequently-occurring serogroups isolated from patients with antibiotic-associated pseudomembranous colitis. [Delmee et al., J. Clin. Microbiol., 28:2210–2214 (1990).] In addition, as this was the same *C. difficile* strain used in all of the previous Examples above, it was again used in order to provide experimental continuity.

On day 3 of the study (24 hrs. post-infection), treatment was started for two of the four groups of animals. Each animal of one group was orally administered 1.0 ml of the CTAB IgY preparation (prepared in section (a) above) at the following timepoints: 0 hrs., 4 hrs., and 8 hrs. The animals in this group were designated "CTAB-24." The animals in the second group were each orally administered 1.0 ml of the pre-immune IgY preparation (also prepared in section (a) above) at the same timepoints as for the CTAB group. These animals were designated "Pre-24." Nothing was done to the remaining two groups of animals on day 3.

On day 4, 48 hrs. post-infection, the treatment described for day 3 above was repeated for the CTAB-24 and Pre-24 groups, and was initiated for the remaining two groups at the same timepoints. The final two groups of animals were designated "CTAB-48" and "Pre-48" respectively.

On days 5 through 9, the animals in all four groups were administered antitoxin or pre-immune IgY, 3× per day, as described for day 4 above. The four experimental groups are summarized in Table 14.

TABLE 14

Experimental Treatment Groups

| Group Designation | Experimental Treatment |
|---|---|
| CTAB-24 | Infected, treatment w/antitoxin IgY started @ 24 hrs. post-infection. |
| Pre-24 | Infected, treatment w/pre-immune IgY started @ 24 hrs. post-infection. |
| CTAB-48 | Infected, treatment w/antitoxin IgY started @ 48 hrs. post-infection. |
| Pre-48 | Infected, treatment w/pre-immune IgY started @ 48 hrs. post-infection. |

All animals were observed for the onset of diarrhea and death through the conclusion of the study on the morning of day 10. The results of this study are displayed in Table 15.

TABLE 15

Experimental Outcome-Day 10

| Treatment Group | No. Animals Surviving | No. Animals Dead |
|---|---|---|
| CTAB-24 | 6 | 1 |
| Pre-24 | 0 | 7 |
| CTAB-48 | 4 | 3 |
| Pre-48 | 2 | 5 |

Eighty-six percent of the animals which began receiving treatment with antitoxin IgY at 24 hrs. post-infection (CTAB-24 above) survived, while 57% of the animals treated with antitoxin IgY starting 48 hrs. post-infection (CTAB-48 above) survived. In contrast, none of the animals receiving pre-immune IgY starting 24 hrs. post-infection (Pre-24 above) survived, and only 29% of the animals which began receiving treatment with pre-immune IgY at 48 hrs. post-infection (Pre-48 above) survived through the conclusion of the study. These results demonstrate that avian antitoxins raised against *C. difficile* toxins A and B are capable of successfully treating established *C. difficile* infections in vivo.

c) Histologic Evaluation of Cecal Tissue

In order to further evaluate the ability of the IgY preparations tested in this study to treat established *C. difficile* infection, histologic evaluations were performed on cecal tissue specimens obtained from representative animals from the study described in section (b) above.

Immediately following death, cecal tissue specimens were removed from animals which died in the Pre-24 and Pre-48 groups. Following the completion of the study, a representative surviving animal was sacrificed and cecal tissue specimens were removed from the CTAB-24 and CTAB-48 groups. A single untreated animal from the same shipment as those used in the study was also sacrificed and a cecal tissue specimen was removed as a normal control. All tissue specimens were fixed overnight at 4° C. in 10% buffered formalin. The fixed tissues were paraffin-embedded, sectioned, and mounted on glass microscope slides. The tissue sections were then stained using hematoxylin and eosin (H and E stain), and were examined by light microscopy.

Upon examination, the tissues obtained from the CTAB-24 and CTAB-48 animals showed no pathology, and were indistinguishable from the normal control. This observation provides further evidence for the ability of avian antitoxins raised against *C. difficile* toxins A and B to effectively treat established *C. difficile* infection, and to prevent the pathologic consequences which normally occur as a result of *C. difficile* disease.

In contrast, characteristic substantial mucosal damage and destruction was observed in the tissues of the animals from the Pre-24 and Pre-48 groups which died from *C. difficile* disease. Normal tissue architecture was obliterated in these two preparations, as most of the mucosal layer was observed to have sloughed away, and there were numerous large hemorrhagic areas containing massive numbers of erythrocytes.

EXAMPLE 11

Cloning and Expression of *C. difficile* Toxin A Fragments

The toxin A gene has been cloned and sequenced, and shown to encode a protein of predicted MW of 308 kd. [Dove et al., Infect. Immun., 58:480–488 (1990).] Given the expense and difficulty of isolating native toxin A protein, it would be advantageous to use simple and inexpensive procaryotic expression systems to produce and purify high levels of recombinant toxin A protein for immunization purposes. Ideally, the isolated recombinant protein would be soluble in order to preserve native antigenicity, since solubilized inclusion body proteins often do not fold into native conformations. To allow ease of purification, the recombinant protein should be expressed to levels greater than 1 mg/liter of *E. coli* culture.

To determine whether high levels of recombinant toxin A protein can be produced in *E. coli*, fragments of the toxin A gene were cloned into various prokaryotic expression vectors, and assessed for the ability to express recombinant toxin A protein in *E. coli*. Three prokaryotic expression systems were utilized. These systems were chosen because they drive expression of either fusion (pMALc and pGEX2T) or native (pET23a–c) protein to high levels in *E. coli*, and allow affinity purification of the expressed protein on a ligand containing column. Fusion proteins expressed from pGEX vectors bind glutathione agarose beads, and are eluted with reduced glutathione. pMAL fusion proteins bind amylose resin, and are eluted with maltose. A poly-histidine tag is present at either the N-terminal (pET16b) or C-terminal (pET23a–c) end of pET fusion proteins. This sequence specifically binds $Ni_2^+$chelate columns, and is eluted with imidazole salts. Extensive descriptions of these vectors are available [Williams et al. (1995) *DNA Cloning 2: Expression Systems*, Glover and Hames, eds. IRL Press, Oxford, pp. 15–58], and will not be discussed in detail here.

The Example involved (a) cloning of the toxin A gene, (b) expression of large fragments of toxin A in various prokaryotic expression systems, (c) identification of smaller toxin A gene fragments that express efficiently in *E. coli*, (d) purification of recombinant toxin A protein by affinity chromatography, and (e) demonstration of functional activity of a recombinant fragment of the toxin A gene.

a) Cloning of the Toxin A Gene

A restriction map of the toxin A gene is shown in FIG. 6. The encoded protein contains a carboxy terminal ligand binding region, containing multiple repeats of a carbohydrate binding domain. [von Eichel-Streiber and Sauerborn, Gene 96:107–113 (1990).] The toxin A gene was cloned in three pieces, by using either the polymerase chain reaction (PCR) to amplify specific regions, (regions 1 and 2, FIG. 6) or by screening a constructed genomic library for a specific toxin A gene fragment (region 3, FIG. 6). The sequences of the utilized PCR primers are P1: 5' GGAAATT TAGCTGCAGCATCTGAC 3' (SEQ ID NO.:1); P2: 5' TCTAGCAAATTCGCTTGT GTTGAA 3' (SEQ ID NO.:2); P3: 5'CTCGCATATAGCATTAGACC 3' (SEQ ID NO.:3); and P4: 5'CTATCTAGGCCTAAAGTAT 3' (SEQ ID NO.:4). These regions were cloned into prokaryotic expression vectors that express either fusion (pMALc and pGEX2T) or native (pET23a–c) protein to high levels in *E. coli*, and allow affinity purification of the expressed protein on a ligand containing column.

*Clostridium difficile* VPI strain 10463 was obtained from the ATCC (ATCC #43255) and grown under anaerobic conditions in brain-heart infusion medium (BBL). High molecular-weight *C. difficile* DNA was isolated essentially as described by Wren and Tabaqchali (1987) J. Clin. Microbiol., 25:2402, except proteinase K and sodium dodecyl sulfate (SDS) was used to disrupt the bacteria, and cetyltrimethylammonium bromide precipitation [as described in Ausubel et al., *Current Protocols in Molecular Biology* (1989)] was used to remove carbohydrates from the cleared lysate. The integrity and yield of genomic DNA was assessed by comparison with a serial dilution of uncut lambda DNA after electrophoresis on an agarose gel.

Fragments 1 and 2 were cloned by PCR, utilizing a proofreading thermostable DNA polymerase (native pfu polymerase; Stratagene). The high fidelity of this polymerase reduces the mutation problems associated with amplification by error prone polymerases (e.g., Taq polymerase). PCR amplification was performed using the indicated PCR primers (FIG. 6) in 50 $\mu$l reactions containing 10 mM Tris-HCl(8.3), 50 mM KCl, 1.5 mM $MgCl_2$, 200 $\mu$M each dNTP, 0.2 $\mu$M each primer, and 50 ng *C. difficile* genomic DNA. Reactions were overlaid with 100 $\mu$l mineral oil, heated to 94° C. for 4 min, 0.5 $\mu$l native pfu polymerase (Stratagene) added, and the reaction cycled 30× at 94° C. for 1 min, 50° C. for 1 min, 72° C. for 4 min, followed by 10 min at 72° C. Duplicate reactions were pooled, chloroform extracted, and ethanol precipitated. After washing in 70% ethanol, the pellets were resuspended in 50 $\mu$l TE buffer [10 mM Tris-HCL, 1 mM EDTA pH 8.0]. Aliquots of 10 $\mu$l each were restriction digested with either EcoRI/HincII (fragment 1) or EcoRI/PstI (fragment 2), and the appropriate restriction fragments were gel purified using the Prep-A-Gene kit (BioRad), and ligated to either EcoRI/SmaI-restricted pGEX2T (Pharmacia) vector (fragment 1), or the EcoRI/PstI pMAlc (New England Biolabs) vector (fragment 2). Both clones are predicted to produce in-frame fusions with either the glutathione-S-transferase protein (pGEX vector) or the maltose binding protein (pMAL vector). Recombinant clones were isolated, and confirmed by restriction digestion, using standard recombinant molecular biology techniques. [Sambrook et al., *Molecular Cloning, A Laboratory Manual* (1989), and designated pGA30–660 and pMA660–1100, respectively (see FIG. 6 for description of the clone designations).]

Fragment 3 was cloned from a genomic library of size selected PstI digested *C. difficile* genomic DNA, using standard molecular biology techniques (Sambrook et al.). Given that the fragment 3 internal PstI site is protected from cleavage in *C. difficile* genomic DNA [Price et al., Curr. Microbiol., 16:55–60 (1987)], a 4.7 kb fragment from PstI restricted *C. difficile* genomic DNA was gel purified, and ligated to PstI restricted, phosphatase treated pUC9 DNA. The resulting genomic library was screened with a oligonucleotide primer specific to fragment 3, and multiple independent clones were isolated. The presence of fragment 3 in several of these clones was confirmed by restriction digestion, and a clone of the indicated orientation (FIG. 6) was restricted with BamHI/HindIII, the released fragment purified by gel electrophoresis, and ligated into similarly restricted pET23c expression vector DNA (Novagen). Recombinant clones were isolated, and confirmed by restriction digestion. This construct is predicted to create both a predicted in frame fusion with the pET protein leader sequence, as well as a predicted C-terminal poly-histidine affinity tag, and is designated pPA1100–2680 (see FIG. 6 for the clone designation).

b) Expression of Large Fragments of Toxin A in *E. coli*

Figure 7:
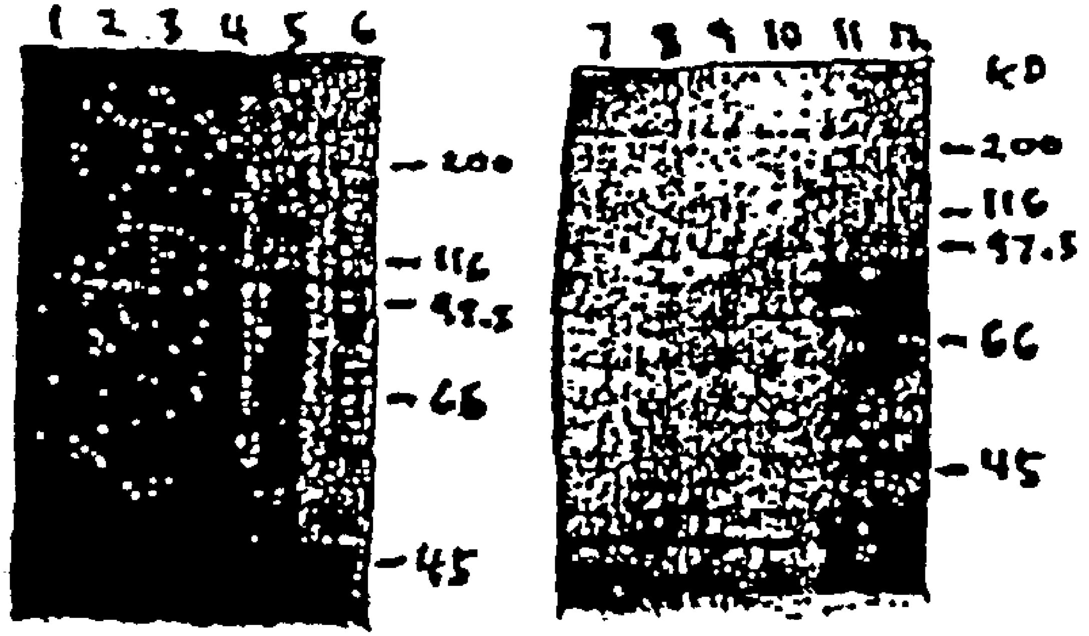
FIG. 7 is a Western blot of *C. difficile* toxin A reactive protein.

Protein expression from the three expression constructs made in (a) was induced, and analyzed by Western blot analysis with an affinity purified, goat polyclonal antiserum directed against the toxin A toxoid (Tech Lab). The procedures utilized for protein induction, SDS-PAGE, and Western blot analysis are described in detail in Williams et al (1995), supra. In brief, 5 ml 2× YT (16 g tryptone, 10 g yeast extract, 5 g NaCl per liter, pH 7.5+100 $\mu$g/ml ampicillin were added to cultures of bacteria (BL21 for pMAI and pGEX plasmids, and BL21(DE3)LysS for pET plasmids) containing the appropriate recombinant clone which were induced to express recombinant protein by addition of IPTG to 1 mM. Cultures were grown at 37° C., and induced when the cell density reached 0.5 $OD_{600}$. Induced protein was allowed to accumulate for two hrs after induction. Protein samples were prepared by pelleting 1 ml aliquots of bacteria by centrifugation (1 min in a microfuge), and resuspension of the pelleted bacteria in 150 $\mu$l of 2× SDS-PAGE sample buffer [Williams et al. (1995), supra]. The samples were heated to 95° C. for 5 min, then cooled and 5 or 10 $\mu$l aliquots loaded on 7.5% SDS-PAGE gels. BioRad high molecular weight protein markers were also loaded, to allow estimation of the MW of identified fusion proteins. After electrophoresis, protein was detected either generally by staining gels with Coomassie blue, or specifically, by blotting to nitrocellulose for Western blot detection of specific immunoreactive protein. Western blots, (performed as described in Example 3) which detect toxin A reactive protein in cell lysates of induced protein from the three expression constructs are shown in FIG. 7. In this figure, lanes 1–3 contain cell lysates prepared from *E. coli* strains containing pPA1100–2860 in B121(DE3)lysE cells; lanes 4–6 contain cell lysates prepared from *E. coli* strains containing pPA1100–2860 in B121(DE3)lysS cells; lanes 7–9 contain cell lysates prepared from *E. coli* strains containing pMA30–660; lanes 10–12 contain cell lysates prepared from *E. coli* strains containing pMA660–1100. The lanes were probed with an affinity purified goat antitoxin A polyclonal antibody (Tech Lab). Control lysates from uninduced cells (lanes 1, 7, and 10) contain very little immunoreactive material compared to the induced samples in the remaining lanes. The highest molecular weight band observed for each clone is consistent with the predicted size of the full length fusion protein.

Figure 8:
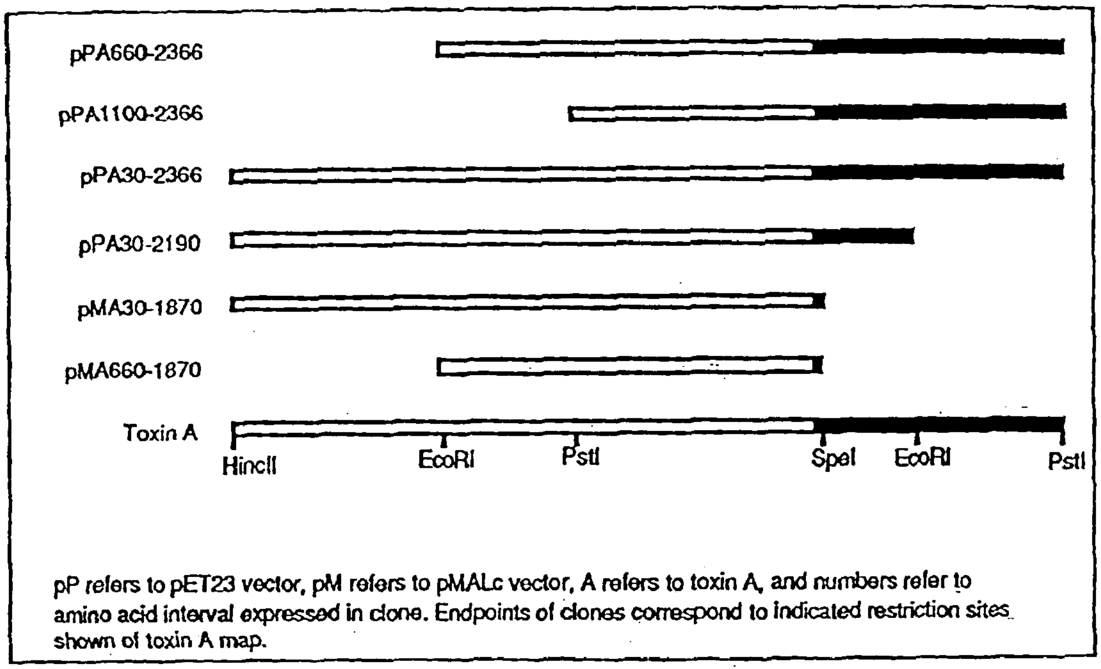
FIG. 8 shows *C. difficile* toxin A expression constructs.

Each construct directs expression of high molecular weight (HMW) protein that is reactive with the toxin A antibody. The size of the largest immunoreactive bands from each sample is consistent with predictions of the estimated MW of the intact fusion proteins. This demonstrates that the three fusions are in-frame, and that none of the clones contain cloning artifacts that disrupt the integrity of the encoded fusion protein. However, the Western blot demonstrates that fusion protein from the two larger constructs (pGA30–660 and pPA1100–2680) are highly degraded. Also, expression levels of toxin A proteins from these two constructs are low, since induced protein bands are not visible by Coomassie staining (not shown). Several other expression constructs that fuse large sub-regions of the toxin A gene to either pMALc or pET23a–c expression vectors, were constructed and tested for protein induction. These constructs were made by mixing gel purified restriction fragments, derived from the expression constructs shown in FIG. 6, with appropriately cleaved expression vectors, ligating, and selecting recombinant clones in which the toxin A restriction fragments had ligated together and into the expression vector as predicted for in-frame fusions. The expressed toxin A interval within these constructs are shown in FIG. 8, as well as the internal restriction sites utilized to make these constructs.

As used herein, the term "interval" refers to any portion (i.e., any segment of the toxin which is less than the whole toxin molecule) of a clostridial toxin. In a preferred embodiment, "interval" refers to portions of *C. difficile* toxins such as toxin A or toxin B. It is also contemplated that these intervals will correspond to epitopes of immunologic importance, such as antigens or immunogens against which a neutralizing antibody response is effected. It is not intended that the present invention be limited to the particular intervals or sequences described in these Examples. It is also contemplated that sub-portions of intervals (e.g., an epitope contained within one interval or which bridges multiple intervals) be used as compositions and in the methods of the present invention.

In all cases, Western blot analysis of each of these constructs with goat antitoxin A antibody (Tech Lab) detected HMW fusion protein of the predicted size (not shown). This confirms that the reading frame of each of these clones is not prematurely terminated, and is fused in the correct frame with the fusion partner. However, the Western blot analysis revealed that in all cases, the induced protein is highly degraded, and, as assessed by the absence of identifiable induced protein bands by Coomassie Blue staining, are expressed only at low levels. These results suggest that expression of high levels of intact toxin A recombinant protein is not possible when large regions of the toxin A gene are expressed in *E. coli* using these expression vectors.

c) High Level Expression of Small Toxin A Protein Fusions in *E. coli*

Figure 9:
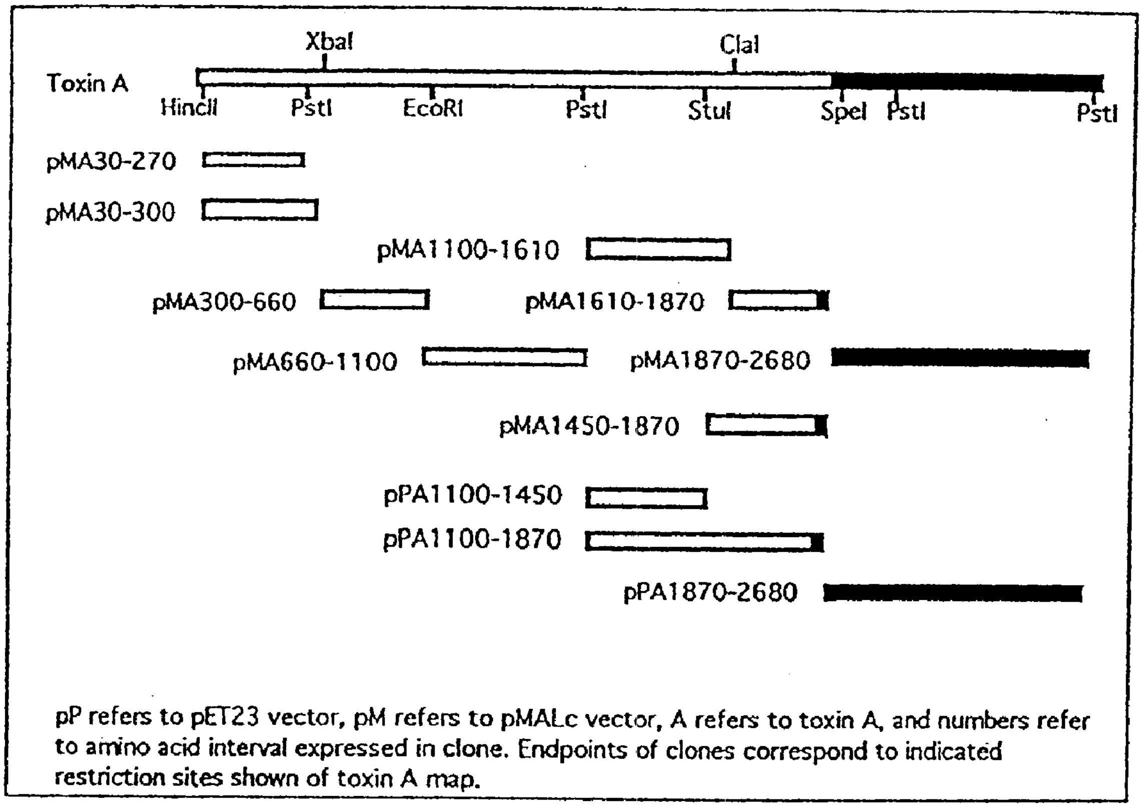
FIG. 9 shows *C. difficile* toxin A expression constructs.

Experience indicates that expression difficulties are often encountered when large (greater than 100 kd) fragments are expressed in *E. coli*. A number of expression constructs containing smaller fragments of the toxin A gene were constructed, to determine if small regions of the gene can be expressed to high levels without extensive protein degradation. A summary of these expression constructs are shown in FIG. 9. All were constructed by in-frame fusions of convenient toxin A restriction fragments to either the pMALc or pET23a–c vectors. Protein preparations from induced cultures of each of these constructs were analyzed by both Coomassie Blue staining and Western analysis as in (b) above. In all cases, higher levels of intact, full length fusion proteins were observed than with the larger recombinants from section (b).

d) Purification of Recombinant Toxin A Protein

Figure 10:
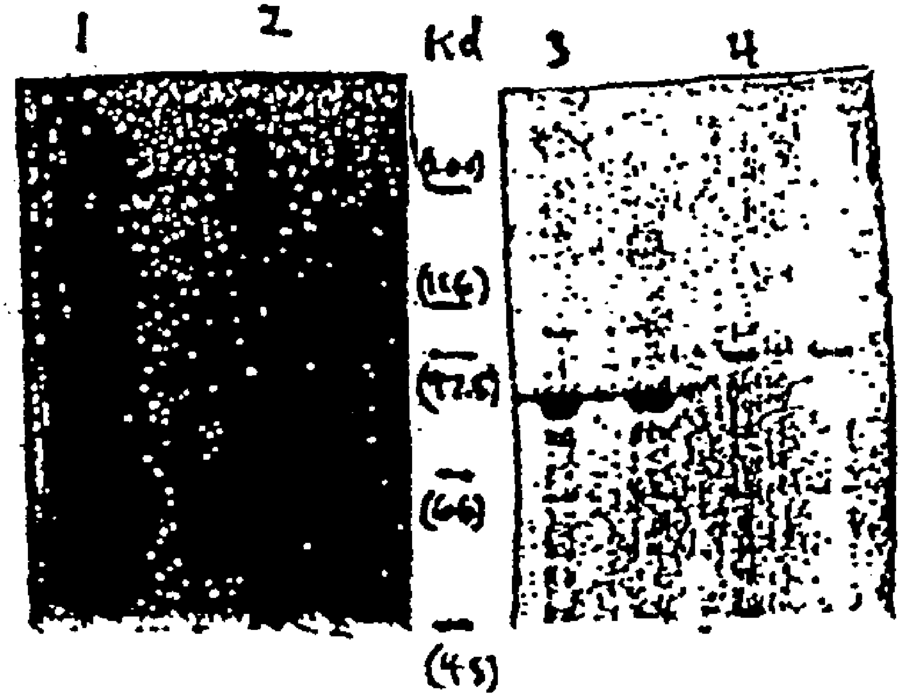
FIG. 10 shows the purification of recombinant *C. difficile* toxin A.

Large scale (500 ml) cultures of each recombinant from (c) were grown, induced, and soluble and insoluble protein fractions were isolated. The soluble protein extracts were affinity chromatographed to isolate recombinant fusion protein, as described [Williams et al. (1994), supra]. In brief, extracts containing tagged pET fusions were chromatographed on a nickel chelate column, and eluted using imidazole salts as described by the distributor (Novagen). Extracts containing soluble pMAL fusion protein were prepared and chromatographed in column buffer (10 mM $NaPO_4$, 0.5M NaCl, 10 mM P-mercaptoethanol, pH 7.2) over an amylose resin column (New England Biolabs), and eluted with column buffer containing 10 mM maltose as described [Williams et al. (1995), supra]. When the expressed protein was found to be predominantly insoluble, insoluble protein extracts were prepared by the method described in Example 17, infra. The results are summarized in Table 16. FIG. 10 shows the sample purifications of recombinant toxin A protein. In this figure, lanes 1 and 2 contain MBP fusion protein purified by affinity purification of soluble protein.

TABLE 16

Purification Of Recombinant Toxin A Protein

| Clone[a] | Protein Solubility | Yield Affinity Purified Soluble Protein[b] | % Intact Soluble Fusion Protein[c] | Yield Intact Insoluble Fusion Protein |
|---|---|---|---|---|
| pMA30–270 | Soluble | 4 mg/500 mls | 10% | NA |
| PMA30–300 | Soluble | 4 mg/500 mls | 5–10% | NA |
| pMA300–660 | In-soluble | — | NA | 10 mg/500 ml |
| pMA660–1100 | Soluble | 4.5 mg/500 mls | 50% | NA |
| pMA1100–1610 | Soluble | 18 mg/500 mls | 10% | NA |
| pMA1610–1870 | Both | 22 mg/500 mls | 90% | 20 mg/500 ml |
| pMA1450–1870 | In-soluble | — | NA | 0.2 mg/500 ml |
| pPA1100–1450 | Soluble | 0.1 mg/500 mls | 90% | NA |
| pPA1100–1870 | Soluble | 0.02 mg/500 mls | 90% | NA |
| pMA1870–2680 | Both | 12 mg/500 mls | 80% | NA |
| pPa1870–2680 | In-soluble | — | NA | 10 mg/500 ml |

[a]pP = pET23 vector, pM = pMALc vector, A = toxin A.
[b]Based on 1.5 $OD_{280}$ = 1 mg/ml (extinction coefficient of MBP).
[c]Estimated by Coomassie staining of SDS-PAGE gels.

Lanes 3 and 4 contain MBP fusion protein purified by solubilization of insoluble inclusion bodies. The purified fusion protein samples are pMA1870–2680 (lane 1), pMA660–1100 (lane 2), pMA300–600 (lane 3) and pMA1450–1870 (lane 4).

Poor yields of affinity purified protein were obtained when poly-histidine tagged pET vectors were used to drive expression (pPA1100–1450, pP1100–1870). However, significant protein yields were obtained from pMAL expression constructs spanning the entire toxin A gene, and yields of full-length soluble fusion protein ranged from an estimated 200–400 μg/500 ml culture (pMA30–300) to greater than 20 mg/500 ml culture (pMA1610–1870). Only one interval was expressed to high levels as strictly insoluble protein (pMA300–660). Thus, although high level expression was not observed when using large expression constructs from the toxin A gene, usable levels of recombinant protein spanning the entire toxin A gene were obtainable by isolating induced protein from a series of smaller pMAL expression constructs that span the entire toxin A gene. This is the first demonstration of the feasibility of expressing recombinant toxin A protein to high levels in *E. coli.* c) Hemagglutination Assay Using the Toxin A Recombinant Proteins

The carboxy terminal end consisting of the repeating units contains the hemagglutination activity or binding domain of *C. difficile* toxin A. To determine whether the expressed toxin A recombinants retain functional activity, hemagglutination assays were performed. Two toxin A recombinant proteins, one containing the binding domain as either soluble affinity purified protein (pMA1870–2680) or SDS solubilized inclusion body protein (pPA1870–2680) and soluble protein from one region outside that domain (pMA1100–1610) were tested using a described procedure. [H. C. Krivan et. al., Infect. Immun., 53:573 (1986).] Citrated rabbit red blood cells (RRBC)(Cocalico) were washed several times with Tris-buffer (0.1M Tris and 50 mM NaCl) by centrifugation at 450×g for 10 minutes at 4° C. A 1% RRBC suspension was made from the packed cells and resuspended in Tris-buffer. Dilutions of the recombinant proteins and native toxin A (Tech Labs) were made in the Tris-buffer and added in duplicate to a round-bottomed 96-well microtiter plate in a final volume of 100 μl. To each well, 50 μl of the 1% RRBC suspension was added, mixed by gentle tapping, and incubated at 4° C. for 34 hours. Significant hemagglutination occurred only in the recombinant proteins containing the binding domain (pMA 1870–2680) and native toxin A. The recombinant protein outside the binding domain (pMA 1100–1610) displayed no hemagglutination activity. Using equivalent protein concentrations, the hemagglutination titer for toxin A was 1:256, while titers for the soluble and insoluble recombinant proteins of the binding domain were 1:256 and about 1:5000. Clearly, the recombinant proteins tested retained functional activity and were able to bind RRBC's.

EXAMPLE 12

Functional Activity of IgY Reactive Against Toxin A Recombinants

The expression of recombinant toxin A protein as multiple fragments in *E. coli* has demonstrated the feasibility of generating toxin A antigen through use of recombinant methodologies (Example 11). The isolation of these recombinant proteins allows the immunoreactivity of each individual subregion of the toxin A protein to be determined (i.e., in a antibody pool directed against the native toxin A protein). This identifies the regions (if any) for which little or no antibody response is elicited when the whole protein is used as a immunogen. Antibodies directed against specific fragments of the toxin A protein can be purified by affinity chromatography against recombinant toxin A protein, and tested for neutralization ability. This identifies any toxin A subregions that are essential for producing neutralizing antibodies. Comparison with the levels of immune response directed against these intervals when native toxin is used as an immunogen predicts whether potentially higher titers of neutralizing antibodies can be produced by using recombinant protein directed against a individual region, rather than the entire protein. Finally, since it is unknown whether antibodies reactive to the recombinant toxin A proteins produced in Example 11 neutralize toxin A as effectively as antibodies raised against native toxin A (Examples 9 and 10), the protective ability of a pool of antibodies affinity purified against recombinant toxin A fragments was assessed for its ability to neutralize toxin A.

This Example involved (a) epitope mapping of the toxin A protein to determine the titre of specific antibodies directed against individual subregions of the toxin A protein when native toxin A protein is used as an immunogen, (b) affinity purification of IgY reactive against recombinant proteins spanning the toxin A gene, (c) toxin A neutralization assays with affinity purified IgY reactive to recombinant toxin A protein to identify subregions of the toxin A protein that induce the production of neutralizing antibodies, and determination of whether complete neutralization of toxin A can be elicited with a mixture of antibodies reactive to recombinant toxin A protein.

a) Epitope Mapping of the Toxin A Gene

The affinity purification of recombinant toxin A protein specific to defined intervals of the toxin A protein allows epitope mapping of antibody pools directed against native toxin A. This has not previously been possible, since previous expression of toxin A recombinants has been assessed only by Western blot analysis, without knowledge of the expression levels of the protein [e.g., von Eichel-Streiber et al, J. Gen. Microbiol., 135:55–64 (1989)]. Thus, high or low reactivity of recombinant toxin A protein on Western blots may reflect protein expression level differences, not immunoreactivity differences. Given that the purified recombinant protein generated in Example 11 have been quantitated, the issue of relative immunoreactivity of individual regions of the toxin A protein was precisely addressed.

For the purposes of this Example, the toxin A protein was subdivided into 6 intervals (1–6), numbered from the amino (interval 1) to the carboxyl (interval 6) termini.

The recombinant proteins corresponding to these intervals were from expression clones (see Example 11(d) for clone designations) pMA30–300 (interval 1), pMA300–660 (interval 2), pMA660–1100 (interval 3), pPA1100–1450 (interval 4), pMA1450–1870 (interval 5) and pMA1870–2680 (interval 6). These 6 clones were selected because they span the entire protein from amino acids numbered 30 through 2680, and subdivide the protein into 6 small intervals. Also, the carbohydrate binding repeat interval is contained specifically in one interval (interval 6), allowing evaluation of the immune response specifically directed against this region. Western blots of 7.5% SDS-PAGE gels, loaded and electrophoresed with defined quantities of each recombinant protein, were probed with either goat antitoxin A polyclonal antibody (Tech Lab) or chicken antitoxin A polyclonal antibody [pCTA IgY, Example 8(c)]. The blots were prepared and developed with alkaline phosphatase as previously described [Williams et al. (1995), supra]. At least 90% of all reactivity, in either goat or chicken antibody pools, was found to be directed against the ligand binding domain (interval 6). The remaining immunoreactivity was directed against all five remaining intervals, and was similar in both antibody pools, except that the chicken antibody showed a much lower reactivity against interval 2 than the goat antibody This clearly demonstrates that when native toxin A is used as an immunogen in goats or chickens, the bulk of the immune response is directed against the ligand binding domain of the protein, with the remaining response distributed throughout the remaining ⅔ of the protein.

b) Affinity Purification of IgY Reactive Against Recombinant Toxin A Protein

Affinity columns, containing recombinant toxin A protein from the 6 defined intervals in (a) above, were made and used to (i) affinity purify antibodies reactive to each individual interval from the CTA IgY preparation [Example 8(c)], and (ii) deplete interval specific antibodies from the CTA IgY preparation. Affinity columns were made by coupling 1 ml of PBS-washed Actigel resin (Sterogene) with region specific protein and 1/10 final volume of Aid-coupling solution (1M sodium cyanoborohydride). The total region specific protein added to each reaction mixture was 2.7 mg (interval 1), 3 mg (intervals 2 and 3), 0.1 mg (interval 4), 0.2 mg (interval 5) and 4 mg (interval 6). Protein for intervals 1, 3, and 6 was affinity purified pMAl fusion protein in column buffer (see Example 11). Interval 4 was affinity purified poly-histidine containing pET fusion in PBS; intervals 2 and 5 were from inclusion body preparations of insoluble pMAL fusion protein, dialyzed extensively in PBS. Aliquots of the supernatants from the coupling reactions, before and after coupling, were assessed by Coomassie staining of 7.5% SDS-PAGE gels. Based on protein band intensities, in all cases greater than 50% coupling efficiencies were estimated. The resins were poured into 5 ml BioRad columns, washed extensively with PBS, and stored at 4° C.

Aliquots of the CTA IgY polyclonal antibody preparation were depleted for each individual region as described below. A 20 ml sample of the CTA IgY preparation [Example 8(c)] was dialyzed extensively against 3 changes of PBS (1 liter for each dialysis), quantitated by absorbance at $OD_{280}$, and stored at 4° C. Six 1 ml aliquots of the dialyzed IgY preparation were removed, and depleted individually for each of the six intervals. Each 1 ml aliquot was passed over the appropriate affinity column, and the eluate twice reapplied to the column. The eluate was collected, and pooled with a 1 ml PBS wash. Bound antibody was eluted from the column by washing with 5 column volumes of 4 M Guanidine-HCl (in 10 mM Tris-HCl, pH 8.0). The column was reequilibrated in PBS, and the depleted antibody stock reapplied as described above. The eluate was collected, pooled with a 1 ml PBS wash, quantitated by absorbance at $OD_{280}$, and stored at 4° C. In this manner, 6 aliquots of the CTA IgY preparation were individually depleted for each of the 6 toxin A intervals, by two rounds of affinity depletion. The specificity of each depleted stock was tested by Western blot analysis. Multiple 7.5% SDS-PAGE gels were loaded with protein samples corresponding to all 6 toxin A subregions. After electrophoresis, the gels were blotted, and protein transfer confirmed by Ponceau S staining [protocols described in Williams et al. (1995), supra]. After blocking the blots 1 hr at 20° C. in PBS+0.1% Tween 20 (PBST) containing 5% milk (as a blocking buffer), 4 ml of either a 1/500 dilution of the dialyzed CTA IgY preparation in blocking buffer, or an equivalent amount of the six depleted antibody stocks (using $OD_{280}$ to standardize antibody concentration) were added and the blots incubated a further 1 hr at room temperature. The blots were washed and developed with alkaline phosphatase (using a rabbit anti-chicken alkaline phosphate conjugate as a secondary antibody) as previously described [Williams et al. (1995), supra]. In all cases, only the target interval was depleted for antibody reactivity, and at least 90% of the reactivity to the target intervals was specifically depleted.

Region specific antibody pools were isolated by affinity chromatography as described below. Ten mls of the dialyzed CTA IgY preparation were applied sequentially to each affinity column, such that a single 10 ml aliquot was used to isolate region specific antibodies specific to each of the six subregions. The columns were sequentially washed with 10 volumes of PBS, 6 volumes of BBS-Tween, 10 volumes of TBS, and eluted with 4 ml Actisep elution media (Sterogene). The eluate was dialyzed extensively against several changes of PBS, and the affinity purified antibody collected and stored at 4° C. The volumes of the eluate increased to greater than 10 mls during dialysis in each case, due to the high viscosity of the Actisep elution media. Aliquots of each sample were 20× concentrated using Centricon 30 microconcentrators (Amicon) and stored at 4° C. The specificity of each region specific antibody pool was tested, relative to the dialyzed CTA IgY preparation, by Western blot analysis, exactly as described above, except that 4 ml samples of blocking buffer containing 100 μl region specific antibody (unconcentrated) were used instead of the depleted CTA IgY preparations. Each affinity purified antibody preparation was specific to the defined interval, except that samples purified against intervals 1–5 also reacted with interval 6. This may be due to non-specific binding to the interval 6 protein, since this protein contains the repetitive ligand binding domain which has been shown to bind antibodies nonspecifically. [Lyerly et al., Curr. Microbiol., 19:303–306 (1989).]

The reactivity of each affinity purified antibody preparation to the corresponding proteins was approximately the same as the reactivity of the 1/500 diluted dialyzed CTA IgY preparation standard. Given that the specific antibody stocks were diluted 1/40, this would indicate that the unconcentrated affinity purified antibody stocks contain 1/10–1/20 the concentration of specific antibodies relative to the starting CTA IgY preparation.

c) Toxin A Neutralization Assay Using Antibodies Reactive Toward Recombinant Toxin A Protein The CHO toxin neutralization assay [Example 8(d)] was used to assess the ability of the depleted or enriched samples generated in (b) above to neutralize the cytotoxicity of toxin A. The general ability of affinity purified antibodies to neutralize toxin A was assessed by mixing together aliquots of all 6 concentrated stocks of the 6 affinity purified samples generated in (b) above, and testing the ability of this mixture to neutralize a toxin A concentration of 0.1 μg/ml. The results, shown in FIG. 11, demonstrate almost complete neutralization of toxin A using the affinity purified (AP) mix. Some epitopes within the recombinant proteins utilized for affinity purification were probably lost when the proteins were denatured before affinity purification [by Guanidine-HCl treatment in (b) above]. Thus, the neutralization ability of antibodies directed against recombinant protein is probably underestimated using these affinity purified antibody pools. This experiment demonstrates that antibodies reactive to recombinant toxin A can neutralize cytotoxicity, suggesting that neutralizing antibodies may be generated by using recombinant toxin A protein as immunogen.

In view of the observation that the recombinant expression clones of the toxin A gene divide the protein into 6 subregions, the neutralizing ability of antibodies directed against each individual region was assessed. The neutralizing ability of antibodies directed against the ligand binding domain of toxin A was determined first.

Figure 11:
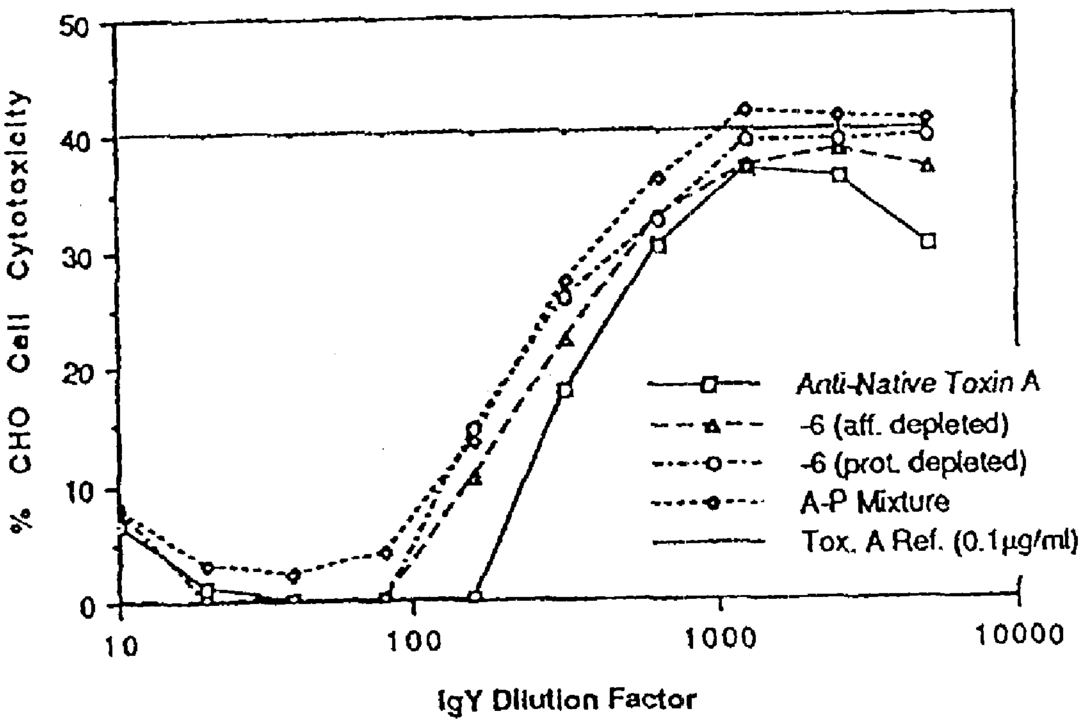
FIG. 11 shows the results of *C. difficile* toxin A neutralization assays with antibodies reactive to recombinant toxin A.

In the toxin neutralization experiment shown in FIG. 11, interval 6 specific antibodies (interval 6 contains the ligand binding domain) were depleted from the dialyzed PEG preparation, and the effect on toxin neutralization assayed. Interval 6 antibodies were depleted either by utilizing the interval 6 depleted CTA IgY preparation from (b) above ("−6 aff. depleted" in FIG. 11), or by addition of interval 6 protein to the CTA IgY preparation (estimated to be a 10 fold molar excess over anti-interval 6 immunoglobulin present in this preparation) to competitively compete for interval 6 protein ("−6 prot depleted" in FIG. 11). In both instances, removal of interval 6 specific antibodies reduces the neutralization efficiency relative to the starting CTA IgY preparation. This demonstrates that antibodies directed against interval 6 contribute to toxin neutralization. Since interval 6 corresponds to the ligand binding domain of the protein, these results demonstrate that antibodies directed against this region in the PEG preparation contribute to the neutralization of toxin A in this assay. However, it is significant that after removal of these antibodies, the PEG preparation retains significant ability to neutralize toxin A (FIG. 11). This neutralization is probably due to the action of antibodies specific to other regions of the toxin A protein, since at least 90% of the ligand binding region reactive antibodies were removed in the depleted sample prepared in (b) above. This conclusion was supported by comparison of the toxin neutralization of the affinity purified (AP) mix compared to affinity purified interval 6 antibody alone. Although some neutralization ability was observed with AP interval 6 antibodies alone, the neutralization was significantly less than that observed with the mixture of all 6 AP antibody stocks (not shown).

Figure 12:
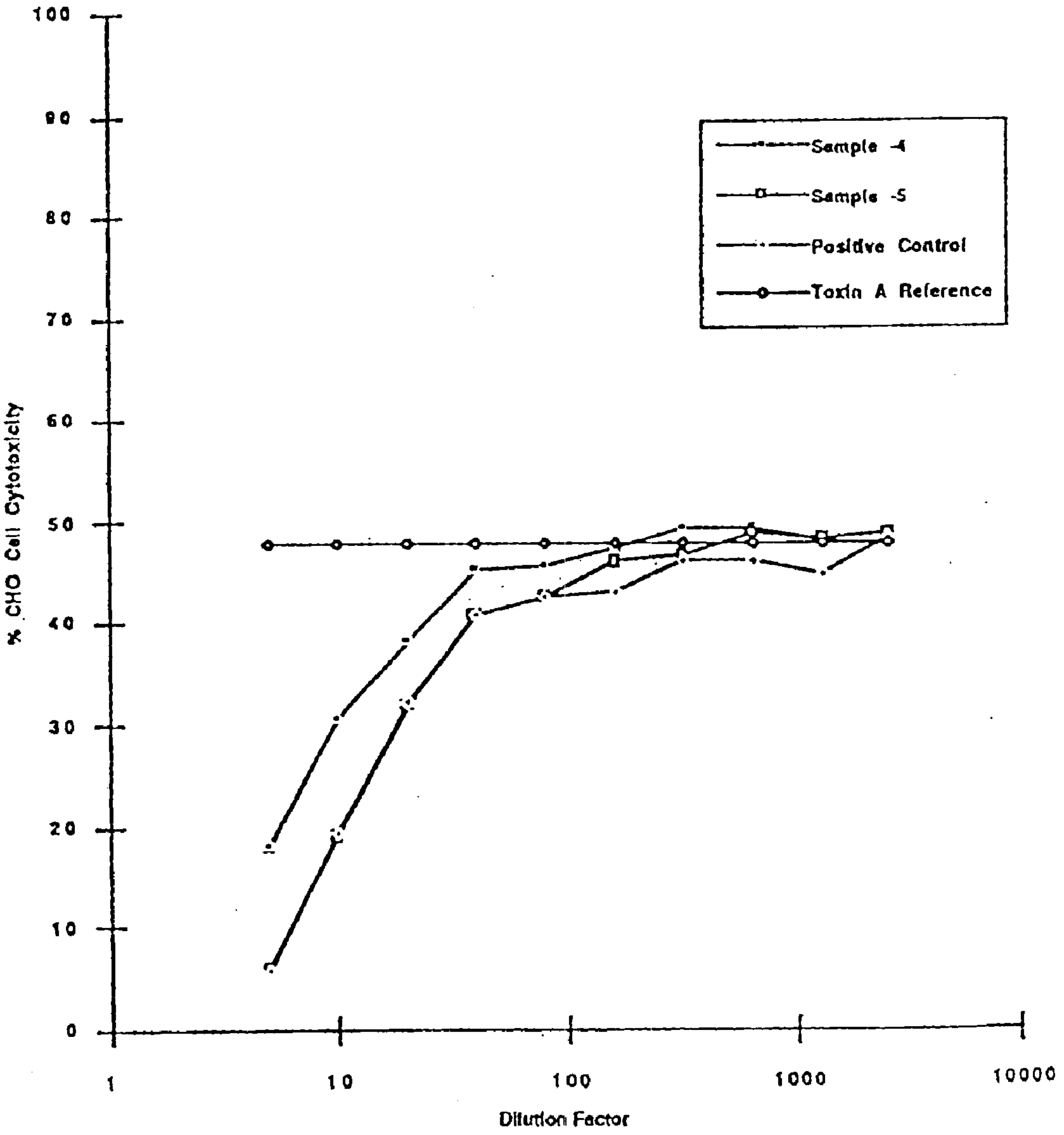
FIG. 12 shows the results for a *C. difficile* toxin A neutralization plate.

Given that the mix of all six affinity purified samples almost completely neutralized the cytotoxicity of toxin A (FIG. 11), the relative importance of antibodies directed against toxin A intervals 1–5 within the mixture was determined. This was assessed in two ways. First, samples containing affinity purified antibodies representing 5 of the 6 intervals were prepared, such that each individual region was depleted from one sample. FIG. 12 demonstrates a sample neutralization curve, comparing the neutralization ability of affinity purified antibody mixes without interval 4 (−4) or 5 (−5) specific antibodies, relative to the mix of all 6 affinity purified antibody stocks (positive control). While the removal of interval 5 specific antibodies had no effect on toxin neutralization (or intervals 1–3, not shown), the loss of interval 4 specific antibodies significantly reduced toxin neutralization (FIG. 12).

Figure 13:
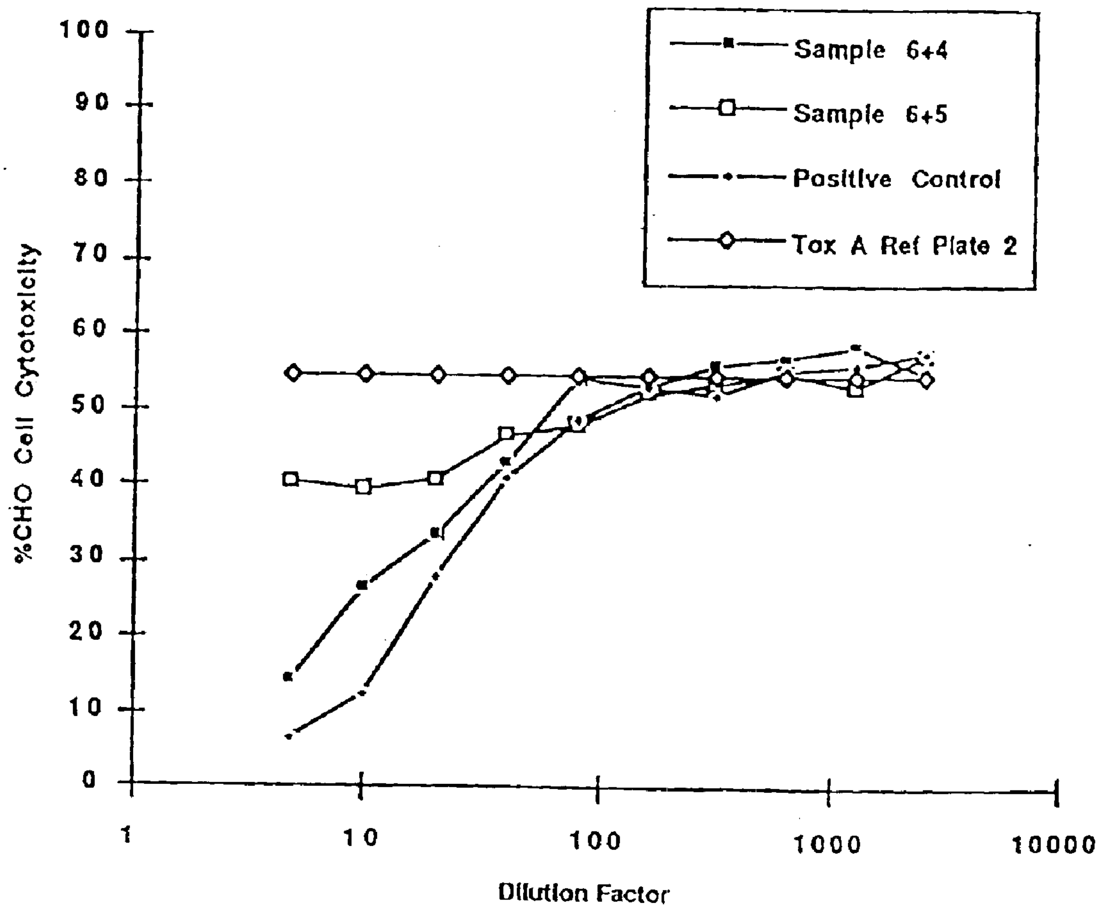
FIG. 13 shows the results for a *C. difficile* toxin A neutralization plate.

Similar results were seen in a second experiment, in which affinity purified antibodies, directed against a single region, were added to interval 6 specific antibodies, and the effects on toxin neutralization assessed. Only interval 4 specific antibodies significantly enhanced neutralization when added to interval 6 specific antibodies (FIG. 13). These results demonstrate that antibodies directed against interval 4 (corresponding to clone pPA1100–1450 in FIG. 9) are important for neutralization of cytotoxicity in this assay. Epitope mapping has shown that only low levels of antibodies reactive to this region are generated when native toxin A is used as an immunogen [Example 12(a)]. It is hypothesized that immunization with recombinant protein specific to this interval will elicit higher titers of neutralizing antibodies. In summary, this analysis has identified two critical regions of the toxin A protein against which neutralizing antibodies are produced, as assayed by the CHO neutralization assay.

EXAMPLE 13

Production and Evaluation of Avian Antitoxin Against *C. difficile* Recombinant Toxin A Polypeptide In Example 12, we demonstrated neutralization of toxin A mediated cytotoxicity by affinity purified antibodies reactive to recombinant toxin A protein. To determine whether antibodies raised against a recombinant polypeptide fragment of *C. difficile* toxin A may be effective in treating clostridial diseases, antibodies to recombinant toxin A protein representing the binding domain were generated. Two toxin A binding domain recombinant polypeptides, expressing the binding domain in either the pMALc (pMA1870–2680) or pET 23(pPA1870–2680) vector, were used as immunogens. The pMAL protein was affinity purified as a soluble product [Example 12(d)] and the pET protein was isolated as insoluble inclusion bodies [Example 12(d)] and solubilized to an immunologically active protein using a proprietary method described in a pending patent application (U.S. patent application Ser. No. 08/129,027). This Example involves (a) immunization, (b) antitoxin collection, (c) determination of antitoxin antibody titer, (d) anti-recombinant toxin A neutralization of toxin A hemagglutination activity in vitro, and (e) assay of in vitro toxin A neutralizing activity.

a) Immunization

The soluble and the inclusion body preparations each were used separately to immunize hens. Both purified toxin A polypeptides were diluted in PBS and emulsified with approximately equal volumes of CFA for the initial immunization or IFA for subsequent booster immunizations. On day zero, for each of the recombinant preparations, two egg laying white Leghorn hens (obtained from local breeder) were each injected at multiple sites (intramuscular and subcutaneous) with 1 ml of recombinant adjuvant mixture containing approximately 0.5 to 1.5 mgs of recombinant toxin A. Booster immunizations of 1.0 mg were given on days 14 and day 28.

b) Antitoxin Collection

Total yolk immune IgY was extracted as described in the standard PEG protocol (as in Example 1) and the final IgY pellet was dissolved in sterile PBS at the original yolk volume. This material is designated "immune recombinant IgY" or "immune IgY."

c) Antitoxin Antibody Titer

To determine if the recombinant toxin A protein was sufficiently immunogenic to raise antibodies in hens, the antibody titer of a recombinant toxin A polypeptide was determined by ELISA. Eggs from both hens were collected on day 32, the yolks pooled and the antibody was isolated using PEG as described. The immune recombinant IgY antibody titer was determined for the soluble recombinant protein containing the maltose binding protein fusion generated in p-Mal (pMA1870–2680). Ninety-six well Falcon Pro-bind plates were coated overnight at 4° C. with 100 $\mu$l/well of toxin A recombinant at 2.5 $\mu$g/$\mu$l in PBS containing 0.05% thimerosal. Another plate was also coated with maltose binding protein (MBP) at the same concentration, to permit comparison of antibody reactivity to the fusion partner. The next day, the wells were blocked with PBS containing 1% bovine serum albumin (BSA) for 1 hour at 37° C. IgY isolated from immune or preimmune eggs was diluted in antibody diluent (PBS containing 1% BSA and 0.05% Tween-20), and added to the blocked wells and incubated for 1 hour at 37° C. The plates were washed three times with PBS with 0.05% Tween-20, then three times with PBS. Alkaline phosphatase conjugated rabbit anti-chicken IgG (Sigma) diluted 1:1000 in antibody diluent was added to the plate, and incubated for 1 hour at 37° C. The plates were washed as before and substrate was added, [p-nitrophenyl phosphate (Sigma)] at 1 mg/ml in 0.05M $Na_2CO_3$, pH 9.5 and 10 mM $MgCl_2$. The plates were evaluated quantitatively on a Dynatech MR 300 Micro EPA plate reader at 410 nm about 10 minutes after the addition of substrate.

Based on these ELISA results, high antibody titers were raised in chickens immunized with the toxin A recombinant polypeptide. The recombinant appeared to be highly immunogenic, as it was able to generate high antibody titers relatively quickly with few immunizations. Immune IgY titer directed specifically to the toxin A portion of the recombinant was higher than the immune IgY titer to its fusion partner, the maltose binding protein, and significantly higher than the preimmune IgY. ELISA titers (reciprocal of the highest dilution of IgY generating a signal) in the preimmune IgY to the MBP or the recombinant was <1:30 while the immune IgY titers to MBP and the toxin A recombinant were 1:18750 and >1:93750 respectively. Importantly, the anti-recombinant antibody titers generated in the hens against the recombinant polypeptide is much higher, compared to antibodies to that region raised using native toxin A. The recombinant antibody titer to region 1870–2680 in the CTA antibody preparation is at least five-fold lower compared to the recombinant generated antibodies (1:18750 versus >1:93750). Thus, it appears a better immune response can be generated against a specific recombinant using that recombinant as the immunogen compared to the native toxin A.

This observation is significant, as it shows that because recombinant portions stimulate the production of antibodies, it is not necessary to use native toxin molecules to produce antitoxin preparations. Thus, the problems associated with the toxicity of the native toxin are avoided and large-scale antitoxin production is facilitated.

d) Anti-Recombinant Toxin A Neutralization of Toxin A Hemagglutination Activity In Vitro Toxin A has hemagglutinating activity besides cytotoxic and enterotoxin properties. Specifically, toxin A agglutinates rabbit erythrocytes by binding to a trisaccharide (gal 1–3B1–4GlcNAc) on the cell surface. [H. Krivan et al., Infect. Immun., 53:573–581 (1986).] We examined whether the anti-recombinant toxin A (immune IgY, antibodies raised against the insoluble product expressed in pET) can neutralize the hemagglutination activity of toxin A in vitro. The hemagglutination assay procedure used was described by H. C. Krivan et al. Polyethylene glycol-fractionated immune or preimmune IgY were pre-absorbed with citrated rabbit erythrocytes prior to performing the hemagglutination assay because we have found that IgY alone can agglutinate red blood cells. Citrated rabbit red blood cells (RRBC's) (Cocalico) were washed twice by centrifugation at 450×g with isotonic buffer (0.1 M Tris-HCl, 0.05 M NaCl, pH 7.2). RRBC-reactive antibodies in the IgY were removed by preparing a 10% RRBC suspension (made by adding packed cells to immune or preimmune IgY) and incubating the mixture for 1 hour at 37° C. The RRBCs were then removed by centrifugation. Neutralization of the hemagglutination activity of toxin A by antibody was tested in round-bottomed 96-well microtiter plates. Twenty-five μl of toxin A (36 μg/ml) (Tech Lab) in isotonic buffer was mixed with an equal volume of different dilutions of immune or preimmune IgY in isotonic buffer, and incubated for 15 minutes at room temperature. Then, 50 μl of a 1% RRBC suspension in isotonic buffer was added and the mixture was incubated for 3 hours at 4° C. Positive control wells containing the final concentration of 9 μg/ml of toxin A after dilution without IgY were also included. Hemagglutination activity was assessed visually, with a diffuse matrix of RRBC's coating the bottom of the well representing a positive hemagglutination reaction and a tight button of RRBC's at the bottom of the well representing a negative reaction. The anti-recombinant immune IgY neutralized toxin A hemagglutination activity, giving a neutralization titer of 1:8. However, preimmune IgY was unable to neutralize the hemagglutination ability of toxin A.

e) Assay of in Vitro Toxin A Neutralizing Activity

Figure 14:
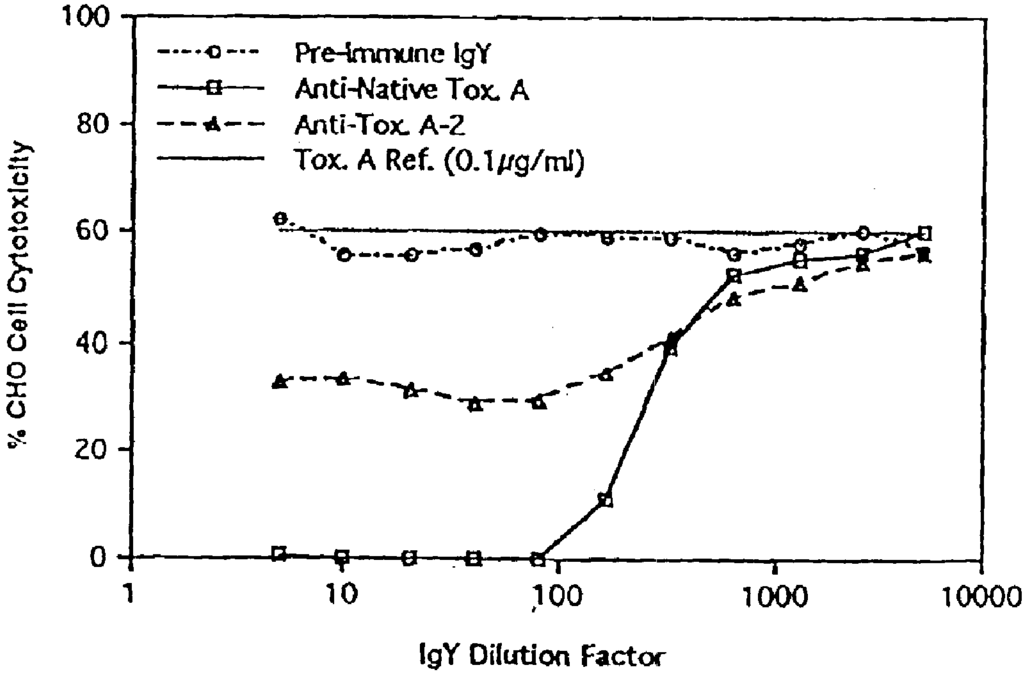
FIG. 14 shows the results of recombinant *C. difficile* toxin A neutralization assays.

The ability of the anti-recombinant toxin A IgY (immune IgY antibodies raised against pMA1870–2680, the soluble recombinant binding domain protein expressed in pMAL, designated as Anti-tox. A-2 in FIG. 14, and referred to as recombinant region 6) and pre-immune IgY, prepared as described in Example 8(c) above, to neutralize the cytotoxic activity of toxin A was assessed in vitro using the CHO cell cytotoxicity assay, and toxin A (Tech Lab) at a concentration of 0.1 μg/ml, as described in Example 8(d) above. As additional controls, the anti-native toxin A IgY (CTA) and pre-immune IgY preparations described in Example 8(c) above were also tested. The results are shown in FIG. 14.

The anti-recombinant toxin A IgY demonstrated only partial neutralization of the cytotoxic activity of toxin A, while the pre-immune IgY did not demonstrate any significant neutralizing activity.

EXAMPLE 14

In vivo Neutralization of *C. difficile* Toxin A

The ability of avian antibodies (IgY) raised against recombinant toxin A binding domain to neutralize the enterotoxin activity of *C. difficile* toxin A was evaluated in vivo using Golden Syrian hamsters. The Example involved: (a) preparation of the avian anti-recombinant toxin A IgY for oral administration;
(b) in vivo protection of hamsters from *C. difficile* toxin A enterotoxicity by treatment of toxin A with avian anti-recombinant toxin A IgY; and (c) histologic evaluation of hamster ceca.

a) Preparation of the Avian Anti-Recombinant Toxin A IgY for Oral Administration Eggs were collected from hens which had been immunized with the recombinant *C. difficile* toxin A fragment pMA1870–2680 (described in Example 13, above). A second group of eggs purchased at a local supermarket was used as a pre-immune (negative) control. Egg yolk immunoglobulin (IgY) was extracted by PEG from the two groups of eggs as described in Example 8(c), and the final IgY pellets were solubilized in one-fourth the original yolk volume using 0.1M carbonate buffer (mixture of $NaHCO_3$ and $Na_2CO_3$), pH 9.5. The basic carbonate buffer was used in order to protect the toxin A from the acidic pH of the stomach environment.

b) In vivo Protection of Hamsters Against *C. difficile* Toxin A Enterotoxicity by Treatment of Toxin A with Avian Anti-recombinant Toxin A IgY In order to assess the ability of the avian anti-recombinant toxin A IgY, prepared in section (a) above to neutralize the in vivo enterotoxin activity of toxin A, an in vivo toxin neutralization model was developed using Golden Syrian hamsters. This model was based on published values for the minimum amount of toxin A required to elicit diarrhea (0.08 mg toxin A/Kg body wt.) and death (0.16 mg toxin A/Kg body wt.) in hamsters when administered orally (Lyerly et al. Infect. Immun., 47:349–352 (1985).

For the study, four separate experimental groups were used, with each group consisting of 7 female Golden Syrian hamsters (Charles River), approx. three and one-half weeks old, weighing approx. 50 gms each. The animals were housed as groups of 3 and 4, and were offered food and water ad libitum through the entire length of the study.

For each animal, a mixture containing either 10 μg of toxin A (0.2 mg/Kg) or 30 μof toxin A (0.6 mg/Kg) (*C. difficile* toxin A was obtained from Tech Lab and 1 ml of either the anti-recombinant toxin A IgY or pre-immune IgY (from section (a) above) was prepared. These mixtures were incubated at 37° C. for 60 min. and were then administered to the animals by the oral route. The animals were then observed for the onset of diarrhea and death for a period of 24 hrs. following the administration of the toxin A+IgY mixtures, at the end of which time, the following results were tabulated and shown in Table 17:

TABLE 17

Study Outcome At 24 Hours

| Experimental Group | Study Outcome at 24 Hours Healthy[1] | Diarrhea[2] | Dead[3] |
|---|---|---|---|
| 10 μg Toxin A + Antitoxin Against Interval 6 | 7 | 0 | 0 |
| 30 μg Toxin A + Antitoxin Against Interval 6 | 7 | 0 | 0 |
| 10 μg Toxin A + Pre-Immune Serum | 0 | 5 | 2 |
| 30 μg Toxin A + Pre-Immune | 0 | 5 | 2 |

[1]Animals remained healthy through the entire 24 hour study period.
[2]Animals developed diarrhea, but did not die.
[3]Animals developed diarrhea, and subsequently died.

Pretreatment of toxin A at both doses tested, using the anti-recombinant toxin A IgY, prevented all overt symptoms of disease in hamsters. Therefore, pretreatment of *C. difficile* toxin A, using the anti-recombinant toxin A IgY, neutralized the in vivo enterotoxin activity of the toxin A. In contrast, all animals from the two groups which received toxin A which had been pretreated using pre-immune IgY developed disease symptoms which ranged from diarrhea to death. The diarrhea which developed in the 5 animals which did not die in each of the two pre-immune groups, spontaneously resolved by the end of the 24 hr. study period.

c) Histologic Evaluation of Hamster Ceca

In order to further assess the ability of anti-recombinant toxin A IgY to protect hamsters from the enterotoxin activity of toxin A, histologic evaluations were performed on the ceca of hamsters from the study described in section (b) above.

Three groups of animals were sacrificed in order to prepare histological specimens. The first group consisted of a single representative animal taken from each of the 4 groups of surviving hamsters at the conclusion of the study described in section (b) above. These animals represented the 24 hr. timepoint of the study.

The second group consisted of two animals which were not part of the study described above, but were separately treated with the same toxin A+pre-immune IgY mixtures as described for the animals in section (b) above. Both of these hamsters developed diarrhea, and were sacrificed 8 hrs. after the time of administration of the toxin A+pre-immune IgY mixtures. At the time of sacrifice, both animals were presenting symptoms of diarrhea. These animals represented the acute phase of the study.

The final group consisted of a single untreated hamster from the same shipment of animals as those used for the two previous groups. This animal served as the normal control.

Samples of cecal tissue were removed from the 7 animals described above, and were fixed overnight at 4° C. using 10% buffered formalin. The fixed tissues were paraffin-embedded, sectioned, and mounted on glass microscope slides. The tissue sections were then stained using hematoxylin and eosin (H and E stain), and were examined by light microscopy.

The tissues obtained from the two 24 hr. animals which received mixtures containing either 10 μg or 30 μg of toxin A and anti-recombinant toxin A IgY were indistinguishable from the normal control, both in terms of gross pathology, as well as at the microscopic level. These observations provide further evidence for the ability of anti-recombinant toxin A IgY to effectively neutralize the in vivo enterotoxin activity of *C. difficile* toxin A, and thus its ability to prevent acute or lasting toxin A-induced pathology.

In contrast, the tissues from the two 24 hr. animals which received the toxin A+pre-immune IgY mixtures demonstrated significant pathology. In both of these groups, the mucosal layer was observed to be less organized than in the normal control tissue. The cytoplasm of the epithelial cells had a vacuolated appearance, and gaps were present between the epithelium and the underlying cell layers. The lamina propria was largely absent. Intestinal villi and crypts were significantly diminished, and appeared to have been overgrown by a planar layer of epithelial cells and fibroblasts. Therefore, although these animals overtly appeared to recover from the acute symptoms of toxin A intoxication, lasting pathologic alterations to the cecal mucosa had occurred.

The tissues obtained from the two acute animals which received mixtures of toxin A and pre-immune IgY demonstrated the most significant pathology. At the gross pathological level, both animals were observed to have severely distended ceca which were filled with watery, diarrhea-like material. At the microscopic level, the animal that was given the mixture containing 10 μg of toxin A and pre-immune IgY was found to have a mucosal layer which had a ragged, damaged appearance, and a disorganized, compacted quality. The crypts were largely absent, and numerous breaks in the epithelium had occurred. There was also an influx of erythrocytes into spaces between the epithelial layer and the underlying tissue. The animal which had received the mixture containing 30 μg of toxin A and pre-immune IgY demonstrated the most severe pathology. The cecal tissue of this animal had an appearance very similar to that observed in animals which had died from *C. difficile* disease. Widespread destruction of the mucosa was noted, and the epithelial layer had sloughed. Hemorrhagic areas containing large numbers of erythrocytes were very prevalent. All semblance of normal tissue architecture was absent from this specimen. In terms of the presentation of pathologic events, this in vivo hamster model of toxin A-intoxication correlates very closely with the pathologic consequences of *C. difficile* disease in hamsters. The results presented in this Example demonstrate that while anti-recombinant toxin A (Interval 6) IgY is capable of only partially neutralizing the cytotoxic activity of *C. difficile* toxin A, the same antibody effectively neutralizes 100% of the in vivo enterotoxin activity of the toxin. While it is not intended that this invention be limited to this mechanism, this may be due to the cytotoxicity and enterotoxicity of *C. difficile* Toxin A as two separate and distinct biological functions.

EXAMPLE 15

In Vivo Neutralization of C. Difficile Toxin A by Antibodies Against Recombinant Toxin A Polypeptides The ability of avian antibodies directed against the recombinant *C. difficile* toxin A fragment 1870–2680 (as expressed by pMA1870–2680; see Example 13) to neutralize the enterotoxic activity of toxin A was demonstrated in Example 14. The ability of avian antibodies (IgYs) directed against other recombinant toxin A epitopes to neutralize native toxin A in vivo was next evaluated. This example involved: (a) the preparation of IgYs against recombinant toxin A polypeptides; (b) in vivo protection of hamsters against toxin A by treatment with anti-recombinant toxin A IgYs and (c) quantification of specific antibody concentration in CTA and Interval 6 IgY PEG preparations.

The nucleotide sequence of the coding region of the entire toxin A protein is listed in SEQ ID NO:5. The amino acid sequence of the entire toxin A protein is listed in SEQ ID NO:6. The amino acid sequence consisting of amino acid residues 1870 through 2680 of toxin A is listed in SEQ ID NO:7. The amino acid sequence consisting of amino acid residues 1870 through 1960 of toxin A is listed in SEQ ID NO:8.

a) Preparation of IgY's Against Recombinant Toxin A Polypeptides

Eggs were collected from Leghorn hens which have been immunized with recombinant *C. difficile* toxin A polypeptide fragments encompassing the entire toxin A protein. The polypeptide fragments used as immunogens were: 1) pMA 1870–2680 (Interval 6), 2) pPA 1100–1450 (Interval 4), and 3) a mixture of fragments consisting of pMA 30–300 (Interval 1), pMA 300–660 (Interval 2), pMA 660–1100 (Interval 3) and pMA 1450–1870 (Interval 5). This mixture of immunogens is referred to as Interval 1235. The location of each interval within the toxin A molecule is shown in FIG. 15A. In FIG. 15A, the following abbreviations are used: pP refers to the pET23 vector (New England BioLabs); pM refers to the pMAL™-c vector (New England BioLabs); A refers to toxin A; the numbers refer to the amino acid interval expressed in the clone. (For example, the designation pMA30–300 indicates that the recombinant clone encodes amino acids 30–300 of toxin A and the vector used was pMAL™-c).

The recombinant proteins were generated as described in Example 11. The IgYs were extracted and solubilized in 0.1M carbonate buffer pH 9.5 for oral administration as described in Example 14(a). The IgY reactivities against each individual recombinant interval was evaluated by ELISA as described in Example 13(c).

b) In Vivo Protection of Hamsters Against Toxin A by Treatment with Anti-Recombinant Toxin A Antibodies The ability of antibodies raised against recombinant toxin A polypeptides to provide in vivo protection against the enterotoxic activity of toxin A was examined in the hamster model system. This assay was performed as described in Example 14(b). Briefly, for each 40–50 gram female Golden Syrian hamster (Charles River), 1 ml of IgY 4× (i.e., resuspended in ¼ of the original yolk volume) PEG prep against Interval 6, Interval 4 or Interval 1235 was mixed with 30 $\mu$g ($LD_{100}$ oral dose) of *C. difficile* toxin A (Tech Lab). Preimmune IgY mixed with toxin A served as a negative control. Antibodies raised against *C. difficile* toxoid A (Example 8) mixed with toxin A (CTA) served as a positive control. The mixture was incubated for 1 hour at 37° C. then orally administered to lightly etherized hamsters using an 18G feeding needle. The animals were then observed for the onset of diarrhea and death for a period of approximately 24 hours. The results are shown in Table 18.

TABLE 18

| | Study Outcome After 24 Hours | | |
|---|---|---|---|
| Treatment group | Healthy[1] | Diarrhea[2] | Dead[3] |
| Preimmune | 0 | 0 | 7 |
| CTA | 5 | 0 | 0 |
| Interval 6 | 6 | 1 | 0 |
| Interval 4 | 0 | 1 | 6 |
| Interval 1235 | 0 | 0 | 7 |

[1]Animal shows no sign of illness.
[2]Animal developed diarrhea, but did not die.
[3]Animal developed diarrhea and died.

Figure 16:
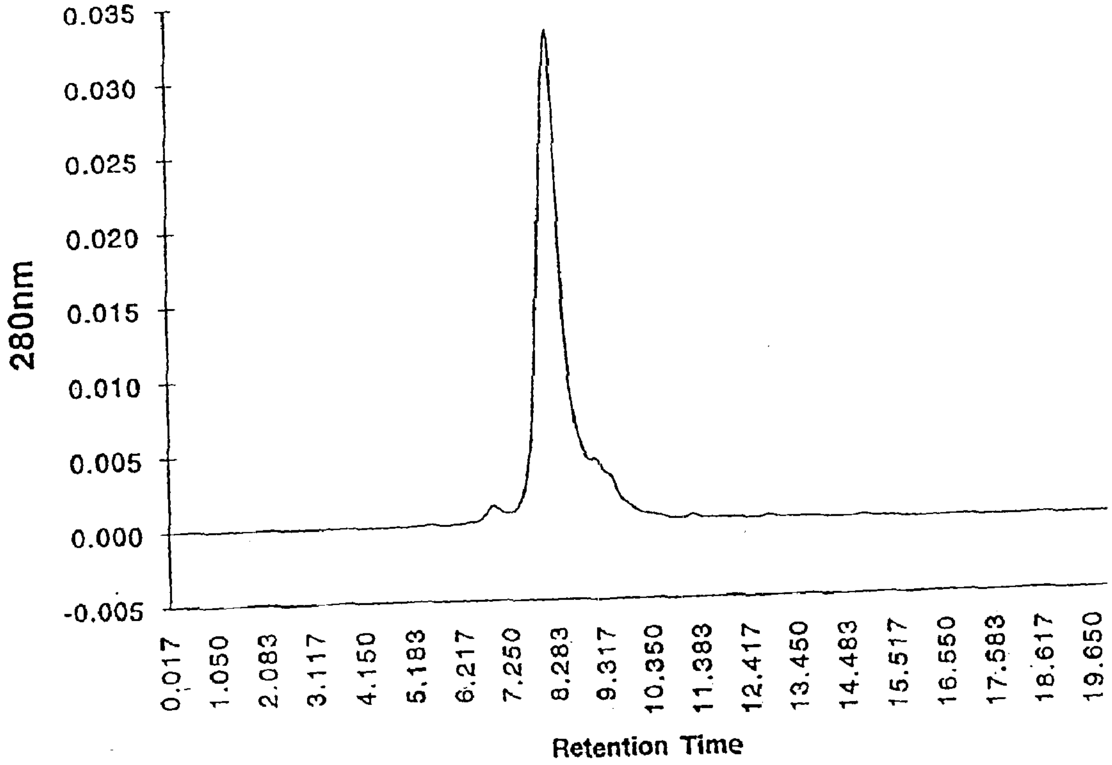
FIG. 16 shows a chromatograph plotting absorbance at 280 nm against retention time for a pMA1870-680 IgY PEG preparation.

Pre-treatment of toxin A with IgYs against Interval 6 prevented diarrhea in 6 of 7 hamsters and completely prevented death in all 7. In contrast, as with preimmune IgY, IgYs against Interval 4 and Interval 1235 had no effect on the onset of diarrhea and death in the hamsters.

c) Quantification of Specific Antibody Concentration in CTA And Interval 6 IgY PEG Preparations To determine the purity of IgY PEG preparations, an aliquot of a pMA1870–2680 (Interval 6) IgY PEG preparation was chromatographed using HPLC and a KW-803 sizing column (Shodex). The resulting profile of absorbance at 280 nm is shown in FIG. 16. The single large peak corresponds to the predicted MW of IgY. Integration of the area under the single large peak showed that greater than 95% of the protein eluted from the column was present in this single peak. This result demonstrated that the majority (>95%) of the material absorbing at 280 nm in the PEG preparation corresponds to IgY. Therefore, absorbance at 280 nm can be used to determine the total antibody concentration in PEG preparations.

To determine the concentration of Interval 6-specific antibodies (expressed as percent of total antibody) within the CTA and pMA1870–2680 (Interval 6) PEG preparations, defined quantities of these antibody preparations were affinity purified on a pPA1870–2680(H) (shown schematically in FIG. 15B) affinity column and the specific antibodies were quantified. In FIG. 15B the following abbreviations are used: pP refers to the pET23 vector (New England BioLabs); pM refers to the pMAL™-c vector (New England BioLabs); pG refers to the pGEX vector (Pharmacia); pB refers to the PinPoint™ Xa vector (Promega); A refers to toxin A; the numbers refer to the amino acid interval expressed in the clone. The solid black ovals represent the MBP; the hatched ovals represent glutathione S-transferase; the hatched circles represent the biotin tag; and HHH represents the polyhistidine tag.

An affinity column containing recombinant toxin A repeat protein was made as follows. Four ml of PBS-washed Actigel resin (Sterogene) was coupled with 5–10 mg of pPA1870–2680 inclusion body protein [prepared as described in Example (17) and dialyzed into PBS] in a 15 ml tube (Falcon) containing 1⁄10 final volume Ald-coupling solution (1 M sodium cyanoborohydride). Aliquots of the supernatant from the coupling reactions, before and after coupling, were assessed by Coomassie staining of 7.5% SDS-PAGE gels. Based upon protein band intensities, greater than 6 mg of recombinant protein was coupled to the resin. The resin was poured into a 10 ml column (BioRad), washed extensively with PBS, pre-eluted with 4 M guanidine-HCl (in 10 mM Tris-HCl, pH 8.0; 0.005% thimerosal) and re-equilibrated with PBS. The column was stored at 4° C.

Aliquots of a pMA1870–2680 (Interval 6) or a CTA IgY polyclonal antibody preparation (PEG prep) were affinity purified on the above affinity column as follows. The column was attached to an UV monitor (ISCO) and washed with PBS. For pMA1870–2680 IgY purification, a 2× PEG prep (filter sterilized using a 0.45μ filter; approximately 500 mg total IgY) was applied. The column was washed with PBS until the baseline was re-established (the column flow-through was saved), washed with BBSTween to elute non-specifically binding antibodies and re-equilibrated with PBS. Bound antibody was eluted from the column in 4 M guanidine-HCl (in 10 mM Tris-HCl, pH 8.0; 0.005% thimerosal). The entire elution peak was collected in a 15 ml tube (Falcon). The column was re-equilibrated and the column eluate was re-chromatographed as described above. The antibody preparation was quantified by UV absorbance (the elution buffer was used to zero the spectrophotometer). Total purified antibody was approximately 9 mg and 1 mg from the first and second chromatography passes, respectively. The low yield from the second pass indicated that most specific antibodies were removed by the first round of chromatography. The estimated percentage of Interval 6 specific antibodies in the pMA1870–2680 PEG prep is approximately 2%.

The percentage of Interval 6 specific antibodies in the CTA PEG prep was determined (utilizing the same column and methodology described above) to be approximately 0.5% of total IgY.

A 4× PEG prep contains approximately 20 mg/ml IgY. Thus in b) above, approximately 400 μg specific antibody in the Interval 6 PEG prep neutralized 30 μg toxin A in vivo.

EXAMPLE 16

In Vivo Treatment Of *C. difficile* Disease In Hamsters By Recombinant Interval 6 Antibodies The ability of antibodies directed against recombinant Interval 6 of toxin A to protect hamsters in vivo from *C. difficile* disease was examined. This example involved: (a) prophylactic treatment of *C. difficile* disease and (b) therapeutic treatment of *C. difficile* disease.

a) Prophylactic Treatment of *C. difficile* Disease

This experiment was performed as described in Example 9(b). Three groups each consisting of 7 female 100 gram Syrian hamsters (Charles River) were prophylactically treated with either preimmune IgYs, IgYs against native toxin A and B [CTAB; see Example 8 (a) and (b)] or IgYs against Interval 6. IgYs were prepared as 4× PEG preparations as described in Example 9(a).

The animals were orally dosed 3 times daily, roughly at 4 hour intervals, for 12 days with 1 ml antibody preparations diluted in Ensure®. Using estimates of specific antibody concentration from Example 15(c), each dose of the Interval 6 antibody prep contained approximately 400 μg of specific antibody. On day 2 each hamster was predisposed to *C. difficile* infection by the oral administration of 3.0 mg of Clindamycin-HCl (Sigma) in 1 ml of water. On day 3 the hamsters were orally challenged with 1 ml of *C. difficile* inoculum strain ATCC 43596 in sterile saline containing approximately 100 organisms. The animals were then observed for the onset of diarrhea and subsequent death during the treatment period. The results are shown in Table 19.

TABLE 19

Lethality After 12 Days Of Treatment

| Treatment Group | Number Animals Alive | Number Animals Dead |
|---|---|---|
| Preimmune | 0 | 7 |
| CTAB | 6 | 1 |
| Interval 6 | 7 | 0 |

Treatment of hamsters with orally-administered IgYs against Interval 6 successfully protected 7 out of 7 (100%) of the animals from *C. difficile* disease. One of the hamsters in this group presented with diarrhea which subsequently resolved during the course of treatment. As shown previously in Example 9, antibodies to native toxin A and toxin B were highly protective. In this Example, 6 out of 7 animals survived in the CTAB treatment group. All of the hamsters treated with preimmune sera came down with diarrhea and died. The survivors in both the CTAB and Interval 6 groups remained healthy throughout a 12 day post-treatment period. In particular, 6 out of 7 Interval 6-treated hamsters survived at least 2 weeks after termination of treatment which suggests that these antibodies provide a long-lasting cure. These results represent the first demonstration that antibodies generated against a recombinant region of toxin A can prevent CDAD when administered passively to be sufficient to protect animals from *C. difficile* disease when administered prophylactically.

Figure 17:
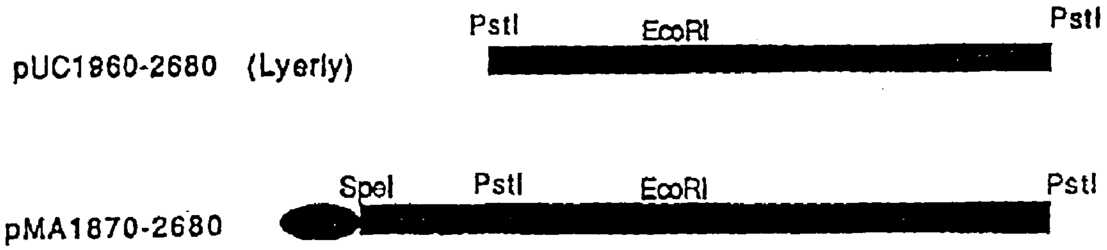
FIG. 17 shows two recombinant *C. difficile* toxin B expression constructs.

Previously others had raised antibodies against toxin A by actively immunizing hamsters against a recombinant polypeptide located within the Interval 6 region [Lyerly, D. M., et al. (1990) Curr. Microbiol. 21:29]. FIG. 17 shows schematically the location of the Lyerly, et al. intra-Interval 6 recombinant protein (cloned into the pUC vector) in comparison with the complete Interval 6 construct (pMA1870–2680) used herein to generate neutralizing antibodies directed against toxin A. In FIG. 17, the solid black oval represents the MBP which is fused to the toxin A Interval 6 in pMA1870–2680.

The Lyerly, et al. antibodies (intra-Interval 6) were only able to partially protect hamsters against *C. difficile* infection in terms of survival (4 out of 8 animals survived) and furthermore, these antibodies did not prevent diarrhea in any of the animals. Additionally, animals treated with the intra-Interval 6 antibodies [Lyerly, et al. (1990), supra] died when treatment was removed.

In contrast, the experiment shown above demonstrates that passive administration of anti-Interval 6 antibodies prevented diarrhea in 6 out of 7 animals and completely prevented death due to CDAD. Furthermore, as discussed above, passive administration of the anti-Interval 6 antibodies provides a long lasting cure (i.e., treatment could be withdrawn without incident).

b) Therapeutic Treatment of *C. difficile* Disease: In Vivo Treatment of an Established *C. difficile* Infection in Hamsters with Recombinant Interval 6 Antibodies The ability of antibodies against recombinant interval 6 of toxin A to therapeutically treat *C. difficile* disease was examined. The experiment was performed essentially as described in Example 10(b). Three groups, each containing seven to eight female Golden Syrian hamsters (100 g each; Charles River) were treated with either preimmune IgY, IgYs against native toxin A and toxin B (CTAB) and IgYs against Interval 6. The antibodies were prepared as described above as 4× PEG preparations.

The hamsters were first predisposed to *C. difficile* infection with a 3 mg dose of Clindamycin-HCl (Sigma) administered orally in 1 ml of water. Approximately 24 hrs later, the animals were orally challenged with 1 ml of *C. difficile* strain ATCC 43596 in sterile saline containing approximately 200 organisms. One day after infection, the presence of toxin A and B was determined in the feces of the hamsters using a commercial immunoassay kit (Cytoclone A+B EPA, Cambridge Biotech) to verify establishment of infection. Four members of each group were randomly selected and tested. Feces from an uninfected hamster was tested as a negative control. All infected animals tested positive for the presence of toxin according to the manufacturer's procedure. The initiation of treatment then started approximately 24 hr post-infection.

The animals were dosed daily at roughly 4 hr intervals with 1 ml antibody preparation diluted in Ensure® (Ross Labs). The amount of specific antibodies given per dose (determined by affinity purification) was estimated to be about 400 $\mu$g of anti-Interval 6 IgY (for animals in the Interval 6 group) and 100 $\mu$g and 70 $\mu$g of antitoxin A (Interval 6-specific) and anti-toxin B (Interval 3-specific; see Example 19), respectively, for the CTAB preparation. The animals were treated for 9 days and then observed for an additional 4 days for the presence of diarrhea and death. The results indicating the number of survivors and the number of dead 4 days post-infection are shown in Table 20.

TABLE 20

In vivo Therapeutic Treatment With Interval 6 Antibodies

| Treatment Group | Number Animals Alive | Number Animals Dead |
|---|---|---|
| Preimmune | 4 | 3 |
| CTAB | 8 | 0 |
| Interval 6 | 8 | 0 |

Antibodies directed against both Interval 6 and CTAB successfully prevented death from *C. difficile* when therapeutically administered 24 hr after infection. This result is significant since many investigators begin therapeutic treatment of hamsters with existing drugs (e.g., vancomycin, phenelfamycins, tiacumicins, etc.) 8 hr post-infection [Swanson, et al. (1991) Antimicrobial Agents and Chemotherapy 35:1108 and (1989) J. Antibiotics 42:94].

Forty-two percent of hamsters treated with preimmune IgY died from CDAD. While the anti-Interval 6 antibodies prevented death in the treated hamsters, they did not eliminate all symptoms of CDAD as 3 animals presented with slight diarrhea. In addition, one CTAB-treated and one preimmune-treated animal also had diarrhea 14 days post-infection. These results indicate that anti-Interval 6 antibodies provide an effective means of therapy for CDAD.

EXAMPLE 17

Induction of Toxin A Neutralizing Antibodies Requires Soluble Interval 6 Protein As shown in Examples 11 (d) and 15, expression of recombinant proteins in *E. coli* may result in the production of either soluble or insoluble protein. If insoluble protein is produced, the recombinant protein is solubilized prior to immunization of animals. To determine whether, one or both of the soluble or insoluble recombinant proteins could be used to generate neutralizing antibodies to toxin A, the following experiment was performed. This example involved a) expression of the toxin A repeats and subfragments of these repeats in *E. coli* using a variety of expression vectors; b) identification of recombinant toxin A repeats and sub-regions to which neutralizing antibodies bind; and c) determination of the neutralization ability of antibodies raised against soluble and insoluble toxin A repeat immunogen.

a) Expression of the Toxin A Repeats and Subfragments of these Repeats in E. coli Using A Variety Of Expression Vectors The Interval 6 immunogen utilized in Examples 15 and 16 was the pMA1870–2680 protein, in which the toxin A repeats are expressed as a soluble fusion protein with the MBP (described in Example 11). Interestingly, expression of this region (from the SpeI site to the end of the repeats, see FIG. 15B) in three other expression constructs, as either native (pPA1870–2680), poly-His tagged [pPA1870–2680 (H)] or biotin-tagged (pBA1870–2680) proteins resulted in completely insoluble protein upon induction of the bacterial host (see FIG. 15B). The host strain BL21 (Novagen) was used for expression of pBA1870–2680 and host strain BL21(DE3) (Novagen) was used for expression of pPA1870–2680 and pPA1870–2680(H). These insoluble proteins accumulated to high levels in inclusion bodies. Expression of recombinant plasmids in *E. coli* host cells grown in 2× YT medium was performed as described [Williams, et al. (1995), supra].

As summarized in FIG. 15B, expression of fragments of the toxin A repeats (as either N-terminal SpeI-EcoR fragments, or C-terminal EcoRI-end fragments) also yielded high levels of insoluble protein using pGEX (pGA1870–2190), PinPoint™-Xa (pBA1870–2190 and pBA2250–2680) and pET expression systems (pPA1870–2190). The pGEX and pET expression systems are described in Example 11. The PinPoint™-Xa expression system drives the expression of fusion proteins in *E. coli*. Fusion proteins from PinPoint™-Xa vectors contain a biotin tag at the amino-terminal end and can be affinity purified SoftLink™ Soft Release avidin resin (Promega) under mild denaturing conditions (5 mM biotin).

The solubility of expressed proteins from the pPG1870–2190 and pPA1870–2190 expression constructs was determined after induction of recombinant protein expression under conditions reported to enhance protein solubility [These conditions comprise growth of the host at reduced temperature (30° C.) and the utilization of high (1 mM IPTG) or low (0.1 mM IPTG) concentrations of inducer [Williams et al. (1995), supra]. All expressed recombinant toxin A protein was insoluble under these conditions. Thus, expression of these fragments of the toxin A repeats in pET and pGEX expression vectors results in the production of insoluble recombinant protein even when the host cells are grown at reduced temperature and using lower concentrations of the inducer. Although expression of these fragments in pMal vectors yielded affinity purifiable soluble fusion protein, the protein was either predominantly insoluble (pMA1870–2190) or unstable (pMA2250–2650). Attempts to solubilize expressed protein from the pMA1870–2190 expression construct using reduced temperature or lower inducer concentration (as described above) did not improve fusion protein solubility.

Collectively, these results demonstrate that expression of the toxin A repeat region in *E. coli* results in the production of insoluble recombinant protein, when expressed as either large (aa 1870–2680) or small (aa 1870–2190 or aa 2250–2680) fragments, in a variety of expression vectors (native or poly-His tagged pET, pGEX or PinPoint™-Xa vectors), utilizing growth conditions shown to enhance protein solubility. The exception to this rule were fusions with the MBP, which enhanced protein solubility, either partially (pMA1870–2190) or fully (pMA1870–2680).

b) Identification of Recombinant Toxin A Repeats and Sub-Regions to which Neutralizing Antibodies Bind Toxin A repeat regions to which neutralizing antibodies bind were identified by utilizing recombinant toxin A repeat region proteins expressed as soluble or insoluble proteins to deplete protective antibodies from a polyclonal pool of antibodies against native *C. difficile* toxin A. An in vivo assay was developed to evaluate proteins for the ability to bind neutralizing antibodies.

The rational for this assay is as follows. Recombinant proteins were first pre-mixed with antibodies against native toxin A (CTA antibody; generated in Example 8) and allowed to react. Subsequently, *C. difficile* toxin A was added at a concentration lethal to hamsters and the mixture was administered to hamsters via IP injection. If the recombinant protein contains neutralizing epitopes, the CTA antibodies would lose their ability to bind toxin A resulting in diarrhea and/or death of the hamsters.

The assay was performed as follows. The lethal dose of toxin A when delivered orally to nine 40 to 50 g Golden Syrian hamsters (Sasco) was determined to be 10 to 30 μg. The PEG-purified CTA antibody preparation was diluted to 0.5× concentration (i.e., the antibodies were diluted at twice the original yolk volume) in 0.1 M carbonate buffer, pH 9.5. The antibodies were diluted in carbonate buffer to protect them from acid degradation in the stomach. The concentration of 0.5× was used because it was found to be the lowest effective concentration against toxin A. The concentration of Interval 6-specific antibodies in the 0.5× CTA prep was estimated to be 10–15 μg/ml (estimated using the method described in Example 15).

Figure 15:
FIG. 15 shows *C. difficile* toxin A expression constructs.

The inclusion body preparation [insoluble Interval 6 protein; pPA1870–2680(H)] and the soluble Interval 6 protein [pMA1870–2680; see FIG. 15] were both compared for their ability to bind to neutralizing antibodies against *C. difficile* toxin A (CTA). Specifically, 1 to 2 mg of recombinant protein was mixed with 5 ml of a 0.5× CTA antibody prep (estimated to contain 60–70 μg of Interval 6-specific antibody). After incubation for 1 hr at 37° C., CTA (Tech Lab) at a final concentration of 30 μg/ml was added and incubated for another 1 hr at 37° C. One ml of this mixture containing 30 μg of toxin A (and 10–15 μg of Interval 6-specific antibody) was administered orally to 40–50 g Golden Syrian hamsters (Sasco). Recombinant proteins that result in the loss of neutralizing capacity of the CTA antibody would indicate that those proteins contain neutralizing epitopes. Preimmune and CTA antibodies (both at 0.5×) without the addition of any recombinant protein served as negative and positive controls, respectively.

Two other inclusion body preparations, both expressed as insoluble products in the pET vector, were tested; one containing a different insert (toxin B fragment) other than Interval 6 called pPB1850–2070 (see FIG. 18) which serves as a control for insoluble Interval 6, the other was a truncated version of the Interval 6 region called pPA1870–2190 (see FIG. 15B). The results of this experiment are shown in Table 21.

TABLE 21

Binding Of Neutralizing Antibodies By Soluble Interval 6 Protein Study Outcome After 24 Hours

| Treatment Group[1] | Healthy[2] | Diarrhea[3] | Dead[4] |
|---|---|---|---|
| Preimmune Ab | 0 | 3 | 2 |
| CTA Ab | 4 | 1 | 0 |
| CTA Ab + Int 6 (soluble) | 1 | 2 | 2 |
| CTA Ab + Int 6 (insoluble) | 5 | 0 | 0 |
| CTA Ab + pPB1850-2070 | 5 | 0 | 0 |
| CTA Ab + pPA1870-2190 | 5 | 0 | 0 |

[1]*C. difficile* toxin A (CTA) was added to each group.
[2]Animals showed no signs of illness.
[3]Animals developed diarrhea but did not die.
[4]Animals developed diarrhea and died.

Preimmune antibody was ineffective against toxin A, while anti-CTA antibodies at a dilute 0.5× concentration almost completely protected the hamsters against the enterotoxic effects of CTA. The addition of recombinant proteins pPB1850–2070 or pPA1870–2190 to the anti-CTA antibody had no effect upon its protective ability, indicating that these recombinant proteins do not bind to neutralizing antibodies. On the other hand, recombinant Interval 6 protein was able to bind to neutralizing anti-CTA antibodies and neutralized the in vivo protective effect of the anti-CTA antibodies. Four out of five animals in the group treated with anti-CTA antibodies mixed with soluble Interval 6 protein exhibited toxin associated toxicity (diarrhea and death). Moreover, the results showed that Interval 6 protein must be expressed as a soluble product in order for it to bind to neutralizing anti-CTA antibodies since the addition of insoluble Interval 6 protein had no effect on the neutralizing capacity of the CTA antibody prep.

c) Determination of Neutralization Ability of Antibodies Raised Against Soluble and Insoluble Toxin A Repeat Immunogen To determine if neutralizing antibodies are induced against solubilized inclusion bodies, insoluble toxin A repeat protein was solubilized and specific antibodies were raised in chickens. Insoluble pPA1870–2680 protein was solubilized using the method described in Williams et al. (1995), supra. Briefly, induced cultures (500 ml) were pelleted by centrifugation at 3,000× g for 10 min at 4° C. The cell pellets were resuspended thoroughly in 10 ml of inclusion body sonication buffer (25 mM HEPES pH 7.7, 100 mM KCl, 12.5 mM $MgCl_2$, 20% glycerol, 0.1% (v/v) Nonidet P-40, 1 mM DTT). The suspension was transferred to a 30 ml non-glass centrifuge tube. Five hundred μl of 10 mg/ml lysozyme was added and the tubes were incubated on ice for min. The suspension was then frozen at −70° C. for at least 1 hr. The suspension was thawed rapidly in a water bath at room temperature and then placed on ice. The suspension was then sonicated using at least eight 15 sec bursts of the microprobe (Branson Sonicator Model No. 450) with intermittent cooling on ice.

The sonicated suspension was transferred to a 35 ml Oakridge tube and centrifuged at 6,000× g for 10 min at 4° C. to pellet the inclusion bodies. The pellet was washed 2 times by pipetting or vortexing in fresh, ice-cold RIPA buffer [0.1% SDS, 1% Triton X-100, 1% sodium deoxycholate in TBS (25 mM Tris-C1 pH 7.5, 150 mM NaCl)]. The inclusion bodies were recentrifuged after each wash. The inclusion bodies were dried and transferred using a small metal spatula to a 15 ml tube (Falcon). One ml of 10% SDS was added and the pellet was solubilized by gently pipetting the solution up and down using a 1 ml micropipettor. The solubilization was facilitated by heating the sample to 95° C. when necessary.

Once the inclusion bodies were in solution, the samples were diluted with 9 volumes of PBS. The protein solutions were dialyzed overnight against a 100-fold volume of PBS containing 0.05% SDS at room temperature. The dialysis buffer was then changed to PBS containing 0.01% SDS and the samples were dialyzed for several hours to overnight at room temperature. The samples were stored at 4° C. until used. Prior to further use, the samples were warmed to room temperature to allow any precipitated SDS to go back into solution.

The inclusion body preparation was used to immunize hens. The protein was dialyzed into PBS and emulsified with approximately equal volumes of CFA for the initial immunization or IFA for subsequent booster immunizations. On day zero, for each of the recombinant preparations, two egg laying white Leghorn hens were each injected at multiple sites (IM and SC) with 1 ml of recombinant protein-adjuvant mixture containing approximately 0.5–1.5 mg of recombinant protein. Booster immunizations of 1.0 mg were given on days 14 and day 28. Eggs were collected on day 32 and the antibody isolated using PEG as described in Example 14(a). High titers of toxin A specific antibodies were present (as assayed by ELISA, using the method described in Example 13). Titers were determined for both antibodies against recombinant polypeptides pPA1870–2680 and pMA1870–2680 and were found to be comparable at >1:62,500.

Antibodies against soluble Interval 6 (pMA1870–2680) and insoluble Interval 6 [(inclusion body), pPA1870–2680] were tested for neutralizing ability against toxin A using the in vivo assay described in Example 15(b). Preimmune antibodies and antibodies against toxin A (CTA) served as negative and positive controls, respectively. The results are shown in Table 22.

TABLE 22

Neutralization Of Toxin A By Antibodies Against Soluble Interval 6 Protein Study Outcome After 24 Hours

| Antibody Treatment Group | Healthy[1] | Diarrhea[2] | Dead[3] |
|---|---|---|---|
| Preimmune | 1 | 0 | 4 |
| CTA | 5 | 0 | 0 |
| Interval 6 (Soluble)[4] | 5 | 0 | 0 |
| Interval 6 (Insoluble) | 0 | 2 | 3 |

[1]Animals showed no sign of illness.
[2]Animal developed diarrhea but did not die.
[3]Animal developed diarrhea and died.
[4]400 μg/ml.

Antibodies raised against native toxin A were protective while preimmune antibodies had little effect. As found using the in vitro CHO assay [described in Example 8(d)] where antibodies raised against the soluble Interval 6 could partially neutralize the effects of toxin A, here they were able to completely neutralize toxin A in vivo. In contrast, the antibodies raised against the insoluble Interval 6 was unable to neutralize the effects of toxin A in vivo as shown above (Table 22) and in vitro as shown in the CHO assay [described in Example 8(d)].

These results demonstrate that soluble toxin A repeat immunogen is necessary to induce the production of neutralizing antibodies in chickens, and that the generation of such soluble immunogen is obtained only with a specific expression vector (pMal) containing the toxin A region spanning aa 1870–2680. That is to say, insoluble protein that is subsequently solubilized does not result in a toxin A antigen that will elicit a neutralizing antibody.

EXAMPLE 18

Cloning and Expression of the *C. difficile* Toxin B Gene

The toxin B gene has been cloned and sequenced; the amino acid sequence deduced from the cloned nucleotide sequence predicts a MW of 269.7 kD for toxin B [Barroso et al., Nucl. Acids Res. 18:4004 (1990)]. The nucleotide sequence of the coding region of the entire toxin B gene is listed in SEQ ID NO:9. The amino acid sequence of the entire toxin B protein is listed in SEQ ID NO:10. The amino acid sequence consisting of amino acid residues 1850 through 2360 of toxin B is listed in SEQ ID NO:11. The amino acid sequence consisting of amino acid residues 1750 through 2360 of toxin B is listed in SEQ ID NO:12.

Given the expense and difficulty of isolating native toxin B protein, it would be advantageous to use simple and inexpensive procaryotic expression systems to produce and purify high levels of recombinant toxin B protein for immunization purposes.

Ideally, the isolated recombinant protein would be soluble in order to preserve native antigenicity, since solubilized inclusion body proteins often do not fold into native conformations. Indeed as shown in Example 17, neutralizing antibodies against recombinant toxin A were only obtained when soluble recombinant toxin A polypeptides were used as the immunogen. To allow ease of purification, the recombinant protein should be expressed to levels greater than 1 mg/liter of *E. coli* culture.

To determine whether high levels of recombinant toxin B protein could be produced in *E. coli*, fragments of the toxin B gene were cloned into various prokaryotic expression vectors, and assessed for the ability to express recombinant toxin B protein in *E. coli*. This Example involved (a) cloning of the toxin B gene and (b) expression of the toxin B gene in *E. coli*.

a) Cloning of the Toxin B Gene

The toxin B gene was cloned using PCR amplification from *C. difficile* genomic DNA. Initially, the gene was cloned in two overlapping fragments, using primer pairs P5/P6 and P7/P8. The location of these primers along the toxin B gene is shown schematically in FIG. 18. The sequence of each of these primers is: P5: 5' TAGAAAAAATGGCAAATGT 3' (SEQ ID NO:11); P6: 5' TTTCATCTTGTA GAGTCAAAG 3' (SEQ ID NO:12); P7: 5' GATGCCACAAGATGATTTAGTG 3' (SEQ ID NO:13); and P8: 5' CTAATTGAGCTGTATCAGGATC 3' (SEQ ID NO:14).

Figure 18:
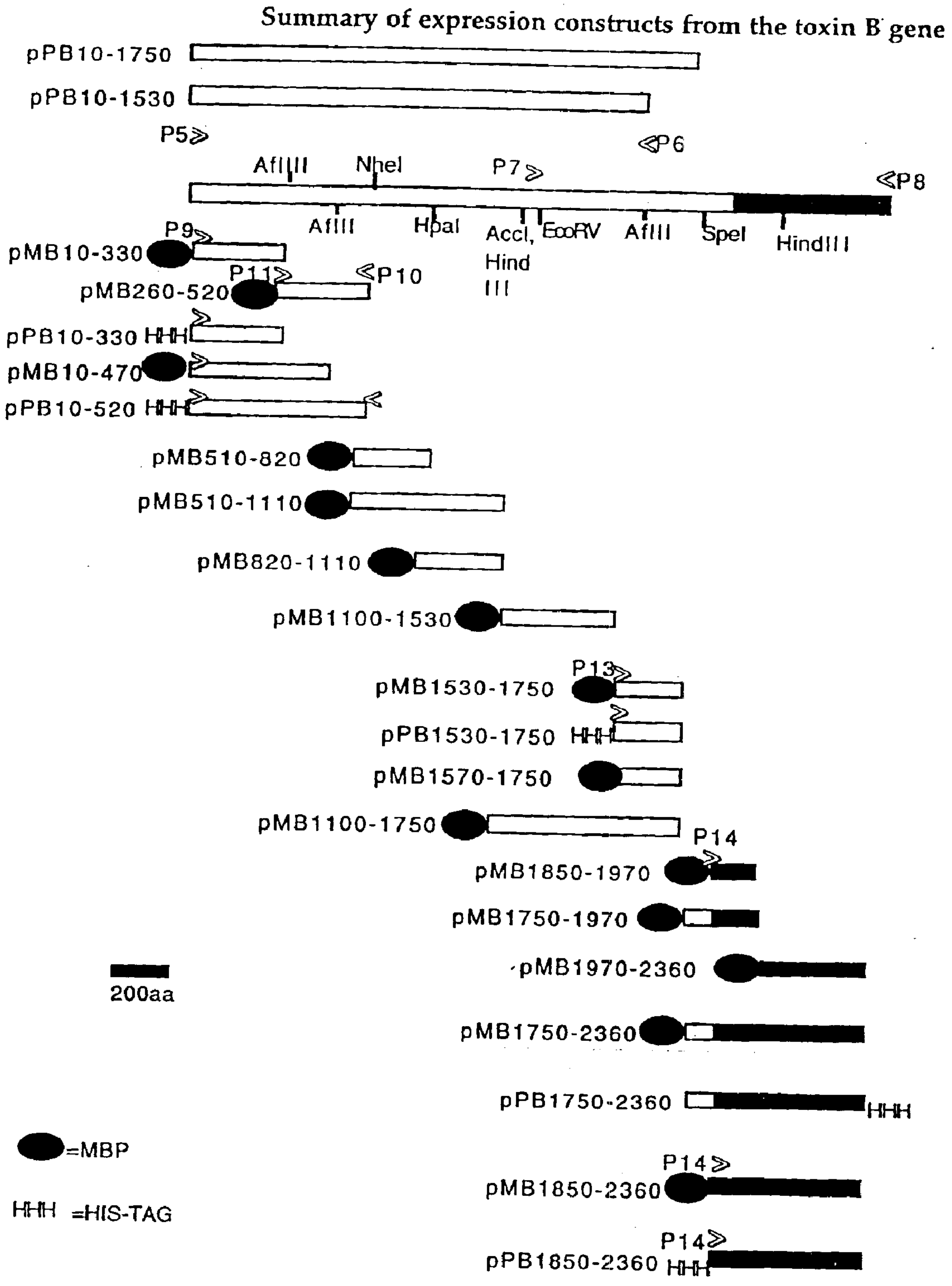
FIG. 18 shows *C. difficile* toxin B expression constructs.

FIG. 18 also shows the location of the following primers along the toxin B gene: P9 which consists of the sequence 5' CGGAATTCCTAGAAAAAATGGCAA ATG 3' (SEQ ID NO:15); P10 which consists of the sequence 5' GCTCTAGAATGA CCATAAGCTAGCCA 3' (SEQ ID NO:16); P11 which consists of the sequence 5' CGGAATTCGAGTTGGTAGAAAGGTGGA 3' (SEQ ID NO:17); P13 which consists of the sequence 5' CGGAATTCGGTTATTATCTTAAGGATG 3' (SEQ ID NO:18); and P14 which consists of the sequence 5' CGGAATTCTTGATAACTGGAT TTGTGAC 3' (SEQ ID NO:19). The amino acid sequence consisting of amino acid residues 1852 through 2362 of toxin B is listed in SEQ ID NO:20. The amino acid sequence consisting of amino acid residues 1755 through 2362 of toxin B is listed in SEQ ID NO:21.

*Clostridium difficile* VPI strain 10463 was obtained from the American Type Culture Collection (ATCC 43255) and grown under anaerobic conditions in brain-heart infusion medium (Becton Dickinson). High molecular-weight *C. difficile* DNA was isolated essentially as described [Wren and Tabaqchali (1987) J. Clin. Microbiol., 25:2402], except 1) 100 μg/ml proteinase K in 0.5% SDS was used to disrupt the bacteria and 2) cetytrimethylammonium bromide (CTAB) precipitation [as described by Ausubel et al., Eds., *Current Protocols in Molecular Biology*, Vol. 2 (1989) Current Protocols] was used to remove carbohydrates from the cleared lysate. Briefly, after disruption of the bacteria with proteinase K and SDS, the solution is adjusted to approximately 0.7 M NaCl by the addition of a 1/7 volume of 5M NaCl. A 1/10 volume of CTAB/NaCl (10% CTAB in 0.7 M NaCl) solution was added and the solution was mixed thoroughly and incubated 10 min at 65° C. An equal volume of chloroform/isoamyl alcohol (24:1) was added and the phases were thoroughly mixed. The organic and aqueous phases were separated by centrifugation in a microfuge for 5 min. The aqueous supernatant was removed and extracted with phenol/chloroform/isoamyl alcohol (25:24:1). The phases were separated by centrifugation in a microfuge for 5 min. The supernatant was transferred to a fresh tube and the DNA was precipitated with isopropanol. The DNA precipitate was pelleted by brief centrifugation in a microfuge. The DNA pellet was washed with 70% ethanol to remove residual CTAB. The DNA pellet was then dried and redissolved in TE buffer (10 mM Tris-HCl pH 80, 1 mM EDTA). The integrity and yield of genomic DNA was assessed by comparison with a serial dilution of uncut lambda DNA after electrophoresis on an agarose gel.

Toxin B fragments were cloned by PCR utilizing a proofreading thermostable DNA polymerase [native Pfu polymerase (Stratagene)]. The high fidelity of this polymerase reduces the mutation problems associated with amplification by error prone polymerases (e.g., Taq polymerase). PCR amplification was performed using the PCR primer pairs P5 (SEQ ID NO:11) with P6 (SEQ ID NO:12) and P7 (SEQ ID NO:13) with P8 (SEQ ID NO:14) in 50 μl reactions containing 10 mM Tris-HCl pH 8.3, 50 mM KCl, 1.5 mM $MgCl_2$, 200 μM of each dNTP, 0.2 μM each primer, and 50 ng *C. difficile* genomic DNA. Reactions were overlaid with 100 μl mineral oil, heated to 94° C. for 4 min, 0.511 native Pfu polymerase (Stratagene) was added, and the reactions were cycled 30 times at 94° C. for 1 min, 50° C. for 1 min, 72° C. (2 min for each kb of sequence to be amplified), followed by 10 min at 72° C. Duplicate reactions were pooled, chloroform extracted, and ethanol precipitated. After washing in 70% ethanol, the pellets were resuspended in 50 μl TE buffer (10 mM Tris-HCl pH 8.0, 1 mM EDTA).

The P5/P6 amplification product was cloned into pUC19 as outlined below. 10 μl aliquots of DNA were gel purified using the Prep-a-Gene kit (BioRad), and ligated to SmaI restricted pUC19 vector. Recombinant clones were isolated and confirmed by restriction digestion using standard recombinant molecular biology techniques (Sambrook et al., 1989). Inserts from two independent isolates were identified in which the toxin B insert was oriented such that the vector BamHI and SacI sites were 5' and 3' oriented, respectively (pUCB10–1530). The insert-containing BamHI/SacI fragment was cloned into similarly cut pET23a–c vector DNA, and protein expression was induced in small scale cultures (5 ml) of identified clones.

Total protein extracts were isolated, resolved on SDS-PAGE gels, and toxin B protein identified by Western analysis utilizing a goat anti-toxin B affinity purified antibody (Tech Lab). Procedures for protein induction, SDS-PAGE, and Western blot analysis were performed as described in Williams et al. (1995), supra. In brief, 5 ml cultures of bacteria grown in 2XYT containing 100 μg/ml ampicillin containing the appropriate recombinant clone were induced to express recombinant protein by addition of IPTG to 1 mM. The *E. coli* hosts used were: BL21(DE3) or BL21(DE3)LysS (Novagen) for pET plasmids.

Cultures were induced by the addition of IPTG to a final concentration of 1.0 mM when the cell density reached 0.5 $OD_{600}$, and induced protein was allowed to accumulate for two hrs after induction. Protein samples were prepared by pelleting 1 ml aliquots of bacteria by centrifugation (1 min in microfuge), and resuspension of the pelleted bacteria in 150 μl of 2× SDS-PAGE sample buffer (0.125 mM Tris-HCl pH 6.8, 2 mM EDTA, 6% SDS, 20% glycerol, 0.025% bromophenol blue; 5-mercaptoethanol is added to 5% before use). The samples were heated to 95° C. for 5 min, then cooled and 5 or 10 μls loaded on 7.5% SDS-PAGE gels. High molecular weight protein markers (BioRad) were also loaded, to allow estimation of the MW of identified fusion proteins. After electrophoresis, protein was detected either generally by staining the gels with Coomassie Blue, or specifically, by blotting to nitrocellulose for Western blot detection of specific immunoreactive protein. The MW of induced toxin B reactive protein allowed the integrity of the toxin B reading frame to be determined.

The pET23b recombinant (pPB10–1530) expressed high MW recombinant toxin B reactive protein, consistent with predicted values. This confirmed that frame terminating errors had not occurred during PCR amplification. A pET23b expression clone containing the 10–1750aa interval of the toxin B gene was constructed, by fusion of the EcoRV-SpeI fragment of the P7/P8 amplification product to the P5-EcoRV interval of the P5/P6 amplification product (see FIG. 18) in pPB10–1530. The integrity of this clone (pPB10–1750) was confirmed by restriction mapping, and Western blot detection of expressed recombinant toxin B protein. Levels of induced protein from both pPB10–1530 and pPB10–1750 were too low to facilitate purification of usable amounts of recombinant toxin B protein. The remaining 1750–2360 aa interval was directly cloned into pMAL or pET expression vectors from the P7/P8 amplification product as described below.

b) Expression of the Toxin B Gene i) Overview of Expression Methodologies

Fragments of the toxin B gene were expressed as either native or fusion proteins in *E. coli*. Native proteins were expressed in either the pET23a–c or pET16b expression vectors (Novagen). The pET23 vectors contain an extensive polylinker sequence in all three reading frames (a–c vectors) followed by a C-terminal poly-histidine repeat. The pET16b vector contains a N-terminal poly-histidine sequence immediately 5' to a small polylinker. The poly-histidine sequence binds to Ni-Chelate columns and allows affinity purification of tagged target proteins [Williams et al. (1995), supra]. These affinity tags are small (10 aa for pET16b, 6 aa for pET23) allowing the expression and affinity purification of native proteins with only limited amounts of foreign sequences.

An N-terminal histidine-tagged derivative of pET16b containing an extensive cloning cassette was constructed to facilitate cloning of N-terminal poly-histidine tagged toxin B expressing constructs. This was accomplished by replacement of the promoter region of the pET23a and b vectors with that of the pET16b expression vector. Each vector was restricted with BglII and NdeI, and the reactions resolved on a 1.2% agarose gel. The pET16b promoter region (contained in a 200 bp BglII-NdeI fragment) and the promoter-less pET23 a or b vectors were cut from the gel, mixed and Prep-A-Gene (BioRad) purified. The eluted DNA was ligated, and transformants screened for promoter replacement by NcoI digestion of purified plasmid DNA (the pET16b promoter contains this site, the pET23 promoter does not). These clones (denoted pETHisa or b) contain the pET16b promoter (consisting of a pT7-lac promoter, ribosome binding site and poly-histidine (10aa) sequence) fused at the NdeI site to the extensive pET23 polylinker.

All MBP fusion proteins were constructed and expressed in the pMAL™-c or pMAL™-p2 vectors (New England Biolabs) in which the protein of interest is expressed as a C-terminal fusion with MBP. All pET plasmids were expressed in either the BL21(DE3) or BL21(DE3)LysS expression hosts, while pMal plasmids were expressed in the BL21 host.

Large scale (500 mls to 1 liter) cultures of each recombinant were grown in 2×YT broth, induced, and soluble protein fractions were isolated as described [Williams, et al. (1995), supra]. The soluble protein extracts were affinity chromatographed to isolate recombinant fusion protein, as described [Williams et al., (1995) supra]. In brief, extracts containing tagged pET fusions were chromatographed on a nickel chelate column, and eluted using imidazole salts or low pH (pH 4.0) as described by the distributor (Novagen or Qiagen). Extracts containing soluble pMAL fusion protein were prepared and chromatographed in PBS buffer over an amylose resin (New England Biolabs) column, and eluted with PBS containing 10 mM maltose as described [Williams et al. (1995), supra).

ii) Overview of Toxin B Expression

In both large expression constructs described in (a) above, only low level (i.e., less than 1 mg/liter of intact or nondegraded recombinant protein) expression of recombinant protein was detected. A number of expression constructs containing smaller fragments of the toxin B gene were then constructed, to determine if small regions of the gene can be expressed to high levels (i.e., greater than 1 mg/liter intact protein) without extensive protein degradation. All were constructed by in frame fusions of convenient toxin B restriction fragments to either the pMAL-c, pET23a–c, pET16b or pETHisa-b expression vectors, or by engineering restriction sites at specific locations using PCR amplification [using the same conditions described in (a) above]. In all cases, clones were verified by restriction mapping, and, where indicated, DNA sequencing.

Protein preparations from induced cultures of each of these constructs were analyzed, by SDS-PAGE, to estimate protein stability (Coomassie Blue staining) and immunoreactivity against anti-toxin B specific antiserum (Western analysis). Higher levels of intact (i.e., nondegraded), full length fusion proteins were observed with the smaller constructs as compared with the larger recombinants, and a series of expression constructs spanning the entire toxin B gene were constructed (FIGS. 18, 19 and 20 and Table 23).

Figure 19:
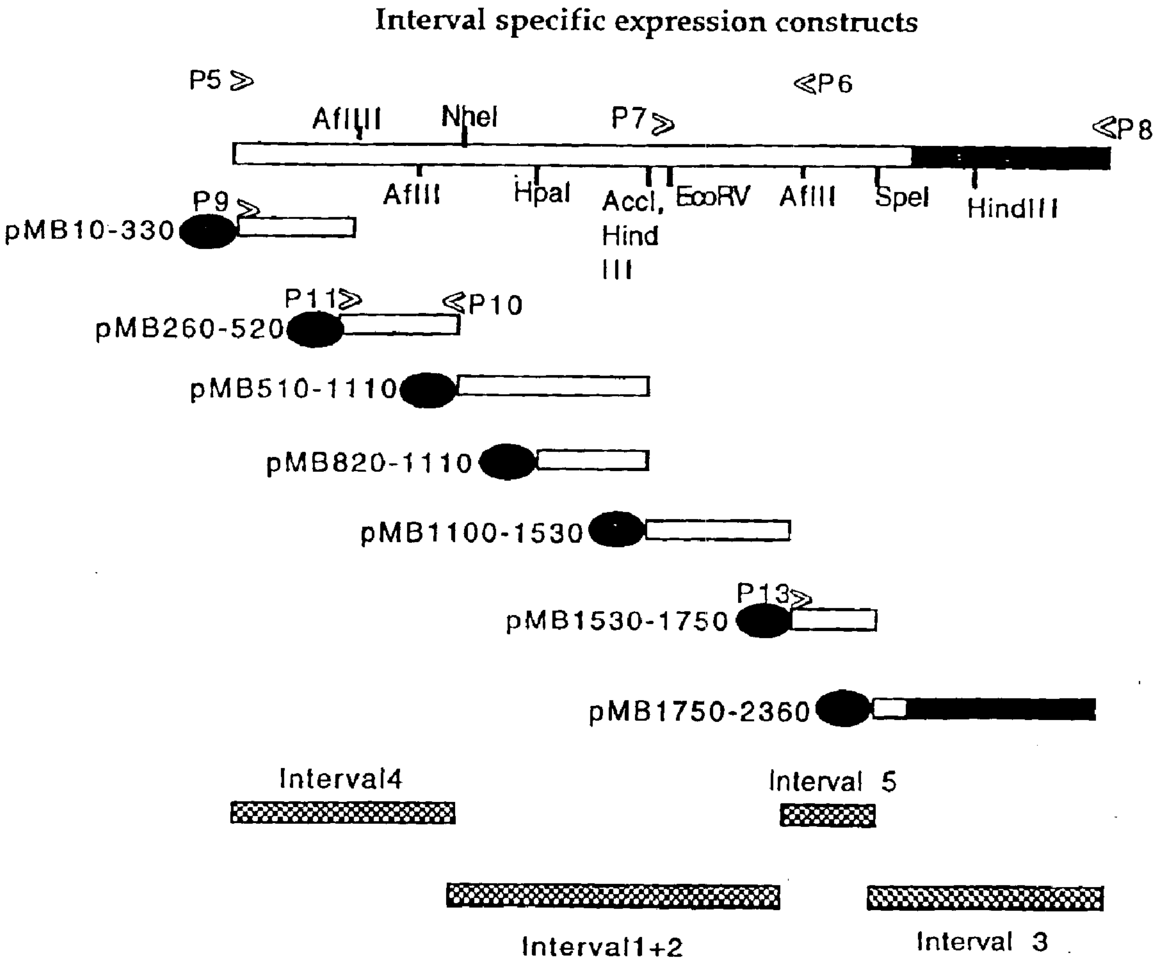
FIG. 19 shows *C. difficile* toxin B expression constructs.
Figure 20:
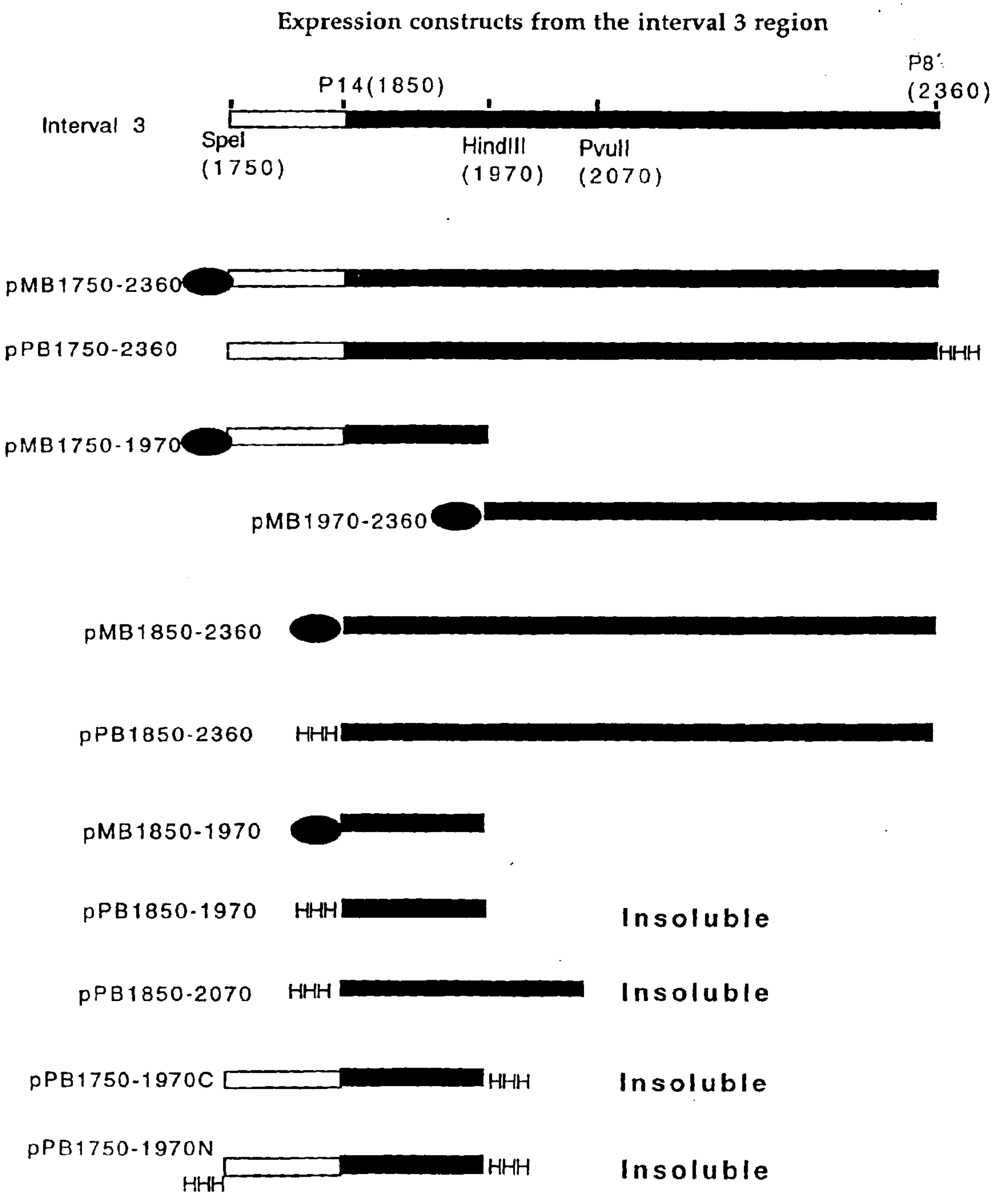
FIG. 20 shows *C. difficile* toxin B expression constructs.

Constructs that expressed significant levels of recombinant toxin B protein (greater than 1 mg/liter intact recombinant protein) in *E. coli* were identified and a series of these clones that spans the toxin B gene are shown in FIG. 19 and summarized in Table 23. These clones were utilized to isolate pure toxin B recombinant protein from the entire toxin B gene. Significant protein yields were obtained from pMAL expression constructs spanning the entire toxin B gene, and yields of full length soluble fusion protein ranged from an estimated 1 mg/liter culture (pMB1100–1530) to greater than 20 mg/liter culture (pMB1750–2360).

Figure 21:
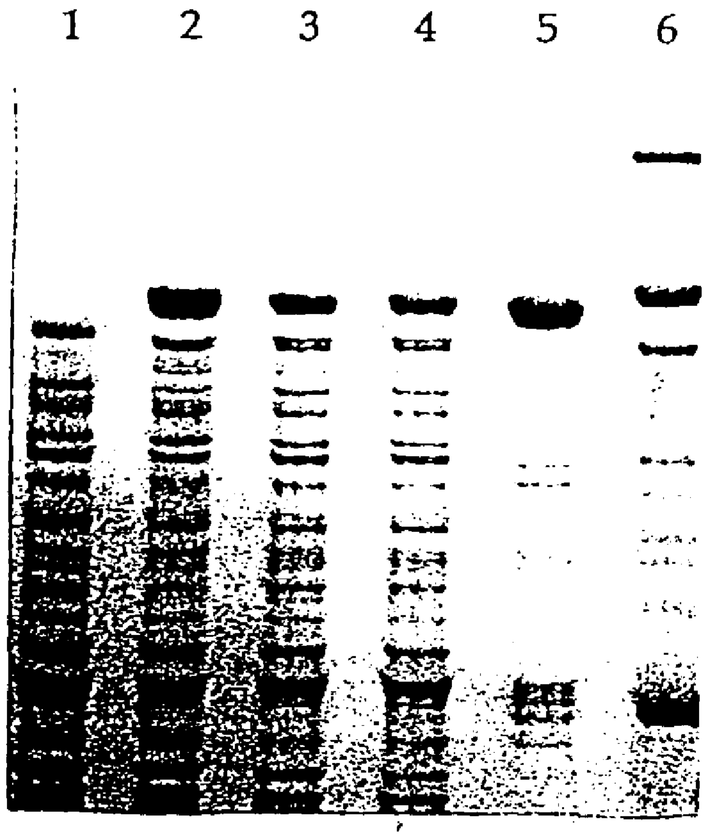
FIG. 21 is an SDS-PAGE gel showing the purification of recombinant *C. difficile* toxin B fusion protein.
Figure 22:
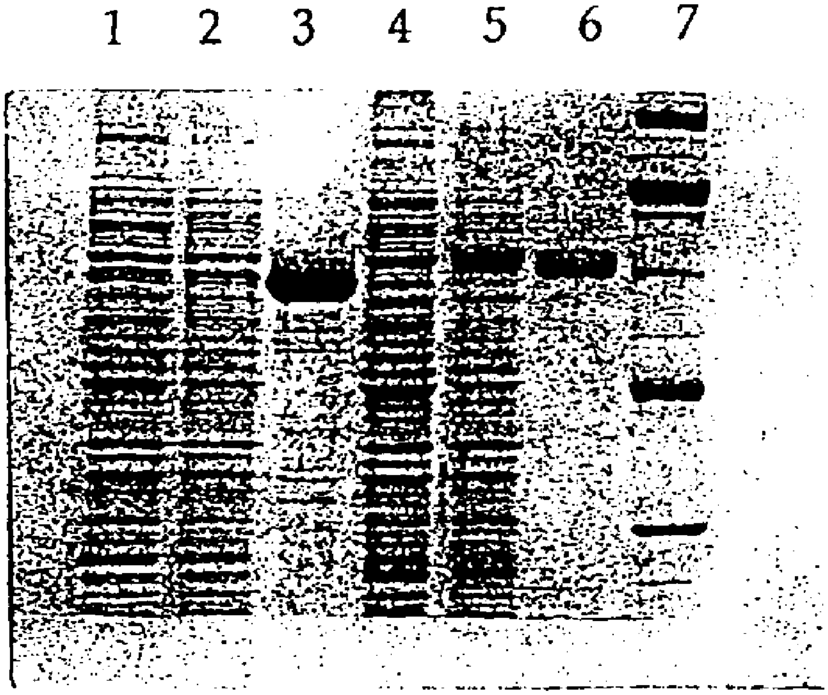
FIG. 22 is an SDS-PAGE gel showing the purification of two histidine-tagged recombinant *C. difficile* toxin B proteins.

Representative purifications of MBP and poly-histidine-tagged toxin B recombinants are shown in FIGS. 21 and 22. FIG. 21 shows a Coomassie Blue stained 7.5% SDS-PAGE gel on which various protein samples extracted from bacteria harboring pMB1850–2360 were electrophoresed. Samples were loaded as follows: Lane 1: protein extracted from uninduced culture; Lane 2: induced culture protein; Lane 3: total protein from induced culture after sonication; Lane 4: soluble protein; and Lane 5: eluted affinity purified protein. FIG. 22 depicts the purification of recombinant proteins expressed in bacteria harboring either pPB1850–2360 (Lanes 1–3) or pPB1750–2360 (Lanes 4–6). Samples were loaded as follows: uninduced total protein (Lanes 1 and 4); induced total protein (Lanes 2 and 5); and eluted affinity purified protein (Lanes 3 and 6). The broad range molecular weight protein markers (BioRad) are shown in Lane 7.

Thus, although high level expression was not attained using large expression constructs from the toxin B gene, usable levels of recombinant protein were obtained by isolating induced protein from a series of smaller pMAL expression constructs that span the entire toxin B gene.

These results represent the first demonstration of the feasibility of expressing recombinant toxin B protein to high levels in *E. coli*. As well, expression of small regions of the putative ligand binding domain (repeat region) of toxin B as native protein yielded insoluble protein, while large constructs, or fusions to MBP were soluble (FIG. 19), demonstrating that specific methodologies are necessary to produce soluble fusion protein from this interval.

iii) Clone Construction and Expression Details

A portion of the toxin B gene containing the toxin B repeat region [amino acid residues 1852–2362 of toxin B (SEQ ID NO:20)] was isolated by PCR amplification of this interval of the toxin B gene from *C. difficile* genomic DNA. The sequence, and location within the toxin B gene, of the two PCR primers [P7 (SEQ ID NO:13) and P8 (SEQ ID NO:14)] used to amplify this region are shown in FIG. 18.

DNA from the PCR amplification was purified by chloroform extraction and ethanol precipitation as described above. The DNA was restricted with SpeI, and the cleaved DNA was resolved by agarose gel electrophoresis. The restriction digestion with SpeI cleaved the 3.6 kb amplification product into a 1.8 kb doublet band. This doublet band was cut from the gel and mixed with appropriately cut, gel purified pMALc or pET23b vector. These vectors were prepared by digestion with HindIII, filling in the overhanging ends using the Klenow enzyme, and cleaving with XbaI (pMALc) or NheI (pET23b). The gel purified DNA fragments were purified using the Prep-A-Gene kit (BioRad) and the DNA was ligated, transformed and putative recombinant clones analyzed by restriction mapping.

pET and pMal clones containing the toxin B repeat insert (aa interval 1750–2360 of toxin B) were verified by restriction mapping, using enzymes that cleaved specific sites within the toxin B region. In both cases fusion of the toxin B SpeI site with either the compatible XbaI site (pMal) or compatible NheI site (pET) is predicted to create an in frame fusion. This was confirmed in the case of the pMB1750–2360 clone by DNA sequencing of the clone junction and 5' end of the toxin B insert using a MBP specific primer (New England Biolabs). In the case of the pET construct, the fusion of the blunt ended toxin B 3' end to the filled HindIII site should create an in-frame fusion with the C-terminal poly-histidine sequence in this vector. The pPB1750–2360 clone selected had lost, as predicted, the HindIII site at this clone junction; this eliminated the possibility that an additional adenosine residue was added to the 3' end of the PCR product by a terminal transferase activity of the Pfu polymerase, since fusion of this adenosine residue to the filled HindIII site would regenerate the restriction site (and was observed in several clones).

One liter cultures of each expression construct were grown, and fusion protein purified by affinity chromatography on either an amylose resin column (pMAL constructs; resin supplied by New England Biolabs) or Ni-chelate column (pET constructs; resin supplied by Qiagen or Novagen) as described [Williams et al. (1995), supra]. The integrity and purity of the fusion proteins were determined by Coomassie staining of SDS-PAGE protein gels as well as Western blot analysis with either an affinity purified goat polyclonal antiserum (Tech Lab), or a chicken polyclonal PEG prep, raised against the toxin B protein (CTB) as described above in Example 8. In both cases, affinity purification resulted in yields in excess of 20 mg protein per liter culture, of which greater than 90% was estimated to be full-length recombinant protein. It should be noted that the poly-histidine affinity tagged protein was released from the Qiagen NI-NTA resin at low imidazole concentration (60 mM), necessitating the use of a 40 mM imidazole rather than a 60 mM imidazole wash step during purification.

A periplasmically secreted version of pMB1750–2360 was constructed by replacement of the promoter and MBP coding region of this construct with that from a related vector (pMAL™-p2; New England Biolabs) in which a signal sequence is present at the N-terminus of the MBP, such that fusion protein is exported. This was accomplished by substituting a BglII-EcoRV promoter fragment from pMAL-p2 into pMB1750–2360. The yields of secreted, affinity purified protein (recovered from osmotic shock extracts as described by Riggs in Current Protocols in Molecular Biology, Vol. 2, Ausubel, et al., Eds. (1989), Current Protocols, pp. 16.6.1–16.6.14] from this vector (pMBp1750–2360) were 6.5 mg/liter culture, of which 50% was estimated to be full-length fusion protein.

The interval was also expressed in two non-overlapping fragments. pMB1750–1970 was constructed by introduction of a frameshift into pMB1750–2360, by restriction with HindIII, filling in the overhanging ends and religation of the plasmid. Recombinant clones were selected by loss of the HindIII site, and further restriction map analysis. Recombinant protein expression from this vector was more than 20 mg/liter of greater than 90% pure protein.

The complementary region was expressed in pMB1970–2360. This construct was created by removal of the 1750–1970 interval of pMB1750–2360. This was accomplished by restriction of this plasmid with EcoRI (in the pMalc polylinker 5' to the insert) and III, filling in the overhanging ends, and religation of the plasmid. The resultant plasmid, pMB1970–2360, was made using both intracellularly and secreted versions of the pMB1750–2360 vector.

No fusion protein was secreted in the pMBp1970–2360 version, perhaps due to a conformational constraint that prevents export of the fusion protein. However, the intracellularly expressed vector produced greater than 40 mg/liter of greater than 90% full-length fusion protein.

Constructs to precisely express the toxin B repeats in either pMalc (pMB1850–2360) or pET16b (pPB1850–2360) were constructed as follows. The DNA interval including the toxin B repeats was PCR amplified as described above utilizing PCR primers P14 (SEQ ID NO:19) and P8 (SEQ ID NO:14). Primer P14 adds a EcoRI site immediately flanking the start of the toxin B repeats.

The amplified fragment was cloned into the pT7 Blue T-vector (Novagen) and recombinant clones in which single copies of the PCR fragment were inserted in either orientation were selected (pT71850–2360) and confirmed by restriction mapping. The insert was excised from two appropriately oriented independently isolated pT71850–2360 plasmids, with EcoRI (5' end of repeats) and PstI (in the flanking polylinker of the vector), and cloned into EcoRI/PstI cleaved pMalc vector. The resulting construct (pMB1850–2360) was confirmed by restriction analysis, and yielded 20 mg/l of soluble fusion protein [greater than 90% intact (i.e., nondegraded)] after affinity chromatography. Restriction of this plasmid with HindIII and religation of the vector resulted in the removal of the 1970–2360 interval. The resultant construct (pMB1850–1970) expressed greater than 70 mg/liter of 90% full length fusion protein.

The pPB1850–2360 construct was made by cloning a EcoRI (filled with Klenow)-BamHI fragment from a pT71850–2360 vector (opposite orientation to that used in the pMB1850–2360 construction) into NdeI (filled)/BamHI cleaved pET16b vector. Yields of affinity purified soluble fusion protein were 15 mg/liter, of greater than 90% full length fusion protein.

Several smaller expression constructs from the 1750–2070 interval were also constructed in His-tagged pET vectors, but expression of these plasmids in the BL21 (DE3) host resulted in the production of high levels of mostly insoluble protein (see Table 23 and FIG. 19). These constructs were made as follows.

pPB1850–1970 was constructed by cloning a BglII-HindIII fragment of pPB1850–2360 into BglII/HindIII cleaved pET23b vector. pPB1850–2070 was constructed by cloning a BglII-PvuII fragment of pPB1850–2360 into BglII/HincII cleaved pET23b vector. pPB1750–1970(c) was constructed by removal of the internal HindIII fragment of a pPB1750–2360 vector in which the vector HindIII site was regenerated during cloning (presumably by the addition of an A residue to the amplified PCR product by terminal transferase activity of Pfu polymerase). The pPB1750–1970 (n) construct was made by insertion of the insert containing the NdeI-HindIII fragment of pPB1750–2360 into identically cleaved pETHisb vector. All constructs were confirmed by restriction digestion.

An expression construct that directs expression of the 10–470 aa interval of toxin B was constructed in the pMalc vector as follows. A NheI (a site 5' to the insert in the pET23 vector)-AflII (filled) fragment of the toxin B gene from pPB10–1530 was cloned into XbaI (compatible with NheI)/HindIII (filled) pMalc vector. The integrity of the construct (pMB10–470) was verified by restriction mapping and DNA sequencing of the 5' clone junction using a MBP specific DNA primer (New England Biolabs). However, all expressed protein was degraded to the MBP monomer MW.

A second construct spanning this interval (aa 10–470) was constructed by cloning the PCR amplification product from a reaction containing the P9 (SEQ ID NO:15) and P10 (SEQ ID NO:16) primers (FIG. 18) into the pETHisa vector. This was accomplished by cloning the PCR product as an EcoRI-blunt fragment into EcoRI-HincII restricted vector DNA; recombinant clones were verified by restriction mapping.

Although this construct (pPB10–520) allowed expression and purification (utilizing the N-terminal polyhistidine affinity tag) of intact fusion protein, yields were estimated at less than 500 μg per liter culture.

Higher yield of recombinant protein from this interval (aa 10–520) were obtained by expression of the interval in two overlapping clones. The 10–330aa interval was cloned in both pETHisa and pMalc vectors, using the BamHI-AflIII (filled) DNA fragment from pPB10–520. This fragment was cloned into BamHI-HindIII (filled) restricted pMalc or BamHI-HincII restricted pETHisa vector. Recombinant clones were verified by restriction mapping. High level expression of either insoluble (pET) or soluble (pMal) fusion protein was obtained. Total yields of fusion protein from the pMB10–330 construct (FIG. 18) were 20 mg/liter culture, of which 10% was estimated to be full-length fusion protein. Although yields of this interval were higher and >90% full-length recombinant protein produced when expressed from the pET construct, the pMal fusion was utilized since the expressed protein was soluble and thus more likely to have the native conformation.

The pMB260–520 clone was constructed by cloning EcoRI-XbaI cleaved amplified DNA from a PCR reaction containing the P11 (SEQ ID NO:17) and P10 (SEQ ID NO:16) DNA primers (FIG. 18) into similarly restricted pMalc vector. Yields of affinity purified protein were 10 mg/liter, of which approximately 50% was estimated to be full-length recombinant protein.

The aa510–1110 interval was expressed as described below. This entire interval was expressed as a pMal fusion by cloning the NheI-HindIII fragment of pUCB10–1530 into XbaI-HindIII cleaved pMalc vector. The integrity of the construct (pMB510–1110) was verified by restriction mapping and DNA sequencing of the 5' clone junction using a MBP specific DNA primer. The yield of affinity purified protein was 25 mg/liter culture, of which 5% was estimated to be full-length fusion protein (1 mg/liter).

To attempt to obtain higher yields, this region was expressed in two fragments (aa510–820, and 820–1110) in the pMalc vector. The pMB510–820 clone was constructed by insertion of a SacI (in the pMalc polylinker 5' to the insert)-HpaI DNA fragment from pMB510–1110 into SacI/StuI restricted pMalc vector. The pMB820–1110 vector was constructed by insertion of the HpaI-HindIII fragment of pUCB10–1530 into BamHI (filled)/HindIII cleaved pMalc vector. The integrity of these constructs were verified by restriction mapping and DNA sequencing of the 5' clone junction using a MBP specific DNA primer.

Recombinant protein expressed from the pMB510–820 vector was highly unstable. However, high levels (20 mg/liter) of >90% full-length fusion protein were obtained from the pMB820–1105 construct. The combination of partially degraded pMB510–1110 protein (enriched for the 510–820 interval) with the pMB820–1110 protein provides usable amounts of recombinant antigen from this interval.

The aa1100–1750 interval was expressed as described below. The entire interval was expressed in the pMalc vector from a construct in which the AccI(filled)-SpeI fragment of pPB10–1750 was inserted into StuI/XbaI (XbaI is compatible with SpeI; StuI and filled AccI sites are both blunt ended) restricted pMalc. The integrity of this construct (PMB1100–1750) was verified by restriction mapping and DNA sequencing of the clone junction using a MBP specific DNA primer. Although 15 mg/liter of affinity purified protein was isolated from cells harboring this construct, the protein was greater than 99% degraded to MBP monomer size.

A smaller derivative of pMB1000–1750 was constructed by restriction of pMB1100–1750 with AflII and SalI (in the pMalc polylinker 3' to the insert), filling in the overhanging ends, and religating the plasmid. The resultant clone (verified by restriction digestion and DNA sequencing) has deleted the aa1530–1750 interval, was designated pMB1100–1530. pMB1100–1530 expressed recombinant protein at a yield of greater than 40 mg/liter, of which 5% was estimated to be full-length fusion protein.

Three constructs were made to express the remaining interval. Initially, a BspHI (filled)-SpeI fragment from pPB10–1750 was cloned into EcoRI(filled)/XbaI cleaved pMalc vector. The integrity of this construct (pMB1570–1750) was verified by restriction mapping and DNA sequencing of the 5' clone junction using a MBP specific DNA primer. Expression of recombinant protein from this plasmid was very low, approximately 3 mg affinity purified protein per liter, and most was degraded to MBP monomer size. This region was subsequently expressed from a PCR amplified DNA fragment. A PCR reaction utilizing primers P13 [SEQ ID NO:18; P13 was engineered to introduce an EcoRI site 5' to amplified toxin B sequences] and P8 (SEQ ID NO: 14) was performed on *C. difficile* genomic DNA as described above. The amplified fragment was cleaved with EcoRI and SpeI, and cloned into EcoRI/XbaI cleaved pMalc vector. The resultant clone (pMB1530–1750) was verified by restriction map analysis, and recombinant protein was expressed and purified. The yield was greater than 20 mg protein per liter culture and it was estimated that 25% was full-length fusion protein; this was a significantly higher yield than the original pMB1570–1750 clone. The insert of pMB1530–1750 (in a EcoRI-SalI fragment) was transferred to the pETHisa vector (EcoRI/XhoI cleaved, XhoI and Sail ends are compatible). No detectable fusion protein was purified on Ni-Chelate columns from soluble lysates of cells induced to express fusion protein from this construct.

TABLE 23

Summary Of Toxin B Expression Constructs[a]

| Clone | Affinity Tag | Yield (mg/liter) | % Full Length |
|---|---|---|---|
| pPB10-1750 | none | low (estimated from Western blot hyb.) | ? |
| pPB10-1530 | none | low (as above) | ? |
| pMB10-470 | MBP | 15 mg/l | 0% |
| pPB10-520 | poly-his | 0.5 mg/l | 20% |
| pPB10-330 | poly-his | >20 mg/l (insoluble) | 90% |
| *pMB10-330* | *MBP* | *20 mg/l* | *10%* |
| *pMB260-520* | *MBP* | *10 mg/l* | *50%* |
| *pMB510-1110* | *MBP* | *25 mg/l* | *5%* |
| pMB510-820 | MBP | degraded (by Western blot hyb) | |
| *pMB820-1110* | *MBP* | *20 mg/l* | *90%* |
| pMB1100-1750 | MBP | 15 mg/l | 0% |
| *pMB1100-1530* | *MBP* | *40 mg/l* | *5%* |
| pMB1570-1750 | MBP | 3 mg/l | <5% |
| pPB1530-1750 | poly-his | no purified protein detected | ? |
| *pMB1530-1750* | *MBP* | *20 mg/l* | *25%* |
| *pMB1750-2360* | *MBP* | *>20 mg/l* | *>90%* |
| pMBp1750-2360 | MBP | 6.5 mg/l (secreted) | 50% |
| pPB1750-2360 | poly-his | >20 mg/l | >90% |
| pMB1750-1970 | MBP | >20 mg/l | >90% |
| pMB1970-2360 | MBP | 40 mg/l | >90% |
| pMBp1970-2360 | MBP | (no secretion) | NA |
| pMB1850-2360 | MBP | 20 mg/l | >90% |
| pPB1850-2360 | poly-his | 15 mg/l | >90% |
| pMB1850-1970 | MBP | 70 mg/l | >90% |
| pPB1850-1970 | poly-his | >10 mg/l (insoluble) | >90% |

TABLE 23-continued

| Summary Of Toxin B Expression Constructs[a] | | | |
|---|---|---|---|
| Clone | Affinity Tag | Yield (mg/liter) | % Full Length |
| pPB1850-2070 | poly-his | >10 mg/l (insoluble) | >90% |
| pPB1750-1970(c) | poly-his | >10 mg/l (insoluble) | >90% |
| pPB1750-1970(n) | poly-his | >10 mg/l (insoluble) | >90% |

[a]Clones in italics are clones currently utilized to purify recombinant protein from each selected interval.

EXAMPLE 19

Identification, Purification and Induction of Neutralizing Antibodies Against Recombinant *C. difficile* Toxin B Protein To determine whether recombinant toxin B polypeptide fragments can generate neutralizing antibodies, typically animals would first be immunized with recombinant proteins and anti-recombinant antibodies are generated. These anti-recombinant protein antibodies are then tested for neutralizing ability in vivo or in vitro. Depending on the immunogenic nature of the recombinant polypeptide, the generation of high-titer antibodies against that protein may take several months. To accelerate this process and identify which recombinant polypeptide(s) may be the best candidate to generate neutralizing antibodies, depletion studies were performed. Specifically, recombinant toxin B polypeptide were pre-screened by testing whether they have the ability to bind to protective antibodies from a CTB antibody preparation and hence deplete those antibodies of their neutralizing capacity. Those recombinant polypeptides found to bind CTB, were then utilized to generate neutralizing antibodies. This Example involved: a) identification of recombinant sub-regions within toxin B to which neutralizing antibodies bind; b) identification of toxin B sub-region specific antibodies that neutralize toxin B in vivo; and c) generation and evaluation of antibodies reactive to recombinant toxin B polypeptides.

a) Identification of Recombinant Sub-Regions within Toxin B to which Neutralizing Antibodies Bind Sub-regions within toxin B to which neutralizing antibodies bind were identified by utilizing recombinant toxin B proteins to deplete protective antibodies from a polyclonal pool of antibodies against native *C. difficile* toxin B. An in vivo assay was developed to evaluate protein preparations for the ability to bind neutralizing antibodies. Recombinant proteins were first pre-mixed with antibodies directed against native toxin B (CTB antibody; see Example 8) and allowed to react for one hour at 37° C. Subsequently, *C. difficile* toxin B (CTB; Tech Lab) was added at a concentration lethal to hamsters and incubated for another hour at 37° C. After incubation this mixture was injected intraperitoneally (IP) into hamsters. If the recombinant polypeptide contains neutralizing epitopes, the CTB antibodies will lose its ability to protect the hamsters against death from CTB. If partial or complete protection occurs with the CTB antibody-recombinant mixture, that recombinant contains only weak or non-neutralizing epitopes of toxin B. This assay was performed as follows.

Antibodies against CTB were generated in egg laying Leghorn hens as described in Example 8. The lethal dosage ($LD_{100}$) of *C. difficile* toxin B when delivered I.P. into 40 g female Golden Syrian hamsters (Charles River) was determined to be 2.5 to 5 μg. Antibodies generated against CTB and purified by PEG precipitation could completely protect the hamsters at the I.P. dosage determined above. The minimal amount of CTB antibody needed to afford good protection against 5 μg of CTB when injected I.P. into hamsters was also determined (1× PEG prep). These experiments defined the parameters needed to test whether a given recombinant protein could deplete protective CTB antibodies.

The cloned regions tested for neutralizing ability cover the entire toxin B gene and were designated as Intervals (INT) 1 through 5 (see FIG. 19). Approximately equivalent final concentrations of each recombinant polypeptide were tested. The following recombinant polypeptides were used: 1) a mixture of intervals 1 and 2 (INT-1,2); 2) a mixture of Intervals 4 and 5 (INT-4, 5) and 3) Interval 3 (INT-3). Recombinant proteins (each at about 1 mg total protein) were first preincubated with a final CTB antibody concentration of 1× [i.e., pellet dissolved in original yolk volume as described in Example 1(c)] in a final volume of 5 mls for 1 hour at 37° C. Twenty-five μg of CTB (at a concentration of 5 μg/ml), enough CTB to kill 5 hamsters, was then added and the mixture was then incubated for 1 hour at 37° C. Five, 40 g female hamsters (Charles River) in each treatment group were then each given 1 ml of the mixture I.P. using a tuberculin syringe with a 27 gauge needle. The results of this experiment are shown in Table 24.

TABLE 24

| Binding Of Neutralizing Antibodies By INT 3 Protein | | |
|---|---|---|
| Treatment Group[1] | Number of Animals Alive | Number Of Animals Dead |
| CTB antibodies | 3 | 2 |
| CTB antibodies + INT1, 2 | 3 | 2 |
| CTB antibodies + INT4, 5 | 3 | 2 |
| CTB antibodies + INT 3 | 0 | 5 |

[1]*C. difficile* toxin B (CTB) was added to each group.

As shown in Table 24, the addition of recombinant proteins from INT-1, 2 or INT-4, 5 had no effect on the in vivo protective ability of the CTB antibody preparation compared to the CTB antibody preparation alone. In contrast, INT-3 recombinant polypeptide was able to remove all of the toxin B neutralizing ability of the CTB antibodies as demonstrated by the death of all the hamsters in that group.

The above experiment was repeated, using two smaller expressed fragments (pMB1750–1970 and pMB1970–2360, see FIG. 19) comprising the INT-3 domain to determine if that domain could be further subdivided into smaller neutralizing epitopes. In addition, full-length INT-3 polypeptide expressed as a nickel tagged protein (pPB1750–2360) was tested for neutralizing ability and compared to the original INT-3 expressed MBP fusion (pMB1750–2360). The results are shown in Table 25.

TABLE 25

| Removal Of Neutralizing Antibodies By Repeat Containing Proteins | | |
|---|---|---|
| Treatment Group[1] | Number Of Animals Alive | Number Of Animals Dead |
| CTB antibodies | 5 | 0 |
| CTB antibodies + pPB1750p–2360 | 0 | 5 |
| CTB antibodies + pMB1750–2360 | 0 | 5 |

TABLE 25-continued

Removal Of Neutralizing Antibodies By Repeat Containing Proteins

| Treatment Group[1] | Number Of Animals Alive | Number Of Animals Dead |
|---|---|---|
| CTB antibodies + pMB1970–2360 | 3 | 2 |
| CTB antibodies + pMB1750–1970 | 2 | 3 |

[1]*C. difficile* toxin B (CTB) was added to each group.

The results summarized in Table 25 indicate that the smaller polypeptide fragments within the INT-3 domain, pMB1750–1970 and pMB1970–2360, partially lose the ability to bind to and remove neutralizing antibodies from the CTB antibody pool. These results demonstrate that the full length INT-3 polypeptide is required to completely deplete the CTB antibody pool of neutralizing antibodies. This experiment also shows that the neutralization epitope of INT-3 can be expressed in alternative vector systems and the results are independent of the vector utilized or the accompanying fusion partner.

Figure 23:
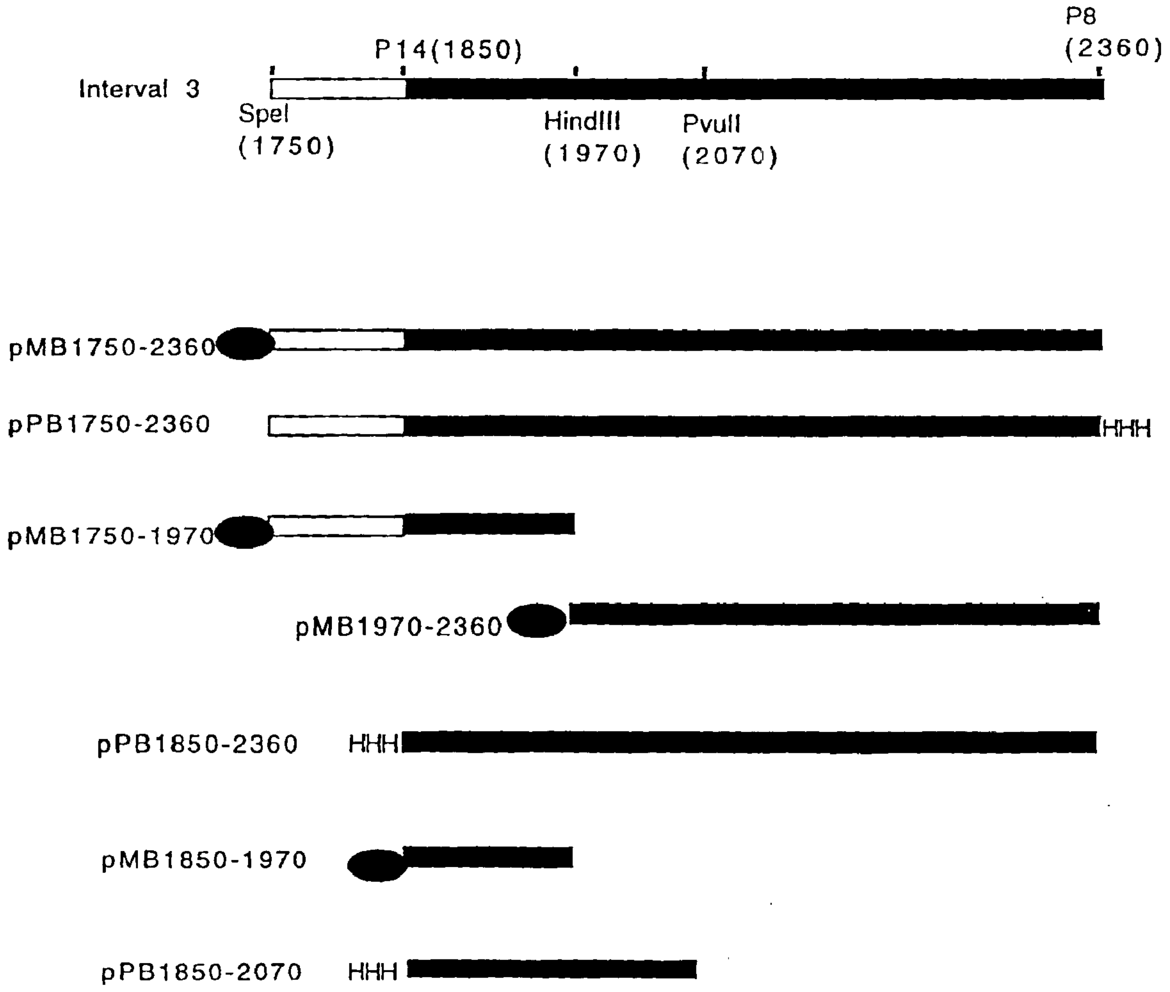
FIG. 23 shows *C. difficile* toxin B expression constructs.

Other Interval 3 specific proteins were subsequently tested for the ability to remove neutralizing antibodies within the CTB antibody pool as described above. The Interval 3 specific proteins used in these studies are summarized in FIG. 23. In FIG. 23 the following abbreviations are used: pP refers to the pET23 vector; pM refers to the pMALc vector; B refers to toxin B; the numbers refer to the amino acid interval expressed in the clone. The solid black ovals represent the MBP; and HHH represents the polyhistidine tag.

Only recombinant proteins comprising the entire toxin B repeat domain (pMB1750–2360, pPB1750–2360 and pPB1850–2360) can bind and completely remove neutralizing antibodies from the CTB antibody pool. Recombinant proteins comprising only a portion of the toxin B repeat domain were not capable of completely removing neutralizing antibodies from the CTB antibody pool (pMB1750–1970 and pMB1970–2360 could partially remove neutralizing antibodies while pMB1850–1970 and pPB1850–2070 failed to remove any neutralizing antibodies from the CTB antibody pool).

The above results demonstrate that only the complete ligand binding domain (repeat region) of the toxin B gene can bind and completely remove neutralizing antibodies from the CTB antibody pool. These results demonstrate that antibodies directed against the entire toxin B repeat region are necessary for in vivo toxin neutralization (see FIG. 23; only the recombinant proteins expressed by the pMB1750–2360, pPB1750–2360 and pPB1850–2360 vectors are capable of completely removing the neutralizing antibodies from the CTB antibody pool).

These results represent the first indication that the entire repeat region of toxin B would be necessary for the generation of antibodies capable of neutralizing toxin B, and that sub-regions may not be sufficient to generate maximal titers of neutralizing antibodies.

b) Identification of Toxin B Sub-Region Specific Antibodies that Neutralize Toxin B In Vivo To determine if antibodies directed against the toxin B repeat region are sufficient for neutralization, region specific antibodies within the CTB antibody preparation were affinity purified, and tested for in vivo neutralization. Affinity columns containing recombinant toxin B repeat proteins were made as described below. A separate affinity column was prepared using each of the following recombinant toxin B repeat proteins: pPB1750–2360, pPB1850–2360, pMB1750–1970 and pMB1970–2360.

For each affinity column to be made, four ml of PBS-washed Actigel resin (Sterogene) was coupled overnight at room temperature with 5–10 mg of affinity purified recombinant protein (first extensively dialyzed into PBS) in 15 ml tubes (Falcon) containing a 1/10 final volume Ald-coupling solution (1 M sodium cyanoborohydride). Aliquots of the supernatants from the coupling reactions, before and after coupling, were assessed by Coomassie staining of 7.5% SDS-PAGE gels. Based on protein band intensities, in all cases greater than 30% coupling efficiencies were estimated. The resins were poured into 10 ml columns (BioRad), washed extensively with PBS, pre-eluted with 4M guanidine-HCl (in 10 mM Tris-HCl, pH 8.0) and reequilibrated in PBS. The columns were stored at 4° C.

Aliquots of a CTB IgY polyclonal antibody preparation (PEG prep) were affinity purified on each of the four columns as described below. The columns were hooked to a UV monitor (ISCO), washed with PBS and 40 ml aliquots of a 2× PEG prep (filter sterilized using a 0.45$\mu$ filter) were applied. The columns were washed with PBS until the baseline value was re-established. The columns were then washed with BBStween to elute nonspecifically binding antibodies, and reequilibrated with PBS. Bound antibody was eluted from the column in 4M guanidine-HCl (in 10 mM Tris-HCl, pH 8.0). The eluted antibody was immediately dialyzed against a 100-fold excess of PBS at 4° C. for 2 hrs. The samples were then dialyzed extensively against at least 2 changes of PBS, and affinity purified antibody was collected and stored at 4° C. The antibody preparations were quantified by UV absorbance. The elution volumes were in the range of 4–8 ml. All affinity purified stocks contained similar total antibody concentrations, ranging from 0.25–0.35% of the total protein applied to the columns.

The ability of the affinity purified antibody preparations to neutralize toxin B in vivo was determined using the assay outlined in a) above. Affinity purified antibody was diluted 1:1 in PBS before testing. The results are shown in Table 26.

In all cases similar levels of toxin neutralization was observed, such that lethality was delayed in all groups relative to preimmune controls. This result demonstrates that antibodies reactive to the repeat region of the toxin B gene are sufficient to neutralize toxin B in vivo. The hamsters will eventually die in all groups, but this death is maximally delayed with the CTB PEG prep antibodies. Thus neutralization with the affinity purified (AP) antibodies is not as complete as that observed with the CTB prep before affinity chromatography. This result may be due to loss of activity during guanidine denaturation (during the elution of the antibodies from the affinity column) or the presence of antibodies specific to other regions of the toxin B gene that can contribute to toxin neutralization (present in the CTB PEG prep).

TABLE 26

Neutralization Of Toxin B By Affinity Purified Antibodies

| Treatment group[a] | Number Animals Alive[b] | Number Animals Dead[b] |
|---|---|---|
| Preimmune[1] | 0 | 5 |
| CTB[1]; 400 $\mu$g | 5 | 0 |
| CTB (AP on pPB1750-2360);[2] 875 $\mu$g | 5 | 0 |

TABLE 26-continued

| Neutralization Of Toxin B By Affinity Purified Antibodies | | |
|---|---|---|
| Treatment group[a] | Number Animals Alive[b] | Number Animals Dead[b] |
| CTB (AP on pMB1750-1970);[2] 875 μg | 5 | 0 |
| CTB (AP on pMB1970-2360);[2] 500 μg | 5 | 0 |

[a]*C. difficile* toxin B (CTB) (Tech Lab; at 5 μg/ml, 25 μg total) at lethal concentration to hamsters is added to antibody and incubated for one hour at 37° C. After incubation this mixture is injected intraperitoneally (IP) into hamsters. Each treatment group received toxin premixed with antibody raised against the indicated protein, as either: [1]4X antibody PEG prep or [2]affinity purified (AP) antibody (from CTB PEG prep, on indicated columns). The amount of specific antibody in each prep is indicated; the amount is directly determined for affinity purified preps and is estimated for the 4X CTB as described in Example 15.
[b]The numbers in each group represent numbers of hamsters dead or alive, 2 hr post IP administration of toxin/antibody mixture.

The observation that antibodies affinity purified against the non-overlapping pMB1750–1970 and pMB1970–2360 proteins neutralized toxin B raised the possibility that either 1) antibodies specific to repeat sub-regions are sufficient to neutralize toxin B or 2) sub-region specific proteins can bind most or all repeat specific antibodies present in the CTB polyclonal pool. This would likely be due to conformational similarities between repeats, since homology in the primary amino acid sequences between different repeats is in the range of only 25–75% [Eichel-Streiber, et al. (1992) Molec. Gen. Genetics 233:260]. These possibilities were tested by affinity chromatography.

The CTB PEG prep was sequentially depleted 2× on the pMB1750–1970 column; only a small elution peak was observed after the second chromatography, indicating that most reactive antibodies were removed. This interval depleted CTB preparation was then chromatographed on the pPB1850–2360 column; no antibody bound to the column. The reactivity of the CTB and CTB (pMB1750–1970 depleted) preps to pPB1750–2360, pPB1850–2360, pMB1750–1970 and pMB1970–2360 proteins was then determined by ELISA using the protocol described in Example 13(c). Briefly, 96-well microtiter plates (Falcon, Pro-Bind Assay Plates) were coated with recombinant protein by adding 100 μl volumes of protein at 1–2 μg/ml in PBS containing 0.005% thimerosal to each well and incubating overnight at 4° C. The next morning, the coating suspensions were decanted and the wells were washed three times using PBS. In order to block non-specific binding sites, 100 μl of 1.0% BSA (Sigma) in PBS (blocking solution) was then added to each well, and the plates were incubated for 1 hr. at 37° C. The blocking solution was decanted and duplicate samples of 150 μl of diluted antibody was added to the first well of a dilution series. The initial testing serum dilution was (1/200 for CTB prep, (the concentration of depleted CTB was standardized by $OD_{280}$) in blocking solution containing 0.5% Tween 20, followed by 5-fold serial dilutions into this solution. This was accomplished by serially transferring 30 μl aliquots to 120 μl buffer, mixing, and repeating the dilution into a fresh well. After the final dilution, 30 μl was removed from the well such that all wells contained 120 μl final volume. A total of 5 such dilutions were performed (4 wells total). The plates were incubated for 1 hr at 37° C. Following this incubation, the serially diluted samples were decanted and the wells were washed three times using PBS containing 0.5% Tween 20 (PBST), followed by two 5 min washes using BBS-Tween and a final three washes using PBST. To each well, 100 μl of 1/1000 diluted secondary antibody [rabbit anti-chicken IgG alkaline phosphatase (Sigma) diluted in blocking solution containing 0.5% Tween 20] was added, and the plate was incubated 1 hr at 37° C. The conjugate solutions were decanted and the plates were washed 6 times in PBST, then once in 50 mM $Na_2CO_3$, 10 mM $MgCl_2$, pH 9.5. The plates were developed by the addition of 100 μl of a solution containing 1 mg/ml para-nitro phenyl phosphate (Sigma) dissolved in 50 mM $Na_2CO_3$, 10 mM $MgCl_2$, pH 9.5 to each well. The plates were then incubated at room temperature in the dark for 545 min. The absorbency of each well was measured at 410 nm using a Dynatech MR 700 plate reader.

As predicted by the affinity chromatography results, depletion of the CTB prep on the pMB1750–1970 column removed all detectable reactivity to the pMB1970–2360 protein. The reciprocal purification of a CTB prep that was depleted on the pMB1970–2360 column yielded no bound antibody when chromatographed on the pMB1750–1970 column. These results demonstrate that all repeat reactive antibodies in the CTB polyclonal pool recognize a conserved structure that is present in non-overlapping repeats. Although it is possible that this conserved structure represents rare conserved linear epitopes, it appears more likely that the neutralizing antibodies recognize a specific protein conformation. This conclusion was also suggested by the results of Western blot hybridization analysis of CTB reactivity to these recombinant proteins.

Western blots of 7.5% SDS-PAGE gels, loaded and electrophoresed with defined quantities of each recombinant protein, were probed with the CTB polyclonal antibody preparation. The blots were prepared and developed with alkaline phosphatase as described in Example 3. The results are shown in FIG. 24.

Figure 24:
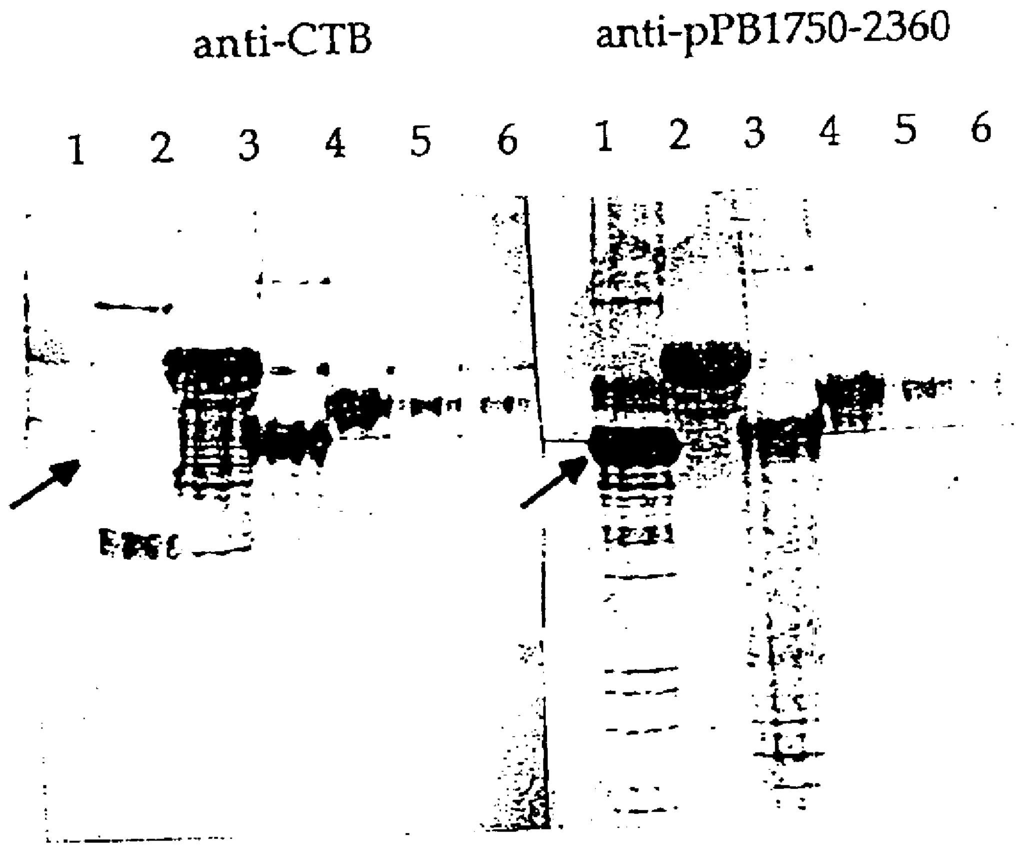
FIG. 24 is a Western blot of *C. difficile* toxin B reactive protein.

FIG. 24 depicts a comparison of immunoreactivity of IgY antibody raised against either native or recombinant toxin B antigen. Equal amounts of pMB1750–1970 (lane 1), pMB1970–2360 (lane 2), pPB1850–2360 (lane 3) as well as a serial dilution of pPB1750–2360 (lanes 4–6 comprising 1×, 1/10× and 1/100× amounts, respectively) proteins were loaded in duplicate and resolved on a 7.5% SDS-PAGE gel. The gel was blotted and each half was hybridized with PEG prep IgY antibodies from chickens immunized with either native CTB or pPB1750–2360 protein. Note that the full-length pMB1750–1970 protein was identified only by antibodies reactive to the recombinant protein (arrows).

Although the CTB prep reacts with the pPB1750–2360, pPB1850–2360, and pMB1970–2360 proteins, no reactivity to the pMB1750–1970 protein was observed (FIG. 24). Given that all repeat reactive antibodies can be bound by this protein during affinity chromatography, this result indicates that the protein cannot fold properly on Western blots. Since this eliminates all antibody reactivity, it is unlikely that the repeat reactive antibodies in the CTB prep recognize linear epitopes. This may indicate that in order to induce protective antibodies, recombinant toxin B protein will need to be properly folded.

c) Generation and Evaluation of Antibodies Reactive to Recombinant Toxin B Polypeptides i) Generation of Antibodies Reactive to Recombinant Toxin B Proteins Antibodies against recombinant proteins were generated in egg laying Leghorn hens as described in Example 13. Antibodies were raised [using Freunds adjuvant (Gibco) unless otherwise indicated] against the following recombinant proteins: 1) a mixture of Interval 1+2 proteins (see FIG. 18); 2) a mixture of interval 4 and 5 proteins (see FIG. 18); 3) pMB1970–2360 protein; 4) pPB1750–2360 protein; 5)

pMB1750–2360; 6) pMB1750–2360 [Titermax adjuvant (Vaxcell)]; 7) pMB1750–2360 [Gerbu adjuvant (Biotech)]; 8) pMBp1750–2360 protein; 9) pPB1850–2360; and 10) pMB1850–2360.

Chickens were boosted at least 3 times with recombinant protein until ELISA reactivity [using the protocol described in b) above with the exception that the plates were coated with pPB1750–2360 protein] of polyclonal PEG preps was at least equal to that of the CTB polyclonal antibody PEG prep. ELISA titers were determined for the PEG preps from all of the above immunogens and were found to be comparable ranging from 1:12500 to 1;62500. High titers were achieved in all cases except in 6) pMB1750–2360 in which strong titers were not observed using the Titermax adjuvant, and this preparation was not tested further.

ii) Evaluation of Antibodies Reactive to Recombinant Proteins by Western Blot Hybridization Western blots of 7.5% SDS-PAGE gels, loaded and electrophoresed with defined quantities of recombinant protein (pMB1750–1970, pPB1850–2360, and pMB1970–2360 proteins and a serial dilution of the pPB1750–2360 to allow quantification of reactivity), were probed with the CTB, pPB1750–2360, pMB1750–2360 and pMB1970–2360 polyclonal antibody preparations (from chickens immunized using Freunds adjuvant). The blots were prepared and developed with alkaline phosphatase as described above in b).

As shown in FIG. 24, the CTB and pMB1970–2360 preps reacted strongly with the pPB1750–2360, pPB1850–2360, and pMB1970–2360 proteins while the pPB1750–2360 and pMB1970–2360 (Gerbu) preparations reacted strongly with all four proteins. The Western blot reactivity of the pPB1750–2360 and pMB1970–2360 (Gerbu) preparations were equivalent to that of the CTB preparation, while reactivity of the pMB1970–2360 preparation was <10% that of the CTB prep. Despite equivalent ELISA reactivities only weak reactivity (approximately 1%) to the recombinant proteins were observed in PEG preps from two independent groups immunized with the pMB1750–2360 protein and one group immunized with the pMB1750–2360 preparation using Freunds adjuvant.

Affinity purification was utilized to determine if this difference in immunoreactivity by Western blot analysis reflects differing antibody titers. Fifty ml 2× PEG preparations from chickens immunized with either pMB1750–2360 or pMB1970–2360 protein were chromatographed on the pPB1750–2360 affinity column from b) above, as described. The yield of affinity purified antibody (% total protein in preparation) was equivalent to the yield obtained from a CTB PEG preparation in b) above. Thus, differences in Western reactivity reflect a qualitative difference in the antibody pools, rather than quantitative differences. These results demonstrate that certain recombinant proteins are more effective at generating high affinity antibodies (as assayed by Western blot hybridization).

iii) In Vivo Neutralization of Toxin B Using Antibodies Reactive to Recombinant Protein The in vivo hamster model [described in Examples 9 and 14(b)] was utilized to assess the neutralizing ability of antibodies raised against recombinant toxin B proteins. The results from three experiments are shown below in Tables 27–29.

The ability of each immunogen to neutralize toxin B in vivo has been compiled and is shown in Table 30. As predicted from the recombinant protein-CTB premix studies (Table 24) only antibodies to Interval 3 (1750–2366) and not the other regions of toxin B (i.e., intervals 1–5) are protective. Unexpectedly, antibodies generated to INT-3 region expressed in pMAL vector (pMB1750–2360 and pMpB1750–2360) using Freunds adjuvant were non-neutralizing. This observation is reproducible, since no neutralization was observed in two independent immunizations with pMB1750–2360 and one immunization with pMpB1750–2360. The fact that 5× quantities of affinity purified toxin B repeat specific antibodies from pMB1750–2360 PEG preps cannot neutralize toxin B while IX quantities of affinity purified anti-CTB antibodies can (Table 28) demonstrates that the differential ability of CTB antibodies to neutralize toxin B is due to qualitative rather than quantitative differences in these antibody preparations. Only when this region was expressed in an alternative vector (pPB1750–2360) or using an alternative adjuvant with the pMB1750–2360 protein were neutralizing antibodies generated. Importantly, antibodies raised using Freunds adjuvant to pPB1850–2360, which contains a fragment that is only 100 amino acids smaller than recombinant pPB1750–2360, are unable to neutralize toxin B in vivo (Table 27); note also that the same vector is used for both pPB1850–2360 and pPB1750–2360.

TABLE 27

In Vivo Neutralization Of Toxin B

| Treatment Group[a] | Number Animals Alive[b] | Number Animals Dead[b] |
|---|---|---|
| Preimmune | 0 | 5 |
| CTB | 5 | 0 |
| INT1 + 2 | 0 | 5 |
| INT 4 + 5 | 0 | 5 |
| pMB1750-2360 | 0 | 5 |
| pMB1970-2360 | 0 | 5 |
| pPB1750-2360 | 5 | 0 |

[a]*C. difficile* toxin B (CTB) (at 5 μg/ml; 25 μg total; Tech Lab) at lethal concentration to hamsters is added to antibody and incubated for one hour at 37° C. After incubation this mixture is injected intraperitoneally (IP) into hamsters. Each treatment group received toxin premixed with antibody raised against the indicated protein, as a 4X antibody PEG prep.

[b]The numbers in each group represent numbers of hamsters dead or alive, 2 hours post IP administration of toxin/antibody mixture.

TABLE 28

In Vivo Neutralization Of Toxin B Using Affinity Purified Antibodies

| Treatment Group[a] | Number Animals Alive[b] | Number Animals Dead[b] |
|---|---|---|
| Preimmune(1) | 0 | 5 |
| CTB(1) | 5 | 0 |
| pPB1750-2360(1) | 5 | 0 |
| 1.5 mg anti-pMB1750-2360(2) | 1 | 4 |
| 1.5 mg anti-pMB1970-2360(2) | 0 | 5 |
| 300 μg anti-CTB(2) | 5 | 0 |

[a]*C. difficile* toxin B (CTB) (at 5 μg/ml; 25 μg total; Tech Lab) at lethal concentration to hamsters is added to antibody and incubated for one hour at 37° C. After incubation, 1 ml of this mixture is injected intraperitoneally (IP) into hamsters. Each treatment group received toxin premixed with antibody raised against the indicated protein, as either (1) 4X antibody PEG prep or (2) affinity purified antibody (on a pPB1750-2360 resin), either 1.5 mg/group (anti-pMB1750-2360 and anti-pMB1970-2360; used undiluted affinity purified antibody) or 350 μg/group (anti-CTB, repeat specific; used ⅕ diluted anti-CTB antibody).

[b]The numbers in each group represent numbers of hamsters dead or alive, 2 hr post-IP administration of toxin/antibody mixture.

TABLE 29

Generation Of Neutralizing Antibodies Utilizing The Gerbu Adjuvant

| Treatment Group[a] | Number Animals Alive[b] | Number Animals Dead[b] |
|---|---|---|
| Preimmune | 0 | 5 |
| CTB | 5 | 0 |
| pMB1970-2360 | 0 | 5 |
| pMB1850-2360 | 0 | 5 |
| pPB1850-2360 | 0 | 5 |
| pMB1750-2360 (Gerbu adj) | 5 | 0 |

[a]*C. difficile* toxin B (CTB) (Tech Lab) at lethal concentration to hamsters is added to antibody and incubated for one hour at 37° C. After incubation this mixture is injected intraperitoneally (IP) into hamsters. Each treatment group received toxin premixed with antibody raised against the indicated protein, as a 4X antibody PEG prep.
[b]The numbers in each group represent numbers of hamsters dead or alive, 2 hrs post IP administration of toxin/antibody mixture.

TABLE 30

In Vivo Neutralization Of Toxin B

| Immunogen | Adjuvant | Tested Preparation[a] | Antigen Utilized For AP | In vivo Neutralization[b] |
|---|---|---|---|---|
| Preimmune | NA[1] | PEG | NA | no |
| CTB (native) | Titermax | PEG | NA | yes |
| CTB (native) | Titermax | AP | pPB1750-2360 | yes |
| CTB (native) | Titermax | AP | pPB1850-2360 | yes |
| CTB (native) | Titermax | AP | pPB1750-1970 | yes |
| CTB (native) | Titermax | AP | pPB1970-2360 | yes |
| pMB1750-2360 | Freunds | PEG | NA | no |
| pMB1750-2360 | Freunds | AP | pPB1750-2360 | no |
| pMB1750-2360 | Gerbu | PEG | NA | yes |
| pMB1970-2360 | Freunds | PEG | NA | no |
| pMB1970-2360 | Freunds | AP | pPB1750-2360 | no |
| pPB1750-2360 | Freunds | PEG | NA | yes |
| pPB1850-2360 | Freunds | PEG | NA | no |
| pMB1850-2360 | Freunds | PEG | NA | no |
| INT 1 + 2 | Freunds | PEG | NA | no |
| INT 4 + 5 | Freunds | PEG | NA | no |

[a]Either PEG preparation (PEG) or affinity purified antibodies (AP).
[b]'Yes' denotes complete neutralization (0/5 dead) while 'no' denotes no neutralization (5/5 dead) of toxin B, 2 hours post-administration of mixture.
[1]'NA' denotes not applicable.

The pPB1750–2360 antibody pool confers significant in vivo protection, equivalent to that obtained with the affinity purified CTB antibodies. This correlates with the observed high affinity of this antibody pool (relative to the pMB1750–2360 or pMB1970–2360 pools) as assayed by Western blot analysis (FIG. 24). These results provide the first demonstration that in vivo neutralizing antibodies can be induced using recombinant toxin B protein as immunogen.

The failure of high concentrations of antibodies raised against the pMB1750–2360 protein (using Freunds adjuvant) to neutralize, while the use of Gerbu adjuvant and pMB1750–2360 protein generates a neutralizing response, demonstrates that conformation or presentation of this protein is essential for the induction of neutralizing antibodies. These results are consistent with the observation that the neutralizing antibodies produced when native CTB is used as an immunogen appear to recognize conformational epitopes [see section b) above]. This is the first demonstration that the conformation or presentation of recombinant toxin B protein is essential to generate high titers of neutralizing antibodies.

EXAMPLE 20

Determination of Quantitative and Qualitative Differences Between pMB1750–2360, pMB1750–2360 (Gerbu) Or pPB1750–2360 IgY Polyclonal Antibody Preparations In Example 19, it was demonstrated that toxin B neutralizing antibodies could be generated using specific recombinant toxin B proteins (pPB1750–2360) or specific adjuvants. Antibodies raised against pMB1750–2360 were capable of neutralizing the enterotoxin effect of toxin B when the recombinant protein was used to immunize hens in conjunction with the Gerbu adjuvant, but not when Freunds adjuvant was used. To determine the basis for these antigen and adjuvant restrictions, toxin B-specific antibodies present in the neutralizing and non-neutralizing PEG preparations were isolated by affinity chromatography and tested for qualitative or quantitative differences. The example involved a) purification of anti-toxin B specific antibodies from pMB1750–2360 and pPB1750–2360 PEG preparations and b) in vivo neutralization of toxin B using the affinity purified antibody.

a) Purification of specific Antibodies from pMB1750–2360 And pPB1750–2360 PEG Preparations To purify and determine the concentration of specific antibodies (expressed as the percent of total antibody) within the pPB1750–2360 (Freunds and Gerbu) and pPB1750–2360 PEG preparations, defined quantities of these antibody preparations were chromatographed on an affinity column containing the entire toxin B repeat region (pPB1750–2360). The amount of affinity purified antibody was then quantified.

An affinity column containing the recombinant toxin B repeat protein, pPB1750–2360, was made as follows. Four ml of PBS-washed Actigel resin (Sterogene) was coupled with 5 mg of pPB1750–2360 affinity purified protein (dialyzed into PBS; estimated to be greater than 95% full length fusion protein) in a 15 ml tube (Falcon) containing 1/10 final volume Aid-coupling solution (1M sodium cyanoborohydride). Aliquots of the supernatant from the coupling reactions, before and after coupling, were assessed by Coomassie staining of 7.5% SDS-PAGE gels. Based on protein band intensities, greater than 95% (approximately 5 mg) of recombinant protein was coupled to the resin. The coupled resin was poured into a 10 ml column (BioRad), washed extensively with PBS, pre-eluted with 4M guanidine-HCl (in 10 mM Tris-HCl, pH 8.0; 0.005% thimerosal) and re-equilibrated in PBS and stored at 4° C.

Aliquots of pMB1750–2360, pMB1750–2360 (Gerbu) or pPB1750–2360 IgY polyclonal antibody preparations (PEG preps) were affinity purified on the above column as follows. The column was attached to an UV monitor (ISCO), and washed with PBS. Forty ml aliquots of 2× PEG preps (filter sterilized using a 0.45$\mu$ filter and quantified by $OD_{280}$ before chromatography) was applied. The column was washed with PBS until the baseline was re-established (the column flow-through was saved), washed with BBSTween to elute non-specifically binding antibodies and re-equilibrated with PBS. Bound antibody was eluted from the column in 4M guanidine-HCl (in 10 mM Tris-HCL, pH 8.0, 0.005% thimerosal) and the entire elution peak collected in a 15 ml tube (Falcon). The column was re-equilibrated, and the column eluate re-chromatographed as described above. The antibody preparations were quantified by UV absorbance (the elution buffer was used to zero the spectrophotometer).

Approximately 10 fold higher concentrations of total purified antibody was obtained upon elution of the first chromatography pass relative to the second pass. The low yield from the second chromatography pass indicated that most of the specific antibodies were removed by the first round of chromatography.

Pools of affinity purified specific antibodies were prepared by dialysis of the column elutes after the first column chromatography pass for the pMB1750–2360, pMB1750–23600 (Gerbu) or pPB1750–2360 IgY polyclonal antibody preparations. The elutes were collected on ice and immediately dialyzed against a 100-fold volume of PBS at 4° C. for 2 hrs. The samples were then dialyzed against 3 changes of a 65-fold volume of PBS at 4° C. Dialysis was performed for a minimum of 8 hrs per change of PBS. The dialyzed samples were collected, centrifuged to remove insoluble debris, quantified by $OD_{280}$, and stored at 4° C.

The percentage of toxin B repeat-specific antibodies present in each preparation was determined using the quantifications of antibody yields from the first column pass (amount of specific antibody recovered after first pass/total protein loaded). The yield of repeat-specific affinity purified antibody (expressed as the percent of total protein in the preparation) in: 1) the pMB1750–2360 PEG prep was approximately 0.5%, 2) the pMB1750–2360 (Gerbu) prep was approximately 2.3%, and 3) the pPB1750–2360 prep was approximately 0.4%. Purification of a CTB IgY polyclonal antibody preparation on the same column demonstrated that the concentration of toxin B repeat specific antibodies in the CTB preparation was 0.35%.

These results demonstrate that 1) the use of Gerbu adjuvant enhanced the titer of specific antibody produced against the pMB1750–2360 protein 5-fold relative to immunization using Freunds adjuvant, and 2) the differences seen in the in vivo neutralization ability of the pMB1750–2360 (not neutralizing) and pPB1750–2360 (neutralizing) and CTB (neutralizing) PEG preps seen in Example 19 was not due to differences in the titers of repeat-specific antibodies in the three preparations because the titer of repeat-specific antibody was similar for all three preps; therefore the differing ability of the three antibody preparations to neutralize toxin B must reflect qualitative differences in the induced toxin B repeat-specific antibodies. To confirm that qualitative differences exist between antibodies raised in hens immunized with different recombinant proteins and/or different adjuvants, the same amount of affinity purified anti-toxin B repeat (aa 1870–2360 of toxin B) antibodies from the different preparations was administered to hamsters using the in vivo hamster model as described below.

b) In vivo Neutralization of Toxin B Using Affinity Purified Antibody

The in vivo hamster model was utilized to assess the neutralizing ability of the affinity purified antibodies raised against recombinant toxin B proteins purified in (a) above. As well, a 4× IgY PEG preparation from a second independent immunization utilizing the pPB1750–2360 antigen with Freunds adjuvant was tested for in vivo neutralization. The results are shown in Table 31.

The results shown in Table 31 demonstrate that:

1) as shown in Example 19 and reproduced here, 1.5 mg of affinity purified antibody from pMB1750–2360 immunized hens using Freunds adjuvant does not neutralize toxin B in vivo. However, 300 μg of affinity purified antibody from similarly immunized hens utilizing Gerbu adjuvant demonstrated complete neutralization of toxin B in vivo. This demonstrates that Gerbu adjuvant, in addition to enhancing the titer of antibodies reactive to the pMB1750–2360 antigen relative to Freunds adjuvant (demonstrated in (a) above), also enhances the yield of neutralizing antibodies to this antigen, greater than 5 fold.
2) Complete in vivo neutralization of toxin B was observed with 1.5 mg of affinity purified antibody from hens immunized with pPB1750–2360 antigen, but not with pMB1750–2360 antigen, when Freunds adjuvant was used. This demonstrates, using standardized toxin B repeat-specific antibody concentrations, that neutralizing antibodies were induced when pPB1750–2360 but not pMB1750–2360 was used as the antigen with Freunds adjuvant.
3) Complete in vivo neutralization was observed with 300 μg of pMB1750–2360 (Gerbu) antibody, but not with 300 μg of pPB1750–2360 (Freunds) antibody. Thus the pMB1750–2360 (Gerbu) antibody has a higher titer of neutralizing antibodies than the pPB1750–2360 (Freunds) antibody.
4) Complete neutralization of toxin B was observed using 300 μg of CTB antibody [affinity purified (AP)] but not 100 μg CTB antibody (AP or PEG prep). This demonstrates that greater than 100 μg of toxin B repeat-specific antibody (anti-CTB) is necessary to neutralize 25 μg toxin B in vivo in this assay, and that affinity purified antibodies specific to the toxin B repeat interval neutralize toxin B as effectively as the PEP prep of IgY raised against the entire CTB protein (shown in this assay).
5) As was observed with the initial pPB1750–2360 (IgY) PEG preparation (Example 19), complete neutralization was observed with a IgY PEG preparation isolated from a second independent group of pPB1750–2360 (Freunds) immunized hens. This demonstrates that neutralizing antibodies are reproducibly produced when hens are immunized with pPB1750–2360 protein utilizing Freunds adjuvant.

TABLE 31

In vivo Neutralization Of Toxin B Using Affinity Purified Antibodies

| Treatment Group[a] | Number Animals Alive[b] | Number Animals Dead[b] |
|---|---|---|
| Preimmune[1] | 0 | 5 |
| CTB (300 μg)[2] | 5 | 0 |
| CTB (100 μg)[2] | 1 | 4 |
| pMB1750-2360 (G) (5 mg)[2] | 5 | 0 |
| pMB1750-2360 (G) (1.5 mg)[2] | 5 | 0 |
| pMB1750-2360 (G) (300 μg)[2] | 5 | 0 |
| pMB1750-2360 (F) (1.5 mg)[2] | 0 | 5 |
| pPB1750-2360 (F) (1.5 mg)[2] | 5 | 0 |
| pPB1750-2360 (F) (300 μg)[2] | 1 | 4 |
| CTB (100 μg)[3] | 2 | 3 |
| pPB1750-2360 (F) (500 μg)[1] | 5 | 0 |

[a]*C. difficile* toxin B (CTB) (Tech Lab) at lethal concentration to hamsters (25 μg) was added to the antibody (amount of specific antibody is indicated) and incubated for one hour at 37° C. After incubation, this mixture was injected IP into hamsters (⅕ total mix injected per hamster). Each treatment group received toxin premixed with antibody raised against the indicated protein (G = gerbu adjuvant, F = Freunds adjuvant). [1]indicates the antibody was a 4X IgY PEG prep; [2]indicates the antibody was affinity purified on a pPB1850-2360 resin; and [3]indicates that the antibody was a IX IgY PEG prep.
[b]The numbers in each group represent numbers of hamsters dead or alive, 2 hrs post IP administration of toxin/antibody mixture.

EXAMPLE 21

Diagnostic Enzyme Immunoassays for *C. difficile* Toxins A and B

The ability of the recombinant toxin proteins and antibodies raised against these recombinant proteins (described in the above examples) to form the basis of diagnostic assays for the detection of clostridial toxin in a sample was examined. Two immunoassay formats were tested to quantitatively detect *C. difficile* toxin A and toxin B from a biological specimen. The first format involved a competitive assay in which a fixed amount of recombinant toxin A or B was immobilized on a solid support (e.g., microtiter plate wells) followed by the addition of a toxin-containing biological specimen mixed with affinity-purified or PEG fractionated antibodies against recombinant toxin A or B. If toxin is present in a specimen, this toxin will compete with the immobilized recombinant toxin protein for binding to the anti-recombinant antibody thereby reducing the signal obtained following the addition of a reporter reagent. The reporter reagent detects the presence of antibody bound to the immobilized toxin protein.

In the second format, a sandwich immunoassay was developed using affinity-purified antibodies to recombinant toxin A and B. The affinity-purified antibodies to recombinant toxin A and B were used to coat microtiter wells instead of the recombinant polypeptides (as was done in the competitive assay format). Biological samples containing toxin A or B were then added to the wells followed by the addition of a reporter reagent to detect the presence of bound toxin in the well.

a) Competitive Immunoassay for the Detection of *C. difficile* Toxin

Recombinant toxin A or B was attached to a solid support by coating 96 well microtiter plates with the toxin protein at a concentration of 1 μg/ml in PBS. The plates were incubated overnight at 2–8° C. The following morning, the coating solutions were removed and the remaining protein binding sites on the wells were blocked by filling each well with a PBS solution containing 0.5% BSA and 0.05% Tween-20. Native *C. difficile* toxin A or B (Tech Lab) was diluted to 4 μg/ml in stool extracts from healthy Syrian hamsters (Sasco). The stool extracts were made by placing fecal pellets in a 15 ml centrifuge tube; PBS was added at 2 ml/pellet and the tube was vortexed to create a uniform suspension. The tube was then centrifuged at 2000 rpm for 5 min at room temperature. The supernatant was removed; this comprises the stool extract. Fifty μl of the hamster stool extract was pipetted into each well of the microtiter plates to serve as the diluent for serial dilutions of the 4 μg/ml toxin samples. One hundred μl of the toxin samples at 4 μg/ml was pipetted into the first row of wells in the microtiter plate, and 50 μl aliquots were removed and diluted serially down the plate in duplicate. An equal volume of affinity purified anti-recombinant toxin antibodies [1 ng/well of anti-pMA1870–2680 antibody was used for the detection of toxin A; 0.5 ng/well of anti-pMB1750–2360(Gerbu) was used for the detection of toxin B] were added to appropriate wells, and the plates were incubated at room temperature for 2 hours with gentle agitation. Wells serving as negative control contained antibody but no native toxin to compete for binding.

Unbound toxin and antibody were removed by washing the plates 3 to 5 times with PBS containing 0.05% Tween-20. Following the wash step, 100 μl of rabbit anti-chicken IgG antibody conjugated to alkaline phosphatase (Sigma) was added to each well and the plates were incubated for 2 hours at room temperature. The plates were then washed as before to remove unbound secondary antibody. Freshly prepared alkaline phosphatase substrate (1 mg/ml p-nitrophenyl phosphate (Sigma) in 50 mM $NaCO_3$, pH 9.5; 10 mM $MgCl_2$) was added to each well. Once sufficient color developed, the plates were read on a Dynatech MR700 microtiter plate reader using a 410 nm filter.

The results are summarized in Tables 32 and 33. For the results shown in Table 32, the wells were coated with recombinant toxin A protein (pMA 1870–2680). The amount of native toxin A added (present as an addition to solubilized hamster stool) to a given well is indicated (0 to 200 ng). Antibody raised against the recombinant toxin A protein, pMA1870–2680, was affinity purified on the an affinity column containing pPA1870–2680 (described in Example 20). As shown in Table 32, the recombinant toxin A protein and affinity-purified antitoxin can be used for the basis of a competitive immunoassay for the detection of toxin A in biological samples.

Similar results were obtained using the recombinant toxin B, pPB1750–2360, and antibodies raised against pMB1750–2360(Gerbu). For the results shown in Table 33, the wells were coated with recombinant toxin B protein (pPB1750–2360). The amount of native toxin B added (present as an addition to solubilized hamster stool) to a given well is indicated (0 to 200 ng). Antibody raised against the recombinant toxin B protein, pMB1750–2360(Gerbu), was affinity purified on the an affinity column containing pPB1850–2360 (described in Example 20). As shown in Table 33, the recombinant toxin B protein and affinity-purified antitoxin can be used for the basis of a competitive immunoassay for the detection of toxin B in biological samples.

In this competition assay, the reduction is considered significant over the background levels at all points; therefore the assay can be used to detect samples containing less than 12.5 ng toxin A/well and as little as 50–100 ng toxin B/well.

TABLE 32

Competitive Inhibition Of Anti-*C. difficile* Toxin A By Native Toxin A

| ng Toxin A/Well | $OD_{410}$ Readout |
|---|---|
| 200 | 0.176 |
| 100 | 0.253 |
| 50 | 0.240 |
| 25 | 0.259 |
| 12.5 | 0.309 |
| 6.25 | 0.367 |
| 3.125 | 0.417 |
| 0 | 0.590 |

TABLE 33

Competitive Inhibition Of Anti-*C. difficile* Toxin B By Native Toxin B

| ng Toxin B/Well | $OD_{410}$ Readout |
|---|---|
| 200 | 0.392 |
| 100 | 0.566 |
| 50 | 0.607 |
| 25 | 0.778 |
| 12.5 | 0.970 |
| 6.25 | 0.902 |
| 3.125 | 1.040 |
| 0 | 1.055 |

These competitive inhibition assays demonstrate that native *C. difficile* toxins and recombinant *C. difficile* toxin proteins can compete for binding to antibodies raised against recombinant *C. difficile* toxins demonstrating that these anti-recombinant toxin antibodies provide effective diagnostic reagents.

b) Sandwich Immunoassay for the Detection of *C. difficile* Toxin

Affinity-purified antibodies against recombinant toxin A or toxin B were immobilized to 96 well microtiter plates as follows. The wells were passively coated overnight at 4° C. with affinity purified antibodies raised against either pMA1870–2680 (toxin A) or pMB1750–2360(Gerbu) (toxin B). The antibodies were affinity purified as described in Example 20. The antibodies were used at a concentration of 1 μg/ml and 100 μl was added to each microtiter well. The wells were then blocked with 200 μl of 0.5% BSA in PBS for 2 hours at room temperature and the blocking solution was then decanted. Stool samples from healthy Syrian hamsters were resuspended in PBS, pH 7.4 (2 ml PBS/stool pellet was used to resuspend the pellets and the sample was centrifuged as described above). The stool suspension was then spiked with native *C. difficile* toxin A or B (Tech Lab) at 4 μg/ml. The stool suspensions containing toxin (either toxin A or toxin B) were then serially diluted two-fold in stool suspension without toxin and 50 μl was added in duplicate to the coated microtiter wells. Wells containing stool suspension without toxin served as the negative control.

The plates were incubated for 2 hours at room temperature and then were washed three times with PBS. One hundred μl of either goat anti-native toxin A or goat anti-native toxin B (Tech Lab) diluted 1:1000 in PBS containing 1% BSA and 0.05% Tween 20 was added to each well. The plates were incubated for another 2 hours at room temperature. The plates were then washed as before and 100 μl of alkaline phosphatase-conjugated rabbit anti-goat IgG (Cappel, Durham, N.C.) was added at a dilution of 1:1000. The plates were incubated for another 2 hours at room temperature. The plates were washed as before then developed by the addition of 100 μl/well of a substrate solution containing 1 mg/ml p-nitrophenyl phosphate (Sigma) in 50 mM $Na_2CO_3$, pH 9.5; 10 mM $MgCl_2$. The absorbance of each well was measured using a plate reader (Dynatech) at 410 nm. The assay results are shown in Tables 34 and 35.

TABLE 34

*C. difficile* Toxin A Detection In Stool Using Affinity-Purified Antibodies Against Toxin A

| ng Toxin A/Well | $OD_{410}$ Readout |
|---|---|
| 200 | 0.9 |
| 100 | 0.8 |
| 50 | 0.73 |
| 25 | 0.71 |
| 12.5 | 0.59 |
| 6.25 | 0.421 |
| 0 | 0 |

TABLE 35

*C. difficile* Toxin B Detection In Stool Using Affinity-Purified Antibodies Against Toxin B

| ng Toxin B/Well | $OD_{410}$ Readout |
|---|---|
| 200 | 1.2 |
| 100 | 0.973 |
| 50 | 0.887 |
| 25 | 0.846 |
| 12.5 | 0.651 |
| 6.25 | 0.431 |
| 0 | 0.004 |

The results shown in Tables 34 and 35 show that antibodies raised against recombinant toxin A and toxin B fragments can be used to detect the presence of *C. difficile* toxin in stool samples. These antibodies form the basis for a sensitive sandwich immunoassay which is capable of detecting as little as 6.25 ng of either toxin A or B in a 50 μl stool sample. As shown above in Tables 34 and 35, the background for this sandwich immunoassay is extremely low; therefore, the sensitivity of this assay is much lower than 6.25 ng toxin/well. It is likely that toxin levels of 0.5 to 1.0 pg/well could be detected by this assay.

The results shown above in Tables 32–35 demonstrate clear utility of the recombinant reagents in *C. difficile* toxin detection systems.

EXAMPLE 22

Construction and Expression of *C. botulinum* C Fragment Fusion Proteins

The *C. botulinum* type A neurotoxin gene has been cloned and sequenced [Thompson, et al., Eur. J. Biochem. 189:73 (1990)]. The nucleotide sequence of the toxin gene is available from the EMBL/GenBank sequence data banks under the accession number X52066; the nucleotide sequence of the coding region is listed in SEQ ID NO:27. The amino acid sequence of the *C. botulinum* type A neurotoxin is listed in SEQ ID NO:28. The type A neurotoxin gene is synthesized as a single polypeptide chain which is processed to form a dimer composed of a light and a heavy chain linked via disulfide bonds. The 50 kD carboxy-terminal portion of the heavy chain is referred to as the C fragment or the $H_C$ domain.

Previous attempts by others to express polypeptides comprising the C fragment of *C. botulinum* type A toxin as a native polypeptide (e.g., not as a fusion protein) in *E. coli* have been unsuccessful [H. F. LaPenotiere, et al. in *Botulinum and Tetanus Neurotoxins*, DasGupta, Ed., Plenum Press, New York (1993), pp. 463–466]. Expression of the C fragment as a fusion with the *E. coli* MBP was reported to result in the production of insoluble protein (H. F. LaPenotiere, et al., supra).

In order to produce soluble recombinant C fragment proteins in *E. coli*, fusion proteins comprising a synthetic C fragment gene derived from the *C. botulinum* type A toxin and either a portion of the *C. difficile* toxin protein or the MBP were constructed. This example involved a) the construction of plasmids encoding C fragment fusion proteins and b) expression of *C. botulinum* C fragment fusion proteins in *E. coli.* a) Construction of Plasmids Encoding C Fragment Fusion Proteins

In Example 11, it was demonstrated that the *C. difficile* toxin A repeat domain can be efficiently expressed and purified in *E. coli* as either native (expressed in the pET 23a vector in clone pPA1870–2680) or fusion (expressed in the pMALc vector as a fusion with the *E. coli* MBP in clone pMA1870–2680) proteins. Fusion proteins comprising a fusion between the MBP, portions of the *C. difficile* toxin A repeat domain (shown to be expressed as a soluble fusion protein) and the C fragment of the *C. botulinum* type A toxin were constructed. A fusion protein comprising the C fragment of the *C botulinum* type A toxin and the MBP was also constructed.

Figure 25:
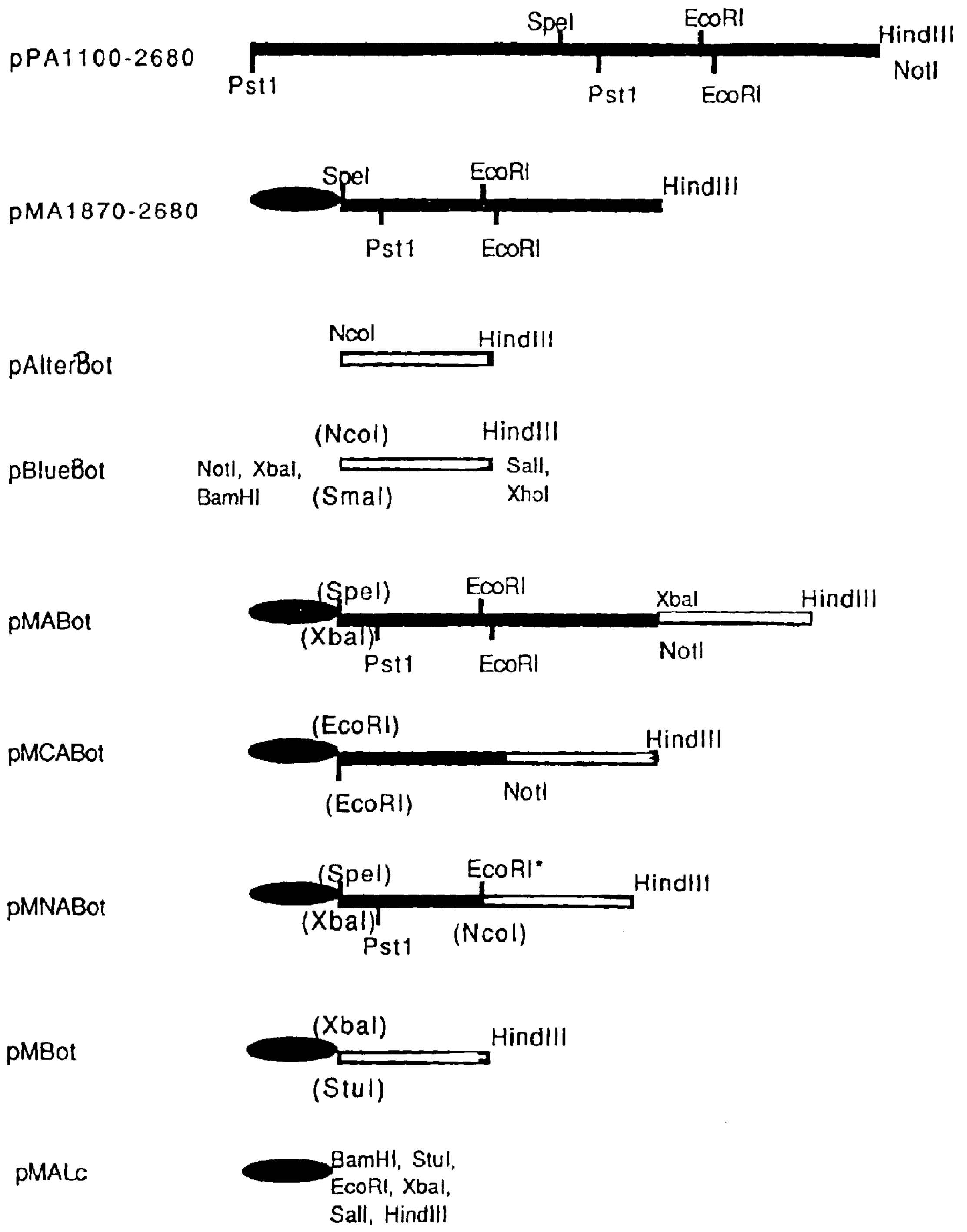
FIG. 25 shows *C. botulinum* type A toxin expression constructs; constructs used to provide *C. botulinum* or *C difficile* sequences are also shown.

FIG. 25 provides a schematic representation of the botulinal fusion proteins along with the donor constructs containing the C difficile toxin A sequences or *C. botulinum* C fragment sequences which were used to generate the botulinal fusion proteins. In FIG. 25, the solid boxes represent *C. difficile* toxin A gene sequences, the open boxes represent *C. botulinum* C fragment sequences and the solid black ovals represent the *E. coli* MBP. When the name for a restriction enzyme appears inside parenthesis, this indicates that the restriction site was destroyed during construction. An asterisk appearing with the name for a restriction enzyme indicates that this restriction site was recreated at the cloning junction.

In FIG. 25, a restriction map of the pMA1870–2680 and pPA1100–2680 constructs (described in Example 11) which contain sequences derived from the *C. difficile* toxin A repeat domain are shown; these constructs were used as the source of *C. difficile* toxin A gene sequences for the construction of plasmids encoding fusions between the *C. botulinum* C fragment gene and the *C. difficile* toxin A gene. The pMA1870–2680 expression construct expresses high levels of soluble, intact fusion protein (20 mg/liter culture) which can be affinity purified on an amylose column (purification described in Example 11 d).

The pAlterBot construct (FIG. 25) was used as the source of *C. botulinum* C fragment gene sequences for the botulinal fusion proteins. pAlterBot was obtained from J. Middlebrook and R. Lemley at the U.S. Department of Defense. pAlterBot contains a synthetic *C. botulinum* C fragment inserted in to the pALTER-1® vector (Promega). This synthetic C fragment gene encodes the same amino acids as does the naturally occurring C fragment gene. The naturally occurring C fragment sequences, like most clostridial genes, are extremely A/T rich (Thompson et al., supra). This high A/T content creates expression difficulties in *E. coli* and yeast due to altered codon usage frequency and fortuitous polyadenylation sites, respectively. In order to improve the expression of C fragment proteins in *E. coli*, a synthetic version of the gene was created in which the non-preferred codons were replaced with preferred codons.

The nucleotide sequence of the *C. botulinum* C fragment gene sequences contained within pAlterBot is listed in SEQ ID NO:22. The first six nucleotides (ATGGCT) encode a methionine and alanine residue, respectively. These two amino acids result from the insertion of the *C. botulinum* C fragment sequences into the pALTER® vector and provide the initiator methionine residue. The amino acid sequence of the *C. botulinum* C fragment encoded by the sequences contained within pAlterBot is listed in SEQ ID NO:23. The first two amino acids (Met Ala) are encoded by vector-derived sequences. From the third amino acid residue onward (Arg), the amino acid sequence is identical to that found in the *C. botulinum* type A toxin gene.

The pMA1870–2680, pPA1100–2680 and pAlterBot constructs were used as progenitor plasmids to make expression constructs in which fragments of the *C. difficile* toxin A repeat domain were expressed as genetic fusions with the *C. botulinum* C fragment gene using the pMAL-c expression vector (New England BioLabs). The pMAL-c expression vector generates fusion proteins which contain the MBP at the amino-terminal end of the protein. A construct, pMBot, in which the *C. botulinum* C fragment gene was expressed as a fusion with only the MBP was constructed (FIG. 25). Fusion protein expression was induced from *E. coli* strains harboring the above plasmids, and induced protein was affinity purified on an amylose resin column.

i) Construction of pBlueBot

In order to facilitate the cloning of the *C. botulinum* C fragment gene sequences into a number of desired constructs, the botulinal gene sequences were removed from pAlterBot and were inserted into the pBluescript plasmid (Stratagene) to generate pBlueBot (FIG. 25). pBlueBot was constructed as follows. Bacteria containing the pAlterBot plasmid were grown in medium containing tetracycline and plasmid DNA was isolated using the QIAprep-spin Plasmid Kit (Qiagen). One microgram of pAlterBot DNA was digested with NcoI and the resulting 3' recessed sticky end was made blunt using the Klenow fragment of DNA polymerase I (here after the Klenow fragment). The pAlterBot DNA was then digested with HindIII to release the botulinal gene sequences (the Bot insert) as a blunt (filled NcoI site)-HindIII fragment. pBluescript vector DNA was prepared by digesting 200 ng of pBluescript DNA with SmaI and HindIII. The digestion products from both plasmids were resolved on an agarose gel. The appropriate fragments were removed from the gel, mixed and purified utilizing the Prep-a-Gene kit (BioRad). The eluted DNA was then ligated using T4 DNA ligase and used to transform competent DH5α cells (Gibco-BRL). Host cells were made competent for transformation using the calcium chloride protocol of Sambrook et al., supra at 1.82–1.83. Recombinant clones were isolated and confirmed by restriction digestion using standard recombinant molecular biology techniques (Sambrook et al, supra). The resultant clone, pBlueBot, contains several useful unique restriction sites flanking the Bot insert (i.e., the *C. botulinum* C fragment sequences derived from pAlterBot) as shown in FIG. 25.

ii) Construction of *C. difficile*/*C. botulinum*/MBP Fusion Proteins

Constructs encoding fusions between the *C. difficile* toxin A gene and the *C. botulinum* C fragment gene and the MBP were made utilizing the same recombinant DNA methodology outlined above; these fusion proteins contained varying amounts of the *C. difficile* toxin A repeat domain.

The pMABot clone contains a 2.4 kb insert derived from the *C. difficile* toxin A gene fused to the Bot insert (i.e, the *C. botulinum* C fragment sequences derived from pAlterBot). pMABot (FIG. 25) was constructed by mixing gel-purified DNA from NotI/HindIII digested pBlueBot (the 1.2 kb Bot fragment), SpeI/NotI digested pPA 1100–2680 (the 2.4 kb *C. difficile* toxin A repeat fragment) and XbaI/HindIII digested pMAL-c vector. Recombinant clones were isolated, confirmed by restriction digestion and purified using the QIAprep-spin Plasmid Kit (Qiagen). This clone expresses the toxin A repeats and the botulinal C fragment protein sequences as an in-frame fusion with the MBP.

The pMCABot construct contains a 1.0 kb insert derived from the *C. difficile* toxin A gene fused to the Bot insert (i.e, the *C. botulinum* C fragment sequences derived from pAlterBot). pMCABot was constructed by digesting the pMABot clone with EcoRI to remove the 5' end of the *C. difficile* toxin A repeat (see FIG. 25, the pMAL-c vector contains a EcoRI site 5' to the *C. difficile* insert in the pMABot clone). The restriction sites were filled and religated together after gel purification. The resultant clone (pMCABot, FIG. 25) generated an in-frame fusion between the MBP and the remaining 3' portion of the *C. difficile* toxin A repeat domain fused to the Bot gene.

The pMNABot clone contains the 1 kb SpeI/EcoRI (filled) fragment from the *C. difficile* toxin A repeat domain (derived from clone pPA 1100–2680) and the 1.2 kb *C. botulinum* C fragment gene as a NcoI (filled)/HindIII fragment (derived from pAlterBot). These two fragments were inserted into the pMAL-c vector digested with XbaI/HindIII. The two insert fragments were generated by digestion of the appropriate plasmid with EcoRI (pPA 100–2680) or NcoI (pAlterBot) followed by treatment with the Klenow fragment. After treatment with the Klenow fragment, the plasmids were digested with the second enzyme (either SpeI or HindIII). All three fragments were gel purified, mixed and Prep-a-Gene purified prior to ligation. Following ligation and transformation, putative recombinants were analyzed by restriction analysis; the EcoRI site was found to be regenerated at the fusion junction, as was predicted for a fusion between the filled EcoRI and NcoI sites.

A construct encoding a fusion protein between the botulinal C fragment gene and the MBP gene was constructed (i.e., this fusion lacks any *C. difficile* toxin A gene sequences) and termed pMBot. The pMBot construct was made by removal of the *C. difficile* toxin A sequences from the pMABot construct and fusing the C fragment gene sequences to the MBP. This was accomplished by digestion of pMABot DNA with StuI (located in the pMALc polylinker 5' to the XbaI site) and XbaI (located 3' to the NotI site at the toxA-Bot fusion junction), filling in the XbaI site using the Klenow fragment, gel purifying the desired restriction fragment, and ligating the blunt ends to circularize the plasmid. Following ligation and transformation, putative recombinants were analyzed by restriction mapping of the Bot insert (i.e, the *C. botulinum* C fragment sequences).

b) Expression of *C. botulinum* C. Fragment Fusion Proteins in *E. coli*

Large scale (1 liter) cultures of the pMAL-c vector, and each recombinant construct described above in (a) were grown, induced, and soluble protein fractions were isolated as described in Example 18. The soluble protein extracts were chromatographed on amylose affinity columns to isolate recombinant fusion protein. The purified recombinant fusion proteins were analyzed by running samples on SDS-PAGE gels followed by Coomassie staining and by Western blot analysis as described [Williams et al, (1994) supra]. In brief, extracts were prepared and chromatographed in column buffer (10 mM $NaPO_4$, 0.5 M NaCl, 10 mM P-mercaptoethanol, pH 7.2) over an amylose resin (New England Biolabs) column, and eluted with column buffer containing 10 mM maltose as described [Williams, et al. (1994), supra]. An SDS-PAGE gel containing the purified protein samples stained with Coomassie blue is shown in FIG. 26.

Figure 26:
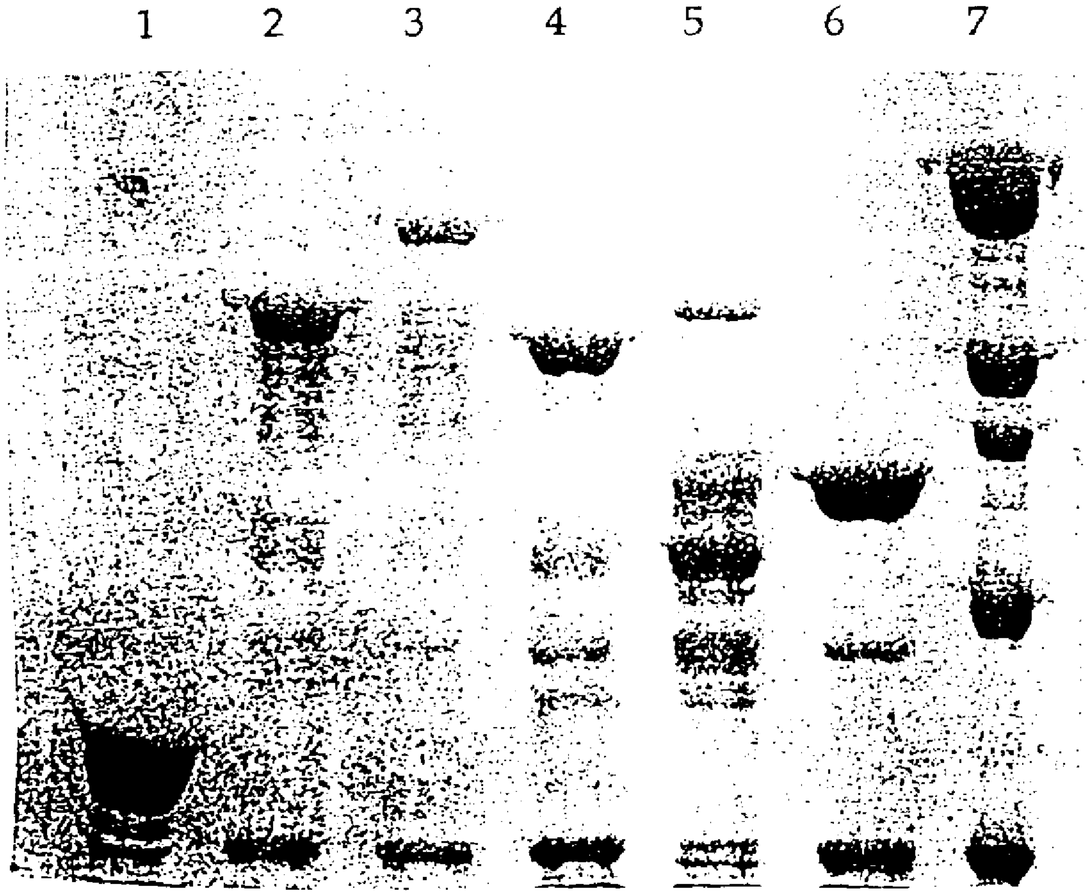
FIG. 26 is an SDS-PAGE gel stained with Coomaisse blue showing the purification of recombinant *C. botulinum* type A toxin fusion proteins.

In FIG. 26, the following samples were loaded. Lanes 1–6 contain protein purified from *E. coli* containing the pMAL-c, pPA1870–2680, pMABot, pMNABot, pMCABot and pMBot plasmids, respectively. Lane 7 contains broad range molecular weight protein markers (BioRad).

The protein samples were prepared for electrophoresis by mixing 5 μl of eluted protein with 5 μl of 2× SDS-PAGE sample buffer (0.125 mM Tris-HCl, pH 6.8, 2 mM EDTA, 6% SDS, 20% glycerol, 0.025% bromophenol blue; P-mercaptoethanol is added to 5% before use). The samples were heated to 95° C. for 5 min, then cooled and loaded on a 7.5% agarose SDS-PAGE gel. Broad range molecular weight protein markers were also loaded to allow estimation of the MW of identified fusion proteins. After electrophoresis, protein was detected generally by staining the gel with Coomassie blue.

In all cases the yields were in excess of 20 mg fusion protein per liter culture (see Table 36) and, with the exception of the pMCABot protein, a high percentage (i.e., greater than 20–50% of total eluted protein) of the eluted fusion protein was of a MW predicted for the full length fusion protein (FIG. 26). It was estimated (by visual inspection) that less than 10% of the pMCABot fusion protein was expressed as the full length fusion protein.

TABLE 36

Yield Of Affinity Purified *C. botulinum* C Fragment/MBP Fusion Proteins

| Construct | Yield (mg/liter of Culture) | Percentage Of Total Soluble Protein |
|---|---|---|
| pMABot | 24 | 5.0 |
| pMCABot | 34 | 5.0 |
| pMNABot | 40 | 5.5 |
| pMBot | 22 | 5.0 |
| pMA1870–2680 | 40 | 4.8 |

These results demonstrate that high level expression of intact *C. botulinum* C fragment/*C. difficile* toxin A fusion proteins in *E. coli* is feasible using the pMAL-c expression system. These results are in contrast to those reported by H. F. LaPenotiere, et al. (1993), supra. In addition, these results show that it is not necessary to fuse the botulinal C fragment gene to the *C. difficile* toxin A gene in order to produce a soluble fusion protein using the pMAL-c system in *E. coli.*

In order to determine whether the above-described botulinal fusion proteins were recognized by anti-*C. botulinum* toxin A antibodies, Western blots were performed. Samples containing affinity-purified proteins from *E. coli* containing the pMABot, pMCABot, pMNABot, pMBot, pMA1870–2680 or pMALc plasmids were analyzed. SDS-PAGE gels (7.5% acrylamide) were loaded with protein samples purified from each expression construct. After electrophoresis, the gels were blotted and protein transfer was confirmed by Ponceau S staining (as described in Example 12b).

Following protein transfer, the blots were blocked by incubation for 1 hr at 20° C. in blocking buffer [PBST (PBS containing 0.1% Tween 20 and 5% dry milk)]. The blots were then incubated in 10 ml of a solution containing the primary antibody; this solution comprised a 1/500 dilution of an anti-*C. botulinum* toxin A IgY PEG prep (described in Example 3) in blocking buffer. The blots were incubated for 1 hr at room temperature in the presence of the primary antibody. The blots were washed and developed using a rabbit anti-chicken alkaline phosphatase conjugate (Boehringer Mannheim) as the secondary antibody as follows. The rabbit anti-chicken antibody was diluted to 1 μg/ml in blocking buffer (10 ml final volume per blot) and the blots were incubated at room temperature for 1 hour in the presence of the secondary antibody. The blots were then washed successively with PBST, BBS-Tween and 50 mM $Na_2CO_3$, pH 9.5. The blots were then developed in freshly-prepared alkaline phosphatase substrate buffer (100 μg/ml nitro blue tetrazolium, 50 μg/ml 5-bromo-chloro-indolylphosphate, 5 mM $MgCl_2$ in 50 mM $NaCO_3$, pH 9.5). Development was stopped by flooding the blots with distilled water and the blots were air dried.

This Western blot analysis detected anti-*C. botulinum* toxin reactive proteins in the pMABot, pMCABot, pMNABot and pMBot protein samples (corresponding to the predicted full length proteins identified above by Coomassie staining in FIG. 26), but not in the pMAI 100–2680 or pMALc protein samples.

These results demonstrate that the relevant fusion proteins purified on an amylose resin as described above in section a) contained immunoreactive *C. botulinum* C fragment protein as predicted.

EXAMPLE 23

Generation of Neutralizing Antibodies by Nasal Administration of pMBot Protein The ability of the recombinant botulinal toxin proteins produced in Example 22 to stimulate a systemic immune response against botulinal toxin epitopes was assessed. This example involved: a) the evaluation of the induction of serum IgG titers produced by nasal or oral administration of botulinal toxin-containing *C. difficile* toxin A fusion proteins and b) the in vivo neutralization of *C. botulinum* type A neurotoxin by anti-recombinant *C. botulinum* C fragment antibodies.

a) Evaluation of the Induction of Serum IgG Titers Produced by Nasal or Oral Administration Of Botulinal Toxin-Containing *C. difficile* Toxin A Fusion Proteins Six groups containing five 6 week old CF female rats (Charles River) per group were immunized nasally or orally with one of the following three combinations using protein prepared in Example 22: (1) 250 μg pMBot protein per rat (nasal and oral); 2) 250 μg pMABot protein per rat (nasal and oral); 3) 125 μg pMBot admixed with 125 μg pMA1870–2680 per rat (nasal and oral). A second set of 5 groups containing 3 CF female rats/group were immunized nasally or orally with one of the following combinations (4) 250 μg pMNABot protein per rat (nasal and oral) or 5) 250 μg pMAL-c protein per rat (nasal and oral).

The fusion proteins were prepared for immunization as follows. The proteins (in column buffer containing 10 mM maltose) were diluted in 0.1 M carbonate buffer, pH 9.5 and administered orally or nasally in a 200 μl volume. The rats were lightly sedated with ether prior to administration. The oral dosing was accomplished using a 20 gauge feeding needle. The nasal dosing was performed using a P-200 micropipettor (Gilson). The rats were boosted 14 days after the primary immunization using the techniques described above and were bled 7 days later. Rats from each group were lightly etherized and bled from the tail. The blood was allowed to clot at 37° C. for 1 hr and the serum was collected.

The serum from individual rats was analyzed using an ELISA to determine the anti-*C. botulinum* type A toxin IgG serum titer. The ELISA protocol used is a modification of that described in Example 13c. Briefly, 96-well microtiter plates (Falcon, Pro-Bind Assay Plates) were coated with *C. botulinum* type A toxoid (prepared as described in Example 3a) by placing 100 μl volumes of *C. botulinum* type A toxoid at 2.5 μg/ml in PBS containing 0.005% thimerosal in each well and incubating overnight at 4° C. The next morning, the coating suspensions were decanted and all wells were washed three times using PBS.

In order to block non-specific binding sites, 100 μl of blocking solution [0.5% BSA in PBS] was then added to each well and the plates were incubated for 1 hr at 37° C. The blocking solution was decanted and duplicate samples of 150 μl of diluted rat serum added to the first well of a dilution series. The initial testing serum dilution was 1:30 in blocking solution containing 0.5% Tween 20 followed by 5-fold dilutions into this solution. This was accomplished by serially transferring 30 μl aliquots to 120 μl blocking solution containing 0.5% Tween 20, mixing, and repeating the dilution into a fresh well. After the final dilution, 30 μl was removed from the well such that all wells contained 120 μl final volume. A total of 3 such dilutions were performed (4 wells total). The plates were incubated 1 hr at 37° C. Following this incubation, the serially diluted samples were decanted and the wells were washed six times using PBS containing 0.5% Tween 20 (PBST). To each well, 100 μl of a rabbit anti-Rat IgG alkaline phosphatase (Sigma) diluted (1/1000) in blocking buffer containing 0.5% Tween 20 was added and the plate was incubated for 1 hr at 37° C. The conjugate solutions were decanted and the plates were washed as described above, substituting 50 mM $Na_2CO_3$, pH 9.5 for the PBST in the final wash. The plates were developed by the addition of 100 μl of a solution containing 1 mg/ml para-nitro phenyl phosphate (Sigma) dissolved in 50 mM $Na_2CO_3$, 10 mM $MgCl_2$, pH 9.5 to each well, and incubating the plates at room temperature in the dark for 5–45 min. The absorbency of each well was measured at 410 nm using a Dynatech MR 700 plate reader. The results are summarized in Tables 37 and 38 and represent mean serum reactivities of individual mice.

TABLE 37

Determination Of Anti-*C. botulinum* Type A Toxin Serum IgG Titers Following Immunization With *C. botulinum* C Fragment-Containing Fusion Proteins

| Route of Immunization | | Nasal | | | Oral | | |
|---|---|---|---|---|---|---|---|
| Immunogen | PRE-IMMUNE | pMBot | pMBot & pMA1870-2680 | pMABot | pMBot | pMBot & pMA1870-2680 | pMABot |
| Dilution | | | | | | | |
| 1:30 | 0.080 | 1.040 | 1.030 | 0.060 | 0.190 | 0.080 | 0.120 |
| 1:150 | 0.017 | 0.580 | 0.540 | 0.022 | 0.070 | 0.020 | 0.027 |
| 1:750 | 0.009 | 0.280 | 0.260 | 0.010 | 0.020 | 0.010 | 0.014 |
| 1:3750 | 0.007 | 0.084 | 0.090 | 0.009 | 0.009 | 0.010 | 0.007 |
| # Rats Tested | | 5 | 5 | 5 | 5 | 2 | 2 |

*Numbers represent the average values obtained from two ELISA plates, standardized utilizing the preimmune control.

TABLE 38

Determination Of Anti-*C. botulinum* Type A Toxin Serum IgG Titers Following Immunization With *C. botulinum* C Fragment-Containing Fusion Proteins

| | Route of Immunization | | | | |
|---|---|---|---|---|---|
| | PRE- | Nasal | | Oral | |
| Immunogen | IMMUNE | pMBot | pMABot | pMNABot | pMNABot |
| Dilution | | | | | |
| 1:30 | 0.040 | 0.557 | 0.010 | 0.015 | 0.010 |
| 1:150 | 0.009 | 0.383 | 0.001 | 0.003 | 0.002 |
| 1:750 | 0.001 | 0.140 | 0.000 | 0.000 | 0.000 |
| 1:3750 | 0.000 | 0.040 | 0.000 | 0.000 | 0.000 |
| # Rats Tested | | 1 | 1 | 3 | 3 |

The above ELISA results demonstrate that reactivity against the botulinal fusion proteins was strongest when the route of administration was nasal; only weak responses were stimulated when the botulinal fusion proteins were given orally. Nasally delivered pMbot and pMBot admixed with pMA1870–2680 invoked the greatest serum IgG response. These results show that only the pMBot protein is necessary to induce this response, since the addition of the pMA1870–2680 protein did not enhance antibody response (Table 37). Placement of the *C. difficile* toxin A fragment between the MBP and the *C. botulinum* C fragment protein dramatically reduced anti-bot IgG titer (see results using pMABot, pMCABot and pMNABot proteins).

This study demonstrates that the pMBot protein induces a strong serum IgG response directed against *C. botulinum* type A toxin when nasally administered.

b) In Vivo Neutralization of *C. botulinum* Type A Neurotoxin by Anti-Recombinant *C. botulinum* C Fragment Antibodies The ability of the anti-*C. botulinum* type A toxin antibodies generated by nasal administration of recombinant botulinal fusion proteins in rats (Example 22) to neutralize *C. botulinum* type A toxin was tested in a mouse neutralization model. The mouse model is the art accepted method for detection of botulinal toxins in body fluids and for the evaluation of anti-botulinal antibodies [E. J. Schantz and D. A. Kautter, J. Assoc. Off. Anal. Chem. 61:96 (1990) and Investigational New Drug (BB-IND-3703) application by the Surgeon General of the Department of the Army to the Federal Food and Drug Administration]. The anti-*C. botulinum* type A toxin antibodies were prepared as follows.

Rats from the group given pMBot protein by nasal administration were boosted a second time with 250 $\mu$g pMBot protein per rat and serum was collected 7 days later. Serum from one rat from this group and from a preimmune rat was tested for anti-*C. botulinum* type A toxin neutralizing activity in the mouse neutralization model described below.

The $LD_{50}$ of a solution of purified *C. botulinum* type A toxin complex, obtained from Dr. Eric Johnson (University of Wisconsin Madison), was determined using the intraperitoneal (IP) method of Schantz and Kautter [J. Assoc. Off. Anal. Chem. 61:96 (1978)] using 18–22 gram female ICR mice and was found to be 3500 $LD_{50}$/ml. The determination of the $LD_{50}$ was performed as follows. A Type A toxin standard was prepared by dissolving purified type A toxin complex in 25 mM sodium phosphate buffer, pH 6.8 to yield a stock toxin solution of $3.15\times10^7$ $LD_{50}$/mg. The $OD_{278}$ of the solution was determined and the concentration was adjusted to 10–20 $\mu$g/ml. The toxin solution was then diluted 1:100 in gel-phosphate (30 mM phosphate, pH 6.4; 0.2% gelatin). Further dilutions of the toxin solution were made as shown below in Table 39. Two mice were injected IP with 0.5 ml of each dilution shown and the mice were observed for symptoms of botulism for a period of 72 hours.

TABLE 39

Determination Of The $LD_{50}$ Of Purified *C. botulinum* Type A Toxin Complex

| Dilution | Number Dead At 72 hr. |
|---|---|
| 1:320 | 2/2 |
| 1:640 | 2/2 |
| 1:1280 | 2/2 |
| 1:2560 | 0/2 (sick after 72 hr) |
| 1:5120 | 0/2 (no symptoms) |

From the results shown in Table 39, the toxin titer was assumed to be between 2560 $LD_{50}$/ml and 5120 $LD_{50}$ (or about 3840 $LD_{50}$/ml). This value was rounded to 3500 $LD_{50}$/ml for the sake of calculation.

The amount of neutralizing antibodies present in the serum of rats immunized nasally with pMBot protein was then determined. Serum from two rats boosted with pMBot protein as described above and preimmune serum from one rat was tested as follows. The toxin standard was diluted 1:100 in gel-phosphate to a final concentration of 350 $LD_{50}$/ml. One milliliter of the diluted toxin standard was mixed with 25 $\mu$l of serum from each of the three rats and 0.2 ml of gel-phosphate. The mixtures were incubated at room temperature for 30 min with occasional mixing. Each of two mice were injected with IP with 0.5 ml of the mixtures. The mice were observed for signs of botulism for 72 hr. Mice receiving serum from rats immunized with pMBot protein neutralized this challenge dose. Mice receiving preimmune rat serum died in less than 24 hr.

The amount of neutralizing anti-toxin antibodies present in the serum of rats immunized with pMBot protein was then quantitated. Serum antibody titrations were performed by mixing 0.1 ml of each of the antibody dilutions (see Table 40) with 0.1 ml of a 1:10 dilution of stock toxin solution ($3.5\times10^4$ $LD_{50}$/ml) with 1.0 ml of gel-phosphate and injecting 0.5 ml IP into 2 mice per dilution. The mice were then observed for signs of botulism for 3 days (72 hr). The results are tabulated in Table 39.

As shown in Table 40 pMBot serum neutralized *C. botulinum* type A toxin complex when used at a dilution of 1:320 or less. A mean neutralizing value of 168 IU/ml was obtained for the pMBot serum (an IU is defined as 10,000 mouse $LD_{50}$). This value translates to a circulating serum titer of about 3.7 IU/mg of serum protein. This neutralizing titer is comparable to the commercially available bottled concentrated (Connaught Laboratories, Ltd.) horse anti-*C. botulinum* antiserum. A 10 ml vial of Connaught antiserum contains about 200 mg/ml of protein; each ml can neutralize 750 IU of *C. botulinum* type A toxin. After administration of one vial to a human, the circulating serum titer of the Connaught preparation would be approximately 25 IU/ml assuming an average serum volume of 3 liters). Thus, the circulating anti-*C. botulinum* titer seen in rats nasally immunized with pMBot protein (168 IU/ml) is 6.7 time higher than the necessary circulation titer of anti-*C. botulinum* antibody needed to be protective in humans.

TABLE 40

Quantitation Of Neutralizing Antibodies In pMBot Sera

| | pMBot[a] | |
|---|---|---|
| Dilution | Rat 1 | Rat 2 |
| 1:20 | 2/2 | 2/2 |
| 1:40 | 2/2 | 2/2 |
| 1:80 | 2/2 | 2/2 |
| 1:160 | 2/2 | 2/2 |
| 1:320 | 2/2[b] | 2/2[b] |
| 1:640 | 0/2 | 0/2 |
| 1:1280 | 0/2 | 0/2 |
| 1:2560 | 0/2 | 0/2 |

[a]Numbers represent the number of mice surviving at 72 hours which received serum taken from rats immunized with the pMBot protein.
[b]These mice survived but were sick after 72 hr.

These results demonstrate that antibodies capable of neutralizing *C. botulinum* type A toxin are induced when recombinant *C. botulinum* C fragment fusion protein produced in *E. coli* is used as an immunogen.

EXAMPLE 24

Production of Soluble *C. botulinum* C Fragment Protein Substantially Free of Endotoxin Contamination Example 23 demonstrated that neutralizing antibodies are generated by immunization with the pMBot protein expressed in *E. coli*. These results showed that the pMBot fusion protein is a good vaccine candidate. However, immunogens suitable for use as vaccines should be pyrogen-free in addition to having the capability of inducing neutralizing antibodies. Expression clones and conditions that facilitate the production of *C. botulinum* C fragment protein for utililization as a vaccine were developed.

The example involved: (a) determination of pyrogen content of the pMBot protein; (b) generation of *C. botulinum* C fragment protein free of the MBP; (c) expression of *C. botulinum* C fragment protein using various expression vectors; and (d) purification of soluble *C. botulinum* C fragment protein substantially free of significant endotoxin contamination.

a) Determination of the Pyrogen Content of the pMBot Protein

In order to use a recombinant antigen as a vaccine in humans or other animals, the antigen preparation must be shown to be free of pyrogens. The most significant pyrogen present in preparations of recombinant proteins produced in gram-negative bacteria, such as *E. coli*, is endotoxin [F. C. Pearson, Pyrogens: endotoxins, LAL testing and depyrogentaion, (1985) Marcel Dekker, New York, pp. 23–56]. To evaluate the utility of the pMBot protein as a vaccine candidate, the endotoxin content in MBP fusion proteins was determined.

The endotoxin content of recombinant protein samples was assayed utilizing the Limulus assay (LAL kit; Associates of Cape Cod) according to the manufacturer's instructions. Samples of affinity-purified pMal-c protein and pMA1870–2680 were found to contain high levels of endotoxin [>50,000 EU/mg protein; EU (endotoxin unit)]. This suggested that MBP— or toxin A repeat-containing fusions with the botulinal C fragment should also contain high levels of endotoxin. Accordingly, removal of endotoxin from affinity-purified pMal-c and pMBot protein preparations was attempted as follows.

Samples of pMal-c and pMBot protein were depyrogenated with polymyxin to determine if the endotoxin could be easily removed. The following amount of protein was treated: 29 ml at 4.8 $OD_{280}$/ml for pMal-c and 19 mls at 1.44 $OD_{280}$/ml for pMBot. The protein samples were dialyzed extensively against PBS and mixed in a 50 ml tube (Falcon) with 0.5 ml PBS-equilibrated polymyxin B (Affi-Prep Polymyxin, BioRad). The samples were allowed to mix by rotating the tubes overnight at 4° C. The polymyxin was pelleted by centrifugation for 30 min in a bench top centrifuge at maximum speed (approximately 2000×g) and the supernatant was removed. The recovered protein (in the supernatant) was quantified by $OD_{280}$, and the endotoxin activity was assayed by LAL. In both cases only approximately ⅓ of the input protein was recovered and the polymyxin-treated protein retained significant endotoxin contamination (approximately 7000 EU/mg of pMBot).

The depyrogenation experiment was repeated using an independently purified pMal-c protein preparation and similar results were obtained. From these studies it was concluded that significant levels of endotoxin copurifies with these MBP fusion proteins using the amylose resin. Furthermore, this endotoxin cannot be easily removed by polymyxin treatment.

These results suggest that the presence of the MBP sequences on the fusion protein complicated the removal of endotoxin from preparations of the pMBot protein.

b) Generation of *C. botulinum* C Fragment Protein Free of the MBP

It was demonstrated that the pMBot fusion protein could not be easily purified from contaminating endotoxin in section a) above. The ability to produce a pyrogen-free (e.g., endotoxin-free) preparation of soluble botulinal C fragment protein free of the MBP tag was next investigated. The pMBot expression construct was designed to facilitate purification of the botulinal C fragment from the MBP tag by cleavage of the fusion protein by utilizing an engineered Factor Xa cleavage site present between the MBP and the botulinal C fragment. The Factor Xa cleavage was performed as follows.

Factor Xa (New England Biolabs) was added to the pMBot protein (using a 0.1–1.0% Factor Xa/pMBot protein ratio) in a variety of buffer conditions [e.g., PBS-NaCl (PBS containing 0.5 M NaCl), PBS-NaCl containing 0.2% Tween 20, PBS, PBS containing 0.2% Tween 20, PBS-C (PBS containing 2 mM $CaCl_2$), PBS-C containing either 0.1 or 0.5% Tween 20, PBS-C containing either 0.1 or 0.5% NP40, PBS-C containing either 0.1 or 0.5% Triton X-100, PBS-C containing 0.1% sodium deoxycholate, PBS-C containing 0.1% SDS]. The Factor Xa digestions were incubated for 12–72 hrs at room temperature.

The extent of cleavage was assessed by Western blot or Coomassie blue staining of proteins following electrophoresis on denaturing SDS-PAGE gels, as described in Example 22. Cleavage reactions (and control samples of uncleaved pMBot protein) were centrifuged for 2 min in a microfuge to remove insoluble protein prior to loading the samples on the gel. The Factor Xa treated samples were compared with uncleaved, uncentrifuged pMBot samples on the same gel. The results of this analysis is summarized below.

1) Most (about 90%) pMBot protein could be removed by centrifugation, even when uncleaved control samples were utilized. This indicated that the pMBot fusion protein was not fully soluble (i.e., it exists as a suspension rather than as a solution). [This result was consistent with the observation that most affinity-purified pMBot protein precipitates after long term storage (>2 weeks) at 4° C. Additionally, the majority (i.e., 75%) of induced pMBot protein remains in the pellet after sonication and clarification of the induced *E. coli*. Resuspension of these insoluble pellets in PBS followed by sonication results in partial solubilization of the insoluble pMBot protein in the pellets.]

2) The portion of pMBot protein that is fully in solution (about 10% of pMBot protein) is completely cleaved by Factor Xa, but the cleaved (released) botulinal C fragment is relatively insoluble such that only the cleaved MBP remains fully in solution.

3) None of the above reaction conditions enhanced solubility without also reducing effective cleavage. Conditions that effectively solubilized the cleaved botulinal C fragment were not identified.

4) The use of 0.1% SDS in the buffer used for Factor Xa cleavage enhanced the solubility of the pMBot protein (all of pMBot protein was soluble). However, the presence of the SDS prevented any cleavage of the fusion protein with Factor Xa.

5) Analysis of pelleted protein from the cleavage reactions indicated that both full length pMBot (i.e., uncleaved) and cleaved botulinal C fragment protein precipitated during incubation.

These results demonstrate that purification of soluble botulinal C fragment protein after cleavage of the pMBot fusion protein is complicated by the insolubility of both the pMBot protein and the cleaved botulinal C fragment protein.

c) Expression of *C. botulinum* C Fragment Using Various Expression Vectors

Figure 27:
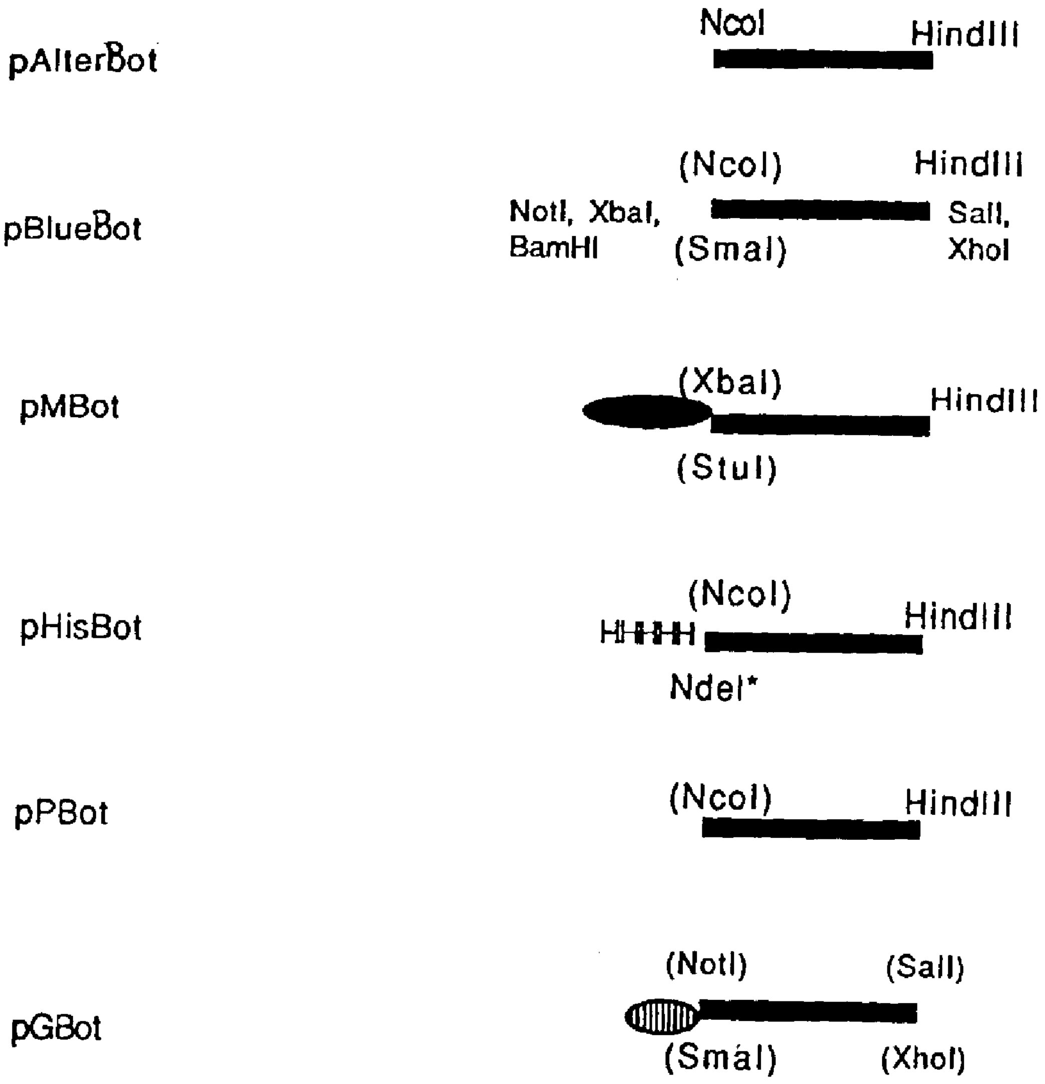
FIG. 27 shows *C. botulinum* type A toxin expression constructs; constructs used to provide *C. botulinum* sequences are also shown.

In order to determine if the solubility of the botulinal C fragment was enhanced by expressing the C fragment protein as a native protein, an N-terminal His-tagged protein or as a fusion with glutathione-S-transferase (GST), alternative expression plasmids were constructed. These expression constructs were generated utilizing the methodologies described in Example 22. FIG. 27 provides a schematic representation of the vectors described below.

In FIG. 27, the following abbreviations are used. pP refers to the pET23 vector. pHIS refers to the pETHisa vector. pBlue refers to the pBluescript vector. pM refers to the pMAL-c vector and pG refers to the pGEX3T vector (described in Example 11). The solid black lines represent *C. botulinum* C fragment gene sequences; the solid black ovals represent the MBP; the hatched ovals represent GST; "HHHHH" represents the poly-histidine tag. In FIG. 27, when the name for a restriction enzyme appears inside parenthesis, this indicates that the restriction site was destroyed during construction. An asterisk appearing with the name for a restriction enzyme indicates that this restriction site was recreated at a cloning junction.

i) Construction of pPBot

In order to express the *C. botulinum* C fragment as a native (i.e., non-fused) protein, the pPBot plasmid (shown schematically in FIG. 27) was constructed as follows. The C fragment sequences present in pAlterBot (Example 22) were removed by digestion of pAlterBot with NcoI and HindIII. The NcoI/HindIII C fragment insert was ligated to pETHisa vector (described in Example 18b) which was digested with NcoI and HindIII. This ligation creates an expression construct in which the NcoI-encoded methionine of the botulinal C fragment is the initiator codon and directs expression of the native botulinal C fragment. The ligation products were used to transform competent BL21(DE3)pLysS cells (Novagen). Recombinant clones were identified by restriction mapping.

ii) Construction of pHisBot

In order to express the *C. botulinum* C fragment containing a poly-histidine tag at the amino-terminus of the recombinant protein, the pHisBot plasmid (shown schematically in FIG. 27) was constructed as follows. The NcoI/HindIII botulinal C fragment insert from pAlterbot was ligated into the pETHisa vector which was digested with NheI and HindIII. The NcoI (on the C fragment insert) and NheI (on the pETHisa vector) sites were filled in using the Klenow fragment prior to ligation; these sites were then blunt end ligated (the NdeI site was regenerated at the clone junction as predicted). The ligation products were used to transform competent BL21(DE3)pLysS cells and recombinant clones were identified by restriction mapping.

The resulting pHisBot clone expresses the botulinal C fragment protein with a histidine-tagged N-terminal extension having the following sequence: MetGlyHisHis HisHisHisHisHisHisHisHisSerSerGlyHisIleGluGlyArgHis MetAla, (SEQ ID NO:24); the amino acids encoded by the botulinal C fragment gene are underlined and the vector encoded amino acids are presented in plain type. The nucleotide sequence present in the pETHisa vector which encodes the pHisBot fusion protein is listed in SEQ ID NO:25. The amino acid sequence of the pHisBot protein is listed in SEQ ID NO:26.

iii) Construction of pGBot

The botulinal C fragment protein was expressed as a fusion with the glutathione-S-transferase protein by constructing the pGBot plasmid (shown schematically in FIG. 27). This expression construct was created by cloning the NotI/SalI C fragment insert present in pBlueBot (Example 22) into the pGEX3T vector which was digested with SmaI and XhoI. The NotI site (present on the botulinal fragment) was made blunt prior to ligation using the Klenow fragment. The ligation products were used to transform competent BL21 cells.

Each of the above expression constructs were tested by restriction digestion to confirm the integrity of the constructs.

Large scale (1 liter) cultures of pPBot [BL21(DE3)pLysS host], pHisBot [BL21(DE3)pLysS host] and pGBot (BL21 host) were grown in 2× YT medium and induced (using IPTG to 0.8–1.0 mM) for 3 hrs as described in Example 22. Total, soluble and insoluble protein preparations were prepared from 1 ml aliquots of each large scale culture [Williams et al. (1994), supra] and analyzed by SDS-PAGE. No obvious induced band was detectable in the pPBot or pHisBot samples by Coomassie staining, while a prominent insoluble band of the anticipated MW was detected in the pGBot sample. Soluble lysates of the pGBot large scale (resuspended in PBS) or pHisBot large scale [resuspended in Novagen 1× binding buffer (5 mM imidazole, 0.5 M NaCl, 20 mM Tris-HCl, pH 7.9)] cultures were prepared and used to affinity purify soluble affinity-tagged protein as follows.

The pGBot lysate was affinity purified on a glutathione-agarose resin (Pharmacia) exactly as described in Smith and Corcoran [Current Protocols in Molecular Biology, Supplement 28 (1994), pp. 16.7.1–16.7.7]. The pHisBot protein was purified on the His-Bind resin (Novagen) utilizing the His-bind buffer kit (Novagen) exactly as described by manufacturer.

Samples from the purification of both the pGBot and pHisBot proteins (including uninduced, induced, total, soluble, and affinity-purified eluted protein) were resolved on SDS-PAGE gels. Following electrophoresis, proteins were analyzed by Coomassie staining or by Western blot detection utilizing a chicken anti-*C. botulinum* Type A toxoid antibody (as described in Example 22).

These studies showed that the pGBot protein was almost entirely insoluble under the utilized conditions, while the pHisBot protein was soluble. Affinity purification of the pHisBot protein on this first attempt was inefficient, both in terms of yield (most of the immunoreactive botulinal protein did not bind to the His-bind resin) and purity (the botulinal protein was estimated to comprise approximately 20% of the total eluted protein).

d) Purification of Soluble *C. botulinum* C Fragment Protein Substantially Free of Endotoxin Contamination The above studies showed that the pHisBot protein was expressed in *E. coli* as a soluble protein. However, the affinity purification of this protein on the His-bind resin was very inefficient. In order to improve the affinity purification of the soluble pHisBot protein (in terms of both yield and purity), an alternative poly-histidine binding affinity resin (Ni-NTA resin; Qiagen) was utilized. The Ni-NTA resin was reported to have a superior binding affinity ($K_d$=1×$10^{-13}$ at pH 8.0; Qiagen user manual) relative to the His-bind resin.

A soluble lysate (in Novagen 1× binding buffer) from an induced 1 liter 2× YT culture was prepared as described above. Briefly, the culture of pHisBot [B121(DE3)pLysS host] was grown at 37° C. to an $OD_{600}$ of 0.7 in 1 liter of 2× YT medium containing 100 μg/ml ampicillin, 34 μg/ml chloramphenicol and 0.2% glucose. Protein expression was induced by the addition of IPTG to 1 mM. Three hours after the addition of the IPTG, the cells were cooled for 15 min in an ice water bath and then centrifuged 10 min at 5000 rpm in a JA10 rotor (Beckman) at 4° C. The pellets were resuspended in a total volume of 40 mls Novagen 1× binding buffer (5 mM imidazole, 0.5 M NaCl, 20 mM Tris-HCl, pH 7.9), transferred to two 35 ml Oakridge tubes and frozen at −70° C. for at least 1 hr. The tubes were thawed and the cells were lysed by sonication (4×20 second bursts using a Branson Sonifier 450 with a power setting of 6–7) on ice. The suspension was clarified by centrifugation for 20 min at 9,000 rpm (10,000×g) in a JA-17 rotor (Beckman).

The soluble lysate was brought to 0.1% NP40 and then was batch absorbed to 7 ml of a 1:1 slurry of Ni-NTA resin:binding buffer by stirring for 1 hr at 4° C. The slurry was poured into a column having an internal diameter of 1 or 2.5 cm (BioRad). The column was then washed sequentially with 15 mls of Novagen 1× binding buffer containing 0.1% NP40, 15 ml of Novagen 1× binding buffer, 15 ml wash buffer (60 mM imidazole, 0.5 M NaCl, 20 mM Tris-HCl, pH 7.9) and 15 ml $NaHPO_4$ wash buffer (50 mM $NaHPO_4$, pH 7.0, 0.3 M NaCl, 10% glycerol). The bound protein was eluted by protonation of the resin using elution buffer (50 mM $NaHPO_4$, pH 4.0, 0.3 M NaCl, 10% glycerol). The eluted protein was stored at 4° C.

Figure 28:
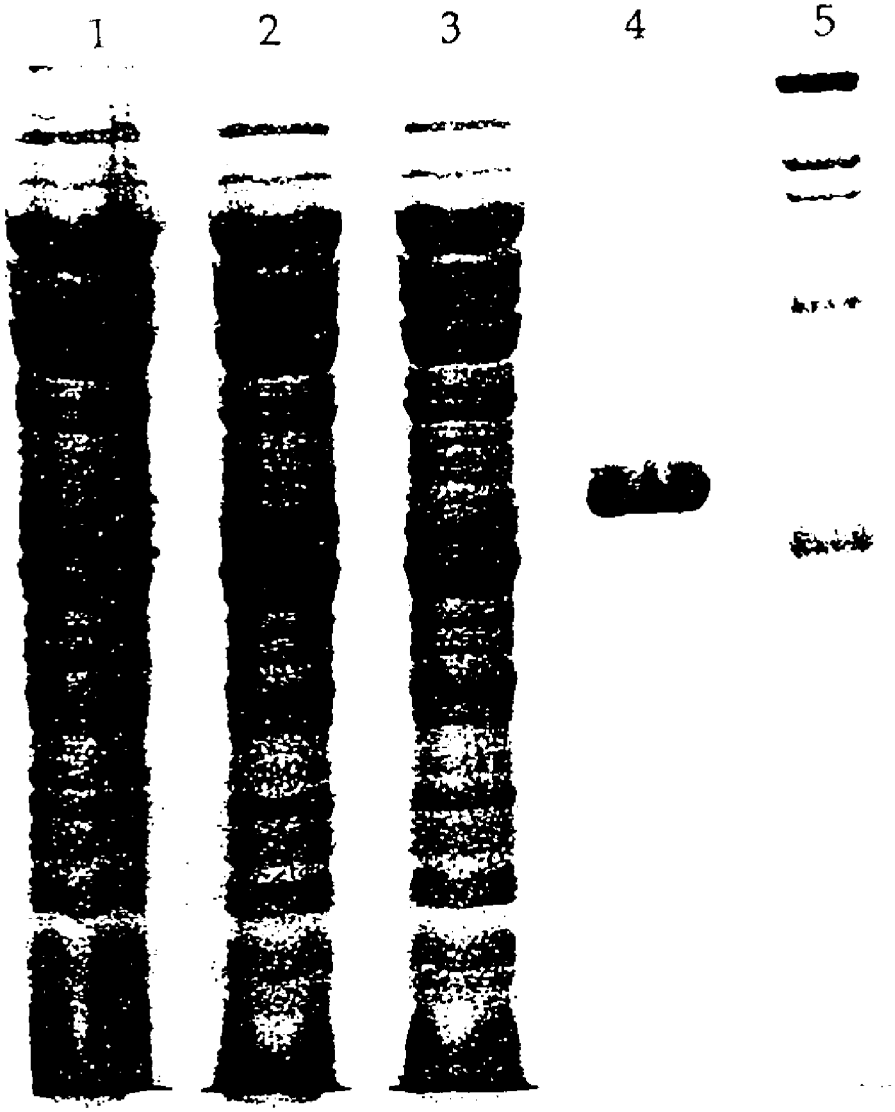
FIG. 28 is an SDS-PAGE gel stained with Coomaisse blue showing the purification of pHisBot protein using the Ni-NTA resin.

Samples of total, soluble and eluted protein were resolved by SDS-PAGE. Protein samples were prepared for electrophoresis as described in Example 22b. Duplicate gels were stained with Coomassie blue to visualize the resolved proteins and *C. botulinum* type A toxin-reactive protein was detected by Western blot analysis as described in Example 22b. A representative Coomassie stained gel is shown in FIG. 28. In FIG. 28, the following samples were loaded on the 12.5% acrylamide gel. Lanes 1–4 contain respectively total protein, soluble protein, soluble protein present in the flow-through of the Ni-NTA column and affinity-purified pHisBot protein (i.e., protein released from the Ni-NTA resin by protonation). Lane 5 contains high molecular weight protein markers (BioRad).

The purification of pHisBot protein resulted in a yield of 7 mg of affinity purified protein from a 1 liter starting culture of BL21(DE3)pLysS cells harboring the pHisBot plasmid. The yield of purified pHisBot protein represented approximately 0.4% of the total soluble protein in the induced culture. Analysis of the purified pHisBot protein by SDS-PAGE revealed that at least 90–95% of the protein was present as a single band (FIG. 28) of the predicted MW (50 kD). This 50 kD protein band was immunoreactive with anti-*C. botulinum* type A toxin antibodies. The extinction coefficient of the protein preparation was determined to be 1.4 (using the Pierce BCA assay) or 1.45 (using the Lowry assay) $OD_{280}$ per 1 mg/ml solution.

Samples of pH neutralized eluted pHisBot protein were resolved on a KB 803 HPLC column (Shodex). Although His-tagged proteins are retained by this sizing column (perhaps due to the inherent metal binding ability of the proteins), the relative mobility of the pHisBot protein was consistent with that expected for a non-aggregated protein in solution. Most of the induced pHisBot protein was determined to be soluble under the growth and solubilization conditions utilized above (i.e., greater than 90% of the pHisBot protein was found to be soluble as judged by comparison of the levels of pHisBot protein seen in total and soluble protein samples prepared from BL21(DE3)pLysS cells containing the pHisBot plasmid). SDS-PAGE analysis of samples obtained after centrifugation, extended storage at −20° C., and at least 2 cycles of freezing and thawing detected no protein loss (due to precipitation), indicating that the pHisBot protein is soluble in the elution buffer (i.e., 50 mM $NaHPO_4$, pH 4.0, 0.3 M NaCl, 10% glycerol).

Determination of endotoxin contamination in the affinity purified pHisBot preparation (after pH neutralization) using the LAL assay (Associates of Cape Cod) detected no significant endotoxin contamination. The assay was performed using the endpoint chromogenic method (without diazo-coupling) according to the manufacturer's instructions. This method can detect concentrations of endotoxin greater than or equal to 0.03 EU/ml (EU refers to endotoxin units). The LAL assay was run using 0.5 ml of a solution comprising 0.5 mg pHisBot protein in 50 mM $NaHPO_4$, pH 7.0, 0.3 M NaCl, 10% glycerol; 30–60 EU were detected in the 0.5 ml sample. Therefore, the affinity purified pHisBot preparation contains 60–120 EU/mg of protein. FDA Guidelines for the administration of parenteral drugs require that a composition to be administered to a human contain less than 5 EU/kg body weight (The average human body weight is 70 kg; therefore up to 349 EU units can be delivered in a parental dose.). Because very small amount of protein are administered in a vaccine preparation (generally in the range of 10–500 μg of protein), administration of affinity purified pHisBot containing 60–120 EU/mg protein would result in delivery of only a small percentage of the permissible endotoxin load. For example, administration of 10–500 μg of purified pHisBot to a 70 kg human, where the protein preparation contains 60 EU/mg protein, results in the introduction of only 0.6 to 30 EU [i.e., 0.2 to 8.6% of the maximum allowable endotoxin burden per parenteral dose (less than 5 EU/kg body weight)].

The above results demonstrate that endotoxin (LPS) does not copurify with the pHisBot protein using the above purification scheme. Preparations of recombinantly produced pHisBot protein containing lower levels of endotoxin (less than or equal to 2 EU/mg recombinant protein) may be produced by washing the Ni-NTA column with wash buffer until the $OD_{280}$ returns to baseline levels (i.e., until no more UV-absorbing material comes off of the column).

The above results illustrate a method for the production and purification of soluble, botulinal C fragment protein substantially free of endotoxin.

EXAMPLE 25

Optimization of the Expression and Purification of pHisBot Protein

The results shown in Example 24d demonstrated that the pHisBot protein is an excellent candidate for use as a vaccine as it could be produced as a soluble protein in *E. coli* and could be purified free of pyrogen activity. In order to optimize the expression and purification of the pHisBot protein, a variety of growth and purification conditions were tested.

a) Growth Parameters i) Host Strains

Figure 29:
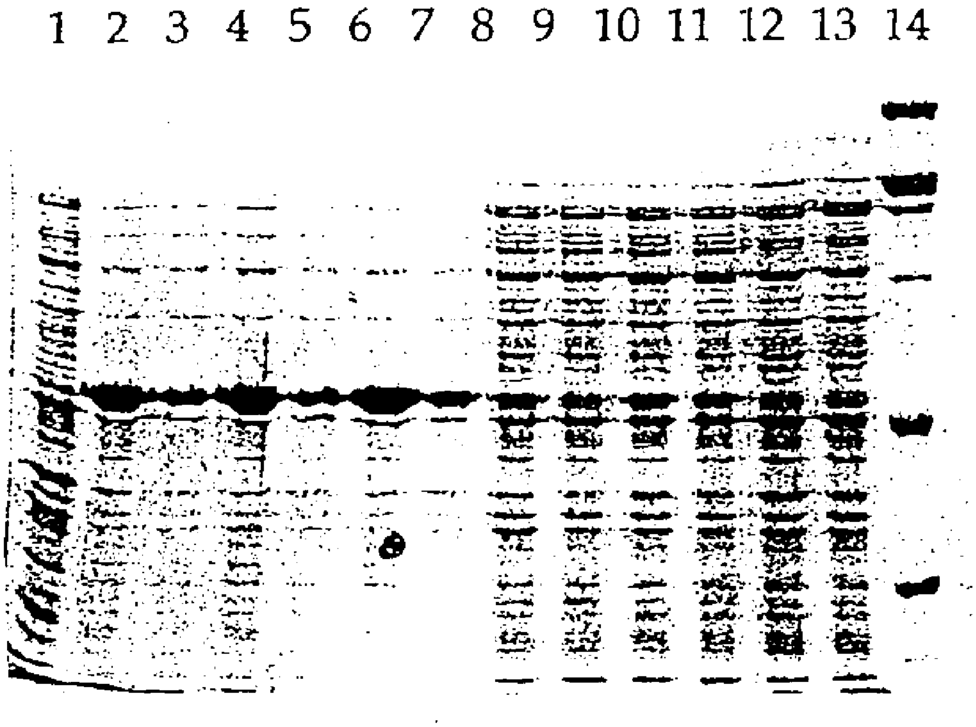
FIG. 29 is an SDS-PAGE gel stained with Coomaisse blue showing the expression of pHisBot protein in BL21(DE3) and BL21(DE3)pLysS host cells.

The influence of the host strain utilized upon the production of soluble pHisBot protein was investigated. A large scale purification of pHisBot was performed [as described in Example 24d above] using the BL21(DE3) host (Novagen) rather than the BL21(DE3)pLysS host. The deletion of the pLysS plasmid in the BL21(DE3) host yielded higher levels of expression due to de-repression of the plasmid's T7-lac promoter. However, the yield of affinity-purified soluble recombinant protein was very low (approximately 600 μg/liter culture) when purified under conditions identical to those described in Example 24d above. This result was due to the fact that expression in the BL21(DE3) host yielded very high level expression of the pHisBot protein as insoluble inclusion bodies as shown by SDS-PAGE analysis of protein prepared from induced BL21(DE3) cultures (FIG. 29, lanes 1–7, described below). These results demonstrate that the pHisBot protein is not inherently toxic to *E. coli* cells and can be expressed to high levels using the appropriate promoter/host combination.

FIG. 29 shows a Coomassie blue stained SDS-PAGE gel (12.5% acrylamide) onto which extracts prepared from BL21(DE3) cells containing the pHisBot plasmid were loaded. Each lane was loaded with 2.5 μl protein sample mixed with 2.5 μl of 2× SDS sample buffer. The samples were handled as described in Example 22b. The following samples were applied to the gel. Lanes 1–7 contain protein isolated from the BL21(DE3) host. Lanes 8–14 contain proteins isolated from the BL21(DE3)pLysS host. Total protein was loaded in lanes 1, 2, 4, 6, 8, 10 and 12. Soluble protein was loaded in Lanes 3, 5, 7, 9, 11 and 13. Lane 1 contains protein from uninduced host cells. Lanes 2–13 contain protein from host cells induced for 3 hours. IPTG was added to a final concentration of 0.1 mM (Lanes 6–7), 0.3 mM (Lanes 4–5) or 1.0 mM (Lanes 2, 3, 8–13). The cultures were grown in LB broth (Lanes 8–9), 2× YT broth (Lanes 10–11) or terrific broth (Lanes 1–7, 12–13). The pHisBot protein seen in Lanes 3, 5 and 7 is insoluble protein which spilled over from Lanes 2, 4 and 6, respectively. High molecular weight protein markers (BioRad) were loaded in Lane 14.

A variety of expression conditions were tested to determine if the BL21(DE3) host could be utilized to express soluble pHisBot protein at suitably high levels (i.e., about 10 mg/ml). The conditions altered were temperature (growth at 37 or 30° C.), culture medium (2× YT, LB or Terrific broth) and inducer levels (0.1, 0.3 or 1.0 mM IPTG). All combinations of these variables were tested and the induction levels and solubility was then assessed by SDS-PAGE analysis of total and soluble extracts [prepared from 1 ml samples as described in Williams et al., (1994), supra].

All cultures were grown in 15 ml tubes (Falcon #2057). All culture medium was prewarmed overnight at the appropriate temperature and were supplemented with 100 μg/ml ampicillin and 0.2% glucose. Terrific broth contains 12 g/l bacto-tryptone, 24 g/l bacto-yeast extract and 100 ml/l of a solution comprising 0.17 M $KH_2PO_4$, 0.72 M $K_2HPO_4$. Cultures were grown in an incubator on a rotating wheel (to ensure aeration) to an $OD_{600}$ of approximately 0.4, and induced by the addition of IPTG. In all cases, high level expression of insoluble pHisBot protein was observed, regardless of temperature, medium or inducer concentration.

The effect of varying the concentration of IPTG upon 2× YT cultures grown at 23° C. was then investigated. IPTG was added to a final concentration of either 1 mM, 0.1 mM, 0.05 mM or 0.01 mM. At this temperature, similar levels of pHisBot protein was induced in the presence of either 1 or 0.1 mM IPTG; these levels of expression was lower than that observed at higher temperatures. Induced protein levels were reduced at 0.05 mM IPTG and absent at 0.01 mM IPTG (relative to 1.0 and 0.1 mM IPTG inductions at 23° C.). However, no conditions were observed in which the induced pHisBot protein was soluble in this host. Thus, although expression levels are superior in the BL21(DE3) host (as compared to the BL21(DE3)pLysS host), conditions that facilitate the production of soluble protein in this host could not be identified.

These results demonstrate that production of soluble pHisBot protein was achieved using the BL21(DE3)pLysS host in conjunction with the T7-lac promoter.

ii) Effect of Varying Temperature, Medium and IPTG Concentration and Length of Induction The effect growing the host cells in various mediums upon the expression of recombinant botulinal protein from the pHisBot expression construct [in the BL21(DE3)pLysS host] was investigated. BL21(DE3)pLysS cells containing the pHisBot plasmid were grown in either LB, 2× YT or Terrific broth at 37° C. The cells were induced using 1 mM IPTG for a 3 hr induction period. Expression of pHisBot protein was found to be the highest when the cells were grown in 2× YT broth (see The cells were then grown at 30° C. in 2× YT broth and the concentration of IPTG was varied from 1.0, 0.3 or 0.1 mM and the length of induction was either 3 or 5 hours. Expression of pHisBot protein was similar at all 3 inducer concentrations utilized and the levels of induced protein were higher after a 5 hr induction as compared to a 3 hr induction.

Using the conditions found to be optimal for the expression of pHisBot protein, a large scale culture was grown in order to provide sufficient material for a large scale purification of the pHisBot protein. Three 1 liter cultures were grown in 2× YT medium containing 100 μg/ml ampicillin, 34 μg/ml chloramphenicol and 0.2% glucose. The cultures were grown at 30° C. and were induced with 1.0 mM IPTG for a 5 hr period. The cultures were harvested and a soluble lysate were prepared as described in Example 18. A large scale purification was performed as described in Example 24d with the exception that except the soluble lysate was batch absorbed for 3 hours rather than for 1 hour. The final yield was 13 mg pHisBot protein/liter culture. The pHisBot protein represented 0.75% of the total soluble protein.

The above results demonstrate growth conditions under which soluble pHisBot protein is produced (i.e., use of the BL21(DE3)pLysS host, 2× YT medium, 30° C., 1.0 mM IPTG for 5 hours).

b) Optimization of Purification Parameters

For optimization of purification conditions, large scale cultures (3×1 liter) were grown at 30° C. and induced with 1 mM IPTG for 5 hours as described above. The cultures were pooled, distributed to centrifuge bottles, cooled and pelleted as described in Example 24d. The cell pellets were frozen at −70° C. until used. Each cell pellet represented ⅓ of a liter starting culture and individual bottles were utilized for each optimization experiment described below. This standardized the input bacteria used for each experiment, such that the yields of affinity purified pHisBot protein could be compared between different optimization experiments.

i) Binding Specificity (pH Protonation)

A lysate of pHisBot culture was prepared in PBS (pH 8.0) and applied to a 3 ml Ni-NTA column equilibrated in PBS (pH 8.0) using a flow rate of 0.2 ml/min (34 column volumes/hr) using an Econo chromatography system (BioRad). The column was washed with PBS (pH 8.0) until the absorbance ($OD_{280}$) of the elute was at baseline levels. The flow rate was then increased to 2 ml/min and the column was equilibrated in PBS (pH 7.0). A pH gradient (pH 7.0 to 4.0 in PBS) was applied in order to elute the bound pHisBot protein from the column. Fractions were collected and aliquots were resolved on SDS-PAGE gels. The PAGE gels were subjected to Western blotting and the pHisBot protein was detected using a chicken anti-*C. botulinum* Type A toxoid antibody as described in Example 22.

From the Western blot analysis it was determined that the pHisBot protein begins to elute from the Ni-NTA column at pH 6.0. This is consistent with the predicted elution of a His-tagged protein monomer at pH 5.9.

These results demonstrate that the pH at which the pHisBot protein is protonated (released) from Ni-NTA resin in PBS buffer is pH 6.0.

ii) Binding Specificity (Imidazole Competition)

In order to define purification conditions under which the native *E. coli* proteins could be removed from the Ni-NTA column while leaving the pHisBot protein bound to the column, the following experiment was performed. A lysate of pHisBot culture was prepared in 50 mM $NaHPO_4$, 0.5 M NaCl, 8 mM imidazole (pH 7.0). This lysate was applied to a 3 ml Ni-NTA column equilibrated in 50 mM $NaHPO_4$, 0.5 M NaCl (pH 7.0) using an Econo chromatography system (BioRad). A flow rate of 0.2 ml/mm (3–4 column volumes/hr) was utilized. The column was washed with 50 mM $NaHPO_4$, 0.5 M NaCl (pH 7.0) until the absorbance of the elute returned to baseline. The flow rate was then increased to 2 ml/min.

The column was eluted using an imidazole step gradient [in 50 mM $NaHPO_4$, 0.5 M NaCl (pH 7.0)]. Elution steps were 20 mM, 40 mM, 60 mM, 80 mM, 100 mM, 200 mM, 1.0 M imidazole, followed by a wash using 0.1 mM EDTA (to strip the nickel from the column and remove any remaining protein). In each step, the wash was continued until the $OD_{280}$ returned to baseline. Fractions were resolved on SDS-PAGE gels, Western blotted, and pHisBot protein detected using a chicken anti-*C. botulinum* Type A toxoid antibody as described in Example 22. Duplicate gels were stained with Coomassie blue to detect eluted protein in each fraction.

The results of the PAGE analysis showed that most of the non-specifically binding bacterial protein was removed by the 20 mM imidazole wash, with the remaining bacterial proteins being removed in the 40 and 60 mM imidazole washes. The pHisBot protein began to elute at 100 mM imidazole and was quantitatively eluted in 200 mM imidazole.

These results precisely defined the window of imidazole wash stringency that optimally removes *E. coli* proteins from the column while specifically retaining the pHisBot protein in this buffer. These results provided conditions under which the pHisBot protein can be purified free of contaminating host proteins.

iii) Purification Buffers and Optimized Purification Protocols

A variety of purification parameters were tested during the development of an optimized protocol for batch purification of soluble pHisBot protein. The results of these analyses are summarized below.

Batch purifications were performed (as described in Example 24d) using several buffers to determine if alternative buffers could be utilized for binding of the pHisBot protein to the Ni-NTA column. It was determined that quantitative binding of pHisBot protein to the Ni-NTA resin was achieved in either Tris-HCl (pH 7.9) or $NaHPO_4$ (pH 8.0) buffers. Binding of the pHisBot protein in $NaHPO_4$ buffer was not inhibited using 5 mM, 8 mM or 60 mM imidazole. Quantitative elution of bound pHisBot protein was obtained in buffers containing 50 mM $NaHPO_4$, 0.3 M NaCl (pH 3.54.0), with or without 10% glycerol. However, quantitation of soluble affinity purified pHisBot protein before and after a freeze thaw (following several weeks storage of the affinity purified elute at −20° C.) revealed that 94% of the protein was recovered using the glycerol-containing buffer, but only 68% of the protein was recovered when the buffer lacking glycerol was employed. This demonstrates that glycerol enhanced the solubility of the pHisBot protein in this low pH buffer when the eluted protein was stored at freezing temperatures (e.g., −20° C.). Neutralization of pH by addition of $NaH_2PO_4$ buffer did not result in obvious protein precipitation.

Figure 30:
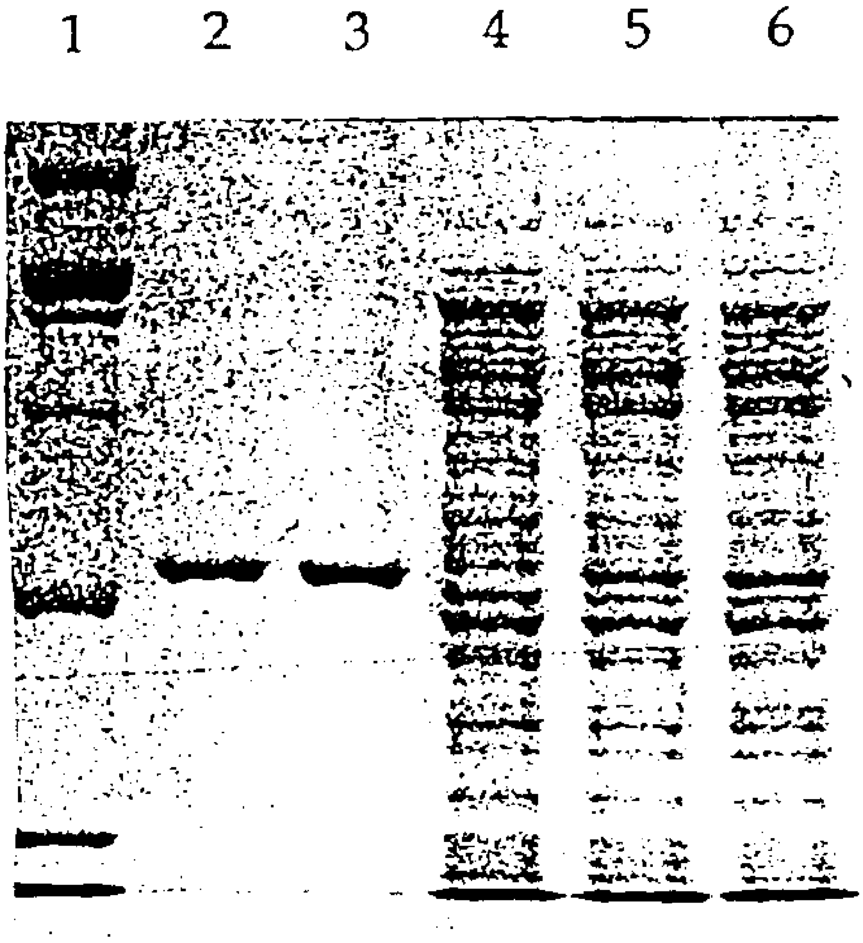
FIG. 30 is an SDS-PAGE gel stained with Coomaisse blue showing the purification of pHisBot protein using a batch absorption procedure.

It was determined that quantitative binding of pHisBot protein using the batch format occurred after 3 hrs (FIG. 30), but not after 1 hr of binding at 4° C. (the resin was stirred during binding). FIG. 30 depicts a Coomassie blue stained SDS-PAGE gel (7.5% acrylamide) containing samples of proteins isolated during the purification of pHisBot protein from lysate prepared from the BL21(DE3)pLysS host. Each lane was loaded with 5 μl of protein sample mixed with 5 μof 2× sample buffer and processed as described in Example 22b. Lane 1 contains high molecular weight protein markers (BioRad). Lanes 2 and 3 contain protein eluted from the Ni-NTA resin. Lane 4 contains soluble protein after a 3 hr batch incubation with the Ni-NTA resin. Lanes 5 and 6 contain soluble and total protein, respectively. FIG. 30 demonstrates that the pHisBot protein is completely soluble [compare Lanes 5 and 6 which show that a similar amount of the 50 kD pHisBot protein is seen in both; if a substantial amount (greater than 20%) of the pHisBot protein were partially insoluble in the host cell, more pHisBot protein would be seen in lane 6 (total protein) as compared to lane 5 (soluble protein)]. FIG. 30 also demonstrates that the pHisBot protein is completely removed from the lysate after batch absorption with the Ni-NTA resin for 3 hours (compare Lanes 4 and 5).

The reported high affinity interaction of the Ni-NTA resin with His-tagged proteins ($K_d$=1×10$^{-13}$ at pH 8.0) suggested that it should be possible to manipulate the resin-protein complexes without significant release of the bound protein. Indeed, it was determined that after the recombinant protein was bound to the Ni-NTA resin, the resin-pHisBot protein complex was highly stable and remained bound following repeated rounds of centrifugation of the resin for 2 min at 1600×g. When this centrifugation step was performed in a 50 ml tube (Falcon), a tight resin pellet formed. This allowed the removal of spent soluble lysate by pouring off the supernatant followed by resuspension of the pellet in wash buffer. Further washes can be performed by centrifugation. The ability to perform additional washes permits the development of protocols for batch absorption of large volumes of lysate with removal of the lysate being performed simply by centrifugation following binding of the recombinant protein to the resin.

A simplified, integrated purification protocol was developed as follows. A soluble lysate was made by resuspending the induced cell pellet in binding buffer [50 mM $NaHPO_4$, 0.5 M NaCl, 60 mM imidazole (pH 8.0)], sonicating 4×20 sec and centrifuging for 20 min at 10,000×g. NP-40 was added to 0.1% and Ni-NTA resin (equilibrated in binding buffer) was added. Eight milliliters of a 1:1 slurry (resin:binding buffer) was used per liter of starting culture. The mixture was stirred for 3 hrs at 4° C. The slurry was poured into a column having a 1 cm internal diameter (BioRad), washed with binding buffer containing 0.1% NP40, then binding buffer until baseline was established (these steps may alternatively be performed by centrifugation of the resin, resuspension in binding buffer containing NP40 followed by centrifugation and resuspension in binding buffer). Imidazole was removed by washing the resin with 50 mM $NaHPO_4$, 0.3M NaCl (pH 7.0). Protein bound to the resin was eluted using the same buffer (50 mM $NaHPO_4$, 0.3M NaCl) having a reduced pH (pH 3.5–4.0).

A pilot purification was performed following this protocol and yielded 18 mg/liter affinity-purified pHisBot. The pHisBot protein was greater than 90% pure as estimated by Coomassie staining of an SDS-PAGE gel. This represents the highest observed yield of soluble affinity-purified pHisBot protein and this protocol eliminates the need for separate imidazole-containing binding and wash buffers. In addition to providing a simplified and efficient protocol for the affinity purification of recombinant pHisBot protein, the above results provide a variety of purification conditions under which pHisBot protein can be isolated.

EXAMPLE 26

The pHisBot Protein is an Effective Immunogen

In Example 23 it was demonstrated that neutralizing antibodies are generated in mouse serum after nasal immunization with the pMBot protein. However, the pMBot protein was found to copurify with significant amounts of endotoxin which could not be easily removed. The pHisBot protein, in contrast, could be isolated free of significant endotoxin contamination making pHisBot a superior candidate for vaccine production. To further assess the suitability of pHisBot as a vaccine, the immunogenicity of the pHisBot protein was determined and a comparison of the relative immunogenicity of pMBot and pHisBot proteins in mice was performed as follows.

Two groups of eight BALBc mice were immunized with either pMBot protein or pHisBot protein using Gerbu GMDP adjuvant (CC Biotech). pMBot protein (in PBS containing 10 mM maltose) or pHisBot protein (in 50 mM $NaHPO_4$, 0.3 M NaCl, 10% glycerol, pH 4.0) was mixed with Gerbu adjuvant and used to immunize mice. Each mouse received an IP injection of 100 µl antigen/adjuvant mix (50 µg antigen plus 1 µg adjuvant) on day 0. Mice were boosted as described above with the exception that the route of administration was IM on day 14 and 28. The mice were bled on day 77 and anti-C. botulinum Type A toxoid titers were determined using serum collected from individual mice in each group (as described in Example 23). The results are shown in Table 41.

TABLE 41

Anti-C. botulinum
Type A Toxoid Serum IgG Titers in Individual Mice Immunized With pMBot or pHisBot Protein

| Mouse # | Preimmune[1] Sample Dilution | | | | pMBot[2] Sample Dilution | | | | pHisBot[2] Sample Dilution | | | |
|---|---|---|---|---|---|---|---|---|---|---|---|---|
| | 1:50 | 1:250 | 1:1250 | 1:6250 | 1:50 | 1:250 | 1:1250 | 1:6250 | 1:50 | 1:250 | 1:1250 | 1:620 |
| 1 | | | | | 0.678 | 0.190 | 0.055 | 0.007 | 1.574 | 0.799 | 0.320 | 0.093 |
| 2 | | | | | 1.161 | 0.931 | 0.254 | 0.075 | 1.513 | 0.829 | 0.409 | 0.134 |
| 3 | | | | | 1.364 | 0.458 | 0.195 | 0.041 | 1.596 | 1.028 | 0.453 | 0.122 |
| 4 | | | | | 1.622 | 1.189 | 0.334 | 0.067 | 1.552 | 0.840 | 0.348 | 0.090 |
| 5 | | | | | 1.612 | 1.030 | 0.289 | 0.067 | 1.629 | 1.580 | 0.895 | 0.233 |
| 6 | | | | | 0.913 | 0.242 | 0.069 | 0.013 | 1.485 | 0.952 | 0.477 | 0.145 |
| 7 | | | | | 0.910 | 0.235 | 0.058 | 0.014 | 1.524 | 0.725 | 0.269 | 0.069 |
| 8 | | | | | 0.747 | 0.234 | 0.058 | 0.014 | 1.274 | 0.427 | 0.116 | 0.029 |
| Mean Titer | 0.048 | 0.021 | 0.011 | 0.002 | 1.133 | 0.564 | 0.164 | 0.037 | 1.518 | 0.896 | 0.411 | 0.114 |

[1]The preimmune sample represents the average from 2 sets of duplicate wells containing serum from a individual mouse immunized with recombinant Staphylococcus enterotoxin B (SEB) antigen. This antigen is immunologically unrelated to C. botulinum toxin and provides a control serum.
[2]Average of duplicate wells.

The results shown above in Table 41 demonstrate that both the pMBot and pHisBot proteins are immunogenic in mice as 100% of the mice (8/8) in each group seroconverted from non-immune to immune status. The results also show that the average titer of anti-C. botulinum Type A toxoid IgG is 2–3 fold higher after immunization with the pHisBot protein relative to immunization with the pMBot protein. This suggests that the pHisBot protein may be a superior immunogen to the pMBot protein.

EXAMPLE 27

Immunization with the Recombinant pHisBot Protein Generates Neutralizing Antibodies The results shown in Example 26 demonstrated that both the pHisBot and pMBot proteins were capable of inducing high titers of anti-C. botulinum type A toxoid-reactive antibodies in immunized hosts. The ability of the immune sera from mice immunized with either the pHisBot or pMBot proteins to neutralize C. botulinum type A toxoid in vivo was determined using the mouse neutralization assay described in Example 23b.

The two groups of eight BALBc mice immunized with either pMBot protein or pHisBot protein in Example 26 were boosted again one week after the bleeding on day 77. The boost was performed by mixing pMBot protein (in PBS containing 10 mM maltose) or pHisBot protein (in 50 mM $NaHPO_4$, 0.3 M NaCl, 10% glycerol, pH 4.0) with Gerbu adjuvant as described in Example 26. Each mouse received an IP injection of 100 $\mu$l antigen/adjuvant mix (50 $\mu$g antigen plus 1 $\mu$g adjuvant). The mice were bled 6 days after this boost and the serum from mice within a group was pooled. Serum from preimmune mice was also collected (this serum is the same serum described in the footnote to Table 41).

The presence of neutralizing antibodies in the pooled or preimmune serum was detected by challenging mice with 5 $LD_{50}$ units of type A toxin mixed with 100 $\mu$l of pooled serum. The challenge was performed by mixing (per mouse to be injected) 100 $\mu$l of serum from each pool with 100 $\mu$l of purified type A toxin standard (50 $LD_{50}$/ml prepared as described in Example 23b) and 500 $\mu$l of gel-phosphate. The mixtures were incubated for 30 min at room temperature with occasional mixing. Each of four mice were injected IP with the mixtures (0.7 ml/mouse). The mice were observed for signs of botulism for 72 hours. Mice receiving toxin mixed with serum from mice immunized with either the pHisBot or pMBot proteins showed no signs of botulism intoxication. In contrast, mice receiving preimmune serum died in less than 24 hours.

These results demonstrate that antibodies capable of neutralizing *C. botulinum* type A toxin are induced when either of the recombinant *C. botulinum* C fragment proteins pHisBot or pMBot are used as immunogens.

EXAMPLE 28

Cloning and Expression of the C Fragment of *C. botulinum* Serotype A Toxin in *E. coli* Utilizing a Native Gene Fragment In Example 22 above, a synthetic gene was used to express the C fragment of *C. botulinum* serotype A toxin in *E. coli*. The synthetic gene replaced non-preferred (i.e., rare) codons present in the C fragment gene with codons which are preferred by *E. coli*i. The synthetic gene was generated because it has been reported that genes which have a high A/T content (such as most clostridial genes) creates expression difficulties in *E. coli* and yeast. Furthermore, LaPenotiere et al. suggested that problems encountered with the stability (non-fusion constructs) and solubility (MBP fusion constructs) of the C fragment of *C. botulinum* serotype A toxin when expressed in *E. coli* was most likely due to the extreme A/F richness of the native *C. botulinum* serotype A toxin gene sequences (LaPenotiere, et al., supra).

In this example, it was demonstrated that successful expression of the C fragment of *C. botulinum* type A toxin gene in *E. coli* does not require the elimination of rare codons (ie., there is no need to use a synthetic gene). This example involved a) the cloning of the native C fragment of the *C. botulinum* serotype A toxin gene and construction of an expression vector and b) a comparison of the expression and purification yields of *C. botulinum* serotype A C fragments derived from native and synthetic expression vectors.

a) Cloning of the Native C Fragment of the *C. botulinum* Serotype A Toxin Gene And Construction of an Expression Vector The serotype A toxin gene was cloned from *C. botulinum* genomic DNA using PCR amplification. The following primer pair was employed: 5'-CGCCATGGCTAG ATTATTATCTACATTTAC-3' (5' primer, NcoI site underlined; SEQ ID NO:29) and 5'-GC AAGCTTCTTGACAGACTCATGTAG-3' (3' primer, HindIII site underlined; SEQ ID NO:30). *C. botulinum* type A strain was obtained from the American Type Culture Collection (ATCC#19397) and grown under anaerobic conditions in Terrific broth medium. High molecular-weight *C. botulinum* DNA was isolated as described in Example 11. The integrity and yield of genomic DNA was assessed by comparison with a serial dilution of uncut lambda DNA after electrophoresis on an agarose gel.

The gene fragment was cloned by PCR utilizing a proofreading thermostable DNA polymerase (native Pfu polymerase). PCR amplification was performed using the above primer pair in a 50 $\mu$l reaction containing 10 mM Tris-HCl (pH 8.3), 50 mM KCl, 1.5 mM $MgCl_2$, 200 $\mu$M each dNTP, 0.21 $\mu$M each primer, and 50 ng *C. botulinum* genomic DNA. Reactions were overlaid with 100 $\mu$l mineral oil, heated to 94° C. 4 min, 0.5 $\mu$l native Pfu polymerase (Stratagene) was added, and thirty cycles comprising 94° C. for 1 min, 50° C. for 2 min, 72° C. for 2 min were carried out followed by 10 min at 72° C. An aliquot (10 $\mu$l) of the reaction mixture was resolved on an agarose gel and the amplified native C fragment gene was gel purified using the Prep-A-Gene kit (BioRad) and ligated to pCRScript vector DNA (Stratagene). Recombinant clones were isolated and confirmed by restriction digestion, using standard recombinant molecular biology techniques [Sambrook et al. (1989), supra]. In addition, the sequence of approximately 300 bases located at the 5' end of the C fragment coding region were obtained using standard DNA sequencing methods. The sequence obtained was identical to that of the published sequence.

An expression vector containing the native *C. botulinum* serotype A C fragment gene was created by ligation of the NcoI-HindIII fragment containing the C fragment gene from the pCRScript clone to NheI-HindIII restricted pETHisa vector (Example 18b). The NcoI and NheI sites were filled in using the Klenow enzyme prior to ligation; these sites were thus blunt-end ligated together. The resulting construct was termed pHisBotA (native). pHisBotA (native) expresses the *C. botulinum* serotype A C fragment with a his-tagged N terminal extension which has the following sequence: Met-GlyHisHisHisHisHisHisHisHisHisHisSerSerGlyHisIleGluGlyArgHisMetAla (SEQ ID NO:24), where the underlining represents amino acids encoded by the *C. botulinum* C fragment gene (this N terminal extension contains the recognition site for Factor Xa protease, shown in italics, which can be employed to remove the polyhistdine tract from the N-terminus of the fusion protein). The pHisBot (native) construct expresses the identical protein as the pHisBot construct (Ex. 24c; herein after the pHisBotA) which contains the synthetic gene.

The predicted DNA sequence encoding the native *C. botulinum* serotype A C fragment gene contained within pHisBotA (native) is listed in SEQ ID NO:31 [the start of translation (ATG) is located at nucleotides 108–110 and the stop of translation (TAA) is located at nucleotides1494–1496 in SEQ ID NO:31] and the corresponding amino acid sequence is listed in SEQ ID NO:26 (i.e., the same amino acid sequence as that produced by pHisBotA containing synthetic gene sequences).

b) Comparison of the Expression and Purification Yields of *C. botulinum* Serotype A C Fragments Derived from Native and Synthetic Expression Vectors Recombinant plasmids containing either the native or the synthetic *C. botulinum* serotype A C fragment genes were transformed into *E. coli* strain B121(DE3) pLysS and protein expression was induced in 1 liter shaker flask cultures. Total protein extracts were isolated, resolved on SDS-PAGE gels and *C. botulinum* C fragment protein was identified by Western analysis utilizing a chicken anti-*C botulinum* serotype A toxoid antiserum as described in Example 22.

Briefly, 1 liter (2XYT+100 μg/ml ampicillin and 34 μg/ml chloramphenicol) cultures of bacteria harboring either the pHisBotA (synthetic) or pHisBotA (native) plasmids in the B121(DE3) pLysS strain were induced to express recombinant protein by addition of IPTG to 1 mM. Cultures were grown at 30–32° C., IPTG was added when the cell density reached an $OD_{600}$ 0.5–1.0 and the induced protein was allowed to accumulate for 3–4 hrs after induction.

The cells were cooled for 15 min in an ice water bath and then centrifuged for 10 min at 5000 rpm in a JA10 rotor (Beckman) at 4° C. The cell pellets were resuspended in a total volume of 40 mls 1× binding buffer (40 mM imidazole, 0.5 M NaCl, 50 mM $NaPO_4$, pH 8.0), transferred to two 50 ml Oakridge tubes and frozen at −70° C. for at least 1 hr. The tubes were then thawed and the cells were lysed by sonication (using four successive 20 second bursts) on ice. The suspension was clarified by centrifugation 20–30 min at 9,000 rpm (10,000 g) in a JA-17 rotor. The soluble lysate was batch absorbed to 7 ml of a 1:1 slurry of NiNTA resin:binding buffer by stirring 2–4 hr at 4° C. The slurry was centrifuged for 1 min at 500 g in 50 ml tube (Falcon), resuspended in 5 mls binding buffer and poured into a 2.5 cm diameter column (BioRad). The column was attached to a UV monitor (ISCO) and the column was washed with binding buffer until a baseline was established. Imidazole was removed by washing with 50 mM $NaPO_4$, 0.3 M NaCl, 10% glycerol, pH 7.0 and bound protein was eluted using 50 mM $NaPO_4$, 0.3 M NaCl, 10% glycerol, pH 3.5–4.0.

The eluted proteins were stored at 4° C. Samples of total, soluble, and eluted proteins were resolved by SDS-PAGE. Protein samples were prepared for electrophoresis by mixing 1 μl total (T) or soluble (S) protein with 4 μl PBS and 5 μl 2× SDS-PAGE sample buffer, or 5 μl eluted (E) protein and 5 μl 2×SDS-PAGE sample buffer. The samples were heated to 95° C. for 5 min, then cooled and 5 or 10 μls were loaded on 12.5% SDS-PAGE gels. Broad range molecular weight protein markers (BioRad) were also loaded to allow the MW of the identified fusion proteins to be estimated. After electrophoresis, protein was detected either generally by staining gels with Coomassie blue, or specifically, by blotting to nitrocellulose for Western blot detection of specific immunoreactive protein.

For Western blot analysis, the gels were blotted, and protein transfer was confirmed by Ponceau S staining as described in Example 22. After blocking the blots for 1 hr at room temperature in blocking buffer (PBST and 5% milk), 10 ml of a 1/500 dilution of an anti-*C. botulinum* toxin A IgY PEG prep (Ex. 3) in blocking buffer was added and the blots were incubated for an additional hour at room temperature. The blots were washed and developed using a rabbit anti-chicken alkaline phosphatase conjugate (Boehringer Mannheim) as the secondary antibody as described in Ex. 22. This analysis detected *C. botulinum* toxin A-reactive proteins in the pHisBotA (native and synthetic) protein samples (corresponding to the predicted full length proteins identified by Coomassie staining).

Figure 31:
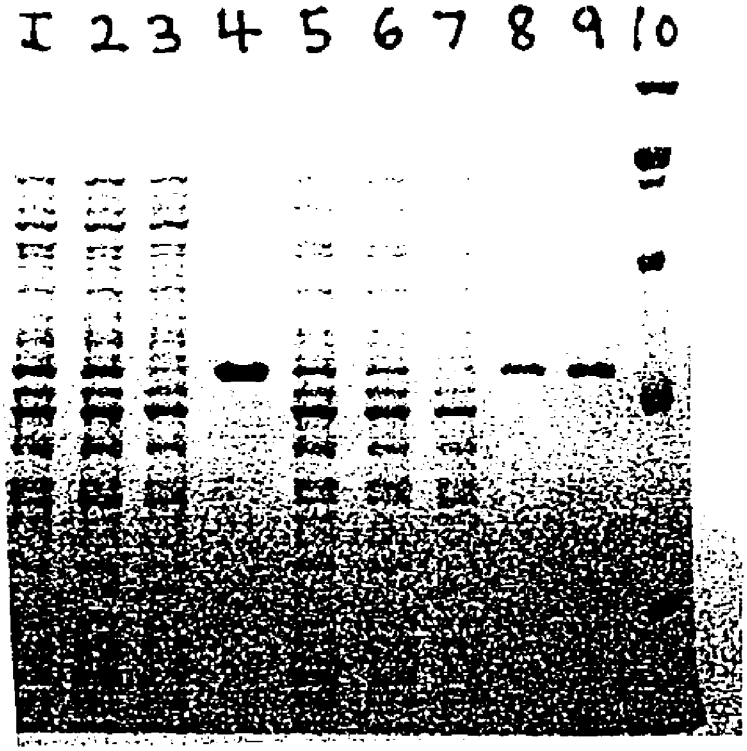
FIG. 31 is an SDS-PAGE gel stained with Coomaisse blue showing the purification of pHisBot and pHisBot(native) proteins using a Ni-NTA column.

A gel containing proteins expressed from the pHisBot and pHisBot (native) constructs during various stages of purification and stained with Coomassie blue is shown in FIG. 31. In FIG. 31, lanes 1–4 and 9 contain proteins expressed by the pHisBotA construct (i.e., the synthetic gene) and lanes 5–8 contain proteins expressed by the pHisBotA (native) construct. Lanes 1 and 5 contain total protein extracts; lanes 2 and 6 contain soluble protein extracts; lanes 3 and 7 contain proteins which flowed through the NiNTA columns; lanes 4, 8 and 9 contain protein eluted from the NiNTA columns and lane 10 contains molecular weight markers.

The above purification resulted in a yield of 3 mg (native gene) or 11 mg (synthetic gene) of affinity purified protein from a 1 liter starting culture, of which at least 90–95% of the protein was a single band of the predicted MW (50 kd) and immunoreactivity for recombinant *C. botulinum* serotype A C fragment protein. Other than the level of expression, no difference was observed between the native and the synthetic gene expression systems.

These results demonstrate that soluble *C. botulinum* serotype A C fragment protein can be expressed in *E. coli* and purified utilizing either native or synthetic gene sequences.

EXAMPLE 29

Generation of Neutralizing Antibodies Using a Recombinant *C. botulinum* Serotype A C Fragment Protein Containing a Six Residue His-Tag In Example 27, neutralizing antibodies were generated utilizing the pHisBot protein, which contains a histidine-tagged N-terminal extension comprising 10 histidine residues. To determine if the generation of neutralizing antibodies is dependent on the presence of this particular his-tag, a protein containing a shorter N-terminal extension (comprising 6 histidine residues) was produced and tested for the ability to generate neutralizing antibodies. This example involved a) the cloning and expression of the p6HisBotA(syn) protein and b) the gene ration and characterization of hyperimmune serum.

a) Cloning and Expression of the p6HisBotA(syn) Protein

The p6HisBotA(syn) construct was generated as described below; the term "syn" designates the presence of synthetic gene sequences. This construct expresses the C fragment of the *C. botulinum* serotype A toxin with a histidine-tagged N terminal extension having the following sequence: MetHisHisHisHisHisHisMetAla (SEQ ID NO:32); the amino acids encoded by the botulinal C fragment gene are underlined and the vector encoded amino acids are presented in plain type. 6×His oligonucleotides [5'-TATGCATCACCATCACCATCA-3' (SEQ ID NO:33) and 5'-CATGTGATGGTGATGGTGATGCA-3' (SEQ ID NO:34) were annealed as follows. One microgram of each oligonucleotide was mixed in total of 20 μl 1× reaction buffer 2 (NEB) and the mixture was heated at 70° C. for 5 min and then incubated at 42° C. for 5 min. The annealed oligonucleotides were then ligated with gel purified NdeI/HindIII cleaved pET23b (T7 promoter) or pET21b (T7lac promoter) DNA and the gel purified NcoI/HindIII *C. botulinum* serotype A C fragment synthetic gene fragment derived from pAlterBot (Ex. 22). Recombinant clones were isolated and confirmed by restriction digestion. The DNA sequence encoding the 6× his-tagged BotA protein contained within p6HisBotA(syn) is listed in SEQ ID NO:35. The amino acid sequence of the p6×HisBotA protein is listed in SEQ ID NO:36.

The resulting recombinant p6×HisBotA plasmid was transformed into the BL21(DE3) pLysS strain, and 1 liter cultures were grown, induced and harvested as described in Example 28. His-tagged protein was purified as described in Example 28, with the following modifications. The binding buffer (BB) contained 5 mM imidazole rather than 40 mM imidazole and NP40 was added to the soluble lysate to a final concentration of 0.1%. The bound material was washed on the column with BB until the baseline was established, then the column was washed successively with BB+20 mM imidazole and BB+40 mM imidazole. The column was eluted as described in Example 28.

In the case of the pET23-derived expression system, high level expression of insoluble 6HisBotA protein was induced. The pET21-derived vector expressed lower levels of soluble protein that bound the NiNTA resin and eluted in the 40 mM imidazole wash rather than during the low pH elution. These results (ie., low level expression of a soluble protein) are consistent with the results obtained with pHisBotA protein (Ex. 25); the pHisBotA construct, like the pET21-derived vector, contains the T7lac rather than T7 promoter.

The 6HisBotA protein thus elutes under less stringent conditions than the 10× histidine-containing pHisBot protein (100–200 mM imidazole; Ex. 25) presumably due to the reduction in the length of the his-tag. The eluted protein was of the predicted size [i.e., slightly reduced in comparison to pHisBotA protein].

b) Generation and Characterization of Hyperimmune Serum

Eight BALBc mice were immunized with purified 6HisBotA protein using Gerbu GMDP adjuvant (CC Biotech). The 40 mM imidazole elution was mixed with Gerbu adjuvant and used to immunize mice. Each mouse received a subcutaneous injection of 100 $\mu$l antigen/adjuvant mix (12 $\mu$g antigen+1 $\mu$g adjuvant) on day 0. Mice were subcutaneously boosted as above on day 14 and bled on day 28. Control mice received pHisBotB protein (prepared as described in Ex. 35 below) in Gerbu adjuvant.

Anti-*C. botulinum* serotype A toxoid titers were determined in serum from individual mice from each group using the ELISA described in Example 23a with the exception that the initial testing serum dilution was 1:100 in blocking buffer containing 0.5% Tween 20, followed by serial 5-fold dilutions into this buffer. The results of the ELISA demonstrated that seroconversion (relative to control mice) occurred in all 8 mice.

The ability of the anti-*C. botulinum* serotype A C fragment antibodies present in serum from the immunized mice to neutralize native *C. botulinum* type A toxin was tested using the mouse neutralization assay described in Example 23b. The amount of neutralizing antibodies present in the serum of the immunized mice was determined using serum antibody titrations. The various serum dilutions (0.01 ml) were mixed with 5 $LD_{50}$ units of *C. botulinum* type A toxin and the mixtures were injected IP into mice. The neutralizations were performed in duplicate. The mice were then observed for signs of botulism for 4 days. Undiluted serum was found to protect 100% of the injected mice while the 1:10 diluted serum did not. This corresponds to a neutralization titer of 0.05–0.5 IU/ml.

These results demonstrate that neutralizing antibodies were induced when the 6HisBotA protein was utilized as the immunogen. Furthermore, these results demonstrate that seroconversion and the generation of neutralizing antibodies does not depend on the specific N terminal extension present on the recombinant *C. botulinum* type A C fragment proteins.

EXAMPLE 30

Construction of Vectors for the Expression of His-Tagged *C. botulinum* Type A Toxin C Fragment Protein Using the Synthetic Gene A number of expression vectors were constructed which contained the synthetic *C. botulinum* type A toxin C fragment gene. These constructs vary as to the promoter (T7 or T7lac) and repressor elements (lacIq) present on the plasmid. The T7 promoter is a stronger promoter than is the T7lac promoter. The various constructs provide varying expression levels and varying levels of plasmid stability. This example involved a) the construction of expression vectors containing the synthetic *C. botulinum* type A C fragment gene and b) the determination of the expression level achieved using plasmids containing either the kanamycin resistance or the ampicillin resistance genes in small scale cultures.

a) Construction of Expression Vectors Containing the Synthetic *C. botulinum* Type A C Fragment Gene Expression vectors containing the synthetic *C. botulinum* type A C fragment gene were engineered to utilize the kanamycin resistance rather than the ampicillin resistance gene. This was done for several reasons including concerns regarding the presence of residual ampicillin in recombinant protein derived from plasmids containing the ampicillin resistance gene. In addition, ampicillin resistant plasmids are more difficult to maintain in culture; the β-lactamase secreted by cells containing ampicillin resistant plasmids rapidly degrades extracellular ampicillin, allowing the growth of plasmid-negative cells.

A second altered feature of the expression vectors is the inclusion of lacIq gene in the plasmid. This repressor lowers expression from lac regulated promoters (the chromosomally located, lactose regulated T7 polymerase gene and the plasmid located T7lac promoter). This down regulates uninduced protein expression and can enhance the stability of recombinant cell lines. The final alteration to the vectors is the inclusion of either the T7 or T7lac promoters that drive high or moderate level expression of recombinant protein, respectively.

The expression plasmids were constructed as follows. In all cases, the protein expressed is the pHisBotA(syn) protein previously described, and the only differences between constructs is the alteration of the various regulatory elements described above.

i) Construction of pHisBotA(syn) kan T7lac

The pHisBotA(syn) kan T7lac construct was made by inserting the SapI/XhoI fragment containing the *C. botulinum* type A C fragment from pHisBotA(syn) into pET24 digested with SapI/XhoI (Novagen; fragment contains kan gene and origin of replication). The desired construct was selected for kanamycin resistance and confirmed by restriction digestion.

ii) Construction of pHisBotA(syn) kan lacIq T7lac

The pHisBotA(syn) kan lacIq T7lac construct was made by inserting the XbaI/HindIII fragment containing the *C. botulinum* type A C fragment from pHisBotA(syn)kanT7lac into the pET24a vector digested with XbaI/HindIII. The resulting construct was confirmed by restriction digestion.

iii) Construction of pHisBotA(syn) kan lacIq T7

The pHisBotA(syn) kan lacIq T7 construct was made by inserting the XbaI/HindIII fragment containing the *C. botulinum* type A C fragment from pHisBotA(syn) kan lacIq T7lac into XbaI/HindIII-digested pHisBotB(syn) kan lacIq T7 (described in Ex 37c below). The resulting construct was confirmed by restriction digestion.

b) Determination of the Expression Level Achieved Using Plasmids Containing Either the Kanamycin Resistance or the Ampicillin Resistance Genes in Small Scale Cultures One liter cultures of pHisBotA(syn) kan T7lac/B121 (DE3)pLysS and pHisBotA(syn) amp T7lac/B121(DE3)

pLysS [this is the previously designated pHisBotA(syn) construct] were grown, induced and his-tagged proteins were purified as described in Example 28. No differences in yield or protein integrity/purity were observed.

These results demonstrate that the antigen induction levels from expression constructs were not affected by the choice of ampicillin versus kanamycin antibiotic resistance genes.

EXAMPLE 31

Fermentation of Cells Expressing Recombinant Botulinal Proteins a) Fermentation Culture of Cells Expressing Recombinant Botulinal Proteins Fermentation cultures were grown under the following conditions which were optimized for growth of the BL21 (DE3) strains containing pET derived expression vectors. An overnight 1 liter feeder culture was prepared by inoculating of 1 liter media (in a 2 L shaker flask) with a fresh colony grown on an LB kan plate. The feeder culture contained: 600 mls nitrogen source [20 gm yeast extract (BBL) and 40 gm tryptone (BBL)/600 mls], 200 mls 5× fermentation salts (per liter: 48.5 gm $K_2HPO_4$, 12 gm $NaH_2PO_4.H_2O$, 5 gm $NH_4Cl$, 2.5 gm NaCl), 180 mls $dH_2O$, 20 mls 20% glucose, 2 mls 1 M $MgSO_4$, 5 mls 0.05M $CaCl_2$ and 4 mls of a 10 mg/ml kanamycin stock. All solutions were sterilized by autoclaving, except the kanamycin stock which was filter sterilized.

An aliquot (5 ml) of the feeder culture broth was removed prior to inoculation, and grown for 2 days at 37° C. as a culture broth sterility control. Growth was not observed in this control culture in any of the fermentations performed.

The inoculated feeder culture was grown for 12–15 hrs (ON) at 30–37° C. Care was taken to prevent oversaturation of this culture. The saturated feeder culture was added to 10 L of fermentation media in fermenter (BiofloIV, New Brunswick Scientific, Edison, N.J.) as follows. The fermenter was sterilized 120 min at 121° C. with $dH_2O$. The sterile water was removed, and fermentation media added as follows: 6 liters nitrogen source, 2 liters 5× fermentation salts, 2 liters 2% glucose, 20 mls 1 M $MgSO_4$, 50 mls 0.05 M $CaCl_2$, 2.5–3.5 mls Macol P 400 antifoam (PPG Industries Inc., Gurnee, Ill.), 40 mls 10 mg/ml kanamycin and 10 mls trace elements (8 gm $FeSO_4.7H_2O$, 2 gm $MnSO_4.H_2O$, 2 gm $AlCl_3.6H_2O$, 0.8 gm $CoCl.6H_2O$, 0.4 gm $ZnSO_4.7H_2O$, 0.4 gm $Na_2MoO_4.2H_2O$, 0.2 gm $CuCl_2.2H_2O$, 0.2 gm $NiCl_2$, 0.1 gm $H_3BO_4$/200 mls 5 M HCl). All solutions were sterilized by autoclaving, except the kanamycin stock which was filter sterilized. Fermentation media was prewarmed to 37° C. before the addition of the feeder culture.

After the addition of the feeder culture, the culture was fermented at 37° C., 400 rpm agitation, and 10 l/min air sparging. The $DO_2$ control was set to 20% PID and dissolved oxygen levels were controlled by increasing the rate of agitation from 400–850 rpm under $DO_2$ control. $DO_2$ levels were maintained at greater than or equal to 20% throughout the entire fermentation. When agitation levels reached 500–600 rpm the temperature was lowered to 30° C. to reduce the oxygen consumption rate. Culture growth was continued until endogenous carbon sources were depleted. In these fermentations, glucose was depleted first [monitored with a glucose monitoring kit (Sigma)], followed by assimilation of acetate and other acidic carbons [monitored using an acetate test kit (Boehringer Mannheim)]. During the assimilation phase, the pH rose from 6.6–6.8 (starting pH) to 7.4–7.5, at which time the bulk of the remaining carbon source was depleted. This was signaled by a drop in agitation rate (from a maximum of 700–800 rpm) and a rise in $DO_2$ levels >30%. This corresponds to a $OD_{600}$ reading of 18–20/ml. At this point a fed batch mode was initiated, in which a feed solution of 50% glucose was added at a rate of approximately 4 gm glucose/liter/hr. The pH was adjusted to 7.0 by the addition of 25% $H_3PO_4$ (approximately 60 mls). Culture growth was continued and reached peak oxygen consumption within the next 3 hrs of growth (while the remaining residual non-glucose carbon sources were assimilated). This phase is characterized by a slow increase in pH, and air sparging was increased to 15 L/min, to keep the maximum rpm below 850.

Once the residual acidic carbon sources are depleted the agitation rate decreases to 650–750 rpm and the pH begins to drop. pH control was maintained at 7.0 PID by regulated pump addition of a sterile 4M NaOH solution which was consumed at a steady rate for the remainder of the fermentation. Growth was continued at 30° C., and the cultures were grown linearly at a growth rate of 4–7 $OD_{600}$ units/hr, to at least 81.5 $OD_{600}$ units/ml (>30 g/l dry cell weight) without induction. Antifoam (a 1:1 dilution with filter sterilized 100% ethanol) was added as necessary throughout the fermentation to prevent foaming.

During the fed batch mode, glucose was assimilated immediately (concentration in media consistently less than 0.1 gm/liter) and acetate was not produced in significant levels by the pET plasmid/BL21(DE3) cell lines tested (approximately 1 gm/liter at end of fermentation; this is lower than that observed in harvests from shaker flask cultures utilizing the same strains). This was fortuitous, since high levels of acetate has been shown to inhibit induction levels in a variety of expression systems. The above described conditions were found to be highly reproducible between fermentations and utilizing different expression plasmids. As a result, glucose and acetate level monitoring were no longer preformed during fermentation.

b) Induction of Fermentation Cultures

Induction with IPTG (250 mg–10 gms, depending on the expression vector and experiment) was initiated 1–3 hrs after initiation of the glucose feed (30–50 $OD_{600}$/ml). The growth rate after induction was monitored on a hourly basis. Aliquots (5–10 ml) of cells were harvested at the time of induction, and at hourly intervals post-induction. Optical density readings were determined by measuring the absorbance at 600 nm of 10 $\mu$l culture in 990 $\mu$l PBS versus a PBS control. The growth rate after induction was found to vary depending on the expression system utilized.

c) Monitoring of Fermentation Cultures

Fermentation cultures were monitored using the following control assays.

i) Colony Forming Ability

An aliquots of cells were removed from the cultures at each timepoint sampled (uninduced and at various times after induction) were serially diluted in PBS (dilution 1=15 $\mu$l cells/3 ml PBS, dilution 2=15 $\mu$l of dilution ⅓ ml PBS, dilution 3=3 or 6 $\mu$l of dilution ⅔ mls PBS) and 100 $\mu$l of dilution 3 was plated on an LB or TSA (trypticase soy agar) plate. The plates were incubated ON at 37° C. and then the colonies are counted and scored for macro or micro growth.

ii) Phenotypic Characterization

Colonies growing on LB or TSA plates (above) from uninduced and induced timepoints were replica plated onto LB+kan, LB+chloramphenicol (for fermentations utilizing LysS or pACYCGro plasmids), LB+kan+1 mM IPTG and LB plates, in this order. The plates were grown 6–8 hrs at 37° C. and growth was scored on each plate for a minimum of 40–50 well isolated colonies. The percentage of cells retaining the plasmid at time of induction (i.e., uninduced cultures immediately prior to the addition of IPTG) was determined to be the # colonies LB+Kan (or chloramphenicol) plate/# colonies LB plate X 100%. The percentage of cells with mutated pET plasmids was determined to be the # colonies LB+Kan+IPTG plate/# colonies LB plate X 100%. Colonies on all LB plates were scored morphologically for *E. coli* phenotype as a contamination control. Morphologically detectable contaminant colonies were not detected in any fermentation.

iii) Recombinant BotA Protein Induction

A total of 10 $OD_{600}$ units of cells (e.g., 200 μl of cells at $OD_{600}$=50/ml) were removed from each timepoint sample to a 1.5 ml microfuge tube and pelleted for 2 min at maximum rpm in a microfuge. The pellets were resuspended in 1 ml of 50 mM $NaHPO_4$, 0.5 M NaCl, 40 mM imidazole buffer (pH 6.8) containing 1 mg/ml lysozyme. The samples were incubated for 20 min at room temperature and stored ON at −70° C. Samples were thawed completely at room temperature and sonicated 2×10 seconds with a Branson Sonifier 450 microtip probe at # 3 power setting. The samples were centrifuged for 5 min at maximum rpm in a microfuge.

An aliquot (20 μl) of the protein samples were removed to 20 μl 2× sample buffer, before or after centrifugation, for total and soluble protein extracts, respectively. The samples were heated to 95° C. for 5 min, then cooled and 5 or 10 μl were loaded onto 12.5% SDS-PAGE gels. High molecular weight protein markers (BioRad) were also loaded to allow for estimation of the MW of identified fusion proteins. After electrophoresis, protein was detected either generally by staining gels with Coomassie blue, or specifically, by blotting onto nitrocellulose (as described in Ex. 28) for Western blot detection of specific his-tagged proteins utilizing a NiNTA-alkaline phosphatase conjugate exactly as described by the manufacturer (Qiagen).

iv) Recombinant Antigen Purification

At the end of each fermentation run, 1–10 liters of culture were harvested from the fermenter and the bacterial cells were pelleted by centrifugation at 6000 rpm for 10 min in a JA10 rotor (Beckman). The cell pellets were stored frozen at −70° C. or utilized immediately without freezing. Cell pellets were resuspended to 15–20% weight to volume in resuspension buffer (generally 50 mM $NaPO_4$, 0.5 M NaCl, 40 mM imidazole, pH 6.8) and lysed utilizing either sonication or high pressure homogenization.

For sonication, the resuspension buffer was supplemented with lysozyme to 1 mg/ml, and the suspension was incubated for 20 min. at room temp. The sample was then frozen ON at −70° C., thawed and sonicated 4×20 seconds at microtip maximum to reduce viscosity. For homogenization, the cells were lyzed by 2 passes through a homogenizer (Rannie Mini-lab type 8.30H) at 600 Bar. Cell lysates were clarified by centrifugation for 30 min at 10,000 rpm in a JA10 rotor.

For IDA chromatography, samples were flocculated utilizing polyethyleneimine (PEI) prior to centrifugation. Cell pellets were resuspended in cell resuspension buffer (CRB: 50 mM $NaPO_4$, 0.5 M NaCl, 40 mM imidazole, pH 6.8) to create a 20% cell suspension (wet weight of cells/volume of CRB) and cell lysates were prepared as described above (sonication or homogenization). PEI (a 2% solution in $dH_2O$, pH 7.5 with HCl) was added to the cell lysate a final concentration of 0.2%, and stirred for 20 min at room temperature prior to centrifugation (8,500 rpm in JA10 rotor for 30 minutes at 4° C.). This treatment removed RNA, DNA and cell wall components, resulting in a clarified, low viscosity lysate ("PEI clarified lysate").

His-tagged proteins were purified from soluble lysates by metal-chelate affinity chromatography using either a NiNTA resin (as described in Ex. 28) or an IDA (iminodiacetic acid) resin as described below.

IDA resin affinity purifications were performed utilizing a low pressure chromatography system (ISCO). A 7 ml (small scale) or 70 ml (large scale) Chelating Sepharose Fast Flow (Pharmacia) affinity column was poured; in addition, a second guard column was poured and attached in line with the first column (to capture Ni ions that leached off the affinity column). The columns were washed with 3 column volumes of $dH_2O$. The guard column was then removed and the affinity column was washed with 0.3 M $NiSO_4$ until resistivity was established, then with $dH_2O$ until the resistivity returned to baseline. The columns were reconnected and equilibrated with cell resuspension buffer (CRB; 50 mM $NaPO_4$, 0.5 M NaCl, 40 mM imidazole, pH 6.8). The clarified sample (in CRB) was loaded. Flow rates were 5 ml/min for small scale columns and 20 ml/min for large scale columns. After sample loading, the column was washed with CRB until a baseline established and bound protein was eluted with elution buffer (50 mM $NaPO_4$, 0.5 M NaCl, 800 mM imidazole, 20% glycerol, pH 6.8 or 8.0). Protein samples were stored at 4° C. or −20° C. The yield of −220eluted protein was established by measuring the $OD_{280}$ of the elutions, with a 1 mg/ml solution of protein assumed to yield an absorbance reading of 2.0.

The IDA columns may be regenerated and reused multiple times (>10). To regenerate the column, the column was washed with 2–3 column volumes of $H_2O$, then 0.05 M EDTA until all of the blue/green color was removed followed by a wash with $dH_2O$. The IDA columns were sterilized with 0.1 M NaOH (using at least 3 column volumes but not more than 50 minutes contact time with column packing material), then washed with 3 column volumes 0.05 M $NaPO_4$, pH 5.0, then $dH_2O$ and stored at room temperature in 20% ethanol.

EXAMPLE 32

Construction of a Folding Chaperone Overexpression System

Co-overexpression of the *E. coli* GroEL/GroES folding chaperones in a cell expressing a recombinant foreign protein has been reported to enhance the solubility of some foreign proteins that are otherwise insoluble when expressed in *E. coli* [Gragerouu et al. (1992) Proc. Natl. Acad. Sci. USA 89:10344]. The improvement in solubility is thought to be due to chaperone-mediated binding and unfolding of insoluble denatured proteins, thus allowing multiple attempts for productive refolding of recombinant proteins. By overexpressing the chaperones, the unfolding/refolding reaction is driven by excess chaperone, resulting, in some cases, in higher yields of soluble protein.

In this example, a chaperone overexpression system, compatible with pET vector expression systems, was constructed to facilitate testing chaperone-mediated solubilization of *C. botulinum* type A proteins. This example involved the cloning of the GroEL/ES operon and construction of a pLysS-based chaperone hyperexpression system.

The GroEL/GroES operon was PCR amplified and cloned into the pCRScript vector as described in Example 28. The following primer pair was used: 5'-CG CATATGAATATTCGTCCATTGCATG-3' (SEQ ID NO:37) [5' primer, start codon of groES gene converted to NdeI site (underlined)] and 5'-GGAAGCTTGCAGGGCAAT TACATCATG (SEQ ID NO:38) (3' primer, stop codon of groEL gene italicized, engineered HindIII site underlined). Following amplification, the chaperone operon was excised as an NdeI/HindIII fragment and cloned into pET23b digested with NdeI and HindIII. This construction places the Gro operon under the control of the T7 promoter of the pET23 vector. The desired construct was confirmed by restriction digestion.

The T7 promoter-Gro operon-T7 terminator expression cassette was then excised as a BglII/BspEI (filled) fragment and cloned into BamHI (compatible with BglII)/HindIII (filled) cleaved pLysS plasmid (this removed the 17 lysozyme gene). The resulting construct was designated pACYCGro, since the plasmid utilizing the pACYC184 origin from the plysS plasmid. Proper construction was confirmed by restriction digestion.

pACYCGro was transformed into BL21(DE3), cultures were grown and induced with 1 mM IPTG as described in preceding examples. Total and soluble protein extracts were generated from cells removed before and after IPTG induction and were resolved on a 12.5% SDS-PAGE gel and stained with Coomassie blue. This analysis revealed that high levels of soluble GroEI and GroES proteins were made in the induced cells. These results demonstrated that the chaperone hyper-expression system was functional.

EXAMPLE 33

Growth of BotA/pACYCGro Cell Lines in Fermentation Cultures

Induction of BL21(DE3) cells lacking the LysS plasmid which contained BotA expression constructs grown in shaker flask or fermentation culture resulted in the expression of primarily insoluble BotA protein. Fermentation cultures were performed to determine if the simultaneous overexpression of the Gro operon and recombinant *C. botulinum* type A proteins (BotA proteins) resulted in enhanced solubility of the recombinant BotA protein. This example involved the fermentation of pHisBotA(syn)kan lacIq T 7lac/pACYCGro BL21(DE3) and pHisBotA(syn)kan lacIq T 7/pACYCGro BL21(DE3) cell lines. The fermentations were repeated exactly as described in Example 31. Chloramphenicol (34 $\mu$g/ml) was included in the feeder and fermentation cultures.

a) Fermentation of pHisBotA(syn)kan lacIq T 7lac/pACYCGro BL21(DE3) Cells

For fermentation of cells containing plasmids comprising the T7lac promoter, induction was with 2 gms IPTG at 1 hr post initiation of glucose feed. The $OD_{600}$ was 35 at time of induction, then 48.5, 61.5, 67 at 1–3 hrs post induction. Viable colony counts decreased from 0–3 hr induction [21 (13), 0, 0, 0; dilution 3 utilized 3 $\mu$l of dilution 2 cells] with numbers in parenthesis for the indicating microcolonies. Of 28 colonies scored at the time of induction, 23 retained the pHisBotA(syn)kan lacIq T7lac plasmid (kan resistant), 22 contained the chaperone plasmid (chloramphenicol resistant) and no colonies at induction grew on IPTG+Kan plates (no mutations detected). These results were indicative of very strong promoter induction, since colony viability dropped immediately after induction.

Total and soluble extracts were resolved on a 12.5% SDS-PAGE gel and stained with Coomassie. High level induction of Gro chaperones was observed, but very low level expression of soluble BotA protein was observed, increasing from 1 to 4.0 hrs post induction (no expression detected in uninduced cells). The dramatically lower expression of the BotA antigen in the presence of chaperone may be due to promoter occlusion (i.e., the stronger T7 promoter on the chaperone plasmid is preferentially utilized).

b) Fermentation of pHisBotA(syn)kan lacIq T 7/pACYCGro BL21(DE3) Cells

A fermentation utilizing the T7-driven BotA expression plasmid was performed. Induction was with 1 gm IPTG at 2 hrs post initiation of glucose feed. The $OD_{600}$ was 41 at time of induction, then 51.5, 61.5, 61.5 and 66 at 1–4 hrs post induction. Viable colony counts decreased from 0–4 hrs induction [71, 1 (34), 1 (1), 1, 0; dilution 3 utilized 6 $\mu$l dilution 2 cells) with numbers in parenthesis for the uninduced timepoint indicating microcolonies. Of 65 colonies scored at the time of induction, all 65 retained both the pHisBotA(syn)kan lacIq T 7 plasmid (kan resistant) and the chaperone plasmid (chloramphenicol resistant) and no colonies at induction grew on IPTG+Kan plates (no mutations detected).

Total and soluble extracts were resolved on a 12.5% SDS-PAGE gel and stained with Coomassie. High level induction of Gro chaperones and moderate level expression of soluble BotA protein was observed, increasing from 1 to 4.0 hrs post induction (no expression detected in uninduced cells).

Figure 32:
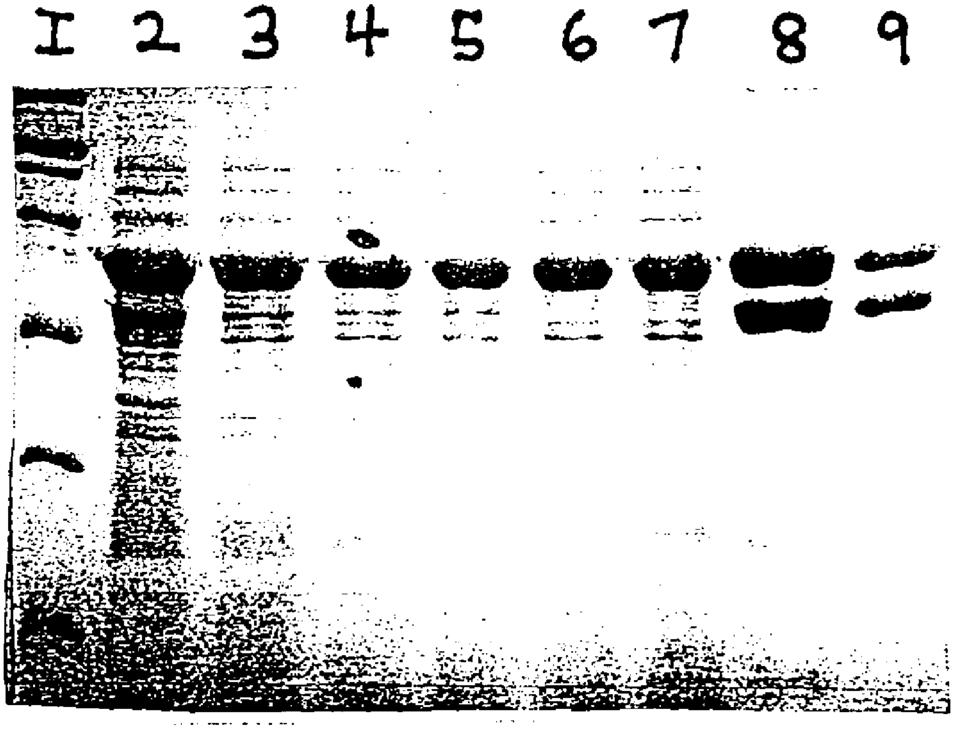
FIG. 32 is an SDS-PAGE gel stained with Coomaisse blue showing the purification of pHisBotA protein expressed in pHisBotA(syn) kan lacIq T7/pACYCGro/BL21(DE3) cells using an IDA column.

A PEI-clarified lysate (0.2% final concentration PEI) [850 ml from 130 gm cell pellet (2 liters fermentation harvest)] was purified on a large scale IDA column. A total of 78 mg of protein was eluted. Extracts from the purification were resolved on a 12.5% SDS-PAGE gel and stained with Coomassie. The elution was found to contain an approximately 1:1 mix of BotA/chaperone protein (FIG. 32). PEI lysates prepared in this manner were typically 16 $OD_{280}$ ml. This was estimated to be 8 mg protein/ml of lysate (by BCA assay). Thus, the eluted recombinant BotA protein represented 0.55% of the total soluble cellular protein applied to the column.

In FIG. 32, lane 1 contains molecular weight markers, lanes 2–9 contain extracts from pHisBotA(syn)kan lacIq 17/pACYCGro/BL21(DE3) cells before or during purification on the IDA column. Lane 2 contains total protein extract; lane 3 contains soluble protein extract; lanes 4 and 5 contain PEI-clarified lysates (duplicates); lanes 6 and 7 contain flow-through from the IDA column (duplicates) and lanes 8 and 9 contain IDA column elute (lane 9 contains 1/10 the amount applied to lane 8).

These results demonstrate, that although the majority of the BotA protein produced was insoluble, 20 mg/liter of soluble recombinant BotA protein can be purified utilizing the pHisBotA(syn)kan lacIq L7/pACYCGro/BL21(DE3) expression system.

EXAMPLE 34

Purification of Recombinant BotA Protein from Folding Chaperones

In this example of size exclusion chromatography was used to purify the recombinant BotA protein away from the folding chaperones and imidazole present in the IDA-purified material (Ex. 33).

To enhance the solubility of the recombinant BotA protein during scale-up, the protein was co-expressed with folding chaperones (Ex. 33). As observed with the recombinant BotB protein (Example 40 below), the folding chaperones co-eluted with the recombinant BotA protein during the Ni-IDA purification step. Because the recombinant BotA and BotB proteins have similar molecular weights (about 1/10 the size of the non-reduced folding chaperone) and the imidazole step gradient strategy was unsuccessful in purifying BotB away from the folding chaperone (see Ex. 40), size exclusion chromatography was examined for the ability to purify the recombinant BotA protein away from the folding chaperones.

A column (2.5×24 cm) containing Sephacryl S-100 HR (Pharmacia) was poured (bed volume ~110 ml). Proteins having molecular weights greater than 100 K are expected to elute in the void volume under these conditions and smaller proteins should be retained by the beads and elute at different times, depending on their molecular weights. To maintain solubility of the purified BotA protein, the Sephacryl column was equilibrated in a buffer having the same salt concentration as the buffer used to elute the BotA protein from the IDA column (i.e., 50 mM sodium phosphate, 0.5 M NaCl, 10% glycerol; all reagents from Mallinkrodt, Chesterfield, Mo.).

Five milliliters of the IDA-purified recombinant BotA protein (Ex. 33) was filtered through a 0.45$\mu$ syringe filter, applied to the column and the equilibration buffer was pumped through the column at a flow rate of 1 ml/minute. Eluted proteins were monitored by absorbance at 280 nin and collected either manually or with a fraction collector (BioRad). Appropriate fractions were pooled, if necessary, and the protein was quantitated by absorbance at 280 nm and/or BCA protein assay (Pierce). The isolated peaks were then analyzed by native and/or SDS-PAGE to identify the proteins present and to evaluate purity. The folding chaperone eluted first, followed by the recombinant BotA protein and then the imidazole peak.

Figure 33:
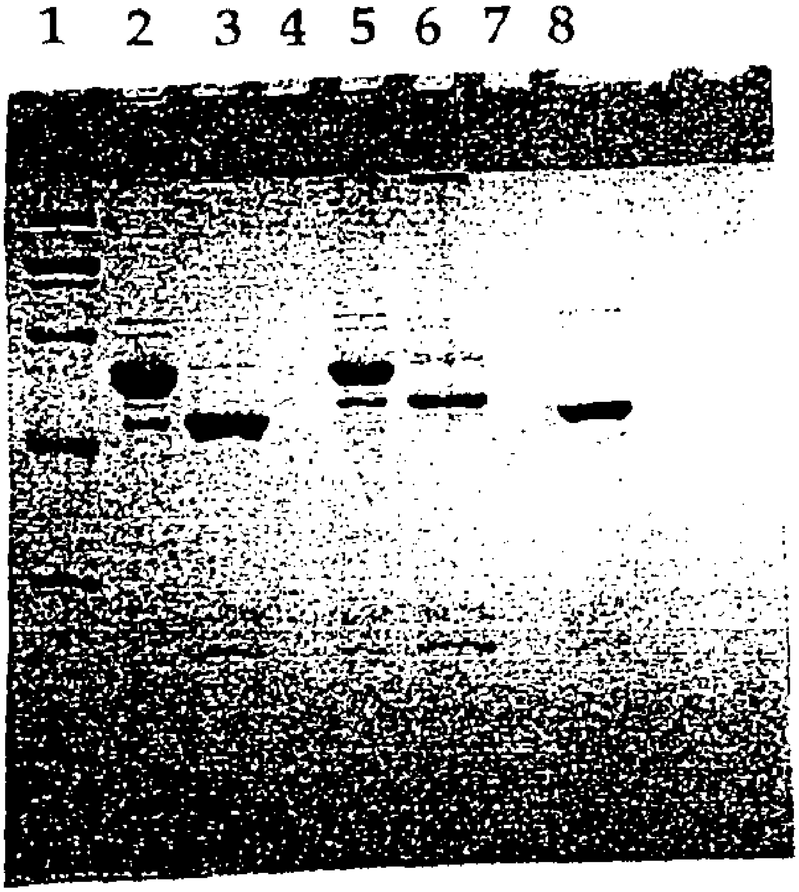
FIG. 33 is an SDS-PAGE gel stained with Coomaisse blue showing the purification of pHisBotA, pHisBotB and pHisBotE proteins by IDA chromatography followed by chromatography on S-100 to remove folding chaperones.

SDS-PAGE analysis (12.5% polyacrylamide, reduced samples) was used to evaluate the purity of the IDA-purified recombinant BotA protein before and after S-100 purification. FIG. 33 shows the difference in purity before and after the S-100 purification step. In FIG. 33, lane 1 contains molecular weight markers (BioRad broad range). Lane 2 shows the IDA-purified recombinant BotA protein preparation, which is contaminated with significant amounts of the folding chaperone. Following S-100 purification, the amount of folding chaperone present in the BotA sample is reduced dramatically (lane 3). Lane 4 contains no protein (i.e., it is a blank lane); lanes 5–8 contain samples of IDA-purified recombinant BotB and BotE proteins and are discussed infra.

Endotoxin levels in the S-100 purified BotA preparation were determined using the LAL assay (Associates of Cape Cod) as describe in Example 24. The purified BotA preparation was found to contain 22.7 to 45.5 EU/mg recombinant protein.

These results demonstrate that size exclusion chromatography was successful in purifying the recombinant BotA protein from folding chaperones and imidazole following an initial IDA purification step. Furthermore, these results demonstrate that the S-100 purified BotA protein was substantially free of endotoxin.

EXAMPLE 35

Cloning and Expression of the C Fragment of the *C. botulinum* Serotype B Toxin Gene The *C. botulinum* type B neurotoxin gene has been cloned and sequenced [Whelan et al. (1992) Appl. Environ. Microbiol. 58:2345 and Hutson et al. (1994) Curr. Microbiol. 28:101]. The nucleotide sequence of the toxin gene derived from the Eklund 17B strain (ATCC 25765) is available from the EMBL/GenBank sequence data banks under the accession number X71343; the nucleotide sequence of the coding region is listed in SEQ ID NO:39. The amino acid sequence of the *C. botulinum* type B neurotoxin derived from the strain Eklund 17B is listed in SEQ ID NO:40. The nucleotide sequence of the *C. botulinum* serotype B toxin gene derived from the Danish strain is listed in SEQ ID NO:41 and the corresponding amino acid sequence is listed in SEQ ID NO:42.

The DNA sequence encoding the native *C. botulinum* serotype B C fragment gene derived from the Eklund 17B strain can be expressed using the pETHisb vector; the resulting coding region is listed in SEQ ID NO:43 and the corresponding amino acid sequence is listed in SEQ ID NO:44. The DNA sequence encoding the native *C. botulinum* serotype B C fragment gene derived from the Danish strain can be expressed using the pETHisb vector; the resulting coding region is listed in SEQ ID NO:45 and the corresponding amino acid sequence is listed in SEQ ID NO:46. The C fragment region from any strain of *C. botulinum* serotype B can be amplified and expressed using the approach illustrated below using the C fragment derived from *C. botulinum* type B 2017 strain.

The *C. botulinum* type B neurotoxin gene is synthesized as a single polypeptide chain which is processed to form a dimer composed of a light and a heavy chain linked via disulfide bonds; the type B neurotoxin has been reported to exist as a mixture of predominatly single chain with some double chain (Whelan et al., supra). The 50 kD carboxy-terminal portion of the heavy chain is referred to as the C fragment or the $H_C$ domain. Expression of the C fragment of *C. botulinum* type B toxin in heterologous hosts (e.g., *E. coli*) has not been previously reported.

The native C fragment of the *C. botulinum* serotype B toxin gene was cloned and expression constructs were made to facilitate protein expression in *E. coli*. This example involved PCR amplification of the gene, cloning, and construction of expression vectors.

The C fragment of the *C. botulinum* serotype B (BotB) toxin gene was cloned using the protocols and conditions described in Example 28 for the isolation of the native BotA gene. The *C. botulinum* type B 2017 strain was obtained from the American Type Culture Collection (ATCC #17843). The following primer pair was used to amplify the BotB gene: 5'-CG <u>CCATGG</u>CTGATACAATACTAATAGAA ATG-3' [5' primer, engineered NcoI site underlined (SEQ ID NO:47)] and 5'-GC<u>AAGCTT</u>TTATTCAGTCCACCCTTCATC-3' [3' primer, engineered HindIII site underlined, native gene termination codon italicized (SEQ ID NO:48)]. After cloning into the pCRscript vector, the NheI(filled)/HindIII fragment was cloned into pETHisb vector as described for BotA C fragment gene in Example 28. The resulting construct was termed pHisBotB.

pHisBotB expresses the BotB gene sequences under the transcriptional control of the T7 lac promoter and the resulting protein contains an N-terminal 10×His-tag affinity tag. The pHisBotB expression construct was transformed into BL21(DE3) pLysS competent cells and 1 liter cultures were grown, induced and his-tagged proteins were purified utilizing a NiNTA resin (eluted in low pH elution buffer) as described in Example 28. Total, soluble and purified proteins were resolved by SDS-PAGE and detected by Coomassie staining and Western blot hybridization utilizing a chicken anti-*C. botulinum* serotype B toxoid primary antibody (generated by immunization of hens using *C. botulinum* serotype B toxoid as described in Example 3). Samples of BotA and BotE C fragment proteins were included on the gels for MW and immunogenicity comparisons. Strong immunoreactivity to only the BotB protein was detected with the anti-*C. botulinum* serotype B toxoid antibodies. The recombinant BotB protein was expressed at low levels (3 mg/liter) as a soluble protein. The purified BotB protein migrated as a single band of the predicted MW (i.e., ~50 kD).

These results demonstrate the cloning of the native *C. botulinum* serotype B C fragment gene, the expression and purification of the recombinant BotB protein as a soluble his-tagged protein in *E. coli.*

EXAMPLE 36

Generation of Neutralizing Antibodies Using the Recombinant pHisBotB Protein The ability of the purified pHisBot protein to generate neutralizing antibodies was examined. Nine BALBc mice were immunized with BotB protein (purified as described in Ex. 35) using Gerbu GMDP adjuvant (CC Biotech). The low pH elution was mixed with Gerbu adjuvant and used to immunize mice. Each mouse received a subcutaneous injection of 100 μl antigen/adjuvant mix (15 μg antigen+1 μg adjuvant) on day 0. Mice were subcutaneously boosted as above on day 14 and bled on day 28. Mice were subsequently boosted 1–2 weeks after bleeding and were then bled on day 70.

Anti-*C. botulinum* serotype B toxoid titers were determined in day 28 serum from individual mice from each group using the ELISA protocol outlined in Example 29 with the exception that the plates were coated with *C. botulinum* serotype B toxoid, and the primary antibody was a chicken anti-*C. botulinum* serotype B toxoid. Seroconversion [relative to control mice immunized with pHisBotE antigen (described below)] was observed with all 9 mice immunized with the purified pHisBotB protein.

The ability of the anti-BotB antibodies to neutralize native *C. botulinum* type B toxin was tested in a mouse-*C. botulinum* neutralization model using pooled mouse serum (see Ex. 23b). The $LD_{50}$ of purified *C. botulinum* type B toxin complex (Dr. Eric Johnson, University of Wisconsin, Madison) was determined by a intraperitoneal (IP) method [Schantz and Kautler (1978), supra] using 18–22 g female ICR mice. The amount of neutralizing antibodies present in the serum of the immunized mice was determined using serum antibody titrations. The various serum dilutions (0.01 ml) were mixed with 5 $LD_{50}$ units of *C. botulinum* type B toxin and the mixtures were injected IP into mice. The neutralizations were performed in duplicate. The mice were then observed for signs of botulism for 4 days. Undiluted serum (day 28 or day 70) was found to protect 100% of the injected mice while the 1:10 diluted serum did not. This corresponds to a neutralization titer of 0.05–0.5 IU/ml.

These results demonstrate that seroconversion occurred and neutralizing antibodies were induced when the pHisBotB protein was utilized as the immunogen.

EXAMPLE 37

Construction of Vectors to Facilitate Expression of His-Tagged BotB Protein in Fermentation Cultures A number of expression vectors were constructed to facilitate the expression of recombinant BotB protein in large scale fermentation culture. These constructs varied as to the strength of the promoter utilized (T7 or T71ac) and the presence of repressor elements (lacIq) on the plasmid. The resulting constructs varied in the level of expression achieved and in plasmid stability which facilitated the selection of an optimal expression system for fermentation scaleup.

The BotB expression vectors created for fermentation culture were engineered to utilize the kanamycin rather than the ampicillin resistance gene, and contained either the T7 or T7lac promoter, with or without the lacIq gene for the reasons outlined in Example 30.

In all cases, the protein expressed by the various expression vectors is the pHisBot B protein described in Example 35, with the only differences between clones being the alteration of various regulatory elements. Using the designations outlined below, the pHisBotB clone (Ex. 35) is equivalent to pHisBotB amp T7lac.

a) Construction of pHisBotB kan T7lac pHisBotB kan T7lac was constructed by insertion of the BglII/HindIII fragment of pHisBotB which contains the BotB gene sequences into the pPA 1870–2680 kan T7lac vector which had been digested with BglII and HindIII (the pPA1870–2680 kan T7lac vector contains the pET24 kan gene in the pET23 vector, such that no lacIq gene is present). Proper construction of pHisBotB kan T7lac was confirmed by restriction digestion.

b) Construction of pHisBotB kan lacIq T7lac pHisBotB kan lacIq T7lac was constructed by insertion of the BglII/HindIII fragment of pHisBotB which contains the BotB gene sequences into similarly cut pET24a vector. Proper construction of pHisBotB kan lacIq T7lac was confirmed by restriction digestion.

c) Construction of pHisBotB kan lacIq T7 pHisBotB kan lacIq T7 was constructed by inserting the NdeI/XhoI fragment from pHisBotE kan lacIq T7lac which contains the BotB gene sequences into similarly cleaved pPA 1870–2680 kan lacIq T7 vector (this vector contains the T7 promoter, the sane N-terminal his-tag as the Bot constructs, the *C. difficile* toxin A insert, and the kan lacIq genes; this cloning replaces the *C. difficile* toxin A insert with the BotB insert). Proper construction was confirmed by restriction digestion.

Expression of recombinant BotB protein from these expression vectors and purification of the BotB protein is described in Example 38 below.

EXAMPLE 38

Fermentation and Purification of Recombinant BotB Protein Utilizing the pHisBotB kan lacIq T7lac, pHisBotB kan T7lac and pHisBotB kan lacIq T7 Vectors The pHisBotB kan lacIq T7lac, pfHisBotB kan T7lac and BotB kan lacIq T7 constructs [all transformed into the B121(DE3) strain] were grown in fermentation cultures to determine the utility of the various constructs for large scale expression and purification of soluble BotB protein. All fermentations were performed as described in Example 31.

a) Fermentation of pHisBotB kan lacIq T7lac/B121(DE3) Cells

The fermentation culture was induced 45 min post start of glucose feed with 1 gm IPTG (final concentration=0.4 mM). pH was maintained at 6.5 rather than 7.0. The $OD_{600}$ was 27 at time of induction, then 35, 38, and 40 at 1–3 hrs post induction. Duplicate platings of diluted 1 hr induction samples (dilutions were prepared as described Ex. 31, dilution 3 utilized 3 μl of dilution 2 cells) on TSA and LB+kan plates yielded 89 TSA colonies and 81 kan colonies (90% kan resistant).

Total and soluble protein extracts were resolved on a 12.5% SDS-PAGE gel and total protein was detected by staining with Coomassie blue. Low level induction of insoluble Bot B protein was observed, increasing from 1 to 3 hrs post induction (no expression was detected in uninduced cells).

b) Fermentation Of pHisBotB kan T7lac/B121(DE3) Cells

The fermentation culture was induced 1 hr post start of glucose feed with 2 gm IPTG (final concentration=0.8 mM). pH was maintained at 6.5 rather than 7.0. The $OD_{600}$ was 24.5 at time of induction, then 31.5, 32, and 33 at 1–3 hrs post induction, respectively. Duplicate platings of diluted 0 hr and 2 hr induction samples (dilutions were prepared as described Ex. 31; dilution 3 utilized 3 μl of dilution 2 cells) on TSA and LB+kan plates yielded 32 TSA colonies and 54 kan colonies (all kan resistant) for uninduced cells, and 1 TSA colony and 0 kan colonies 2 hr post induction. These results were indicative of strong induction, since viable counts decreased dramatically 2 hrs post induction.

Total and soluble extracts were resolved on a 10% SDS-PAGE gel and total protein was detected by staining with Coomassie blue. Moderate induction of insoluble BotB protein was observed, increasing from 1 to 3 hrs post induction (no expression was detected in uninduced cells).

c) Fermentation of pHisBotB kan lacIq T7/B121(DE3) Cells

The fermentation was induced 2 hr post start of glucose feed with 4 gm IPTG (final concentration=1.6 mM). pH was maintained at 6.5 rather than 7.0. The $OD_{600}$ was 45 at time of induction, then 47, 50, and 50 and 55 at 1–4 hrs post induction, respectively. Viable colony counts decreased after induction (96, 1, 1, 2, 3; dilution 3 utilized 3 μl of dilution 2 cells). Of 63 colonies scored at the time of induction, all 63 retaining the BotB plasmid (kan resistant) and no colonies at induction grew on IPTG+Kan plates (no mutations detected).

Total and soluble extracts were resolved on a 12.5% SDS-PAGE gel and total protein was detected by staining with Coomassie blue. Moderate level induction of insoluble BotB protein was observed, increasing from 1 to 4 hrs post induction (lower level expression was detected in uninduced cells, since the T7 rather than T7lac promoter was utilized).

d) Purification of pHisBotB Protein from pHisBotB amp T7lac/B121(DE3) Cells

Figure 34:
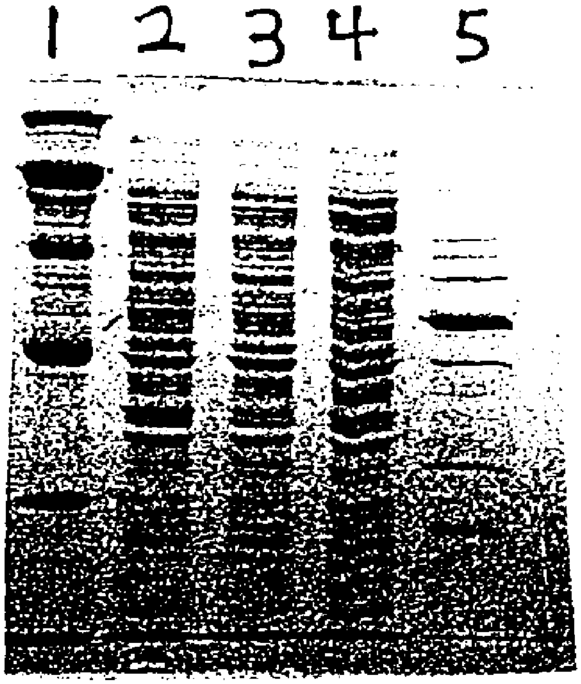
FIG. 34 is an SDS-PAGE gel stained with Coomaisse blue showing the extracts derived from pHisBotB amp T7lac/BL21(DE3) cells before and after purification on a Ni-NTA column.

Soluble recombinant BotB protein was purified utilizing NiNTA resin from 80 ml of cell lysate generated from cells harvested from a pHisBotB fermentation [using the pHisBotB amp T7lac/B121(DE3) strain]. As predicted from the small scale results above, the majority of the induced protein was insoluble. As well, the eluted material was contaminated with multiple *E. coli* contaminant proteins. A Coomassie blue-stained SDS-PAGE gel containing extracts derived from pHisBotB amp T7lac/B121(DE3) cells before and during purification is shown in FIG. 34. In FIG. 34, lane 1 contains broad range protein MW markers (BioRad). Lanes 2–5 contain extracts prepared from pHisBotB amp T7lac/B121(DE3) cells grown in fermentation culture; lane 2 contains total protein; lane 3 contains soluble protein; lane 4 contains protein which did not bind to the NiNTA column (i.e., the flow-through) and lane 5 contains protein eluted from the NiNTA column.

Similar results were obtained using a small scale IDA column utilizing a cell lysate from the pHisBotB kan lacIq T7 fermentation described above. 250 mls of a 20% w/v PEI clarified lysate (50 gms cell pellet) of botB kan lacIq T7/B121(DE3) cells were purified on a small scale IDA column. The total yield of eluted protein was 21 mg protein (assuming 1 mg/ml solution=2 $OD_{280}$/ml). When analyzed by SDS-PAGE and Coomassie staining, the BotB protein was found to comprise approximately 50% of the eluted protein with the remainder being a ladder of *E. coli* proteins similar to that observed with the NiNTA purification.

The NiNTA alkaline phosphatase conjugate was utilized to detect his-tagged proteins on a Western blot containing total, soluble, soluble (PEI clarified), soluble (after IDA column) and elution samples from the IDA column purification. The results demonstrated that a small percentage of BotB protein was soluble, that the soluble protein was not precipitated by PEI treatment and was quantitatively bound by the IDA column. Since a 1 liter fermentation harvest yielded a 67.5 gm cell pellet, this indicated that the yield of soluble affinity purified BotB protein from the IDA column was 14 mg/liter.

EXAMPLE 39

Co-Expression of Recombinant BotB Proteins and Folding Chaperones in Fermentation Cultures Fermentations were performed to determine if the simultaneous overexpression of folding chaperones (i.e., the Gro operon) and the BotB protein resulted in enhanced solubility of the BotB protein. This example involved fermentation of the pHisBotBkan lacIq T7lac/pACYCGro BL21(DE3), pHisBotB kan T7lac/pACYCGro B121(DE3) and pHisBotBkan lacIq T7/pACYCGro BL21(DE3) cell lines. Fermentation was carried out as described in Example 31; 34 μg/ml chloramphenicol was included in the feeder and fermentation cultures.

a) Fermentation of pHisBotBkan lacIq T7lac/pACYCGro BL21(DE3) Cells

Induction was with 4 gms IPTG at 1 hr 15 min post initiation of the glucose feed. The $OD_{600}$ was 38 at time of induction, then 50, 58.5, 62 and 68 at 1–4 hrs post induction. Viable colony counts decreased during induction (24, 0, 0, 2, 0 at 0–4 hr induction; dilution 3 utilized 3 μl of dilution 2 cells). Of 24 colonies scored at the time of induction, 24 retained the BotB plasmid (kan resistant), 24 contained the chaperone plasmid (chloramphenicol resistant) and no colonies at induction grew on IPTG+Kan plates (no mutations detected).

Total and soluble extracts were resolved on 12.5% SDS-PAGE gels and were either stained with Coomassie blue or subjected to Western blotting (his-tagged proteins were detected utilizing the NiNTA-alkaline phosphatase conjugate). This analysis revealed that the Gro chaperones were induced to high levels, but very low level expression of soluble BotB protein was observed, increasing from 1 to 4.0 hrs post induction (no expression detected in uninduced cells, induced protein detected only on Western blot). The dramatically lower expression of BotB protein in the presence of chaperone may be due to promoter occlusion (i.e., the stronger T7 promoter on the chaperone plasmid was preferentially utilized).

b) Fermentation of pHisBotB kan T7lac/pACYCGro/B121(DE3) Cells

Induction was with 4 gms IPTG at 1 hr post initiation of the glucose feed. The $OD_{600}$ was 33.5 at time of induction, then 44, 51, 58.5 and 69 at 1–4 hrs post induction. Viable colony counts decreased after 2 hrs induction (43, 65, 74, 0 (70), 0 (70) at 0–4 hr induction; bracketed numbers represent microcolonies; dilution 3 utilized 3 $\mu$l of dilution 2 cells). Most colonies at induction retained the BotB plasmid (kan resistant) and the chaperone plasmid (chloramphenicol resistant) and no colonies at induction grew on IPTG+Kan plates (no mutations detected).

Total and soluble extracts were resolved on a 12.5% SDS-PAGE gel and subjected to Western blotting; his-tagged proteins were detected utilizing the NiNTA-alkaline phosphatase conjugate. This analysis revealed that the Gro chaperones were induced to high levels and low level expression of soluble Bot B protein was observed, increasing from 1 to 4.0 hrs post induction (no expression detected in uninduced cells).

A small scale IDA purification of BotB protein from a 250 ml PEI clarified 15% w/v extract (37.5 gm cell pellet) yielded approximately 12.5 mg protein, of which approximately 50% was BotB protein and 50% was GroEL chaperone (assessed by Coomassie staining of a 10% SDS-PAGE gel). The NiNTA alkaline phosphatase conjugate was utilized to detect his-tagged proteins on a Western blot containing total, soluble, soluble (PEI clarified), soluble (after IDA column) and elution samples from the IDA column purification. The results demonstrated that all of the BotB protein produced by the pHisBotB kan T7lac/pACYCGro/B121(DE3) cells was soluble; the BotB protein was not precipitated by PEI treatment and was quantitatively bound by the IDA column. Since a 1 liter fermentation harvest yielded a 75 gm cell pellet, this indicated that the yield of soluble affinity purified BotB protein from this fermentation was 12.5 mg/liter. These results also demonstrated that additional purification steps are necessary to separate the chaperone proteins from the BotB protein.

c) Fermentation of pHisBotBkan lacIq T7/pACYCGro/BL21(DE3) Cells

Induction was with 4 gms IPTG at 2 hr post initiation of the glucose feed. The $OD_{600}$ was 46 at time of induction, then 56, 63, 69 and 71.5 at 1–4 hrs post induction. Viable colony counts decreased after induction (58, 3(5), 3, 0, 0 at 0–4 hr induction; bracketed numbers represent microcolonies; dilution 3 utilized 3 $\mu$l of dilution 2 cells). All (53/53) colonies scored at the time of induction retained the BotB plasmid (kan resistant) and the chaperone plasmid (chloramphenicol resistant) and no colonies at induction grew on IPTG+Kan plates (no mutations detected).

Total and soluble extracts were resolved on a 10% SDS-PAGE gels and Western blotted and his-tagged proteins were detected utilizing the NiNTA-alkaline phosphatase conjugate. This analysis revealed that the Gro chaperones were induced to high levels (observed by ponceau S staining), and a much higher expression of soluble BotB protein (compared to expression in the pHisBotB kan T7lac/pACYCGro fermentation) was observed at all timepoints, including uninduced cells (some increase in BotB protein levels were observed after induction).

A small scale IDA purification of BotB protein from a 100 ml PEI clarified 15% w/v extract (15 gm cell pellet) yielded approximately 40 mg protein, of which approximately 50% was BotB protein and 50% was GroEL chaperone, as assessed by Coomassie staining of a 10% SDS-PAGE gel. The NiNTA alkaline phosphatase conjugate was utilized to detect his-tagged proteins on a Western blot containing total, soluble, soluble (PEI clarified), soluble (after IDA column) and elution samples from the IDA column purification. The results demonstrated that a significant percentage (i.e., ~10–20%) of BotB protein was soluble, that the solubilized protein was not precipitated by PEI treatment and was quantitatively bound by the IDA column. Since a 10 liter fermentation yielded a 108 gm cell pellet, this indicated that the yield of soluble affinity purified BotB protein from this fermentation was 144 mg/liter.

In a scale up experiment, 2 liters of a 20% w/v PEI clarified lysate of pHisBotB kan lacIq T7/pACYCGro/BL21 (DE3) cells were purified on a large scale IDA column. The purification was performed in duplicate. The total yield of BotB protein was 220 and 325 mgs protein in the two experiments (assuming 1 mg/ml solution=2.0 $OD_{280}$/ml). This represents 0.7% or 1.0%, respectively, of the total soluble cellular protein (assuming a PEI lystate having a concentration of 8 mg protein/ml and that the eluted material comprises a 1:1 mixture of BotB and folding chaperone). The NiNTA alkaline phosphatase conjugate was utilized to detect his-tagged proteins on a Western blot containing total, soluble, soluble (PEI clarified), soluble (after IDA column) and elution samples from the IDA column purification. These results demonstrated that a significant percentage (i.e., ~10–20%) of the BotB protein was soluble, that the solubilized protein was not precipitated by PEI treatment and was quantitatively bound by the IDA column. Since a 1 liter fermentation harvest yielded a 108 gm cell pellet, this indicated that the yield of soluble affinity purified BotB protein from the large scale purification was 60 mg or 89 mg/liter. These results also demonstrated that further purification would be necessary to remove the contaminating chaperone protein.

The above results provide methodologies for the purification of soluble BotB protein from fermentation cultures, in a form contaminated predominantly with a single *E. coli* protein (the folding chaperone utilized to enhance solubility). In the next example, methods are provided for the removal of the contaminating chaperone protein.

EXAMPLE 40

Removal of Contaminating Folding Chaperone Protein From Purified Recombinant *C. botulinum* Type B Protein In this example size exclusion chromatography and ultrafiltration was used to purify recombinant BotB protein from the folding chaperones and imidazole in IDA-purified material.

Figure 35:
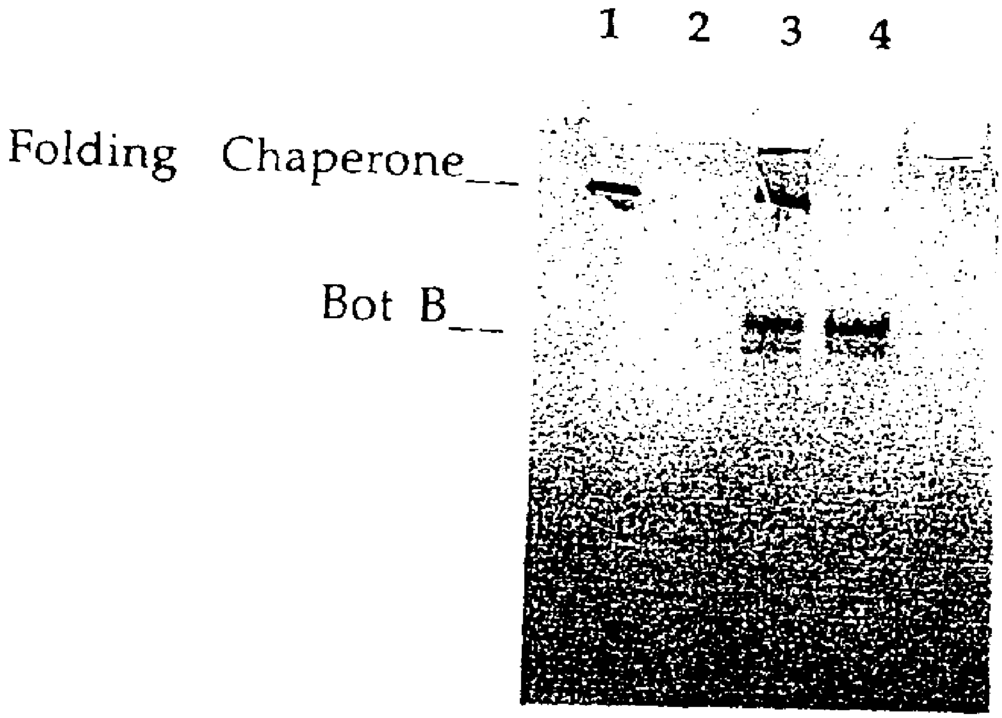
FIG. 35 is an SDS-PAGE gel run under native conditions and stained with Coomaisse blue showing the removal of folding chaperones from IDA-purified BotB protein using a S-100 column.

To enhance the solubility of the recombinant BotB protein during scale-up, the protein was co-expressed with folding chaperones (see Ex. 39). During the Ni-IDA purification step, the folding chaperones co-eluted with the BotB protein in 800 mM imidazole; therefore, a second purification step was required to isolate the BotB protein free of folding chaperones. Lane 3 of FIG. 35 contains proteins eluted from an IDA column to which a lysate of pHisBotB kan lacIq T7/pACYCGro/BL21(DE3) cells had been applied; the proteins were resolved on a 4–15% polyacrylamide pre-cast gradient gel (Bio-Rad, Hercules, Calif.) run under native conditions and then stained with Coomassie blue. In FIG. 35, lanes 1 and 4 contain proteins present in peak 1 and peak 2 from a Sephacryl S-100 column run as described below; lane 2 is blank.

As seen in lane 3 of FIG. 35, the IDA-purified sample consists primarily of the folding chaperones and the BotB protein. The fact that the chaperones and the BotB antigen appear as two distinct bands under native conditions suggested they were not complexed together and therefore, it should be possible to separate them, using either a gradient of imidazole concentrations or size exclusion methods.

In order to determine whether a gradient of imidazole concentrations could be used to separate the chaperone from the BotB protein, a step gradient using imidazole at 200, 400, 600, and 800 mM in 50 mM sodium phosphate, 0.5 M NaCl and 10% glycerol, pH 6.8 was applied to an IDA column (containing proteins bound from a lysate of pHis-BotB kan lacIq T7/pACYCGro/BL21(DE3) cells). By narrowing the range of imidazole concentrations, it was hoped that the BotB and chaperone proteins would differentially elute at different concentrations of imidazole. Eluted proteins were monitored by absorbance at 280 nm and collected either manually or with a fraction collector (BioRad). Protein was found to elute at 200 and 400 mM imidazole only.

Figure 36:
FIG. 36 is an SDS-PAGE gel stained with Coomaisse blue showing proteins that eluted during an imidazole step gradient applied to a IDA column containing a lysate of pHisBotB kan lacIq T7/pACYCGro/BL21(DE3) cells.

FIG. 36 shows a Coomassie stained SDS-PAGE gel containing protein eluted during the imidazole step gradient. Lane 1 contains broad range MW markers (BioRad). Lane 2 contains BotB protein purified by IDA chromatography of an extract of pHisBotB/BL21(DE3) pLysS cells grown in shaker flask culture (i.e., no co-expression of chaperones; Ex. 35). Lane 3 contains a 20% w/v PEI clarified lysate of pHisBotB kan lacIq T7/pACYCGro/BL21(DE3) cells (i.e., the lysate prior to purification by IDA chromatography). Lanes 4 and 5 contain protein which eluted at 200 or 400 mM imidazole, respectively. Lane 6 is blank. Lanes 7 and 8 contain ⅕ the load present in lanes 4 and 5.

As shown in FIG. 36, both the chaperone and the BotB protein eluted in 200 mM imidazole, and more chaperone elutes in 400 mM imidazole, however no concentration of imidazole tested permitted the elution of BotB protein alone. Consequently, no significant purification was achieved using imidazole at these concentrations.

Because of the considerable difference in molecular weights between the folding chaperone, which is a multimer with a total molecular weight around 400 kD (as determined on a Shodex KB 804 sizing column by HPLC), and the recombinant BotB protein (molecular weight around 50 kD), size exclusion chromatography was next examined for the ability to separate these proteins.

a) Size Exclusion Chromatography

A column containing Sephacryl S-100 HR(S-100) (Pharmacia) was poured (2.5 cm×24 cm; ~110 ml bed volume). The column was equilibrated in a buffer consisting of phosphate buffered saline (10 mM potassium phosphate, 150 mM NaCl, pH 7.2) and 10% glycerol (Mallinkrodt). Typically, 5 ml of the IDA-purified BotB protein was filtered through a 0.45 $\mu$l syringe filter and applied to the column, and the equilibration buffer was pumped through the column at a flow rate of 1 ml/minute. Eluted proteins were monitored by absorbance at 280 nm and collected either manually or with a fraction collector. Appropriate tubes were pooled, if necessary, and the protein was quantitated by absorbance at 280 nm and/or by BCA protein assay. The isolated peaks were then analyzed by native and/or SDS-PAGE to identify the protein and evaluate the purity.

Because of its larger size, the folding chaperone eluted first, followed by the recombinant BotB protein. A smaller third peak was observed which failed to stain when analyzed by SDS-PAGE and therefore was presumed to be imidazole.

SDS-PAGE analysis (12.5% polyacrylamide, reduced samples) was used to evaluate the purity of the IDA-purified recombinant BotB protein before and after S-100 purification. The results are shown in FIG. 33.

In FIG. 33, lane 1 contains broad range MW markers (BioRad). Lane 5 contains IDA-purified BotB protein. Lane 6 contains IDA-purified BotB protein following S-100 purification. Lane 7 is blank (lanes 24 were discussed in Ex. 34 above).

The results shown in FIG. 33 show that the IDA-purified BotB is significantly contaminated with the folding chaperone (molecular weight about 60 kD under reducing conditions; lane 6). Following S-100 purification, the amount of folding chaperone present in the BotB sample was reduced dramatically (lane 7). Visual inspection of the Coomassie stained SDS-PAGE gel revealed that after S-100 purification, >90% of the total protein present was BotB.

The IDA-purified BotB and the S-100-purified BotB samples were analyzed by HPLC on a size exclusion column (Shodex KB 804); this analysis revealed that the BotB protein represented 64% of the total protein in the IDA-purified sample and that following S-100 purification, the BotB protein represented >95% of the total protein in the sample.

The IDA-purified BotB material was also applied to a ACA 44 (SpectraPor, Houston, Tex.) column. The ACA 44 resin is equivalent to the S-100 resin and chromatography using the ACA 44 resin was carried out exactly as described above for the S-100 resin. The ACA 44 resin was found to separate the recombinant BotB protein from the folding chaperone. The ACA 44-purified BotB sample was analyzed for endotoxin using the LAL assay (Associates of Cape Cod) as describe in Example 24. Two aliqouts of the ACA 44-purified BotB preparation were analyzed and were found to contain either 58 to 116 EU/mg recombinant protein or 94 to 189 EU/mg recombinant protein.

These results demonstrate that size exclusion chromatography can be used to purify the recombinant BotB protein from the folding chaperone and imidazole in IDA-purified material.

b) Ultrafiltration for the Separation of Recombinant BotB Protein and Chaperones Ultrafiltration was examined as an alternative method for the separation recombinant BotB protein and folding chaperones in IDA-purified material. While in this example only mixtures of BotB and chaperones were separated by ultrafiltration, this technique is suitable for use with recombinant BotA and BotE proteins as well provided that the wash buffers used are altered as necessary to take into account different requirements for solubility.

The recombinant BotB protein and folding chaperones were separated using a two-step sequential ultrafiltration method. The first membrane used had a nominal molecular weight cutoff (MWCO) of approximately 100 kD; this membrane retains the larger folding chaperone while allowing the smaller recombinant protein to pass through. The addition of several volumes of wash buffer may be required to efficiently wash the recombinant protein through the membrane. The second step utilized a membrane with a nominal MWCO of approximately 10 kD. During this step, the recombinant antigen was retained by the membrane and could be concentrated to the degree desired and the imidazole and excess wash buffer passed through the membrane.

Twenty-seven milliliters of an IDA-purified BotB preparation was ultrafiltered through a 47 mm YM 100 (100 kD MWCO) membrane (Amicon) in a 50 ml stirred cell (Amicon). The membrane was washed in dd $H_2O$ prior to use as recommended by the manufacturer. Six volumes of 10% glycerol in PBS were washed through to remove most of the recombinant BotB protein and this wash was collected in a separate vessel. The resulting BotB protein-rich filtrate was then concentrated 12-fold using a YM 10 (10 kD MWCO) membrane (Amicon), to a final volume of 14 ml. The YM 100 and YM 10 concentrates were analyzed along with the lysate starting material by native PAGE using a 4–15% pre-cast gradient gel (BioRad). The results are shown in FIG. 37.

Figure 37:
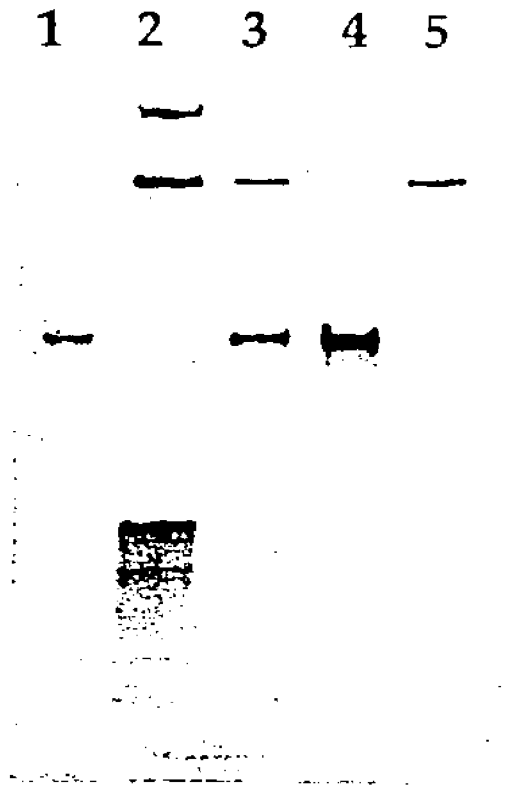
FIG. 37 is an SDS-PAGE gel run under native conditions and stained with Coomaisse blue showing IDA-purified BotB protein before and after ultrafiltration.

In FIG. 37, lane 1 contains IDA-purified BotB derived from a shaker flask culture (Le., no co-expression of chaperones; Ex. 35); lane 2 contains a 20% w/v PEI clarified lysate of pHisBotB kan lacIq T7/pACYCGro/BL21 (DE3) cells; lane 3 shows the lysate of lane 3 after IDA purification; lane 4 contains the YM 10 concentrate and lane 5 contains the YM 100 concentrate.

The results shown in FIG. 37 demonstrate that the recombinant BotB protein can be purified away from the folding chaperone by ultrafiltration through a 100 kD MWCO membrane (lane 4), leaving the chaperone protein in the 100 kD concentrate (lane 5). Analysis of the sample in lane 5 also showed that very little of the BotB protein was retained by the 100 kD MWCO membrane after 6 volumes of wash buffer had been applied.

The BotB samples following IDA chromatography and following ultrafiltration through the YM 100 membrane were anlyzed by HPLC on a size exclusion column (Shodex KB 804); this analysis revealed that the BotB protein represented 64% of the total protein in the IDA-purified sample and that following ultrafiltration through the YM 100 membrane, the BotB protein represented >96% of the total protein in the sample.

The BotB protein purified by ultrafiltration through the YM 100 membrane was examined for endotoxin using the LAL assay (Associates of Cape Cod) as described in Example 24. Two aliqouts of the YM 100-purified BotB preparation were analyzed and were found to contain either 18 to 36 EU/mg recombinant protein or 125 to 250 EU/mg recombinant protein.

The above results demonstrate that size exclusion chromatography and ultrafiltration can be used to purify recombinant botulinal toxin proteins away from folding chaperones.

EXAMPLE 41

Cloning and Expression of the C Fragment of the *C. botulinum* Serotype E Toxin Gene The *C. botulinum* type E neurotoxin gene has been cloned and sequenced from several different strains [Poulet et al. (1992) Biochem. Biophys. Res. Commun. 183:107 (strain Beluga); Whelan et al. (1992) Eur. J. Biochem. 204:657 (strain NCTC 11219); Fujii et al. (1990) Microbiol. Immunol. 34:1041 (partial sequence of strains Mashike, Iwani and Otaru) and Fujii et al. (1993) J. Gen. Microbiol. 139:79 (strain Mashike)]. The nucleotide sequence of the type E toxin gene is available from the EMBL sequence data bank under accession numbers X62089 (strain Beluga) and X62683 (strain NCTC 11219). The nucleotide sequence of the coding region (strain Beluga) is listed in SEQ ID NO:49. The amino acid sequence of the *C. botulinum* type E neurotoxin derived from strain Belgua is listed in SEQ ID NO:50. The nucleotide sequence of the coding region (strain NCTC 11219) is listed in SEQ ID NO:51. The amino acid sequence of the *C. botulinum* type E neurotoxin derived from strain NCTC 11219 is listed in SEQ ID NO:52.

The DNA sequence encoding the native *C. botulinum* serotype E C fragment gene derived from the Beluga strain can be expressed as a histidine-tagged protein using the pETHisb vector; the resulting coding region is listed in SEQ ID NO:53 and the corresponding amino acid sequence is listed in SEQ ID NO:54. The DNA sequence encoding the C fragment of the native *C. botulinum* serotype E gene derived from the NCTC 11219 strain can be expressed as a histidine-tagged fusion protein using the pETHisb vector; the resulting coding region is listed in SEQ ID NO:55 and the corresponding amino acid sequence is listed in SEQ ID NO:56. The C fragment region from any strain of *C .botulinum* serotype E can be amplified and expressed using the approach illustrated below using the C fragment derived from *C. botulinum* type E 2231 strain (ATCC #17786).

The type E neurotoxin gene is synthesized as a single polypeptide chain which may be converted to a double-chain form (i.e., a heavy chain and a light chain) by cleavage with trypsin; unlike the type A neurotoxin, the type E neurotoxin exists essentially only in the single-chain form. The 50 kD carboxy-terminal portion of the heavy chain is referred to as the C fragment or the $H_C$ domain. Expression of the C fragment of *C. botulinum* type E toxin in heterologous hosts (e.g., *E. coli* i) has not been previously reported.

The native C fragment of the *C. botulinum* serotype E toxin (BotE) gene was cloned and inserted into expression vectors to facilitate expression of the recombinant BotE protein in *E. coli*. This example involved PCR amplification of the gene, cloning, and construction of expression vectors.

The BotE serotype gene was isolated using PCR as described for the BotA serotype gene in Example 28. The *C. botulinum* type E strain was obtained from the American Type Culture Collection (ATCC #17786; strain 2231). The following primer pair was used in the PCR amplification: 5'-CGCCATGGCTCTTTCTTCTTAT ACAGATGAT-3' (5' primer, engineered NcoI site underlined) (SEQ ID NO:57) and 5'-GCAAGCTTTTATTTTTCTTGCCATCCATG-3' (3' primer, engineered HindIII site underlined, native gene termination codon italicized) (SEQ ID NO:58). The PCR product was inserted into pCRscript as described in Example 28. The resulting pCRscript BotE clone was confirmed by restriction digestion, as well as, by obtaining the sequence of approximately 300 bases located at the 5' end of the C fragment coding region using standard DNA sequencing methods. The resulting BotE sequence was identical to that of the published *C. botulinum* type E toxin sequence [Whelan et al (1992), supra].

The NheI(filled)/HindIII fragment from a pCRscript BotE recombinant was cloned into pETHisb vector as described for BotA C fragment in Example 28. The resulting construct was termed pHisBotE. pHisBotE expresses the BotE gene under the control of the T7 lac promoter and the resulting protein contains an N-terminal 10×His-tag affinity tag.

The pHisBotE expression construct was transformed into BL21(DE3) pLysS competent cells and 1 liter cultures were grown, induced and his-tagged proteins were purified utilizing a NiNTA resin (eluted in low pH elution buffer) as described in Example 28. Total, soluble and purified proteins were resolved by SDS-PAGE and detected by Coomassie staining. The results are shown in FIG. 38.

Figure 38:
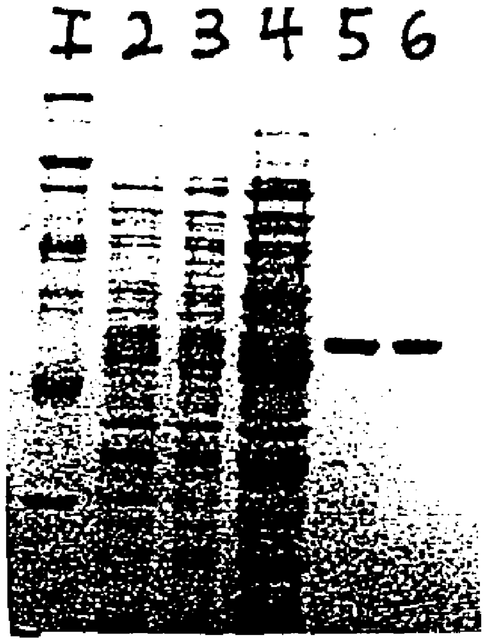
FIG. 38 is an SDS-PAGE gel stained with Coomaisse blue showing the purification of BotE protein using a NiNTA column.

In FIG. 38, lane 1 contains broad range MW markers (BioRad); lane 2 contains a total protein extract; lane 3 contains a soluble protein extract; lane 4 contains proteins present in the flow through from the NiNTA column (this sample was not diluted prior to loading and therefore represents a load 5× that of the load applied for the total and soluble extracts in lanes 2 and 3); lane 5 contains proteins eluted from the NiNTA column; lane 6 contains protein eluted from a NiNTA column which had been stored at −20° C. for 1 year.

The pHisBotE protein was expressed at moderate levels (7 mg/liter) as a totally soluble protein. The purified protein migrated as a single band of the predicted MW.

Western blot hybridization utilizing a chicken anti-*C. botulinum* serotype E toxoid primary antibody (generated by immunization of hens as described in Example 3 using *C. botulinum* serotype E toxoid) was also performed on the total, soluble and purified BotE proteins. Samples of BotA and BotB C fragments were also included on the gels to facilitate MW and immunogenicity comparisons. Strong immunoreactivity was detected using the anti-*C. botulinum* type E toxoid antibody only with the BotE protein.

These results demonstrate that the native BotE gene sequences can be expressed as a soluble his-tagged protein in *E. coli* and purified by metal-chelation affinity chromatography.

EXAMPLE 42

Generation of Neutralizing Antibodies Using the Recombinant pHisBotE Protein The ability of the purified pHisBotE protein to generate neutralizing antibodies was examined. Nine BALBc mice were immunized with BotE protein (purified as described in Ex. 41) using Gerbu GMDP adjuvant (CC Biotech). The low pH elution was mixed with Gerbu adjuvant and used to immunize mice. Each mouse received a subcutaneous injection of 100 $\mu$l antigen/adjuvant mix (35 $\mu$g antigen+1 $\mu$g adjuvant) on day 0. Mice were subcutaneously boosted as above on day 14 and bled on day 28. Mice were subsequently boosted and bled on day 70.

Anti-*C. botulinum* serotype E toxoid titers were determined in day 28 serum from individual mice from each group using the ELISA protocol outlined in Example 29 with the exception that the plates were coated with *C. botulinum* serotype E toxoid, and the primary antibody was a chicken anti-*C. botulinum* serotype E toxoid. Seroconversion [relative to control mice immunized with the p6xHisBotA antigen (Ex. 29)] was observed with all 9 mice immunized with the purified pHisBotE protein.

The ability of the anti-BotE antibodies to neutralize native *C. botulinum* type E toxin was tested in a mouse-*C. botulinum* neutralization model using pooled mouse serum (see Ex. 23b). The $LD_{50}$ of purified *C. botulinum* type E toxin complex (Dr. Eric Johnson, University of Wisconsin, Madison) was determined by a intraperitoneal (IP) method [Schantz and Kautler (1978), supra] using 18–22 g female ICR mice. The amount of neutralizing antibodies present in the serum of the immunized mice was determined using serum antibody titrations. The various serum dilutions (0.01 ml) were mixed with 5 $LD_{50}$ units of *C. botulinum* type E toxin and the mixtures were injected IP into mice. The neutralizations were performed in duplicate. The mice were then observed for signs of botulism for 4 days. Undiluted serum from day 28 did not protect, while undiluted, 1/10 diluted and 1/100 diluted day 70 serum protected (1005 of animals) while 1/1000 diluted day 70 serum did not. This corresponds to a neutralization titer of 50–500 IU/ml.

These results demonstrate that seroconversion occurred and neutralizing antibodies were induced when the recombinant BotE protein was utilized as the immunogen.

EXAMPLE 43

Construction of Vectors To Facilitate Expression of His-Tagged BotE Protein in Fermentation Cultures A number of expression vectors were constructed to facilitate the expression of recombinant BotE protein in large scale fermentation culture. These constructs varied as to the strength of the promoter utilized (T7 or T7lac) and the presence of repressor elements (lacIq) on the plasmid. The resulting constructs varied in the level of expression achieved and in plasmid stability which facilitated the selection of an optimal expression system for fermentation scaleup. This example involved a) construction of BotE expression vectors and b) determination of expression levels in small scale cultures.

a) Construction of BotE Expression Vectors

The BotE expression vectors created for fermentation culture were engineered to utilize the kanamycin rather than the ampicillin resistance gene, and contained either the T7 or T7lac promoter, with or without the lacIq gene for the reasons outlined in Example 30.

In all cases, the protein expressed by the various expression vectors is the pHisBotE protein described in Example 41, with the only differences between clones being the alteration of various regulatory elements. Using the designations outlined below, the pHisBotE clone (Ex. 41) is equivalent to pHisBotE amp T7lac.

i) Construction of pHisBotE kan lacIq T7lac pHisBotE kan lacIq T7lac was constructed by inserting the XbaI/HindIII fragment of pHisBotE which contains the BotE gene sequences into XbaI/HindIII-cleaved pET24a vector. Proper construction was confirmed by restriction digestion.

ii) Construction of pHisBotE kan T7 pHisBotE kan T7 was constructed by ligating the BotE-containing XbaI/SapI fragment of pHisBotE kan lacIq T7lac to the T7 promoter-containing XbaI/SapI fragment of pET23a. Proper construction was confirmed by restriction digestion.

iii) Construction of pHisBotE kan lacIqT7 pHisBotE kan lacIqT7 was constructed by inserting the BglII/HindIII fragment from pHisBotE kan T7 which contains the BotE gene sequences into BglII/HindIII-cleaved pET24 vector. Proper construction was confirmed by restriction digestion.

b) Determination of BotE Expression Levels in Small Scale Cultures

The three BotE kan expression vectors described above were transformed into B121(DE3) competent cells and 50 ml (2XYT+40 $\mu$g/ml kan) cultures were grown and induced with ITPG as described in Example 28. Total and soluble protein extracts from before and after induction made as described in Example 28. The total and soluble extracts were resolved on a 12.5% SDS-PAGE gel, and his-tagged proteins were detected on a Western blot utilizing the NiNTA-alkaline phosphatase conjugate as described in Example 31(c)(iii). The results showed that all three BotE cell lines expressed his-tagged proteins of the predicted MW for the BotE protein upon induction. The results also demonstrated that the two constructs that contained the T7 promoter expressed the BotE protein before induction, while the T7lac promoter construct did not. Upon induction, the T7 promoter-containing constructs induced to higher levels than the T71α-containing construct, with the pHisBotE kan lacIqT7/B1121(DE3) cells accumulating the maximal levels of BotE protein.

EXAMPLE 44

Expression and Purification of pHisBotE from Fermentation Cultures

Based on the small scale inductions performed in Example 43, the pHisBotE kan lacIq T7/B121(DE3) strain was selected for fermentation scaleup. This example involved the fermentation and purification of recombinant BotE C fragment protein.

A fermentation with the pHisBotE kan lacIq T7/B121 (DE3) strain was performed as described in Example 31. The fermentation culture was induced 2 hrs post start of the glucose feed with 4 gm IPTG (final concentration=1.6 mM). The $OD_{600}$ was 42 at time of induction, then 46.5, 48, 53 and 54 at 1–4 hrs post induction. Viable colony counts decreased from 0–4 hr induction [131, 4 (28), 7 (3), 7, 8; dilution 3 utilized 6 $\mu$l of dilution 2 cells; bracketed colonies are microcolonies]. All (32/32) colonies scored at the time of induction retained the BotE plasmid (kan resistant) and no colonies at induction grew on IPTG+Kan plates (no mutations detected). These results were indicative of strong promoter induction, since colony viability reduced after induction, and the culture stopped growing during fermentation (stopped at 54 $OD_{600}$/ml).

Total and soluble extracts were resolved on a 12.5% SDS-PAGE gel and total protein was detected by staining with Coomassie blue. The results are shown in FIG. 39.

Figure 39:
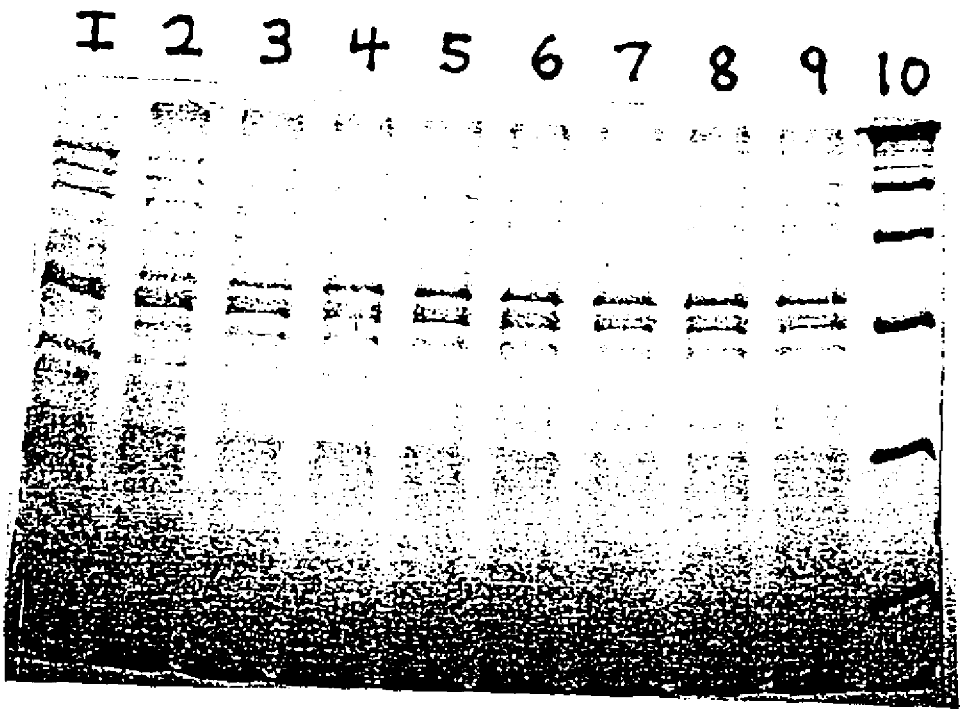
FIG. 39 is an SDS-PAGE gel stained with Coomaisse blue showing extracts derived from pHisBotA kan T7 lac/BL21 (DE3) pLysS cells grown in fermentation culture.

In FIG. 39, lane 1 contains total protein from a pHisBotA kan T7 lac/B121(DE3) pLysS fermentation (Ex. 24). Lanes 2–9 contain extracts prepared from the above pHisBotE kan lacIq T7/B121(DE3) fermentation; lanes 2–4 contain total protein extracts prepared at 0, 1 and 2 hours post-induction, respectively. Lane 5 contains a soluble protein extract prepared at 2 hours post-induction. Lanes 6 and 7 contain total and soluble extracts prepared at 3 hours post-induction, respectively. Lanes 8 and 9 contain total and soluble extracts prepared at 4 hours post-induction, respectively. Lane 10 contains broad range MW markers (BiORad).

The results shown in FIG. 39 demonstrate that moderate level induction of totally soluble Bot E protein was observed, increasing from 1 to 4 hrs post induction (no expression was detected in uninduced cells). From a 2 liter fermentation harvest a 155 gm (wet wt) cell pellet was obtained and used to make a PEI-clarified lysate (1 liter in CRB, pH 6.8). The lysate was applied to a large scale IDA column and 200 mg of BotE protein, which was found to be greater than 95% pure (as judged by visual inspection of a Coomassie stained SDS-PAGE gel), was recovered. This represents 2.5% of the total soluble cellular protein (assuming a PEI lysate having a concentration of 8 mg protein/ml) and corresponds to a yield of 100 mg BotE protein/liter of fermentation culture.

The above results demonstrate that high levels of the recombinant BotE protein can be expressed and purified from fermentation cultures.

EXAMPLE 45

Removal of Imidazole from Purified Recombinant BotE Protein Preparations

The expression of recombinant BotE protein, unlike the BotA and BotB proteins, did not require the presence of folding chaperones to maintain solubility during scale-up. A size exclusion chromatography step was included however to remove the imidazole from the sample and exchange the IDA elution buffer for one consistent with the BotA antigen.

A Sephacryl S-100 HR(S-100; Pharmacia) column was poured (2.5 cm×24 cm; bed volume ~110 ml). Under these conditions, the BotE protein should be retained by the beads to a lesser degree than the smaller imidazole, therefore the BotE protein should elute from the column before the imidazole. The column was equilibrated in a buffer consisting of 50 mM sodium phosphate, 0.5 M NaCl, and 10% glycerol (all reagents from Mallinkrodt). Five milliliters of the IDA-purified BotE protein (Ex. 44) was filtered through a 0.45% syringe filter and applied to the S-100 column, and equilibration buffer was pumped through the column at a flow rate of 1 ml/minute. Eluted proteins were monitored by absorbance at 280 nm, and collected either manually or with a fraction collector. Appropriate tubes were pooled if necessary, and the protein was quantitated by absorbance at 280 nm and/or BCA protein assay. The isolated peaks were then analyzed by native and/or SDS-PAGE to identify the protein(s) and evaluate the purity.

Figure 40:
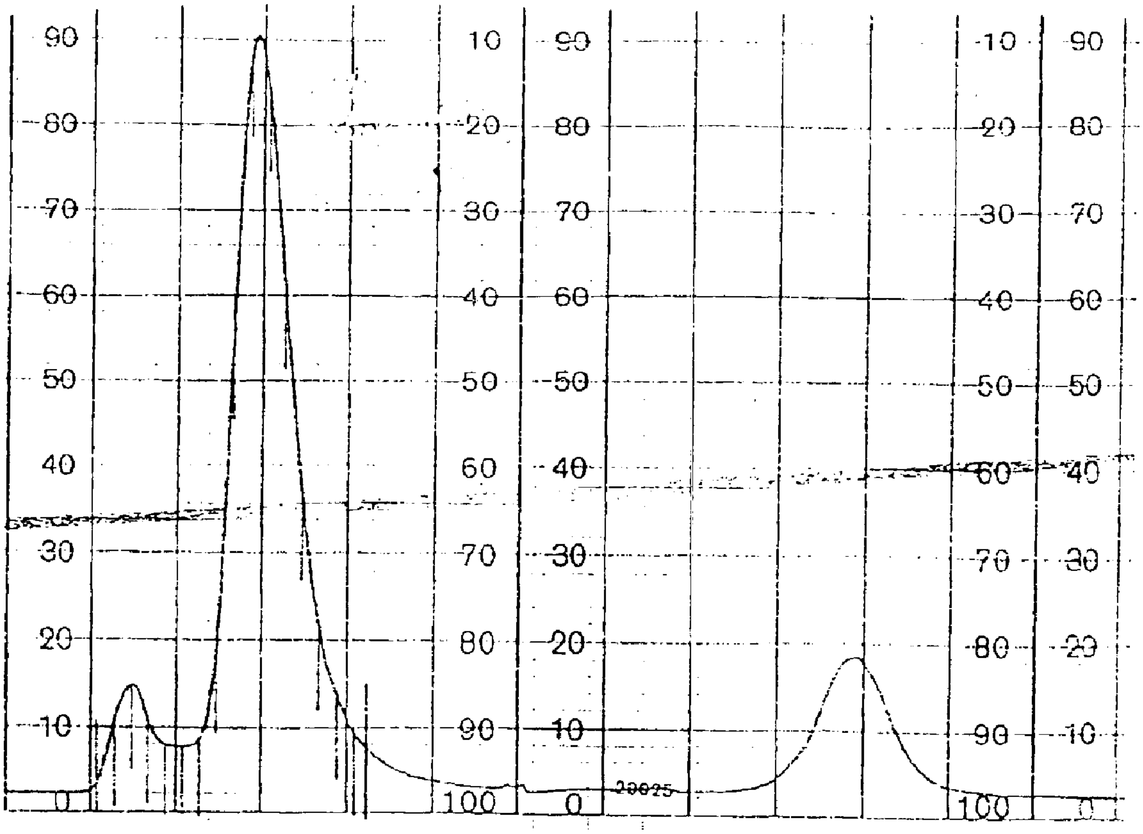
FIG. 40 is a chromatogram showing proteins present after IDA-purified BotE protein was applied to a S-100 column.

FIG. 40 provides a representative chromatogram showing the purification of IDA-purified BotE on the S-100 column. Even though folding chaperones were not over-expressed with this antigen, a small amount of protein eluted at a time consistent with the folding chaperones expressed with BotA and BotB proteins (Gro) (see the first peak). The second peak in the chromatogram contained the BotE protein, and the third peak was presumably imidazole. This presumed imidazole peak was isolated in comparable levels in IDA-purified BotA and BotB protein preparations as well.

These results demonstrate that size exclusion chromatography can be used to remove imidazole and traces of contaminating high molecular weight proteins from IDA-purified BotE protein preparations.

The S-100-purified BotE protein was tested for endotoxin contamination using the LAL assay as described in Example 24. This preparation was found to contain 64 to 128 EU/mg recombinant protein and is therefore substantially free of endotoxin.

The S-100 purified BotE was mixed with purified preparations of BotA and BotB proteins and used to immunize mice; 5 $\mu$g of each Bot protein was used per immunization and alum was included as an adjuvant. After two immunizations with this trivalent vaccine, the immunized mice were challenged with *C. botulinum* toxin. The immunized mice contained neutralizing antibodies sufficient to neutralize between 100,000 to 1,000,000 $LD_{50}$ of either toxin A or toxin B and between 1,000 to 10,000 $LD_{50}$ of toxin E. The titer of neutralizing antibodies directed against toxin E would be expected to increase following subsequent boosts with the vaccine. These results demonstrate that a trivalent vaccine containing recombinant BotA, BotB and BotE proteins provokes neutralizing antibodies.

EXAMPLE 46

Expression of the C Fragment of the *C. botulinum* Serotype C Toxin Gene and Generation of Neutralizing Antibodies The *C. botulinum* type C1 neurotoxin gene has been cloned and sequenced [Kimura et al. (1990) Biochem. Biophys. Res. Comm. 171:1304]. The nucleotide sequence of the toxin gene derived from the *C. botulinum* type C strain C-Stockholm is available from the EMBL/GenBank sequence data banks under the accession number D90210; the nucleotide sequence of the coding region is listed in SEQ ID NO:59. The amino acid sequence of the *C. botulinum* type C1 neurotoxin derived from this strain is listed in SEQ ID NO:60.

The DNA sequence encoding the native *C. botulinum* serotype $C_1$-C fragment gene derived from the C-Stockholm strain can be expressed using the pETHisb vector; the resulting coding region is listed in SEQ ID NO:61 and the corresponding amino acid sequence is listed in SEQ ID NO:62. The C fragment region from any strain of *C. botulinum* serotype C can be amplified and expressed using the approach illustrated below using the C fragment derived from *C. botulinum* type C C-Stockholm strain. Expression of the C fragment of *C. botulinum* type C1 toxin in heterologous hosts (e.g., *E. coli*) has not been previously reported.

The C fragment of the *C. botulinum* serotype C1 (BotC1) toxin gene is cloned using the protocols and conditions described in Example 28 for the isolation of the native BotA gene. A number of *C. botulinum* serotype C strains (expressing either or both C1 and C2 toxin) are available from the ATCC [e.g., 2220 (ATCC 17782), 2239 (ATCC 17783), 2223 (ATCC 17784; a type C-βstrain; C-βstrains produce C2 toxin), 662 (ATCC 17849; a type C-α strain; C-α strains produce mainly C1 toxin and a small amount of C2 toxin), 2021 (ATCC 17850; a type C-α strain) and VPI 3803 (ATCC 25766)]. Alternatively, other type C strains may be employed for the isolation of sequences encoding the C fragment of *C. botulinum* serotype C toxin.

The following primer pair is used to amplify the BotC gene: 5'-CGCCATGGC TTTATTAAAAGATATAATTAATG-3' [5' primer, engineered NcoI site underlined (SEQ ID NO:63)] and 5'-GC AAGCTTTTATTCACTTACAGGTAC AAAACC-3' [3' primer, engineered HindIII site underlined, native gene termination codon italicized (SEQ ID NO:64)]. Following PCR amplification, the PCR product is inserted into the pCRscript vector and then the 1.5 kb fragment is cloned into pETHisb vector as described for BotA C fragment gene in Example 28. The resulting construct is termed pHisBotC. Proper construction is confirmed by DNA sequencing of the BotC sequences contained within pHisBotC.

pHisBotC expresses the BotC gene sequences under the transcriptional control of the T7 lac promoter and the resulting protein contains an N-terminal 10×His-tag affinity tag. The pHisBotC expression construct is transformed into BL21(DE3) pLysS competent cells and 1 liter cultures are grown, induced and his-tagged proteins are purified utilizing a NiNTA resin (eluted in 250 mM imidazole, 20% glycerol) as described in Example 28. Total, soluble and purified proteins are resolved by SDS-PAGE and detected by Coomassie staining and Western blot hybridization utilizing a Ni-NTA-alkaline phosphatase conjugate (Qiagen) which recognizes his-tagged proteins as described in Example 31(c)(iii). This analysis permits the determination of expression levels of the pHisBotC protein (i.e., number of mg/liter expressed as a soluble protein). The purified BotC protein will migrate as a single band of the predicted MW (i.e., ~50 kD).

The level of expression of the pHisBotC protein may be modified (increased) by substitution of the T7 promoter for the T7lac promoter, or by inclusion of the lacIq gene on the expression plasmid, and plasmid expressed in BL21(DE3) cell lines in fermentation cultures as described in Example 30. If only very low levels (i.e., less than 0.5%) of soluble pHisBotC protein are expressed using the above expression systems, the pHisBotC construct may be co-expressed with pACYCGro construct as described in Example 32. In this case, the recombinant BotC protein may co-purify with the folding chaperones. The contaminating chaperones may be removed as described in Example 34. Preparations of purified pHisBotC protein are tested for endotoxin contamination using the LAL assay as described in Example 24.

The purifed pHisBotC protein is used to generate neutralizing antibodies. BALBc mice are immunized with the BotC protein using Gerbu GMDP adjuvant (CC Biotech) as described in Example 36. The ability of the anti-BotC antibodies to neutralize native *C. botulinum* type C toxin is demonstrated using the mouse-*C. botulinum* neutralization model described in Example 36.

EXAMPLE 47

Expression of the C Fragment of the *C. botulinum* Serotype D Toxin Gene And Generation of Neutralizing Antibodies The *C. botulinum* type D neurotoxin gene has been cloned and sequenced [Sunagawa et al. (1992) J. Vet. Med. Sci. 54:905 and Binz et al. (1990) Nucleic Acids Res. 18:5556]. The nucleotide sequence of the toxin gene derived from the CB16 strain is available from the EMBL/GenBank sequence data banks under the accession number S49407; the nucleotide sequence of the coding region is listed in SEQ ID NO:65. The amino acid sequence of the *C. botulinum* type D neurotoxin derived from the CB16 strain is listed in SEQ ID NO:66.

The DNA sequence encoding the native *C. botulinum* serotype D C fragment gene derived from a BotD expressing strain can be expressed using the pETHisb vector; the resulting coding region is listed in SEQ ID NO:67 and the corresponding amino acid sequence is listed in SEQ ID NO:68. The C fragment region from any strain of *C. botulinum* serotype D can be amplified and expressed using the approach illustrated below using the C fragment derived from *C. botulinum* type D CB16 strain. Expression of the C fragment of *C. botulinum* type D toxin in heterologous hosts (e.g., *E. coli*) has not been previously reported.

The C fragment of the *C. botulinum* serotype D (BotD) toxin gene is cloned using the protocols and conditions described in Example 28 for the isolation of the native BotA gene. A number of *C. botulinum* type D strains are available from the ATCC [e.g., ATCC 9633, 2023 (ATCC 17851), and VPI 5995 (ATCC 27517)].

The following primer pair is used to amplify the BotD gene: 5'-CGCCATGGC TTTATTAAAAGATATAATTAATG-3' [5' primer, engineered NcoI site underlined (SEQ ID NO:63)] and 5'-GC AAGCTTTTACTCTACCCATCCTGGATCCCT-3' [3' primer, engineered HindIII site underlined, native gene termination codon italicized (SEQ ID NO:69)]. Following PCR amplification, the PCR product is inserted into the pCRscript vector and then the 1.5 kb fragment is cloned into pETHisb vector as described for BotA C fragment gene in Example 28. The resulting construct is termed pHisBotD.

pHisBotD expresses the BotD gene sequences under the transcriptional control of the T7 lac promoter and the resulting protein contains an N-terminal 10×His-tag affinity tag. The pHisBotD expression construct is transformed into BL21(DE3) pLysS competent cells and 1 liter cultures are grown, induced and his-tagged proteins are purified utilizing a NiNTA resin as described in Example 28. Total, soluble and purified proteins are resolved by SDS-PAGE and detected by Coomassie staining and Western blot hybridization utilizing a Ni-NTA-alkaline phosphatase conjugate (Qiagen) which recognizes his-tagged proteins as described in Example 31(c)(iii). This analysis permits the determination of expression levels of the pHisBotD protein (i.e., number of mg/liter expressed as a soluble protein). The purified BotD protein will migrate as a single band of the predicted MW (i.e., ~50 kD).

The level of expression of the pHisBotD protein may be modified (increased) by substitution of the T7 promoter for the T7lac promoter, or by inclusion of the lacIq gene on the expression plasmid, and plasmid expressed in BL21(DE3) cell lines in fermentation cultures as described in Example 30. If only very low levels (ie., less than about 0.5%) of soluble pHisBotD protein are expressed using the above expression systems, the pHisBotD construct may be co-expressed with pACYCGro construct as described in Example 32. In this case, the recombinant BotD protein may co-purify with the folding chaperones. The contaminating chaperones may be removed as described in Example 34. Preparations of purified pHisBotD protein are tested for endotoxin contamination using the LAL assay as described in Example 24.

The purifed pHisBotD protein is used to generate neutralizing antibodies. BALBc mice are immunized with the BotD protein using Gerbu GMDP adjuvant (CC Biotech) as described in Example 36. The ability of the anti-BotD antibodies to neutralize native *C. botulinum* type D toxin is demonstrated using the mouse-*C. botulinum* neutralization model described in Example 36.

EXAMPLE 48

Expression of the C Fragment of the *C. botulinum* Serotype F Toxin Gene and Generation of Neutralizing Antibodies The *C. botulinum* type F neurotoxin gene has been cloned and sequenced [East et al. (1992) FEMS Microbiol. Lett. 96:225]. The nucleotide sequence of the toxin gene derived from the 202F strain (ATCC 23387) is available from the EMBL/GenBank sequence data banks under the accession number M92906; the nucleotide sequence of the coding region is listed in SEQ ID NO:70. The amino acid sequence of the *C. botulinum* type F neurotoxin derived from the 202F strain is listed in SEQ ID NO:71.

The DNA sequence encoding the native *C. botulinum* serotype F C fragment gene derived from the 202F strain can be expressed using the pETHisb vector; the resulting coding region is listed in SEQ ID NO:72 and the corresponding amino acid sequence is listed in SEQ ID NO:73. The C fragment region from any strain of *C. botulinum* serotype F can be amplified and expressed using the approach illustrated below using the C fragment derived from *C. botulinum* type F 202F strain. Expression of the C fragment of *C. botulinum* type F toxin in heterologous hosts (e.g., *E. coli*) has not been previously reported.

The C fragment of the *C. botulinum* serotype F (BotF) toxin gene is cloned using the protocols and conditions described in Example 28 for the isolation of the native BotA gene. The *C. botulinum* type F 202F strain is obtained from the American Type Culture Collection (ATCC 23387). Alternatively, sequences encoding the BotF toxin may be isolated from any BotF expressing strain [e.g., VPI 4404 (ATCC 25764), VPI 2382 (ATCC 27321) and Langeland (ATCC 35415)].

The following primer pair is used to amplify the BotF gene: 5'-CGCCATGGC TATTCTAATTATATATTTTAATAG-3' [5' primer, engineered NcoI site underlined (SEQ ID NO:74)] and 5'-GC AAGCTTTCATTCTTTCCATCCATTCTC-3' [3' primer, engineered HindIII site underlined, native gene termination codon italicized (SEQ ID NO:75)]. Following PCR amplification, the PCR product is inserted into the pCRscript vector and then the 1.5 kb fragment is cloned into pETHisb vector as described for BotA C fragment gene in Example 28. The resulting construct is termed pHisBotF.

pHisBotF expresses the BotF gene sequences under the transcriptional control of the T7 lac promoter and the resulting protein contains an N-terminal 10×His-tag affinity tag. The pHisBotF expression construct is transformed into BL21(DE3) pLysS competent cells and 1 liter cultures are grown, induced and his-tagged proteins are purified utilizing a NiNTA resin as described in Example 28. Total, soluble and purified proteins are resolved by SDS-PAGE and detected by Coomassie staining and Western blot hybridization utilizing a Ni-NTA-alkaline phosphatase conjugate (Qiagen) which recognizes his-tagged proteins as described in Example 31 (c)(iii). This analysis permits the determination of expression levels of the pHisBotF protein (i.e., number of mg/liter expressed as a soluble protein). The purified BotF protein will migrate as a single band of the predicted MW (i.e., ~50 kD).

The level of expression of the pHisBotF protein may be modified (increased) by substitution of the T7 promoter for the T7lac promoter, or by inclusion of the lacIq gene on the expression plasmid, and plasmid expressed in BL21(DE3) cell lines in fermentation cultures as described in Example 30. If only very low levels (i.e., less than about 0.5%) of soluble pHisBotF protein are expressed using the above expression systems, the pHisBotF construct may be co-expressed with pACYCGro construct as described in Example 32. In this case, the recombinant BotF protein may co-purify with the folding chaperones. The contaminating chaperones may be removed as described in Example 34. Preparations of purified pHisBotF protein are tested for endotoxin contamination using the LAL assay as described in Example 24.

The purifed pHisBotF protein is used to generate neutralizing antibodies. BALBc mice are immunized with the BotF protein using Gerbu GMDP adjuvant (CC Biotech) as described in Example 36. The ability of the anti-BotF antibodies to neutralize native *C. botulinum* type F toxin is demonstrated using the mouse-*C. botulinum* neutralization model described in Example 36.

EXAMPLE 49

Expression of the C Fragment of the *C. botulinum* Serotype G Toxin Gene and Generation of Neutralizing Antibodies The *C. botulinum* type G neurotoxin gene has been cloned and sequenced [Campbell et al. (1993) Biochimica et Biophysica Acta 1216:487 and Binz et al. (1990) Nucleic Acids Res. 18:5556]. The nucleotide sequence of the toxin gene derived from the 113/30 strain (NCFB 3012) is available from the EMBL/GenBank sequence data banks under the accession number X74162; the nucleotide sequence of the coding region is listed in SEQ ID NO:76. The amino acid sequence of the *C. botulinum* type G neurotoxin derived from this strain is listed in SEQ ID NO:77.

The DNA sequence encoding the native *C. botulinum* serotype G C fragment gene derived from the 113/30 strain can be expressed using the pETHisb vector; the resulting coding region is listed in SEQ ID NO:78 and the corresponding amino acid sequence is listed in SEQ ID NO:79. The C fragment region from any strain of *C. botulinum* serotype G can be amplified and expressed using the approach illustrated below using the C fragment derived from *C. botulinum* type G 113/30 strain. Expression of the C fragment of *C .botulinum* type G toxin in heterologous hosts (e.g., *E. coli*) has not been previously reported.

The C fragment of the *C. botulinum* serotype G (BotG) toxin gene is cloned using the protocols and conditions described in Example 28 for the isolation of the native BotA gene. The *C. botulinum* type G 113/30 strain is obtained from the NCFB. The following primer pair is used to amplify the BotG gene: 5'-CGCCATGGCTGACACAATTTTAATACA AGT-3' [5' primer, engineered NcoI site underlined (SEQ ID NO:80)] and 5'-GC CTCGAGTTATTCTGTCCATCCTTCATCCAC-3' [3' primer, engineered XhoI site underlined, native gene termination codon italicized (SEQ ID NO:81)]. Following PCR amplification, the PCR product is inserted into the pCRscript vector and then the 1.5 kb fragment is cloned into pETHisb vector as described for BotA C fragment gene in Example 28 with the exception that the sequences encoding BotG are excised from the pCRscript vector by digestion with NcoI and XhoI and the NcoI site is blunted (the BotG sequences contain an internal HindIII site). This NcoI(filled)/XhoI fragment is then ligated to the pETHisb vector which has been digested with NheI and SalI and the NheI site is blunted. The resulting construct is termed pHisBotG.

pHisBotG expresses the BotG gene sequences under the transcriptional control of the T7 lac promoter and the resulting protein contains an N-terminal 10×His-tag affinity tag. The pHisBotG expression construct is transformed into BL21(DE3) pLysS competent cells and 1 liter cultures are grown, induced and his-tagged proteins are purified utilizing a NiNTA resin as described in Example 28. Total, soluble and purified proteins are resolved by SDS-PAGE and detected by Coomassie staining and Western blot hybridization utilizing a Ni-NTA-alkaline phosphatase conjugate (Qiagen) which recognizes his-tagged proteins as described in Example 31(c)(iii). This analysis permits the determination of expression levels of the pHisBotG protein (i.e., number of mg/liter expressed as a soluble protein). The purified BotG protein will migrate as a single band of the predicted MW (i.e., –50 kD).

The level of expression of the pHisBotG protein may be modified (increased) by substitution of the T7 promoter for the T7lac promoter, or by inclusion of the lacIq gene on the expression plasmid, and plasmid expressed in BL21(DE3) cell lines in fermentation cultures as described in Example 30. If only very low levels (i.e., less than about 0.5%) of soluble pHisBotG protein are expressed using the above expression systems, the pHisBotG construct may be co-expressed with pACYCGro construct as described in Example 32. In this case, the recombinant BotG protein may co-purify with the folding chaperones. The contaminating chaperones may be removed as described in Example 34. Preparations of purified pHisBotG protein are tested for endotoxin contamination using the LAL assay as described in Example 24.

The purifed pHisBotG protein is used to generate neutralizing antibodies. BALBc mice are immunized with the BotG protein using Gerbu GMDP adjuvant (CC Biotech) as described in Example 36. The ability of the anti-BotG antibodies to neutralize native *C. botulinum* type G toxin is demonstrated using the mouse-*C. botulinum* neutralization model described in Example 36.

EXAMPLE 50

Expression of Recombinant Botulinal Toxin Proteins in Eucaryotic Host Cells

Recombinant botulinal C fragment proteins may be expressed in eucaryotic host cells, such as yeast and insect cells.

a) Expression in Yeast

Botulinal C fragments derived from serotypes A, B, C, D, E, F and G may be expressed in yeast cells using a variety of commercially available vectors. For example, the pPIC3K and pPIC9K expression vectors (Invitrogen) may be employed for expression in the methylotrophic yeast, *Pichia pastoris*. When the pPIC3K vector is employed, expression of the botulinal C fragment protein will be intracellular. When the pPIC3K vector is employed, the botulinal C fragment protein will be secreted (the alpha factor secretion signal is provided on the pPIC9K vector).

DNA sequences encoding the desired C fragment is inserted into these vectors using techniques known to the art. Briefly, the desired botulinal expression cassette (including sequences encoding the his-tag; described in the preceding examples) is amplified using the PCR in conjunction with primers that incorporate unique restriction sites at the termini of the amplified fragment. Suitable restriction enzyme sites include SnaBI, EcoRI, AvrII and NotI. When the botulinal C fragment is to be expressed using the pPIC3K vector, the initiator methionine (ATG) is provided by the desired Bot gene sequence and a Kozak consensus sequence is engineered upstream of the ATG (e.g., ACCATGG).

The amplified restriction fragment containing the botulinal C fragment gene is then cloned into the desired expression vector. Recombinant clones are integrated into the *Pichia pastoris* genome and recombinant protein expression is induced using methanol following the manufacturer's instructions (Invitrogen *Pichia* expression kit manual).

*C. botulinum* genes are A/T rich and contain multiple sequences that are similar to yeast transcriptional termination signals (e.g., TTTTTTATA). If premature transcription termination is observed when the botulinal C fragment genes are expressed in yeast, the transcription termination signals present in the C fragment genes can be removed by either site directed mutagenesis (utilizing the pALTER system; Promega) or by construction of synthetic genes utilizing overlapping synthetic primers.

The botulinal C fragment genes may be expressed in other yeast cells using other commercially available vectors [e.g., using the pYES2 vector (Invitrogen) and *S. cerevisiae* cells (Invitrogen)].

b) Expression in Insect Cells

Botulinal C fragments derived from serotypes A, B, C, D, E, F and G may be expressed in insect cells using a variety of commercially available vectors. For example, the pBlueBac4 transfer vector (Invitrogen) may be employed for expression in *Spodoptera frugiperda* (Sf9) insect cells (baculovirus expression system) (equivalent baculovirus vectors and host cells are avaialble from other vendors, e.g., Pharmingen, San Diego, Calif.). Botulinal C fragments contained on NcoI/HindIII fragments contained within the pHisBotA-G expression constructs (described in the preceding examples) are cloned into the pBlueBac4 vector (digested with NcoI and HindIII); the NcoI site present on the C fragment constructs overlaps with the start codon of the fusion proteins. In the case of botulinal C fragment clones that contain internal HindIII sites (e.g., using the BotG sequences described in Ex. 49), the C fragment gene is contained within a NcoI/XhoI fragment on the pHisBot construct. This NcoI/XhoI fragment is excised from pHisBot and inserted into pBlueBac4 digested with NcoI and SalI. Recombinant baculoviruses are made and the desired recombinant C fragment is expressed in Sf9 cells using the protocols provided by the manufacturer (Invitrogen MaxBac manual). The resulting constructs will express the pHisBot protein intracellularly (including the N-terminal his-tag) under the control of the polyhedrin promoter. For extracellular secretion of botulinal C fragment proteins, the C fragment sequences from the pHisBot constructs are cloned into the pMelBacB vector (Invitrogen) as described above for the pBlueBac4 vector. When the pMelBacB vector is employed, the his-tagged botulinal C fragment proteins are secreted (utilizing a vector-encoded honeybee melittin secretion signal) and contain a nine amino acid extension at the N-terminus.

His-tagged botulinal C fragments expressed in yeast or insect cells are purified using metal chelation columns as described in the preceding examples.

From the above it is clear that the present invention provides compositions and methods for the preparation of effective multivalent vaccines against *C. botulinum* neurotoxin. It is also contemplated that the recombinant botulinal proteins be used for the production of antitoxins. All publications and patents mentioned in the above specification are herein incorporated by reference. Various modifications and variations of the described method and system of the invention will be apparent to those skilled in the art without departing from the scope and spirit of the invention.

What is claimed is:

1. A method of making a soluble botulinum toxin type A comprising:

expressing a botulinum toxin from a prokaryotic expression vector comprising a botulinum toxin nucleotide sequence in a prokaryotic host cell wherein the prokaryotic expression vector is T7lac promoter thereby making a soluble botulinum toxin.

2. The method of claim 1 wherein the prokaryotic host cell is *E. coli.*

3. The method of claim 2 wherein the *E. coli* is strain BL21 (DE3).

4. The method of claim 3 wherein a pLys gene is included in the host cell.

5. The method of claim 4 wherein the pLys gene is plasmid encoded.

6. The method of claim 1 wherein the host cell includes a lacIq gene.

7. The method of claim 1 wherein the botulinum toxin nucleotide sequence specifically hybridizes under highly stringent conditions to SEQ ID NO:27.

* * * * *